(12) United States Patent
Kawamura et al.

(10) Patent No.: US 9,944,634 B2
(45) Date of Patent: Apr. 17, 2018

(54) PYRAZOLOPYRIDINE DERIVATIVES AS TTX-S BLOCKERS

(71) Applicant: RaQualia Pharma Inc., Aichi (JP)

(72) Inventors: Kiyoshi Kawamura, Aichi (JP); Tatsuya Yamagishi, Aichi (JP); Yoshimasa Arano, Aichi (JP); Mikio Morita, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 6 days.

(21) Appl. No.: 14/434,203

(22) PCT Filed: Oct. 31, 2013

(86) PCT No.: PCT/JP2013/006475
§ 371 (c)(1),
(2) Date: Apr. 8, 2015

(87) PCT Pub. No.: WO2014/068988
PCT Pub. Date: May 8, 2014

(65) Prior Publication Data
US 2015/0291582 A1    Oct. 15, 2015

Related U.S. Application Data

(60) Provisional application No. 61/720,974, filed on Oct. 31, 2012.

(51) Int. Cl.
| | | |
|---|---|---|
| *C07D 471/04* | (2006.01) |
| *A61K 31/437* | (2006.01) |
| *A61K 31/444* | (2006.01) |
| *A61K 31/4545* | (2006.01) |
| *A61K 31/4725* | (2006.01) |
| *A61K 31/497* | (2006.01) |
| *A61K 31/501* | (2006.01) |
| *A61K 31/5377* | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/4725* (2013.01); *A61K 31/497* (2013.01); *A61K 31/501* (2013.01); *A61K 31/5377* (2013.01)

(58) Field of Classification Search
None
See application file for complete search history.

(56) References Cited

FOREIGN PATENT DOCUMENTS

| EP | 2 380 881 | 10/2011 |
|---|---|---|
| WO | 2005/014558 | 2/2005 |
| WO | 2009/000411 | 12/2008 |
| WO | 2009/073777 | 6/2009 |
| WO | 2010/106333 | 9/2010 |
| WO | 2011/153588 | 12/2011 |
| WO | 2011/158108 | 12/2011 |
| WO | WO 2011/153588 A1 * | 12/2011 |
| WO | 2012/053186 | 4/2012 |
| WO | WO 2012/066061 A1 * | 5/2012 |

OTHER PUBLICATIONS

Bourzat, JD. et al. New method of synthesis of pyrazolo[4,3-c]pyridines. Tetrahedron. 1973, vol. 29, p. 441.*
Carey, FA. Organic Chemistry 6th Ed. McGraw Hill. 2006, chapter 1, p. 9.*
Greenwald, RB. et al. Drug Delivery Systems: Water Soluble Taxol 2'-Poly(ethylene glycol) Ester Prodrugs—Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
International Search Report dated Dec. 17, 2013 in International (PCT) Application No. PCT/JP2013/006475.
Written Opinion of the International Searching Authority dated Dec. 17, 2013 in International (PCT) Application No. PCT/JP2013/006475.
Kayano et al., "Primary structure of rat brain sodium channel III deduced from the cDNA sequence", FEBS Lett., vol. 228, No. 1, Feb. 1988, pp. 187-194.
Lu et al., "Isolation of a Human-Brain Sodium-Channel Gene Encoding Two Isoforms of the Subtype III α-Subunit", Journal of Molecular Neuroscience, vol. 10, No. 1, 1998, pp. 67-70.
Chen et al., "Cloning, distribution and functional analysis of the type III sodium channel from human brain", European Journal of Neuroscience, vol. 12, No. 12, 2000, pp. 4281-4289.
Black et al., "Upregulation of a Silent Sodium Channel After Peripheral, but not Central, Nerve Injury in DRG Neurons", J Neurophysiol, vol. 82, 1999, pp. 2776-2785.
Craner et al., "Changes of Sodium Channel Expression in Experimental Painful Diabetic Neuropathy", Ann Neurol, vol. 52, 2002, pp. 786-792.

(Continued)

*Primary Examiner* — Heidi Reese
(74) *Attorney, Agent, or Firm* — Wenderoth, Lind & Ponack, L.L.P.

(57) ABSTRACT

The present invention relates to pyrazolopyridine derivatives which have blocking activities of voltage gated sodium channels as the TTX-S channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

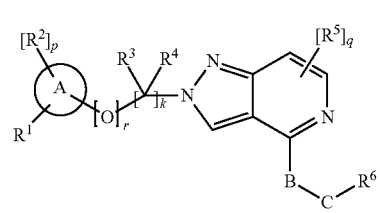

(I)

15 Claims, No Drawings

(56) References Cited

OTHER PUBLICATIONS

Hong et al., "Early Painful Diabetic Neuropathy Is Associated with Differential Changes in Tetrodotoxin-sensitive and -resistant Sodium Channels in Dorsal Root Ganglion Neurons in the Rat", J. Biol. Chem., vol. 279, May 3, 2004, pp. 29341-29350.
Kim et al., "The changes in expression of three subtypes of TTX sensitive sodium channels in sensory neurons after spinal nerve ligation", Molecular Brain Research, vol. 95, 2001, pp. 153-161.
Hains et al., "Altered Sodium Channel Expression in Second-Order Spinal Sensory Neurons Contributes to Pain after Peripheral Nerve Injury", The Journal of Neuroscience, vol. 24(20), May 19, 2004, pp. 4832-4839.
Cox et al., "An SCN9A channelopathy causes congenital inability to experience pain", Nature, vol. 444, Dec. 14, 2006, pp. 894-898.
Baker et al., "Involvement of $Na^+$ channels in pain pathways", TRENDS in Pharmacological Sciences, vol. 22, No. 1, Jan. 2001, pp. 27-31.
Lyu et al., "Low dose of tetrodotoxin reduces neuropathic pain behaviors in an animal model", Brain Research, vol. 871, 2000, pp. 98-103.
Extended European Search Report dated Mar. 21, 2016 in corresponding European Patent Application No. 13851886.5.

\* cited by examiner

PYRAZOLOPYRIDINE DERIVATIVES AS TTX-S BLOCKERS

TECHNICAL FIELD

The present invention relates to the pyrazolopyridine derivatives which are sodium channel blockers and have a number of therapeutic applications, particularly in the treatment of pain.

BACKGROUND ART

The pyrazolopyridine derivatives of the present invention are sodium channel blockers and have a number of therapeutic applications, particularly in the treatment of pain. More particularly, the pyrazolopyridine derivatives of the invention are selective tetrodotoxin-sensitive (TTX-S) blockers. In the discussion that follows, the invention is exemplified by reference to the inhibition of $Na_{v1.3}$ or $Na_{v1.7}$ channel as the TTX-S channels. They show the affinity for $Na_{v1.3}$ or $Na_{v1.7}$ channel which is significantly greater than their affinity for $Na_{v1.5}$ channel as the tetrodotoxin-resistant (TTX-R) sodium channels. The pyrazolopyridine derivatives of the invention show good selectivity for the $Na_{v1.3}$ or $Na_{v1.7}$ channel as compared with $Na_{v1.5}$ channel.

The rat $Na_{v1.3}$ channel and the human $Na_{v1.3}$ channel have been cloned in 1988, 1998, 2000 respectively (NPL 1, NPL 2, and NPL 3). The $Na_{v1.3}$ channel was formerly known as brain type III sodium channel. $Na_{v1.3}$ is present at relatively high levels in the nervous system of rat embryos but is barely detectable in adult rats. $Na_{v1.3}$ is upregulated following axotomy in the Spinal Nerve Ligation (SNL), Chronic Constriction Injury (CCI), and diabetic neuropathy models (NPL 4, NPL 5, NPL 6, and NPL 7). The upregulation of $Na_{v1.3}$ channel contributes to rapidly repriming sodium current in small dorsal root ganglion (DRG) neurons (NPL 3). These observations suggest that $Na_{v1.3}$ may make a key contribution to neuronal hyperexcitability.

In order to validate the contribution of $Na_{v1.3}$ sodium channel in the pain states, specific antisense oligonucleotides (ASO) were used in animal pain models. $Na_{v1.3}$ sodium channel ASO treatment significantly attenuated pain-related behaviors after CCI operation (NPL 8). These findings suggest that $Na_{v1.3}$ sodium channel antagonist is useful to treat neuropathic pain conditions.

The $Na_{v1.7}$ channel appears to be the best 'validated' pain target. The most exciting findings with respect to $Na_{v1.7}$ have come from human genetic studies. Cox et al. (NPL 9) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both TTX-R and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (NPL 10). In rats, application of a very low dose of TTX to the DRG of the injured segment of the L5 spinal nerve significantly reduces mechanical allodynic behavior (NPL 11). This suggests that TTX-S subtypes of sodium channels play an important role in maintaining allodynic behaviors in an animal model of neuropathic pain.

The $Na_{v1.5}$ channel is also a member of TTX-resistant sodium channels. The $Na_{v1.5}$ channel is almost exclusively expressed in cardiac tissue and has been shown to underlie a variety of cardiac arrhythmias and conduction disorders.

CITATION LIST

Non Patent Literature

{NPL 1} FEBS Lett. 228 (1), 187-194, 1988.
{NPL 2} J. Mol. Neurosci., 10 (1), 67-70, 1998.
{NPL 3} Eur. J. Neurosci. 12 (12), 4281-4289, 2000
{NPL 4} J Neurophysiol 82, 2776-2785, 1999. J. A. Black et al.
{NPL 5} Ann Neurol 52, 786-792, 2002. M. J. Cranner et al.
{NPL 6} J Biol Chem 279, 29341-29350, 2004. S. Hong et al.
{NPL 7} Mol Brain Res 95, 153-161, 2001. C. H. Kim et al.
{NPL 8} J. Neurosci. 24, 4832-4839, 2004, Hains, B. C. et al.
{NPL 9} Nature 444, 894-898, 2006.
{NPL 10} Trends in Pharm. Sci 22, 27-31, 2001, Baker, M. D. et al.
{NPL 11} Brain Res 871, 98-103, 2000, Lyu, Y. S. et al.

SUMMARY OF INVENTION

Technical Problem

It is an objective of the invention to provide new TTX-S blockers that are good drug candidates. Preferred compounds should bind potently to the TTX-S($Na_{v1.3}$ and/or $Na_{v1.7}$) channels whilst showing little affinity for other sodium channels, particularly the $Na_{v1.5}$ channel. They should be well absorbed from the gastrointestinal tract, be metabolically stable and possess favorable pharmacokinetic properties. They should be non-toxic and demonstrate few side-effects. Furthermore, the ideal drug candidate will exist in a physical form that is stable, non-hygroscopic and easily formulated.

In particular, the pyrazolopyridine derivatives of the present invention are selective for the TTX-S channels over the $Na_{v1.5}$ channel, leading to improvements in the side-effect profile.

The pyrazolopyridine derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back pain, orofacial pain and chemo-induced pain.

Other conditions that may be treated with the pyrazolopyridine derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The compounds showed activities against $Na_{V1.3}$ or $Na_{V1.7}$ channel. In addition they showed selectivity for the $Na_{V1.3}$ or $Na_{V1.7}$ channel as compared with $Na_{V1.5}$ channel.

Solution to Problem

With respect to other compounds disclosed in the art, the compounds of the present invention may show less toxicity, good plasma absorption and distribution, good solubility, less plasma protein binding, less drug-drug interaction, good metabolic stability, reduced inhibitory activity at HERG channel, and/or reduced QT prolongation.

[1] This invention provides a compound of the following formula (I):

[Chem. 1]

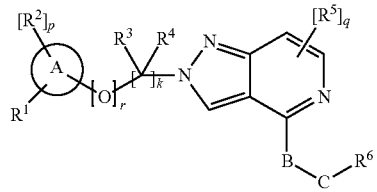

Wherein:
A is aryl; preferable aryl is pyridyl, phenyl, pyrazinyl, pyridazinyl, pyrazole, triazolyl, indolyl, benzimidazolyl, or isoquinolinyl; more preferable aryl is pyridyl, phenyl, pyrazinyl, or pyridazinyl; the most preferable aryl is pyridyl, or phenyl;
B is selected from the group consisting of a chemical bond, —$C_{1-6}$ alkylene-, —$C_{1-6}$ alkylene-$NR^2$—, —$NR^2$—, and —(C=O)—;
C is selected from the group consisting of a chemical bond, —(C=O)—, and —$NR^2$—;
$R^1$ is independently selected from the group consisting of:
(1) hydrogen, (2) —$O_n$—$C_{1-6}$ alkyl where the alkyl is unsubstituted or substituted with one or more substituents independently selected from $R^{11}$, (3) —$O_n$—$C_{3-7}$ cycloalkyl where the cycloalkyl is unsubstituted or substituted with one or more substituents independently selected from $R^{11}$, (4) —$O_n$-aryl where the aryl is unsubstituted or substituted with one or more substituents independently selected from $R^{11}$, (5) —S—$C_{1-6}$ alkyl, where the alkyl is unsubstituted or substituted with one or more substituents independently selected from $R^{11}$, (6) —S-aryl where the aryl is unsubstituted or substituted with one or more substituents independently selected from $R^{11}$; (7) —NH—$C_{1-6}$ alkyl, where the alkyl is unsubstituted or substituted with one or more substituents independently selected from $R^{11}$, and (8) —NH-aryl, where the aryl is unsubstituted or substituted with one or more substituents independently selected from $R^{11}$;
preferable $R^1$ is independently selected from the group consisting of;
(2) —$O_n$—$C_{1-6}$ alkyl where the alkyl is unsubstituted or substituted with one or more substituents independently selected from $R^{11}$, (3) —$O_n$—$C_{3-7}$ cycloalkyl where the cycloalkyl is unsubstituted or substituted with one or more substituents independently selected from $R^{11}$, (4) —$O_n$-aryl where the aryl is unsubstituted or substituted with one or more substituents independently selected from $R^{11}$, and (7) —NH—$C_{1-6}$ alkyl, where the alkyl is unsubstituted or substituted with one or more substituents independently selected from $R^{11}$;
wherein n is independently 0 or 1, when n is 0, a chemical bond is present in the place of —$O_n$—;
$R^2$ is independently selected from the group consisting of:
(1) hydrogen, (2) halogen, (3) hydroxyl, (4) —$O_n$—$C_{1-6}$ alkyl, where the alkyl is unsubstituted or substituted with one or more substituents independently selected from $R^7$, (5) —$O_n$—$C_{3-6}$ cycloalkyl, where the cycloalkyl is unsubstituted or substituted with one or more substituents independently selected from $R^7$, (6) —$O_n$—$C_{2-4}$ alkenyl, where the alkenyl is unsubstituted or substituted with one or more substituents independently selected from $R^7$, (7) —$O_n$-phenyl or —$O_n$-naphthyl, where the phenyl or naphthyl is unsubstituted or substituted with one or more substituents independently selected from $R^7$, (8) —$O_n$-heterocyclyl, where the heterocyclyl is unsubstituted or substituted with one or more substituents independently selected from $R^7$, (9) —(C=O)—$NR^8R^9$, (10) —$NR^8R^9$, (11) —$S(O)_2$—$NR^8R^9$, (12) —$NR^8$—$S(O)_2R^9$, (13) —$S(O)_t$—$R^9$, where t is 0, 1 or 2, (14) —$NR^8$ (C=O)$R^9$, (15) —CN, and (16) —$NO_2$;
wherein n is independently 0 or 1, when n is 0, a chemical bond is present in the place of —$O_n$—; preferable $R^2$ is independently selected from the group consisting of: (1) hydrogen, (2) halogen, (3) $C_{1-6}$ alkyl, and (4) —O—$C_{1-6}$ alkyl; more preferable $R^2$ is independently selected from the group consisting of: (1) hydrogen, (2) halogen, (3) methyl, and (4) methoxy;
p is 1, 2, 3, or 4; when p is two or more than two, $R^2$ may be same or different; preferable p is 1;
$R^3$ and $R^4$ are independently hydrogen or $C_{1-6}$ alkyl which is unsubstituted or substituted with one or more substituents independently selected from halogen, hydroxyl, and —O—$C_{1-6}$ alkyl; or $R^3$ form a 3 to 7 membered ring with $R^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^{11}$, (5) $C_{3-6}$ cycloalkyl, which is unsubstituted or substituted with one or more substituents independently selected from $R^{11}$, (6) —O—$C_{1-6}$ alkyl, where the alkyl is unsubstituted or substituted with one or more substituents independently selected from $R^{11}$, and (7) —O—$C_{3-6}$ cycloalkyl, where the cycloalkyl is unsubstituted or substituted with one or more substituents independently selected from $R^{11}$; preferable $R^3$ is hydrogen; preferable $R^4$ is hydrogen or $C_{1-6}$ alkyl; more preferable $R^4$ is hydrogen or methyl; $R^5$ is independently selected from the group consisting of:
(1) hydrogen, (2) halogen, (3) —$O_n$—$C_{1-6}$ alkyl, where the alkyl is unsubstituted or substituted with one or more substituents independently selected from $R^7$, (4) —$O_n$—$C_{3-6}$ cycloalkyl, where the cycloalkyl is unsubstituted or substituted with one or more substituents independently selected from $R^7$, and (5) —$O_n$—$C_{2-4}$ alkenyl, where the alkenyl is unsubstituted or substituted with one or more substituents independently selected from $R^7$;

wherein n is independently 0 or 1, when n is 0, a chemical bond is present in the place of —$O_n$—; preferable $R^5$ is hydrogen or $C_{1-6}$ alkyl; more preferable $R^5$ is hydrogen or methyl;

$R^5$ may be anywhere on the pyrazolopyridine ring;

q is 1, 2 or 3; when q is two or more than two, $R^5$ may be same or different; preferable q is 1;

$R^6$ is independently hydrogen, $C_{1-6}$ alkyl, $C_{1-6}$ alkoxy, $C_{2-6}$ alkenyl, $C_{3-7}$ cycloalkyl, —$NR^8R^9$, heterocyclyl, aryl, aryl-$C_{1-6}$ alkyl, or heterocyclyl-$C_{1-6}$ alkyl, where the $C_{1-6}$ alkyl, the $C_{1-6}$ alkoxy, the $C_{2-6}$ alkenyl, the $C_{3-7}$ cycloalkyl, the heterocyclyl, the aryl, the aryl-$C_{1-6}$ alkyl, or the heterocyclyl-$C_{1-6}$ alkyl, is unsubstituted or substituted with one or more substituents independently selected from halogen, hydroxyl, $C_{1-6}$ alkyl, —O—$C_{1-6}$ alkyl, —$C_{3-7}$ cycloalkyl, —O—$C_{3-7}$ cycloalkyl, hydroxyl-$C_{1-6}$ alkoxy, —CN, —$NR^8R^9$, —(C=O)—$R^8$, —(C=O)—$NR^8R^9$, —$NR^8$—(C=O)—$R^9$, —$NR^8$—(C=O)—$NR^9R^{10}$, —$NR^8$—(C=O)—$OR^9$, —$NR^8$—S(O)$_2$—$R^9$, —$NR^8$—S(O)$_2$—$NR^9R^{10}$, and —S(O)$_2$—$R^8$;

when B is —$NR^2$— and C is —(C=O)—, $R^6$ may form the 4-7 membered ring with $R^2$; preferable $R^6$ is independently hydrogen, $C_{1-6}$ alkyl, $C_{3-7}$ cycloalkyl, heterocyclyl, or aryl, where the $C_{1-6}$ alkyl, the $C_{3-7}$ cycloalkyl, the heterocyclyl, or the aryl, is unsubstituted or substituted with one or more substituents independently selected from halogen, hydroxyl, $C_{1-6}$ alkyl, —O—$C_{1-6}$ alkyl, —CN, —$NR^8R^9$, and —$NR^8$—(C=O)—$R^9$; more preferable $R^6$ is selected from the group consisting of methyl, ethyl, isopropyl, and cyclopropyl, heterocyclyl, or aryl which is unsubstituted or substituted with one or more substituents independently selected from halogen, hydroxyl, $C_{1-6}$ alkyl, —O—$C_{1-6}$ alkyl, —CN;

more preferable $R^6$ is also selected from the group consisting of methyl, ethyl, propyl, and cyclopropyl, which is unsubstituted or substituted with one or more substituents independently selected from halogen, hydroxyl, $C_{1-6}$ alkyl, —O—$C_{1-6}$ alkyl, —CN, —$NR^8R^9$, and —$NR^8$—(C=O)—$R^9$;

$R^7$ is selected from the group consisting of:
(1) hydrogen, (2) halogen, (3) hydroxyl, (4) —(C=O)$_m$—$O_l$—$C_{1-6}$ alkyl, where the alkyl is unsubstituted or substituted with one or more substituents independently selected from $R^{11}$, (5) —$O_l$—(C$_{1-3}$)perfluoroalkyl, (6) —(C=O)$_m$—$O_l$—$C_{3-6}$ cycloalkyl, where the cycloalkyl is unsubstituted or substituted with one or more substituents independently selected from $R^{11}$, (7) —(C=O)$_m$—$O_l$—$C_{2-4}$alkenyl, where the alkenyl is unsubstituted or substituted with one or more substituents independently selected from $R^{11}$, (8) —(C=O)$_m$—$O_l$-phenyl or —(C=O)$_m$—$O_l$-naphthyl, where the phenyl or naphthyl is unsubstituted or substituted with one or more substituents independently selected from $R^{11}$, (9) —(C=O)$_m$—$O_l$-heterocyclyl, where the heterocyclyl is unsubstituted or substituted with one or more substituents independently selected from $R^{11}$, (10) —(C=O)—$NR^8R^9$, (11) —$NR^8R^9$, (12) —S(O)$_2$—$NR^8R^9$, (13) —S(O)$_t$—$R^8$, where t is 0, 1 or 2, (14) —CO$_2$H, (15) —CN, and (16) —NO$_2$;

wherein l is 0 or 1 and m is 0 or 1; when l is 0 or m is 0, a chemical bond is present in the place of —$O_l$— or —(C=O)$_m$—, and when l is 0 and m is 0, a chemical bond is present in the place of —(C=O)$_m$—$O_l$—;

preferable $R^7$ is hydrogen;

$R^8$, $R^9$, and $R^{10}$ are independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, —O—$C_{1-6}$ alkyl, $C_{3-7}$ cycloalkyl, and —O—$C_{3-7}$ cycloalkyl; or $R^8$ form a 4 to 7 membered ring with $R^9$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^{11}$, (5) $C_{3-6}$ cycloalkyl, which is unsubstituted or substituted with one or more substituents independently selected from $R^{11}$, (6) —O—$C_{1-6}$ alkyl, where the alkyl is unsubstituted or substituted with one or more substituents independently selected from $R^{11}$, and (7) —O—$C_{3-6}$ cycloalkyl, where the cycloalkyl is unsubstituted or substituted with one or more substituents independently selected from $R^{11}$;

preferable $R^8$, $R^9$, and $R^{10}$ are independently hydrogen, $C_{1-6}$ alkyl, or $C_{3-7}$ cycloalkyl;

$R^{11}$ is independently selected from the group consisting of: (1) hydrogen, (2) hydroxyl, (3) halogen, (4) —$C_{1-6}$ alkyl, which is unsubstituted or substituted with one or more halogen, (5) —$C_{3-6}$ cycloalkyl, (6) —O—$C_{1-6}$ alkyl, where the alkyl is unsubstituted or substituted with one or more halogen, (7) —O(C=O)—$C_{1-6}$ alkyl, (8) —NH—$C_{1-6}$ alkyl, (9) phenyl, (10) heterocyclyl, (11) —CN, and (12) —Si($C_{1-6}$ alkyl)$_3$;

preferable $R^{11}$ is halogen or —$C_{3-6}$ cycloalkyl;

k is 1 or 2; preferable k is 1;

r is 0 or 1, when r is 0, a chemical bond is present in the place of —[O]$_r$—; preferable r is 0;

or a prodrug thereof or a pharmaceutically acceptable salt thereof.

[2] This invention provides a compound represented by above formula (I) according to [1]
wherein:
k is 1;
r is 0;
or a prodrug thereof or a pharmaceutically acceptable salt thereof.

[3] Preferable compounds of this invention are represented by the following formula (II):

[Chem. 2]

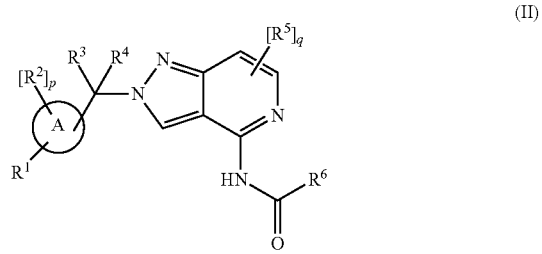

wherein:
A is aryl; preferable aryl is pyridyl, phenyl, pyrazinyl, pyridazinyl, pyrazole, triazolyl, indolyl, benzimidazolyl, or isoquinolinyl; more preferable aryl is pyridyl, phenyl, pyrazinyl, or pyridazinyl; the most preferable aryl is pyridyl, or phenyl;

$R^1$ is independently selected from the group consisting of:
(1) hydrogen, (2) —$O_n$—$C_{1-6}$ alkyl where the alkyl is unsubstituted or substituted with one or more substituents independently selected from $R^{11}$, (3) —$O_n$—$C_{3-7}$ cycloalkyl where the cycloalkyl is unsubstituted or substituted with one or more substituents independently selected from $R^{11}$, (4) —$O_n$-aryl where the aryl is unsubstituted or substituted with one or more substituents independently selected from $R^{11}$, (5) —S—$C_{1-6}$ alkyl, where the alkyl is unsubstituted or substituted with one or more substituents independently selected from $R^{11}$, (6) —S-aryl where the aryl is unsubstituted or substituted with one or more substituents independently selected from $R^{11}$; (7) —NH—$C_{1-6}$ alkyl, where the alkyl is unsubstituted or substituted with one or more substituents independently selected from $R^{11}$, and (8) —NH-aryl, where the aryl is unsubstituted or substituted with one or more substituents independently selected from $R^{11}$;

preferable $R^1$ is independently selected from the group consisting of:
(2) —$O_n$—$C_{1-6}$ alkyl where the alkyl is unsubstituted or substituted with one or more substituents independently selected from $R^{11}$, (3) —$O_n$—$C_{3-7}$ cycloalkyl where the cycloalkyl is unsubstituted or substituted with one or more substituents independently selected from $R^{11}$, (4) —$O_n$-aryl where the aryl is unsubstituted or substituted with one or more substituents independently selected from $R^{11}$ and (7) —NH—$C_{1-6}$ alkyl, where the alkyl is unsubstituted or substituted with one or more substituents independently selected from $R^{11}$;

wherein n is independently 0 or 1, when n is 0, a chemical bond is present in the place of —$O_n$—;

$R^2$ is independently selected from the group consisting of:
(1) hydrogen, (2) halogen, (3) hydroxyl, (4) —$O_n$—$C_{1-6}$ alkyl, where the alkyl is unsubstituted or substituted with one or more substituents independently selected from $R^7$, (5) —$O_n$—$C_{3-6}$ cycloalkyl, where the cycloalkyl is unsubstituted or substituted with one or more substituents independently selected from $R^7$, (6) —$O_n$—$C_{2-4}$ alkenyl, where the alkenyl is unsubstituted or substituted with one or more substituents independently selected from $R^7$, (7) —$O_n$-phenyl or —$O_n$-naphthyl, where the phenyl or naphthyl is unsubstituted or substituted with one or more substituents independently selected from $R^7$, (8) —$O_n$-heterocyclyl, where the heterocyclyl is unsubstituted or substituted with one or more substituents independently selected from $R^7$, (9) —(C=O)—$NR^8R^9$, (10) —$NR^8R^9$, (11) —$S(O)_2$—$NR^8R^9$, (12) —$NR^8$—$S(O)_2R^9$, (13) —$S(O)_t$—$R^9$, where t is 0, 1 or 2, (14) —$NR^8$(C=O)$R^9$, (15) —CN, and (16) —$NO_2$;

wherein n is independently 0 or 1, when n is 0, a chemical bond is present in the place of —$O_n$—;

preferable $R^2$ is independently selected from the group consisting of: (1) hydrogen, (2) halogen, (3) $C_{1-6}$ alkyl, and (4) —O—$C_{1-6}$ alkyl; more preferable $R^2$ is independently selected from the group consisting of: (1) hydrogen, (2) halogen, (3) methyl, and (4) methoxy;

p is 1, 2, 3, or 4; when p is two or more than two, $R^2$ may be same or different; preferable p is 1;

$R^3$ and $R^4$ are independently hydrogen or $C_{1-6}$ alkyl which is unsubstituted or substituted with one or more substituents independently selected from halogen, hydroxyl, and —O—$C_{1-6}$ alkyl; or $R^3$ form a 3 to 7 membered ring with $R^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^{11}$, (5) $C_{3-6}$ cycloalkyl, which is unsubstituted or substituted with one or more substituents independently selected from $R^{11}$, (6) —O—$C_{1-6}$ alkyl, where the alkyl is unsubstituted or substituted with one or more substituents independently selected from $R^{11}$, and (7) —O—$C_{3-6}$ cycloalkyl, where the cycloalkyl is unsubstituted or substituted with one or more substituents independently selected from $R^{11}$;

preferable $R^3$ is hydrogen; preferable $R^4$ is hydrogen or $C_{1-6}$ alkyl; more preferable $R^4$ is hydrogen or methyl;

$R^5$ is independently selected from the group consisting of:
(1) hydrogen, (2) halogen, (3) —$O_n$—$C_{1-6}$ alkyl, where the alkyl is unsubstituted or substituted with one or more substituents independently selected from $R^7$, (4) —$O_n$—$C_{3-6}$ cycloalkyl, where the cycloalkyl is unsubstituted or substituted with one or more substituents independently selected from $R^7$, and (5) —$O_n$—$C_{2-4}$ alkenyl, where the alkenyl is unsubstituted or substituted with one or more substituents independently selected from $R^7$;

wherein n is independently 0 or 1, when n is 0, a chemical bond is present in the place of —$O_n$—;

preferable $R^5$ is hydrogen or $C_{1-6}$ alkyl; more preferable $R^5$ is hydrogen or methyl;

$R^5$ may be anywhere on the pyrazolopyridine ring;

q is 1, 2 or 3; when q is two or more than two, $R^5$ may be same or different; preferable q is 1;

$R^6$ is independently hydrogen, $C_{1-6}$ alkyl, $C_{1-6}$ alkoxy, $C_{2-6}$ alkenyl, $C_{3-7}$ cycloalkyl, —$NR^8R^9$, heterocyclyl, aryl, aryl-$C_{1-6}$ alkyl, or heterocyclyl-$C_{1-6}$ alkyl, where the $C_{1-6}$ alkyl, the $C_{1-6}$ alkoxy, the $C_{2-6}$ alkenyl, the $C_{3-7}$ cycloalkyl, the heterocyclyl, the aryl, the aryl-$C_{1-6}$ alkyl, or the heterocyclyl-$C_{1-6}$ alkyl, is unsubstituted or substituted with one or more substituents independently selected from halogen, hydroxyl, $C_{1-6}$ alkyl, —O—$C_{1-6}$ alkyl, —$C_{3-7}$ cycloalkyl, —O—$C_{3-7}$ cycloalkyl, hydroxyl-$C_{1-6}$ alkoxy, —CN, —$NR^8R^9$, —(C=O)—$R^8$, —(C=O)—$NR^8R^9$, —$NR^8$—(C=O)—$R^9$, —$NR^8$—(C=O)—$NR^9R^{10}$, —$NR^8$—$S(O)_2$—$R^9$, —$NR^8$—$S(O)_2$—$NR^9R^{10}$, and —$S(O)_2$—$R^8$;

preferable $R^6$ is independently hydrogen, $C_{1-6}$ alkyl, $C_{3-7}$ cycloalkyl, heterocyclyl, or aryl, where the $C_{1-6}$ alkyl, the $C_{3-7}$ cycloalkyl, the heterocyclyl, or the aryl, is unsubstituted or substituted with one or more substituents independently selected from halogen, hydroxyl, $C_{1-6}$ alkyl, —O—$C_{1-6}$ alkyl, —CN, —$NR^8R^9$, and —$NR^8$—(C=O)—$R^9$; more preferable $R^6$ is selected from the group consisting of methyl, ethyl, isopropyl, and cyclopropyl, heterocyclyl, or aryl which is unsubstituted or substituted with one or more substituents independently selected from halogen, hydroxyl, $C_{1-6}$ alkyl, —O—$C_{1-6}$ alkyl, —CN;

$R^7$ is selected from the group consisting of:
(1) hydrogen, (2) halogen, (3) hydroxyl, (4) —(C=O)$_m$—$O_t$—$C_{1-6}$ alkyl, where the alkyl is unsubstituted or substituted with one or more substituents independently selected from $R^{11}$, (5) —$O_t$—$(C_{1-3})$perfluoroalkyl, (6) —(C=O)$_m$—$O_t$—$C_{3-6}$ cycloalkyl, where the cycloalkyl is unsubstituted or substituted with one or more substituents independently selected from $R^{11}$, (7) —(C=O)$_m$—$O_t$—$C_{2-4}$alkenyl, where the alkenyl is unsubstituted or substituted with one or more substituents independently selected from $R^{11}$, (8) —(C=O)$_m$—$O_t$-phenyl or —(C=O)$_m$—O$_l$-naphthyl, where the phenyl or naphthyl is unsubstituted or substituted with one or more substituents independently selected from R$^{11}$, (9) —(C=O)$_m$—O$_l$-heterocyclyl, where the heterocyclyl is unsubstituted or substituted with one or more substituents independently selected from R$^{11}$, (10) —(C=O)—NR$^8$R$^9$, (11) —NR$^8$R$^9$, (12) —S(O)$_2$—NR$^8$R$^9$, (13) —S(O)$_t$—R$^8$, where t is 0, 1 or 2, (14) —CO$_2$H, (15) —CN, and (16) —NO$_2$;

wherein l is 0 or 1 and m is 0 or 1; when l is 0 or m is 0, a chemical bond is present in the place of —O$_l$ or —(C=O)$_m$—, and when l is 0 and m is 0, a chemical bond is present in the place of —(C=O)$_m$—O$_l$—;

preferable R$^7$ is hydrogen;

R$^8$, R$^9$, and R$^{10}$ are independently hydrogen, C$_{1-6}$ alkyl, C$_{2-6}$ alkenyl, C$_{3-7}$ cycloalkyl, or aryl, which is unsubstituted or substituted with one or more substituents independently selected from halogen, hydroxyl, C$_{1-6}$ alkyl, —O—C$_{1-6}$ alkyl, C$_{3-7}$ cycloalkyl, and —O—C$_{3-7}$ cycloalkyl; or R$^8$ form a 4 to 7 membered ring with R$^9$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) C$_{1-6}$ alkyl, which is unsubstituted or substituted with one or more substituents independently selected from R$^{11}$, (5) C$_{3-6}$ cycloalkyl, which is unsubstituted or substituted with one or more substituents independently selected from R$^{11}$, (6) —O—C$_{1-6}$ alkyl, where the alkyl is unsubstituted or substituted with one or more substituents independently selected from R$^{11}$, and (7) —O—C$_{3-6}$ cycloalkyl, where the cycloalkyl is unsubstituted or substituted with one or more substituents independently selected from R$^{11}$;

preferable R$^8$, R$^9$, and R$^{10}$ are independently hydrogen, C$_{1-6}$ alkyl, or C$_{3-7}$ cycloalkyl; R$^{11}$ is independently selected from the group consisting of:

(1) hydrogen, (2) hydroxyl, (3) halogen, (4) —C$_{1-6}$ alkyl, which is unsubstituted or substituted with one or more halogen, (5) —C$_{3-6}$ cycloalkyl, (6) —O—C$_{1-6}$ alkyl, where the alkyl is unsubstituted or substituted with one or more halogen, (7) —O(C=O)—C$_{1-6}$ alkyl, (8) —NH—C$_{1-6}$ alkyl, (9) phenyl, (10) heterocyclyl, (11) —CN, and (12) —Si(C$_{1-6}$ alkyl)$_3$; preferable R$^{11}$ is halogen or —C$_{3-6}$ cycloalkyl;

or a prodrug thereof or a pharmaceutically acceptable salt thereof.

[4] Compounds described in [3] are further preferred wherein:

R$^2$ is independently selected from the group consisting of:
(1) hydrogen, (2) halogen, (3) methyl, and (4) methoxy;
p is 1;
R$^3$ is hydrogen;
R$^4$ is hydrogen or methyl;
R$^6$ is selected from the group consisting of methyl, ethyl, isopropyl, and cyclopropyl, heterocyclyl, or aryl which is unsubstituted or substituted with one or more substituents independently selected from halogen, hydroxyl, C$_{1-6}$ alkyl, —O—C$_{1-6}$ alkyl, —CN;

or a prodrug thereof or a pharmaceutically acceptable salt thereof.

[5] Preferable compounds of this invention are represented by the following formula (III):

[Chem. 3]

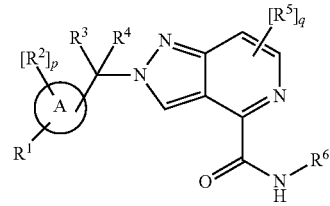

(III)

wherein:

A is aryl; preferable aryl is pyridyl, phenyl, pyrazinyl, pyridazinyl, pyrazole, triazolyl, indolyl, benzimidazolyl, or isoquinolinyl; more preferable aryl is pyridyl, phenyl, pyrazinyl, or pyridazinyl; the most preferable aryl is pyridyl, or phenyl;

R$^1$ is independently selected from the group consisting of;
(1) hydrogen, (2) —O$_n$—C$_{1-6}$ alkyl where the alkyl is unsubstituted or substituted with one or more substituents independently selected from R$^{11}$, (3) —O$_n$—C$_{3-7}$ cycloalkyl where the cycloalkyl is unsubstituted or substituted with one or more substituents independently selected from R$^{11}$, (4) —O$_n$-aryl where the aryl is unsubstituted or substituted with one or more substituents independently selected from R$^{11}$, (5) —S—C$_{1-6}$ alkyl, where the alkyl is unsubstituted or substituted with one or more substituents independently selected from R$^{11}$, (6) —S-aryl where the aryl is unsubstituted or substituted with one or more substituents independently selected from R$^{11}$; (7) —NH—C$_{1-6}$ alkyl, where the alkyl is unsubstituted or substituted with one or more substituents independently selected from R$^{11}$, and (8) —NH-aryl, where the aryl is unsubstituted or substituted with one or more substituents independently selected from R$^{11}$;

preferable R$^1$ is independently selected from the group consisting of;
(2) —O$_n$—C$_{1-6}$ alkyl where the alkyl is unsubstituted or substituted with one or more substituents independently selected from R$^{11}$, (3) —O$_n$—C$_{3-7}$ cycloalkyl where the cycloalkyl is unsubstituted or substituted with one or more substituents independently selected from R$^{11}$, (4) —O$_n$-aryl where the aryl is unsubstituted or substituted with one or more substituents independently selected from R$^{11}$ and (7) —NH—C$_{1-6}$ alkyl, where the alkyl is unsubstituted or substituted with one or more substituents independently selected from R$^{11}$;

wherein n is independently 0 or 1, when n is 0, a chemical bond is present in the place of —O$_n$—;

R$^2$ is independently selected from the group consisting of:
(1) hydrogen, (2) halogen, (3) hydroxyl, (4) —O$_n$—C$_{1-6}$ alkyl, where the alkyl is unsubstituted or substituted with one or more substituents independently selected from R$^7$, (5) —O$_n$—C$_{3-6}$ cycloalkyl, where the cycloalkyl is unsubstituted or substituted with one or more substituents independently selected from R$^7$, (6) —O$_n$—C$_{2-4}$ alkenyl, where the alkenyl is unsubstituted or substituted with one or more substituents independently selected from R$^7$, (7) —O$_n$-phenyl or —O$_n$-naphthyl, where the phenyl or naphthyl is unsubstituted or substituted with one or more substituents independently selected from R$^7$, (8) —O$_n$-heterocyclyl, where the heterocyclyl is unsubstituted or substituted with one or more substituents independently selected from R$^7$, (9) —(C=O)—NR$^8$R$^9$, (10) —NR$^8$R$^9$, (11) —S(O)$_2$—NR$^8$R$^9$, (12) —NR$^8$—S(O)$_2$R$^9$, (13)

—S(O)$_t$—R$^9$, where t is 0, 1 or 2, (14) —NR$^8$(C=O)R$^9$, (15) —CN, and (16) —NO$_2$;

wherein n is independently 0 or 1, when n is 0, a chemical bond is present in the place of —O$_n$—; preferable R$^2$ is independently selected from the group consisting of: (1) hydrogen, (2) halogen, (3) C$_{1-6}$ alkyl, and (4) —O—C$_{1-6}$ alkyl; more preferable R$^2$ is independently selected from the group consisting of: (1) hydrogen, (2) halogen, (3) methyl, and (4) methoxy;

p is 1, 2, 3, or 4; when p is two or more than two, R$^2$ may be same or different; preferable p is 1;

R$^3$ and R$^4$ are independently hydrogen or C$_{1-6}$ alkyl which is unsubstituted or substituted with one or more substituents independently selected from halogen, hydroxyl, and —O—C$_{1-6}$ alkyl; or R$^3$ form a 3 to 7 membered ring with R$^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) C$_{1-6}$ alkyl, which is unsubstituted or substituted with one or more substituents independently selected from R$^{11}$, (5) C$_{3-6}$ cycloalkyl, which is unsubstituted or substituted with one or more substituents independently selected from R$^{11}$, (6) —O—C$_{1-6}$ alkyl, where the alkyl is unsubstituted or substituted with one or more substituents independently selected from R$^{11}$, and (7) —O—C$_{3-6}$ cycloalkyl, where the cycloalkyl is unsubstituted or substituted with one or more substituents independently selected from R$^{11}$;

preferable R$^3$ is hydrogen; preferable R$^4$ is hydrogen or C$_{1-6}$ alkyl; more preferable R$^4$ is hydrogen or methyl;

R$^5$ is independently selected from the group consisting of:
(1) hydrogen, (2) halogen, (3) —O$_n$—C$_{1-6}$ alkyl, where the alkyl is unsubstituted or substituted with one or more substituents independently selected from R$^7$, (4) —O$_n$—C$_{3-6}$ cycloalkyl, where the cycloalkyl is unsubstituted or substituted with one or more substituents independently selected from R$^7$, and (5) —O$_n$—C$_{2-4}$ alkenyl, where the alkenyl is unsubstituted or substituted with one or more substituents independently selected from R$^7$;

wherein n is independently 0 or 1, when n is 0, a chemical bond is present in the place of —O$_n$—;

preferable R$^5$ is hydrogen or C$_{1-6}$ alkyl; more preferable R$^5$ is hydrogen or methyl; R$^5$ may be anywhere on the pyrazolopyridine ring;

q is 1, 2 or 3; when q is two or more than two, R$^5$ may be same or different; preferable q is 1;

R$^6$ is independently hydrogen, C$_{1-6}$ alkyl, C$_{1-6}$ alkoxy, C$_{2-6}$ alkenyl, C$_{3-7}$ cycloalkyl, heterocyclyl, aryl, aryl-C$_{1-6}$ alkyl, or heterocyclyl-C$_{1-6}$ alkyl, where the C$_{1-6}$ alkyl, the C$_{1-6}$ alkoxy, the C$_{2-6}$ alkenyl, the C$_{3-7}$ cycloalkyl, the heterocyclyl, the aryl, the aryl-C$_{1-6}$ alkyl, or the heterocyclyl-C$_{1-6}$ alkyl, is unsubstituted or substituted with one or more substituents independently selected from halogen, hydroxyl, C$_{1-6}$ alkyl, —O—C$_{1-6}$ alkyl, —C$_{3-7}$ cycloalkyl, —O—C$_{3-7}$ cycloalkyl, hydroxyl-C$_{1-6}$ alkoxy, —CN, —NR$^8$R$^9$, —(C=O)—R$^8$, —(C=O)—NR$^8$R$^9$, —NR$^8$—(C=O)—R$^9$, —NR$^8$—(C=O)—NR$^9$R$^{10}$, —NR$^8$—(C=O)—OR$^9$, —NR$^8$—S(O)$_2$—R$^9$, —NR$^8$—S(O)$_2$—NR$^9$R$^{10}$, and —S(O)$_2$—R$^8$; preferable R$^6$ is independently hydrogen, C$_{1-6}$ alkyl, C$_{3-7}$ cycloalkyl, heterocyclyl, or aryl, where the C$_{1-6}$ alkyl, the C$_{3-7}$ cycloalkyl, the heterocyclyl, or the aryl, is unsubstituted or substituted with one or more substituents independently selected from halogen, hydroxyl, C$_{1-6}$ alkyl, —O—C$_{1-6}$ alkyl, —CN, —NR$^8$R$^9$, and —NR$^8$—(C=O)—R$^9$; more preferable R$^6$ is selected from the group consisting of methyl, ethyl, propyl, and cyclopropyl, which is unsubstituted or substituted with one or more substituents independently selected from halogen, hydroxyl, C$_{1-6}$ alkyl, —O—C$_{1-6}$ alkyl, —CN, —NR$^8$R$^9$, and —NR$^8$—(C=O)—R$^9$;

R$^7$ is selected from the group consisting of:
(1) hydrogen, (2) halogen, (3) hydroxyl, (4) —(C=O)$_m$—O$_l$—C$_{1-6}$ alkyl, where the alkyl is unsubstituted or substituted with one or more substituents independently selected from R$^{11}$, (5) —O$_l$—(C$_{1-3}$)perfluoroalkyl, (6) —(C=O)$_m$—O$_l$—C$_{3-6}$ cycloalkyl, where the cycloalkyl is unsubstituted or substituted with one or more substituents independently selected from R$^{11}$, (7) —(C=O)$_m$—O$_l$—C$_{2-4}$alkenyl, where the alkenyl is unsubstituted or substituted with one or more substituents independently selected from R$^{11}$, (8) —(C=O)$_m$—O$_l$-phenyl or —(C=O)$_m$—O$_l$-naphthyl, where the phenyl or naphthyl is unsubstituted or substituted with one or more substituents independently selected from R$^{11}$, (9) —(C=O)$_m$—O$_l$-heterocyclyl, where the heterocyclyl is unsubstituted or substituted with one or more substituents independently selected from R$^{11}$, (10) —(C=O)—NR$^8$R$^9$, (11) —NR$^8$R$^9$, (12) —S(O)$_2$—NR$^8$R$^9$, (13) —S(O)—R$^8$, where t is 0, 1 or 2, (14) —CO$_2$H, (15) —CN, and (16) —NO$_2$;

wherein l is 0 or 1 and m is 0 or 1; when l is 0 or m is 0, a chemical bond is present in the place of —O$_l$— or —(C=O)$_m$—, and when l is 0 and m is 0, a chemical bond is present in the place of —(C=O)$_m$—O$_l$—;

preferable R$^7$ is hydrogen;

R$^8$, R$^9$, and R$^{10}$ are independently hydrogen, C$_{1-6}$ alkyl, C$_{2-6}$ alkenyl, C$_{3-7}$ cycloalkyl, or aryl, which is unsubstituted or substituted with one or more substituents independently selected from halogen, hydroxyl, C$_{1-6}$ alkyl, —O—C$_{1-6}$ alkyl, C$_{3-7}$ cycloalkyl, and —O—C$_{3-7}$ cycloalkyl; or R$^8$ form a 4 to 7 membered ring with R$^9$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) C$_{1-6}$ alkyl, which is unsubstituted or substituted with one or more substituents independently selected from R$^{11}$, (5) C$_{3-6}$ cycloalkyl, which is unsubstituted or substituted with one or more substituents independently selected from R$^{11}$, (6) —O—C$_{1-6}$ alkyl, where the alkyl is unsubstituted or substituted with one or more substituents independently selected from R$^{11}$, and (7) —O—C$_{3-6}$ cycloalkyl, where the cycloalkyl is unsubstituted or substituted with one or more substituents independently selected from R$^{11}$;

preferable R$^8$, R$^9$, and R$^{10}$ are independently hydrogen, C$_{1-6}$ alkyl, or C$_{3-7}$ cycloalkyl;

R$^{11}$ is independently selected from the group consisting of:
(1) hydrogen, (2) hydroxyl, (3) halogen, (4) —C$_{1-6}$ alkyl, which is unsubstituted or substituted with one or more halogen, (5) —C$_{3-6}$ cycloalkyl, (6) —O—C$_{1-6}$ alkyl, where the alkyl is unsubstituted or substituted with one or more halogen, (7) —O(C=O)—C$_{1-6}$ alkyl, (8) —NH—C$_{1-6}$ alkyl, (9) phenyl, (10) heterocyclyl, (11) —CN, and (12) —Si(C$_{1-6}$ alkyl)$_3$;

preferable R$^{11}$ is halogen or —C$_{3-6}$ cycloalkyl;

or a prodrug thereof or a pharmaceutically acceptable salt thereof.

[6] Compounds described in [5] are further preferred wherein:
R$^2$ is independently selected from the group consisting of: (1) hydrogen, (2) halogen, (3) methyl, and (4) methoxy;
p is 1;
R$^3$ is hydrogen;
R$^4$ is hydrogen or methyl;
R$^6$ is selected from the group consisting of methyl, ethyl, isopropyl, propyl, or butyl which is unsubstituted or substituted with one or more substituents independently selected from hydroxyl, C$_{1-6}$ alkyl, C$_{3-7}$ cycloalkyl, —O—C$_{1-6}$ alkyl, —CN, and —NR$^8$—(C=O)—R$^9$ in which each of R$^8$ and R$^9$ has the same meaning as above;
or a prodrug thereof or a pharmaceutically acceptable salt thereof.

[7] Suitable individual compounds of the invention are:
N-(2-((5-methyl-6-(2,2,2-trifluoroethoxy)pyridin-3-yl)methyl)-2H-pyrazolo[4,3-c]pyridin-4-yl)-isobutyramide;
2-hydroxy-2-methyl-N-(2-((5-methyl-6-(2,2,2-trifluoroethoxy)pyridin-3-yl)methyl)-2H-pyrazolo[4,3-c]pyridin-4-yl)propanamide;
N-(2-((5-methyl-6-(2,2,2-trifluoroethoxy)pyridin-3-yl)methyl)-2H-pyrazolo[4,3-c]pyridin-4-yl)-acetamide;
N-(2-((6-(2,2-difluoroethoxy)-5-methylpyridin-3-yl)methyl)-2H-pyrazolo[4,3-c]pyridin-4-yl)-isobutyramide;
N-(2-((6-(2,2-difluoroethoxy)-5-methylpyridin-3-yl)methyl)-2H-pyrazolo[4,3-c]pyridin-4-yl)-acetamide;
N-(2-((6-(2,2-difluoroethoxy)-5-methylpyridin-3-yl)methyl)-2H-pyrazolo[4,3-c]pyridin-4-yl)-propionamide;
N-(2-((6-(2,2-difluoroethoxy)-5-methylpyridin-3-yl)methyl)-2H-pyrazolo[4,3-c]pyridin-4-yl)-cyclopropanecarboxamide;
N-(2-((6-(2,2-difluoroethoxy)-5-methylpyridin-3-yl)methyl)-2H-pyrazolo[4,3-c]pyridin-4-yl)-2-hydroxy-2-methylpropanamide;
N-(2-(1-(5-methyl-6-(2,2,2-trifluoroethoxy)pyridin-3-yl)ethyl)-2H-pyrazolo[4,3-c]pyridin-4-yl)-acetamide;
N-(2-(1-(5-methyl-6-(2,2,2-trifluoroethoxy)pyridin-3-yl)ethyl)-2H-pyrazolo[4,3-c]pyridin-4-yl)-propionamide;
N-(2-(1-(5-methyl-6-(2,2,2-trifluoroethoxy)pyridin-3-yl)ethyl)-2H-pyrazolo[4,3-c]pyridin-4-yl)-isobutyramide;
N-(2-(1-(5-methyl-6-(2,2,2-trifluoroethoxy)pyridin-3-yl)ethyl)-2H-pyrazolo[4,3-c]pyridin-4-yl)-tetrahydro-2H-pyran-4-carboxamide;
N-(2-((6-(2,2,2-trifluoroethoxy)pyridin-3-yl)methyl)-2H-pyrazolo[4,3-c]pyridin-4-yl)-cyclopropanecarboxamide;
N-(2-((6-(2,2,2-trifluoroethoxy)pyridin-3-yl)methyl)-2H-pyrazolo[4,3-c]pyridin-4-yl)-isobutyramide;
N-(2-((5-chloro-6-(2,2,2-trifluoroethoxy)pyridin-3-yl)methyl)-2H-pyrazolo[4,3-c]pyridin-4-yl)-isobutyramide;
N-(2-((5-chloro-6-(2,2,2-trifluoroethoxy)pyridin-3-yl)methyl)-2H-pyrazolo[4,3-c]pyridin-4-yl)-propionamide;
N-(2-((5-chloro-6-(2,2,2-trifluoroethoxy)pyridin-3-yl)methyl)-2H-pyrazolo[4,3-c]pyridin-4-yl)-tetrahydro-2H-pyran-4-carboxamide;
N-(2-((5-chloro-6-(2,2-difluoroethoxy)pyridin-3-yl)methyl)-2H-pyrazolo[4,3-c]pyridin-4-yl)-acetamide;
N-(2-((5-chloro-6-(2,2-difluoroethoxy)pyridin-3-yl)methyl)-2H-pyrazolo[4,3-c]pyridin-4-yl)-propionamide;
N-(2-((5-chloro-6-(2,2-difluoroethoxy)pyridin-3-yl)methyl)-2H-pyrazolo[4,3-c]pyridin-4-yl)-isobutyramide;
N-(2-((5-chloro-6-(2,2,2-trifluoroethoxy)pyridin-3-yl)methyl)-2H-pyrazolo[4,3-c]pyridin-4-yl)-acetamide;
N-(2-((5-methyl-6-(2,2,2-trifluoroethoxy)pyridin-3-yl)methyl)-2H-pyrazolo[4,3-c]pyridin-4-yl)-tetrahydro-2H-pyran-4-carboxamide;
N-(2-((5-methyl-6-(2,2,2-trifluoroethoxy)pyridin-3-yl)methyl)-2H-pyrazolo[4,3-c]pyridin-4-yl)-oxazole-5-carboxamide;
1,1-dimethyl-3-(2-((5-methyl-6-(2,2,2-trifluoroethoxy)pyridin-3-yl)methyl)-2H-pyrazolo[4,3-c]pyridin-4-yl)urea;
2-((5-methyl-6-(2,2,2-trifluoroethoxy)pyridin-3-yl)methyl)-2H-pyrazolo[4,3-c]pyridin-4-amine;
3-(2-((5-methyl-6-(2,2,2-trifluoroethoxy)pyridin-3-yl)methyl)-2H-pyrazolo[4,3-c]pyridin-4-yl)-oxazolidin-2-one;
ethyl-(2-((5-methyl-6-(2,2,2-trifluoroethoxy)pyridin-3-yl)methyl)-2H-pyrazolo[4,3-c]pyridin-4-yl)-carbamate;
N-(2-((6-(2,2,2-trifluoroethoxy)pyridin-3-yl)methyl)-2H-pyrazolo[4,3-c]pyridin-4-yl)acetamide;
N-(2-((6-(2,2,2-trifluoroethoxy)pyridin-3-yl)methyl)-2H-pyrazolo[4,3-c]pyridin-4-yl)-propionamide;
4-methoxy-2-((5-methyl-6-(2,2,2-trifluoroethoxy)pyridin-3-yl)methyl)-2H-pyrazolo[4,3-c]-pyridine;
2-((5-methyl-6-(2,2,2-trifluoroethoxy)pyridin-3-yl)methyl)-2H-pyrazolo[4,3-c]pyridine-4-carboxamide;
N-methyl-2-((5-methyl-6-(2,2,2-trifluoroethoxy)pyridin-3-yl)methyl)-2H-pyrazolo[4,3-c]-pyridine-4-carboxamide;
N-isopropyl-2-((5-methyl-6-(2,2,2-trifluoroethoxy)pyridin-3-yl)methyl)-2H-pyrazolo[4,3-c]-pyridine-4-carboxamide;
N-(2-((5-methyl-6-(2,2,2-trifluoroethoxy)pyridin-3-yl)methyl)-2H-pyrazolo[4,3-c]pyridin-4-yl)-cyclopropanecarboxamide;
N-(2-((6-(2,2-difluoroethoxy)-5-fluoropyridin-3-yl)methyl)-2H-pyrazolo[4,3-c]pyridin-4-yl)-cyclopropanecarboxamide;
N-(2-((6-(2,2-difluoroethoxy)-5-fluoropyridin-3-yl)methyl)-2H-pyrazolo[4,3-c]pyridin-4-yl)-isobutyramide;
N-(2-((6-(2,2,2-trifluoroethoxy)pyridazin-3-yl)methyl)-2H-pyrazolo[4,3-c]pyridin-4-yl)-isobutyramide;
N-(2-((6-(2,2,2-trifluoroethoxy)pyridazin-3-yl)methyl)-2H-pyrazolo[4,3-c]pyridin-4-yl)-cyclopropanecarboxamide;
N-(2-((5-(2,2,2-trifluoroethoxy)pyridin-2-yl)methyl)-2H-pyrazolo[4,3-c]pyridin-4-yl)-isobutyramide;
N-(2-((5-(2,2,2-trifluoroethoxy)pyridin-2-yl)methyl)-2H-pyrazolo[4,3-c]pyridin-4-yl)-cyclopropanecarboxamide;
N-(2-((6-(3,3,3-trifluoropropoxy)pyridin-3-yl)methyl)-2H-pyrazolo[4,3-c]pyridin-4-yl)-isobutyramide;
N-(2-((6-(3,3,3-trifluoropropoxy)pyridin-3-yl)methyl)-2H-pyrazolo[4,3-c]pyridin-4-yl)-cyclopropanecarboxamide;
N-(2-(1-(5-methyl-6-(2,2,2-trifluoroethoxy)pyridin-3-yl)ethyl)-2H-pyrazolo[4,3-c]pyridin-4-yl)-isobutyramide;
N-(2-(1-(5-methyl-6-(2,2,2-trifluoroethoxy)pyridin-3-yl)ethyl)-2H-pyrazolo[4,3-c]pyridin-4-yl)-cyclopropanecarboxamide;
N-(2-(1-(5-methyl-6-(2,2,2-trifluoroethoxy)pyridin-3-yl)ethyl)-2H-pyrazolo[4,3-c]pyridin-4-yl)-acetamide;
N-(2-(1-(5-methyl-6-(2,2,2-trifluoroethoxy)pyridin-3-yl)ethyl)-2H-pyrazolo[4,3-c]pyridin-4-yl)-propionamide;
N-(2-(1-(5-methyl-6-(2,2,2-trifluoroethoxy)pyridin-3-yl)ethyl)-2H-pyrazolo[4,3-c]pyridin-4-yl)-tetrahydro-2H-pyran-4-carboxamide;
N-(2-((5-fluoro-6-(2,2,2-trifluoroethoxy)pyridin-3-yl)methyl)-2H-pyrazolo[4,3-c]pyridin-4-yl)-propionamide;
N-(2-((5-fluoro-6-(2,2,2-trifluoroethoxy)pyridin-3-yl)methyl)-2H-pyrazolo[4,3-c]pyridin-4-yl)-cyclopropanecarboxamide;
N-(2-((5-fluoro-6-(2,2,2-trifluoroethoxy)pyridin-3-yl)methyl)-2H-pyrazolo[4,3-c]pyridin-4-yl)-isobutyramide;
N-(2-((5-methyl-6-(2,2,2-trifluoroethoxy)pyridin-3-yl)methyl)-2H-pyrazolo[4,3-c]pyridin-4-yl)-pivalamide;
N-(2-((5-methyl-6-(2,2,2-trifluoroethoxy)pyridin-3-yl)methyl)-2H-pyrazolo[4,3-c]pyridin-4-yl)-nicotinamide;

1-(2-((5-methyl-6-(2,2,2-trifluoroethoxy)pyridin-3-yl)
methyl)-2H-pyrazolo[4,3-c]pyridin-4-yl)-pyrrolidin-2-
one;
1-(2-((5-methyl-6-(2,2,2-trifluoroethoxy)pyridin-3-yl)
methyl)-2H-pyrazolo[4,3-c]pyridin-4-yl)-imidazolidin-2-
one;
4-(2-((5-methyl-6-(2,2,2-trifluoroethoxy)pyridin-3-yl)
methyl)-2H-pyrazolo[4,3-c]pyridin-4-yl)-morpholine;
N-(1-methyl-1H-pyrazol-3-yl)-2-((5-methyl-6-(2,2,2-trifluoroethoxy)pyridin-3-yl)methyl)-2H-pyrazolo[4,3-c]
pyridin-4-amine;
2-((5-methyl-6-(2,2,2-trifluoroethoxy)pyridin-3-yl)methyl)-
N-(pyrimidin-2-yl)-2H-pyrazolo[4,3-c]-pyridin-4-amine;
N-(2-((6-(2,2,3,3-tetrafluoropropoxy)pyridin-3-yl)methyl)-
2H-pyrazolo[4,3-c]pyridin-4-yl)-cyclopropanecarboxamide;
N-(2-((6-(2,2-difluoroethoxy)-5-methylpyridin-3-yl)
methyl)-2H-pyrazolo[4,3-c]pyridin-4-yl)-tetrahydro-2H-
pyran-4-carboxamide;
3-(2-((6-(2,2-difluoroethoxy)-5-methylpyridin-3-yl)
methyl)-2H-pyrazolo[4,3-c]pyridin-4-yl)-1,1-dimethylurea;
N-(2-((6-(2,2-difluoroethoxy)-5-methylpyridin-3-yl)
methyl)-2H-pyrazolo[4,3-c]pyridin-4-yl)-pivalamide;
N-(2-(4-(2,2,2-trifluoroethoxy)benzyl)-2H-pyrazolo[4,3-c]
pyridin-4-yl)isobutyramide;
N-(2-(4-(2,2,2-trifluoroethoxy)benzyl)-2H-pyrazolo[4,3-c]
pyridin-4-yl)-cyclopropanecarboxamide;
2-((5-methyl-6-(2,2,2-trifluoroethoxy)pyridin-3-yl)methyl)-
4-(1H-pyrazol-5-yl)-2H-pyrazolo[4,3-c]pyridine;
N-(2-((6-(2,2,3,3,3-pentafluoropropoxy)pyridin-3-yl)
methyl)-2H-pyrazolo[4,3-c]pyridin-4-yl)isobutyramide;
N-(2-((6-(2,2,3,3,3-pentafluoropropoxy)pyridin-3-yl)
methyl)-2H-pyrazolo[4,3-c]pyridin-4-yl)-cyclopropanecarboxamide;
N-(2-(4-(trifluoromethoxy)benzyl)-2H-pyrazolo[4,3-c]pyridin-4-yl)isobutyramide;
2-(1-(5-methyl-6-(2,2,2-trifluoroethoxy)pyridin-3-yl)ethyl)-
2H-pyrazolo[4,3-c]pyridine-4-carboxamide;
N-ethyl-2-((5-methyl-6-(2,2,2-trifluoroethoxy)pyridin-3-yl)
methyl)-2H-pyrazolo[4,3-c]-pyridine-4-carboxamide;
(S)-2-((5-methyl-6-(2,2,2-trifluoroethoxy)pyridin-3-yl)
methyl)-N-(tetrahydrofuran-3-yl)-2H-pyrazolo[4,3-c]
pyridine-4-carboxamide;
N-cyclopropyl-2-((5-methyl-6-(2,2,2-trifluoroethoxy)pyridin-3-yl)methyl)-2H-pyrazolo[4,3-c]-pyridine-4-carboxamide;
N-cyclobutyl-2-((5-methyl-6-(2,2,2-trifluoroethoxy)pyridin-3-yl)methyl)-2H-pyrazolo[4,3-c]-pyridine-4-carboxamide;
N-(cyclopropylmethyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-
N-((tetrahydro-2H-pyran-4-yl)-methyl)-2H-pyrazolo[4,
3-c]pyridine-4-carboxamide;
N-(2-methoxyethyl)-2-((5-methyl-6-(2,2,2-trifluoroethoxy)
pyridin-3-yl)methyl)-2H-pyrazolo[4,3-c]pyridine-4-carboxamide;
(R)-N-(1-hydroxypropan-2-yl)-2-((5-methyl-6-(2,2,2-trifluoroethoxy)pyridin-3-yl)methyl)-2H-pyrazolo[4,3-c]
pyridine-4-carboxamide;
N-(3-methyl-2-((5-methyl-6-(2,2,2-trifluoroethoxy)pyridin-
3-yl)methyl)-2H-pyrazolo[4,3-c]-pyridin-4-yl)propionamide;
N-(3-methyl-2-((5-methyl-6-(2,2,2-trifluoroethoxy)pyridin-
3-yl)methyl)-2H-pyrazolo[4,3-c]-pyridin-4-yl)cyclopropanecarboxamide;
N-(2-((6-(2,2,3,3-tetrafluoropropoxy)pyridin-3-yl)methyl)-
2H-pyrazolo[4,3-c]pyridin-4-yl)-isobutyramide;
N-(2-(1-(6-(2,2-difluoroethoxy)-5-methylpyridin-3-yl)
ethyl)-2H-pyrazolo[4,3-c]pyridin-4-yl)-cyclopropanecarboxamide;
N-(2-(2-(6-(2,2,2-trifluoroethoxy)pyridin-3-yl)ethyl)-2H-
pyrazolo[4,3-c]pyridin-4-yl)cyclopropanecarboxamide;
N-(2-((6-(4-fluorophenoxy)-5-methylpyridin-3-yl)methyl)-
2H-pyrazolo[4,3-c]pyridin-4-yl)-isobutyramide;
N-(2-((6-(4-fluorophenoxy)-5-methylpyridin-3-yl)methyl)-
2H-pyrazolo[4,3-c]pyridin-4-yl)-cyclopropanecarboxamide;
N-methyl-N-(2-((5-methyl-6-(2,2,2-trifluoroethoxy)pyridin-3-yl)methyl)-2H-pyrazolo[4,3-c]-pyridin-4-yl)isobutyramide;
(S)-N-(2-((5-methyl-6-(2,2,2-trifluoroethoxy)pyridin-3-yl)
methyl)-2H-pyrazolo[4,3-c]pyridin-4-yl)tetrahydrofuran-
2-carboxamide;
(S)-N-(2-((6-(2,2-difluoroethoxy)-5-methylpyridin-3-yl)
methyl)-2H-pyrazolo[4,3-c]pyridin-4-yl)tetrahydrofuran-
2-carboxamide;
N-(2-((6-(2,2-difluoroethoxy)-5-methylpyridin-3-yl)
methyl)-2H-pyrazolo[4,3-c]pyridin-4-yl)-nicotinamide;
(R)-2-hydroxy-N-(2-((5-methyl-6-(2,2,2-trifluoroethoxy)
pyridin-3-yl)methyl)-2H-pyrazolo[4,3-c]pyridin-4-yl)
propanamide;
(S)-2-hydroxy-N-(2-((5-methyl-6-(2,2,2-trifluoroethoxy)
pyridin-3-yl)methyl)-2H-pyrazolo[4,3-c]pyridin-4-yl)
propanamide;
N-(2-((5-methyl-6-(2,2,2-trifluoroethoxy)pyridin-3-yl)
methyl)-2H-pyrazolo[4,3-c]pyridin-4-yl)-pyrrolidine-1-
carboxamide;
1-acetyl-N-(2-((5-methyl-6-(2,2,2-trifluoroethoxy)pyridin-
3-yl)methyl)-2H-pyrazolo[4,3-c]-pyridin-4-yl)piperidine-4-carboxamide;
N-isopropyl-2-(1-(5-methyl-6-(2,2,2-trifluoroethoxy)pyridin-3-yl)ethyl)-2H-pyrazolo[4,3-c]-pyridine-4-carboxamide;
2-((5-methyl-6-(2,2,2-trifluoroethoxy)pyridin-3-yl)methyl)-
N-propyl-2H-pyrazolo[4,3-c]-pyridine-4-carboxamide;
N-isobutyl-2-((5-methyl-6-(2,2,2-trifluoroethoxy)pyridin-3-
yl)methyl)-2H-pyrazolo[4,3-c]-pyridine-4-carboxamide;
N-(2-ethoxyethyl)-2-((5-methyl-6-(2,2,2-trifluoroethoxy)
pyridin-3-yl)methyl)-2H-pyrazolo[4,3-c]pyridine-4-carboxamide;
N-(cyanomethyl)-2-((5-methyl-6-(2,2,2-trifluoroethoxy)
pyridin-3-yl)methyl)-2H-pyrazolo[4,3-c]pyridine-4-carboxamide;
(S)-2-((5-methyl-6-(2,2,2-trifluoroethoxy)pyridin-3-yl)
methyl)-N-((tetrahydrofuran-2-yl)-methyl)-2H-pyrazolo
[4,3-c]pyridine-4-carboxamide;
N-(2-(dimethylamino)ethyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-
N-(pyridin-3-ylmethyl)-2H-pyrazolo[4,3-c]pyridine-4-
carboxamide;
N-((5-methyl-1,2,4-oxadiazol-3-yl)methyl)-2-((5-methyl-6-
(2,2,2-trifluoroethoxy)pyridin-3-yl)methyl)-2H-pyrazolo
[4,3-c]pyridine-4-carboxamide;
2-((5-methyl-6-(2,2,2-trifluoroethoxy)pyridin-3-yl)methyl)-
N-(pyridin-3-yl)-2H-pyrazolo[4,3-c]pyridine-4-carboxamide;

(R)-N-(2-((5-methyl-6-(2,2,2-trifluoroethoxy)pyridin-3-yl)
methyl)-2H-pyrazolo[4,3-c]pyridin-4-yl)tetrahydrofuran-
2-carboxamide;

(R)-N-(2-((6-(2,2-difluoroethoxy)-5-methylpyridin-3-yl)
methyl)-2H-pyrazolo[4,3-c]pyridin-4-yl)tetrahydrofuran-
2-carboxamide;

N-(3-methoxypropyl)-2-((5-methyl-6-(2,2,2-trifluoroethoxy)pyridin-3-yl)methyl)-2H-pyrazolo[4,3-c]pyridine-4-
carboxamide;

N-((1-hydroxycyclohexyl)methyl)-2-((5-methyl-6-(2,2,2-
trifluoroethoxy)pyridin-3-yl)methyl)-2H-pyrazolo[4,3-c]
pyridine-4-carboxamide;

N-(6-methyl-2-((5-methyl-6-(2,2,2-trifluoroethoxy)pyridin-
3-yl)methyl)-2H-pyrazolo[4,3-c]-pyridin-4-yl)propiona-
mide;

N-(6-methyl-2-((5-methyl-6-(2,2,2-trifluoroethoxy)pyridin-
3-yl)methyl)-2H-pyrazolo[4,3-c]-pyridin-4-yl)cyclopro-
panecarboxamide;

N-(6-methyl-2-((5-methyl-6-(2,2,2-trifluoroethoxy)pyridin-
3-yl)methyl)-2H-pyrazolo[4,3-c]-pyridin-4-yl)isobutyr-
amide;

2-hydroxy-2-methyl-N-(6-methyl-2-((5-methyl-6-(2,2,2-tri-
fluoroethoxy)pyridin-3-yl)methyl)-2H-pyrazolo[4,3-c]
pyridin-4-yl)propanamide;

N-(7-methyl-2-((5-methyl-6-(2,2,2-trifluoroethoxy)pyridin-
3-yl)methyl)-2H-pyrazolo[4,3-c]-pyridin-4-yl)propiona-
mide;

N-(7-methyl-2-((5-methyl-6-(2,2,2-trifluoroethoxy)pyridin-
3-yl)methyl)-2H-pyrazolo[4,3-c]-pyridin-4-yl)isobutyr-
amide;

2-((6-(2,2-difluoroethoxy)-5-methylpyridin-3-yl)methyl)-
N-ethyl-2H-pyrazolo[4,3-c]pyridine-4-carboxamide;

2-((6-(2,2-difluoroethoxy)-5-methylpyridin-3-yl)methyl)-
N-methyl-2H-pyrazolo[4,3-c]pyridine-4-carboxamide;

1-isobutyryl-N-(2-((5-methyl-6-(2,2,2-trifluoroethoxy)pyri-
din-3-yl)methyl)-2H-pyrazolo[4,3-c]pyridin-4-yl)piperi-
dine-4-carboxamide;

N-(2-((5-methyl-6-(2,2,2-trifluoroethoxy)pyridin-3-yl)
methyl)-2H-pyrazolo[4,3-c]pyridin-4-yl)-1-(methylsulfo-
nyl)piperidine-4-carboxamide;

(S)-1-acetyl-N-(2-((5-methyl-6-(2,2,2-trifluoroethoxy)pyri-
din-3-yl)methyl)-2H-pyrazolo[4,3-c]pyridin-4-yl)pyrroli-
dine-2-carboxamide;

(R)-1-acetyl-N-(2-((5-methyl-6-(2,2,2-trifluoroethoxy)pyri-
din-3-yl)methyl)-2H-pyrazolo[4,3-c]pyridin-4-yl)pyrroli-
dine-2-carboxamide;

N-methyl-N-(2-((2-((5-methyl-6-(2,2,2-trifluoroethoxy)
pyridin-3-yl)methyl)-2H-pyrazolo[4,3-c]pyridin-4-yl)
amino)-2-oxoethyl)acetamide;

(S)-2-methoxy-N-(2-((5-methyl-6-(2,2,2-trifluoroethoxy)
pyridin-3-yl)methyl)-2H-pyrazolo[4,3-c]pyridin-4-yl)
propanamide;

(S)-N-(2-((6-(2,2-difluoroethoxy)-5-methylpyridin-3-yl)
methyl)-2H-pyrazolo[4,3-c]pyridin-4-yl)-2-methoxypro-
panamide;

(R)-N-(2-((6-(2,2-difluoroethoxy)-5-methylpyridin-3-yl)
methyl)-2H-pyrazolo[4,3-c]pyridin-4-yl)-2-hydroxypro-
panamide;

(S)-N-(2-((6-(2,2-difluoroethoxy)-5-methylpyridin-3-yl)
methyl)-2H-pyrazolo[4,3-c]pyridin-4-yl)-2-hydroxypro-
panamide;

2-((6-(2,2-difluoroethoxy)-5-methylpyridin-3-yl)methyl)-
N-isopropyl-2H-pyrazolo[4,3-c]-pyridine-4-carboxam-
ide;

N-cyclopropyl-2-((6-(2,2-difluoroethoxy)-5-methylpyridin-
3-yl)methyl)-2H-pyrazolo[4,3-c]-pyridine-4-carboxam-
ide;

N-(cyclopropylmethyl)-2-((6-(2,2-difluoroethoxy)-5-meth-
ylpyridin-3-yl)methyl)-2H-pyrazolo[4,3-c]pyridine-4-
carboxamide;

2-((6-(2,2-difluoroethoxy)-5-methylpyridin-3-yl)methyl)-
N-(2-(dimethylamino)ethyl)-2H-pyrazolo[4,3-c]pyri-
dine-4-carboxamide;

2-((5-methyl-6-(2,2,2-trifluoroethoxy)pyridin-3-yl)methyl)-
N-(2-morpholinoethyl)-2H-pyrazolo[4,3-c]pyridine-4-
carboxamide;

N-(2-((5-methyl-6-(2,2,2-trifluoroethoxy)pyridin-3-yl)
methyl)-2H-pyrazolo[4,3-c]pyridin-4-yl)-2-(pyridin-2-
yl)acetamide;

N-(2-((5-methyl-6-(2,2,2-trifluoroethoxy)pyridin-3-yl)
methyl)-2H-pyrazolo[4,3-c]pyridin-4-yl)-2-(pyridin-3-
yl)acetamide;

N-isopropyl-2-((6-(2,2,2-trifluoroethoxy)pyridin-3-yl)
methyl)-2H-pyrazolo[4,3-c]pyridine-4-carboxamide;

N-ethyl-2-((6-(2,2,2-trifluoroethoxy)pyridin-3-yl)methyl)-
2H-pyrazolo[4,3-c]pyridine-4-carboxamide;

N-cyclopropyl-2-((6-(2,2,2-trifluoroethoxy)pyridin-3-yl)
methyl)-2H-pyrazolo[4,3-c]pyridine-4-carboxamide;

N-(cyclopropylmethyl)-2-((6-(2,2,2-trifluoroethoxy)pyri-
din-3-yl)methyl)-2H-pyrazolo[4,3-c]-pyridine-4-carbox-
amide;

N-(2-((5-methyl-6-(2,2,2-trifluoroethoxy)pyridin-3-yl)
methyl)-2H-pyrazolo[4,3-c]pyridin-4-yl)-2-(pyridin-4-
yl)acetamide;

N-(cyanomethyl)-2-((6-(2,2-difluoroethoxy)-5-methylpyri-
din-3-yl)methyl)-2H-pyrazolo[4,3-c]-pyridine-4-carbox-
amide;

2-((6-(2,2-difluoroethoxy)-5-methylpyridin-3-yl)methyl)-
N-propyl-2H-pyrazolo[4,3-c]pyridine-4-carboxamide;

N-(2-cyanopropan-2-yl)-2-((5-methyl-6-(2,2,2-trifluoroeth-
oxy)pyridin-3-yl)methyl)-2H-pyrazolo[4,3-c]pyridine-4-
carboxamide;

N-(2-hydroxy-2-methylpropyl)-2-((5-methyl-6-(2,2,2-trif-
luoroethoxy)pyridin-3-yl)methyl)-2H-pyrazolo[4,3-c]
pyridine-4-carboxamide;

N-(3-(dimethylamino)propyl)-2-((5-methyl-6-(2,2,2-trifluo-
roethoxy)pyridin-3-yl)methyl)-2H-pyrazolo[4,3-c]pyri-
dine-4-carboxamide;

N-(2-aminoethyl)-2-((5-methyl-6-(2,2,2-trifluoroethoxy)
pyridin-3-yl)methyl)-2H-pyrazolo[4,3-c]pyridine-4-car-
boxamide;

N-(2-hydroxyethyl)-2-((5-methyl-6-(2,2,2-trifluoroethoxy)
pyridin-3-yl)methyl)-2H-pyrazolo[4,3-c]pyridine-4-car-
boxamide;

2-((5-methyl-6-(2,2,2-trifluoroethoxy)pyridin-3-yl)methyl)-
N-(oxetan-3-yl)-2H-pyrazolo[4,3-c]pyridine-4-carbox-
amide;

N-methyl-2-((4-methyl-6-(2,2,2-trifluoroethoxy)pyridin-3-
yl)methyl)-2H-pyrazolo[4,3-c]-pyridine-4-carboxamide;

N-ethyl-2-((4-methyl-6-(2,2,2-trifluoroethoxy)pyridin-3-yl)
methyl)-2H-pyrazolo[4,3-c]-pyridine-4-carboxamide;

N-(2-((6-(2,2-difluoroethoxy)-5-methylpyridin-3-yl)
methyl)-2H-pyrazolo[4,3-c]pyridin-4-yl)-2-(pyridin-4-
yl)acetamide;

2-(pyridin-4-yl)-N-(2-((6-(2,2,2-trifluoroethoxy)pyridin-3-
yl)methyl)-2H-pyrazolo[4,3-c]pyridin-4-yl)acetamide;

N-(2-((6-(2,2-difluoroethoxy)-5-methylpyridin-3-yl)
methyl)-2H-pyrazolo[4,3-c]pyridin-4-yl)-2-(pyridin-3-
yl)acetamide;

2-((6-(2,2-difluoroethoxy)-5-methylpyridin-3-yl)methyl)-
N-(2-hydroxyethyl)-2H-pyrazolo[4,3-c]pyridine-4-car-
boxamide;

N-(2-hydroxyethyl)-2-((5-methyl-6-(3,3,3-trifluoro-propoxy)pyridin-3-yl)methyl)-2H-pyrazolo[4,3-c]pyridine-4-carboxamide;

N-(2-hydroxyethyl)-2-((4-methyl-6-(2,2,2-trifluoroethoxy)pyridin-3-yl)methyl)-2H-pyrazolo[4,3-c]pyridine-4-carboxamide;

N-(2-((5-methyl-6-(3,3,3-trifluoropropoxy)pyridin-3-yl)methyl)-2H-pyrazolo[4,3-c]pyridin-4-yl)-isobutyramide;

N-(2-((5-methyl-6-(3,3,3-trifluoropropoxy)pyridin-3-yl)methyl)-2H-pyrazolo[4,3-c]pyridin-4-yl)-cyclopropanecarboxamide;

2-hydroxy-2-methyl-N-(2-((5-methyl-6-(3,3,3-trifluoropropoxy)pyridin-3-yl)methyl)-2H-pyrazolo[4,3-c]pyridin-4-yl)propanamide;

N-methyl-2-((5-methyl-6-(3,3,3-trifluoropropoxy)pyridin-3-yl)methyl)-2H-pyrazolo[4,3-c]-pyridine-4-carboxamide;

N-ethyl-2-((5-methyl-6-(3,3,3-trifluoropropoxy)pyridin-3-yl)methyl)-2H-pyrazolo[4,3-c]-pyridine-4-carboxamide;

N-isopropyl-2-((5-methyl-6-(3,3,3-trifluoropropoxy)pyridin-3-yl)methyl)-2H-pyrazolo[4,3-c]-pyridine-4-carboxamide;

N-(2-((5-methyl-6-(2,2,2-trifluoroethoxy)pyridazin-3-yl)methyl)-2H-pyrazolo[4,3-c]pyridin-4-yl)isobutyramide;

N-(2-((5-methyl-6-(2,2,2-trifluoroethoxy)pyridazin-3-yl)methyl)-2H-pyrazolo[4,3-c]pyridin-4-yl)cyclopropanecarboxamide;

N-methyl-2-((5-methyl-6-(2,2,2-trifluoroethoxy)pyridazin-3-yl)methyl)-2H-pyrazolo[4,3-c]pyridine-4-carboxamide;

N-ethyl-2-((5-methyl-6-(2,2,2-trifluoroethoxy)pyridazin-3-yl)methyl)-2H-pyrazolo[4,3-c]-pyridine-4-carboxamide;

N-(2-((5-methyl-6-(2,2,2-trifluoroethoxy)pyridin-3-yl)methyl)-2H-pyrazolo[4,3-c]pyridin-4-yl)-2-(2-methylthiazol-4-yl)acetamide;

N-(2-((5-methyl-6-(3,3,3-trifluoropropoxy)pyridin-3-yl)methyl)-2H-pyrazolo[4,3-c]pyridin-4-yl)-2-(pyridin-3-yl)acetamide;

N-(2-((5-methyl-6-(3,3,3-trifluoropropoxy)pyridin-3-yl)methyl)-2H-pyrazolo[4,3-c]pyridin-4-yl)-2-(pyridin-4-yl)acetamide;

2-(3,5-dimethylisoxazol-4-yl)-N-(2-((5-methyl-6-(2,2,2-trifluoroethoxy)pyridin-3-yl)methyl)-2H-pyrazolo[4,3-c]pyridin-4-yl)acetamide;

N-isopropyl-2-((5-methyl-6-(2,2,2-trifluoroethoxy)pyridazin-3-yl)methyl)-2H-pyrazolo[4,3-c]-pyridine-4-carboxamide;

(R)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;

N-(2-((4-methyl-5-(2,2,2-trifluoroethoxy)pyridin-2-yl)methyl)-2H-pyrazolo[4,3-c]pyridin-4-yl)-cyclopropanecarboxamide;

2-hydroxy-2-methyl-N-(2-((4-methyl-5-(2,2,2-trifluoroethoxy)pyridin-2-yl)methyl)-2H-pyrazolo[4,3-c]pyridin-4-yl)propanamide;

N-methyl-2-((4-methyl-5-(2,2,2-trifluoroethoxy)pyridin-2-yl)methyl)-2H-pyrazolo[4,3-c]-pyridine-4-carboxamide;

N-ethyl-2-((4-methyl-5-(2,2,2-trifluoroethoxy)pyridin-2-yl)methyl)-2H-pyrazolo[4,3-c]-pyridine-4-carboxamide;

N-isopropyl-2-((4-methyl-5-(2,2,2-trifluoroethoxy)pyridin-2-yl)methyl)-2H-pyrazolo[4,3-c]-pyridine-4-carboxamide;

N-(2-hydroxyethyl)-2-((4-methyl-5-(2,2,2-trifluoroethoxy)pyridin-2-yl)methyl)-2H-pyrazolo[4,3-c]pyridine-4-carboxamide;

(S)-N-(1-hydroxypropan-2-yl)-2-((5-methyl-6-(2,2,2-trifluoroethoxy)pyridin-3-yl)methyl)-2H-pyrazolo[4,3-c]pyridine-4-carboxamide;

N-(2-amino-2-oxoethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-(2-(methylsulfonamido)ethyl)-2H-pyrazolo[4,3-c]pyridine-4-carboxamide;

N-(2-hydroxyethyl)-2-((5-methyl-6-(2,2,2-trifluoroethoxy)pyridazin-3-yl)methyl)-2H-pyrazolo[4,3-c]pyridine-4-carboxamide;

N-(3-hydroxypropyl)-2-((5-methyl-6-(2,2,2-trifluoroethoxy)pyridin-3-yl)methyl)-2H-pyrazolo[4,3-c]pyridine-4-carboxamide;

2-((6-(2,2-difluoroethoxy)-5-methylpyridin-3-yl)methyl)-N-(3-hydroxypropyl)-2H-pyrazolo[4,3-c]pyridine-4-carboxamide;

N-(2-cyanoethyl)-2-((5-methyl-6-(2,2,2-trifluoroethoxy)pyridin-3-yl)methyl)-2H-pyrazolo[4,3-c]pyridine-4-carboxamide;

N-(2-cyanoethyl)-2-((6-(2,2-difluoroethoxy)-5-methylpyridin-3-yl)methyl)-2H-pyrazolo[4,3-c]pyridine-4-carboxamide;

N-(2-acetamidoethyl)-2-((5-methyl-6-(2,2,2-trifluoroethoxy)pyridin-3-yl)methyl)-2H-pyrazolo[4,3-c]pyridine-4-carboxamide;

N-(2-((5-methoxy-6-(2,2,2-trifluoroethoxy)pyridin-3-yl)methyl)-2H-pyrazolo[4,3-c]pyridin-4-yl)isobutyramide;

N-(2-((5-methoxy-6-(2,2,2-trifluoroethoxy)pyridin-3-yl)methyl)-2H-pyrazolo[4,3-c]pyridin-4-yl)cyclopropanecarboxamide;

2-((5-methoxy-6-(2,2,2-trifluoroethoxy)pyridin-3-yl)methyl)-N-methyl-2H-pyrazolo[4,3-c]-pyridine-4-carboxamide;

N-ethyl-2-((5-methoxy-6-(2,2,2-trifluoroethoxy)pyridin-3-yl)methyl)-2H-pyrazolo[4,3-c]-pyridine-4-carboxamide;

N-isopropyl-2-((5-methoxy-6-(2,2,2-trifluoroethoxy)pyridin-3-yl)methyl)-2H-pyrazolo[4,3-c]-pyridine-4-carboxamide;

N-(2-hydroxyethyl)-2-((5-methoxy-6-(2,2,2-trifluoroethoxy)pyridin-3-yl)methyl)-2H-pyrazolo[4,3-c]pyridine-4-carboxamide;

N-(2-(2-hydroxyethoxy)ethyl)-2-((5-methyl-6-(2,2,2-trifluoroethoxy)pyridin-3-yl)methyl)-2H-pyrazolo[4,3-c]pyridine-4-carboxamide;

N-(2-((4-methyl-5-(2,2,2-trifluoroethoxy)pyridin-2-yl)methyl)-2H-pyrazolo[4,3-c]pyridin-4-yl)-isobutyramide;

N-ethyl-2-((5-fluoro-6-(2,2,2-trifluoroethoxy)pyridin-3-yl)methyl)-2H-pyrazolo[4,3-c]pyridine-4-carboxamide;

2-((5-fluoro-6-(2,2,2-trifluoroethoxy)pyridin-3-yl)methyl)-N-isopropyl-2H-pyrazolo[4,3-c]-pyridine-4-carboxamide;

2-((5-chloro-6-(2,2,2-trifluoroethoxy)pyridin-3-yl)methyl)-N-(2-hydroxyethyl)-2H-pyrazolo[4,3-c]pyridine-4-carboxamide;

2-((5-chloro-6-(2,2-difluoroethoxy)pyridin-3-yl)methyl)-N-methyl-2H-pyrazolo[4,3-c]pyridine-4-carboxamide;

2-((5-chloro-6-(2,2-difluoroethoxy)pyridin-3-yl)methyl)-N-ethyl-2H-pyrazolo[4,3-c]pyridine-4-carboxamide;

2-((5-chloro-6-(2,2-difluoroethoxy)pyridin-3-yl)methyl)-N-(2-hydroxyethyl)-2H-pyrazolo[4,3-c]pyridine-4-carboxamide;
2-((5-chloro-6-(2,2-difluoroethoxy)pyridin-3-yl)methyl)-N-isopropyl-2H-pyrazolo[4,3-c]-pyridine-4-carboxamide;
(R)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;
N-(2-hydroxyethyl)-2-(4-(2,2,2-trifluoroethoxy)benzyl)-2H-pyrazolo[4,3-c]pyridine-4-carboxamide;
2-((6-(4-fluorophenoxy)-5-methylpyridin-3-yl)methyl)-N-(2-hydroxyethyl)-2H-pyrazolo[4,3-c]pyridine-4-carboxamide;
N-(2-hydroxyethyl)-2-((6-(2,2,3,3,3-pentafluoropropoxy)pyridin-3-yl)methyl)-2H-pyrazolo[4,3-c]pyridine-4-carboxamide;
N-methyl-2-((6-(3,3,3-trifluoropropoxy)pyridin-3-yl)methyl)-2H-pyrazolo[4,3-c]pyridine-4-carboxamide;
N-ethyl-2-((6-(3,3,3-trifluoropropoxy)pyridin-3-yl)methyl)-2H-pyrazolo[4,3-c]pyridine-4-carboxamide;
N-isopropyl-2-((6-(3,3,3-trifluoropropoxy)pyridin-3-yl)methyl)-2H-pyrazolo[4,3-c]pyridine-4-carboxamide;
N-(2-hydroxyethyl)-2-((6-(3,3,3-trifluoropropoxy)pyridin-3-yl)methyl)-2H-pyrazolo[4,3-c]-pyridine-4-carboxamide;
(S)-N-(1-amino-1-oxopropan-2-yl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(2-(methylamino)-2-oxoethyl)-2H-pyrazolo[4,3-c]pyridine-4-carboxamide;
N-(3-amino-3-oxopropyl)-2-((5-methyl-6-(2,2,2-trifluoroethoxy)pyridin-3-yl)methyl)-2H-pyrazolo[4,3-c]pyridine-4-carboxamide;
N-(3-hydroxy-2,2-dimethylpropyl)-2-((5-methyl-6-(2,2,2-trifluoroethoxy)pyridin-3-yl)methyl)-2H-pyrazolo[4,3-c]pyridine-4-carboxamide;
N-(2-hydroxyethyl)-2-((6-(2,2,2-trifluoroethoxy)pyridin-3-yl)methyl)-2H-pyrazolo[4,3-c]-pyridine-4-carboxamide;
N-(4-hydroxybutyl)-2-((5-methyl-6-(2,2,2-trifluoroethoxy)pyridin-3-yl)methyl)-2H-pyrazolo[4,3-c]pyridine-4-carboxamide;
N-(3-hydroxypropyl)-2-((6-(2,2,2-trifluoroethoxy)pyridin-3-yl)methyl)-2H-pyrazolo[4,3-c]-pyridine-4-carboxamide;
N-(2-hydroxyethyl)-2-(3-methyl-4-(2,2,2-trifluoroethoxy)benzyl)-2H-pyrazolo[4,3-c]pyridine-4-carboxamide;
N-ethyl-2-((6-(2,2,3,3-tetrafluoropropoxy)pyridin-3-yl)methyl)-2H-pyrazolo[4,3-c]-pyridine-4-carboxamide;
N-(2-hydroxyethyl)-2-((6-(2,2,3,3-tetrafluoropropoxy)pyridin-3-yl)methyl)-2H-pyrazolo[4,3-c]pyridine-4-carboxamide;
N-(3-acetamidopropyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(3-(methylsulfonamido) propyl)-2H-pyrazolo[4,3-c]pyridine-4-carboxamide;
N-isopropyl-2-((6-(2,2,3,3-tetrafluoropropoxy)pyridin-3-yl)methyl)-2H-pyrazolo[4,3-c]-pyridine-4-carboxamide;
2-(4-((2,2-difluoroethoxy)-3-methylbenzyl)-N-(2-hydroxyethyl)-2H-pyrazolo[4,3-c]pyridine-4-carboxamide;
2-(4-((2,2-difluoroethoxy)-3-methylbenzyl)-N-(3-hydroxypropyl)-2H-pyrazolo[4,3-c]pyridine-4-carboxamide;
N-(2-hydroxyethyl)-2-((5-methyl-6-(2,2,3,3-tetrafluoropropoxy)pyridin-3-yl)methyl)-2H-pyrazolo[4,3-c]pyridine-4-carboxamide;
N-(3-hydroxypropyl)-2-((5-methyl-6-(2,2,3,3-tetrafluoropropoxy)pyridin-3-yl)methyl)-2H-pyrazolo[4,3-c]pyridine-4-carboxamide;
2-((5-chloro-6-(2,2,2-trifluoroethoxy)pyridin-3-yl)methyl)-N-(3-hydroxypropyl)-2H-pyrazolo[4,3-c]pyridine-4-carboxamide;
2-((5-chloro-6-(2,2-difluoroethoxy)pyridin-3-yl)methyl)-N-(3-hydroxypropyl)-2H-pyrazolo[4,3-c]pyridine-4-carboxamide;
N-(3-hydroxypropyl)-2-(4-(2,2,2-trifluoroethoxy)benzyl)-2H-pyrazolo[4,3-c]pyridine-4-carboxamide;
N-(2-((2-methyl-6-(2,2,2-trifluoroethoxy)pyridin-4-yl)methyl)-2H-pyrazolo[4,3-c]pyridin-4-yl)-isobutyramide;
N-(2-((2-methyl-6-(2,2,2-trifluoroethoxy)pyridin-4-yl)methyl)-2H-pyrazolo[4,3-c]pyridin-4-yl)-cyclopropanecarboxamide;
N-(3-hydroxypropyl)-2-(3-methyl-4-(2,2,2-trifluoroethoxy)benzyl)-2H-pyrazolo[4,3-c]-pyridine-4-carboxamide;
N-(3-hydroxypropyl)-2-((5-methyl-6-(3,3,3-trifluoropropoxy)pyridin-3-yl)methyl)-2H-pyrazolo[4,3-c]pyridine-4-carboxamide;
N-(3-hydroxypropyl)-2-((5-methyl-6-(2,2,2-trifluoroethoxy)pyridazin-3-yl)methyl)-2H-pyrazolo[4,3-c]pyridine-4-carboxamide;
N-(3-hydroxypropyl)-2-((4-methyl-5-(2,2,2-trifluoroethoxy)pyridin-2-yl)methyl)-2H-pyrazolo[4,3-c]pyridine-4-carboxamide;
N-(3-hydroxypropyl)-2-((5-methoxy-6-(2,2,2-trifluoroethoxy)pyridin-3-yl)methyl)-2H-pyrazolo[4,3-c]pyridine-4-carboxamide;
2-((5-fluoro-6-(2,2,2-trifluoroethoxy)pyridin-3-yl)methyl)-N-(3-hydroxypropyl)-2H-pyrazolo[4,3-c]pyridine-4-carboxamide;
2-((6-(4-fluorophenoxy)-5-methylpyridin-3-yl)methyl)-N-(3-hydroxypropyl)-2H-pyrazolo[4,3-c]pyridine-4-carboxamide;
N-(3-hydroxypropyl)-2-((6-(2,2,3,3,3-pentafluoropropoxy)pyridin-3-yl)methyl)-2H-pyrazolo[4,3-c]pyridine-4-carboxamide;
N-(3-hydroxypropyl)-2-((6-(3,3,3-trifluoropropoxy)pyridin-3-yl)methyl)-2H-pyrazolo[4,3-c]-pyridine-4-carboxamide;
N-methyl-2-((2-methyl-6-(2,2,2-trifluoroethoxy)pyridin-4-yl)methyl)-2H-pyrazolo[4,3-c]-pyridine-4-carboxamide;
N-ethyl-2-((2-methyl-6-(2,2,2-trifluoroethoxy)pyridin-4-yl)methyl)-2H-pyrazolo[4,3-c]pyridine-4-carboxamide;
N-isopropyl-2-((2-methyl-6-(2,2,2-trifluoroethoxy)pyridin-4-yl)methyl)-2H-pyrazolo[4,3-c]-pyridine-4-carboxamide;
N-(2-hydroxyethyl)-2-((2-methyl-6-(2,2,2-trifluoroethoxy)pyridin-4-yl)methyl)-2H-pyrazolo[4,3-c]pyridine-4-carboxamide;
N-(3-hydroxypropyl)-2-((2-methyl-6-(2,2,2-trifluoroethoxy)pyridin-4-yl)methyl)-2H-pyrazolo[4,3-c]pyridine-4-carboxamide;
N-(2-((6-methyl-5-(2,2,2-trifluoroethoxy)pyridin-2-yl)methyl)-2H-pyrazolo[4,3-c]pyridin-4-yl)-isobutyramide;
N-(2-((6-methyl-5-(2,2,2-trifluoroethoxy)pyridin-2-yl)methyl)-2H-pyrazolo[4,3-c]pyridin-4-yl)-cyclopropanecarboxamide;
(S)-N-(2-hydroxypropyl)-2-((5-methyl-6-(3,3,3-trifluoropropoxy)pyridin-3-yl)methyl)-2H-pyrazolo[4,3-c]pyridine-4-carboxamide;
(R)-N-(2-hydroxypropyl)-2-((5-methyl-6-(3,3,3-trifluoropropoxy)pyridin-3-yl)methyl)-2H-pyrazolo[4,3-c]pyridine-4-carboxamide;

(S)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;

(R)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;

(S)-N-(2,3-dihydroxypropyl)-2-((4-methyl-5-(2,2,2-trifluoroethoxy)pyridin-2-yl)methyl)-2H-pyrazolo[4,3-c]pyridine-4-carboxamide;

N-isopropyl-2-((1-(5-(trifluoromethyl)pyridin-2-yl)-1H-pyrazol-3-yl)methyl)-2H-pyrazolo[4,3-c]pyridine-4-carboxamide;

N-(2-hydroxyethyl)-2-((1-(5-(trifluoromethyl)pyridin-2-yl)-1H-pyrazol-3-yl)methyl)-2H-pyrazolo[4,3-c]pyridine-4-carboxamide;

N-(3-hydroxypropyl)-2-((1-(5-(trifluoromethyl)pyridin-2-yl)-1H-pyrazol-3-yl)methyl)-2H-pyrazolo[4,3-c]pyridine-4-carboxamide;

N-methyl-2-((1-(5-(trifluoromethyl)pyridin-2-yl)-1H-pyrazol-3-yl)methyl)-2H-pyrazolo[4,3-c]-pyridine-4-carboxamide;

N-ethyl-2-((1-(5-(trifluoromethyl)pyridin-2-yl)-1H-pyrazol-3-yl)methyl)-2H-pyrazolo[4,3-c]-pyridine-4-carboxamide;

(S)-N-(2-hydroxypropyl)-2-((4-methyl-5-(2,2,2-trifluoroethoxy)pyridin-2-yl)methyl)-2H-pyrazolo[4,3-c]pyridine-4-carboxamide;

(R)-N-(2-hydroxypropyl)-2-((4-methyl-5-(2,2,2-trifluoroethoxy)pyridin-2-yl)methyl)-2H-pyrazolo[4,3-c]pyridine-4-carboxamide;

(S)-N-(1-hydroxypropan-2-yl)-2-((5-methyl-6-(3,3,3-trifluoropropoxy)pyridin-3-yl)methyl)-2H-pyrazolo[4,3-c]pyridine-4-carboxamide;

(S)-N-(1-hydroxypropan-2-yl)-2-((4-methyl-5-(2,2,2-trifluoroethoxy)pyridin-2-yl)methyl)-2H-pyrazolo[4,3-c]pyridine-4-carboxamide;

N-(2-cyanoethyl)-2-((4-methyl-5-(2,2,2-trifluoroethoxy)pyridin-2-yl)methyl)-2H-pyrazolo[4,3-c]pyridine-4-carboxamide;

N-(2-cyanoethyl)-2-((5-methyl-6-(3,3,3-trifluoropropoxy)pyridin-3-yl)methyl)-2H-pyrazolo[4,3-c]pyridine-4-carboxamide;

N-(2-acetamidoethyl)-2-((5-methyl-6-(3,3,3-trifluoropropoxy)pyridin-3-yl)methyl)-2H-pyrazolo[4,3-c]pyridine-4-carboxamide;

N-(2-amino-2-oxoethyl)-2-((5-methyl-6-(3,3,3-trifluoropropoxy)pyridin-3-yl)methyl)-2H-pyrazolo[4,3-c]pyridine-4-carboxamide;

N-(2-methoxyethyl)-2-((5-methyl-6-(3,3,3-trifluoropropoxy)pyridin-3-yl)methyl)-2H-pyrazolo[4,3-c]pyridine-4-carboxamide;

N-(2-((5-methyl-6-(2-(2,2,2-trifluoroethoxy)ethoxy)pyridin-3-yl)methyl)-2H-pyrazolo[4,3-c]-pyridin-4-yl)isobutyramide;

N-(2-((5-methyl-6-(2-(2,2,2-trifluoroethoxy)ethoxy)pyridin-3-yl)methyl)-2H-pyrazolo[4,3-c]-pyridin-4-yl)cyclopropanecarboxamide;

2-hydroxy-2-methyl-N-(2-((5-methyl-6-(2-(2,2,2-trifluoroethoxy)ethoxy)pyridin-3-yl)methyl)-2H-pyrazolo[4,3-c]pyridin-4-yl)propanamide;

N-(2-((2-methoxy-6-(2,2,2-trifluoroethoxy)pyridin-3-yl)methyl)-2H-pyrazolo[4,3-c]pyridin-4-yl)isobutyramide;

N-(2-((2-methoxy-6-(2,2,2-trifluoroethoxy)pyridin-3-yl)methyl)-2H-pyrazolo[4,3-c]pyridin-4-yl)cyclopropanecarboxamide;

N-(2-hydroxyethyl)-2-((5-methyl-6-(2-(2,2,2-trifluoroethoxy)ethoxy)pyridin-3-yl)methyl)-2H-pyrazolo[4,3-c]pyridine-4-carboxamide;

N-(3-hydroxypropyl)-2-((5-methyl-6-(2-(2,2,2-trifluoroethoxy)ethoxy)pyridin-3-yl)methyl)-2H-pyrazolo[4,3-c]pyridine-4-carboxamide;

N-methyl-2-((5-methyl-6-(2-(2,2,2-trifluoroethoxy)ethoxy)pyridin-3-yl)methyl)-2H-pyrazolo[4,3-c]pyridine-4-carboxamide;

N-ethyl-2-((5-methyl-6-(2-(2,2,2-trifluoroethoxy)ethoxy)pyridin-3-yl)methyl)-2H-pyrazolo[4,3-c]pyridine-4-carboxamide;

N-(2-hydroxyethyl)-2-((2-methoxy-6-(2,2,2-trifluoroethoxy)pyridin-3-yl)methyl)-2H-pyrazolo[4,3-c]pyridine-4-carboxamide;

N-(3-hydroxypropyl)-2-((2-methoxy-6-(2,2,2-trifluoroethoxy)pyridin-3-yl)methyl)-2H-pyrazolo[4,3-c]pyridine-4-carboxamide; 2-((2-methoxy-6-(2,2,2-trifluoroethoxy)pyridin-3-yl)methyl)-N-methyl-2H-pyrazolo[4,3-c]-pyridine-4-carboxamide;

N-ethyl-2-((2-methoxy-6-(2,2,2-trifluoroethoxy)pyridin-3-yl)methyl)-2H-pyrazolo[4,3-c]-pyridine-4-carboxamide;

N-isopropyl-2-((5-methyl-6-(2-(2,2,2-trifluoroethoxy)ethoxy)pyridin-3-yl)methyl)-2H-pyrazolo[4,3-c]pyridine-4-carboxamide;

N-isopropyl-2-((2-methoxy-6-(2,2,2-trifluoroethoxy)pyridin-3-yl)methyl)-2H-pyrazolo[4,3-c]-pyridine-4-carboxamide;

N-methyl-2-(2-(4-(trifluoromethyl)phenoxy)ethyl)-2H-pyrazolo[4,3-c]pyridine-4-carboxamide;

N-ethyl-2-(2-(4-(trifluoromethyl)phenoxy)ethyl)-2H-pyrazolo[4,3-c]pyridine-4-carboxamide;

N-isopropyl-2-(2-(4-(trifluoromethyl)phenoxy)ethyl)-2H-pyrazolo[4,3-c]pyridine-4-carboxamide;

N-(2-hydroxyethyl)-2-(2-(4-(trifluoromethyl)phenoxy)ethyl)-2H-pyrazolo[4,3-c]pyridine-4-carboxamide;

N-(3-hydroxypropyl)-2-(2-(4-(trifluoromethyl)phenoxy)ethyl)-2H-pyrazolo[4,3-c]pyridine-4-carboxamide;

N-(2-((6-methyl-5-(2,2,2-trifluoroethoxy)pyrazin-2-yl)methyl)-2H-pyrazolo[4,3-c]pyridin-4-yl)-isobutyramide;

N-(2-((6-methyl-5-(2,2,2-trifluoroethoxy)pyrazin-2-yl)methyl)-2H-pyrazolo[4,3-c]pyridin-4-yl)cyclopropanecarboxamide;

N-(2-((6-(2,2-difluoropropoxy)-5-methylpyridin-3-yl)methyl)-2H-pyrazolo[4,3-c]pyridin-4-yl)-isobutyramide;

N-(2-((6-(2,2-difluoropropoxy)-5-methylpyridin-3-yl)methyl)-2H-pyrazolo[4,3-c]pyridin-4-yl)-cyclopropanecarboxamide;

N-(2-((6-(2,2-difluoropropoxy)-5-methylpyridin-3-yl)methyl)-2H-pyrazolo[4,3-c]pyridin-4-yl)-2-hydroxy-2-methylpropanamide;

2-(2-((3-chloro-5-(trifluoromethyl)pyridin-2-yl)oxy)ethyl)-N-methyl-2H-pyrazolo[4,3-c]-pyridine-4-carboxamide;

2-(2-((3-chloro-5-(trifluoromethyl)pyridin-2-yl)oxy)ethyl)-N-ethyl-2H-pyrazolo[4,3-c]pyridine-4-carboxamide;

2-(2-((3-chloro-5-(trifluoromethyl)pyridin-2-yl)oxy)ethyl)-N-isopropyl-2H-pyrazolo[4,3-c]-pyridine-4-carboxamide;

2-(2-((3-chloro-5-(trifluoromethyl)pyridin-2-yl)oxy)ethyl)-N-(2-hydroxyethyl)-2H-pyrazolo[4,3-c]pyridine-4-carboxamide;

2-(2-((3-chloro-5-(trifluoromethyl)pyridin-2-yl)oxy)ethyl)-N-(3-hydroxypropyl)-2H-pyrazolo[4,3-c]pyridine-4-carboxamide;

2-((5-cyclopropyl-6-(2,2,2-trifluoroethoxy)pyridin-3-yl)methyl)-N-methyl-2H-pyrazolo[4,3-c]-pyridine-4-carboxamide;

2-((5-cyclopropyl-6-(2,2,2-trifluoroethoxy)pyridin-3-yl)methyl)-N-ethyl-2H-pyrazolo[4,3-c]-pyridine-4-carboxamide;
2-((5-cyclopropyl-6-(2,2,2-trifluoroethoxy)pyridin-3-yl)methyl)-N-isopropyl-2H-pyrazolo[4,3-c]pyridine-4-carboxamide;
2-((5-cyclopropyl-6-(2,2,2-trifluoroethoxy)pyridin-3-yl)methyl)-N-(2-hydroxyethyl)-2H-pyrazolo[4,3-c]pyridine-4-carboxamide;
2-((5-cyclopropyl-6-(2,2,2-trifluoroethoxy)pyridin-3-yl)methyl)-N-(3-hydroxypropyl)-2H-pyrazolo[4,3-c]pyridine-4-carboxamide;
2-((6-(2,2-difluoropropoxy)-5-methylpyridin-3-yl)methyl)-N-methyl-2H-pyrazolo[4,3-c]-pyridine-4-carboxamide;
2-((6-(2,2-difluoropropoxy)-5-methylpyridin-3-yl)methyl)-N-ethyl-2H-pyrazolo[4,3-c]-pyridine-4-carboxamide;
2-((6-(2,2-difluoropropoxy)-5-methylpyridin-3-yl)methyl)-N-(2-hydroxyethyl)-2H-pyrazolo[4,3-c]pyridine-4-carboxamide;
2-((6-(2,2-difluoropropoxy)-5-methylpyridin-3-yl)methyl)-N-(3-hydroxypropyl)-2H-pyrazolo[4,3-c]pyridine-4-carboxamide;
N-methyl-2-((6-methyl-5-(2,2,2-trifluoroethoxy)pyrazin-2-yl)methyl)-2H-pyrazolo[4,3-c]-pyridine-4-carboxamide;
N-ethyl-2-((6-methyl-5-(2,2,2-trifluoroethoxy)pyrazin-2-yl)methyl)-2H-pyrazolo[4,3-c]-pyridine-4-carboxamide;
N-(3-hydroxypropyl)-2-((6-methyl-5-(2,2,2-trifluoroethoxy)pyrazin-2-yl)methyl)-2H-pyrazolo[4,3-c]pyridine-4-carboxamide;
2-((6-(2,2-difluoropropoxy)-5-methylpyridin-3-yl)methyl)-N-isopropyl-2H-pyrazolo[4,3-c]-pyridine-4-carboxamide;
N-isopropyl-2-((6-methyl-5-(2,2,2-trifluoroethoxy)pyrazin-2-yl)methyl)-2H-pyrazolo[4,3-c]-pyridine-4-carboxamide;
2-((6-(4-chloro-1H-pyrazol-1-yl)-5-methylpyridin-3-yl)methyl)-N-methyl-2H-pyrazolo[4,3-c]-pyridine-4-carboxamide;
2-((6-(4-chloro-1H-pyrazol-1-yl)-5-methylpyridin-3-yl)methyl)-N-ethyl-2H-pyrazolo[4,3-c]-pyridine-4-carboxamide;
N-(2-hydroxyethyl)-2-(1-(5-methyl-6-(2,2,2-trifluoroethoxy)pyridin-3-yl)ethyl)-2H-pyrazolo[4,3-c]-pyridine-4-carboxamide;
N-(3-hydroxypropyl)-2-(1-(5-methyl-6-(2,2,2-trifluoroethoxy)pyridin-3-yl)ethyl)-2H-pyrazolo[4,3-c]-pyridine-4-carboxamide;
N-methyl-2-(1-(5-methyl-6-(2,2,2-trifluoroethoxy)pyridin-3-yl)ethyl)-2H-pyrazolo[4,3-c]-pyridine-4-carboxamide;
N-ethyl-2-(1-(5-methyl-6-(2,2,2-trifluoroethoxy)pyridin-3-yl)ethyl)-2H-pyrazolo[4,3-c]-pyridine-4-carboxamide;
N-(2-hydroxyethyl)-2-(1-(5-methyl-6-(2,2,2-trifluoroethoxy)pyridin-3-yl)ethyl)-2H-pyrazolo[4,3-c]-pyridine-4-carboxamide;
N-(3-hydroxypropyl)-2-(1-(5-methyl-6-(2,2,2-trifluoroethoxy)pyridin-3-yl)ethyl)-2H-pyrazolo[4,3-c]-pyridine-4-carboxamide;
N-methyl-2-(1-(5-methyl-6-(2,2,2-trifluoroethoxy)pyridin-3-yl)ethyl)-2H-pyrazolo[4,3-c]-pyridine-4-carboxamide;
N-ethyl-2-(1-(5-methyl-6-(2,2,2-trifluoroethoxy)pyridin-3-yl)ethyl)-2H-pyrazolo[4,3-c]-pyridine-4-carboxamide;
N-methyl-2-((5-methyl-2-phenyl-2H-1,2,3-triazol-4-yl)methyl)-2H-pyrazolo[4,3-c]pyridine-4-carboxamide;
N-(2-methoxyethyl)-2-((4-methyl-5-(2,2,2-trifluoroethoxy)pyridin-2-yl)methyl)-2H-pyrazolo[4,3-c]pyridine-4-carboxamide;
2-((6-(4-chloro-1H-pyrazol-1-yl)-5-methylpyridin-3-yl)methyl)-N-isopropyl-2H-pyrazolo[4,3-c]pyridine-4-carboxamide;
2-((6-(4-chloro-1H-pyrazol-1-yl)-5-methylpyridin-3-yl)methyl)-N-(2-hydroxyethyl)-2H-pyrazolo[4,3-c]pyridine-4-carboxamide;
N-(2-(1-(5-methyl-6-(2,2,2-trifluoroethoxy)pyridin-3-yl)ethyl)-2H-pyrazolo[4,3-c]pyridin-4-yl)isobutyramide;
2-hydroxy-2-methyl-N-(2-(1-(5-methyl-6-(2,2,2-trifluoroethoxy)pyridin-3-yl)ethyl)-2H-pyrazolo[4,3-c]pyridin-4-yl)propanamide;
N-(2-((5-methyl-2-phenyl-2H-1,2,3-triazol-4-yl)methyl)-2H-pyrazolo[4,3-c]pyridin-4-yl)-cyclopropanecarboxamide;
N-(2-((6-(2,2,2-trifluoroethoxy)pyridin-2-yl)methyl)-2H-pyrazolo[4,3-c]pyridin-4-yl)-isobutyramide;
N-(2-((6-(2,2,2-trifluoroethoxy)pyridin-2-yl)methyl)-2H-pyrazolo[4,3-c]pyridin-4-yl)-cyclopropanecarboxamide;
N-(2-((6-(cyclopropylmethoxy)-5-methylpyridin-3-yl)methyl)-2H-pyrazolo[4,3-c]pyridin-4-yl)isobutyramide;
N-(2-((6-(cyclopropylmethoxy)-5-methylpyridin-3-yl)methyl)-2H-pyrazolo[4,3-c]pyrdin-4-yl)cyclopropanecarboxamide;
N-(2-((6-(cyclopropylmethoxy)-5-methylpyridin-3-yl)methyl)-2H-pyrazolo[4,3-c]pyridin-4-yl)-2-hydroxy-2-methylpropanamide;
N,6-dimethyl-2-((5-methyl-6-(2,2,2-trifluoroethoxy)pyridin-3-yl)methyl)-2H-pyrazolo[4,3-c]pyridine-4-carboxamide;
N-ethyl-6-methyl-2-((5-methyl-6-(2,2,2-trifluoroethoxy)pyridin-3-yl)methyl)-2H-pyrazolo[4,3-c]pyridine-4-carboxamide;
N-ethyl-2-((5-methyl-6-((2,2,2-trifluoroethyl)amino)pyridin-3-yl)methyl)-2H-pyrazolo[4,3-c]pyridine-4-carboxamide;
N-isopropyl-2-((5-methyl-6-((2,2,2-trifluoroethyl)amino)pyridin-3-yl)methyl)-2H-pyrazolo[4,3-c]pyridine-4-carboxamide;
N-(2-hydroxyethyl)-2-((5-methyl-6-((2,2,2-trifluoroethyl)amino)pyridin-3-yl)methyl)-2H-pyrazolo[4,3-c]pyridine-4-carboxamide;
N-(3-hydroxypropyl)-2-((5-methyl-6-((2,2,2-trifluoroethyl)amino)pyridin-3-yl)methyl)-2H-pyrazolo[4,3-c]pyridine-4-carboxamide;
2-((6-(cyclopropylmethoxy)-5-methylpyridin-3-yl)methyl)-N-isopropyl-2H-pyrazolo[4,3-c]pyridine-4-carboxamide;
N-methyl-2-((6-(2,2,2-trifluoroethoxy)pyridin-2-yl)methyl)-2H-pyrazolo[4,3-c]pyridine-4-carboxamide;
N-ethyl-2-((6-(2,2,2-trifluoroethoxy)pyridin-2-yl)methyl)-2H-pyrazolo[4,3-c]pyridine-4-carboxamide;
N-(2-hydroxyethyl)-2-((6-(2,2,2-trifluoroethoxy)pyridin-2-yl)methyl)-2H-pyrazolo[4,3-c]pyridine-4-carboxamide;
N-(3-hydroxypropyl)-2-((6-(2,2,2-trifluoroethoxy)pyridin-2-yl)methyl)-2H-pyrazolo[4,3-c]pyridine-4-carboxamide;
2-((6-(cyclopropylmethoxy)-5-methylpyridin-3-yl)methyl)-N-methyl-2H-pyrazolo[4,3-c]pyridine-4-carboxamide;
2-((6-(cyclopropylmethoxy)-5-methylpyridin-3-yl)methyl)-N-ethyl-2H-pyrazolo[4,3-c]pyridine-4-carboxamide;
2-((6-(cyclopropylmethoxy)-5-methylpyridin-3-yl)methyl)-N-(2-hydroxyethyl)-2H-pyrazolo[4,3-c]pyridine-4-carboxamide;
2-((6-(cyclopropylmethoxy)-5-methylpyridin-3-yl)methyl)-N-(3-hydroxypropyl)-2H-pyrazolo[4,3-c]pyridine-4-carboxamide;
N-ethyl-2-(3-methyl-4-(trifluoromethoxy)benzyl)-2H-pyrazolo[4,3-c]pyridine-4-carboxamide;

N-isopropyl-2-(3-methyl-4-(trifluoromethoxy)benzyl)-2H-pyrazolo[4,3-c]pyridine-4-carboxamide;
N-(2-hydroxyethyl)-2-(3-methyl-4-(trifluoromethoxy)benzyl)-2H-pyrazolo[4,3-c]pyridine-4-carboxamide;
N-(3-hydroxypropyl)-2-(3-methyl-4-(trifluoromethoxy)benzyl)-2H-pyrazolo[4,3-c]pyridine-4-carboxamide;
N-ethyl-2-((2-(2,2,2-trifluoroethoxy)pyridin-4-yl)methyl)-2H-pyrazolo[4,3-c]pyridine-4-carboxamide;
N-(2-((5-phenyl-6-(2,2,2-trifluoroethoxy)pyridin-3-yl)methyl)-2H-pyrazolo[4,3-c]pyridin-4-yl)cyclopropanecarboxamide;
N-methyl-2-(3-methyl-4-(trifluoromethoxy)benzyl)-2H-pyrazolo[4,3-c]pyridine-4-carboxamide;
2-((6-(4-chloro-1H-pyrazol-1-yl)-5-methylpyridin-3-yl)methyl)-N-(3-hydroxypropyl)-2H-pyrazolo[4,3-c]pyridine-4-carboxamide;
N-isopropyl-2-((2-(2,2,2-trifluoroethoxy)pyridin-4-yl)methyl)-2H-pyrazolo[4,3-c]pyridine-4-carboxamide;
2-((6-(4-fluorophenoxy)-5-methylpyridin-3-yl)methyl)-N-methyl-2H-pyrazolo[4,3-c]pyridine-4-carboxamide;
N-ethyl-2-((6-(4-fluorophenoxy)-5-methylpyridin-3-yl)methyl)-2H-pyrazolo[4,3-c]pyridine-4-carboxamide;
N-(2-hydroxyethyl)-6-methyl-2-((5-methyl-6-(2,2,2-trifluoroethoxy)pyridin-3-yl)methyl)-2H-pyrazolo[4,3-c]pyridine-4-carboxamide;
N-(3-hydroxypropyl)-6-methyl-2-((5-methyl-6-(2,2,2-trifluoroethoxy)pyridin-3-yl)methyl)-2H-pyrazolo[4,3-c]pyridine-4-carboxamide;
2-((5-methyl-6-(3,3,3-trifluoropropoxy)pyridin-3-yl)methyl)-N-(3-(methylsulfonyl)propyl)-2H-pyrazolo[4,3-c]pyridine-4-carboxamide;
N-methyl-2-((1-(2,2,2-trifluoroethoxy)isoquinolin-4-yl)methyl)-2H-pyrazolo[4,3-c]pyridine-4-carboxamide;
N-ethyl-2-((1-(2,2,2-trifluoroethoxy)isoquinolin-4-yl)methyl)-2H-pyrazolo[4,3-c]pyridine-4-carboxamide;
N-isopropyl-2-((1-(2,2,2-trifluoroethoxy)isoquinolin-4-yl)methyl)-2H-pyrazolo[4,3-c]pyridine-4-carboxamide;
N-(2-hydroxyethyl)-2-((1-(2,2,2-trifluoroethoxy)isoquinolin-4-yl)methyl)-2H-pyrazolo[4,3-c]pyridine-4-carboxamide;
N-(3-hydroxypropyl)-2-((1-(2,2,2-trifluoroethoxy)isoquinolin-4-yl)methyl)-2H-pyrazolo[4,3-c]pyridine-4-carboxamide;
N-ethyl-2-(4-((2,2,2-trifluoroethoxy)methyl)benzyl)-2H-pyrazolo[4,3-c]pyridine-4-carboxamide;
N-(3-hydroxypropyl)-2-(4-((2,2,2-trifluoroethoxy)methyl)benzyl)-2H-pyrazolo[4,3-c]pyridine-4-carboxamide;
N-isopropyl-2-(4-((2,2,2-trifluoroethoxy)methyl)benzyl)-2H-pyrazolo[4,3-c]pyridine-4-carboxamide;
(S)-4-hydroxy-1-(2-((5-methyl-6-(2,2,2-trifluoroethoxy)pyridin-3-yl)methyl)-2H-pyrazolo[4,3-c]pyridin-4-yl)pyrrolidin-2-one;
2-((5-(2,2-difluoroethoxy)-4-methylpyridin-2-yl)methyl)-N-(2-hydroxyethyl)-2H-pyrazolo[4,3-c]pyridine-4-carboxamide;
2-((5-(2,2-difluoroethoxy)-4-methylpyridin-2-yl)methyl)-N-(3-hydroxypropyl)-2H-pyrazolo[4,3-c]pyridine-4-carboxamide;
N-methyl-2-((1-methyl-5-(trifluoromethoxy)-1H-indol-2-yl)methyl)-2H-pyrazolo[4,3-c]pyridine-4-carboxamide;
N-ethyl-2-((1-methyl-5-(trifluoromethoxy)-1H-indol-2-yl)methyl)-2H-pyrazolo[4,3-c]pyridine-4-carboxamide;
N-isopropyl-2-((1-methyl-5-(trifluoromethoxy)-1H-indol-2-yl)methyl)-2H-pyrazolo[4,3-c]pyridine-4-carboxamide;
N-(2-hydroxyethyl)-2-((1-methyl-5-(trifluoromethoxy)-1H-indol-2-yl)methyl)-2H-pyrazolo[4,3-c]pyridine-4-carboxamide;
2-(3-chloro-4-(2,2-difluoroethoxy)benzyl)-N-(2-hydroxyethyl)-2H-pyrazolo[4,3-c]pyridine-4-carboxamide;
2-(3-chloro-4-(2,2-difluoroethoxy)benzyl)-N-(3-hydroxypropyl)-2H-pyrazolo[4,3-c]pyridine-4-carboxamide;
N-(2-((5-methyl-6-((2,2,2-trifluoroethoxy)methyl)pyridin-3-yl)methyl)-2H-pyrazolo[4,3-c]pyridin-4-yl)isobutyramide;
2-((5-methyl-6-(2,2,2-trifluoroethoxy)pyridin-3-yl)methyl)-N-(3-(methylsulfonyl)propyl)-2H-pyrazolo[4,3-c]pyridine-4-carboxamide;
N-ethyl-2-((5-methyl-6-((2,2,2-trifluoroethoxy)methyl)pyridin-3-yl)methyl)-2H-pyrazolo[4,3-c]pyridine-4-carboxamide;
N-isopropyl-2-((5-methyl-6-((2,2,2-trifluoroethoxy)methyl)pyridin-3-yl)methyl)-2H-pyrazolo[4,3-c]pyridine-4-carboxamide;
N-(2-hydroxyethyl)-2-((5-methyl-6-((2,2,2-trifluoroethoxy)methyl)pyridin-3-yl)methyl)-2H-pyrazolo[4,3-c]pyridine-4-carboxamide;
N-(3-hydroxypropyl)-2-((5-methyl-6-((2,2,2-trifluoroethoxy)methyl)pyridin-3-yl)methyl)-2H-pyrazolo[4,3-c]pyridine-4-carboxamide;
N-(3-hydroxypropyl)-2-((1-methyl-5-(trifluoromethoxy)-1H-indol-2-yl)methyl)-2H-pyrazolo[4,3-c]pyridine-4-carboxamide;
N-(2-((5-methyl-6-((2,2,2-trifluoroethoxy)methyl)pyridin-3-yl)methyl)-2H-pyrazolo[4,3-c]pyridin-4-yl)cyclopropanecarboxamide;
N-(2-((5-(2,2-difluoroethoxy)-4-methylpyridin-2-yl)methyl)-2H-pyrazolo[4,3-c]pyridin-4-yl)isobutyramide;
N-(2-((5-(2,2-difluoroethoxy)-4-methylpyridin-2-yl)methyl)-2H-pyrazolo[4,3-c]pyridin-4-yl)cyclopropanecarboxamide;
N-(2-((5-(2,2-difluoroethoxy)-4-methylpyridin-2-yl)methyl)-2H-pyrazolo[4,3-c]pyridin-4-yl)-2-hydroxy-2-methylpropanamide;
N-(2-(3-(trifluoromethoxy)benzyl)-2H-pyrazolo[4,3-c]pyridin-4-yl)cyclopropanecarboxamide;
N-(2-(3-(trifluoromethoxy)benzyl)-2H-pyrazolo[4,3-c]pyridin-4-yl)isobutyramide;
2-hydroxy-2-methyl-N-(2-(3-(trifluoromethoxy)benzyl)-2H-pyrazolo[4,3-c]pyridin-4-yl)propanamide;
N-(2-(2-((3-fluoro-5-(trifluoromethyl)pyridin-2-yl)oxy)ethyl)-2H-pyrazolo[4,3-c]pyridin-4-yl)cyclopropanecarboxamide;
N-(2-(2-((3-fluoro-5-(trifluoromethyl)pyridin-2-yl)oxy)ethyl)-2H-pyrazolo[4,3-c]pyridin-4-yl)isobutyramide;
N-methyl-2-(3-(trifluoromethoxy)benzyl)-2H-pyrazolo[4,3-c]pyridine-4-carboxamide;
N-isopropyl-2-(3-(trifluoromethoxy)benzyl)-2H-pyrazolo[4,3-c]pyridine-4-carboxamide;
N-(2-hydroxyethyl)-2-(3-(trifluoromethoxy)benzyl)-2H-pyrazolo[4,3-c]pyridine-4-carboxamide;
N-(3-hydroxypropyl)-2-(3-(trifluoromethoxy)benzyl)-2H-pyrazolo[4,3-c]pyridine-4-carboxamide;
N-ethyl-2-(2-((3-fluoro-5-(trifluoromethyl)pyridin-2-yl)oxy)ethyl)-2H-pyrazolo[4,3-c]pyridine-4-carboxamide;
2-(2-((3-fluoro-5-(trifluoromethyl)pyridin-2-yl)oxy)ethyl)-N-isopropyl-2H-pyrazolo[4,3-c]pyridine-4-carboxamide;
2-(2-((3-fluoro-5-(trifluoromethyl)pyridin-2-yl)oxy)ethyl)-N-(3-hydroxypropyl)-2H-pyrazolo[4,3-c]pyridine-4-carboxamide;
N-(2-((5-(2,2,3,3,3-pentafluoropropoxy)pyridin-2-yl)methyl)-2H-pyrazolo[4,3-c]pyridin-4-yl)isobutyramide;

N-(2-((5-(2,2,3,3,3-pentafluoropropoxy)pyridin-2-yl)methyl)-2H-pyrazolo[4,3-c]pyridin-4-yl)cyclopropanecarboxamide;

N-(2-hydroxyethyl)-2-(4-(1,1,2,2-tetrafluoroethoxy)benzyl)-2H-pyrazolo[4,3-c]pyridine-4-carboxamide;

N-(3-hydroxypropyl)-2-(4-(1,1,2,2-tetrafluoroethoxy)benzyl)-2H-pyrazolo[4,3-c]pyridine-4-carboxamide;

N-ethyl-2-((5-(2,2,3,3,3-pentafluoropropoxy)pyridin-2-yl)methyl)-2H-pyrazolo[4,3-c]pyridine-4-carboxamide;

N-isopropyl-2-((5-(2,2,3,3,3-pentafluoropropoxy)pyridin-2-yl)methyl)-2H-pyrazolo[4,3-c]pyridine-4-carboxamide;

N-(3-hydroxypropyl)-2-((5-(2,2,3,3,3-pentafluoropropoxy)pyridin-2-yl)methyl)-2H-pyrazolo[4,3-c]pyridine-4-carboxamide;

2-((5-(2,2-difluoroethoxy)-4-methylpyridin-2-yl)methyl)-N-isopropyl-2H-pyrazolo[4,3-c]pyridine-4-carboxamide;

2-((5-(2,2-difluoroethoxy)-4-methylpyridin-2-yl)methyl)-N-methyl-2H-pyrazolo[4,3-c]pyridine-4-carboxamide;

2-((5-(2,2-difluoroethoxy)-4-methylpyridin-2-yl)methyl)-N-ethyl-2H-pyrazolo[4,3-c]pyridine-4-carboxamide;

N-ethyl-2-((5-(2,2,3,3-tetrafluoropropoxy)pyridin-2-yl)methyl)-2H-pyrazolo[4,3-c]pyridine-4-carboxamide;

N-(2-hydroxyethyl)-2-((5-(2,2,3,3-tetrafluoropropoxy)pyridin-2-yl)methyl)-2H-pyrazolo[4,3-c]pyridine-4-carboxamide;

N-(3-hydroxypropyl)-2-((5-(2,2,3,3-tetrafluoropropoxy)pyridin-2-yl)methyl)-2H-pyrazolo[4,3-c]pyridine-4-carboxamide;

N-(2-((5-chloro-6-(2,2,3,3-tetrafluoropropoxy)pyridin-3-yl)methyl)-2H-pyrazolo[4,3-c]pyridin-4-yl)isobutyramide;

N-(2-((5-chloro-6-(2,2,3,3-tetrafluoropropoxy)pyridin-3-yl)methyl)-2H-pyrazolo[4,3-c]pyridin-4-yl)cyclopropanecarboxamide;

N-(2-((5-chloro-6-(2,2,3,3-tetrafluoropropoxy)pyridin-3-yl)methyl)-2H-pyrazolo[4,3-c]pyridin-4-yl)-2-hydroxy-2-methylpropanamide;

N-(2-((5-(2,2,3,3-tetrafluoropropoxy)pyridin-2-yl)methyl)-2H-pyrazolo[4,3-c]pyridin-4-yl)isobutyramide;

N-(2-acetamidoethyl)-2-((5-methyl-6-(2,2,3,3-tetrafluoropropoxy)pyridin-3-yl)methyl)-2H-pyrazolo[4,3-c]pyridine-4-carboxamide;

(S)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;

(S)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;

N-(2-(3-(trifluoromethyl)benzyl)-2H-pyrazolo[4,3-c]pyridin-4-yl)cyclopropanecarboxamide;

N-(2-(3-(trifluoromethyl)benzyl)-2H-pyrazolo[4,3-c]pyridin-4-yl)isobutyramide;

N-methyl-2-(3-(trifluoromethyl)benzyl)-2H-pyrazolo[4,3-c]pyridine-4-carboxamide;

N-ethyl-2-(3-(trifluoromethyl)benzyl)-2H-pyrazolo[4,3-c]pyridine-4-carboxamide;

N-isopropyl-2-(3-(trifluoromethyl)benzyl)-2H-pyrazolo[4,3-c]pyridine-4-carboxamide;

N-(3-hydroxypropyl)-2-(3-(trifluoromethyl)benzyl)-2H-pyrazolo[4,3-c]pyridine-4-carboxamide;

(R)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;

(R)-N-(2,3-dihydroxypropyl)-2-((5-methyl-6-(2,2,3,3-tetrafluoropropoxy)pyridin-3-yl) methyl)-2H-pyrazolo[4,3-c]pyridine-4-carboxamide;

2-(3-chloro-4-(2,2-difluoroethoxy)benzyl)-N-methyl-2H-pyrazolo[4,3-c]pyridine-4-carboxamide;

N-methyl-2-(4-(1,1,2,2-tetrafluoroethoxy)benzyl)-2H-pyrazolo[4,3-c]pyridine-4-carboxamide;

2-((5-chloro-6-(2,2,2-trifluoroethoxy)pyridin-3-yl)methyl)-N-methyl-2H-pyrazolo[4,3-c]pyridine-4-carboxamide;

2-(3-chloro-4-(2,2-difluoroethoxy)benzyl)-N-ethyl-2H-pyrazolo[4,3-c]pyridine-4-carboxamide;

N-ethyl-2-(4-(1,1,2,2-tetrafluoroethoxy)benzyl)-2H-pyrazolo[4,3-c]pyridine-4-carboxamide;

2-((5-chloro-6-(2,2,2-trifluoroethoxy)pyridin-3-yl)methyl)-N-ethyl-2H-pyrazolo[4,3-c]pyridine-4-carboxamide;

N-methyl-2-(1-(4-methyl-5-(2,2,2-trifluoroethoxy)pyridin-2-yl)ethyl)-2H-pyrazolo[4,3-c]pyridine-4-carboxamide;

N-ethyl-2-(1-(4-methyl-5-(2,2,2-trifluoroethoxy)pyridin-2-yl)ethyl)-2H-pyrazolo[4,3-c]pyridine-4-carboxamide;

N-(2-acetamidoethyl)-2-(1-(4-methyl-5-(2,2,2-trifluoroethoxy)pyridin-2-yl)ethyl)-2H-pyrazolo[4,3-c]pyridine-4-carboxamide;

N-(2-hydroxyethyl)-2-(1-(4-methyl-5-(2,2,2-trifluoroethoxy)pyridin-2-yl)ethyl)-2H-pyrazolo[4,3-c]pyridine-4-carboxamide;

N-(3-hydroxypropyl)-2-(1-(4-methyl-5-(2,2,2-trifluoroethoxy)pyridin-2-yl)ethyl)-2H-pyrazolo[4,3-c]pyridine-4-carboxamide;

N-((S)-2-hydroxypropyl)-2-(1-(4-methyl-5-(2,2,2-trifluoroethoxy)pyridin-2-yl)ethyl)-2H-pyrazolo[4,3-c]pyridine-4-carboxamide;

N-methyl-2-((5-methyl-6-(3,3,3-trifluoropropyl)pyridin-3-yl)methyl)-2H-pyrazolo[4,3-c]pyridine-4-carboxamide;

N-ethyl-2-((5-methyl-6-(3,3,3-trifluoropropyl)pyridin-3-yl)methyl)-2H-pyrazolo[4,3-c]pyridine-4-carboxamide;

N-isopropyl-2-((5-methyl-6-(3,3,3-trifluoropropyl)pyridin-3-yl)methyl)-2H-pyrazolo[4,3-c]pyridine-4-carboxamide;

N-(2-hydroxyethyl)-2-((5-methyl-6-(3,3,3-trifluoropropyl)pyridin-3-yl)methyl)-2H-pyrazolo[4,3-c]pyridine-4-carboxamide;

N-(3-hydroxypropyl)-2-((5-methyl-6-(3,3,3-trifluoropropyl)pyridin-3-yl)methyl)-2H-pyrazolo[4,3-c]pyridine-4-carboxamide;

N-methyl-2-((4-methyl-5-(3,3,3-trifluoropropoxy)pyridin-2-yl)methyl)-2H-pyrazolo[4,3-c]pyridine-4-carboxamide;

N-ethyl-2-((4-methyl-5-(3,3,3-trifluoropropoxy)pyridin-2-yl)methyl)-2H-pyrazolo[4,3-c]pyridine-4-carboxamide;

N-(2-hydroxyethyl)-2-((4-methyl-5-(3,3,3-trifluoropropoxy)pyridin-2-yl)methyl)-2H-pyrazolo[4,3-c]pyridine-4-carboxamide;

N-isopropyl-2-((4-methyl-5-(3,3,3-trifluoropropoxy)pyridin-2-yl)methyl)-2H-pyrazolo[4,3-c]pyridine-4-carboxamide;

2-((5-chloro-6-(2,2,3,3-tetrafluoropropoxy)pyridin-3-yl)methyl)-N-methyl-2H-pyrazolo[4,3-c]pyridine-4-carboxamide;

2-((5-chloro-6-(2,2,3,3-tetrafluoropropoxy)pyridin-3-yl)methyl)-N-ethyl-2H-pyrazolo[4,3-c]pyridine-4-carboxamide;

2-((5-chloro-6-(2,2,3,3-tetrafluoropropoxy)pyridin-3-yl)methyl)-N-isopropyl-2H-pyrazolo[4,3-c]pyridine-4-carboxamide;

2-((5-chloro-6-(2,2,3,3-tetrafluoropropoxy)pyridin-3-yl)methyl)-N-(2-hydroxyethyl)-2H-pyrazolo[4,3-c]pyridine-4-carboxamide;

2-((5-chloro-6-(2,2,3,3-tetrafluoropropoxy)pyridin-3-yl)methyl)-N-(3-hydroxypropyl)-2H-pyrazolo[4,3-c]pyridine-4-carboxamide;

(S)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;

(R)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;

(S)-2-((5-chloro-6-(2,2,3,3-tetrafluoropropoxy)pyridin-3-yl)methyl)-N-(2,3-dihydroxypropyl)-2H-pyrazolo[4,3-c]pyridine-4-carboxamide;

(R)-2-((5-chloro-6-(2,2,3,3-tetrafluoropropoxy)pyridin-3-yl)methyl)-N-(2,3-dihydroxypropyl)-2H-pyrazolo[4,3-c]pyridine-4-carboxamide;

(S)-2-((5-chloro-6-(2,2,3,3-tetrafluoropropoxy)pyridin-3-yl)methyl)-N-(1-hydroxypropan-2-yl)-2H-pyrazolo[4,3-c]pyridine-4-carboxamide;

N-(2-acetamidoethyl)-2-((5-chloro-6-(2,2,3,3-tetrafluoropropoxy)pyridin-3-yl)methyl)-2H-pyrazolo[4,3-c]pyridine-4-carboxamide;

N-(2-(1-(4-methyl-5-(2,2,2-trifluoroethoxy)pyridin-2-yl)ethyl)-2H-pyrazolo[4,3-c]pyridin-4-yl)isobutyramide;

N-(2-((5-methyl-6-(2,2,3,3-tetrafluoropropoxy)pyridin-3-yl)methyl)-2H-pyrazolo[4,3-c]pyridin-4-yl)isobutyramide;

N-(2-((5-methyl-6-(2,2,3,3-tetrafluoropropoxy)pyridin-3-yl)methyl)-2H-pyrazolo[4,3-c]pyridin-4-yl)cyclopropanecarboxamide;

2-hydroxy-2-methyl-N-(2-((5-methyl-6-(2,2,3,3-tetrafluoropropoxy)pyridin-3-yl)methyl)-2H-pyrazolo[4,3-c]pyridin-4-yl)propanamide;

N-methyl-2-((5-methyl-6-(2,2,3,3-tetrafluoropropoxy)pyridin-3-yl)methyl)-2H-pyrazolo[4,3-c]pyridine-4-carboxamide;

N-ethyl-2-((5-methyl-6-(2,2,3,3-tetrafluoropropoxy)pyridin-3-yl)methyl)-2H-pyrazolo[4,3-c]pyridine-4-carboxamide;

N-(2-((4-methyl-5-(3,3,3-trifluoropropoxy)pyridin-2-yl)methyl)-2H-pyrazolo[4,3-c]pyridin-4-yl)isobutyramide;

N-(2-((4-methyl-5-(3,3,3-trifluoropropoxy)pyridin-2-yl)methyl)-2H-pyrazolo[4,3-c]pyridin-4-yl)cyclopropanecarboxamide;

N-(2-((5-methyl-6-(3,3,3-trifluoropropyl)pyridin-3-yl)methyl)-2H-pyrazolo[4,3-c]pyridin-4-yl)cyclopropanecarboxamide;

N-(2-((5-methyl-6-(3,3,3-trifluoropropyl)pyridin-3-yl)methyl)-2H-pyrazolo[4,3-c]pyridin-4-yl)isobutyramide;

2-((5-chloro-6-(2,2-difluoropropoxy)pyridin-3-yl)methyl)-N-methyl-2H-pyrazolo[4,3-c]pyridine-4-carboxamide;

2-((5-chloro-6-(2,2-difluoropropoxy)pyridin-3-yl)methyl)-N-ethyl-2H-pyrazolo[4,3-c]pyridine-4-carboxamide;

2-((5-chloro-6-(2,2-difluoropropoxy)pyridin-3-yl)methyl)-N-isopropyl-2H-pyrazolo[4,3-c]pyridine-4-carboxamide;

2-((5-chloro-6-(2,2-difluoropropoxy)pyridin-3-yl)methyl)-N-(3-hydroxypropyl)-2H-pyrazolo[4,3-c]pyridine-4-carboxamide;

2-((5-chloro-6-(2,2-difluoropropoxy)pyridin-3-yl)methyl)-N-(2-hydroxyethyl)-2H-pyrazolo[4,3-c]pyridine-4-carboxamide;

N-isopropyl-2-((5-methyl-6-(2,2,3,3-tetrafluoropropoxy)pyridin-3-yl)methyl)-2H-pyrazolo[4,3-c]pyridine-4-carboxamide;

(S)-N-(1-hydroxypropan-2-yl)-2-((5-methyl-6-(2,2,3,3-tetrafluoropropoxy)pyridin-3-yl)methyl)-2H-pyrazolo[4,3-c]pyridine-4-carboxamide;

N-(2-((5-chloro-6-(3,3,3-trifluoropropoxy)pyridin-3-yl)methyl)-2H-pyrazolo[4,3-c]pyridin-4-yl)isobutyramide;

N-(2-((5-chloro-6-(3,3,3-trifluoropropoxy)pyridin-3-yl)methyl)-2H-pyrazolo[4,3-c]pyridin-4-yl)cyclopropanecarboxamide;

N-(2-((5-chloro-6-(3,3,3-trifluoropropoxy)pyridin-3-yl)methyl)-2H-pyrazolo[4,3-c]pyridin-4-yl)-2-hydroxy-2-methylpropanamide;

N-(2-((1-methyl-5-(trifluoromethyl)-1H-benzo[d]imidazol-2-yl)methyl)-2H-pyrazolo[4,3-c]pyridin-4-yl)cyclopropanecarboxamide;

N-(2-((1-methyl-5-(trifluoromethyl)-1H-benzo[d]imidazol-2-yl)methyl)-2H-pyrazolo[4,3-c]pyridin-4-yl)isobutyramide;

2-((5-chloro-6-(3,3,3-trifluoropropoxy)pyridin-3-yl)methyl)-N-methyl-2H-pyrazolo[4,3-c]pyridine-4-carboxamide;

2-((5-chloro-6-(3,3,3-trifluoropropoxy)pyridin-3-yl)methyl)-N-ethyl-2H-pyrazolo[4,3-c]pyridine-4-carboxamide;

2-((5-chloro-6-(3,3,3-trifluoropropoxy)pyridin-3-yl)methyl)-N-isopropyl-2H-pyrazolo[4,3-c]pyridine-4-carboxamide;

2-((5-chloro-6-(3,3,3-trifluoropropoxy)pyridin-3-yl)methyl)-N-(2-hydroxyethyl)-2H-pyrazolo[4,3-c]pyridine-4-carboxamide;

2-((5-chloro-6-(3,3,3-trifluoropropoxy)pyridin-3-yl)methyl)-N-(3-hydroxypropyl)-2H-pyrazolo[4,3-c]pyridine-4-carboxamide;

N-(2-(3-chloro-4-(2,2-difluoroethoxy)benzyl)-2H-pyrazolo[4,3-c]pyridin-4-yl)isobutyramide;

N-(2-(3-chloro-4-(2,2-difluoroethoxy)benzyl)-2H-pyrazolo[4,3-c]pyridin-4-yl)cyclopropanecarboxamide;

N-methyl-2-((1-methyl-5-(trifluoromethyl)-1H-benzo[d]imidazol-2-yl)methyl)-2H-pyrazolo[4,3-c]pyridine-4-carboxamide;

N-ethyl-2-((1-methyl-5-(trifluoromethyl)-1H-benzo[d]imidazol-2-yl)methyl)-2H-pyrazolo[4,3-c]pyridine-4-carboxamide;

N-isopropyl-2-((1-methyl-5-(trifluoromethyl)-1H-benzo[d]imidazol-2-yl)methyl)-2H-pyrazolo[4,3-c]pyridine-4-carboxamide;

N-(2-hydroxyethyl)-2-((1-methyl-5-(trifluoromethyl)-1H-benzo[d]imidazol-2-yl)methyl)-2H-pyrazolo[4,3-c]pyridine-4-carboxamide;

N-(3-hydroxypropyl)-2-((1-methyl-5-(trifluoromethyl)-1H-benzo[d]imidazol-2-yl)methyl)-2H-pyrazolo[4,3-c]pyridine-4-carboxamide;

N-(2-(4-((2,2-difluoroethoxy)-3-methylbenzyl)-2H-pyrazolo[4,3-c]pyridin-4-yl)isobutyramide;

N-(2-(4-((2,2-difluoroethoxy)-3-methylbenzyl)-2H-pyrazolo[4,3-c]pyridin-4-yl)cyclopropanecarboxamide;

N-(2-(4-((2,2-difluoroethoxy)-3-methylbenzyl)-2H-pyrazolo[4,3-c]pyridin-4-yl)-2-hydroxy-2-methylpropanamide;

2-hydroxy-2-methyl-N-(2-(3-methyl-4-(2,2,2-trifluoroethoxy)benzyl)-2H-pyrazolo[4,3-c]pyridin-4-yl)propanamide;

2-hydroxy-2-methyl-N-(2-(3-methyl-4-(trifluoromethoxy)benzyl)-2H-pyrazolo[4,3-c]pyridin-4-yl)propanamide;

2-hydroxy-2-methyl-N-(2-(2-(4-(trifluoromethyl)phenoxy)ethyl)-2H-pyrazolo[4,3-c]pyridin-4-yl)propanamide;

N-(2-((6-(4-chloro-1H-pyrazol-1-yl)-5-methylpyridin-3-yl)methyl)-2H-pyrazolo[4,3-c]pyridin-4-yl)-2-hydroxy-2-methylpropanamide;

2-(4-(2,2-difluoroethoxy)-3-methylbenzyl)-N-methyl-2H-pyrazolo[4,3-c]pyridine-4-carboxamide;

2-(4-(2,2-difluoroethoxy)-3-methylbenzyl)-N-ethyl-2H-pyrazolo[4,3-c]pyridine-4-carboxamide;

N-(2-((5-chloro-6-(2,2-difluoropropoxy)pyridin-3-yl)methyl)-2H-pyrazolo[4,3-c]pyridin-4-yl)cyclopropanecarboxamide;

N-(2-((5-chloro-6-(2,2-difluoropropoxy)pyridin-3-yl)methyl)-2H-pyrazolo[4,3-c]pyridin-4-yl)isobutyramide;

2-((5-methyl-6-(2,2,2-trifluoroethoxy)pyridin-3-yl)methyl)-N-(2-propionamidoethyl)-2H-pyrazolo[4,3-c]pyridine-4-carboxamide;

N-(2-isobutyramidoethyl)-2-((5-methyl-6-(2,2,2-trifluoroethoxy)pyridin-3-yl)methyl)-2H-pyrazolo[4,3-c]pyridine-4-carboxamide;

N-(2-(cyclopropanecarboxamido)ethyl)-2-((5-methyl-6-(2,2,2-trifluoroethoxy)pyridin-3-yl)methyl)-2H-pyrazolo[4,3-c]pyridine-4-carboxamide;

ethyl(2-(2-((5-methyl-6-(2,2,2-trifluoroethoxy)pyridin-3-yl)methyl)-2H-pyrazolo[4,3-c]pyridine-4-carboxamido)ethyl)carbamate;

N-(2-benzamidoethyl)-2-((5-methyl-6-(2,2,2-trifluoroethoxy)pyridin-3-yl)methyl)-2H-pyrazolo[4,3-c]pyridine-4-carboxamide;

N-(2-(2-hydroxy-2-methylpropanamido)ethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-(2-(N-methylacetamido)ethyl)-2H-pyrazolo[4,3-c]pyridine-4-carboxamide;

N-(2-butyramidoethyl)-2-((5-methyl-6-(2,2,2-trifluoroethoxy)pyridin-3-yl)methyl)-2H-pyrazolo[4,3-c]pyridine-4-carboxamide;

N-(2-(cyclobutanecarboxamido)ethyl)-2-((5-methyl-6-(2,2,2-trifluoroethoxy)pyridin-3-yl)methyl)-2H-pyrazolo[4,3-c]pyridine-4-carboxamide;

N-(2-(cyclohexanecarboxamido)ethyl)-2-((5-methyl-6-(2,2,2-trifluoroethoxy)pyridin-3-yl)methyl)-2H-pyrazolo[4,3-c]pyridine-4-carboxamide;

N-(2-(3-ethylureido)ethyl)-2-((5-methyl-6-(2,2,2-trifluoroethoxy)pyridin-3-yl)methyl)-2H-pyrazolo[4,3-c]pyridine-4-carboxamide;

N-(2-acetamidoethyl)-2-((5-chloro-6-(2,2,2-trifluoroethoxy)pyridin-3-yl)methyl)-2H-pyrazolo[4,3-c]pyridine-4-carboxamide;

N-(2-acetamidoethyl)-2-((6-(cyclopropylmethoxy)-5-methylpyridin-3-yl)methyl)-2H-pyrazolo[4,3-c]pyridine-4-carboxamide;

N-(2-acetamidoethyl)-2-(3-methyl-4-(trifluoromethoxy)benzyl)-2H-pyrazolo[4,3-c]pyridine-4-carboxamide;

N-(2-acetamidoethyl)-2-(3-methyl-4-(2,2,2-trifluoroethoxy)benzyl)-2H-pyrazolo[4,3-c]pyridine-4-carboxamide;

N-(2-acetamidoethyl)-2-(4-((2,2-difluoroethoxy)-3-methylbenzyl)-2H-pyrazolo[4,3-c]pyridine-4-carboxamide;

N-(2-acetamidoethyl)-2-((5-chloro-6-(3,3,3-trifluoropropoxy)pyridin-3-yl)methyl)-2H-pyrazolo[4,3-c]pyridine-4-carboxamide;

N-(2-acetamidoethyl)-2-((1-methyl-5-(trifluoromethoxy)-1H-indol-2-yl)methyl)-2H-pyrazolo[4,3-c]pyridine-4-carboxamide;

2-hydroxy-2-methyl-N-(2-((4-methyl-5-(3,3,3-trifluoropropoxy)pyridin-2-yl)methyl)-2H-pyrazolo[4,3-c]pyridin-4-yl)propanamide;

2-((5-methyl-6-(2,2,2-trifluoroethoxy)pyridin-3-yl)methyl)-N-(2-(picolinamido)ethyl)-2H-pyrazolo[4,3-c]pyridine-4-carboxamide;

2-((5-methyl-6-(2,2,2-trifluoroethoxy)pyridin-3-yl)methyl)-N-(2-(nicotinamido)ethyl)-2H-pyrazolo[4,3-c]pyridine-4-carboxamide;

N-(2-(isonicotinamido)ethyl)-2-((5-methyl-6-(2,2,2-trifluoroethoxy)pyridin-3-yl)methyl)-2H-pyrazolo[4,3-c]pyridine-4-carboxamide;

N-(2-(1-hydroxycyclohexanecarboxamido)ethyl)-2-((5-methyl-6-(2,2,2-trifluoroethoxy) pyridin-3-yl)methyl)-2H-pyrazolo[4,3-c]pyridine-4-carboxamide;

N-(2-acetamidoethyl)-2-(3-chloro-4-(2,2,2-trifluoroethoxy)benzyl)-2H-pyrazolo[4,3-c]pyridine-4-carboxamide;

N-(2-((4-methyl-5-(2,2,3,3-tetrafluoropropoxy)pyridin-2-yl)methyl)-2H-pyrazolo[4,3-c]pyridin-4-yl)cyclopropanecarboxamide;

2-hydroxy-2-methyl-N-(2-((4-methyl-5-(2,2,3,3-tetrafluoropropoxy)pyridin-2-yl)methyl)-2H-pyrazolo[4,3-c]pyridin-4-yl)propanamide;

N-(2-((5-chloro-6-(cyclopropylmethoxy)pyridin-3-yl)methyl)-2H-pyrazolo[4,3-c]pyridin-4-yl)isobutyramide;

N-(2-((5-chloro-6-(cyclopropylmethoxy)pyridin-3-yl)methyl)-2H-pyrazolo[4,3-c]pyridin-4-yl)cyclopropanecarboxamide;

N-(2-((5-chloro-6-(cyclopropylmethoxy)pyridin-3-yl)methyl)-2H-pyrazolo[4,3-c]pyridin-4-yl)-2-hydroxy-2-methylpropanamide;

N-methyl-2-((4-methyl-5-(2,2,3,3-tetrafluoropropoxy)pyridin-2-yl)methyl)-2H-pyrazolo[4,3-c]pyridine-4-carboxamide;

N-ethyl-2-((4-methyl-5-(2,2,3,3-tetrafluoropropoxy)pyridin-2-yl)methyl)-2H-pyrazolo[4,3-c]pyridine-4-carboxamide;

N-isopropyl-2-((4-methyl-5-(2,2,3,3-tetrafluoropropoxy)pyridin-2-yl)methyl)-2H-pyrazolo[4,3-c]pyridine-4-carboxamide;

N-(2-acetamidoethyl)-2-((4-methyl-5-(2,2,3,3-tetrafluoropropoxy)pyridin-2-yl)methyl)-2H-pyrazolo[4,3-c]pyridine-4-carboxamide;

N-(2-hydroxyethyl)-2-((4-methyl-5-(2,2,3,3-tetrafluoropropoxy)pyridin-2-yl)methyl)-2H-pyrazolo[4,3-c]pyridine-4-carboxamide;

N-(3-hydroxypropyl)-2-((4-methyl-5-(2,2,3,3-tetrafluoropropoxy)pyridin-2-yl)methyl)-2H-pyrazolo[4,3-c]pyridine-4-carboxamide;

N-methyl-2-(1-(4-methyl-5-(2,2,2-trifluoroethoxy)pyridin-2-yl)ethyl)-2H-pyrazolo[4,3-c]pyridine-4-carboxamide;

N-ethyl-2-(1-(4-methyl-5-(2,2,2-trifluoroethoxy)pyridin-2-yl)ethyl)-2H-pyrazolo[4,3-c]pyridine-4-carboxamide;

N-isopropyl-2-(1-(4-methyl-5-(2,2,2-trifluoroethoxy)pyridin-2-yl)ethyl)-2H-pyrazolo[4,3-c]pyridine-4-carboxamide;

N-(2-acetamidoethyl)-2-((2-methyl-6-(2,2,2-trifluoroethoxy)pyridin-4-yl)methyl)-2H-pyrazolo[4,3-c]pyridine-4-carboxamide;

N-(2-acetamidoethyl)-2-(2-(4-(trifluoromethyl)phenoxy)ethyl)-2H-pyrazolo[4,3-c]pyridine-4-carboxamide;

N-(2-acetamidoethyl)-2-((6-(4-chloro-1H-pyrazol-1-yl)-5-methylpyridin-3-yl)methyl)-2H-pyrazolo[4,3-c]pyridine-4-carboxamide;

N-(2-acetamidoethyl)-2-((1-(2,2,2-trifluoroethoxy)isoquinolin-4-yl)methyl)-2H-pyrazolo[4,3-c]pyridine-4-carboxamide;

N-(2-acetamidoethyl)-2-(4-(1,1,2,2-tetrafluoroethoxy)benzyl)-2H-pyrazolo[4,3-c]pyridine-4-carboxamide;

N-(2-acetamidoethyl)-2-((2-methoxy-6-(2,2,2-trifluoroethoxy)pyridin-3-yl)methyl)-2H-pyrazolo[4,3-c]pyridine-4-carboxamide;

N-(2-acetamidoethyl)-2-((6-(2,2-difluoropropoxy)-5-methylpyridin-3-yl)methyl)-2H-pyrazolo[4,3-c]pyridine-4-carboxamide;

N-(2-acetamidoethyl)-2-((6-(2,2,2-trifluoroethoxy)pyridin-2-yl)methyl)-2H-pyrazolo[4,3-c]pyridine-4-carboxamide;

N-(2-(1-(4-methyl-5-(2,2,2-trifluoroethoxy)pyridin-2-yl)ethyl)-2H-pyrazolo[4,3-c]pyridin-4-yl)cyclopropanecarboxamide;

N-(2-(1-(4-methyl-5-(2,2,2-trifluoroethoxy)pyridin-2-yl)ethyl)-2H-pyrazolo[4,3-c]pyridin-4-yl)isobutyramide;

2-((5-chloro-6-(cyclopropylmethoxy)pyridin-3-yl)methyl)-N-methyl-2H-pyrazolo[4,3-c]pyridine-4-carboxamide;

2-((5-chloro-6-(cyclopropylmethoxy)pyridin-3-yl)methyl)-N-ethyl-2H-pyrazolo[4,3-c]pyridine-4-carboxamide;

N-(2-acetamidoethyl)-2-((5-chloro-6-(cyclopropylmethoxy)pyridin-3-yl)methyl)-2H-pyrazolo[4,3-c]pyridine-4-carboxamide;

2-((5-chloro-6-(cyclopropylmethoxy)pyridin-3-yl)methyl)-N-isopropyl-2H-pyrazolo[4,3-c]pyridine-4-carboxamide;

2-((5-chloro-6-(cyclopropylmethoxy)pyridin-3-yl)methyl)-N-(2-hydroxyethyl)-2H-pyrazolo[4,3-c]pyridine-4-carboxamide;

2-((5-chloro-6-(cyclopropylmethoxy)pyridin-3-yl)methyl)-N-(3-hydroxypropyl)-2H-pyrazolo[4,3-c]pyridine-4-carboxamide;

N-(2-((6-((4-fluorobenzyl)oxy)-5-methylpyridin-3-yl)methyl)-2H-pyrazolo[4,3-c]pyridin-4-yl)isobutyramide;

N-(2-((6-((4-fluorobenzyl)oxy)-5-methylpyridin-3-yl)methyl)-2H-pyrazolo[4,3-c]pyridin-4-yl)cyclopropanecarboxamide;

N-(2-((6-((4-fluorobenzyl)oxy)-5-methylpyridin-3-yl)methyl)-2H-pyrazolo[4,3-c]pyridin-4-yl)-2-hydroxy-2-methylpropanamide;

2-((6-((4-fluorobenzyl)oxy)-5-methylpyridin-3-yl)methyl)-N-methyl-2H-pyrazolo[4,3-c]pyridine-4-carboxamide;

N-ethyl-2-((6-((4-fluorobenzyl)oxy)-5-methylpyridin-3-yl)methyl)-2H-pyrazolo[4,3-c]pyridine-4-carboxamide;

N-(2-acetamidoethyl)-2-((6-((4-fluorobenzyl)oxy)-5-methylpyridin-3-yl)methyl)-2H-pyrazolo[4,3-c]pyridine-4-carboxamide;

2-((6-((4-fluorobenzyl)oxy)-5-methylpyridin-3-yl)methyl)-N-isopropyl-2H-pyrazolo[4,3-c]pyridine-4-carboxamide;

2-((6-((4-fluorobenzyl)oxy)-5-methylpyridin-3-yl)methyl)-N-(2-hydroxyethyl)-2H-pyrazolo[4,3-c]pyridine-4-carboxamide;

2-((6-((4-fluorobenzyl)oxy)-5-methylpyridin-3-yl)methyl)-N-(3-hydroxypropyl)-2H-pyrazolo[4,3-c]pyridine-4-carboxamide;

N-(2-((6-cyclobutoxy-5-methylpyridin-3-yl)methyl)-2H-pyrazolo[4,3-c]pyridin-4-yl)isobutyramide;

N-(2-((6-cyclobutoxy-5-methylpyridin-3-yl)methyl)-2H-pyrazolo[4,3-c]pyridin-4-yl)cyclopropanecarboxamide;

N-(2-((6-cyclobutoxy-5-methylpyridin-3-yl)methyl)-2H-pyrazolo[4,3-c]pyridin-4-yl)-2-hydroxy-2-methylpropanamide;

N-(2-((4-methyl-5-(2,2,3,3-tetrafluoropropoxy)pyridin-2-yl)methyl)-2H-pyrazolo[4,3-c]pyridin-4-yl)isobutyramide;

2-((6-cyclobutoxy-5-methylpyridin-3-yl)methyl)-N-methyl-2H-pyrazolo[4,3-c]pyridine-4-carboxamide;

2-((6-cyclobutoxy-5-methylpyridin-3-yl)methyl)-N-ethyl-2H-pyrazolo[4,3-c]pyridine-4-carboxamide;

N-(2-acetamidoethyl)-2-((6-cyclobutoxy-5-methylpyridin-3-yl)methyl)-2H-pyrazolo[4,3-c]pyridine-4-carboxamide;

2-((6-cyclobutoxy-5-methylpyridin-3-yl)methyl)-N-isopropyl-2H-pyrazolo[4,3-c]pyridine-4-carboxamide;

2-((6-cyclobutoxy-5-methylpyridin-3-yl)methyl)-N-(2-hydroxyethyl)-2H-pyrazolo[4,3-c]pyridine-4-carboxamide;

2-((6-cyclobutoxy-5-methylpyridin-3-yl)methyl)-N-(3-hydroxypropyl)-2H-pyrazolo[4,3-c]pyridine-4-carboxamide;

N-(2-((5-(cyclopropylmethoxy)-4-methylpyridin-2-yl)methyl)-2H-pyrazolo[4,3-c]pyridin-4-yl)isobutyramide;

N-(2-((5-(cyclopropylmethoxy)-4-methylpyridin-2-yl)methyl)-2H-pyrazolo[4,3-c]pyridin-4-yl)cyclopropanecarboxamide;

N-(2-((5-(cyclopropylmethoxy)-4-methylpyridin-2-yl)methyl)-2H-pyrazolo[4,3-c]pyridin-4-yl)-2-hydroxy-2-methylpropanamide;

2-((5-(cyclopropylmethoxy)-4-methylpyridin-2-yl)methyl)-N-methyl-2H-pyrazolo[4,3-c]pyridine-4-carboxamide;

2-((5-(cyclopropylmethoxy)-4-methylpyridin-2-yl)methyl)-N-ethyl-2H-pyrazolo[4,3-c]pyridine-4-carboxamide;

N-(2-acetamidoethyl)-2-((5-(cyclopropylmethoxy)-4-methylpyridin-2-yl)methyl)-2H-pyrazolo[4,3-c]pyridine-4-carboxamide;

2-((5-(cyclopropylmethoxy)-4-methylpyridin-2-yl)methyl)-N-isopropyl-2H-pyrazolo[4,3-c]pyridine-4-carboxamide;

2-((5-(cyclopropylmethoxy)-4-methylpyridin-2-yl)methyl)-N-(2-hydroxyethyl)-2H-pyrazolo[4,3-c]pyridine-4-carboxamide;

2-((5-(cyclopropylmethoxy)-4-methylpyridin-2-yl)methyl)-N-(3-hydroxypropyl)-2H-pyrazolo[4,3-c]pyridine-4-carboxamide;

N-methyl-2-((5-methyl-6-(2,2,3,3-tetrafluoropropoxy)pyridazin-3-yl)methyl)-2H-pyrazolo[4,3-c]pyridine-4-carboxamide;

N-ethyl-2-((5-methyl-6-(2,2,3,3-tetrafluoropropoxy)pyridazin-3-yl)methyl)-2H-pyrazolo[4,3-c]pyridine-4-carboxamide;

N-isopropyl-2-((5-methyl-6-(2,2,3,3-tetrafluoropropoxy)pyridazin-3-yl)methyl)-2H-pyrazolo[4,3-c]pyridine-4-carboxamide;

N-(2-hydroxyethyl)-2-((5-methyl-6-(2,2,3,3-tetrafluoropropoxy)pyridazin-3-yl)methyl)-2H-pyrazolo[4,3-c]pyridine-4-carboxamide;

N-(3-hydroxypropyl)-2-((5-methyl-6-(2,2,3,3-tetrafluoropropoxy)pyridazin-3-yl)methyl)-2H-pyrazolo[4,3-c]pyridine-4-carboxamide;

N-(2-((5-(2,2-difluoropropoxy)-4-methylpyridin-2-yl)methyl)-2H-pyrazolo[4,3-c]pyridin-4-yl)isobutyramide;

N-(2-((5-(2,2-difluoropropoxy)-4-methylpyridin-2-yl)methyl)-2H-pyrazolo[4,3-c]pyridin-4-yl)cyclopropanecarboxamide;

2-((5-(2,2-difluoropropoxy)-4-methylpyridin-2-yl)methyl)-N-methyl-2H-pyrazolo[4,3-c]pyridine-4-carboxamide;

2-((5-(2,2-difluoropropoxy)-4-methylpyridin-2-yl)methyl)-N-ethyl-2H-pyrazolo[4,3-c]pyridine-4-carboxamide;

N-(2-acetamidoethyl)-2-((5-(2,2-difluoropropoxy)-4-methylpyridin-2-yl)methyl)-2H-pyrazolo[4,3-c]pyridine-4-carboxamide;

2-((5-(2,2-difluoropropoxy)-4-methylpyridin-2-yl)methyl)-N-isopropyl-2H-pyrazolo[4,3-c]pyridine-4-carboxamide;

2-((5-(2,2-difluoropropoxy)-4-methylpyridin-2-yl)methyl)-N-(2-hydroxyethyl)-2H-pyrazolo[4,3-c]pyridine-4-carboxamide;

2-((5-(2,2-difluoropropoxy)-4-methylpyridin-2-yl)methyl)-N-(3-hydroxypropyl)-2H-pyrazolo[4,3-c]pyridine-4-carboxamide;

N-(2-((5-(2,2-difluoropropoxy)-4-methylpyridin-2-yl)methyl)-2H-pyrazolo[4,3-c]pyridin-4-yl)-2-hydroxy-2-methylpropanamide;

(R)-2-((6-(2,2-difluoropropoxy)-5-methylpyridin-3-yl)methyl)-N-(2-hydroxypropyl)-2H-pyrazolo[4,3-c]pyridine-4-carboxamide;

(S)-2-((6-(2,2-difluoropropoxy)-5-methylpyridin-3-yl)methyl)-N-(2-hydroxypropyl)-2H-pyrazolo[4,3-c]pyridine-4-carboxamide;
(S)-2-((6-(2,2-difluoropropoxy)-5-methylpyridin-3-yl)methyl)-N-(1-hydroxypropan-2-yl)-2H-pyrazolo[4,3-c]pyridine-4-carboxamide;
(S)-2-((6-(2,2-difluoropropoxy)-5-methylpyridin-3-yl)methyl)-N-(2,3-dihydroxypropyl)-2H-pyrazolo[4,3-c]pyridine-4-carboxamide;
(R)-2-((6-(2,2-difluoropropoxy)-5-methylpyridin-3-yl)methyl)-N-(2,3-dihydroxypropyl)-2H-pyrazolo[4,3-c]pyridine-4-carboxamide;
N-(2-cyanoethyl)-2-((6-(2,2-difluoropropoxy)-5-methylpyridin-3-yl)methyl)-2H-pyrazolo[4,3-c]pyridine-4-carboxamide;
N-(2-(4-(2,2-difluoropropoxy)-3-methylbenzyl)-2H-pyrazolo[4,3-c]pyridin-4-yl)isobutyramide;
N-(2-(4-(2,2-difluoropropoxy)-3-methylbenzyl)-2H-pyrazolo[4,3-c]pyridin-4-yl)cyclopropanecarboxamide;
N-(2-(4-(2,2-difluoropropoxy)-3-methylbenzyl)-2H-pyrazolo[4,3-c]pyridin-4-yl)-2-hydroxy-2-methylpropanamide;
2-(4-(2,2-difluoropropoxy)-3-methylbenzyl)-N-methyl-2H-pyrazolo[4,3-c]pyridine-4-carboxamide;
2-(4-(2,2-difluoropropoxy)-3-methylbenzyl)-N-ethyl-2H-pyrazolo[4,3-c]pyridine-4-carboxamide;
N-(2-acetamidoethyl)-2-(4-(2,2-difluoropropoxy)-3-methylbenzyl)-2H-pyrazolo[4,3-c]pyridine-4-carboxamide;
2-(4-(2,2-difluoropropoxy)-3-methylbenzyl)-N-isopropyl-2H-pyrazolo[4,3-c]pyridine-4-carboxamide;
2-(4-(2,2-difluoropropoxy)-3-methylbenzyl)-N-(2-hydroxyethyl)-2H-pyrazolo[4,3-c]pyridine-4-carboxamide;
2-(4-(2,2-difluoropropoxy)-3-methylbenzyl)-N-(3-hydroxypropyl)-2H-pyrazolo[4,3-c]pyridine-4-carboxamide;
N-(2-(1-(5-methyl-6-(2,2,2-trifluoroethoxy)pyridin-3-yl)ethyl)-2H-pyrazolo[4,3-c]pyridin-4-yl)oxazole-5-carboxamide;
2-hydroxy-2-methyl-N-(2-(1-(5-methyl-6-(2,2,2-trifluoroethoxy)pyridin-3-yl)ethyl)-2H-pyrazolo[4,3-c]pyridin-4-yl)propanamide;
(S)-2-(4-(2,2-difluoroethoxy)-3-methylbenzyl)-N-(2-hydroxypropyl)-2H-pyrazolo[4,3-c]pyridine-4-carboxamide;
(R)-2-(4-(2,2-difluoroethoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((R)-2-hydroxypropyl)-2H-pyrazolo[4,3-c]pyridine-4-carboxamide;
(R)-2-(4-(2,2-difluoroethoxy)-3,5-dimethylbenzyl)-N-(2-hydroxypropyl)-2H-pyrazolo[4,3-c]pyridine-4-carboxamide;
(R)-2-(3-(2,2-difluoroethoxy)-4-methylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((R)-2-hydroxypropyl)-2H-pyrazolo[4,3-c]pyridine-4-carboxamide;
2-(1-(4-(2,2-difluoroethoxy)-3-methylphenyl)ethyl)-N-((R)-2-hydroxypropyl)-2H-pyrazolo[4,3-c]pyridine-4-carboxamide;
(S)-2-(4-(2,2-difluoropropoxy)-3-methylbenzyl)-N-(2-hydroxypropyl)-2H-pyrazolo[4,3-c]pyridine-4-carboxamide;
(R)-2-(4-(2,2-difluoropropoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((S)-2-hydroxypropyl)-2H-pyrazolo[4,3-c]pyridine-4-carboxamide;
(S)-2-(4-(2,2-difluoroethoxy)-3,5-dimethylbenzyl)-N-(2-hydroxypropyl)-2H-pyrazolo[4,3-c]pyridine-4-carboxamide;
(S)-2-(3-(2,2-difluoroethoxy)-4-methylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((S)-2-hydroxypropyl)-2H-pyrazolo[4,3-c]pyridine-4-carboxamide;
2-(1-(4-(2,2-difluoroethoxy)-3-methylphenyl)ethyl)-N-((S)-2-hydroxypropyl)-2H-pyrazolo[4,3-c]pyridine-4-carboxamide;
(R)-2-(1-(4-(2,2-difluoroethoxy)-3-methylphenyl)ethyl)-N-(2-hydroxyethyl)-2H-pyrazolo[4,3-c]pyridine-4-carboxamide;
2-(4-(2,2-difluoroethoxy)-3,5-dimethylbenzyl)-N-(2-hydroxyethyl)-2H-pyrazolo[4,3-c]pyridine-4-carboxamide;
2-(3-(2,2-difluoroethoxy)-4-methylbenzyl)-N-(2-hydroxyethyl)-2H-pyrazolo[4,3-c]pyridine-4-carboxamide;
2-(1-(4-(2,2-difluoropropoxy)-3-methylphenyl)ethyl)-N-(2-hydroxyethyl)-2H-pyrazolo[4,3-c]pyridine-4-carboxamide;
2-(1-(4-(2,2-difluoroethoxy)-3-methylphenyl)ethyl)-N-(2-hydroxyethyl)-2H-pyrazolo[4,3-c]pyridine-4-carboxamide;
2-(1-(4-(2,2-difluoroethoxy)-3-methylphenyl)ethyl)-N-(3-hydroxypropyl)-2H-pyrazolo[4,3-c]pyridine-4-carboxamide;
2-(4-(2,2-difluoroethoxy)-3,5-dimethylbenzyl)-N-(3-hydroxypropyl)-2H-pyrazolo[4,3-c]pyridine-4-carboxamide;
2-(3-(2,2-difluoroethoxy)-4-methylbenzyl)-N-(3-hydroxypropyl)-2H-pyrazolo[4,3-c]pyridine-4-carboxamide;
2-(1-(4-(2,2-difluoropropoxy)-3-methylphenyl)ethyl)-N-(3-hydroxypropyl)-2H-pyrazolo[4,3-c]pyridine-4-carboxamide;
2-(1-(4-(2,2-difluoroethoxy)-3-methylphenyl)ethyl)-N-(3-hydroxypropyl)-2H-pyrazolo[4,3-c]pyridine-4-carboxamide;
2-(4-(2,2-difluoropropoxy)-3-methylbenzyl)-2H-pyrazolo[4,3-c]pyridine-4-carboxamide;
2-(4-(difluoromethoxy)-3-methylbenzyl)-N-methyl-2H-pyrazolo[4,3-c]pyridine-4-carboxamide;
2-(4-(difluoromethoxy)-3-methylbenzyl)-N-ethyl-2H-pyrazolo[4,3-c]pyridine-4-carboxamide;
N-(2-acetamidoethyl)-2-(4-(difluoromethoxy)-3-methylbenzyl)-2H-pyrazolo[4,3-c]pyridine-4-carboxamide;
2-(4-(difluoromethoxy)-3-methylbenzyl)-N-(2-hydroxyethyl)-2H-pyrazolo[4,3-c]pyridine-4-carboxamide;
2-(4-(difluoromethoxy)-3-methylbenzyl)-N-(3-hydroxypropyl)-2H-pyrazolo[4,3-c]pyridine-4-carboxamide;
(R)-2-(4-(difluoromethoxy)-3-methylbenzyl)-N-(2-hydroxypropyl)-2H-pyrazolo[4,3-c]pyridine-4-carboxamide;
(S)-2-(4-(difluoromethoxy)-3-methylbenzyl)-N-(2-hydroxypropyl)-2H-pyrazolo[4,3-c]pyridine-4-carboxamide;
and
2-(4-(difluoromethoxy)-3-methylbenzyl)-N-isopropyl-2H-pyrazolo[4,3-c]pyridine-4-carboxamide;
or a prodrug thereof or a pharmaceutically acceptable salt thereof.

[8] More suitable individual compounds of the invention are:

N-(2-((5-methyl-6-(2,2,2-trifluoroethoxy)pyridin-3-yl)
methyl)-2H-pyrazolo[4,3-c]pyridin-4-yl)isobutyramide;
2-hydroxy-2-methyl-N-(2-((5-methyl-6-(2,2,2-trifluoroethoxy)pyridin-3-yl)methyl)-2H-pyrazolo[4,3-c]pyridin-4-yl)propanamide;
N-(2-((6-(2,2-difluoroethoxy)-5-methylpyridin-3-yl)
methyl)-2H-pyrazolo[4,3-c]pyridin-4-yl)isobutyramide;
N-(2-((6-(2,2,2-trifluoroethoxy)pyridin-3-yl)methyl)-2H-pyrazolo[4,3-c]pyridin-4-yl)isobutyramide;
N-(2-((5-chloro-6-(2,2,2-trifluoroethoxy)pyridin-3-yl)
methyl)-2H-pyrazolo[4,3-c]pyridin-4-yl)acetamide;
N-methyl-2-((5-methyl-6-(2,2,2-trifluoroethoxy)pyridin-3-yl)methyl)-2H-pyrazolo[4,3-c]pyridine-4-carboxamide;
N-isopropyl-2-((5-methyl-6-(2,2,2-trifluoroethoxy)pyridin-3-yl)methyl)-2H-pyrazolo[4,3-c]pyridine-4-carboxamide;
N-(2-(1-(5-methyl-6-(2,2,2-trifluoroethoxy)pyridin-3-yl)
ethyl)-2H-pyrazolo[4,3-c]pyridin-4-yl)isobutyramide;
N-(2-(1-(5-methyl-6-(2,2,2-trifluoroethoxy)pyridin-3-yl)
ethyl)-2H-pyrazolo[4,3-c]pyridin-4-yl)acetamide;
N-(2-(1-(5-methyl-6-(2,2,2-trifluoroethoxy)pyridin-3-yl)
ethyl)-2H-pyrazolo[4,3-c]pyridin-4-yl)tetrahydro-2H-pyran-4-carboxamide;
N-(2-((6-(2,2-difluoroethoxy)-5-methylpyridin-3-yl)
methyl)-2H-pyrazolo[4,3-c]pyridin-4-yl)pivalamide;
N-ethyl-2-((5-methyl-6-(2,2,2-trifluoroethoxy)pyridin-3-yl)
methyl)-2H-pyrazolo[4,3-c]pyridine-4-carboxamide;
N-(2-methoxyethyl)-2-((5-methyl-6-(2,2,2-trifluoroethoxy)
pyridin-3-yl)methyl)-2H-pyrazolo[4,3-c]pyridine-4-carboxamide;
2-((5-methyl-6-(2,2,2-trifluoroethoxy)pyridin-3-yl)methyl)-
N-propyl-2H-pyrazolo[4,3-c]pyridine-4-carboxamide;
N-(2-(dimethylamino)ethyl)-2-((5-methyl-6-(2,2,2-trifluoroethoxy)pyridin-3-yl)methyl)-2H-pyrazolo[4,3-c]pyridine-4-carboxamide;
2-hydroxy-2-methyl-N-(6-methyl-2-((5-methyl-6-(2,2,2-trifluoroethoxy)pyridin-3-yl)methyl)-2H-pyrazolo[4,3-c]pyridin-4-yl)propanamide;
2-((6-(2,2-difluoroethoxy)-5-methylpyridin-3-yl)methyl)-
N-ethyl-2H-pyrazolo[4,3-c]pyridine-4-carboxamide;
N-(2-hydroxyethyl)-2-((5-methyl-6-(2,2,2-trifluoroethoxy)
pyridin-3-yl)methyl)-2H-pyrazolo[4,3-c]pyridine-4-carboxamide;
2-((6-(2,2-difluoroethoxy)-5-methylpyridin-3-yl)methyl)-
N-(2-hydroxyethyl)-2H-pyrazolo[4,3-c]pyridine-4-carboxamide;
N-(2-hydroxyethyl)-2-((5-methyl-6-(3,3,3-trifluoropropoxy)pyridin-3-yl)methyl)-2H-pyrazolo[4,3-c]pyridine-4-carboxamide;
N-(2-((5-methyl-6-(3,3,3-trifluoropropoxy)pyridin-3-yl)
methyl)-2H-pyrazolo[4,3-c]pyridin-4-yl)isobutyramide;
2-hydroxy-2-methyl-N-(2-((5-methyl-6-(3,3,3-trifluoropropoxy)pyridin-3-yl)methyl)-2H-pyrazolo[4,3-c]pyridin-4-yl)propanamide;
N-isopropyl-2-((5-methyl-6-(3,3,3-trifluoropropoxy)pyridin-3-yl)methyl)-2H-pyrazolo[4,3-c]pyridine-4-carboxamide;
N-(2-((5-methyl-6-(2,2,2-trifluoroethoxy)pyridazin-3-yl)
methyl)-2H-pyrazolo[4,3-c]pyridin-4-yl)isobutyramide;
N-(2-((5-methyl-6-(2,2,2-trifluoroethoxy)pyridazin-3-yl)
methyl)-2H-pyrazolo[4,3-c]pyridin-4-yl)cyclopropanecarboxamide;
N-methyl-2-((5-methyl-6-(2,2,2-trifluoroethoxy)pyridazin-3-yl)methyl)-2H-pyrazolo[4,3-c]pyridine-4-carboxamide;
N-ethyl-2-((5-methyl-6-(2,2,2-trifluoroethoxy)pyridazin-3-yl)methyl)-2H-pyrazolo[4,3-c]pyridine-4-carboxamide;
(R)-N-(2-hydroxypropyl)-2-((5-methyl-6-(2,2,2-trifluoroethoxy)pyridin-3-yl)methyl)-2H-pyrazolo[4,3-c]pyridine-4-carboxamide;
(S)-N-(2-hydroxypropyl)-2-((5-methyl-6-(2,2,2-trifluoroethoxy)pyridin-3-yl)methyl)-2H-pyrazolo[4,3-c]pyridine-4-carboxamide;
(S)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;
N-(2-((4-methyl-5-(2,2,2-trifluoroethoxy)pyridin-2-yl)
methyl)-2H-pyrazolo[4,3-c]pyridin-4-yl)cyclopropanecarboxamide;
N-methyl-2-((4-methyl-5-(2,2,2-trifluoroethoxy)pyridin-2-yl)methyl)-2H-pyrazolo[4,3-c]pyridine-4-carboxamide;
N-ethyl-2-((4-methyl-5-(2,2,2-trifluoroethoxy)pyridin-2-yl)
methyl)-2H-pyrazolo[4,3-c]pyridine-4-carboxamide;
N-isopropyl-2-((4-methyl-5-(2,2,2-trifluoroethoxy)pyridin-2-yl)methyl)-2H-pyrazolo[4,3-c]pyridine-4-carboxamide;
N-(2-hydroxyethyl)-2-((4-methyl-5-(2,2,2-trifluoroethoxy)
pyridin-2-yl)methyl)-2H-pyrazolo[4,3-c]pyridine-4-carboxamide;
N-(2-hydroxyethyl)-2-((5-methyl-6-(2,2,2-trifluoroethoxy)
pyridazin-3-yl)methyl)-2H-pyrazolo[4,3-c]pyridine-4-carboxamide;
N-(3-hydroxypropyl)-2-((5-methyl-6-(2,2,2-trifluoroethoxy)pyridin-3-yl)methyl)-2H-pyrazolo[4,3-c]pyridine-4-carboxamide;
2-((6-(2,2-difluoroethoxy)-5-methylpyridin-3-yl)methyl)-
N-(3-hydroxypropyl)-2H-pyrazolo[4,3-c]pyridine-4-carboxamide;
N-(2-cyanoethyl)-2-((5-methyl-6-(2,2,2-trifluoroethoxy)
pyridin-3-yl)methyl)-2H-pyrazolo[4,3-c]pyridine-4-carboxamide;
N-(2-cyanoethyl)-2-((6-(2,2-difluoroethoxy)-5-methylpyridin-3-yl)methyl)-2H-pyrazolo[4,3-c]pyridine-4-carboxamide;
N-(2-acetamidoethyl)-2-((5-methyl-6-(2,2,2-trifluoroethoxy)pyridin-3-yl)methyl)-2H-pyrazolo[4,3-c]pyridine-4-carboxamide;
N-(2-((5-methoxy-6-(2,2,2-trifluoroethoxy)pyridin-3-yl)
methyl)-2H-pyrazolo[4,3-c]pyridin-4-yl)isobutyramide;
N-ethyl-2-((5-methoxy-6-(2,2,2-trifluoroethoxy)pyridin-3-yl)methyl)-2H-pyrazolo[4,3-c]pyridine-4-carboxamide;
N-(2-(2-hydroxyethoxy)ethyl)-2-((5-methyl-6-(2,2,2-trifluoroethoxy)pyridin-3-yl)methyl)-2H-pyrazolo[4,3-c]pyridine-4-carboxamide;
N-(2-((4-methyl-5-(2,2,2-trifluoroethoxy)pyridin-2-yl)
methyl)-2H-pyrazolo[4,3-c]pyridin-4-yl)isobutyramide;
2-((5-chloro-6-(2,2,2-trifluoroethoxy)pyridin-3-yl)methyl)-
N-(2-hydroxyethyl)-2H-pyrazolo[4,3-c]pyridine-4-carboxamide;
2-((5-chloro-6-(2,2-difluoroethoxy)pyridin-3-yl)methyl)-N-
ethyl-2H-pyrazolo[4,3-c]pyridine-4-carboxamide;
2-((5-chloro-6-(2,2-difluoroethoxy)pyridin-3-yl)methyl)-N-
(2-hydroxyethyl)-2H-pyrazolo[4,3-c]pyridine-4-carboxamide;
(R)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;
N-(2-hydroxyethyl)-2-((6-(2,2,3,3,3-pentafluoropropoxy)
pyridin-3-yl)methyl)-2H-pyrazolo[4,3-c]pyridine-4-carboxamide;
N-(4-hydroxybutyl)-2-((5-methyl-6-(2,2,2-trifluoroethoxy)
pyridin-3-yl)methyl)-2H-pyrazolo[4,3-c]pyridine-4-carboxamide;

N-(2-hydroxyethyl)-2-(3-methyl-4-(2,2,2-trifluoroethoxy)benzyl)-2H-pyrazolo[4,3-c]pyridine-4-carboxamide;
N-(3-acetamidopropyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(3-(methylsulfonamido)propyl)-2H-pyrazolo[4,3-c]pyridine-4-carboxamide;
2-(4-((2,2-difluoroethoxy)-3-methylbenzyl)-N-(2-hydroxyethyl)-2H-pyrazolo[4,3-c]pyridine-4-carboxamide;
2-(4-((2,2-difluoroethoxy)-3-methylbenzyl)-N-(3-hydroxypropyl)-2H-pyrazolo[4,3-c]pyridine-4-carboxamide;
N-(2-hydroxyethyl)-2-((5-methyl-6-(2,2,3,3-tetrafluoropropoxy)pyridin-3-yl)methyl)-2H-pyrazolo[4,3-c]pyridine-4-carboxamide;
N-(3-hydroxypropyl)-2-((5-methyl-6-(2,2,3,3-tetrafluoropropoxy)pyridin-3-yl)methyl)-2H-pyrazolo[4,3-c]pyridine-4-carboxamide; 2-((5-chloro-6-(2,2,2-trifluoroethoxy)pyridin-3-yl)methyl)-N-(3-hydroxypropyl)-2H-pyrazolo[4,3-c]pyridine-4-carboxamide;
N-(2-((2-methyl-6-(2,2,2-trifluoroethoxy)pyridin-4-yl)methyl)-2H-pyrazolo[4,3-c]pyridin-4-yl)isobutyramide;
N-(3-hydroxypropyl)-2-(3-methyl-4-(2,2,2-trifluoroethoxy)benzyl)-2H-pyrazolo[4,3-c]pyridine-4-carboxamide;
N-(3-hydroxypropyl)-2-((5-methyl-6-(3,3,3-trifluoropropoxy)pyridin-3-yl)methyl)-2H-pyrazolo[4,3-c]pyridine-4-carboxamide;
N-(3-hydroxypropyl)-2-((4-methyl-5-(2,2,2-trifluoroethoxy)pyridin-2-yl)methyl)-2H-pyrazolo[4,3-c]pyridine-4-carboxamide;
N-methyl-2-((2-methyl-6-(2,2,2-trifluoroethoxy)pyridin-4-yl)methyl)-2H-pyrazolo[4,3-c]pyridine-4-carboxamide;
N-ethyl-2-((2-methyl-6-(2,2,2-trifluoroethoxy)pyridin-4-yl)methyl)-2H-pyrazolo[4,3-c]pyridine-4-carboxamide;
N-isopropyl-2-((2-methyl-6-(2,2,2-trifluoroethoxy)pyridin-4-yl)methyl)-2H-pyrazolo[4,3-c]pyridine-4-carboxamide;
N-(2-hydroxyethyl)-2-((2-methyl-6-(2,2,2-trifluoroethoxy)pyridin-4-yl)methyl)-2H-pyrazolo[4,3-c]pyridine-4-carboxamide;
N-(3-hydroxypropyl)-2-((2-methyl-6-(2,2,2-trifluoroethoxy)pyridin-4-yl)methyl)-2H-pyrazolo[4,3-c]pyridine-4-carboxamide;
(S)-N-(2-hydroxypropyl)-2-((5-methyl-6-(3,3,3-trifluoropropoxy)pyridin-3-yl)methyl)-2H-pyrazolo[4,3-c]pyridine-4-carboxamide;
(R)-N-(2-hydroxypropyl)-2-((5-methyl-6-(3,3,3-trifluoropropoxy)pyridin-3-yl)methyl)-2H-pyrazolo[4,3-c]pyridine-4-carboxamide;
(S)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;
(R)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;
N-(3-hydroxypropyl)-2-((1-(5-(trifluoromethyl)pyridin-2-yl)-1H-pyrazol-3-yl)methyl)-2H-pyrazolo[4,3-c]pyridine-4-carboxamide;
N-ethyl-2-((1-(5-(trifluoromethyl)pyridin-2-yl)-1H-pyrazol-3-yl)methyl)-2H-pyrazolo[4,3-c]pyridine-4-carboxamide;
(S)-N-(2-hydroxypropyl)-2-((4-methyl-5-(2,2,2-trifluoroethoxy)pyridin-2-yl)methyl)-2H-pyrazolo[4,3-c]pyridine-4-carboxamide;
(S)-N-(1-hydroxypropan-2-yl)-2-((5-methyl-6-(3,3,3-trifluoropropoxy)pyridin-3-yl)methyl)-2H-pyrazolo[4,3-c]pyridine-4-carboxamide;
N-(2-cyanoethyl)-2-((4-methyl-5-(2,2,2-trifluoroethoxy)pyridin-2-yl)methyl)-2H-pyrazolo[4,3-c]pyridine-4-carboxamide;
N-(2-cyanoethyl)-2-((5-methyl-6-(3,3,3-trifluoropropoxy)pyridin-3-yl)methyl)-2H-pyrazolo[4,3-c]pyridine-4-carboxamide;
N-(2-acetamidoethyl)-2-((5-methyl-6-(3,3,3-trifluoropropoxy)pyridin-3-yl)methyl)-2H-pyrazolo[4,3-c]pyridine-4-carboxamide;
N-(2-hydroxyethyl)-2-((5-methyl-6-(2-(2,2,2-trifluoroethoxy)ethoxy)pyridin-3-yl)methyl)-2H-pyrazolo[4,3-c]pyridine-4-carboxamide;
N-(2-hydroxyethyl)-2-((2-methoxy-6-(2,2,2-trifluoroethoxy)pyridin-3-yl)methyl)-2H-pyrazolo[4,3-c]pyridine-4-carboxamide;
N-(3-hydroxypropyl)-2-((2-methoxy-6-(2,2,2-trifluoroethoxy)pyridin-3-yl)methyl)-2H-pyrazolo[4,3-c]pyridine-4-carboxamide;
2-((2-methoxy-6-(2,2,2-trifluoroethoxy)pyridin-3-yl)methyl)-N-methyl-2H-pyrazolo[4,3-c]pyridine-4-carboxamide;
N-ethyl-2-((2-methoxy-6-(2,2,2-trifluoroethoxy)pyridin-3-yl)methyl)-2H-pyrazolo[4,3-c]pyridine-4-carboxamide;
N-isopropyl-2-(2-(4-(trifluoromethyl)phenoxy)ethyl)-2H-pyrazolo[4,3-c]pyridine-4-carboxamide;
N-(3-hydroxypropyl)-2-(2-(4-(trifluoromethyl)phenoxy)ethyl)-2H-pyrazolo[4,3-c]pyridine-4-carboxamide;
N-(2-((6-methyl-5-(2,2,2-trifluoroethoxy)pyrazin-2-yl)methyl)-2H-pyrazolo[4,3-c]pyridin-4-yl)isobutyramide;
N-(2-((6-(2,2-difluoropropoxy)-5-methylpyridin-3-yl)methyl)-2H-pyrazolo[4,3-c]pyridin-4-yl)-2-hydroxy-2-methylpropanamide;
2-(2-((3-chloro-5-(trifluoromethyl)pyridin-2-yl)oxy)ethyl)-N-(2-hydroxyethyl)-2H-pyrazolo[4,3-c]pyridine-4-carboxamide;
2-((5-cyclopropyl-6-(2,2,2-trifluoroethoxy)pyridin-3-yl)methyl)-N-ethyl-2H-pyrazolo[4,3-c]pyridine-4-carboxamide;
2-((5-cyclopropyl-6-(2,2,2-trifluoroethoxy)pyridin-3-yl)methyl)-N-isopropyl-2H-pyrazolo[4,3-c]pyridine-4-carboxamide;
2-((5-cyclopropyl-6-(2,2,2-trifluoroethoxy)pyridin-3-yl)methyl)-N-(2-hydroxyethyl)-2H-pyrazolo[4,3-c]pyridine-4-carboxamide;
2-((6-(2,2-difluoropropoxy)-5-methylpyridin-3-yl)methyl)-N-methyl-2H-pyrazolo[4,3-c]pyridine-4-carboxamide;
2-((6-(2,2-difluoropropoxy)-5-methylpyridin-3-yl)methyl)-N-ethyl-2H-pyrazolo[4,3-c]pyridine-4-carboxamide;
2-((6-(2,2-difluoropropoxy)-5-methylpyridin-3-yl)methyl)-N-(2-hydroxyethyl)-2H-pyrazolo[4,3-c]pyridine-4-carboxamide;
2-((6-(2,2-difluoropropoxy)-5-methylpyridin-3-yl)methyl)-N-(3-hydroxypropyl)-2H-pyrazolo[4,3-c]pyridine-4-carboxamide;
N-ethyl-2-((6-methyl-5-(2,2,2-trifluoroethoxy)pyrazin-2-yl)methyl)-2H-pyrazolo[4,3-c]pyridine-4-carboxamide;
2-((6-(2,2-difluoropropoxy)-5-methylpyridin-3-yl)methyl)-N-isopropyl-2H-pyrazolo[4,3-c]pyridine-4-carboxamide;
N-isopropyl-2-((6-methyl-5-(2,2,2-trifluoroethoxy)pyrazin-2-yl)methyl)-2H-pyrazolo[4,3-c]pyridine-4-carboxamide;
2-((6-(4-chloro-1H-pyrazol-1-yl)-5-methylpyridin-3-yl)methyl)-N-methyl-2H-pyrazolo[4,3-c]pyridine-4-carboxamide;
2-((6-(4-chloro-1H-pyrazol-1-yl)-5-methylpyridin-3-yl)methyl)-N-ethyl-2H-pyrazolo[4,3-c]pyridine-4-carboxamide;

N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide;

N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide;

N-methyl-2-(1-(5-methyl-6-(2,2,2-trifluoroethoxy)pyridin-3-yl)ethyl)-2H-pyrazolo[4,3-c]pyridine-4-carboxamide;

N-ethyl-2-(1-(5-methyl-6-(2,2,2-trifluoroethoxy)pyridin-3-yl)ethyl)-2H-pyrazolo[4,3-c]pyridine-4-carboxamide;

N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide;

N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide;

N-ethyl-2-(1-(5-methyl-6-(2,2,2-trifluoroethoxy)pyridin-3-yl)ethyl)-2H-pyrazolo[4,3-c]pyridine-4-carboxamide;

2-((6-(4-chloro-1H-pyrazol-1-yl)-5-methylpyridin-3-yl)methyl)-N-isopropyl-2H-pyrazolo[4,3-c]pyridine-4-carboxamide;

2-((6-(4-chloro-1H-pyrazol-1-yl)-5-methylpyridin-3-yl)methyl)-N-(2-hydroxyethyl)-2H-pyrazolo[4,3-c]pyridine-4-carboxamide;

N-(2-(1-(5-methyl-6-(2,2,2-trifluoroethoxy)pyridin-3-yl)ethyl)-2H-pyrazolo[4,3-c]pyridin-4-yl)isobutyramide;

N-(2-((6-(cyclopropylmethoxy)-5-methylpyridin-3-yl)methyl)-2H-pyrazolo[4,3-c]pyridin-4-yl)-2-hydroxy-2-methylpropanamide;

N,6-dimethyl-2-((5-methyl-6-(2,2,2-trifluoroethoxy)pyridin-3-yl)methyl)-2H-pyrazolo[4,3-c]pyridine-4-carboxamide;

N-ethyl-6-methyl-2-((5-methyl-6-(2,2,2-trifluoroethoxy)pyridin-3-yl)methyl)-2H-pyrazolo[4,3-c]pyridine-4-carboxamide;

N-ethyl-2-((5-methyl-6-((2,2,2-trifluoroethyl)amino)pyridin-3-yl)methyl)-2H-pyrazolo[4,3-c]pyridine-4-carboxamide;

N-(3-hydroxypropyl)-2-((5-methyl-6-((2,2,2-trifluoroethyl)amino)pyridin-3-yl)methyl)-2H-pyrazolo[4,3-c]pyridine-4-carboxamide;

2-((6-(cyclopropylmethoxy)-5-methylpyridin-3-yl)methyl)-N-isopropyl-2H-pyrazolo[4,3-c]pyridine-4-carboxamide;

2-((6-(cyclopropylmethoxy)-5-methylpyridin-3-yl)methyl)-N-methyl-2H-pyrazolo[4,3-c]pyridine-4-carboxamide;

2-((6-(cyclopropylmethoxy)-5-methylpyridin-3-yl)methyl)-N-ethyl-2H-pyrazolo[4,3-c]pyridine-4-carboxamide;

2-((6-(cyclopropylmethoxy)-5-methylpyridin-3-yl)methyl)-N-(2-hydroxyethyl)-2H-pyrazolo[4,3-c]pyridine-4-carboxamide;

2-((6-(cyclopropylmethoxy)-5-methylpyridin-3-yl)methyl)-N-(3-hydroxypropyl)-2H-pyrazolo[4,3-c]pyridine-4-carboxamide;

N-(2-hydroxyethyl)-2-(3-methyl-4-(trifluoromethoxy)benzyl)-2H-pyrazolo[4,3-c]pyridine-4-carboxamide;

N-(3-hydroxypropyl)-2-(3-methyl-4-(trifluoromethoxy)benzyl)-2H-pyrazolo[4,3-c]pyridine-4-carboxamide;

2-((6-(4-chloro-1H-pyrazol-1-yl)-5-methylpyridin-3-yl)methyl)-N-(3-hydroxypropyl)-2H-pyrazolo[4,3-c]pyridine-4-carboxamide;

N-ethyl-2-((6-(4-fluorophenoxy)-5-methylpyridin-3-yl)methyl)-2H-pyrazolo[4,3-c]pyridine-4-carboxamide;

N-(2-hydroxyethyl)-6-methyl-2-((5-methyl-6-(2,2,2-trifluoroethoxy)pyridin-3-yl)methyl)-2H-pyrazolo[4,3-c]pyridine-4-carboxamide;

N-(3-hydroxypropyl)-6-methyl-2-((5-methyl-6-(2,2,2-trifluoroethoxy)pyridin-3-yl)methyl)-2H-pyrazolo[4,3-c]pyridine-4-carboxamide;

2-((5-methyl-6-(3,3,3-trifluoropropoxy)pyridin-3-yl)methyl)-N-(3-(methylsulfonyl)propyl)-2H-pyrazolo[4,3-c]pyridine-4-carboxamide;

N-methyl-2-((1-(2,2,2-trifluoroethoxy)isoquinolin-4-yl)methyl)-2H-pyrazolo[4,3-c]pyridine-4-carboxamide;

N-ethyl-2-((1-(2,2,2-trifluoroethoxy)isoquinolin-4-yl)methyl)-2H-pyrazolo[4,3-c]pyridine-4-carboxamide;

N-(2-hydroxyethyl)-2-((1-(2,2,2-trifluoroethoxy)isoquinolin-4-yl)methyl)-2H-pyrazolo[4,3-c]pyridine-4-carboxamide;

N-(3-hydroxypropyl)-2-((1-(2,2,2-trifluoroethoxy)isoquinolin-4-yl)methyl)-2H-pyrazolo[4,3-c]pyridine-4-carboxamide;

2-(3-chloro-4-(2,2-difluoroethoxy)benzyl)-N-(3-hydroxypropyl)-2H-pyrazolo[4,3-c]pyridine-4-carboxamide;

N-(2-((5-methyl-6-((2,2,2-trifluoroethoxy)methyl)pyridin-3-yl)methyl)-2H-pyrazolo[4,3-c]pyridin-4-yl)isobutyramide;

2-((5-methyl-6-(2,2,2-trifluoroethoxy)pyridin-3-yl)methyl)-N-(3-(methylsulfonyl)propyl)-2H-pyrazolo[4,3-c]pyridine-4-carboxamide;

N-(3-hydroxypropyl)-2-((1-methyl-5-(trifluoromethoxy)-1H-indol-2-yl)methyl)-2H-pyrazolo[4,3-c]pyridine-4-carboxamide;

N-(2-((5-(2,2-difluoroethoxy)-4-methylpyridin-2-yl)methyl)-2H-pyrazolo[4,3-c]pyridin-4-yl)isobutyramide;

N-(2-((5-(2,2-difluoroethoxy)-4-methylpyridin-2-yl)methyl)-2H-pyrazolo[4,3-c]pyridin-4-yl)cyclopropanecarboxamide;

N-(2-hydroxyethyl)-2-(3-(trifluoromethoxy)benzyl)-2H-pyrazolo[4,3-c]pyridine-4-carboxamide;

N-(2-((5-(2,2,3,3,3-pentafluoropropoxy)pyridin-2-yl)methyl)-2H-pyrazolo[4,3-c]pyridin-4-yl)isobutyramide;

N-ethyl-2-((5-(2,2,3,3,3-pentafluoropropoxy)pyridin-2-yl)methyl)-2H-pyrazolo[4,3-c]pyridine-4-carboxamide;

2-((5-(2,2-difluoroethoxy)-4-methylpyridin-2-yl)methyl)-N-isopropyl-2H-pyrazolo[4,3-c]pyridine-4-carboxamide;

2-((5-(2,2-difluoroethoxy)-4-methylpyridin-2-yl)methyl)-N-methyl-2H-pyrazolo[4,3-c]pyridine-4-carboxamide;

2-((5-(2,2-difluoroethoxy)-4-methylpyridin-2-yl)methyl)-N-ethyl-2H-pyrazolo[4,3-c]pyridine-4-carboxamide;

N-ethyl-2-((5-(2,2,3,3-tetrafluoropropoxy)pyridin-2-yl)methyl)-2H-pyrazolo[4,3-c]pyridine-4-carboxamide;

N-(2-((5-chloro-6-(2,2,3,3-tetrafluoropropoxy)pyridin-3-yl)methyl)-2H-pyrazolo[4,3-c]pyridin-4-yl)-2-hydroxy-2-methylpropanamide;

N-(2-((5-(2,2,3,3-tetrafluoropropoxy)pyridin-2-yl)methyl)-2H-pyrazolo[4,3-c]pyridin-4-yl)isobutyramide;

N-(2-acetamidoethyl)-2-((5-methyl-6-(2,2,3,3-tetrafluoropropoxy)pyridin-3-yl)methyl)-2H-pyrazolo[4,3-c]pyridine-4-carboxamide;

(S)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;

(S)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;

N-(3-hydroxypropyl)-2-(3-(trifluoromethyl)benzyl)-2H-pyrazolo[4,3-c]pyridine-4-carboxamide;

(R)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;

(R)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;
2-(3-chloro-4-(2,2-difluoroethoxy)benzyl)-N-methyl-2H-pyrazolo[4,3-c]pyridine-4-carboxamide;
2-((5-chloro-6-(2,2,2-trifluoroethoxy)pyridin-3-yl)methyl)-N-methyl-2H-pyrazolo[4,3-c]pyridine-4-carboxamide;
2-(3-chloro-4-(2,2-difluoroethoxy)benzyl)-N-ethyl-2H-pyrazolo[4,3-c]pyridine-4-carboxamide;
N-ethyl-2-(4-(1,1,2,2-tetrafluoroethoxy)benzyl)-2H-pyrazolo[4,3-c]pyridine-4-carboxamide;
2-((5-chloro-6-(2,2,2-trifluoroethoxy)pyridin-3-yl)methyl)-N-ethyl-2H-pyrazolo[4,3-c]pyridine-4-carboxamide;
N-methyl-2-(1-(4-methyl-5-(2,2,2-trifluoroethoxy)pyridin-2-yl)ethyl)-2H-pyrazolo[4,3-c]pyridine-4-carboxamide;
N-ethyl-2-(1-(4-methyl-5-(2,2,2-trifluoroethoxy)pyridin-2-yl)ethyl)-2H-pyrazolo[4,3-c]pyridine-4-carboxamide;
N-(2-acetamidoethyl)-2-(1-(4-methyl-5-(2,2,2-trifluoroethoxy)pyridin-2-yl)ethyl)-2H-pyrazolo[4,3-c]pyridine-4-carboxamide;
N-(2-hydroxyethyl)-2-(1-(4-methyl-5-(2,2,2-trifluoroethoxy)pyridin-2-yl)ethyl)-2H-pyrazolo[4,3-c]pyridine-4-carboxamide;
N-(3-hydroxypropyl)-2-(1-(4-methyl-5-(2,2,2-trifluoroethoxy)pyridin-2-yl)ethyl)-2H-pyrazolo[4,3-c]pyridine-4-carboxamide;
N-((S)-2-hydroxypropyl)-2-(1-(4-methyl-5-(2,2,2-trifluoroethoxy)pyridin-2-yl)ethyl)-2H-pyrazolo[4,3-c]pyridine-4-carboxamide;
N-methyl-2-((5-methyl-6-(3,3,3-trifluoropropyl)pyridin-3-yl)methyl)-2H-pyrazolo[4,3-c]pyridine-4-carboxamide;
N-ethyl-2-((5-methyl-6-(3,3,3-trifluoropropyl)pyridin-3-yl)methyl)-2H-pyrazolo[4,3-c]pyridine-4-carboxamide;
N-isopropyl-2-((5-methyl-6-(3,3,3-trifluoropropyl)pyridin-3-yl)methyl)-2H-pyrazolo[4,3-c]pyridine-4-carboxamide;
N-(2-hydroxyethyl)-2-((5-methyl-6-(3,3,3-trifluoropropyl)pyridin-3-yl)methyl)-2H-pyrazolo[4,3-c]pyridine-4-carboxamide;
N-(3-hydroxypropyl)-2-((5-methyl-6-(3,3,3-trifluoropropyl)pyridin-3-yl)methyl)-2H-pyrazolo[4,3-c]pyridine-4-carboxamide;
N-methyl-2-((4-methyl-5-(3,3,3-trifluoropropoxy)pyridin-2-yl)methyl)-2H-pyrazolo[4,3-c]pyridine-4-carboxamide;
N-ethyl-2-((4-methyl-5-(3,3,3-trifluoropropoxy)pyridin-2-yl)methyl)-2H-pyrazolo[4,3-c]pyridine-4-carboxamide;
N-(2-hydroxyethyl)-2-((4-methyl-5-(3,3,3-trifluoropropoxy)pyridin-2-yl)methyl)-2H-pyrazolo[4,3-c]pyridine-4-carboxamide;
N-isopropyl-2-((4-methyl-5-(3,3,3-trifluoropropoxy)pyridin-2-yl)methyl)-2H-pyrazolo[4,3-c]pyridine-4-carboxamide;
2-((5-chloro-6-(2,2,3,3-tetrafluoropropoxy)pyridin-3-yl)methyl)-N-methyl-2H-pyrazolo[4,3-c]pyridine-4-carboxamide;
2-((5-chloro-6-(2,2,3,3-tetrafluoropropoxy)pyridin-3-yl)methyl)-N-ethyl-2H-pyrazolo[4,3-c]pyridine-4-carboxamide;
2-((5-chloro-6-(2,2,3,3-tetrafluoropropoxy)pyridin-3-yl)methyl)-N-isopropyl-2H-pyrazolo[4,3-c]pyridine-4-carboxamide;
2-((5-chloro-6-(2,2,3,3-tetrafluoropropoxy)pyridin-3-yl)methyl)-N-(2-hydroxyethyl)-2H-pyrazolo[4,3-c]pyridine-4-carboxamide;
2-((5-chloro-6-(2,2,3,3-tetrafluoropropoxy)pyridin-3-yl)methyl)-N-(3-hydroxypropyl)-2H-pyrazolo[4,3-c]pyridine-4-carboxamide;
(S)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;
(R)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;
(S)-2-((5-chloro-6-(2,2,3,3-tetrafluoropropoxy)pyridin-3-yl)methyl)-N-(1-hydroxypropan-2-yl)-2H-pyrazolo[4,3-c]pyridine-4-carboxamide;
N-(2-acetamidoethyl)-2-((5-chloro-6-(2,2,3,3-tetrafluoropropoxy)pyridin-3-yl)methyl)-2H-pyrazolo[4,3-c]pyridine-4-carboxamide;
N-(2-(1-(4-methyl-5-(2,2,2-trifluoroethoxy)pyridin-2-yl)ethyl)-2H-pyrazolo[4,3-c]pyridin-4-yl)isobutyramide;
2-hydroxy-2-methyl-N-(2-((5-methyl-6-(2,2,3,3-tetrafluoropropoxy)pyridin-3-yl)methyl)-2H-pyrazolo[4,3-c]pyridin-4-yl)propanamide;
N-methyl-2-((5-methyl-6-(2,2,3,3-tetrafluoropropoxy)pyridin-3-yl)methyl)-2H-pyrazolo[4,3-c]pyridine-4-carboxamide;
N-ethyl-2-((5-methyl-6-(2,2,3,3-tetrafluoropropoxy)pyridin-3-yl)methyl)-2H-pyrazolo[4,3-c]pyridine-4-carboxamide;
N-(2-((4-methyl-5-(3,3,3-trifluoropropoxy)pyridin-2-yl)methyl)-2H-pyrazolo[4,3-c]pyridin-4-yl)cyclopropanecarboxamide;
N-(2-((5-methyl-6-(3,3,3-trifluoropropyl)pyridin-3-yl)methyl)-2H-pyrazolo[4,3-c]pyridin-4-yl)cyclopropanecarboxamide;
2-((5-chloro-6-(2,2-difluoropropoxy)pyridin-3-yl)methyl)-N-methyl-2H-pyrazolo[4,3-c]pyridine-4-carboxamide;
2-((5-chloro-6-(2,2-difluoropropoxy)pyridin-3-yl)methyl)-N-ethyl-2H-pyrazolo[4,3-c]pyridine-4-carboxamide;
2-((5-chloro-6-(2,2-difluoropropoxy)pyridin-3-yl)methyl)-N-(3-hydroxypropyl)-2H-pyrazolo[4,3-c]pyridine-4-carboxamide;
2-((5-chloro-6-(2,2-difluoropropoxy)pyridin-3-yl)methyl)-N-(2-hydroxyethyl)-2H-pyrazolo[4,3-c]pyridine-4-carboxamide;
N-isopropyl-2-((5-methyl-6-(2,2,3,3-tetrafluoropropoxy)pyridin-3-yl)methyl)-2H-pyrazolo[4,3-c]pyridine-4-carboxamide;
(S)-N-(1-hydroxypropan-2-yl)-2-((5-methyl-6-(2,2,3,3-tetrafluoropropoxy)pyridin-3-yl)methyl)-2H-pyrazolo[4,3-c]pyridine-4-carboxamide;
2-((5-chloro-6-(3,3,3-trifluoropropoxy)pyridin-3-yl)methyl)-N-methyl-2H-pyrazolo[4,3-c]pyridine-4-carboxamide;
2-((5-chloro-6-(3,3,3-trifluoropropoxy)pyridin-3-yl)methyl)-N-ethyl-2H-pyrazolo[4,3-c]pyridine-4-carboxamide;
2-((5-chloro-6-(3,3,3-trifluoropropoxy)pyridin-3-yl)methyl)-N-isopropyl-2H-pyrazolo[4,3-c]pyridine-4-carboxamide;
2-((5-chloro-6-(3,3,3-trifluoropropoxy)pyridin-3-yl)methyl)-N-(2-hydroxyethyl)-2H-pyrazolo[4,3-c]pyridine-4-carboxamide;
2-((5-chloro-6-(3,3,3-trifluoropropoxy)pyridin-3-yl)methyl)-N-(3-hydroxypropyl)-2H-pyrazolo[4,3-c]pyridine-4-carboxamide;
N-ethyl-2-((1-methyl-5-(trifluoromethyl)-1H-benzo[d]imidazol-2-yl)methyl)-2H-pyrazolo[4,3-c]pyridine-4-carboxamide;

N-(3-hydroxypropyl)-2-((1-methyl-5-(trifluoromethyl)-1H-benzo[d]imidazol-2-yl)methyl)-2H-pyrazolo[4,3-c]pyridine-4-carboxamide;

2-hydroxy-2-methyl-N-(2-(3-methyl-4-(2,2,2-trifluoroethoxy)benzyl)-2H-pyrazolo[4,3-c]pyridin-4-yl)propanamide;

2-hydroxy-2-methyl-N-(2-(3-methyl-4-(trifluoromethoxy)benzyl)-2H-pyrazolo[4,3-c]pyridin-4-yl)propanamide;

2-(4-(2,2-difluoroethoxy)-3-methylbenzyl)-N-methyl-2H-pyrazolo[4,3-c]pyridine-4-carboxamide;

2-(4-(2,2-difluoroethoxy)-3-methylbenzyl)-N-ethyl-2H-pyrazolo[4,3-c]pyridine-4-carboxamide;

N-(2-acetamidoethyl)-2-((6-(cyclopropylmethoxy)-5-methylpyridin-3-yl)methyl)-2H-pyrazolo[4,3-c]pyridine-4-carboxamide;

N-(2-acetamidoethyl)-2-(3-methyl-4-(2,2,2-trifluoroethoxy)benzyl)-2H-pyrazolo[4,3-c]pyridine-4-carboxamide;

N-(2-acetamidoethyl)-2-(4-(2,2-difluoroethoxy)-3-methylbenzyl)-2H-pyrazolo[4,3-c]pyridine-4-carboxamide;

2-hydroxy-2-methyl-N-(2-((4-methyl-5-(3,3,3-trifluoropropoxy)pyridin-2-yl)methyl)-2H-pyrazolo[4,3-c]pyridin-4-yl)propanamide;

N-ethyl-2-(1-(4-methyl-5-(2,2,2-trifluoroethoxy)pyridin-2-yl)ethyl)-2H-pyrazolo[4,3-c]pyridine-4-carboxamide;

N-(2-acetamidoethyl)-2-((6-(2,2-difluoropropoxy)-5-methylpyridin-3-yl)methyl)-2H-pyrazolo[4,3-c]pyridine-4-carboxamide;

N-(2-(1-(4-methyl-5-(2,2,2-trifluoroethoxy)pyridin-2-yl)ethyl)-2H-pyrazolo[4,3-c]pyridin-4-yl)isobutyramide;

2-((5-chloro-6-(cyclopropylmethoxy)pyridin-3-yl)methyl)-N-methyl-2H-pyrazolo[4,3-c]pyridine-4-carboxamide;

2-((5-chloro-6-(cyclopropylmethoxy)pyridin-3-yl)methyl)-N-ethyl-2H-pyrazolo[4,3-c]pyridine-4-carboxamide;

2-((5-chloro-6-(cyclopropylmethoxy)pyridin-3-yl)methyl)-N-isopropyl-2H-pyrazolo[4,3-c]pyridine-4-carboxamide;

2-((5-chloro-6-(cyclopropylmethoxy)pyridin-3-yl)methyl)-N-(2-hydroxyethyl)-2H-pyrazolo[4,3-c]pyridine-4-carboxamide;

2-((5-chloro-6-(cyclopropylmethoxy)pyridin-3-yl)methyl)-N-(3-hydroxypropyl)-2H-pyrazolo[4,3-c]pyridine-4-carboxamide;

2-((6-((4-fluorobenzyl)oxy)-5-methylpyridin-3-yl)methyl)-N-(2-hydroxyethyl)-2H-pyrazolo[4,3-c]pyridine-4-carboxamide;

N-(2-((6-cyclobutoxy-5-methylpyridin-3-yl)methyl)-2H-pyrazolo[4,3-c]pyridin-4-yl)-2-hydroxy-2-methylpropanamide;

2-((6-cyclobutoxy-5-methylpyridin-3-yl)methyl)-N-ethyl-2H-pyrazolo[4,3-c]pyridine-4-carboxamide;

N-(2-acetamidoethyl)-2-((6-cyclobutoxy-5-methylpyridin-3-yl)methyl)-2H-pyrazolo[4,3-c]pyridine-4-carboxamide;

2-((6-cyclobutoxy-5-methylpyridin-3-yl)methyl)-N-isopropyl-2H-pyrazolo[4,3-c]pyridine-4-carboxamide;

2-((6-cyclobutoxy-5-methylpyridin-3-yl)methyl)-N-(2-hydroxyethyl)-2H-pyrazolo[4,3-c]pyridine-4-carboxamide;

2-((6-cyclobutoxy-5-methylpyridin-3-yl)methyl)-N-(3-hydroxypropyl)-2H-pyrazolo[4,3-c]pyridine-4-carboxamide;

N-(2-((5-(cyclopropylmethoxy)-4-methylpyridin-2-yl)methyl)-2H-pyrazolo[4,3-c]pyridin-4-yl)-2-hydroxy-2-methylpropanamide;

2-((5-(cyclopropylmethoxy)-4-methylpyridin-2-yl)methyl)-N-ethyl-2H-pyrazolo[4,3-c]pyridine-4-carboxamide;

2-((5-(cyclopropylmethoxy)-4-methylpyridin-2-yl)methyl)-N-isopropyl-2H-pyrazolo[4,3-c]pyridine-4-carboxamide;

2-((5-(cyclopropylmethoxy)-4-methylpyridin-2-yl)methyl)-N-(2-hydroxyethyl)-2H-pyrazolo[4,3-c]pyridine-4-carboxamide;

2-((5-(cyclopropylmethoxy)-4-methylpyridin-2-yl)methyl)-N-(3-hydroxypropyl)-2H-pyrazolo[4,3-c]pyridine-4-carboxamide;

N-methyl-2-((5-methyl-6-(2,2,3,3-tetrafluoropropoxy)pyridazin-3-yl)methyl)-2H-pyrazolo[4,3-c]pyridine-4-carboxamide;

N-ethyl-2-((5-methyl-6-(2,2,3,3-tetrafluoropropoxy)pyridazin-3-yl)methyl)-2H-pyrazolo[4,3-c]pyridine-4-carboxamide;

N-(3-hydroxypropyl)-2-((5-methyl-6-(2,2,3,3-tetrafluoropropoxy)pyridazin-3-yl)methyl)-2H-pyrazolo[4,3-c]pyridine-4-carboxamide;

N-(2-((5-(2,2-difluoropropoxy)-4-methylpyridin-2-yl)methyl)-2H-pyrazolo[4,3-c]pyridin-4-yl)isobutyramide;

2-((5-(2,2-difluoropropoxy)-4-methylpyridin-2-yl)methyl)-N-methyl-2H-pyrazolo[4,3-c]pyridine-4-carboxamide;

2-((5-(2,2-difluoropropoxy)-4-methylpyridin-2-yl)methyl)-N-ethyl-2H-pyrazolo[4,3-c]pyridine-4-carboxamide;

2-((5-(2,2-difluoropropoxy)-4-methylpyridin-2-yl)methyl)-N-isopropyl-2H-pyrazolo[4,3-c]pyridine-4-carboxamide;

2-((5-(2,2-difluoropropoxy)-4-methylpyridin-2-yl)methyl)-N-(2-hydroxyethyl)-2H-pyrazolo[4,3-c]pyridine-4-carboxamide;

2-((5-(2,2-difluoropropoxy)-4-methylpyridin-2-yl)methyl)-N-(3-hydroxypropyl)-2H-pyrazolo[4,3-c]pyridine-4-carboxamide;

N-(2-cyanoethyl)-2-((6-(2,2-difluoropropoxy)-5-methylpyridin-3-yl)methyl)-2H-pyrazolo[4,3-c]pyridine-4-carboxamide;

2-(4-(2,2-difluoropropoxy)-3-methylbenzyl)-N-methyl-2H-pyrazolo[4,3-c]pyridine-4-carboxamide;

2-(4-(2,2-difluoropropoxy)-3-methylbenzyl)-N-ethyl-2H-pyrazolo[4,3-c]pyridine-4-carboxamide;

2-(4-(2,2-difluoropropoxy)-3-methylbenzyl)-N-isopropyl-2H-pyrazolo[4,3-c]pyridine-4-carboxamide;

2-(4-(2,2-difluoropropoxy)-3-methylbenzyl)-N-(2-hydroxyethyl)-2H-pyrazolo[4,3-c]pyridine-4-carboxamide;

2-(4-(2,2-difluoropropoxy)-3-methylbenzyl)-N-(3-hydroxypropyl)-2H-pyrazolo[4,3-c]pyridine-4-carboxamide;

(R)-2-(4-(2,2-difluoroethoxy)-3-methylbenzyl)-N-(2-hydroxypropyl)-2H-pyrazolo[4,3-c]pyridine-4-carboxamide;

2-(1-(4-(2,2-difluoroethoxy)-3-methylphenyl)ethyl)-N-((R)-2-hydroxypropyl)-2H-pyrazolo[4,3-c]pyridine-4-carboxamide;

(R)-2-(4-(2,2-difluoroethoxy)-3,5-dimethylbenzyl)-N-(2-hydroxypropyl)-2H-pyrazolo[4,3-c]pyridine-4-carboxamide;

2-(1-(4-(2,2-difluoropropoxy)-3-methylphenyl)ethyl)-N-((R)-2-hydroxypropyl)-2H-pyrazolo[4,3-c]pyridine-4-carboxamide;

(S)-2-(4-(2,2-difluoropropoxy)-3-methylbenzyl)-N-(2-hydroxypropyl)-2H-pyrazolo[4,3-c]pyridine-4-carboxamide;

(R)-2-(4-(2,2-difluoropropoxy)-3-methylbenzyl)-N-(2-hydroxypropyl)-2H-pyrazolo[4,3-c]pyridine-4-carboxamide;

2-(1-(4-(2,2-difluoroethoxy)-3-methylphenyl)ethyl)-N-((S)-2-hydroxypropyl)-2H-pyrazolo[4,3-c]pyridine-4-carboxamide;

(S)-2-(4-(2,2-difluoroethoxy)-3,5-dimethylbenzyl)-N-(2-hydroxypropyl)-2H-pyrazolo[4,3-c]pyridine-4-carboxamide;

2-(1-(4-(2,2-difluoropropoxy)-3-methylphenyl)ethyl)-N-((S)-2-hydroxypropyl)-2H-pyrazolo[4,3-c]pyridine-4-carboxamide;

(R)-2-(1-(4-(2,2-difluoroethoxy)-3-methylphenyl)ethyl)-N-(2-hydroxyethyl)-2H-pyrazolo[4,3-c]pyridine-4-carboxamide;

2-(4-(2,2-difluoroethoxy)-3,5-dimethylbenzyl)-N-(2-hydroxyethyl)-2H-pyrazolo[4,3-c]pyridine-4-carboxamide;

2-(1-(4-(2,2-difluoropropoxy)-3-methylphenyl)ethyl)-N-(2-hydroxyethyl)-2H-pyrazolo[4,3-c]pyridine-4-carboxamide;

2-(1-(4-(2,2-difluoroethoxy)-3-methylphenyl)ethyl)-N-(3-hydroxypropyl)-2H-pyrazolo[4,3-c]pyridine-4-carboxamide;

2-(4-(2,2-difluoroethoxy)-3,5-dimethylbenzyl)-N-(3-hydroxypropyl)-2H-pyrazolo[4,3-c]pyridine-4-carboxamide;

2-(1-(4-(2,2-difluoropropoxy)-3-methylphenyl)ethyl)-N-(3-hydroxypropyl)-2H-pyrazolo[4,3-c]pyridine-4-carboxamide;

2-(4-(2,2-difluoropropoxy)-3-methylbenzyl)-2H-pyrazolo[4,3-c]pyridine-4-carboxamide;

2-(4-(difluoromethoxy)-3-methylbenzyl)-N-(3-hydroxypropyl)-2H-pyrazolo[4,3-c]pyridine-4-carboxamide;

and 2-(4-(difluoromethoxy)-3-methylbenzyl)-N-isopropyl-2H-pyrazolo[4,3-c]pyridine-4-carboxamide;

or a prodrug thereof or a pharmaceutically acceptable salt thereof.

[9] The present invention provides a pharmaceutical composition comprising a compound or a prodrug thereof or a pharmaceutically acceptable salt thereof, as described in any one of [1] to [8], and a pharmaceutically acceptable carrier.

[10] The present invention provides the pharmaceutical composition as described in [9], further comprising another pharmacologically active agent.

[11] The present invention provides a method for the treatment of a condition or disorder in which TTX-S channel blockers are involved, in an animal, including a human, which comprises administering to the animal in need of such treatment a therapeutically effective amount of a compound or a prodrug thereof or a pharmaceutically acceptable salt thereof, as described in any one of [1] to [8].

[12] The present invention provides the method as described in [11], wherein said condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia; and combinations thereof.

[13] The present invention provides a use of a compound described in any one of [1] to [8] or a pharmaceutically acceptable salt, prodrug, solvate or composition thereof for the manufacture of a medicament for the treatment of a condition or disorder in which TTX-S channel blockers are involved.

[14] The present invention provides the use as described in [13], wherein said condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder, causalgia, and chemo-induced pain;

and combinations thereof.

[15] The present invention provides a compound described in any one of [1] to [8] or a prodrug or a pharmaceutically acceptable salt for use in the treatment of a condition or disorder in which TTX-S channel blockers are involved.

[16] The present invention provides a process for preparing a pharmaceutical composition comprising mixing a compound described in any one of [1] to [8] or a prodrug thereof or a pharmaceutically acceptable salt thereof and a pharmaceutically acceptable carrier or excipient.

Advantageous Effects of Invention

The pyrazolopyridine derivatives of the present invention are sodium channel blockers and have a number of therapeutic applications, particularly in the treatment of pain.

More particularly, the pyrazolopyridine derivatives of the invention are selective tetrodotoxin-sensitive (TTX-S) blockers. In the discussion that follows, the invention is exemplified by reference to the inhibition of $Na_{V1.3}$ or $Na_{V1.7}$ channel as the TTX-S channels.

They show the affinity for $Na_{V1.3}$ or $Na_{V1.7}$ channel which is significantly greater than their affinity for $Na_{V1.5}$ channel as the tetrodotoxin-resistant (TTX-R) sodium channels.

The pyrazolopyridine derivatives of the invention show good selectivity for the $Na_{V1.3}$ or $Na_{V1.7}$ channel as compared with $Na_{V1.5}$ channel.

In particular, the pyrazolopyridine derivatives of the present invention are selective for the TTX-S channels over the $Na_{V1.5}$ channel, leading to improvements in the side-effect profile.

The pyrazolopyridine derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back pain, orofacial pain and chemo-induced pain.

Other conditions that may be treated with the pyrazolopyridine derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

DESCRIPTION OF EMBODIMENTS

Examples of conditions or disorders mediated by TTX-S channels include, but are not limited to, TTX-S channels related diseases. The compounds of the present invention show the TTX-S channels blocking activity. The compounds of the present invention may show less toxicity, good absorption and distribution, good solubility, less protein binding affinity other than TTX-S channels, less drug-drug interaction, good metabolic stability, reduced inhibitory activity at HERG channel, and/or reduced QT prolongation.

As appreciated by those of skill in the art, "halogen" or "halo" as used herein is intended to include fluoro, chloro, bromo and iodo. Similarly, 1-6, as in $C_{1-6}$ is defined to identify the number as having 1, 2, 3, 4, 5 or 6. According to the definition, for example, $C_{1-6}$, as in $C_{1-6}$ alkyl is defined to identify the alkyl group as having 1, 2, 3, 4, 5 or 6 carbons. Similarly, $C_{2-6}$ alkenyl is defined to identify the alkenyl group as having 2, 3, 4, 5 or 6 carbons. A group which is designated as being independently substituted with substituents may be independently substituted with multiple numbers of such substituents.

The term "alkyl", as used herein, means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

The term "alkoxy", as used herein, means an —O-alkyl such as, but not limited to, methoxy, ethoxy, propoxy, or 2-propoxy, butoxy (including all isomeric forms), and the like.

The term "alkylthio", as used herein, means a —S-alkyl such as, but not limited to, methylthio, ethylthio, and the like.

The term "alkylamino", as used herein, means a —NH-alkyl such as, but not limited to, methylamino, ethylamino, propylamino, 2-propylamino, and the like.

The term "alkenyl", as used herein, means a hydrocarbon radical having at least one double bond, which may be in a E- or a Z-arrangement, including, but not limited to, ethenyl, propenyl, 1-butenyl, 2-butenyl and the like.

The term "cycloalkyl", as used herein, means a mono- or bicyclic ring such as, but not limited to, cyclopropyl, cyclobutyl, cyclopentyl, cyclohexyl, cycloheptyl, norboranyl, adamantyl groups, and the like.

The term "alkylene", as used herein, means a linear saturated divalent hydrocarbon radical of one to six carbon atoms or a branched saturated divalent hydrocarbon radical of three to six carbon atoms unless otherwise stated, e.g., but not limited to, methylene, ethylene, propylene, 1-methylpropylene, 2-methylpropylene, butylene, pentylene, and the like.

The term "cycloalkylene", as used herein, means a mono- or bicyclic ring such as, but not limited to, cyclopropylene, cyclobutylene, cyclopentylene, cyclohexylene, cycloheptylene, and the like.

The term "aryl", as used herein, means mono- or bi-carbocyclic or mono- or bi-heterocyclic ring which may contain 0-4 heteroatoms selected from O, N and S such as, but not limited to, phenyl, naphthyl, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, phthalazyl, pyrazolopyridyl, pyrazolopyrimidinyl, pyrazolyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof.

The term "heterocyclyl" as used herein includes both unsaturated and saturated heterocyclic moieties, wherein the unsaturated heterocyclic moieties (i.e. "heteroaryl") include, but not limited to, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof, and wherein the saturated heterocyclic moieties include, but not limited to, azetidinyl, 1,4-dioxanyl, hexahydroazepinyl, piperazinyl, piperidinyl, pyridin-2-onyl, pyrrolidinyl, morpholinyl, tetrahydrofuranyl, tetrahydropyranyl, thiomorpholinyl, triazolopyrimidyl, tetrahydrothienyl, pyrrolidinonyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, and N-oxides thereof and S-oxides thereof.

The term "$C_0$", as used herein, means direct bond.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 2007).

The terms "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder".

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

Compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g., but not limited to, hydrochloric, hydrobromic, sulfuric, nitric or phosphoric acid; and organic acids e.g., but not limited to, succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases such as choline, arginine, benzathine, diethylamine, glycine, lysine, meglumine, olamine, 2-amino-2-methylpropan-1-ol, benethamine, tert-butylamine, epolamine, ethylenediamine, hydrabamine, morpholine, piperazine, procaine, triethanolamine, diethanolamine, monoethanolamine, triisopropanolamine, and tromethamine.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formula (I) contains an amino group, a pyrazolopyridine derivative prepared by reacting with a suitable acid halide or a suitable acid anhydride is exemplified as a prodrug. A particularly preferred pyrazolopyridine derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Compounds of formula (I) and salts thereof may be prepared in crystalline or noncrystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Compounds of formula (I) may have polymorphs in crystalline form, which are within the scope of the present invention.

Additionally, compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be one or more chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{2}H$, $^{3}H$, $^{11}C$, $^{13}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{123}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as increased metabolic stability, enhanced oral bioavailability or absorption, and/or decreased drug-drug interactions.

The compounds of formula (I), being $Na_{V1.3}$ and/or $Na_{V1.7}$ channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strain-ssprains, burns, myocardial infarction and acute pancreatitis, post-operative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central poststroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

(i) pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

(ii) heart and vascular pain, including pain caused by angina, myocardial infarction, mitral stenosis, pericarditis, Raynaud's phenomenon, scleredoma and skeletal muscle ischemia;

(iii) head pain, such as migraine (including migraine with aura and migraine without aura), cluster headache, tension-type headache mixed headache and headache associated with vascular disorders; and (vi) orofacial pain, including dental pain, otic pain, burning mouth syndrome and temporomandibular myofascial pain.

Compounds of formula (I) are also expected to be useful in the treatment of multiple sclerosis.

The invention also relates to therapeutic use of compounds of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder, causalgia, and chemo-induced pain.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a prodrug thereof or a pharmaceutically acceptable salt or solvate thereof, as defined above, may be administered simultaneously, sequentially or separately in combination with one or more agents selected from

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine; —a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex™, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g. oxybutynin, tolterodine, propiverine, trospium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion™ or sarizotan;
- a vanilloid receptor agonist (e.g. resiniferatoxin) or antagonist (e.g. capsazepine);
- a transient receptor potential cation channel subtype (V1, V2, V3, V4, M8, M2, A1) agonist or antagonist;
- a beta-adrenergic such as propranolol;
- a local anaesthetic such as mexiletine;
- a corticosteroid such as dexamethasone;
- a 5-HT receptor agonist or antagonist, particularly a 5-HT1B1D agonist such as eletriptan, sumatriptan, naratriptan, zolmitriptan or rizatriptan;
- a 5-HT2A receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol™;

- a PDEV inhibitor, such as 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino[2',1':6,1] pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
- an alpha-2-delta ligand such as gabapentin, pregabalin, 3-methylgabapentin, (3-(aminomethyl)bicyclo[3.2.0] hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl) cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, and (3R,4R,5R)-3-amino-4,5-dimethyloctanoic acid;
a cannabinoid;
a metabotropic glutamate subtype 1 receptor (mGluR1) antagonist;
a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
a noradrenaline (norepinephrine) reuptake inhibitor, such as maprotiline, lofepramine, mirtazapine, oxaprotiline, fezolamine, tomoxetine, mianserin, buproprion, buproprion metabolite hydroxybuproprion, nomifensine and viloxazine (Vivalan™) especially a selective noradrenaline reuptake inhibitor such as reboxetine, in particular (S,S)-reboxetine;
a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;
an acetylcholinesterase inhibitor such as donepezil;
a prostaglandin E2 subtype 4 (EP4) antagonist such as N-[({2-[4-(2-ethyl-4,6-dimethyl-1H-imidazo[4,5-c] pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;
a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,
a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);
a sodium channel blocker, such as lidocaine;
a calcium channel blocker, such as ziconotide, zonisamide, mibefradil;
a 5-HT3 antagonist, such as ondansetron;
a chemotherapy drug such as oxaliplatin, 5-fluorouracil, leukovolin, paclitaxel;
a calcitonin gene related peptide (CGRP) antagonist;
a bradykinin (BK1 and BK2) antagonist;
a voltage gated sodium dependent channel blocker ($Na_{V1.3}$, $Na_{V1.7}$, $Na_{V1.8}$);
a voltage dependent calcium channel blocker (N-type, T-type);
a P2X (ion channel type ATP receptor) antagonist;
an acid-sensing ion channel (ASIC1a, ASIC3) antagonist;
an Angiotensin AT2 antagonist;
a Chemokine CCR2B receptor antagonist;
a Cathepsin (B, S, K) inhibitor;
a sigma1 receptor agonist or antagonist;
and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formula (I) or pharmaceutically acceptable salts thereof may also be formulated in rectal compositions such as suppositories or retention enemas, e.g. containing conventional suppository bases such as cocoa butter or other glycerides.

Compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:
DCM Dichloromethane
DMF N,N-Dimethylformamide
DMA N,N-Dimethylacetamide
DME 1,2-DimethoxyethaneDMSO Dimethyl sulfoxide
EDC 1-Ethyl-3-(3-dimethylaminopropyl)carbodiimide Hydrochloride
e.e. Enantiomeric Excess
ESI Electrospray Ionization
EtOAc Ethyl acetate
EtOH Ethanol
HOBT 1-Hydroxybenztriazole
HBTU O-(Benzotriazol-1-yl)-N,N,N',N'-tetramethyluronium Hexafluorophosphate
HPLC High-Performance Liquid Chromatography
LC Liquid Chromatography
LG Leaving Group
tR Retention Time
MeCN Acetonitrile
MeOH Methanol
MHz Megahertz
MS Mass Spectrometry
NMR Nuclear Magnetic Resonance
PG Protecting Group
rt Room Temperature
TFA Trifluoroacetic Acid
THF Tetrahydrofuran
TLC Thin Layer Chromatography
UV Ultraviolet The term of "base" is likewise no particular restriction on the nature of the bases used, and any base commonly used in reactions of this type may equally be used here. Examples of such bases include, but not limited to: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo [5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18-25° C.; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography is carried out using Merck silica gel 60 (230-400 mesh ASTM), Fuji Silysia Chromatorex (registered trade mark) DU3050 (Amino Type), Wako Wakogel C300-HG, Biotage silica KP-Sil, Yamazen Hi-FLASH column, YMC DispoPack-SIL, or Biotage amino bounded silica KP-NH. The purification of compounds using HPLC (preparative LC-MS) is performed by the following apparatus and conditions.

Apparatus; Waters MS-trigger AutoPurification(trademark) system

Column; Waters XTerra C18, 19×50 mm, 5 micrometer particle

Condition A: Methanol or acetonitrile/0.01%(vv) ammonia aqueous solution

Condition B: Methanol or acetonitrile/0.05%(vv) formic acid aqueous solution

Low-resolution mass spectral data (ESI) are obtained by the following apparatus and conditions: Apparatus; Waters Alliance HPLC system on ZQ or ZMD mass spectrometer and UV detector. NMR data are determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L(liter(s)), mL (milliliter(s)), g (gram(s)), mg(milligram(s)), mol (moles), mmol (millimoles).

Each prepared compound is generally named by ChemBioDraw (Ultra, version 12.0, CambridgeSoft).

Conditions for determining HPLC retention time:
Method: QC1
Apparatus: Waters ACQUITY Ultra Parformance LC with TUV Detector and ZQ mass spectrometer
Column: Waters ACQUITY C18, 2.1×100 mm, 1.7 micrometer particle size
Column Temperature: 60° C.
Flow rate: 0.7 mL/min
Run time: 3 min
UV detection: 210 nm
MS detection: ESI positive/negative mode
Mobile phases:
A1: 10 mM Ammonium acetate
B1: acetonitrile
Gradient program: (QC_neutral_full_3 min)

TABLE 1

| Time (min) | A1 (%) | B1 (%) |
|---|---|---|
| 0 | 95 | 5 |
| 0.1 | 95 | 5 |
| 1.8 | 5 | 95 |
| 2.3 | 95 | 5 |

Method: QC2
Apparatus: Waters 2795 Alliance HPLC with ZQ2000 mass spectrometer and 2996 PDA Detector
Column: XBridge C18, 2.1×50 mm, 3.5 micrometer particle size
Column Temperature: 45° C.
Flow rate: 1.2 mL/min
Run time: 4.5 min
UV detection: 210-400 nm scan
MS detection: ESI positive/negative mode
Mobile phases:
A: Water
B: MeCN
C: 1% aqueous HCOOH solution
D: 1% aqueous $NH_3$ solution
Gradient Program:

TABLE 2

| Time (min) | A (%) | B (%) | C (%) | D (%) |
|---|---|---|---|---|
| 0 | 85 | 10 | 2.5 | 2.5 |
| 0.2 | 85 | 10 | 2.5 | 2.5 |
| 3.2 | 0 | 95 | 2.5 | 2.5 |
| 3.7 | 0 | 95 | 2.5 | 2.5 |
| 3.71 | 85 | 10 | 2.5 | 2.5 |
| 4.5 | 85 | 10 | 2.5 | 2.5 |

All of the pyrazolopyridine derivatives of the formula (I) can be prepared by the procedures described in the general methods presented below or by the specific methods described in the Example synthesis part and Intermediate synthesis part, or by routine modifications thereof. The present invention also encompasses any one or more of these processes for preparing the pyrazolopyridine derivatives of formula (I), in addition to any novel intermediates used therein.

In the following general methods, descriptors are as previously defined for the pyrazolopyridine derivatives of the formula (I) unless otherwise stated.

<Scheme A>

[Chem.4]

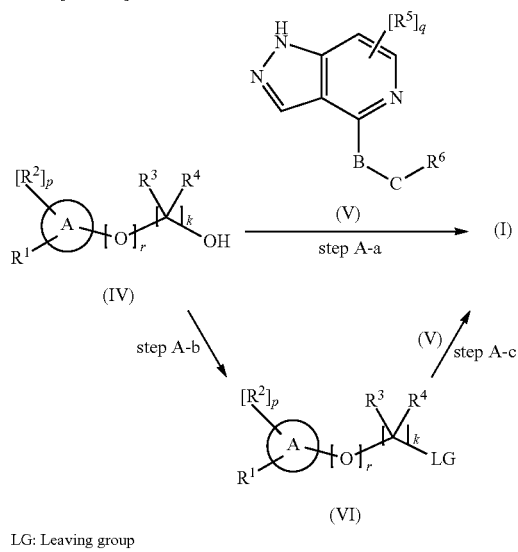

LG: Leaving group

In Step A-a, a compound of formula (I) can be prepared from a compound of formula (IV) by Mitsunobu reaction with a compound of formula (V) using a suitable reagent in organic solvent in the presence of coupling reagent, but not limited to, such as diethyl azodicarboxylate triphenylphosphine, diisopropyl azodicarboxylate triphenylphosphine, di-ter-butyl azodicarboxylate triphenylphosphine, and cyanomethylenetributylphosphorane. Examples of suitable organic solvent include such as THF, 1,4-dioxane, DMF, MeCN, and toluene. The reaction can be carried out at a temperature of from about −20 to 180° C., more preferably from about 20 to 150° C. Reaction times are, in general, from about 30 minutes to 48 hours, more preferably from about 30 minutes to 24 hours.

When LG is such as O-trifluoromethanesulfonate, O-tosylate, O-mesylate, iodide, bromide, and chloride, in Step A-b, a compound of formula (VI) can be prepared by sulfonylation or substitution with halogen of a compound of formula (IV) under, for example, known sulfonylation condition or known halogenation conditions in an inert solvent. In case of sulfonylation, the reaction can be carried out in the presence of a base in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as TEA, tributylamine, diisopropylethylamine, 2,6-lutidine, pyridine or dimethylaminopyridine. Examples of suitable inert aqueous or non-aqueous organic solvents include: alcohols, such as methanol or ethanol; ethers, such as THF or 1,4-dioxane; acetone; DMF; halogenated hydrocarbons, such as DCM, 1,2-dichloroethane or chloroform; and pyridine; or mixtures thereof. The reaction can be carried out at a temperature in the range of from about −10° C. to 200° C., preferably in the range of from about 20 to 100° C. Reaction times are, in general, from about 10 minutes to 4 days, preferably from about 10 minutes to 24 hours. In case of halogenation, example of halogen source is such as thionyl chloride, N-bromosuccinimide, N-chlorosuccinimide, iodine, bromine, phosphorous trichloride, phosphorous tribromide, carbon tetrachloride, or carbon tetrabromide. In the halogenation reaction, the reaction can be carried out in the presence of reducing agent such as triphenylphosphine. Examples of suitable organic solvent include such as THF, 1,4-dioxane, DCM, 1,2-dichloroethane, carbon tetrachloride, toluene, and DMF.

In Step A-c, a compound of formula (I) can be prepared from a compound of formula (VI) and formula (V) in the presence of a suitable base in an inert solvent. Examples of a suitable base include, but not limited to, such as sodium hydride, potassium carbonate, potassium bicarbonate, cesium carbonate, sodium carbonate, sodium bicarbonate, tripotassium phosphate, potassium tert-butoxide, triethylamine, N,N-diisopropylethylamine, and dicyclohexylamine. Examples of suitable organic solvent include such as THF, 1,4-dioxane, DMF, MeCN, DMA, and toluene. The reaction can be carried out at a temperature of from about −20 to 150° C., more preferably from about 0 to 100° C. Reaction times are, in general, from about 30 minutes to 48 hours, more preferably from about 30 minutes to 24 hours.

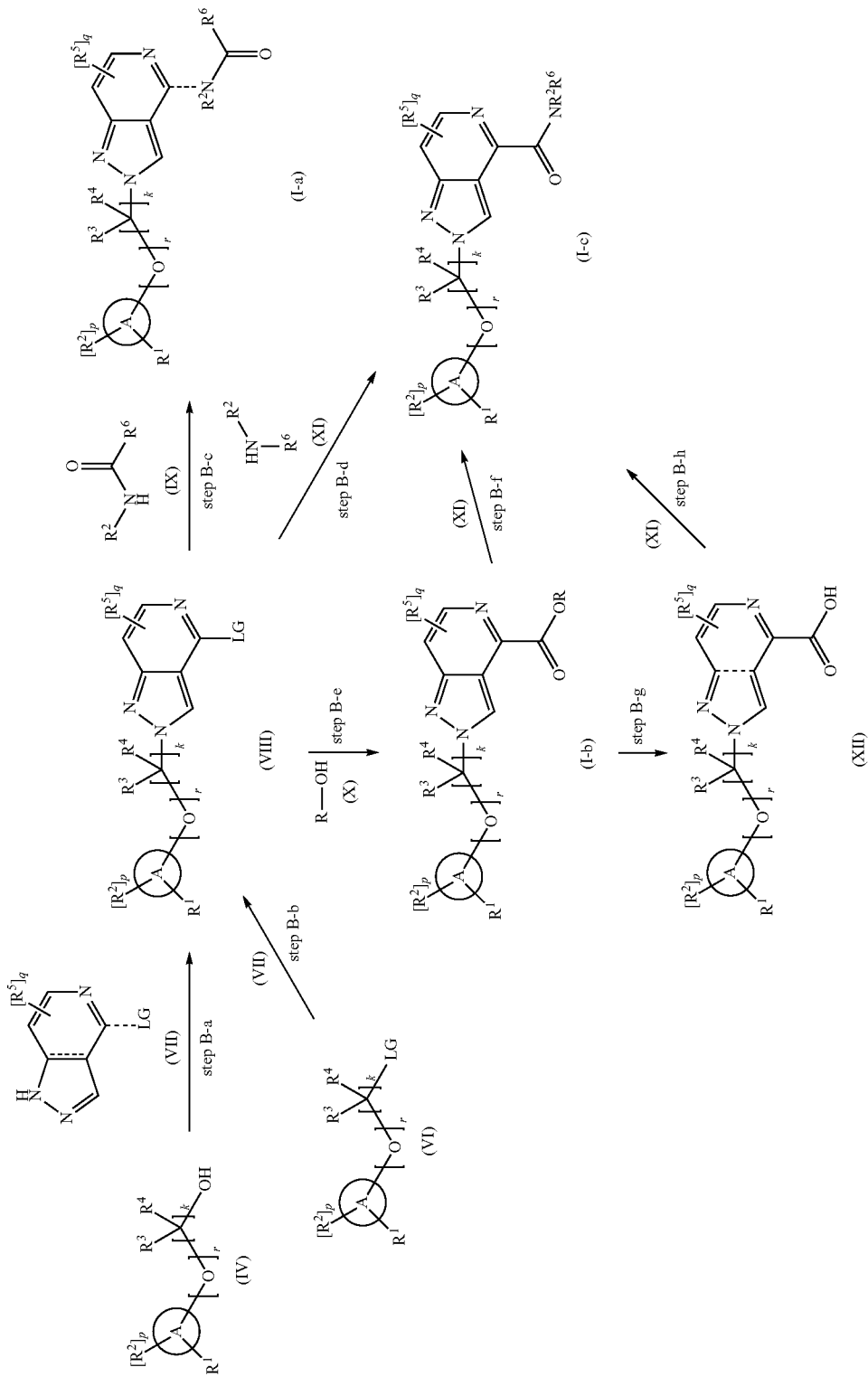

In Step B-a, a compound of formula (VIII) can be prepared from a compound of formula (IV) and a compound of formula (VII) by Mitsunobu reaction as described in Step A-a.

In Step B-b, a compound of formula (VIII) can be prepared from a compound of formula (VI) and a compound of formula (VII) as described in Step A-c.

When —B—C—$R^6$ component of formula (I) is —$NHR^2$—(C=O)—$R^6$, in Step B-c, a compound of (I-a) can be prepared by coupling of formula (VIII) with a suitable reagent of formula (IX) under coupling conditions in suitable organic solvents in the presence of a suitable transition metal catalyst and in the presence or absence of a base. Examples of suitable transition metal catalysts include, but not limited to: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper (II) chloride, copper(II) iodide, copper(II) oxide, copper(II) trifluoromethanesulfonate, palladium(II) acetate, palladium (II) chloride, bis(acetonitrile)dichloropalladium(II ), bis (dibenzylideneacetone)palladium(0), tris(dibenzylideneacetone)dipalladium(0) and [1,1'-bis(diphenylphosphino) ferrocene]palladium(II) dichloride. Preferred catalysts are tetrakis(triphenylphosphine)palladium(0), bis(triphenylphosphine)palladium(II) chloride, palladium(II) acetate, palladium(II) chloride, bis(acetonitrile)dichloropalladium (0), bis(dibenzylideneacetone)palladium(0), tris(dibenzylideneacetone)dipalladium(0) and [1,1-bis(diphenylphosphino)ferrocene]palladium(II) dichloride. Examples of suitable carboxamide represented by formula (IX) include, but not limited to, carboximides such as acetamide, propionamide, isobutyramide and cyclopropanecarboxamide. Examples of suitable organic solvent include: THF; 1,4-dioxane; DMF; MeCN; alcohols, such as methanol or ethanol; halogenated hydrocarbons, such as DCM, 1,2-dichloroethane, chloroform or carbon tetrachloride; and diethyl ether; in the presence or absence of base such as tripotassium phosphate, sodium bicarbonate, sodium cabonate or potassium carbonate. This reaction can be carried out in the presence of a suitable additive. Examples of such an additive include, but not limited to: 4,5-Bis(diphenylphosphino)-9, 9-dimethylxanthene, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, and triphenylarsine. The reaction can be carried out at a temperature of from about 50 to 200° C., more preferably from about 80 to 150° C. Reaction times are, in general, from about 5 minutes to 48 hours, more preferably from about 30 minutes to 24 hours. In an alternative case, the reaction can be carried out with microwave system. The reaction can be carried out at a temperature in the range from about 100 to 200° C., preferably in the range from about 120 to 180° C. Reaction times are, in general, from about 10 minutes to 3 hours, preferably from about 15 minutes to 1 hour.

When —B—C—$R^6$ component of formula (I) is —(C=O)—$NR^2R^6$, in Step B-d, a compound of (I-c) can be prepared from a compound of formula (VIII) and a compound of formula (XI) by CO insertion reaction in suitable organic solvents in the presence of suitable transition metal catalyst in the presence or absence of a base under carbon monoxide atmosphere. Example of suitable transition metal catalysts include, but not limited to: palladium metal, palladium-carbon, palladium(II) acetate, tris(dibenzylideneacetone)dipalladiumchloroform, [1,2-bis(diphenylphosphino) ethane]palladium dichloride, bis(tri-o-toluylphosphine) palladium dichloride, bis(triphenylphosphine)palladium dichloride, tetrakis(triphenylphosphine)palladium, dichloro [1,1'-bis(diphenylphosphino)ferrocene]palladium, or a catalyst produced in solution by adding a ligand into the reaction solution of these. The ligand added into the reaction solution may be a phosphoric ligand such as 1,1'-bis(diphenylphosphino)ferrocene, bis(2-diphenylphosphinophenyl)ether, 2,2'-bis(diphenylphosphino)-1,1'-binaphthol, 1,3-bis(diphenylphosphino)propane, 1,4-bis(diphenylphosphino)butane, tri-o-toluylphosphine, triphenylphosphine, 2-diphenylphosphino-2'-methoxy-1,1'-binaphthyl or 2,2-bis (diphenylphosphino)-1,1'-binaphthyl. Examples of suitable organic solvent include: THF; 1,4-dioxane; DMF; DMA; MeCN; toluene; halogenated hydrocarbons, such as DCM, 1,2-dichloroethane, chloroform or carbon tetrachloride; and diethyl ether; in the presence or absence of base such as triethylamine, N,N-diisopropylethylamine, tripotassium phosphate, sodium bicarbonate, sodium cabonate or potassium carbonate. This reaction can be carried out in the presence of a suitable additive agent. Examples of such additive agents include: 4,5-bis(diphenylphosphino)-9,9-dimethylxanthene, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, and triphenylarsine. The reaction can be carried out at a temperature of from about 50 to 200° C., more preferably from about 60 to 150° C. Reaction times are, in general, from about 5 minutes to 48 hours, more preferably from about 30 minutes to 24 hours. Instead of carbon monoxide, other carbon monoxide source such as molybdenumhexacarbonyl and DMFpotassium tert-butoxide can be employed.

In an alternative case, the reaction can be carried out with microwave system. The reaction can be carried out at a temperature in the range from about 100 to 200° C., preferably in the range from about 120 to 180° C. Reaction times are, in general, from about 10 minutes to 3 hours, preferably from about 15 minutes to 1 hour.

In Step B-e, a compound of formula (I-b) can be prepared from a compound of formula (VIII) and alcohol of formula (X) by CO insertion reaction as described in Step B-d. Alternatively, the reaction can be carried out with other carbon monoxide source such as phenyl formate triethylamine and molybdenum hexacarbonyl.

In Step B-f, a compound of formula (I-c) can be prepared from a compound of formula (I-b) and formula (XI) in suitable solvents. Examples of suitable solvents include, but not limited to: THF, 1,4-dioxane, DMF, MeCN, MeOH, EtOH, and water. The reaction can be carried out at a temperature of from about 0 to 200° C., more preferably from about 20 to 150° C. Reaction times are, in general, from about 5 minutes to 48 hours, more preferably from about 30 minutes to 24 hours.

In Step B-g, a compound of formula (XII) can be prepared by hydrolysis of the ester compound of formula (I-b). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, for example, but not limited to: water, alcohols such as methanol, ethanol, propanol, butanol, 2-methoxyethanol, and ethylene gylcol; ethers such as THF, DME, and 1,4-dioxane; amides such as DMF and hexamethylphospholic triamide; and sulfoxides such as DMSO. Preferred solvents are water, methanol, ethanol, propanol, THF, DME, 1,4-dioxane, DMF, and DMSO. This reaction can be carried out at a temperature in the range of from about 20 to 100° C. for from about 30 minutes to 24 hours.

In Step B-h, a compound of formula (I-c) can be prepared from a compound of formula (XII) by amidation with a compound of formula (XI) using a suitable condensation agent such as HBTU and EDC-HOBT, preferably under the presence of a base such as triethylamine and N,N-diisopropylethylamine in a suitable solvent such as DMF, DMA and DCM at a temperature of from about 5 to 60° C. for about 1-24 hours. In addition, a compound of formula (I-c) can be also prepared from a compound of formula (III) by amidation with an acid halide prepared from a compound of formula (XII) using thionyl chloride or oxalyl chloride, preferably under the presence of a base such as triethylamine, pyridine, and N,N-diisopropylethylamine in a suitable solvent such as DCM at a temperature of from about 5 to 40° C. for about 1-24 hours.

(IV) isopropoxide, titanium(IV) ethoxide, molecular sieves, magnesium sulfate, copper(II) sulfate, hydrochloric acid, acetic acid, p-toluenesulfonic acid, trifluoromethanesulfonic acid, and 10-camphorsulfonic acid. This reaction can be carried out at a temperature in the range of from about 0 to 150° C. for from about 30 minutes to 48 hours.

In Step C-b, a compound of formula (I) can be prepared from a compound of formula (XV) in a presence of a suitable reagent such as triethyl phosphite and iodobenzene diacetate in an inert solvent or without a solvent. A preferred solvent is selected from DMF, DMA, MeOH, EtOH, DCM, 1,2-dichloroethane, and toluene. This reaction can be carried out at a temperature in the range of from about 0 to 150° C. for from about 30 minutes to 48 hours.

In Step C-c, a compound of formula (XVII) can be prepared from a compound of formula (XIII) and a compound of formula (XVI) as described in Step C-a.

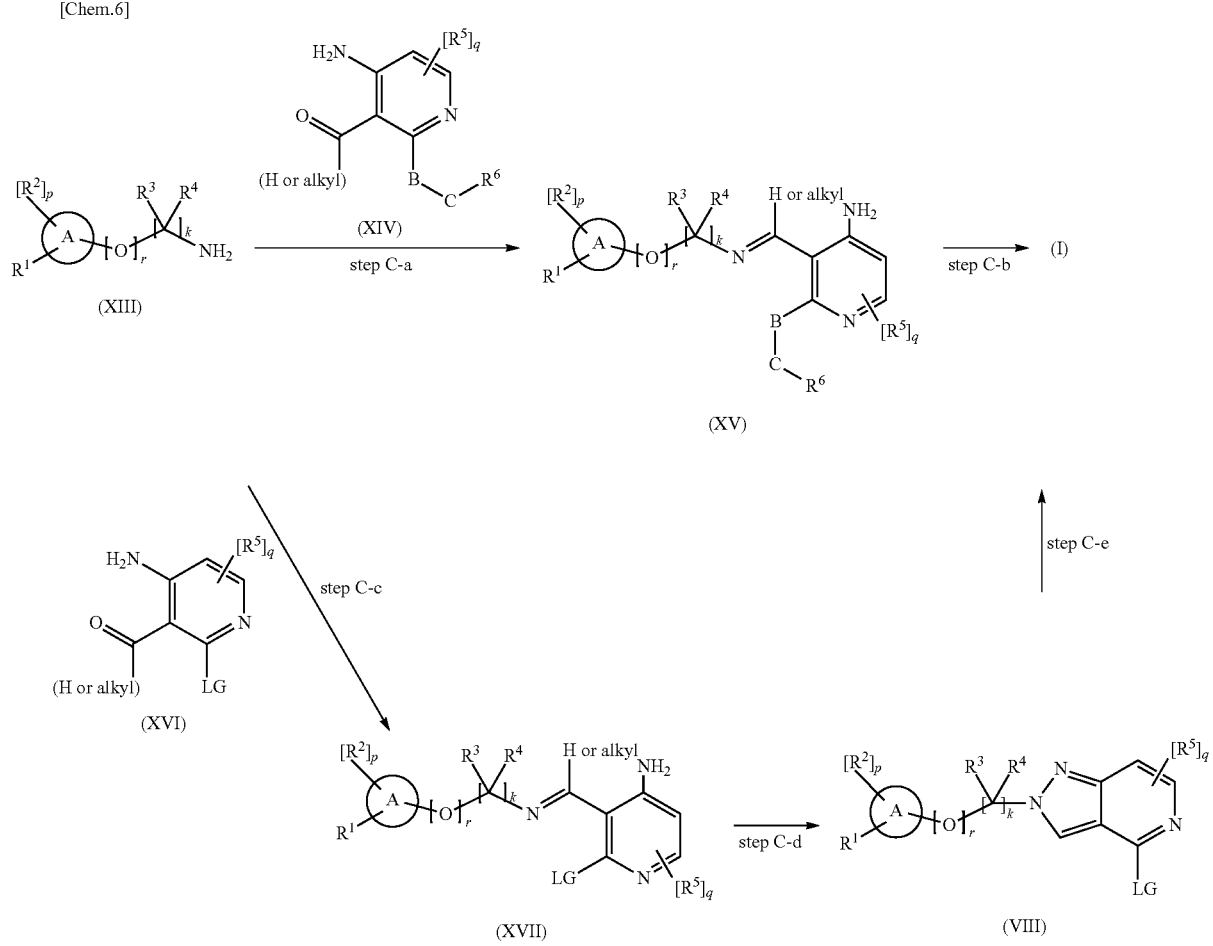

In Step C-a, a compound of formula (XV) can be prepared from amine of formula (XIII) and a compound of formula (XIV) in suitable solvents such as toluene, THF, dioxane, diethyl ether, DCM, 1,2-dichloroethane, chloroform, hexane, MeOH, and EtOH. The reaction can be carried out in a presence of a suitable additive reagent. Examples of such additive reagents include, but not limited to, titanium In Step C-d, a compound of formula (VIII) can be prepared from a compound of formula (XVII) as described in Step C-b.

In Step C-e, a compound of formula (I) can be prepared from a compound of formula (VIII) in a similar manner to B-c, B-d, B-e, B-f, B-g, and B-h in Scheme B.

<Scheme D>

[Chem.7]

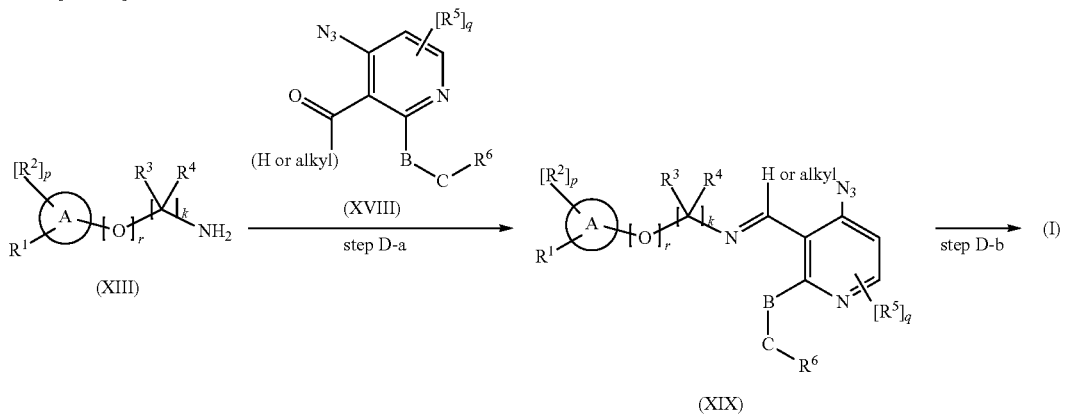

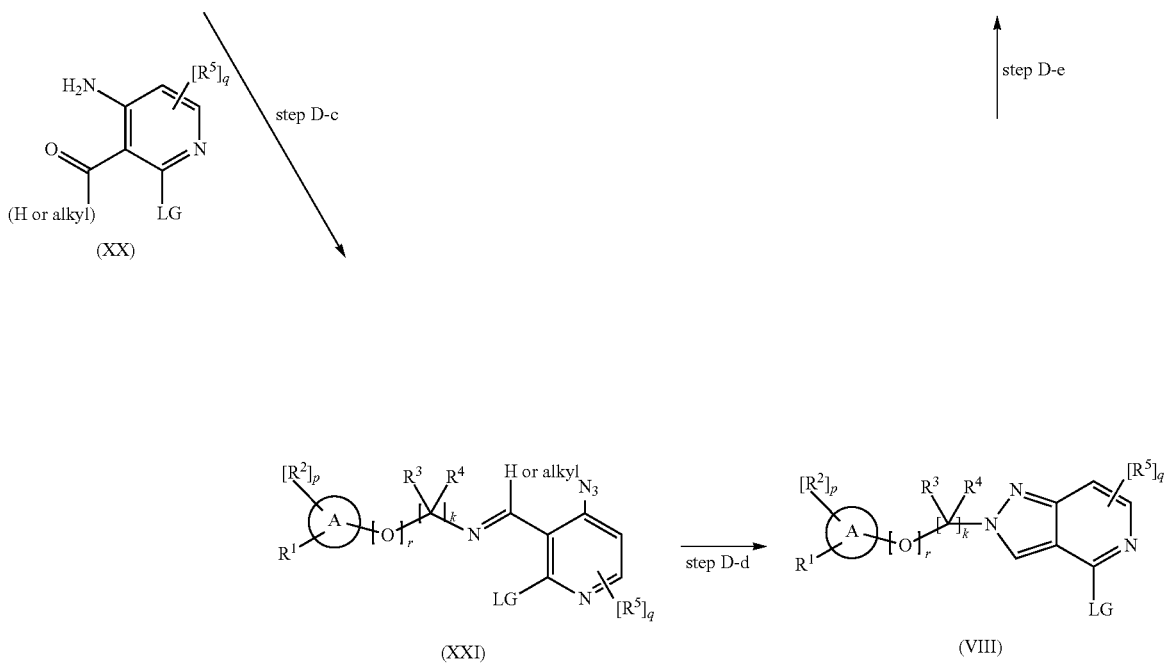

LG: Leaving group

In Step D-a, a compound of formula (XIX) can be prepared from a compound of formula (XIII) and a compound of formula (XVIII) as described in Step C-a.

In Step D-b, a compound of formula (I) can be prepared from a compound of formula (XIX) with or without a suitable additive in a suitable solvent. Examples of suitable additive include, but not limited to, such as copper(I) iodide/N,N,N',N'-tetramethylethylenediamine. Examples of a suitable solvent include, but not limited to, such as toluene, 1,2-dichlorobenzene, DMF, DMA, THF, 1,4-dioxane, DCM, and 1,2-dichloroethane. The reaction can be carried out at a temperature of from about 20 to 180° C. Reaction times are, in general, from about 30 minutes to 48 hours.

In Step D-c, a compound of formula (XXI) can be prepared from a compound of formula (XIII) and a compound of formula (XX) as described in Step C-a.

In Step D-d, a compound of formula (VIII) can be prepared from a compound of formula (XXI) as described in Step D-b.

In Step D-e, a compound of formula (I) can be prepared from a compound of formula (VIII) in a similar manner to B-c, B-d, B-e, B-f, B-g, and B-h in Scheme B.

Scheme E

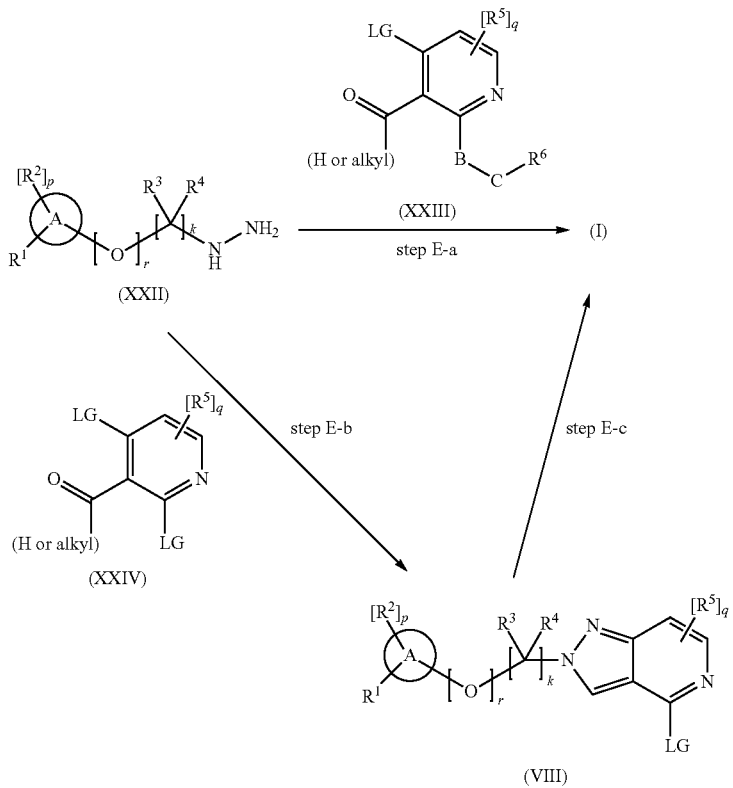

LG: Leaving group

In Step E-a, a compound of formula (I) can be prepared from a compound of formula (XXII) and a compound of formula (XXIII) in a suitable organic solvent. Examples of suitable organic solvent include, but not limited to, such as MeOH, EtOH, toluene, THF, 1,4-dioxane, DMF, MeCN, 1,2-dichloroethane, and toluene. The reaction can be carried out at a temperature of from about 20 to 180° C., more preferably from about 50 to 150° C. Reaction times are, in general, from about 30 minutes to 48 hours, more preferably from about 30 minutes to 24 hours.

In Step E-b, a compound of formula (VIII) can be prepared from a compound of formula (XXII) and a compound of formula (XXIV) as described in Step E-a.

In Step E-c, a compound of formula (I) can be prepared from a compound of formula (VIII) in a similar manner to B-c, B-d, B-e, B-f, B-g, and B-h in Scheme B.

The key intermediate amines of formula (XIII) can be prepared by the following general synthetic route of Scheme F and G.

Scheme F

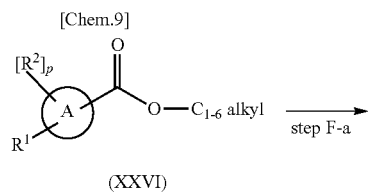

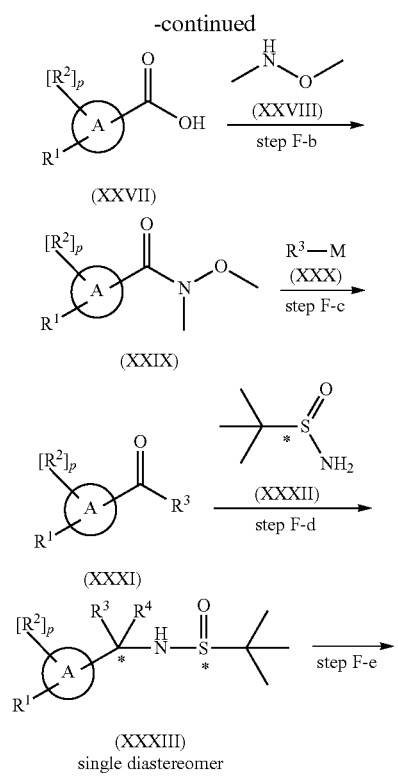

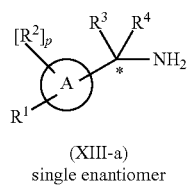

(XIII-a)
single enantiomer

*chiral

When —(O)$_r$—(CR$^3$R$^4$)$_k$—NH$_2$ component of formula (XIII) is —(CR$^3$R$^4$)—NH$_2$, a compound of formula (XIII-a) can be prepared according to Scheme F and G.

In Step F-a, a compound of formula (XXVII) can be prepared by hydrolysis of the ester compound of formula (XXVI) as described in Step B-g.

In Step F-b, a compound of formula (XXIX) can be prepared from acid of the formula (XXVII) and N,O-dimethylhydroxylamine (XXVIII) by amidation (Weinreb amide formation) as described in Step B-h.

In Step F-c, a compound of formula (XXXI) can be prepared from compound of formula (XXIX) by the treatment with a suitable alkyl-metal reagent (XXX) in an inert solvent. Examples of suitable alkyl-metal reagent include, but not limited to, such as methyllitium, ethyllithium, methylmagnesium chloride, methylmagnesium bromide, and methylmagnesium iodide. Examples of inert solvent include, but not limited to, such as THF, diethyl ether, DME, and 1,4-dioxane. The reaction can be carried out at a temperature of from about -40 to 100° C., more preferably from about 0 to 50° C. Reaction times are, in general, from about 5 minutes to 48 hours, more preferably from about 30 minutes to 24 hours.

In Step F-d, a compound of formula (XXXIII) can be prepared as a single diastereomer from carbonyl compound of formula (XXXI) and a chiral tert-butanesulfinamide (XXXII) by the conventional methods known to those skilled in the art (Pure Appl. Chem., 75, 39-46, 2003; Tetrahedron Lett., 45, 6641-6643, 2004). In the following intermediate and example sections, a compound name of formula (XXXIII) is described as an (R) or (S) isomer, which represents the configuration of a sulfur atom.

In Step F-e, a compound of formula (XIII-a) can be prepared as a single enantiomer from a compound of formula (XXXIII) by the treatment with acidic condition by the conventional methods known to those skilled in the art (Pure Appl. Chem., 75, 39-46, 2003; Tetrahedron Lett., 45, 6641-6643, 2004).

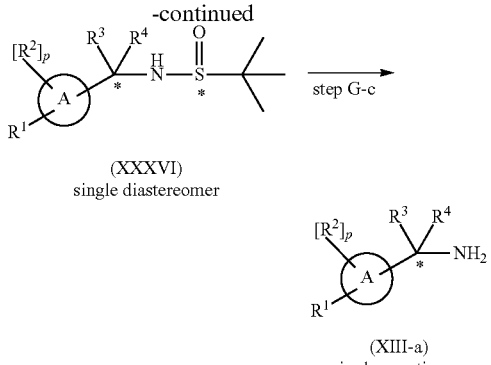

(XXXVI)
single diastereomer step G-c (XIII-a)
single enantiomer

*chiral

In Step G-a, a compound of formula (XXXV) can be prepared from aldehyde of formula (XXXIV) and chiral tert-butanesulfinamide (XXXII) by the conventional methods known to those skilled in the art (Pure Appl. Chem., 75, 39-46, 2003; Tetrahedron Lett., 45, 6641-6643, 2004).

In Step G-b, a compound of (XXXVI) can be prepared as a single diastereomer from chiral sulfinyl imine of formula (XXXV) and alkyl-metal reagent or hydride reagent by the conventional methods known to those skilled in the art (Pure Appl. Chem., 75, 39-46, 2003; Tetrahedron Lett., 45, 6641-6643, 2004). In the following intermediate and example sections, a compound name of formula (XXXVI) is described as an (R) or (S) isomer, which represents the configuration of a sulfur atom.

In Step G-c, a compound of formula (XIII-a) can be prepared as a single enantiomer from a compound of formula (XXXVI) by the treatment with acidic condition by the conventional methods known to those skilled in the art (Pure Appl. Chem., 75, 39-46, 2003; Tetrahedron Lett., 45, 6641-6643, 2004).

When —(O)$_r$—(CR$^3$R$^4$)$_k$—OH component of the key intermediate alcohols of formula (IV) is —(CR$^3$R$^4$)—OH, a compound of formula (IV-a) can be prepared by the following general synthetic route of Scheme H.

The key intermediate alcohols of formula (IV-a) can be prepared by the following general synthetic route of Scheme H.

<Scheme G>

[Chem.10]

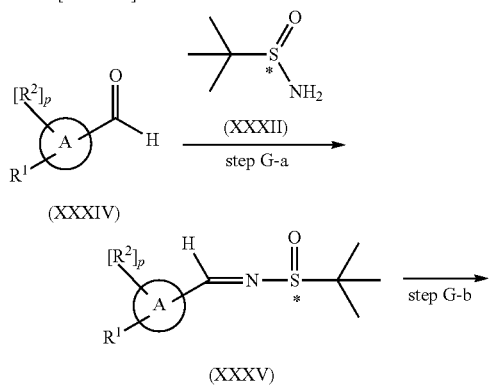

<Scheme H>

[Chem.11]

(XXXVII) → step H-a → (IV-a)

step H-b ↘      ↗ step H-c (XXXVIII)

In Step H-a, a compound of formula (IV-a) can be prepared by reduction of a compound of formula (XXXVII).

The reduction may be carried out in the presence of a suitable reducing reagent in an inert solvent or without solvent. A preferred reducing agent is selected from, for example, but not limited to, such as sodium borohydride, lithium aluminum hydride, lithium borohydride, boran-complex, and diisobutylaluminium hydride. Reaction temperatures are generally in the range of from about -78 to 100° C., preferably in the range of from about -70 to 60° C. Reaction times are, in general, from about 30 minute to a day. Examples of suitable solvents include, but not limited to: THF; 1,4-dioxane; DMF; MeCN; alcohols, such as MeOH or EtOH, and halogenated hydrocarbons, such as DCM, 1,2-dichloroethane, chloroform or carbon tetrachloride.

In Step H-b, a compound of formula (XXXVIII) can be prepared by the hydrolysis of the ester compound of formula (XXXVII) as described in Step B-g.

In Step H-c, a compound of formula (IV-a) can be prepared by the reduction of the carboxylic acid of formula (XXXVIII) as described in Step H-a.

The key intermediate pyrazolopyridine of formula (V) and (VII) can be prepared by the following general synthetic route of Scheme J.

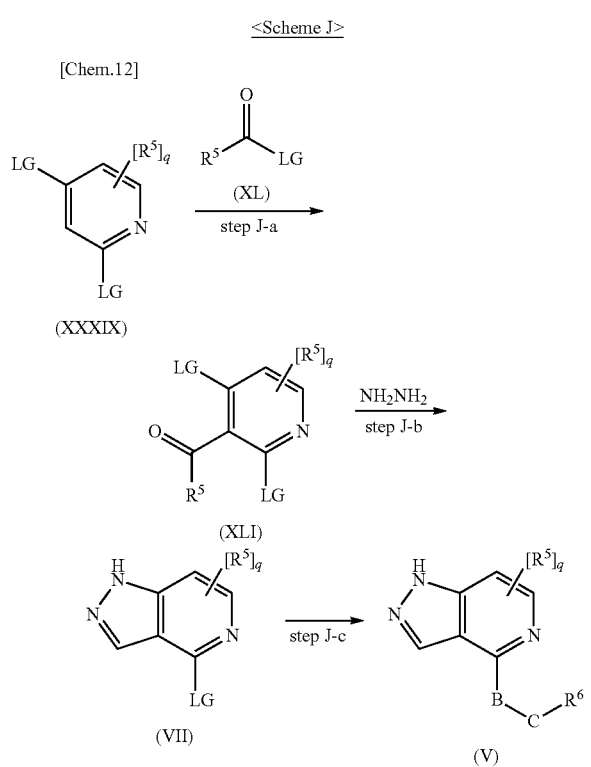

LG: Leaving group

In Step J-a, a compound of formula (XLI) can be prepared by metalation of a compound of formula (XXXIX) and trapping by a carbonyl compound of formula (XL). Metalation can be carried out by a base such as n-butyllitium, sec-butyllithium, tert-butyllithium, and lithium diisopropylamide. Examples of the carbonyl compound of formula (XL) include, but not limited to, such as DMF, acetyl chloride, propionyl chloride, and benzoyl chloride. Examples of suitable organic solvent include such as THF, diethyl ether, 1,4-dioxane, and hexane. The reaction can be carried out at a temperature of from about -78 to 20° C. Reaction times are, in general, from about 30 minutes to 24 hours.

In Step J-b, a compound of formula (VII) can be prepared from the carbonyl compound of formula (XLI) and hydrazine as described in Step E-a.

In Step J-c, a compound of formula (V) can be prepared from the compound of formula (VII) in a similar manner to B-c, B-d, B-e, B-f, B-g, and B-h in Scheme B.

The key intermediate of formula (XVI) can be prepared by the following general synthetic route of Scheme K.

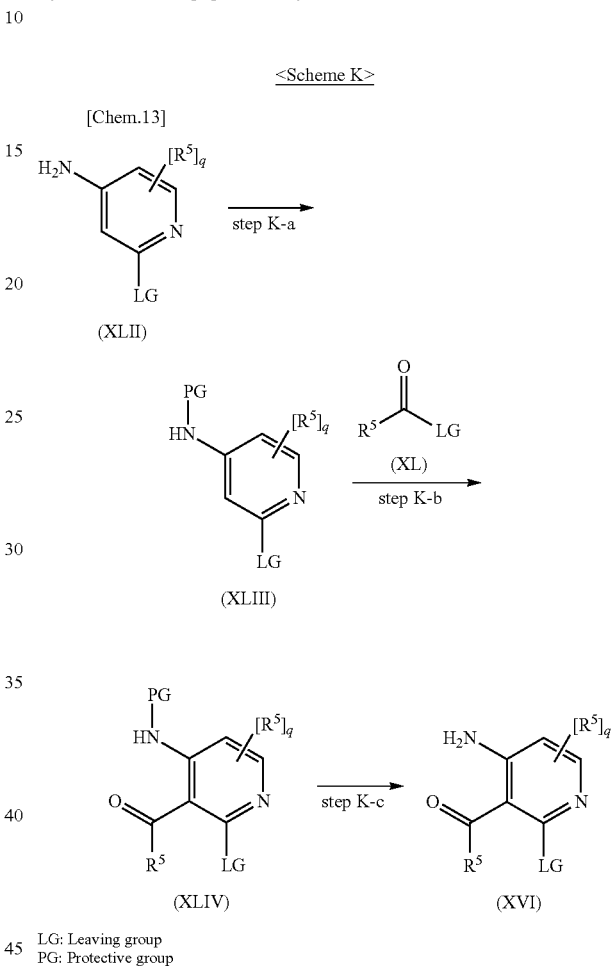

LG: Leaving group
PG: Protective group

In Step K-a, a protecting group can be introduced by the conventional methods known to those skilled in the art (typical amino protecting groups described in "Protective Groups in Organic Synthesis Forth Edition" edited by T. W. Greene et al. (John Wiley & Sons, 2007)).

In Step K-b, a compound of formula (XLIV) can be prepared from the compound of formula (XLIII) and a compound of formula (XL) as described in Step J-a.

In Step K-c, a compound of formula (XVI) can be prepared by de-protection of a compound of formula (XLIV) by the conventional methods known to those skilled in the art (typical amino protecting groups described in "Protective Groups in Organic Synthesis Forth Edition" edited by T. W. Greene et al. (John Wiley & Sons, 2007)).

All starting materials and intermediates in the following syntheses may be commercially available or obtained by the conventional methods known to those skilled in the art, otherwise noted in the intermediate synthesis part.

INTERMEDIATE SYNTHESIS PART

Intermediate compounds are prepared as follows.

Intermediate-A1

(5-methyl-6-(2,2,2-trifluoroethoxy)pyridin-3-yl)methanol

<Step-1>: 5-methyl-6-(2,2,2-trifluoroethoxy)nicotinic acid

To a stirred mixture of sodium hydride (9.28 g, 232 mmol, 60% in oil, washed with hexane before use) in DMA (60 mL) is added 2,2,2-trifluoroethanol (6.68 mL, 93 mmol) at 0° C. and stirred at rt for 20 minutes. To the mixture is added a solution of 6-fluoro-5-methylnicotinic acid (12.0 g, 77 mmol) in DMA (160 mL) at rt and the resulting mixture is stirred at 70° C. for 6 hours and continued stirred at rt overnight. The reaction mixture is diluted with water (800 mL) and acidified by the addition of 2 M hydrochloric acid. The white precipitate is collected by the filtration, washed with water and hexane, and dried in vacuo at 50° C. for 3 hours to give 15.1 g (83% yield) of the title compound as a white solid.

The symbol 'δ' is written "deltas" hereafter.

$^1$H-NMR (300 MHz, CDCl$_3$) delta 8.72 (1H, s), 8.10 (1H, s), 4.84 (2H, q, J=8.8 Hz), 2.30 (3H, s) (a signal due to COOH is not observed), MS (ESI) m/z: 234 (M−H)$^-$.

<Step-2>: (5-methyl-6-(2,2,2-trifluoroethoxy)pyridin-3-yl)methanol

To a stirred solution of 5-methyl-6-(2,2,2-trifluoroethoxy) nicotinic acid (15.0 g, 63.8 mmol, Step-1) in THF (120 mL) is added portionwise lithium aluminum hydride (3.20 g, 84 mmol) at 0° C. The reaction mixture is stirred at rt for 2 hours. The reaction mixture is quenched with saturated aqueous ammonium chloride solution at 0° C. The resulting slurry is filtered through a pad of Celite and is washed with EtOAc (100 mL x 4). The combined filtrate is washed with water and brine, dried over sodium sulfate, then filtered and concentrated to give 13.51 g (96% yield) of the title compound as a pale yellow solid.

$^1$H-NMR (300 MHz, CDCl$_3$) delta 7.93 (1H, s), 7.51 (1H, s), 4.76 (2H, q, J=8.8 Hz), 4.63 (2H, br), 2.24 (3H, s) (a signal due to OH is not observed), MS (ESI) m/z: 222 (M+H)$^+$.

Intermediate-A2

(6-(2,2-difluoroethoxy)-5-methylpyridin-3-yl)methanol

<Step-1>: 6-(2,2-difluoroethoxy)-5-methylnicotinic acid

The title compound is prepared in 94% yield (6.57 g, a white solid) from 6-fluoro-5-methylnicotinic acid (5.00 g, 32.2 mmol) and 2,2-difluoroethanol (5.29 g, 64.5 mmol) in a similar manner to Step-1 of Intermediate-A1.

$^1$H-NMR (300 MHz, DMSO-d$_6$) delta 13.09 (1H, br s), 8.56 (1H, d, J=2.2 Hz), 8.07 (1H, d, J=2.2 Hz), 6.42 (1H, tt, J=54.3, 3.7 Hz), 4.66 (2H, td, J=14.7, 3.7 Hz), 2.21 (3H, s), MS (ESI) m/z: 218 (M+H)$^+$.

<Step-2>: methyl 6-(2,2-difluoroethoxy)-5-methylnicotinate

To a mixture of 6-(2,2-difluoroethoxy)-5-methylnicotinic acid (3.19 g, 14.7 mmol, Step-1) and potassium carbonate (4.06 g, 29.4 mmol) in DMF (37 mL) is added iodomethane (1.4 mL, 22 mmol), and the mixture is stirred at rt for 1 hour. The mixture is poured onto water (300 mL), and the aqueous layer is extracted with EtOAc (300 mL). The separated organic layer is washed with water (100 mL), dried over sodium sulfate, and concentrated in vacuo. The residue is purified by chromatography on silica gel eluting with n-hexane/EtOAc (10:1-4:1) to give 2.99 g (88% yield) of the title compound as a white solid.

$^1$H-NMR (300 MHz, CDCl$_3$) delta 8.64 (1H, d, J=1.8 Hz), 8.03 (1H, d, J=1.8 Hz), 6.15 (1H, tt, J=55.8, 4.4 Hz), 4.61 (2H, td, J=13.2, 4.4 Hz), 3.91 (3H, s), 2.25 (3H, s), MS (ESI) m/z: 232 (M+H)$^+$.

<Step-3>: (6-(2,2-difluoroethoxy)-5-methylpyridin-3-yl)methanol

The title compound is prepared in quantitative yield (2.62 g, colorless oil) from methyl 6-(2,2-difluoroethoxy)-5-methylnicotinate (2.99 g, 12.9 mmol, Step-2) in a similar manner to Step-2 of Intermediate-A1.

$^1$H-NMR (300 MHz, CDCl$_3$) delta 7.92 (1H, d, J=1.8 Hz), 7.48 (1H, d, J=1.8 Hz), 6.14 (1H, tt, J=55.8, 4.0 Hz), 4.62-4.49 (4H, m), 2.22 (3H, s), 1.80 (1H, t, J=5.9 Hz), MS (ESI) m/z: 204 (M+H)$^+$.

Intermediate-A3

(5-chloro-6-(2,2,2-trifluoroethoxy)pyridin-3-yl)methanol

<Step-1>: 5-chloro-6-(2,2,2-trifluoroethoxy)nicotinic acid

To a suspension of sodium hydride (5.00 g, 60% in oil, 125 mmol) in DMA is added 2,2,2-trifluoroethanol (5.8 mL, 94 mmol) at 0° C. After stirring at 0° C. for 20 minutes, 5,6-dichloronicotinic acid (12.0 g, 62.5 mmol) is added to the mixture, and this is stirred at 90° C. for 2 hours. After cooling to rt, the mixture is poured onto 0.3 M hydrochloric acid (700 mL). The formed white precipitate is collected by filtration and washed with water and hexane to give 16.6 g (quantitative yield) of the title compound as a white solid. This is used for the next step without further purification.

$^1$H-NMR (300 MHz, DMSO-d$_6$) delta 8.66 (1H, d, J=2.2 Hz), 8.32 (1H, d, J=2.2 Hz), 5.15 (2H, q, J=8.8 Hz), MS (ESI) m/z: 256 (M+H)$^+$.

<Step-2>: (5-chloro-6-(2,2,2-trifluoroethoxy)pyridin-3-yl)methanol

To a stirred solution of 5-chloro-6-(2,2,2-trifluoroethoxy) nicotinic acid (5.00 g, 19.5 mmol, Step-1) in THF (50 mL) is added N,N'-carbonyldiimidazole (4.76 g, 29.3 mmol) at rt. After stirring at rt for 2 hours, a solution of sodium borohydride (3.70 g, 98.0 mmol) in water (50 mL) is added slowly to the mixture at 0° C. After stirring at 0° C. for 15 minutes, 2 M hydrochloric acid (50 mL) is added to the mixture at 0° C. After 30 minutes, the mixture is poured onto saturated sodium bicarbonate solution (100 mL) carefully. This is extracted with EtOAc (200 mL), and the organic layer is dried over sodium sulfate. After removal of the organic solvent, the residue is purified by column chromatography on silica-gel eluting with n-hexane/EtOAc (2:1) to give 4.63 g (98% yield) of the title compound as a pale yellow solid.

¹H-NMR (300 MHz, CDCl₃) delta 8.00 (1H, d, J=2.2 Hz), 7.76 (1H, d, J=2.2 Hz), 4.82 (2H, q, J=8.8 Hz), 4.66 (2H, s), MS (ESI) m/z: 242 (M+H)⁺.

Intermediate-A4

(5-chloro-6-(2,2-difluoroethoxy)pyridin-3-yl)methanol

<Step-1>: 5-chloro-6-(2,2-difluoroethoxy)nicotinic acid

The title compound is prepared in 83% yield (4.12 g, a white solid) from 5,6-dichloronicotinic acid (4.00 g, 20.8 mmol) and 2,2-difluoroethanol in a similar manner to Step-1 of Intermediate-A3.
¹H-NMR (300 MHz, DMSO-d₆) delta 13.4 (1H, br s), 8.65 (1H, d, J=1.8 Hz), 8.28 (1H, d, J=1.8 Hz), 6.44 (1H, tt, J=54.3, 3.3 Hz), 4.73 (2H, td, J=15.0, 3.3 Hz), MS (ESI) m/z: 236 (M−H)⁻.

<Step-2>: methyl 5-chloro-6-(2,2-difluoroethoxy)nicotinate

To a solution of 5-chloro-6-(2,2-difluoroethoxy)nicotinic acid (1.5 g, 6.31 mmol, Step-1) in MeOH (100 ml) is added dropwise thionyl chloride (1.38 ml, 18.9 mmol) at 0° C. Then the reaction mixture is refluxed with stirring for 2 hours. After removing solvent to give 1.57 g (quantitative yield) of the title compound as a white solid.
¹H-NMR (300 MHz, DMSO-d₆) delta 8.68 (1H, d, J=2.2 Hz), 8.33 (1H, d, J=2.2 Hz), 6.44 (1H, tt, J=54.3, 3.3 Hz), 4.74 (2H, td, J=14.7, 3.3 Hz), 3.86 (3H, s), MS (ESI) m/z: 252 (M+H)⁺.

<Step-3>: (5-chloro-6-(2,2-difluoroethoxy)pyridin-3-yl)methanol

The title compound is prepared in 62% yield (0.87 g, colorless oil) from methyl 5-chloro-6-(2,2-difluoroethoxy) nicotinate (1.57 g, 6.25 mmol, Step-2) in a similar manner to Step-2 of Intermediate-A1.
¹H-NMR (300 MHz, CDCl₃) delta 7.99 (1H, d, J=2.2 Hz), 7.74 (1H, d, J=2.2 Hz), 6.16 (1H, tt, J=55.4, 4.4 Hz), 4.65 (2H, d, J=5.5 Hz), 4.60 (2H, td, J=13.2, 4.0 Hz), a signal due to OH is not observed, MS (ESI) m/z: 224 (M+H)⁺.

Intermediate-A5

(5-fluoro-6-(2,2,2-trifluoroethoxy)pyridin-3-yl)methanol

<Step-1>: 2-chloro-5-fluoro-6-(2,2,2-trifluoroethoxy)nicotinic acid

A mixture of 2,6-dichloro-5-fluoronicotinic acid (25.0 g, 119 mmol), 2,2,2-trifluoroethanol (17.1 mL, 238 mmol) and sodium hydroxide (14.3 g, 357 mmol) in water (600 mL) is stirred at 80° C. for 40 hours. After cooling to 0° C., the mixture is acidified with conc. hydrochloric acid (pH 2). The resulting white precipitate is collected by filtration and dried to give 32.2 g of the title compound as a crude. This is used for the next step without further purification.
MS (ESI) m/z: 274 (M+H)⁺.

<Step-2>: 5-fluoro-6-(2,2,2-trifluoroethoxy)nicotinic acid

A mixture of 2-chloro-5-fluoro-6-(2,2,2-trifluoroethoxy) nicotinic acid (32.2 g, 118 mmol, Step-1), triethylamine (23 mL, 165 mmol), and 10% Pd-C(12.5 g) in EtOH is stirred at rt for 5 hours under hydrogen atmosphere. Then the mixture is filtered through a pad of Celite, and the filtrate is concentrated in vacuo. The residue is dissolved in water (300 mL), and the solution is acidified by conc. Hydrochloric acid. The formed white precipitate is collected by filtration to give 21.0 g (75%) of the title compound as a white solid.
¹H-NMR (300 MHz, DMSO-d₆) delta 13.40 (1H, br), 8.55 (1H, d, J=1.8 Hz), 8.13 (1H, dd, J=10.3, 1.8 Hz), 5.16 (2H, q, J=9.2 Hz), MS (ESI) m/z: 238 (M−H)⁻.

<Step-3>: (5-fluoro-6-(2,2,2-trifluoroethoxy)pyridin-3-yl)methanol

The title compound is prepared in 91% yield (1.11 g, a brown oil) from 5-fluoro-6-(2,2,2-trifluoroethoxy)nicotinic acid (1.29 g, 5.39 mmol, Step-2) in a similar manner to Step-2 of Intermediate-A1.
¹H-NMR (300 MHz, CDCl₃) delta 7.88 (1H, s), 7.48 (1H, dd, J=9.9, 1.5 Hz), 4.84 (2H, q, J=8.4 Hz), 4.68 (2H, d, J=5.9 Hz), 1.76 (1H, m), MS (ESI) m/z: 226 (M+H)+

Intermediate-A6

(6-(3,3,3-trifluoropropoxy)pyridin-3-yl)methanol

<Step-1>: methyl 6-(3,3,3-trifluoropropoxy)nicotinate

Potassium tert-butoxide (2.45 g, 21.9 mmol) is added to a solution of 3,3,3-trifluoropropan-1-ol (1.67 mL, 18.9 mmol) in THF (30 mL) and stirred for 5 minutes. Then methyl 6-chloronicotinate (2.5 g, 14.6 mmol) is added there and stirred for 2 hours. The reaction mixture is poured into water, extracted with EtOAc. The organic layer is dried over sodium sulfate and concentrated in vacuo to give 2.21 g (61% yield) of the title compound as a colorless oil. This material is used for the next reaction (Step-2) without further purification.
¹H-NMR (300 MHz, CDCl₃) delta 8.81 (1H, d, J=2.2 Hz), 8.17 (1H, dd, J=8.8, 2.2 Hz), 6.79 (1H, d, J=8.8 Hz), 4.62 (2H, t, J=6.2 Hz), 3.91 (3H, s), 2.63 (2H, m), MS (ESI) m/z: 250 (M+H)⁺.

<Step-2>: 6-(3,3,3-trifluoropropoxy)nicotinic acid

To a solution of methyl 6-(3,3,3-trifluoropropoxy)nicotinate (1.37 g, 5.50 mmol, Step-1) in MeOH (30 mL) is added 2 M sodium hydroxide (5 mL), and stirred for 2 hours at 60° C. After removal of the solvent, the residue is dissolved in water (30 mL) and acidified with conc. hydrochloric acid (pH 2). The resulting white precipitate is collected by filtration and dried to give 1.11 g (86% yield) of the title compound as a white solid.
¹H-NMR (300 MHz, CDCl₃) delta 8.90 (1H, d, J=2.2 Hz), 8.23 (1H, dd, J=8.8, 2.2 Hz), 6.83 (1H, d, J=8.8 Hz), 4.65 (2H, t, J=6.2 Hz), 2.65 (2H, m), MS (ESI) m/z: 236 (M+H)⁺.

<Step-3>: (6-(3,3,3-trifluoropropoxy)pyridin-3-yl)methanol

The title compound is prepared in 91% yield (858 mg, 4.25 mmol, a brown oil) from 6-(3,3,3-trifluoropropoxy) nicotinic acid (1.00 g, 4.25 mmol, Step-2) in a similar manner to Step-2 of Intermediate-A1.
¹H-NMR (300 MHz, CDCl₃) delta 8.11 (1H, d, J=2.2 Hz), 7.64 (1H, dd, J=8.4, 2.6 Hz), 6.77 (1H, d, J=8.1 Hz), 4.64

(2H, s), 4.55 (2H, t, J=6.6 Hz), 2.70-2.54 (2H, m), 1.67 (1H, br s), MS (ESI) m/z: 222 (M+H)+.

Intermediate-A7

1(5-methyl-6-(2,2,2-trifluoroethoxy)pyridin-3-yl)ethanamine hydrochloride (single enantiomer; antipode of Intermediate-A27)

<Step-1>: N-methoxy-N,5-dimethyl-6-(2,2,2-trifluoroethoxy)nicotinamide

A mixture of 5-methyl-6-(2,2,2-trifluoroethoxy)nicotinic acid (2.27 g, 9.67 mmol, Step-1 of Intermediate-A1), N,O-dimethylhydroxylamine hydrochloride (1.04 g, 10.64 mmol), HBTU (5.50 g, 14.51 mmol) and triethylamine (5.39 mL, 38.7 mmol) in DCM (30 mL) is stirred at rt for 1.5 hours. The reaction mixture is poured into saturated aqueous sodium hydrogen carbonate solution (300 mL) and extracted with DCM (500 mL). The organic layer is washed with saturated aqueous sodium hydrogen carbonate (300 mL×2) and dried over sodium sulfate, and concentrated in vacuo. The residue is purified by column chromatography on silica gel eluting with n-hexane/EtOAc (4:1) to give 2.03 g (76% yield) of the title compound as a colorless oil.
$^1$H-NMR (300 MHz, CDCl$_3$) delta 8.43 (1H, d, J=2.2 Hz), 7.86 (1H, m), 4.82 (2H, q, J=8.4 Hz), 3.60 (3H, s), 3.38 (3H, s), 2.26 (3H, s), MS (ESI) m/z: 279 (M+H)+.

<Step-2>: 1-(5-methyl-6-(2,2,2-trifluoroethoxy)pyridin-3-yl)ethanone

To a solution of N-methoxy-N,5-dimethyl-6-(2,2,2-trifluoroethoxy)nicotinamide (2.03 g, 7.31 mmol, Step-1) in THF (25 mL) is added dropwise a solution of methylmagnesium bromide in THF (1.12 M, 13.1 mL, 14.6 mmol) at 0° C. After stirring at rt for 1.5 h, the reaction is quenched with saturated aqueous sodium bicarbonate solution (150 mL), and the aqueous layer is extracted with EtOAc (150 mL×2). The combined organic layer is dried over sodium sulfate and concentrated in vacuo. The residual solid is washed with hexane to give 1.47 g (86% yield) of the title compound as a white solid.
$^1$H-NMR (300 MHz, CDCl$_3$) delta 8.59 (1H, d, J=2.0 Hz), 8.03 (1H, d, J=2.2 Hz), 4.84 (2H, q, J=8.4 Hz), 2.57 (3H, s), 2.27 (3H, s), MS (ESI) m/z: 234 (M+H)+.

<Step-3>: (R)-2-methyl-N-(1-(5-methyl-6-(2,2,2-trifluoroethoxy)pyridin-3-yl)ethyl)propane-2-sulfinamide (single diastereomer)

To a mixture of 1-(5-methyl-6-(2,2,2-trifluoroethoxy)pyridin-3-yl)ethanone (1.47 g, 6.32 mmol, Step-2) and (R)-2-methylpropane-2-sulfinamide (1.15 g, 9.48 mmol) in THF (10 mL) is added titanium(IV) ethoxide (1.99 mL, 9.48 mmol), and the mixture is stirred at 70° C. for 22 hours. After cooling to 0° C., sodium borohydride (717 mg, 19.0 mmol) is added to the mixture. After stirring at 0° C. for 1 h, the reaction is quenched with saturated aqueous sodium bicarbonate solution (150 mL), and the aqueous layer is extracted with EtOAc (150 mL). The separated organic layer is washed with water, dried over sodium sulfate, and concentrated in vacuo. The residue is purified by column chromatography on silica gel eluting with n-hexane/EtOAc (4:1-1:1.5) to give 1.70 g (79%) of the title compound as a colorless oil.
$^1$H-NMR (300 MHz, CDCl$_3$) delta 7.94 (1H, d, J=2.2 Hz), 7.45 (1H, d, J=2.2 Hz), 4.76 (2H, q, J=8.8 Hz), 4.56-4.43 (1H, m), 3.32 (1H, d, J=2.6 Hz), 2.24 (3H, s), 1.51 (3H, d, J=6.6 Hz), 1.23 (9H, s), MS (ESI) m/z: 339 (M+H)+.

<Step-4>: 1-(5-methyl-6-(2,2,2-trifluoroethoxy)pyridin-3-yl)ethanamine hydrochloride (single enantiomer; antipode of Intermediate-A27)

A mixture of (R)-2-methyl-N-(1-(5-methyl-6-(2,2,2-trifluoroethoxy)pyridin-3-yl)ethyl)-propane-2-sulfinamide (single diastereomer, Step-3) (1.70 g, 5.01 mmol) and 8 M HCl-MeOH (10 mL) is stirred at rt for 1 hour. After removing the solvent, the residual solid is crystallized from EtOAc/hexane to give 1.27 g (94%) of the title compound as a white solid.
$^1$H-NMR (300 MHz, DMSO-d$_6$) delta 8.56 (2H, br s), 8.16 (1H, d, J=2.0 Hz), 7.87 (1H, d, J=2.0 Hz), 5.03 (2H, q, J=9.2 Hz), 4.50-4.28 (1H, m), 2.20 (3H, s), 1.50 (3H, d, J=7.0 Hz), MS (ESI) m/z: 235 (M+H)+.

Intermediate-A8

(6-(2,2-difluoroethoxy)-5-fluoropyridin-3-yl)methanol

<Step-1>: 2-chloro-6-(2,2-difluoroethoxy)-5-fluoronicotinic acid

The title compound is prepared in 55% yield (6.76 g, a white solid) from 2,6-dichloro-5-fluoronicotinic acid (10.0 g, 47.6 mmol) and 2,2-difluoroethanol in a similar manner to Step-1 of Intermediate-A5.
$^1$H-NMR (300 MHz, CDCl$_3$) delta 8.10 (1H, d, J=9.5 Hz), 6.17 (1H, tt, J=55.0, 4.1 Hz), 4.68 (2H, td, J=12.8, 4.1 Hz) (a signal due to COOH is not observed), MS (ESI) m/z: 256 (M+H)+.

<Step-2>: 6-(2,2-difluoroethoxy)-5-fluoronicotinic acid

The title compound is prepared in 55% yield (2.1 g, a white solid) from 2-chloro-6-(2,2-difluoroethoxy)-5-fluoronicotinic acid (4.5 g, 17.6 mmol, Step-1) in a similar manner to Step-2 of Intermediate-A5.
$^1$H-NMR (300 MHz, DMSO-d$_6$) delta 8.55 (1H, d, J=2.2 Hz), 8.08 (1H, dd, J=12.5, 2.2 Hz), 6.44 (1H, tt, J=54.3, 3.3 Hz), 4.75 (2H, td, J=15.0, 3.3 Hz) (a signal due to COOH is not observed), MS (ESI) m/z: 220 (M−H)−.

<Step-3>: methyl 6-(2,2-difluoroethoxy)-5-fluoronicotinate

The title compound is prepared in 71% yield (1.6 g, a white solid) from 6-(2,2-difluoroethoxy)-5-fluoronicotinic acid (2.1 g, 9.7 mmol, Step-2) in a similar manner to Step-2 of Intermediate-A4.
$^1$H-NMR (300 MHz, CDCl$_3$) delta 8.59 (1H, s), 7.95 (1H, d, J=11.1 Hz), 6.18 (1H, tt, J=55.4, 4.0 Hz), 4.68 (2H, td, J=13.2, 3.7 Hz), 3.94 (3H, s), MS (ESI) m/z: 236 (M+H)+.

<Step-4>: (6-(2,2-difluoroethoxy)-5-fluoropyridin-3-yl)methanol

The title compound is prepared in 88% yield (1.24 g, a colorless oil) from methyl 6-(2,2-difluoroethoxy)-5-fluoronicotinate (1.6 g, 6.8 mmol, Step-3) in a similar manner to Step-2 of Intermediate-A1.

¹H-NMR (300 MHz, CDCl₃) delta 7.87 (1H, s), 7.45 (1H, d, J=10.3 Hz), 6.16 (1H, tt, J=55.4, 4.4 Hz), 4.66 (2H, d, J=5.9 Hz), 4.60 (2H, td, J=13.2, 3.7 Hz) (a signal due to OH is not observed), MS (ESI) m/z: 208 (M+H)⁺, 206 (M−H)⁻.

Intermediate-A9

(6-(2,2,3,3-tetrafluoropropoxy)pyridin-3-yl)methanol

The title compound is prepared in 78% yield (12.6 g, a yellow semi-solid) from 6-(2,2,3,3-tetrafluoropropoxy)nicotinic acid (1.29 g, 5.39 mmol) in a similar manner to Step-2 of Intermediate-A1.

¹H-NMR (300 MHz, CDCl₃) delta 8.13 (1H, d, J=2.2 Hz), 7.69 (1H, dd, J=8.8, 2.2 Hz), 6.84 (1H, d, J=8.8 Hz), 6.02 (1H, tt, J=53.1, 4.6 Hz), 4.78-4.66 (4H, m), 1.69 (1H, t, J=5.9 Hz), MS (ESI) m/z: 240 (M+H)⁺.

Intermediate-A10

(6-(2,2,3,3,3-pentafluoropropoxy)pyridin-3-yl)methanol

<Step-1>: methyl 6-(2,2,3,3,3-pentafluoropropoxy)nicotinate

To a stirred suspension of sodium hydride (3.85 g, 96 mmol, 60% in oil) in DMA (120 mL) is added dropwise 2,2,3,3,3-pentafluoropropan-1-ol (6.4 mL, 64 mmol) at 0° C. After stirring for 10 minutes, a solution of methyl 6-chloronicotinate (5.5 g, 32 mmol) in DMA (40 mL) is added dropwise at 0° C., and the mixture is stirred for 30 minutes at rt. Then the mixture is stirred at 90° C. for 2 hours. After cooled to rt, 2 M aqueous sodium hydroxide is added (pH is around 6). The mixture is extracted with n-hexane/EtOAc (1:2, 200 mL). The organic layer is washed with water, brine, dried over sodium sulfate, and concentrated in vacuo. The residue is purified by column chromatography on NH-gel eluting with n-hexane/EtOAc (30:1) to give 3.07 g (34% yield) of the title compound as a brown oil.

¹H-NMR (300 MHz, CDCl₃) delta 8.12 (1H, d, J=2.2 Hz), 8.24 (1H, dd, J=8.4, 2.6 Hz), 6.90 (1H, d, J=8.1 Hz), 4.90 (2H, t, J=12.5 Hz), 3.93 (3H, s), MS (ESI) m/z: 286 (M+H)⁺.

<Step-2>: (6-(2,2,3,3,3-pentafluoropropoxy)pyridin-3-yl)methanol

The title compound is prepared in 83% yield (2.31 g, a brown oil) from methyl 6-(2,2,3,3,3-pentafluoropropoxy)nicotinate (3.07 g, 10.8 mmol, Step-1) in a similar manner to Step-2 of Intermediate-A1.

¹H-NMR (300 MHz, CDCl₃) delta 8.13 (1H, d, J=1.5 Hz), 7.69 (1H, dd, J=8.8, 2.2 Hz), 6.87 (1H, d, J=8.8 Hz), 4.84 (2H, t, J=12.8 Hz), 4.66 (2H, d, J=5.1 Hz), 1.73 (1H, t, J=5.1 Hz), MS (ESI) m/z: 258 (M+H)⁺.

Intermediate-A11

(+)-1-(6-(2,2-difluoroethoxy)-5-methylpyridin-3-yl)ethanamine hydrochloride (single enantiomer)

<Step-1>: 6-(2,2-difluoroethoxy)-N-methoxy-N,5-dimethylnicotinamide

The title compound is prepared in 98% yield (1.20 g, a white solid) from 6-(2,2-difluoroethoxy)-5-methylnicotinic acid (1.02 g, 4.70 mmol, Step-1 of Intermediate-A2) in a similar manner to Step-1 of Intermediate-A7.

¹H-NMR (300 MHz, CDCl₃) delta 8.43 (1H, d, J=2.2 Hz), 7.84 (1H, br s), 6.16 (1H, tt, J=55.8, 4.4 Hz), 4.60 (2H, td, J=13.2, 4.4 Hz), 3.58 (3H, s), 3.37 (3H, s), 2.25 (3H, s), MS (ESI) m/z: 261 (M+H)⁺.

<Step-2>: 1-(6-(2,2-difluoroethoxy)-5-methylpyridin-3-yl)ethanone

The title compound is prepared in quantitative yield (0.99 g, a white solid) from 6-(2,2-difluoroethoxy)-N-methoxy-N,5-dimethylnicotinamide (1.20 g, 4.61 mmol, Step-1) in a similar manner to Step-2 of Intermediate-A7.

¹H-NMR (270 MHz, CDCl₃) delta 8.58 (1H, d, J=2.0 Hz), 8.01-8.00 (1H, m), 6.16 (1H, tt, J=55.4, 4.0 Hz), 4.63 (2H, td, J=13.2, 4.0 Hz), 2.57 (3H, s), 2.26 (3H, s), MS (ESI) m/z: 216 (M+H)⁺.

<Step-3>: (R)—N-(1-(6-(2,2-difluoroethoxy)-5-methylpyridin-3-yl)ethyl)-2-methylpropane-2-sulfinamide (single diastereomer)

The title compound is prepared in 82% yield (1.22 g, colorless oil) from 1-(6-(2,2-difluoroethoxy)-5-methylpyridin-3-yl)ethanone (0.99 g, 4.61 mmol, Step-2) and (R)-2-methylpropane-2-sulfinamide in a similar manner to Step-3 of Intermediate-A7.

¹H-NMR (300 MHz, CDCl₃) delta 7.97 (1H, d, J=2.2 Hz), 7.43 (1H, br s), 6.14 (1H, tt, J=55.8, 4.4 Hz), 4.59-4.46 (3H, m), 3.32 (1H, br s), 2.22 (3H, s), 1.50 (3H, d, J=6.6 Hz), 1.23 (9H, s), MS (ESI) m/z: 321 (M+H)⁺.

<Step-4>: (+)-1-(6-(2,2-difluoroethoxy)-5-methylpyridin-3-yl)ethanamine hydrochloride (single enantiomer)

The title compound is prepared in 94% yield (0.91 g, a white solid) from (R)—N-(1-(6-(2,2-difluoroethoxy)-5-methylpyridin-3-yl)ethyl)-2-methylpropane-2-sulfinamide (single diastereomer) (1.22 g, 3.80 mmol, Step-3) in a similar manner to Step-4 of Intermediate-A7.

¹H-NMR (270 MHz, DMSO-d₆) delta 8.58 (2H, br s), 8.13 (1H, d, J=2.0 Hz), 7.82 (1H, br s), 6.40 (1H, tt, J=54.7, 3.3 Hz), 4.60 (2H, td, J=15.2, 3.3 Hz), 4.42-4.36 (1H, m), 2.19 (3H, s), 1.52 (3H, d, J=6.6 Hz), MS (ESI) m/z: 217 (M+H)⁺.

$[\alpha]_D^{26}$=+3.09 (c=1.18, methanol)

Intermediate-A12

(6-(4-fluorophenoxy)-5-methylpyridin-3-yl)methanol

<Step-1>: methyl 6-(4-fluorophenoxy)-5-methylnicotinate

A mixture of methyl 6-fluoro-5-methylnicotinate (2.40 g, 14.2 mmol), 4-fluorophenol (2.39 g, 21.3 mmol), and potassium carbonate (3.92 g, 28.4 mmol) in DMF (45 mL) is stirred at 90° C. for 3 hours. After cooling to rt, the mixture is filtered through a pad of Celite and rinsed with EtOAc (200 mL). The filtrate is washed with water (200 mL) and brine (200 mL), dried over sodium sulfate, and concentrated in vacuo. The residue is purified by chromatography on silica gel eluting with n-hexane/EtOAc (20:1) to give 3.46 g (93% yield) of the title compound as a white solid.

¹H-NMR (300 MHz, CDCl₃) delta 8.59 (1H, d, J=2.2 Hz), 8.12 (1H, d, J=2.2 Hz), 7.15-7.06 (4H, m), 3.90 (3H, s), 2.40 (3H, s), MS (ESI) m/z: 262 (M+H)⁺.

<Step-2>: 6-(4-fluorophenoxy)-5-methylnicotinic acid

The title compound is prepared in 91% yield (2.98 g, a white solid) from methyl 6-(4-fluorophenoxy)-5-methylnicotinate (3.46 g, 13.2 mmol, Step-1) in a similar manner to Step-2 of Intermediate-A6.
¹H-NMR (300 MHz, CDCl₃) delta 8.67 (1H, d, J=2.2 Hz), 8.16 (1H, d, J=2.2 Hz), 7.18-7.06 (4H, m), 2.40 (3H, s) (a signal due to COOH is not observed), MS (ESI) m/z: 248 (M+H)⁺.

<Step-3>: (6-(4-fluorophenoxy)-5-methylpyridin-3-yl)methanol

The title compound is prepared in 98% yield (417 mg, a white solid) from 6-(4-fluorophenoxy)-5-methylnicotinic acid (450 mg, 1.82 mmol, Step-2) in a similar manner to Step-2 of Intermediate-A3.
¹H-NMR (300 MHz, CDCl₃) delta 7.93 (1H, s), 7.59 (1H, s), 7.15-7.03 (4H, m), 4.62 (2H, d, J=5.5 Hz), 2.36 (3H, s), 1.65 (1H, t, J=5.5 Hz), MS (ESI) m/z: 234 (M+H)⁺.

Intermediate-A13

(5-methyl-6-(3,3,3-trifluoropropoxy)pyridin-3-yl)methanol

<Step-1>:
5-methyl-6-(3,3,3-trifluoropropoxy)nicotinic acid

To a solution of sodium hydride (0.844 g, 21.1 mmol) in THF (10 mL), 3,3,3-trifluoropropan-1-ol (1.61 g, 14.1 mmol) in THF (10 mL) is added at 0° C., and stirred for 5 minutes. Then methyl 6-fluoro-5-methylnicotinate (1.19 g, 7.04 mmol) in THF (10 mL) is added dropwise the reaction mixture and the resulting mixture is stirred at rt for 2 hours. The reaction mixture is diluted with water (30 mL) and stirred overnight. After removal of THF, the mixture is acidified with 2 M hydrochloric acid (11 mL). The resulting white precipitate is collected by filtration and dried to give 1.76 g (quantitative yield) of the title compound as a white solid. This material is used for the next reaction (Step-2) without further purification.
MS (ESI) m/z: 250 (M+H)⁺.

<Step-2>: (5-methyl-6-(3,3,3-trifluoropropoxy)pyridin-3-yl)methanol

The title compound is prepared in 95% yield (2.43 g, a white solid) from 5-methyl-6-(3,3,3-trifluoropropoxy)nicotinic acid (2.71 g, 10.9 mmol, Step-1) in a similar manner to Step-2 of Intermediate-A3.
¹H-NMR (270 MHz, CDCl₃) delta 7.94 (1H, s), 7.47 (1H, s), 4.62-4.54 (4H, m), 2.71-2.56 (2H, m), 2.19 (3H, s), 1.62 (1H, t, J=5.9 Hz), MS (ESI) m/z: 236 (M+H)⁺.

Intermediate-A14

(5-methyl-6-(2,2,2-trifluoroethoxy)pyridazin-3-yl)methanol

<Step-1>: A mixture of 6-chloro-4-methyl-3-(2,2,2-trifluoroethoxy)pyridazine and 3-chloro-4-methyl-6-(2,2,2-trifluoroethoxy)pyridazine (2:1)

To a stirred solution of 2,2,2-trifluoroethanol (2.03 g, 20.2 mmol), DMF (20 mL) and THF (10 mL) is added 60% sodium hydride (0.78 g, 20.2 mmol) at 0° C. carefully. After stirring at rt for 1 hour, this solution is added to a solution of 3,6-dichloro-4-methylpyridazine (3.00 g, 18.4 mmol) in DMF (20 mL) at 0° C. slowly. The resulting mixture is stirred at rt for 1 hour. The mixture is poured onto ice-water, and extracted with EtOAc (200 mL). The organic layer is washed with water (200 mL×2), and dried over sodium sulfate. After removal of the organic solvent, the residue is purified by column chromatography on silica-gel eluting with n-hexane/EtOAc (9:1) to give 3.40 g of a mixture of the title compound (81% yield) as a white solid.
MS (ESI) m/z: 227 (M+H)⁺.

<Step-2>: ethyl 5-methyl-6-(2,2,2-trifluoroethoxy)pyridazine-3-carboxylate and ethyl 4-methyl-6-(2,2,2-trifluoroethoxy)pyridazine-3-carboxylate A mixture of 6-chloro-4-methyl-3-(2,2,2-trifluoroethoxy)pyridazine and 3-chloro-4-methyl-6-(2,2,2-trifluoroethoxy)pyridazine (3.40 g, 15.0 mmol, Step-1), palladium(II) acetate (0.34 g, 1.50 mmol), 1,3-bis(diphenylphosphino)propane (1.24 g, 3.00 mmol), triethylamine (6.27 mL, 45.0 mmol), DMF (40 mL), and EtOH (20 mL) is stirred at 80° C. under carbon monoxide atmosphere (1 atm) for 20 hours. After cooling to rt, the mixture is diluted with EtOAc (200 mL). This is washed with water (200 mL×2), and the organic layer is dried over sodium sulfate. After removal of the organic solvent, the residue is purified by column chromatography on silica-gel eluting with n-hexane/EtOAc (8:1-5:1) to give 2.15 g of ethyl 5-methyl-6-(2,2,2-trifluoroethoxy)pyridazine-3-carboxylate (54% yield, more polar product) as an off-white solid and 0.63 g of ethyl 4-methyl-6-(2,2,2-trifluoroethoxy)pyridazine-3-carboxylate (16% yield, less polar product) as pale yellow oil.

ethyl 5-methyl-6-(2,2,2-trifluoroethoxy)pyridazine-3-carboxylate (more polar)

¹H-NMR (300 MHz, CDCl₃) delta 7.99 (1H, d, J=1.5 Hz), 5.02 (2H, q, J=8.1 Hz), 4.50 (2H, q, J=7.3 Hz), 2.36 (3H, s), 1.46 (3H, t, J=7.3 Hz), MS (ESI) m/z: 265 (M+H)⁺.

ethyl 4-methyl-6-(2,2,2-trifluoroethoxy)pyridazine-3-carboxylate (less polar)

¹H-NMR (300 MHz, CDCl₃) delta 7.00 (1H, s), 4.99 (2H, q, J=8.1 Hz), 4.49 (2H, q, J=7.3 Hz), 2.58 (3H, s), 1.46 (3H, t, J=7.3 Hz), MS (ESI) m/z: 265 (M+H)⁺.

<Step-3>: (5-methyl-6-(2,2,2-trifluoroethoxy)pyridazin-3-yl)methanol

The title compound is prepared in 30% yield (373 mg, a brown oil) from ethyl 5-methyl-6-(2,2,2-trifluoroethoxy)pyridazine-3-carboxylate (1.5 g, 5.7 mmol, Step-2) in a similar manner to Step-2 of Intermediate-A1.
¹H-NMR (300 MHz, CDCl₃) delta 7.31 (1H, s), 4.93 (2H, q, J=8.1 Hz), 4.86 (2H, s), 2.31 (3H, s) (a signal due to OH is not observed), MS (ESI) m/z: 223 (M+H)⁺.

Intermediate-A15

4-methyl-5-(2,2,2-trifluoroethoxy)pyridin-2-yl)methanol

<Step-1>: 2-chloro-4-methyl-5-(2,2,2-trifluoroethoxy)pyridine

To a mixture of 6-chloro-4-methylpyridin-3-ol (2.00 g, 13.9 mmol) and cesium carbonate (6.81 g, 20.9 mmol) in DMF (40 mL) is added dropwise 2,2,2-trifluoroethyl trifluoromethanesulfonate (3.56 g, 15.3 mmol) at 0° C. After stirring at rt for 1 hour, the mixture is poured onto water (300 mL). The aqueous layer is extracted with EtOAc (300 mL). The separated organic layer is washed with water (200 mL), dried over sodium sulfate, and concentrated in vacuo. The residue is purified by column chromatography on silica gel eluting with n-hexane/EtOAc (9:1) to give 3.00 g (95% yield) of the title compound as a white solid.

$^1$H-NMR (300 MHz, CDCl$_3$) delta 7.90 (1H, s), 7.17 (1H, s), 4.43 (2H, q, J=7.3 Hz), 2.28 (3H, s), MS (ESI) m/z: 226 (M+H)$^+$.

<Step-2>: ethyl 4-methyl-5-(2,2,2-trifluoroethoxy)picolinate

The title compound is prepared in 90% yield (3.14 g, a white solid) from 2-chloro-4-methyl-5-(2,2,2-trifluoroethoxy)pyridine (3.00 g, 13.3 mmol, step-1) in a similar manner to Step-2 of Intermediate-A14.

$^1$H-NMR (300 MHz, CDCl$_3$) delta 8.24 (1H, s), 8.00 (1H, s), 4.57-4.42 (4H, m), 2.35 (3H, s), 1.44 (3H, t, J=6.6 Hz), MS (ESI) m/z: 264 (M+H)$^+$.

<Step-3>: (4-methyl-5-(2,2,2-trifluoroethoxy)pyridin-2-yl)methanol

The title compound is prepared in 72% yield (913 mg, a pale yellow solid) from ethyl 4-methyl-5-(2,2,2-trifluoroethoxy)picolinate (1.50 g, 5.7 mmol, Step-2) in a similar manner to Step-2 of Intermediate-A1.

$^1$H-NMR (300 MHz, CDCl$_3$) delta 8.09 (1H, s), 7.09 (1H, s), 4.68 (2H, d, J=3.7 Hz), 4.44 (2H, q, J=8.1 Hz), 3.44 (1H, br s), 2.30 (3H, s), MS (ESI) m/z: 222 (M+H)$^+$.

Intermediate-A16

(3-methyl-4-(2,2,2-trifluoroethoxy)phenyl)methanol

<Step-1>: 3-methyl-4-(2,2,2-trifluoroethoxy)benzoic acid

To a stirred solution of 4-hydroxy-3-methylbenzoic acid (10 g, 65.7 mmol) and cesium carbonate (64.2 g, 197 mmol) in DMF (150 mL) is added 2,2,2-trifluoroethyl trifluoromethanesulfonate (33.6 g, 145 mmol) at 0° C. The mixture is stirred at 0° C. for 10 minutes then stirred at rt for 2 days. To the mixture are added water (150 mL) and NaOH pellet (15 g), and the resulting mixture is stirred for 20 hours at rt. The mixture is diluted with water (100 mL), washed with ether (100 mL×2), and the water layer is acidified with conc. hydrochloric acid (pH 4) at 0° C. to give a white solid. The solid is collected by filtration, washed successively with water and n-hexane, and dried in vacuo at 50° C. to give 14.8 g (96% yield) of the title compound as a white solid.

$^1$H-NMR (300 MHz, CDCl$_3$) delta 7.98-7.90 (2H, m), 6.83 (1H, d, J=8.0 Hz), 4.43 (2H, q, J=7.3 Hz), 2.31 (3H, s) (a signal due to COOH is not observed), MS (ESI) m/z: 233 (M−H)$^-$.

<Step-2>: (3-methyl-4-(2,2,2-trifluoroethoxy)phenyl)methanol

The title compound is prepared in 80% yield (5.26 g, a white solid) from 3-methyl-4-(2,2,2-trifluoroethoxy)benzoic acid (7.00 g, 29.9 mmol, Step-1) in a similar manner to Step-2 of Intermediate-A1.

$^1$H-NMR (300 MHz, CDCl$_3$) delta 7.19-7.16 (2H, m), 6.78 (1H, d, J=8.4 Hz), 4.62 (2H, d, J=5.9 Hz), 4.35 (2H, q, J=8.7 Hz), 2.27 (3H, s) (a signal due to OH is not observed), MS (ESI) m/z: positive ion of a fragment signal 203 is observed.

Intermediate-A17

(4-(2,2-difluoroethoxy)-3-methylphenyl)methanol

<Step-1>: methyl 4-(2,2-difluoroethoxy)-3-methylbenzoate

To a stirred solution of methyl 4-hydroxy-3-methylbenzoate (1.5 g, 9.0 mmol), 2,2-difluoroethanol (0.90 g, 10.8 mmol), triphenylphosphine (3.6 g, 13.5 mmol) in THF (40 mL) is added dropwise diethyl azodicarboxylate (4.9 mL, 10.8 mmol, 40% solution in toluene) at 0° C. The mixture is stirred at rt for 30 minutes. Then the reaction mixture is stirred at 60° C. for 2 hours. After cooling to rt, the mixture is concentrated under reduced pressure. The residue is purified by column chromatography on silica gel eluting with n-hexane/EtOAc (18:1) to give 1.9 g (90% yield) of the title compound as a white solid.

$^1$H-NMR (300 MHz, CDCl$_3$) delta 7.90-7.85 (2H, m), 6.79 (1H, d, J=8.8 Hz), 6.13 (1H, tt, J=54.9, 4.4 Hz), 4.24 (2H, td, J=12.5, 3.7 Hz), 3.89 (3H, s), 2.27 (3H, s).

<Step-2>: (4-(2,2-difluoroethoxy)-3-methylphenyl)methanol

The title compound is prepared in quantitative yield (712 mg, a colorless oil) from methyl 4-(2,2-difluoroethoxy)-3-methylbenzoate (750 mg, 3.3 mmol, Step-1) in a similar manner to Step-2 of Intermediate-A1.

$^1$H-NMR (300 MHz, CDCl$_3$) delta 7.18-7.15 (2H, m), 6.78 (1H, d, J=8.1 Hz), 6.11 (1H, tt, J=54.9, 4.2 Hz), 4.61 (2H, d, J=5.9 Hz), 4.19 (2H, tt, J=13.0, 4.2 Hz), 2.25 (3H, s) (a signal due to OH is not observed).

Intermediate-A18

(5-methyl-6-(2,2,3,3-tetrafluoropropoxy)pyridin-3-yl)methanol

<Step-1>: 5-methyl-6-(2,2,3,3-tetrafluoropropoxy)nicotinic acid

The title compound is prepared in quantitative yield (3.7 g, a white solid) from 6-fluoro-5-methylnicotinic acid (2.0 g, 12.9 mmol) and 2,2,3,3-tetrafluoropropan-1-ol (3.4 g, 25.8 mmol) in a similar manner to Step-1 of Intermediate-A1.

$^1$H-NMR (300 MHz, CDCl$_3$) delta 8.74 (1H, d, J=2.2 Hz), 8.09 (1H, d, J=2.2 Hz), 6.00 (1H, tt, J=52.7, 3.7 Hz), 4.84 (2H, t, J=12.5 Hz), 2.28 (3H, s), a signal due to COOH is not observed, MS (ESI) m/z: 268 (M+H)$^+$.

<Step-2>: (5-methyl-6-(2,2,3,3-tetrafluoropropoxy)pyridin-3-yl)methanol

The title compound is prepared in 98% yield (0.93 g, a yellow oil) from 5-methyl-6-(2,2,3,3-tetrafluoropropoxy)nicotinic acid (1.00 g, 3.74 mmol) in a similar manner to Step-2 of Intermediate-A1.

$^1$H-NMR (300 MHz, DMSO-d$_6$) delta 7.93 (1H, s), 7.57 (1H, s), 6.68 (1H, tt, J=52.0, 5.9 Hz), 5.19 (1H, t, J=5.9 Hz), 4.84 (2H, t, J=13.9 Hz), 4.43 (2H, d, J=5.9 Hz), 2.18 (3H, s), MS (ESI) m/z: 254 (M+H)⁺.

Intermediate-A19

(2-methyl-6-(2,2,2-trifluoroethoxy)pyridin-4-yl)methanol

<Step-1>: ethyl 2-methyl-6-(2,2,2-trifluoroethoxy)isonicotinate

The title compound is prepared in 83% yield (2.42 g, a colorless oil) from ethyl 2-hydroxy-6-methylisonicotinate (2.0 g, 11.0 mmol) and 2,2,2-trifluoroethyl trifluoromethanesulfonate (2.82 g, 12.1 mmol) in a similar manner to Step-1 of Intermediate-A15.
¹H-NMR (270 MHz, CDCl₃) delta 7.36 (1H, s), 7.23 (1H, s), 4.78 (2H, q, J=8.6 Hz), 4.38 (2H, q, J=7.3 Hz), 2.50 (3H, s), 1.39 (3H, t, J=7.3 Hz), MS (ESI) m/z: 264 (M+H)⁺.

<Step-2>: (2-methyl-6-(2,2,2-trifluoroethoxy)pyridin-4-yl)methanol

The title compound is prepared in 90% yield (753 mg, a colorless oil) from ethyl 2-methyl-6-(2,2,2-trifluoroethoxy)isonicotinate (1.00 g, 3.8 mmol, Step-1) in a similar manner to Step-2 of Intermediate-A1.
¹H-NMR (300 MHz, CDCl₃) delta 6.80 (1H, s), 6.66 (1H, s), 4.76 (2H, d, J=8.8 Hz), 4.67 (2H, q, J=5.9 Hz), 2.43 (3H, s), 1.81 (1H, t, J=5.9 Hz), MS (ESI) m/z: 222 (M+H)⁺.

Intermediate-A20

(1-(5-(trifluoromethyl)pyridin-2-yl)-1H-pyrazol-3-yl)methanol

The title compound is prepared in 92% yield (1.04 g, colorless oil) from 1-(5-(trifluoromethyl)pyridin-2-yl)-1H-pyrazole-3-carboxylic acid (1.2 g, 4.7 mmol) in a similar manner to Step-2 of Intermediate-A3.
¹H-NMR (300 MHz, CDCl₃) delta 8.66 (1H, s), 8.56 (1H, d, J=2.2 Hz), 8.08-8.00 (2H, m), 6.50 (1H, d, J=2.9 Hz), 4.81 (2H, d, J=5.8 Hz), MS (ESI) m/z: 244 (M+H)⁺.

Intermediate-A21

(6-(cyclopropylmethoxy)-5-methylpyridin-3-yl)methanol

<Step-1>: 6-(cyclopropylmethoxy)-5-methylnicotinic acid

To a suspension of sodium hydride (2.04 g, 60% in oil, 53.2 mmol) in THF (30 mL), cyclopropylmethanol (3.84 g, 53.2 mmol) and methyl 6-fluoro-5-methylnicotinate (1.50 g, 8.9 mmol) are added, and the mixture is stirred at 0° C. for 1 hour. Then, 1 M aqueous sodium hydroxide solution (20 mL), EtOH (10 mL), and THF (10 mL) are added, and the mixture is stirred at 60° C. for 1 hour. After cooling to rt, the mixture is acidified by 2 M hydrochloric acid (pH 4), and the aqueous layer is extracted with EtOAc (100 mL). The organic layer is dried over sodium sulfate and concentrated in vacuo. The residue is purified by column chromatography on silica gel eluting with DCM/MeOH (20:1) to give 1.72 g of the title compound (containing ca 20% of 6-methoxy-5-methylnicotinic acid) as a white solid. This is used for the next step without further purification.
MS (ESI) m/z: 206 (M–H)⁻.

<Step-2>: (6-(cyclopropylmethoxy)-5-methylpyridin-3-yl)methanol

The title compound is prepared in 68% yield (1.10 g, a white solid) from 6-(cyclopropylmethoxy)-5-methylnicotinic acid (1.72 g, 8.30 mmol, Step-1) in a similar manner to Step-2 of Intermediate-A1.
¹H-NMR (300 MHz, CDCl₃) delta, 7.92 (1H, s), 7.45 (1H, s), 4.59 (2H, d, J=5.9 Hz), 4.15 (2H, d, J=6.6 Hz), 2.22 (3H, s), 1.54 (1H, t, J=5.9 Hz), 1.35-1.24 (1H, m), 0.62-0.55 (2H, m), 0.37-0.32 (2H, m), MS (ESI) m/z: 194 (M+H)⁺.

Intermediate-A22

(2-methoxy-6-(2,2,2-trifluoroethoxy)pyridin-3-yl)methanol

<Step-1>: methyl 2-methoxy-6-(2,2,2-trifluoroethoxy)nicotinate

The title compound is prepared in 54% yield (1.79 g, colorless oil) from methyl 6-chloro-2-methoxynicotinate (2.5 g, 12.4 mmol) and 2,2,2-trifluoroethanol (2.78 g, 24.8 mmol) in a similar manner to Step-1 of Intermediate-A6.
¹H-NMR (300 MHz, CDCl₃) delta 8.21 (1H, d, J=8.0 Hz), 6.47 (1H, d, J=8.0 Hz), 4.79 (2H, q, J=8.8 Hz), 4.07 (3H, s), 3.87 (3H, s), MS (ESI) m/z: 266 (M+H)⁺.

<Step-2>: (2-methoxy-6-(2,2,2-trifluoroethoxy)pyridin-3-yl)methanol

The title compound is prepared in 74% yield (1.19 g, a white solid) from methyl 2-methoxy-6-(2,2,2-trifluoroethoxy)nicotinate (1.79 g, 6.75 mmol, Step-1) in a similar manner to Step-2 of Intermediate-A1.
¹H-NMR (300 MHz, CDCl₃) delta 7.54 (1H, d, J=8.0 Hz), 6.41 (1H, d, J=8.0 Hz), 4.72 (2H, q, J=8.8 Hz), 4.59 (2H, s), 3.97 (3H, s), 2.10 (1H, br s), MS (ESI) m/z: 238 (M+H)⁺.

Intermediate-A23

(6-methyl-5-(2,2,2-trifluoroethoxy)pyrazin-2-yl)methanol

<Step-1>: methyl 6-methyl-5-(2,2,2-trifluoroethoxy)pyrazine-2-carboxylate

A mixture of methyl 5-chloro-6-methylpyrazine-2-carboxylate (3.00 g, 16.1 mmol), 2,2,2-trifluoroethanol (32.2 g, 322 mmol), and potassium carbonate (3.33 g, 24.1 mmol) in DMF (30 mL) is stirred at 60° C. for 2 hours. After cooling to rt, the mixture is filtered off, and the filtrate is diluted with EtOAc (300 mL). The organic layer is washed with water (100 mL×3), dried over sodium sulfate, and concentrated in vacuo. The residue is purified by column chromatography on silica gel eluting EtOAc to give 3.91 g (97% yield) of the title compound as a white solid.
MS (ESI) m/z: 251 (M+H)⁺.

<Step-2>: 6-methyl-5-(2,2,2-trifluoroethoxy)pyrazine-2-carboxylic acid

The title compound is prepared in 66% yield (2.44 g, a white solid) from methyl 6-methyl-5-(2,2,2-trifluoroethoxy)

pyrazine-2-carboxylate (3.91 g, 15.6 mmol, Step-1) in a similar manner to Step-2 of Intermediate-A6.

$^1$H-NMR (300 MHz, DMSO-d$_6$) delta 13.36 (1H, br s), 8.67 (1H, s), 5.11 (2H, q, J=8.8 Hz), 2.48 (3H, s), MS (ESI) m/z: 235 (M−H)$^−$.

<Step-3>: (6-methyl-5-(2,2,2-trifluoroethoxy)pyrazin-2-yl)methanol

The title compound is prepared in quantitative yield (1.9 g, a white solid) from 6-methyl-5-(2,2,2-trifluoroethoxy)pyrazine-2-carboxylic acid (2.0 g, 8.5 mmol, Step-2) in a similar manner to Step-2 of Intermediate-A3.

$^1$H-NMR (300 MHz, DMSO-d$_6$) delta 8.07 (1H, s), 5.46 (1H, t, J=1.5 Hz), 5.08-4.99 (2H, m), 4.54 (2H, d, J=5.8 Hz), 2.42 (3H, s), MS (ESI) m/z: 223 (M+H)$^+$ Intermediate-A24

(6-(2,2-difluoropropoxy)-5-methylpyridin-3-yl)methanol

<Step-1>: 6-(2,2-difluoropropoxy)-5-methylnicotinic acid

The title compound is prepared in 87% yield (2.14 g, a white solid) from methyl 6-fluoro-5-methylnicotinate (1.80 g, 10.6 mmol) and 2,2-difluoropropan-1-ol (1.13 g, 11.7 mmol) in a similar manner to Step-1 of Intermediate-A21.

$^1$H-NMR (300 MHz, DMSO-d$_6$) delta 8.56 (1H, d, J=1.5 Hz), 8.07 (1H, d, J=1.5 Hz), 4.64 (2H, t, J=13.2 Hz), 2.22 (3H, s), 1.75 (3H, t, J=19.1 Hz) (a signal due to COOH is not observed), MS (ESI) m/z: 230 (M−H)$^−$.

<Step-2>: (6-(2,2-difluoropropoxy)-5-methylpyridin-3-yl)methanol

The title compound is prepared in 93% yield (1.31 g, a colorless oil) from 6-(2,2-difluoropropoxy)-5-methylnicotinic acid (1.5 g, 6.5 mmol, Step-1) in a similar manner to Step-2 of Intermediate-A3.

$^1$H-NMR (300 MHz, DMSO-d$_6$) delta 7.91 (1H, s), 7.55 (1H, s), 5.17 (1H, t, J=5.8 Hz), 4.54 (2H, t, J=13.2 Hz), 4.41 (2H, d, J=5.8 Hz), 2.17 (3H, s), 1.73 (3H, t, J=19.1 Hz), MS (ESI) m/z: 218 (M+H)+

Intermediate-A25

(5-cyclopropyl-6-(2,2,2-trifluoroethoxy)pyridin-3-yl)methanol

<Step-1>: methyl 5-cyclopropyl-6-(2,2,2-trifluoroethoxy)nicotinate

A mixture of methyl 5-bromo-6-(2,2,2-trifluoroethoxy)nicotinate (1.00 g, 3.18 mmol), cyclopropylboronic acid (821 mg, 9.6 mmol), palladium(II) acetate (36 mg, 0.16 mmol), tricyclohexylphosphine (15% toluene solution, 595 mg, 0.32 mmol), and potassium phosphate (1.69 g, 7.96 mmol) in toluene-water (10:1, 11 mL) is refluxed with stirring for 12 hours. After cooling to rt, the mixture is filtered through a pad of Celite. The filtrate is concentrated in vacuo. The residue is purified by chromatography on silica gel eluting with n-hexane/EtOAc (20:1) to give 854 mg (97% yield) of the title compound as a white solid.

$^1$H-NMR (300 MHz, CDCl$_3$) delta 8.59-8.57 (1H, m), 7.76-7.74 (1H, m), 4.90-4.79 (2H, m), 3.91 (3H, s), 2.12-2.06 (1H, m), 1.04-0.98 (2H, m), 0.78-0.74 (2H, m), MS (ESI) m/z: 276 (M+H)$^+$.

<Step-2>: (5-cyclopropyl-6-(2,2,2-trifluoroethoxy)pyridin-3-yl)methanol

The title compound is prepared in 86% yield (657 mg, a white solid) from methyl 5-cyclopropyl-6-(2,2,2-trifluoroethoxy)nicotinate (850 mg, 3.09 mmol, Step-1) in a similar manner to Step-2 of Intermediate-A1.

$^1$H-NMR (300 MHz, CDCl$_3$) delta 7.88 (1H, d, J=2.2 Hz), 7.23 (1H, d, J=2.2 Hz), 4.78 (2H, q, J=8.0 Hz), 4.60 (2H, d, J=5.9), 2.13-2.04 (1H, m), 1.71 (1H, br s), 1.02-0.95 (2H, m), 0.73-0.68 (2H, m) MS (ESI) m/z: 248 (M+H)$^+$.

Intermediate-A26

(6-(4-chloro-1H-pyrazol-1-yl)-5-methylpyridin-3-yl)methanol

<Step-1>: methyl 6-(4-chloro-1H-pyrazol-1-yl)-5-methylnicotinate

A mixture of methyl 6-fluoro-5-methylnicotinate (800 mg, 4.73 mmol), 4-chloro-1H-pyrazole (509 mg, 4.97 mmol), and cesium carbonate (3.08 g, 9.46 mmol) in DMF (16 mL) stirred at 60° C. for 1 hour. After cooling to rt, the mixture is diluted with EtOAc (150 mL) and washed with water (100 mL×3). The organic phase is filtered through silica gel, and the filtrate is concentrated to give 1.19 g (quantitative yield) of the title compound as a white solid.

$^1$H-NMR (300 MHz, CDCl$_3$) delta 8.88 (1H, d, J=1.5 Hz), 8.43 (1H, s), 8.26 (1H, s), 7.68 (1H, s), 3.97 (3H, s), 2.68 (3H, s), MS (ESI) m/z: 252 (M+H)$^+$.

<Step-2>: 6-(4-chloro-1H-pyrazol-1-yl)-5-methylnicotinic acid

The title compound is prepared in 80% yield (904 mg, a white solid) from methyl 6-(4-chloro-1H-pyrazol-1-yl)-5-methylnicotinate (1.19 g, 4.7 mmol, Step-1) in a similar manner to Step-2 of Intermediate-A6.

$^1$H-NMR (300 MHz, DMSO-d$_6$) delta 8.81 (1H, s), 8.69 (1H, s), 8.36 (1H, s), 7.99 (1H, s), 2.56 (3H, s) (a signal due to COOH is not observed), MS (ESI) m/z: 236 (M−H)$^−$.

<Step-3>: (6-(4-chloro-1H-pyrazol-1-yl)-5-methylpyridin-3-yl)methanol

The title compound is prepared in 96% yield (791 mg, a white solid) from 6-(4-chloro-1H-pyrazol-1-yl)-5-methylnicotinic acid (880 mg, 3.70 mmol, Step-2) in a similar manner to Step-2 of Intermediate-A3.

$^1$H-NMR (300 MHz, CDCl$_3$) delta 8.28 (1H, br s), 8.21 (1H, s), 7.70 (1H, br s), 7.65 (1H, s), 4.76 (2H, d, J=5.3 Hz), 2.56 (3H, s), 1.93 (1H, t, J=5.3 Hz), MS (ESI) m/z: 224 (M+H)$^+$.

Intermediate-A27

1-(5-methyl-6-(2,2,2-trifluoroethoxy)pyridin-3-yl)ethanamine hydrochloride (single enantiomer; antipode of Intermediate-A7)

<Step-1>: (S)-2-methyl-N-(1-(5-methyl-6-(2,2,2-trifluoroethoxy)pyridin-3-yl)ethyl)propane-2-sulfinamide (single diastereomer)

The title compound is prepared in 83% yield (0.79 g, colorless oil) from 1-(5-methyl-6-(2,2,2-trifluoroethoxy)

pyridin-3-yl)ethanone (0.66 g, 2.81 mmol, Step-2 of Intermediate-A7) and (S)-2-methylpropane-2-sulfinamide in a similar manner to Step-3 of Intermediate-A7.

$^1$H-NMR (300 MHz, CDCl$_3$) delta 7.93 (1H, d, J=1.84 Hz), 7.44 (1H, s), 4.76 (2H, q, J=8.4 Hz), 4.54-4.46 (1H, m), 3.32 (1H, d, J=2.6 Hz), 2.24 (3H, s), 1.51 (3H, d, J=6.6 Hz), 1.23 (9H, s), MS (ESI) m/z: 339 (M+H)$^+$.

<Step-2>: 1-(5-methyl-6-(2,2,2-trifluoroethoxy)pyridin-3-yl)ethanamine hydrochloride (single enantiomer; antipode of Intermediate-A7)

The title compound is prepared in 88% yield (0.56 g, a white solid) from (S)-2-methyl-N-(1-(5-methyl-6-(2,2,2-trifluoroethoxy)pyridin-3-yl)ethyl)propane-2-sulfinamide (single diastereomer) (0.79 g, 2.33 mmol, Step-1) in a similar manner to Step-4 of Intermediate-A7.

$^1$H-NMR (300 MHz, DMSO-d$_6$) delta 8.41 (2H, br s), 8.13 (1H, d, J=2.2 Hz), 7.82 (1H, d, J=1.8 Hz), 5.02 (2H, q, J=9.2 Hz), 4.44-4.37 (1H, m), 2.19 (3H, s), 1.50 (3H, d, J=7.0 Hz), MS (ESI) m/z: 235 (M+H)$^+$.

Intermediate-A28

(5-methyl-6-(2-(2,2,2-trifluoroethoxy)ethoxy)pyridin-3-yl)methanol

<Step-1>: 5-methyl-6-(2-(2,2,2-trifluoroethoxy)ethoxy)nicotinic acid

The title compound is prepared in 73% yield (1.95 g, a white solid) from methyl 6-fluoro-5-methylnicotinate (1.60 g, 9.46 mmol) and 2-(2,2,2-trifluoroethoxy)ethanol (1.64 g, 11.4 mmol) in a similar manner to Step-1 of Intermediate-A21.

$^1$H-NMR (300 MHz, DMSO-d$_6$) delta 12.98 (1H, br s), 8.55 (1H, s), 8.01 (1H, s), 4.52-4.49 (2H, m), 4.16 (2H, q, J=9.5 Hz), 3.98-3.95 (2H, m), 2.19 (3H, s), MS (ESI) m/z: 278 (M−H)$^-$.

<Step-2>: (5-methyl-6-(2-(2,2,2-trifluoroethoxy)ethoxy)pyridin-3-yl)methanol

The title compound is prepared in 85% yield (0.97 g, colorless oil) from 5-methyl-6-(2-(2,2,2-trifluoroethoxy)ethoxy)nicotinic acid (1.2 g, 4.3 mmol, Step-1) in a similar manner to Step-2 of Intermediate-A3.

$^1$H-NMR (300 MHz, DMSO-d$_6$) delta 7.89 (1H, s), 7.49 (1H, s), 5.12 (1H, t, J=5.8 Hz), 4.41-4.38 (4H, m), 4.13 (2H, q, J=9.5 Hz), 3.92 (2H, t, J=4.4 Hz), 2.14 (3H, s), MS (ESI) m/z: 266 (M+H)$^+$.

Intermediate-A29

(5-methyl-6-((2,2,2-trifluoroethyl)amino)pyridin-3-yl)methanol

<Step-1>: 5-methyl-6-((2,2,2-trifluoroethyl)amino)nicotinic acid

A mixture of methyl 6-fluoro-5-methylnicotinate (2.00 g, 11.8 mmol) and 2,2,2-trifluoroethanamine (9.37 g, 95 mmol) in N-methylpyrrolidone (24 mL) is stirred at 220° C. for 2.5 hours under microwave irradiation. The mixture is diluted with MeOH (30 mL), and 2 M aqueous sodium hydroxide solution (15 mL) is added to the mixture. After stirring at 50° C. for 1 hour, the mixture is acidified by 2 M hydrochloric acid, and extracted with EtOAc/hexane (100 mL×3). The combined organic layer is washed with water (100 mL), dried over sodium sulfate, and concentrated in vacuo. The residue is crystallized from diisopropyl ether to give 884 mg (32%) of the title compound as a pale pink solid.

$^1$H-NMR (300 MHz, DMSO-d$_6$) delta 8.49 (1H, s), 7.78 (1H, s), 7.17 (1H, t, J=6.6 Hz), 4.35-4.21 (2H, m), 2.14 (3H, s) (a signal due to COOH is not observed), MS (ESI) m/z: 233 (M−H)$^-$.

<Step-2>: (5-methyl-6-((2,2,2-trifluoroethyl)amino)pyridin-3-yl)methanol

The title compound is prepared in 85% yield (623 mg, a white solid) from 5-methyl-6-((2,2,2-trifluoroethyl)amino)nicotinic acid (780 mg, 3.3 mmol, Step-1) in a similar manner to Step-2 of Intermediate-A3.

$^1$H-NMR (300 MHz, CDCl$_3$) delta 7.99 (1H, br s), 7.36 (1H, br s), 4.56 (2H, d, J=5.5 Hz), 4.46-4.30 (1H, m), 4.30-4.21 (2H, m), 2.15 (3H, s), 1.51 (1H, t, J=5.5 Hz), MS (ESI) m/z: 221 (M+H)$^+$.

Intermediate-A30

(3-methyl-4-(trifluoromethoxy)phenyl)methanol

<Step-1>: ethyl 3-methyl-4-(trifluoromethoxy)benzoate

The title compound is prepared in 88% yield (1.72 g, a colorless oil) from 4-bromo-2-methyl-1-(trifluoromethoxy)benzene (2.00 g, 7.84 mmol) in a similar manner to Step-2 of Intermediate-A14.

$^1$H-NMR (300 MHz, CDCl$_3$) delta 7.95-7.88 (2H, m), 7.26-7.24 (1H, m), 4.38 (2H, q, J=7.3 Hz), 2.36 (3H, s), 1.40 (3H, t, J=7.3 Hz).

<Step-2>: (3-methyl-4-(trifluoromethoxy)phenyl)methanol

The title compound is prepared in 93% yield (620 mg, a colorless oil) from ethyl 3-methyl-4-(trifluoromethoxy)benzoate (0.80 g, 3.22 mmol, Step-1) in a similar manner to Step-2 of Intermediate-A1.

$^1$H-NMR (300 MHz, CDCl$_3$) delta 7.35-7.15 (3H, m), 4.67 (2H, d, J=5.6 Hz), 2.32 (3H, s), 1.74 (1H, t, J=5.6 Hz).

Intermediate-A31

(2-(2,2,2-trifluoroethoxy)pyridin-4-yl)methanol

The title compound is prepared in 87% yield (816 mg, a colorless oil) from 2-(2,2,2-trifluoroethoxy)isonicotinic acid (1.00 g, 4.5 mmol) in a similar manner to Step-2 of Intermediate-A3.

$^1$H-NMR (300 MHz, CDCl$_3$) delta 8.10 (1H, d, J=5.1 Hz), 6.95 (1H, d, J=5.1 Hz), 6.88 (1H, s), 4.77 (2H, q, J=8.6 Hz), 4.72 (2H, d, J=5.8 Hz), 1.91 (1H, t, J=5.8 Hz), MS (ESI) m/z: 208 (M+H)$^+$.

Intermediate-A32

(5-phenyl-6-(2,2,2-trifluoroethoxy)pyridin-3-yl)methanol

<Step-1>: methyl 5-phenyl-6-(2,2,2-trifluoroethoxy)nicotinate

A mixture of methyl 5-bromo-6-(2,2,2-trifluoroethoxy)nicotinate (2.00 g, 6.37 mmol), phenylboronic acid (932 mg, 7.64 mmol), tetrakis(triphenylphosphine)palladium(0) (368 mg, 0.32 mmol), and sodium bicarbonate (1.07 g, 12.7 mmol) in dioxane-water (10:1, 22 mL) is refluxed with stirring for 18 hours. After cooling to rt, the mixture is poured onto water (30 mL), and the aqueous layer is extracted with EtOAc (30 mL×3). The combined organic layer is dried over sodium sulfate and concentrated in vacuo. The residue is purified by column chromatography on silica gel eluting with n-hexane/EtOAc (10:1) to give 1.99 g (quantitative yield) of the title compound as a white solid.

$^1$H-NMR (300 MHz, CDCl$_3$) delta 8.78 (1H, d, J=2.2 Hz), 8.31 (1H, d, J=2.2 Hz), 7.57 (2H, d, J=6.6 Hz), 7.48-7.40 (3H, m), 4.88 (2H, q, J=8.0 Hz), 3.95 (3H, s), MS (ESI) m/z: 312 (M+H)$^+$.

<Step-2>: (5-phenyl-6-(2,2,2-trifluoroethoxy)pyridin-3-yl)methanol

The title compound is prepared in 73% yield (1.26 g, a white solid) from methyl 5-phenyl-6-(2,2,2-trifluoroethoxy) nicotinate (1.90 g, 6.10 mmol) in a similar manner to Step-2 of Intermediate-A1.

$^1$H-NMR (300 MHz, CDCl$_3$) delta 8.10 (1H, d, J=2.2 Hz), 7.76 (1H, d, J=2.2 Hz), 7.6-7.3 (5H, m), 4.83 (2H, q, J=8.1 Hz), 4.72 (2H, s), 1.81 (1H, br s), MS (ESI) m/z: 284 (M+H)$^+$.

Intermediate-A33

(1-(2,2,2-trifluoroethoxy)isoquinolin-4-yl)methanol

<Step-1>: methyl 1-(2,2,2-trifluoroethoxy)isoquinoline-4-carboxylate

The title compound is prepared in 88% yield (1.14 g, a white solid) from methyl 1-chloroisoquinoline-4-carboxylate (1.00 g, 4.5 mmol) in a similar manner to Step-1 of Intermediate-A10.

$^1$H-NMR (300 MHz, CDCl$_3$) delta 8.97 (1H, d, J=8.8 Hz), 8.77 (1H, s), 8.35 (1H, d, J=8.1 Hz), 7.87-7.81 (1H, m), 7.65 (1H, t, J=8.1 Hz), 5.01 (2H, q, J=8.1 Hz), 3.99 (3H, s), MS (ESI) m/z: 286 (M+H)$^+$.

<Step-2>: (1-(2,2,2-trifluoroethoxy)isoquinolin-4-yl)methanol

The title compound is prepared in quantitative yield (0.88 g, a white solid) from methyl 1-(2,2,2-trifluoroethoxy)isoquinoline-4-carboxylate (0.98 g, 3.4 mmol, Step-1) in a similar manner to Step-2 of Intermediate-A1.

$^1$H-NMR (300 MHz, CDCl$_3$) delta 8.33 (1H, d, J=8.2 Hz), 8.12 (1H, d, J=8.2 Hz), 7.97 (1H, s), 7.83-7.78 (1H, m), 7.68-7.60 (1H, m), 5.02 (2H, d, J=5.9 Hz), 4.95 (2H, q, J=8.4 Hz), 1.68 (1H, t, J=5.9 Hz), MS (ESI) m/z: 258 (M+H)$^+$.

Intermediate-A34

(5-(2,2-difluoroethoxy)-4-methylpyridin-2-yl)methanamine

<Step-1>: 2-chloro-5-(2,2-difluoroethoxy)-4-methylpyridine

The title compound is prepared in 95% yield (4.14 g, a white solid) from 6-chloro-4-methylpyridin-3-ol (3.0 g, 20.9 mmol) and 2,2-difluoroethyl trifluoromethanesulfonate (4.92 g, 23.0 mmol) in a similar manner to Step-1 of Intermediate-A15.

$^1$H-NMR (300 MHz, CDCl$_3$) delta, 7.89 (1H, s), 7.14 (1H, s), 6.11 (1H, tt, J=54.3, 4.4 Hz), 4.26 (2H, td, J=13.2, 4.4 Hz), 2.26 (3H, s), MS (ESI) m/z: 208 (M+H)$^+$.

<Step-2>: ethyl 5-(2,2-difluoroethoxy)-4-methylpicolinate

The title compound is prepared in 87% yield (4.24 g, a white solid) from 2-chloro-5-(2,2-difluoroethoxy)-4-methylpyridine (4.14 g, 19.9 mmol, Step-1) in a similar manner to Step-2 of Intermediate-A14.

$^1$H-NMR (300 MHz, CDCl$_3$) delta, 8.24 (1H, s), 7.99 (1H, s), 6.14 (1H, tt, J=55.0, 4.4 Hz), 4.49-4.32 (4H, m), 2.32 (3H, s), 1.44 (3H, t, J=6.6 Hz), MS (ESI) m/z: 246 (M+H)$^+$.

<Step-3>: (5-(2,2-difluoroethoxy)-4-methylpyridin-2-yl)methanol

A mixture of ethyl 5-(2,2-difluoroethoxy)-4-methylpicolinate (2.0 g, 8.2 mmol, Step-2) and calcium chloride (3.62 g, 32.6 mmol) in THF-EtOH (1:1, 60 mL) is stirred at rt for 30 minutes. Then, the mixture is cooled to 0° C., and sodium borohydride (771 mg, 20.4 mmol) is added portionwise to it. After stirring 1 day, the reaction is quenched with saturated aqueous ammonium chloride solution (200 mL), and the aqueous layer is extracted with DCM (200 mL×2). The combined organic layer is dried over sodium sulfate and concentrated in vacuo. The residue is purified by column chromatography on silica gel eluting with n-hexane/EtOAc (10:1 then EtOAc only) to give 1.61 g (97% yield) of the title compound as a white solid.

$^1$H-NMR (300 MHz, DMSO-d$_6$) delta 8.18 (1H, s), 7.26 (1H, s), 6.41 (1H, tt, J=54.2, 3.7 Hz), 5.31 (1H, t, J=5.9 Hz), 4.47-4.37 (4H, m), 2.21 (3H, s), MS (ESI) m/z: 204 (M+H)

<Step-4>: 2-((5-(2,2-difluoroethoxy)-4-methylpyridin-2-yl)methyl)isoindoline-1,3-dione The title compound is prepared in 74% yield (720 mg, a white solid) from (5-(2,2-difluoroethoxy)-4-methylpyridin-2-yl)methanol (594 mg, 2.92 mmol, Step-3) and phthalimide (473 mg, 3.22 mmol) in a similar manner to Step-1 of Intermediate-A17.

$^1$H-NMR (300 MHz, CDCl$_3$) delta 8.05 (1H, s), 7.91-7.86 (2H, m), 7.78-7.70 (2H, m), 7.12 (1H, s) 6.08 (1H, tt, J=54.9, 4.5 Hz), 4.93 (2H, s), 4.27-4.17 (2H, m), 2.23 (3H, s), MS (ESI) m/z: 333 (M+H)$^+$.

<Step-5>: (5-(2,2-difluoroethoxy)-4-methylpyridin-2-yl)methanamine

To a suspension of 2-((5-(2,2-difluoroethoxy)-4-methylpyridin-2-yl)methyl)isoindoline-1,3-dione (720 mg, 2.17 mmol, Step-4) in MeOH (30 mL) is added hydrazine hydrate (0.32 mL, 6.50 mmol), and the mixture is stirred at 60° C. for 5 hours. After removal of the solvent, to the residue is added 1 M aqueous sodium hydroxide solution (100 mL), and the aqueous layer is extracted with DCM (100 mL), dried over sodium sulfate, filtered and concentrated to give 307 mg (70% yield) of the title compound as a colorless oil.

$^1$H-NMR (300 MHz, DMSO-d$_6$) delta 8.19 (1H, s), 7.25 (1H, s), 6.40 (1H, tt, J=54.2, 3.6 Hz), 4.41 (td, 1H, J=14.7

Hz, 3.6 Hz), 3.69 (2H, s), 2.19 (3H, s) (a signal due to NH2 is not observed), MS (ESI) m/z: 203 (M+H)⁺.

Intermediate-A35

(1-methyl-5-(trifluoromethoxy)-1H-indol-2-yl) methanol

<Step-1>: ethyl 1-methyl-5-(trifluoromethoxy)-1H-indole-2-carboxylate

The title compound is prepared in 99% yield (1.01 g, a brown oil) from ethyl 5-(trifluoromethoxy)-1H-indole-2-carboxylate (975 mg, 3.6 mmol, Step-1) in a similar manner to Step-2 of Intermediate-A2.

¹H-NMR (300 MHz, CDCl₃) delta 7.52 (1H, br s), 7.40-7.34 (1H, m), 7.32-7.18 (2H, m), 4.39 (2H, q, J=7.0 Hz), 4.09 (3H, s), 1.42 (3H, t, J=7.0 Hz), MS (ESI) m/z: 288 (M+H)⁺.

<Step-2>: (1-methyl-5-(trifluoromethoxy)-1H-indol-2-yl)methanol

The title compound is prepared in quantitative yield (0.88 g, a white solid) from ethyl 1-methyl-5-(trifluoromethoxy)-1H-indole-2-carboxylate (0.96 g, 3.3 mmol, Step-1) in a similar manner to Step-2 of Intermediate-A1.

¹H-NMR (300 MHz, CDCl₃) delta 7.44 (1H, s), 7.35-7.24 (1H, m), 7.20-7.05 (1H, m), 6.47 (1H, s), 4.81 (2H, d, J=5.6 Hz), 3.82 (3H, s), 1.63 (1H, t, J=5.6 Hz), MS (ESI) m/z: 246 (M+H)⁺.

Intermediate-A36

(3-chloro-4-(2,2-difluoroethoxy)phenyl)methanol

<Step-1>: methyl 3-chloro-4-(2,2-difluoroethoxy)benzoate

The title compound is prepared in 98% yield (2.0 g, a white solid) from methyl 3-chloro-4-hydroxybenzoate (1.5 g, 8.0 mmol) in a similar manner to Step-1 of Intermediate-A17.

¹H-NMR (300 MHz, CDCl₃) delta 8.09 (1H, d, J=2.2 Hz), 7.94 (1H, dd, J=8.8, 2.2 Hz), 6.94 (1H, d, J=8.0 Hz), 6.18 (1H, tt, J=54.9, 4.4 Hz), 4.30 (2H, td, J=12.5, 4.4 Hz), 3.91 (3H, s).

<Step-2>: (3-chloro-4-(2,2-difluoroethoxy)phenyl)methanol

The title compound is prepared in quantitative yield (860 mg, clear colorless oil) from methyl 3-chloro-4-(2,2-difluoroethoxy)benzoate (930 mg, 3.7 mmol, Step-1) in a similar manner to Step-2 of Intermediate-A1.

¹H-NMR (300 MHz, CDCl₃) delta 7.42 (1H, d, J=2.2 Hz), 7.22 (1H, dd, J=8.1, 2.2 Hz), 6.93 (1H, d, J=8.8 Hz), 6.15 (1H, tt, J=54.9, 4.4 Hz), 4.63 (2H, d, J=5.1 Hz), 4.24 (2H, td, J=12.8, 4.4 Hz), 1.75-1.65 (1H, m).

Intermediate-A37

5-(chloromethyl)-3-methyl-2-((2,2,2-trifluoroethoxy) methyl)pyridine hydrochloride <Step-1>: diethyl 3-methylpyridine-2,5-dicarboxylate The title compound is prepared in 72% yield (2.05 g, a yellow oil) from 2,5-dibromo-3-methylpyridine (3.00 g, 12.0 mmol) in a similar manner to Step-2 of Intermediate-A14.

¹H-NMR (300 MHz, CDCl₃) delta 9.10 (1H, d, J=1.5 Hz), 8.21 (1H, s), 4.52-4.39 (4H, m), 2.62 (3H, s), 1.48-1.40 (6H, m), MS (ESI) m/z: 238 (M+H)⁺.

<Step-2>: ethyl 6-(hydroxymethyl)-5-methylnicotinate

The title compound is prepared in 74% yield (1.25 g, a pale yellow solid) from diethyl 3-methylpyridine-2,5-dicarboxylate (2.05 g, 8.6 mmol) in a similar manner to Step-3 of Intermediate-A34.

¹H-NMR (300 MHz, CDCl₃) delta 9.02 (1H, s), 8.08 (1H, s), 4.74 (2H, s), 4.42 (2H, q, J=7.3 Hz), 2.28 (3H, s), 1.42 (3H, t, J=7.3 Hz), MS (ESI) m/z: 196 (M+H)⁺.

<Step-3>: ethyl 6-(chloromethyl)-5-methylnicotinate hydrochloride

To a solution of ethyl 6-(hydroxymethyl)-5-methylnicotinate (1.25 g, 6.40 mmol) in DCM (25 mL) is added thionyl chloride (0.93 mL, 12.8 mmol) at 0° C. After stirring at rt for 1 hour, the solvent is removed in vacuo to give 1.37 g (quantitative yield) of the title compound as a pale yellow solid.

MS (ESI) m/z: 214 (M+H)⁺.

<Step-4>: 5-methyl-6-((2,2,2-trifluoroethoxy) methyl)nicotinic acid

To a mixture of 2,2,2-trifluoroethanol (3.84 g, 38.4 mmol) and cesium carbonate (8.33 g, 25.6 mmol) in DMF (20 mL) is added ethyl 6-(chloromethyl)-5-methylnicotinate hydrochloride (1.37 g, 6.39 mmol). After stirring at 40° C. for 20 hours, 2 M aqueous sodium hydroxide solution (20 mL), water (20 mL), THF (20 mL), and EtOH (20 mL) are added to the mixture. After stirring at 60° C. for 3 hours, the mixture is acidified by 2 M hydrochloric acid (pH 4). The organic solvent is removed by evaporation, and the residual aqueous layer is extracted with EtOAc/hexane. The separated organic layer is washed with water, dried over sodium sulfate, and concentrated in vacuo. The residue is crystallized from hexane to give 1.06 g (66%) of the title compound as a white solid.

¹H-NMR (300 MHz, DMSO-d₆) delta 8.85 (1H, d, J=1.5 Hz), 8.11 (1H, s), 4.84 (2H, s), 4.22-4.12 (2H, m), 2.40 (3H, s) (a signal due to COOH is not observed), MS (ESI) m/z: 248 (M−H)⁻.

<Step-5>: (5-methyl-6-((2,2,2-trifluoroethoxy) methyl)pyridin-3-yl)methanol

The title compound is prepared in 86% yield (843 mg, a colorless oil) from 5-methyl-6-((2,2,2-trifluoroethoxy) methyl)nicotinic acid (1.04 g, 4.17 mmol, Step-4) in a similar manner to Step-2 of Intermediate-A3.

¹H-NMR (300 MHz, CDCl₃) delta 8.37 (1H, d, J=1.4 Hz), 7.56 (1H, d, J=1.4 Hz), 4.82 (2H, s), 4.72 (2H, s), 3.88 (2H, q, J=8.8 Hz), 2.42 (3H, s), 2.21-2.02 (1H, m), MS (ESI) m/z: 236 (M+H)⁺.

<Step-6>: 5-(chloromethyl)-3-methyl-2-((2,2,2-trifluoroethoxy)methyl)pyridine hydrochloride The title compound is prepared in quantitative yield (830 mg, a white solid) from (5-methyl-6-((2,2,2-trifluoroethoxy) methyl)pyridin-3-yl)methanol (693 mg, 2.95 mmol, Step-5) in a similar manner to Step-3.

¹H-NMR (300 MHz, CDCl₃) delta 8.71 (1H, s), 8.23 (1H, s), 5.28 (2H, s), 4.72 (2H, s), 4.17 (2H, q, J=8.4 Hz), 2.63 (3H, s), MS (ESI) m/z: 254 (M+H)⁺.

Intermediate-A38

2-((3-fluoro-5-(trifluoromethyl)pyridin-2-yl)oxy) ethanol

The title compound is prepared in 64% yield (785 mg, a colorless oil) from 2,3-difluoro-5-(trifluoromethyl)pyridine (1.00 g, 5.46 mmol) and ethane-1,2-diol (678 mg, 10.9 mmol) in a similar manner to Step-1 of Intermediate-A10.
¹H-NMR (300 MHz, CDCl₃) delta 8.22 (1H, s), 7.57 (1H, dd, J=9.5, 1.5 Hz), 4.62-4.59 (2H, m), 4.05-4.00 (2H, m), 2.49 (1H, t, J=5.9 Hz), MS (ESI) m/z: 226 (M+H)⁺.

Intermediate-A39: (5-(2,2,3,3,3-pentafluoropropoxy) pyridin-2-yl)methanol

<Step-1>:
2-bromo-5-(2,2,3,3,3-pentafluoropropoxy)pyridine

The title compound is prepared in quantitative yield (2.11 g, a yellow solid) from 6-bromo-4-methylpyridin-3-ol (1.20 g, 6.90 mmol) and 2,2,3,3,3-pentafluoropropyl trifluoromethanesulfonate (13.8 mmol) in a similar manner to Step-1 of Intermediate-A15.
¹H-NMR (300 MHz, CDCl₃) delta 8.13 (1H, d, J=3.4 Hz), 7.45 (1H, d, J=8.8 Hz), 7.19 (1H, dd, J=8.8, 3.4 Hz), 4.46 (2H, t, J=11.4 Hz), MS (ESI) m/z: 306 (M+H)⁺.

<Step-2>: ethyl 5-(2,2,3,3,3-pentafluoropropoxy)picolinate

The title compound is prepared in 72% yield (1.89 g, a pale orange solid) from 2-bromo-5-(2,2,3,3,3-pentafluoropropoxy)pyridine (2.11 g, 6.9 mmol) in a similar manner to Step-2 of Intermediate-A14.
¹H-NMR (300 MHz, CDCl₃) delta 8.47 (1H, d, J=2.9 Hz), 8.16 (1H, d, J=8.6 Hz), 7.34 (1H, dd, J=8.6, 2.9 Hz), 4.60-4.40 (4H, m), 1.45 (3H, t, J=7.0 Hz), MS (ESI) m/z: 300 (M+H)⁺.

<Step-3>: (5-(2,2,3,3,3-pentafluoropropoxy)pyridin-2-yl)methanol

The title compound is prepared in 80% yield (847 mg, a colorless oil) from ethyl 5-(2,2,3,3,3-pentafluoropropoxy) picolinate (1.23 g, 4.10 mmol) in a similar manner to Step-3 of Intermediate-A34.
¹H-NMR (300 MHz, CDCl₃) delta 8.31 (1H, d, J=2.6 Hz), 7.36-7.21 (2H, m), 4.74 (2H, d, J=4.9 Hz), 4.49 (2H, t, J=12.1 Hz), 3.34 (1H, t, J=4.9 Hz), MS (ESI) m/z: 258 (M+H)⁺.

Intermediate-A40

(4-(1,1,2,2-tetrafluoroethoxy)phenyl)methanol

The title compound is prepared in 82% yield (464 mg, a colorless oil) from 4-(1,1,2,2-tetrafluoroethoxy)benzoic acid (600 mg, 2.52 mmol) in a similar manner to Step-2 of Intermediate-A3.
¹H-NMR (300 MHz, CDCl₃) delta 7.39 (2H, d, J=8.4 Hz), 7.21 (2H, d, J=8.4 Hz), 5.91 (1H, tt, J=52.9, 2.9 Hz), 4.71 (2H, d, J=5.7 Hz), 1.74 (1H, t, J=5.7 Hz).

Intermediate-A41

(5-(2,2,3,3-tetrafluoropropoxy)pyridin-2-yl)methanol

<Step-1>:
2-bromo-5-(2,2,3,3-tetrafluoropropoxy)pyridine

The title compound is prepared in quantitative yield (2.25 g, a yellow solid) from 6-bromopyridin-3-ol (1.30 g, 7.47 mmol) and 2,2,3,3-tetrafluoropropan-1-ol (3.94 g, 14.9 mmol) in a similar manner to Step-1 of Intermediate-A15.
¹H-NMR (300 MHz, CDCl₃) delta 8.12 (1H, d, J=2.9 Hz), 7.44 (1H, d, J=8.8 Hz), 7.16 (1H, dd, J=8.8, 2.9 Hz), 6.03 (1H, tt, J=52.7, 4.4 Hz), 4.40 (2H, t, J=11.7 Hz), MS (ESI) m/z: 288 and 290 (M+H)⁺.

<Step-2>: ethyl 5-(2,2,3,3-tetrafluoropropoxy)picolinate

The title compound is prepared in 94% yield (2.07 g, a pale yellow solid) from 2-bromo-5-(2,2,3,3-tetrafluoropropoxy)pyridine (2.25 g, 7.81 mmol, Step-1) in a similar manner to Step-2 of Intermediate-A14.
¹H-NMR (300 MHz, CDCl₃) delta 8.46 (1H, d, J=2.9 Hz), 8.16 (1H, d, J=8.8 Hz), 8.33 (1H, dd, J=8.8, 2.9 Hz), 6.06 (1H, tt, J=52.7, 4.4 Hz), 4.52-4.44 (4H, m), 1.45 (3H, t, J=6.6 Hz), MS (ESI) m/z: 282 (M+H)⁺.

<Step-3>: (5-(2,2,3,3-tetrafluoropropoxy)pyridin-2-yl)methanol

The title compound is prepared in 91% yield (717 mg, a white solid) from ethyl 5-(2,2,3,3-tetrafluoropropoxy)picolinate (923 mg, 3.28 mmol, Step-2) in a similar manner to Step-3 of Intermediate-A34.
¹H-NMR (300 MHz, DMSO-d₆) delta 8.29 (1H, s), 7.57-7.40 (2H, m), 6.70 (1H, tt, J=52.0, 5.9 Hz), 5.37 (1H, t, J=5.9 Hz), 4.68 (2H, t, J=13.9 Hz), 4.50 (2H, d, J=5.9 Hz), MS (ESI) m/z: 240 (M+H)⁺.

Intermediate-A42

(5-chloro-6-(2,2,3,3-tetrafluoropropoxy)pyridin-3-yl)methanol

<Step-1>:
5-chloro-6-(2,2,3,3-tetrafluoropropoxy)nicotinic acid

The title compound is prepared in 97% yield (7.29 g, a pale brown solid) from 5,6-dichloronicotinic acid (5.00 g, 26.0 mmol) and 2,2,3,3-tetrafluoropropan-1-ol (5.16 g, 39.1 mmol) in a similar manner to Step-1 of Intermediate-A3.
¹H-NMR (300 MHz, CDCl₃) delta 8.77 (1H, d, J=1.5 Hz), 8.34 (1H, d, J=2.2 Hz), 6.08 (1H, tt, J=52.8, 4.5 Hz), 4.88 (2H, t, J=12.5 Hz) (a signal due to COOH is not observed), MS (ESI) m/z: 286 (M−H)⁻.

<Step-2>: (5-chloro-6-(2,2,3,3-tetrafluoropropoxy) pyridin-3-yl)methanol

The title compound is prepared in 96% yield (2.49 g, a white solid) from 5-chloro-6-(2,2,3,3-tetrafluoropropoxy) nicotinic acid (2.49 g, 8.66 mmol, Step-1) in a similar manner to Step-2 of Intermediate-A3.
¹H-NMR (300 MHz, CDCl₃) delta 8.02 (1H, d, J=2.0 Hz), 7.71 (1H, d, J=2.0 Hz), 6.09 (1H, tt, J=52.9, 4.8 Hz), 4.78

(2H, tt, J=12.2, 1.5 Hz), 4.67 (2H, d, J=5.3 Hz), 1.80 (1H, t, J=5.3 Hz), MS (ESI) m/z: 274 (M+H)$^+$.

Intermediate-A43

1-(4-methyl-5-(2,2,2-trifluoroethoxy)pyridin-2-yl) ethanamine hydrochloride (single enantiomer)

<Step-1>: 4-methyl-5-(2,2,2-trifluoroethoxy)picolinic acid

The title compound is prepared in 92% yield (2.72 g, a white solid) from ethyl 4-methyl-5-(2,2,2-trifluoroethoxy) picolinate (3.30 g, 12.5 mmol, Step-2 of Intermediate-A 15) in a similar manner to Step-2 of Intermediate-A6.
$^1$H-NMR (300 MHz, CDCl$_3$) delta 8.12 (1H, s), 8.09 (1H, s), 4.55 (2H, q, J=7.6 Hz), 2.39 (3H, s), a signal due to COOH is not observed, MS (ESI) m/z: 236 (M+H)$^+$, 234 (M−H)$^−$.

<Step-2>: N-methoxy-N,4-dimethyl-5-(2,2,2-trifluoroethoxy)picolinamide

The title compound is prepared in quantitative yield (1.6 g, an off-white solid) from 4-methyl-5-(2,2,2-trifluoroethoxy)picolinic acid (1.0 g, 4.3 mmol, Step-1) in a similar manner to Step-1 of Intermediate-A7.
$^1$H-NMR (300 MHz, CDCl$_3$, 1 drop of DMSO-d$_6$ is added) delta 8.14 (1H, s), 7.58 (1H, br s), 4.51 (2H, q, J=8.1 Hz), 3.76 (3H, s), 3.41 (3H, s), 2.32 (3H, s), MS (ESI) m/z: 279 (M+H)$^+$.

<Step-3>: 4-methyl-5-(2,2,2-trifluoroethoxy)picolinaldehyde

The title compound is prepared in 95% yield (1.2 g, a pale brown solid) from N-methoxy-N,4-dimethyl-5-(2,2,2-trifluoroethoxy)picolinamide (1.6 g, 5.8 mmol, Step-2) and lithium aluminum hydride (80 mg, 2.9 mmol) in a similar manner to Step-2 of Intermediate-A1.
$^1$H-NMR (300 MHz, CDCl$_3$) delta 9.98 (1H, s), 8.29 (1H, s), 7.85 (1H, s), 4.57 (2H, q, J=8.1 Hz), 2.36 (3H, s), MS (ESI) m/z: 220 (M+H)$^+$.

<Step-4>: (R,E)-2-methyl-N-((4-methyl-5-(2,2,2-trifluoroethoxy)pyridin-2-yl)methyl ene) -propane-2-sulfinamide (single enantiomer)

A mixture of 4-methyl-5-(2,2,2-trifluoroethoxy)picolinaldehyde (1.6 g, 7.3 mmol, Step-3), (R)-2-methylpropane-2-sulfinamide (1.33 g, 11.0 mmol), and titanium tetraethoxide (2.50 g, 11.0 mmol) in THF (30 mL) is refluxed with stirring for 2 hours. After cooling to 0° C., water (30 mL) and EtOAc (80 mL) are added to the mixture, and this is filtered through a pad of Celite. The filtrate is washed successively with water and brine, dried over sodium sulfate, and concentrated in vacuo. The residue is purified by column chromatography on silica-gel eluting with n-hexane/EtOAc (4:1-2:1) to give 1.14 g (48% yield) of the title compound as a pale yellow solid.
$^1$H-NMR (300 MHz, CDCl$_3$) delta 8.62 (1H, s), 8.25 (1H, s), 7.88 (1H, s), 4.53 (2H, q, J=8.0 Hz), 2.36 (3H, s), 1.28 (9H, s), MS (ESI) m/z: 323 (M+H)$^+$.

<Step-5>: (R)-2-methyl-N-(1-(4-methyl-5-(2,2,2-trifluoroethoxy)pyridin-2-yl)ethyl)propane-2-sulfinamide (single diastereomer)

To a solution of (R,E)-2-methyl-N-((4-methyl-5-(2,2,2-trifluoroethoxy)pyridin-2-yl)methylene)propane-2-sulfinamide (1.1 g, 3.4 mmol, Step-4) in DCM (50 mL) is added dropwise a solution of methylmagnesium bromide in THF (0.97 M, 7.0 mL, 6.8 mmol) at −78° C. After stirring at −78° C. for 1 h, the reaction is quenched with saturated aqueous ammonium chloride solution (100 mL). The aqueous layer is extracted with DCM (100 mL×2). The combined organic layer is washed with water (100 mL), dried over sodium sulfate, and concentrated in vacuo. The residue is purified by column chromatography on silica-gel eluting with n-hexane/EtOAc (1:3) to give 1.09 g (94% yield) of the title compound as a colorless oil.
$^1$H-NMR (300 MHz, CDCl$_3$) delta 8.08 (1H, s), 7.12 (1H, s), 4.65 (1H, d, J=5.4 Hz), 4.54-4.46 (1H, m), 4.42 (2H, q, J=7.9 Hz), 2.28 (3H, s), 1.48 (3H, d, J=6.6 Hz), 1.25 (9H, s), MS (ESI) m/z: 337 (M−H)$^−$.

<Step-6>: 1-(4-methyl-5-(2,2,2-trifluoroethoxy) pyridin-2-yl)ethanamine hydrochloride (single enantiomer)

The title compound is prepared in quantitative yield (1.1 g, a white solid) from (R)-2-methyl-N-(1-(4-methyl-5-(2,2,2-trifluoroethoxy)pyridin-2-yl)ethyl)propane-2-sulfinamide (1.1 g, 3.3 mmol, Step-5) in a similar manner to Step-4 of Intermediate-A7.
$^1$H-NMR (300 MHz, DMSO-d$_6$) delta 8.42 (2H, br s), 8.38 (1H, s), 7.43 (1H, s), 4.95 (2H, q, J=8.8 Hz), 4.50-4.38 (1H, m), 2.22 (3H, s), 1.45 (3H, d, J=6.6 Hz), MS (ESI) m/z: 235 (M+H)$^+$.

Intermediate-A44

(5-methyl-6-(3,3,3-trifluoropropyl)pyridin-3-yl) methanol

<Step-1>: methyl 6-chloro-5-methylnicotinate

The title compound is prepared in 93% yield (2.02 g, a white solid) from 6-chloro-5-methylnicotinic acid (2.00 g, 11.7 mmol) in a similar manner to Step-2 of Intermediate-A2.
$^1$H-NMR (300 MHz, CDCl$_3$) delta 8.83 (1H, s, J=2.2 Hz), 8.16 (1H, s), 3.95 (3H, s), 2.44 (3H, s), MS (ESI) m/z: 186 (M+H)$^+$.

<Step-2>: methyl 5-methyl-6-(3,3,3-trifluoropropyl)nicotinate

To a suspension of zinc powder (2.49 g, 38.1 mmol) in THF (15 mL), 1,2-dibromoethane (0.21 g, 1.1 mmol) and trimethylsilyl chloride (0.12 g, 1.1 mmol) are added. After stirring at rt for 20 minutes, 1,1,1-trifluoro-3-iodopropane (6.10 g, 27.2 mmol) is added, and the mixture is stirred at 55° C. for 1 hour to give a solution of (3,3,3-trifluoropropyl) zinc iodide in THF. To a mixture of methyl 6-chloro-5-methylnicotinate (2.02 g, 10.9 mmol, Step-1) and tetrakis (triphenylphosphine)palladium(0) (1.01 g, 0.87 mmol) in DMF (15 mL) is added the zinc reagent, and the mixture is stirred at 55° C. for 12 hours. After cooling to rt, the mixture is poured onto water (100 mL), and the aqueous layer is extracted with EtOAc (30 mL×2). The combined organic layer is dried over sodium sulfate and concentrated in vacuo. The residue is purified by column chromatography on silica-gel eluting with n-hexane/EtOAc (5:1 to EtOAc only) to give 2.32 g (86% yield) of the title compound as an orange solid.

¹H-NMR (300 MHz, CDCl₃) delta 8.97 (1H, d, J=1.5 Hz), 8.05 (1H, d, J=1.5 Hz), 3.94 (3H, s), 3.10-3.04 (2H, m), 2.76-2.62 (2H, m), 2.38 (3H, s) MS (ESI) m/z: 248 (M+H)⁺.

<Step-3>: (5-methyl-6-(3,3,3-trifluoropropyl)pyridin-3-yl)methanol

The title compound is prepared in quantitative yield (1.16 g, a pale yellow solid) from methyl 5-methyl-6-(3,3,3-trifluoropropyl)nicotinate (1.30 g, 5.26 mmol, Step-2) in a similar manner to Step-2 of Intermediate-A1.
¹H-NMR (300 MHz, CDCl₃) delta 8.31 (1H,s), 7.49 (1H, s), 4.67 (2H, d, J=5.9 Hz), 3.03-2.98 (2H, m), 2.68-2.51 (2H, m), 2.33 (4H, s), MS (ESI) m/z: 220 (M+H)⁺.

Intermediate-A45

(4-methyl-5-(3,3,3-trifluoropropoxy)pyridin-2-yl)methanol

<Step-1>: 2-chloro-4-methyl-5-(3,3,3-trifluoropropoxy)pyridine

The title compound is prepared in quantitative yield (3.64 g, a pale yellow solid) from 6-chloro-4-methylpyridin-3-ol (3.00 g, 20.9 mmol) and 3,3,3-trifluoropropan-1-ol (5.72 g, 50.1 mmol) in a similar manner to Step-1 of Intermediate-A17.
¹H-NMR (300 MHz, CDCl₃) delta, 7.87 (1H, s), 7.12 (1H, s), 4.27 (2H, t, J=6.6 Hz), 2.78-2.59 (2H, m), 2.22 (3H, s), MS (ESI) m/z: 240 (M+H)⁺.

<Step-2>: ethyl 4-methyl-5-(3,3,3-trifluoropropoxy)picolinate

The title compound is prepared in 93% yield (3.92 g, a pale yellow solid) from 2-chloro-4-methyl-5-(3,3,3-trifluoropropoxy)pyridine (3.64 g, 15.2 mmol, Step-1) in a similar manner to Step-2 of Intermediate-A14.
¹H-NMR (300 MHz, CDCl₃) delta, 8.24 (1H, s), 7.97 (1H, s), 4.49-4.36 (4H, m), 2.78-2.62 (2H, m), 2.29 (3H, s), 1.44 (3H, t, J=6.6 Hz), MS (ESI) m/z: 278 (M+H)⁺.

<Step-3>: (4-methyl-5-(3,3,3-trifluoropropoxy)pyridin-2-yl)methanol

The title compound is prepared in 93% yield (807 mg, a white solid) from ethyl 4-methyl-5-(3,3,3-trifluoropropoxy)picolinate (1.0 g, 3.6 mmol, Step-2) in a similar manner to Step-3 of Intermediate-A34.
¹H-NMR (300 MHz, DMSO-d₆) delta 8.16 (1H, s), 7.26 (1H, s), 5.28 (1H, t, J=5.8 Hz), 4.45 (2H, d, J=5.8 Hz), 4.30 (2H, t, J=5.8 Hz), 2.89-2.74 (2H, m), 2.17 (3H, s), MS (ESI) m/z: 236 (M+H)⁺.

Intermediate-A46

(5-chloro-6-(2,2-difluoropropoxy)pyridin-3-yl)methanol

<Step-1>: 5-chloro-6-(2,2-difluoropropoxy)nicotinic acid

The title compound is prepared in 85% yield (1.12 g, a colorless oil) from 5,6-dichloronicotinic acid (1.00 g, 5.21 mmol) and 2,2-difluoropropan-1-ol (0.50 g, 5.21 mmol) in a similar manner to Step-1 of Intermediate-A3.

¹H-NMR (300 MHz, CDCl₃) delta 8.77 (1H, d, J=2.2 Hz), 8.31 (1H, d, J=2.2 Hz), 4.64 (2H, t, J=11.7 Hz), 1.80 (3H, t, J=18.3 Hz) (a signal due to COOH is not observed), MS (ESI) m/z: 252 (M+H)⁺.

<Step-2>: (5-chloro-6-(2,2-difluoropropoxy)pyridin-3-yl)methanol

The title compound is prepared in 73% yield (689 mg, a colorless oil) from 5-chloro-6-(2,2-difluoropropoxy)nicotinic acid (1.00 g, 3.97 mmol, Step-1) in a similar manner to Step-2 of Intermediate-A3.
¹H-NMR (300 MHz, CDCl₃) delta 8.00 (1H, s), 7.74 (1H, d, J=1.5 Hz), 4.65 (2H, t, J=5.9 Hz), 4.55 (2H, d, J=11.7 Hz), 1.78 (3H, t, J=19.1 Hz), 1.6-1.5 (1H, m), MS (ESI) m/z: 238(M+H)⁺.

Intermediate-A47

(5-chloro-6-(3,3,3-trifluoropropoxy)pyridin-3-yl)methanol

<Step-1>: 5-chloro-6-(3,3,3-trifluoropropoxy)nicotinic acid

¹H-NMR (300 MHz, CDCl₃) delta 8.77 (1H, d, J=2.2 Hz), 8.29 (1H, d, J=1.5 Hz), 4.72 (2H, t, J=6.6 Hz), 2.78-2.63 (2H, m) (a signal due to COOH is not observed), MS (ESI) m/z: 270 (M+H)⁺.

<Step-2>: (5-chloro-6-(3,3,3-trifluoropropoxy)pyridin-3-yl)methanol

¹H-NMR (300 MHz, CDCl₃) delta 8.00 (1H, d, J=1.8 Hz), 7.72 (1H, d, J=1.8 Hz), 4.75-4.55 (4H, m), 2.76-2.56 (2H, m), 1.80 (1H, br s), MS (ESI) m/z: 256 (M+H)⁺.

Intermediate-A48

1-(5-methyl-6-(2,2,2-trifluoroethoxy)pyridin-3-yl)ethanol

To a solution of 1-(5-methyl-6-(2,2,2-trifluoroethoxy)pyridin-3-yl)ethanone (3.41 g, 14.6 mmol, Step-2 of Intermediate-A7) in MeOH (70 mL) is added sodium borohydride (1.11 g, 29.2 mmol) at 0° C., and the mixture is stirred at rt for 3 hours. Then, the reaction is quenched with water, and the mixture is filtered through a pad of Celite. The filtrate is extracted with EtOAc, dried over sodium sulfate, and concentrated in vacuo. The residue is purified by column chromatography on silica gel eluting with EtOAc to give 3.39 g (99%) of the title compound as a colorless oil.
¹H-NMR (300 MHz, CDCl₃) delta 7.93 (1H, s), 7.52 (1H, s), 4.93-4.83 (1H, m), 4.76 (2H, q, J=8.8 Hz), 2.24 (3H, s), 1.49 (3H, d, J=5.9 Hz), MS (ESI) m/z: 236 (M+H)⁺.

Intermediate-A49

(4-methyl-5-(2,2,3,3-tetrafluoropropoxy)pyridin-2-yl)methanamine hydrochloride

<Step-1>: 2-chloro-4-methyl-5-(2,2,3,3-tetrafluoropropoxy)pyridine

To a mixture of 6-chloro-4-methylpyridin-3-ol (5.00 g, 34.8 mmol) and cesium carbonate (34.0 g, 104 mmol) in DMF (140 mL) is added 1,1,2,2-tetrafluoro-3-iodopropane (16.9 g, 69.7 mmol), and the mixture is stirred at 90 deg for 19 hours. After cooling to rt, the mixture is poured into water (500 mL), and the aqueous layer is extracted with EtOAc/hexane (3:1. 500 mL). The separated organic layer is washed with water (300 mL), dried over sodium sulfate, and concentrated in vacuo. The residue is purified by chromatography on silica gel eluting with n-hexane/EtOAc (20:1-4:1) to give 7.97 g (89% yield) of the title compound as a pale yellow solid.

$^1$H-NMR (300 MHz, CDCl$_3$) delta 7.91 (1H, s), 7.16 (1H, s), 6.02 (1H, tt, J=53.1, 4.0 Hz), 4.43 (2H, t, J=11.7 Hz), 2.26 (3H, s), MS (ESI) m/z: 258 (M+H)$^+$.

<Step-2>: ethyl 4-methyl-5-(2,2,3,3-tetrafluoropropoxy)picolinate

The title compound is prepared in 90% yield (5.55 g, a white solid) from 2-chloro-4-methyl-5-(2,2,3,3-tetrafluoropropoxy)pyridine (5.39 g, 20.9 mmol, Step-1) in a similar manner to Step-2 of Intermediate-A14.

$^1$H-NMR (300 MHz, CDCl$_3$) delta 8.26 (1H, s), 8.00 (1H, s), 6.04 (1H, tt, J=53.1, 4.0 Hz), 4.60-4.35 (4H, m), 2.32 (3H, s), 1.44 (3H, t, J=7.1 Hz), MS (ESI) m/z: 296 (M+H)$^+$.

<Step-3>: (4-methyl-5-(2,2,3,3-tetrafluoropropoxy)pyridin-2-yl)methanol

The title compound is prepared in 80% yield (1.36 g, a colorless oil) from ethyl 4-methyl-5-(2,2,3,3-tetrafluoropropoxy)picolinate (2.00 g, 6.77 mmol, Step-2) in a similar manner to Step-3 of Intermediate-A34.

$^1$H-NMR (300 MHz, CDCl$_3$) delta 8.10 (1H, s), 7.10 (1H, s), 6.05 (1H, tt, J=53.0, 4.4 Hz), 4.68 (2H, s), 4.45 (2H, t, J=11.7 Hz), 3.58 (1H, br s), 2.28 (3H, s), MS (ESI) m/z: 254 (M+H)$^+$.

<Step-4>: 2-((4-methyl-5-(2,2,3,3-tetrafluoropropoxy)pyridin-2-yl)methyl)isoindoline-1,3-dione The title compound is prepared in 82% yield (1.70 g, a white solid) from (4-methyl-5-(2,2,3,3-tetrafluoropropoxy)pyridin-2-yl)methanol (1.36 g, 5.39 mmol, Step-3) and phthalimide (873 mg, 5.93 mmol) in a similar manner to Step-1 of Intermediate-A 17.

$^1$H-NMR (300 MHz, CDCl$_3$) delta 8.06 (1H, s), 7.93-7.83 (2H, m), 7.79-7.70 (2H, m), 7.14 (1H, s), 6.02 (1H, tt, J=53.1, 4.4 Hz), 4.93 (2H, s), 4.39 (2H, t, J=11.7 Hz), 2.28 (3H, s), MS (ESI) m/z: 383 (M+H)$^+$.

<Step-5>: (4-methyl-5-(2,2,3,3-tetrafluoropropoxy)pyridin-2-yl)methanamine hydrochloride The title compound is prepared in >99% yield (1.35 g, a white solid) from 2-((4-methyl-5-(2,2,3,3-tetrafluoropropoxy)pyridin-2-yl)methyl)isoindoline-1,3-dione (1.70 g, 4.44 mmol, Step-4) in a similar manner to Step-5 of Intermediate-A34.

$^1$H-NMR (300 MHz, DMSO-d$_6$) delta 8.45 (3H, br s), 8.41 (1H, s), 7.43 (1H, s), 6.74 (1H, tt, J=51.6, 5.5 Hz), 4.80 (2H, t, J=13.2 Hz), 4.15-4.03 (2H, m), 2.25 (3H, s), MS (ESI) m/z: 253 (M+H)$^+$.

Intermediate-A50: (5-chloro-6-(cyclopropylmethoxy)pyridin-3-yl)methanamine hydrochloride <Step-1>: 5-chloro-6-(cyclopropylmethoxy)nicotinic acid The title compound is prepared in 98% yield (4.65 g, a white solid) from 5,6-dichloronicotinic acid (4.00 g, 20.8 mmol) and cyclopropylmethanol (2.25 g, 31.3 mmol) in a similar manner to Step-1 of Intermediate-A3.

$^1$H-NMR (300 MHz, DMSO-d$_6$) delta 8.63 (1H, d, J=2.2 Hz), 8.22 (1H, d, J=2.2 Hz), 4.28 (2H, d, J=7.3 Hz), 1.38-1.20 (1H, m), 0.63-0.54 (2H, m), 0.42-0.34 (2H, m) (a signal due to COOH is not observed), MS (ESI) m/z: 226 (M−H)$^−$.

<Step-2>: (5-chloro-6-(cyclopropylmethoxy)pyridin-3-yl)methanol

The title compound is prepared in 80% yield (1.50 g, a colorless oil) from 5-chloro-6-(cyclopropylmethoxy)nicotinic acid (2.00 g, 8.79 mmol, Step-1) in a similar manner to Step-2 of Intermediate-A3.

$^1$H-NMR (300 MHz, CDCl$_3$) delta 7.98 (1H, d, J=2.2 Hz), 7.70 (1H, d, J=2.2 Hz), 4.62 (2H, d, J=5.5 Hz), 4.22 (2H, d, J=7.0 Hz), 1.71 (1H, t, J=5.6 Hz), 1.42-1.20 (1H, m), 0.66-0.51 (2H, m), 0.47-0.33 (2H, m), MS (ESI) m/z: 214 (M+H)$^+$.

<Step-3>: 2-((5-chloro-6-(cyclopropylmethoxy)pyridin-3-yl)methyl)isoindoline-1,3-dione The title compound is prepared in 74% yield (1.79 g, a white solid) from (5-chloro-6-(cyclopropylmethoxy)pyridin-3-yl)methanol (1.50 g, 7.00 mmol, Step-2) and phthalimide (1.13 g, 7.70 mmol) in a similar manner to Step-1 of Intermediate-A17.

$^1$H-NMR (300 MHz, CDCl$_3$) delta 8.12 (1H, d, J=2.2 Hz), 7.90-7.80 (2H, m), 7.76-7.70 (3H, m), 4.76 (2H, s), 4.19 (2H, d, J=7.4 Hz), 1.35-1.24 (1H, m), 0.69-0.50 (2H, m), 0.43-0.31 (2H, m), MS (ESI) m/z: 343 (M+H)$^+$.

<Step-4>: (5-chloro-6-(cyclopropylmethoxy)pyridin-3-yl)methanamine hydrochloride The title compound is prepared in 86% yield (1.12 g, a white solid) from 2-((5-chloro-6-(cyclopropylmethoxy)pyridin-3-yl)methyl)isoindoline-1,3-dione (1.79 g, 5.23 mmol, Step-3) in a similar manner to Step-5 of Intermediate-A34.

$^1$H-NMR (300 MHz, DMSO-d$_6$) delta 8.33 (3H, br s), 8.19 (1H, d, J=1.8 Hz), 8.07 (1H, d, J=1.8 Hz), 4.20 (2H, d, J=7.3 Hz), 4.05-3.94 (2H, m), 1.32-1.20 (1H, m), 0.61-0.51 (2H, m), 0.39-0.31 (2H, m), MS (ESI) m/z: 213 (M+H)$^+$.

Intermediate-A51

1-(4-methyl-5-(2,2,2-trifluoroethoxy)pyridin-2-yl)ethanamine hydrochloride (single enantiomer) (antipode of Intermediate-A43)

The title compound is prepared according to the procedure of Intermediate-A43 using (S)-2-methylpropane-2-sulfinamide instead of (R)-2-methylpropane-2-sulfinamide.

Intermediate-A52

(3-chloro-4-(2,2,2-trifluoroethoxy)phenyl)methanamine hydrochloride

<Step-1>: (3-chloro-4-(2,2,2-trifluoroethoxy)phenyl)methanol

The title compound is prepared in 69% yield (767 mg, a colorless oil) from 3-chloro-4-(2,2,2-trifluoroethoxy)benzoic acid (1.18 g, 4.63 mmol) in a similar manner to Step-2 of Intermediate-A3.

¹H-NMR (300 MHz, CDCl₃) delta 7.43 (1H, d, J=2.2 Hz), 7.26-7.22 (1H, m), 6.97 (1H, d, J=8.1 Hz), 4.65 (2H, d, J=5.9 Hz), 4.41 (2H, q, J=8.1 Hz), 1.71 (1H, t, J=5.5 Hz).

<Step-2>: 2-(3-chloro-4-(2,2,2-trifluoroethoxy)benzyl)isoindoline-1,3-dione

The title compound is prepared in 77% yield (894 mg, a white solid) from (3-chloro-4-(2,2,2-trifluoroethoxy)phenyl)methanol (760 mg, 3.16 mmol, Step-1) in a similar manner to Step-1 of Intermediate-A17.

¹H-NMR (300 MHz, CDCl₃) delta 7.89-7.73 (2H, m), 7.74-7.71 (2H, m), 7.50 (1H, d, J=2.2 Hz) 7.33 (1H, dd, J=8.1, 2.2 Hz), 6.91 (1H, d, J=8.1 Hz), 4.78 (2H, s), 4.36 (2H, q, J=8.1 Hz).

<Step-3>: (3-chloro-4-(2,2,2-trifluoroethoxy)phenyl)methanamine hydrochloride

The title compound is prepared in 89% yield (593 mg, an off-white solid) from 2-(3-chloro-4-(2,2,2-trifluoroethoxy)benzyl)isoindoline-1,3-dione (890 mg, 2.41 mmol, Step-2) in a similar manner to Step-5 of Intermediate-A34.

¹H-NMR (300 MHz, DMSO-d₆) delta 8.47 (3H, br s), 7.68 (1H, s), 7.48 (1H, d, J=8.8 Hz), 7.33 (1H, d, J=8.8 Hz), 4.91 (2H, q, J=8.8 Hz), 3.98 (2H, d, J=5.1 Hz), MS (ESI) m/z: positive ion of a fragment signal 223 is observed.

Intermediate-A53

(6-((4-fluorobenzyl)oxy)-5-methylpyridin-3-yl)methanamine hydrochloride

<Step-1>: 6-((4-fluorobenzyl)oxy)-5-methylnicotinic acid

The title compound is prepared in 69% yield (4.26 g, a white solid) from methyl 6-fluoro-5-methylnicotinate (4.00 g, 23.7 mmol) in a similar manner to Step-1 of Intermediate-A21.

¹H-NMR (300 MHz, CDCl₃DMSO-d₆) delta 8.69 (1H, d, J=2.2 Hz), 8.01 (1H, d, J=2.2 Hz), 7.45 (2H, dd, J=8.0, 5.1 Hz), 7.06 (2H, t, J=8.8 Hz), 5.43 (2H, s), 2.24 (3H, s) (a signal due to COOH is not observed), MS (ESI) m/z: 260 (M−H)⁻.

<Step-2>: (6-((4-fluorobenzyl)oxy)-5-methylpyridin-3-yl)methanol

The title compound is prepared in 91% yield (1.30 g, a white solid) from 6-((4-fluorobenzyl)oxy)-5-methylnicotinic acid (1.50 g, 5.74 mmol, Step-1) in a similar manner to Step-2 of Intermediate-A3.

¹H-NMR (300 MHz, CDCl₃) delta 7.96 (1H, d, J=1.9 Hz), 7.51-7.38 (3H, m), 7.12-7.01 (2H, m), 5.37 (2H, s), 4.60 (2H, d, J=2.2 Hz), 2.23 (3H, s), 1.68 (1H, br s), MS (ESI) m/z: 248 (M+H)⁺.

<Step-3>: 2-((6-((4-fluorobenzyl)oxy)-5-methylpyridin-3-yl)methyl)isoindoline-1,3-dione The title compound is prepared in 74% yield (1.46 g, a white solid) from (6-((4-fluorobenzyl)oxy)-5-methylpyridin-3-yl)methanol (1.30 g, 5.25 mmol, Step-2) in a similar manner to Step-1 of Intermediate-A17.

¹H-NMR (300 MHz, CDCl₃) delta 8.03 (1H, d, J=2.2 Hz), 7.83-7.70 (2H, m), 7.68-7.60 (2H, m), 7.44 (1H, d, J=1.4 Hz), 7.38-7.30 (2H, m), 7.02-6.90 (2H, m), 5.26 (2H, s), 4.68 (2H, s), 2.11 (3H, s), MS (ESI) m/z: 377 (M+H)⁺.

<Step-4>: (6-((4-fluorobenzyl)oxy)-5-methylpyridin-3-yl)methanamine hydrochloride The title compound is prepared in 92% yield (1.01 g, a pale yellow solid) from 2-((6-((4-fluorobenzyl)oxy)-5-methylpyridin-3-yl)methyl)isoindoline-1,3-dione (1.46 g, 3.88 mmol, Step-3) in a similar manner to Step-5 of Intermediate-A34.

¹H-NMR (300 MHz, DMSO-d₆) delta 8.24 (3H, br s), 8.07 (1H, d, J=1.8 Hz), 7.70 (1H, d, J=1.8 Hz), 7.55-7.43 (2H, m), 7.26-7.15 (2H, m), 5.38 (2H, s), 3.99-3.90 (2H, m), 2.19 (3H, s), MS (ESI) m/z: 247 (M+H)⁺.

Intermediate-A54

(6-cyclobutoxy-5-methylpyridin-3-yl)methanamine hydrochloride

<Step-1>: 6-cyclobutoxy-5-methylnicotinic acid

The title compound is prepared in 88% yield (1.18 g, a white solid) from 6-fluoro-5-methylnicotinic acid (1.00 g, 6.45 mmol) and cyclobutanol (837 mg, 11.6 mmol) in a similar manner to Step-1 of Intermediate-A1.

¹H-NMR (300 MHz, DMSO-d₆) delta 8.50 (1H, s), 7.97 (1H, s), 5.21 (1H, quintet, J=7.3 Hz), 2.48-2.35 (2H, m), 2.16 (3H, s), 2.15-1.99 (2H, m), 1.84-1.57 (2H, m) (a signal due to COOH is not observed), MS (ESI) m/z: 208 (M+H)⁺.

<Step-2>: (6-cyclobutoxy-5-methylpyridin-3-yl)methanol

The title compound is prepared in 87% yield (2.22 g, a white solid) from 6-cyclobutoxy-5-methylnicotinic acid (2.74 g, 13.2 mmol, Step-1) in a similar manner to Step-2 of Intermediate-A3.

¹H-NMR (300 MHz, CDCl₃) delta 7.91 (1H, s), 7.43 (1H, s), 5.21 (1H, quintet, J=7.3 Hz), 4.57 (2H, d, J=5.1 Hz), 2.58-2.41 (2H, m), 2.32-2.04 (3H, m), 2.19 (3H, s), 1.91-1.58 (2H, m), MS (ESI) m/z: 194 (M+H)⁺.

<Step-3>: 2-((6-cyclobutoxy-5-methylpyridin-3-yl)methyl)isoindoline-1,3-dione

The title compound is prepared in 83% yield (3.07 g, a white solid) from (6-cyclobutoxy-5-methylpyridin-3-yl)methanol (2.22 g, 11.5 mmol, Step-2) in a similar manner to Step-1 of Intermediate-A17.

¹H-NMR (300 MHz, CDCl₃) delta 8.05 (1H, d, J=1.8 Hz), 7.92-7.78 (2H, m), 7.74-7.68 (2H, m), 7.46 (1H, d, J=1.8 Hz), 5.17 (1H, quintet, J=7.3 Hz), 4.73 (2H, s), 2.49-2.36 (2H, m), 2.20-2.00 (2H, m), 2.14 (3H, s), 1.86-1.56 (2H, m), MS (ESI) m/z: 323 (M+H)⁺.

<Step-4>: (6-cyclobutoxy-5-methylpyridin-3-yl)methanamine hydrochloride

The title compound is prepared in 96% yield (2.10 g, a white solid) from 2-((6-cyclobutoxy-5-methylpyridin-3-yl)methyl)isoindoline-1,3-dione (3.07 g, 9.52 mmol, Step-3) in a similar manner to Step-5 of Intermediate-A34.

¹H-NMR (300 MHz, DMSO-d₆) delta 8.21 (3H, br s), 8.02 (1H, s), 7.65 (1H, s), 5.15 (1H, quintet, J=7.0 Hz), 4.00-3.88 (2H, m), 2.48-2.33 (2H, m), 2.14 (3H, s), 2.11-1.95 (2H, m), 1.84-1.55 (2H, m), MS (ESI) m/z: 193 (M+H)$^+$.

Intermediate-A55

(5-(cyclopropylmethoxy)-4-methylpyridin-2-yl)methanamine hydrochloride

<Step-1>:
2-chloro-5-(cyclopropylmethoxy)-4-methylpyridine

The title compound is prepared in 86% yield (3.57 g, a colorless oil) from 6-chloro-4-methylpyridin-3-ol (3.00 g, 20.9 mmol) and (bromomethyl)cyclopropane (3.39 g, 25.1 mmol) in a similar manner to Step-1 of Intermediate-A15.
$^1$H-NMR (300 MHz, CDCl$_3$) delta 7.84 (1H, s), 7.10 (1H, s), 3.88 (2H, d, J=6.6 Hz), 2.25 (3H, s), 1.37-1.22 (1H, m), 0.72-0.62 (2H, m), 0.43-0.33 (2H, m), MS (ESI) m/z: 198 (M+H)$^+$.

<Step-2>: ethyl 5-(cyclopropylmethoxy)-4-methylpicolinate

The title compound is prepared in 52% yield (2.21 g, a white solid) from 2-chloro-5-(cyclopropylmethoxy)-4-methylpyridine (3.57 g, 18.1 mmol, Step-1) in a similar manner to Step-2 of Intermediate-A14.
$^1$H-NMR (300 MHz, CDCl$_3$) delta 8.21 (1H, s), 7.95 (1H, s), 4.44 (2H, q, J=6.6 Hz), 3.99 (2H, d, J=6.6 Hz), 2.31 (3H, s), 1.43 (3H, t, J=6.6 Hz), 1.39-1.23 (1H, m), 0.72-0.63 (2H, m), 0.45-0.36 (2H, m), MS (ESI) m/z: 236 (M+H)$^+$.

<Step-3>: (5-(cyclopropylmethoxy)-4-methylpyridin-2-yl)methanol

The title compound is prepared in 73% yield (597 mg, a colorless oil) from ethyl 5-(cyclopropylmethoxy)-4-methylpicolinate (1.00 g, 4.25 mmol, Step-2) in a similar manner to Step-3 of Intermediate-A34.
$^1$H-NMR (300 MHz, CDCl$_3$) delta 8.05 (1H, s), 7.03 (1H, s), 4.62 (2H, s), 3.90 (2H, d, J=6.6 Hz), 2.27 (3H, s), 1.35-1.20 (1H, m), 0.69-0.60 (2H, m), 0.41-0.32 (2H, m), MS (ESI) m/z: 194 (M+H)$^+$.

<Step-4>: 2-((5-(cyclopropylmethoxy)-4-methylpyridin-2-yl)methyl)isoindoline-1,3-dione The title compound is prepared in 77% yield (767 mg, a white solid) from (5-(cyclopropylmethoxy)-4-methylpyridin-2-yl)methanol (597 mg, 3.09 mmol, Step-3) and phthalimide (500 mg, 3.40 mmol) in a similar manner to Step-1 of Intermediate-A17.
$^1$H-NMR (300 MHz, CDCl$_3$) delta 8.03 (1H, s), 7.90-7.82 (2H, m), 7.78-7.65 (2H, m), 7.09 (1H, s), 4.91 (2H, s), 3.85 (2H, d, J=6.6 Hz), 2.22 (3H, s), 1.39-1.18 (1H, m), 0.68-0.55 (2H, m), 0.38-0.28 (2H, m), MS (ESI) m/z: 323 (M+H)$^+$.

<Step-5>: (5-(cyclopropylmethoxy)-4-methylpyridin-2-yl)methanamine hydrochloride The title compound is prepared in >99% yield (581 mg, a white solid) from 2-((5-(cyclopropylmethoxy)-4-methylpyridin-2-yl)methyl)isoindoline-1,3-dione (767 mg, 2.38 mmol, Step-4) in a similar manner to Step-5 of Intermediate-A34.
$^1$H-NMR (300 MHz, DMSO-d$_6$) delta 8.39 (3H, br s), 8.27 (1H, s), 7.43 (1H, s), 4.18-4.01 (2H, m), 4.00 (2H, d, J=6.9 Hz), 2.24 (3H, s), 1.30-1.19 (1H, m), 0.64-0.53 (2H, m), 0.41-0.30 (2H, m), MS (ESI) m/z: 193 (M+H)$^+$.

Intermediate-A56

(5-methyl-6-(2,2,3,3-tetrafluoropropoxy)pyridazin-3-yl)methanol

<Step-1>: A mixture of 6-chloro-4-methyl-3-(2,2,3,3-tetrafluoropropoxy)pyridazine and 3-chloro-4-methyl-6-(2,2,3,3-tetrafluoropropoxy)pyridazine (ca 1.5:1)

The title compound is prepared in 85% yield (5.42 g, a colorless oil) from 3,6-dichloro-4-methylpyridazine (4.00 g, 24.5 mmol) and 2,2,3,3-tetrafluoropropan-1-ol (3.56 g, 27.0 mmol) in a similar manner to Step-1 of Intermediate-A 14.
MS (ESI) m/z: 259 (M+H)$^+$.

<Step-2>: ethyl 5-methyl-6-(2,2,3,3-tetrafluoropropoxy)pyridazine-3-carboxylate

The title compound is prepared in 27% yield (1.66 g, a yellow solid) from a mixture of 6-chloro-4-methyl-3-(2,2,3,3-tetrafluoropropoxy)pyridazine and 3-chloro-4-methyl-6-(2,2,3,3-tetrafluoropropoxy)pyridazine (ca 1.5:1) (5.40 g, 20.9 mmol, Step-1) in a similar manner to Step-2 of Intermediate-A14.
$^1$H-NMR (300 MHz, CDCl$_3$) delta 7.99 (1H, s), 6.02 (1H, tt, J=53.1, 3.7 Hz), 5.04 (2H, t, J=12.5 Hz), 4.50 (2H, q, J=7.3 Hz), 2.34 (3H, s), 1.46 (3H, t, J=7.3 Hz), MS (ESI) m/z: 297 (M+H)$^+$.

<Step-3>: 5-methyl-6-(2,2,3,3-tetrafluoropropoxy)pyridazine-3-carboxylic acid

The title compound is prepared in >99% yield (909 mg, a white solid) from a mixture of ethyl 5-methyl-6-(2,2,3,3-tetrafluoropropoxy)pyridazine-3-carboxylate (980 mg, 3.31 mmol, Step-2) in a similar manner to Step-2 of Intermediate-A5.
$^1$H-NMR (300 MHz, DMSO-d$_6$) delta 8.00 (1H, s), 6.75 (1H, tt, J=51.2, 5.1 Hz), 5.01 (2H, t, J=13.1 Hz), 2.26 (3H, s) (a signal due to COOH is not observed), MS (ESI) m/z: 267 (M−H)$^-$.

<Step-4>: (5-methyl-6-(2,2,3,3-tetrafluoropropoxy)pyridazin-3-yl)methanol

The title compound is prepared in 88% yield (670 mg, a white solid) from 5-methyl-6-(2,2,3,3-tetrafluoropropoxy)pyridazine-3-carboxylic acid (800 mg, 2.98 mmol, Step-3) in a similar manner to Step-2 of Intermediate-A3.
$^1$H-NMR (300 MHz, CDCl$_3$) delta 7.32 (1H, s), 6.00 (1H, tt, J=52.7, 3.7 Hz), 4.91 (2H, t, J=12.4 Hz), 4.85 (2H, s), 3.62 (1H, br s), 2.28 (3H, s), MS (ESI) m/z: 255 (M+H)$^+$.

Intermediate-A57

(5-(2,2-difluoropropoxy)-4-methylpyridin-2-yl)methanamine hydrochloride

<Step-1>:
2-chloro-5-(2,2-difluoropropoxy)-4-methylpyridine

The title compound is prepared in 98% yield (4.52 g, a pale yellow oil) from 6-chloro-4-methylpyridin-3-ol (3.00 g, 20.9 mmol) and 2,2-difluoropropyl trifluoromethanesulfonate (11.9 g, 52.2 mmol) in a similar manner to Step-1 of Intermediate-A15.

$^1$H-NMR (270 MHz, CDCl$_3$) delta 7.88 (1H, s), 7.14 (1H, s), 4.18 (2H, t, J=11.2 Hz), 2.27 (3H, s), 1.80 (3H, t, J=18.5 Hz), MS (ESI) m/z: 222 (M+H)$^+$.

<Step-2>: ethyl 5-(2,2-difluoropropoxy)-4-methylpicolinate

The title compound is prepared in 92% yield (5.35 g, a pale yellow solid) from 2-chloro-5-(2,2-difluoropropoxy)-4-methylpyridine (4.99 g, 22.5 mmol, Step-1) in a similar manner to Step-2 of Intermediate-A14.

$^1$H-NMR (300 MHz, CDCl$_3$) delta 8.23 (1H, s), 7.99 (1H, s), 4.46 (2H, q, J=7.3 Hz), 4.28 (2H, t, J=11.0 Hz), 2.33 (3H, s), 1.81 (3H, t, J=19.1 Hz), 1.44 (3H, t, J=7.3 Hz), MS (ESI) m/z: 260 (M+H)$^+$.

<Step-3>: (5-(2,2-difluoropropoxy)-4-methylpyridin-2-yl)methanol

The title compound is prepared in 62% yield (1.05 g, a colorless oil) from ethyl 5-(2,2-difluoropropoxy)-4-methylpicolinate (2.00 g, 7.71 mmol, Step-2) in a similar manner to Step-3 of Intermediate-A34.

$^1$H-NMR (300 MHz, CDCl$_3$) delta 8.07 (1H, s), 7.07 (1H, s), 4.68 (2H, s), 4.20 (2H, t, J=11.3 Hz), 2.28 (3H, s), 1.81 (3H, t, J=18.7 Hz) (a signal due to OH is not observed), MS (ESI) m/z: 218 (M+H)$^+$.

<Step-4>: 2-((5-(2,2-difluoropropoxy)-4-methylpyridin-2-yl)methyl)isoindoline-1,3-dione The title compound is prepared in 34% yield (1.05 g, a white solid) from (5-(2,2-difluoropropoxy)-4-methylpyridin-2-yl)methanol (1.05 g, 4.81 mmol, Step-3) and phthalimide (779 mg, 4.81 mmol) in a similar manner to Step-1 of Intermediate-A17.

$^1$H-NMR (300 MHz, CDCl$_3$) delta 8.04 (1H, s), 7.92-7.83 (2H, m), 7.79-7.70 (2H, m), 7.13 (1H, s), 4.93 (2H, s), 4.14 (2H, t, J=11.0 Hz), 2.24 (3H, s), 1.77 (3H, t, J=18.7 Hz), MS (ESI) m/z: 347 (M+H)$^+$.

<Step-5>: (5-(2,2-difluoropropoxy)-4-methylpyridin-2-yl)methanamine hydrochloride The title compound is prepared in >99% yield (1.35 g, a white solid) from 2-((5-(2,2-difluoropropoxy)-4-methylpyridin-2-yl)methyl)isoindoline-1,3-dione (1.70 g, 4.44 mmol, Step-4) in a similar manner to Step-5 of Intermediate-A34.

$^1$H-NMR (300 MHz, DMSO-d$_6$) delta 8.33 (1H, s), 8.31 (3H, br s), 7.36 (1H, s), 4.47 (2H, t, J=12.6 Hz), 4.08 (2H, q, J=5.5 Hz), 2.23 (3H, s), 1.77 (3H, t, J=19.4 Hz), MS (ESI) m/z: 217 (M+H)$^+$.

Intermediate-A58

(4-(2,2-difluoropropoxy)-3-methylphenyl)methanamine hydrochloride

<Step-1>: methyl 4-(2,2-difluoropropoxy)-3-methylbenzoate

The title compound is prepared in 76% yield (2.09 g, a white solid) from methyl 4-hydroxy-3-methylbenzoate (1.86 g, 11.2 mmol) and 2,2-difluoropropyl trifluoromethanesulfonate (6.37 g, 27.9 mmol) in a similar manner to Step-1 of Intermediate-A15.

$^1$H-NMR (300 MHz, CDCl$_3$) delta 7.92-7.85 (2H, m), 6.79 (1H, d, J=8.1 Hz), 4.16 (2H, t, J=11.0 Hz), 3.89 (3H, s), 2.28 (3H, s), 1.81 (3H, t, J=19.1 Hz), MS (ESI) m/z: 245 (M+H)$^+$.

<Step-2>: (4-(2,2-difluoropropoxy)-3-methylphenyl)methanol

The title compound is prepared in >99% yield (805 mg, a white solid) from methyl 4-(2,2-difluoropropoxy)-3-methylbenzoate (900 mg, 3.68 mmol, Step-1) in a similar manner to Step-2 of Intermediate-A1.

$^1$H-NMR (300 MHz, CDCl$_3$) delta 7.23-7.12 (2H, m), 6.77 (1H, d, J=8.0 Hz), 4.61 (2H, d, J=5.9 Hz), 4.11 (2H, t, J=11.0 Hz), 2.26 (3H, s), 1.80 (3H, t, J=19.1 Hz), 1.56 (1H, t, J=5.9 Hz).

<Step-3>: 2-(4-(2,2-difluoropropoxy)-3-methylbenzyl)isoindoline-1,3-dione

The title compound is prepared in 85% yield (1.10 g, a white solid) from (4-(2,2-difluoropropoxy)-3-methylphenyl)methanol (805 mg, 3.72 mmol, Step-2) and phthalimide (603 mg, 4.10 mmol) in a similar manner to Step-1 of Intermediate-A17.

$^1$H-NMR (300 MHz, CDCl$_3$) delta 7.91-7.80 (2H, m), 7.78-7.65 (2H, m), 7.32-7.23 (2H, m), 6.71 (1H, d, J=8.8 Hz), 4.76 (2H, s), 4.06 (2H, t, J=11.4 Hz), 2.21 (3H, s), 1.76 (3H, t, J=18.7 Hz), MS (ESI) m/z: 346 (M+H)$^+$.

<Step-4>: (4-(2,2-difluoropropoxy)-3-methylphenyl)methanamine hydrochloride

The title compound is prepared in >99% yield (796 mg, a white solid) from 2-(4-(2,2-difluoropropoxy)-3-methylbenzyl)isoindoline-1,3-dione (1.10 g, 3.17 mmol, Step-3) in a similar manner to Step-5 of Intermediate-A34.

$^1$H-NMR (300 MHz, DMSO-d$_6$) delta 8.20 (3H, br s), 7.32-7.22 (2H, m), 7.04 (1H, d, J=8.8 Hz), 4.30 (2H, t, J=12.5 Hz), 3.92 (2H, q, J=5.9 Hz), 2.18 (3H, s), 1.76 (3H, t, J=19.1 Hz), MS (ESI) m/z: 216 (M+H)$^+$.

Intermediate-A59

1-(4-(2,2-difluoroethoxy)-3-methylphenyl)ethanamine hydrochloride (single enantiomer)

<Step-1>: methyl 4-(2,2-difluoroethoxy)-3-methylbenzoate

To a stirred solution of methyl 4-hydroxy-3-methylbenzoate (1.5 g, 9.0 mmol), 2,2-difluoroethanol (0.90 g, 10.8 mmol), triphenylphosphine (3.6 g, 13.5 mmol) in THF (40 mL) is added dropwise diethyl azodicarboxylate (4.9 mL, 10.8 mmol, 40% solution in toluene) at 0° C. The mixture is stirred at rt for 30 minutes. Then the reaction mixture is stirred at 60° C. for 2 hours. After cooling to rt, the mixture is concentrated under reduced pressure. The residue is purified by column chromatography on silica gel eluting with n-hexane/EtOAc (18:1) to give 1.9 g (90% yield) of the title compound as white solid.

$^1$H-NMR (300 MHz, CDCl$_3$) delta 7.90-7.85 (2H, m), 6.79 (1H, d, J=8.8 Hz), 6.13 (1H, tt, J=54.9, 4.4 Hz), 4.24 (2H, td, J=12.5, 3.7 Hz), 3.89 (3H, s), 2.27 (3H, s).

<Step-2>: 4-(2,2-difluoroethoxy)-3-methylbenzoic acid

The title compound is prepared in >99% yield (1.1 g, white solid) from methyl 4-(2,2-difluoroethoxy)-3-methylbenzoate (1.0 g, 4.3 mmol, Step-1) in a similar manner to Step-2 of Intermediate-A6.

$^1$H-NMR (300 MHz, CDCl$_3$) delta 7.97-7.90 (2H, m), 6.83 (1H, d, J=8.1 Hz), 6.14 (1H, tt, J=54.9, 4.4 Hz), 4.26 (2H, td, J=12.5, 4.4 Hz), 2.28 (3H, s) (a signal due to COOH is not observed), MS (ESI) m/z: 215 (M−H)$^−$.

<Step-3>: 4-(2,2-difluoroethoxy)-N-methoxy-N,3-dimethylbenzamide

The title compound is prepared in 94% yield (900 mg, clear colorless oil) from 4-(2,2-difluoroethoxy)-3-methylbenzoic acid (800 mg, 3.7 mmol, Step-2) in a similar manner to Step-1 of Intermediate-A7.

$^1$H-NMR (300 MHz, CDCl$_3$) delta 7.60-7.50 (2H, m), 6.78 (1H, d, J=8.0 Hz), 6.13 (1H, tt, J=54.9, 4.4 Hz), 4.23 (2H, td, J=12.4, 3.7 Hz), 3.56 (3H, s), 3.35 (3H, s), 2.26 (3H, s), MS (ESI) m/z: 260 (M+H)$^+$.

<Step-4>: 1-(4-(2,2-difluoroethoxy)-3-methylphenyl)ethanone

The title compound is prepared in 98% yield (730 mg, pale yellow oil) from 4-(2,2-difluoroethoxy)-N-methoxy-N,3-dimethylbenzamide (900 mg, 3.4 mmol, Step-3) in a similar manner to Step-2 of Intermediate-A7.

$^1$H-NMR (300 MHz, CDCl$_3$) delta 7.84-7.80 (2H, m), 6.81 (1H, d, J=8.0 Hz), 6.14 (1H, tt, J=54.9, 3.7 Hz), 4.25 (2H, td, J=12.5, 3.7 Hz), 2.82 (3H, s), 2.28 (3H, s), MS (ESI) m/z: 215 (M+H)$^+$.

<Step-5>: (R)—N-(1-(4-(2,2-difluoroethoxy)-3-methylphenyl)ethyl)-2-methylpropane-2-sulfinamide (single diastereomer)

The title compound is prepared in 47% yield (520 mg, clear colorless oil) from 1-(4-(2,2-difluoroethoxy)-3-methylphenyl)ethanone (750 mg, 3.5 mmol, Step-4) and (R)-2-methylpropane-2-sulfinamide in a similar manner to Step-3 of Intermediate-A7.

$^1$H-NMR (300 MHz, CDCl$_3$) delta 7.14 (2H, br), 6.75 (1H, d, J=8.8 Hz), 6.10 (1H, tt, J=54.9, 4.4 Hz), 4.50-4.40 (1H, m), 4.17 (2H, td, J=13.2, 4.4 Hz), 3.33 (1H, br s), 2.24 (3H, s), 1.47 (3H, d, J=6.6 Hz), 1.23 (9H, s).

<Step-6>: 1-(4-(2,2-difluoroethoxy)-3-methylphenyl)ethanamine hydrochloride (single enantiomer)

The title compound is prepared in 96% yield (390 mg, white solid) from (R)—N-(1-(4-(2,2-difluoroethoxy)-3-methylphenyl)ethyl)-2-methylpropane-2-sulfinamide (single diastereomer) (750 mg, 3.5 mmol, Step-5) in a similar manner to Step-4 of Intermediate-A7.

$^1$H-NMR (300 MHz, DMSO-d$_6$) delta 8.23 (2H, br s), 7.31-7.25 (2H, m), 7.06 (1H, d, J=8.8 Hz), 6.40 (1H, tt, J=54.2, 2.9 Hz), 4.33 (2H, td, J=14.7, 3.7 Hz), 2.18 (3H, s), 1.47 (3H, d, J=6.6 Hz) (a signal due to CHNH$_2$ (benzylic proton) is not observed).

Intermediate-A60

1-(4-(2,2-difluoropropoxy)-3-methylphenyl)ethanamine hydrochloride (single enantiomer)

The title compound is prepared from 2,2-difluoropropan-1-ol instead of 2,2-difluoroethanol in a similar manner to Intermediate-A59.

$^1$H-NMR (300 MHz, DMSO-d$_6$) delta 8.24 (3H, br s), 7.32-7.26 (2H, m), 7.03 (1H, d, J=8.4 Hz), 4.35-4.20 (3H, m), 2.18 (3H, s), 1.74 (3H, t, J=19.1 Hz), 1.45 (3H, d, J=6.6 Hz), MS (ESI) m/z: 230 (M+H)$^+$.

Intermediate-A61

1-(4-(2,2-difluoroethoxy)-3-methylphenyl)ethanamine hydrochloride (single enantiomer, antipode of Intermediate-A59)

The title compound is prepared from (S)-2-methylpropane-2-sulfinamide instead of (R)-2-methylpropane-2-sulfinamide in a similar manner to Intermediate-A59.

The following intermediate compounds are commercially available or synthesized by the known procedures.

Intermediate B1: 4-chloro-1H-pyrazolo[4,3-c]pyridine

Intermediate B2: 4-chloro-6-methyl-1H-pyrazolo[4,3-c]pyridine

Intermediate B3: 4-chloro-7-methyl-1H-pyrazolo[4,3-c]pyridine

Intermediate B4: 4-chloro-3-methyl-1H-pyrazolo[4,3-c]pyridine

Intermediate B5: 4-amino-2-chloronicotinaldehyde 2,2,2-trifluoroacetic acid salt Representative Procedure for Method A The following preparation of Intermediate-1a represents the Method A.

Intermediate-1a 4-chloro-2-((5-methyl-6-(2,2,2-trifluoroethoxy)pyridin-3-yl)methyl)-2H-pyrazolo[4,3-c]pyridine To a solution of 4-chloro-2H-pyrazolo[4,3-c]pyridine (1.50 g, 9.77 mmol, Intermediate-B1) (5-methyl-6-(2,2,2-trifluoroethoxy)pyridin-3-yl)methanol (2.38 g, 10.7 mmol, Intermediate-A1) and triphenylphosphine (3.84 g, 14.7 mmol) in THF (40 mL) is added 2.2M toluene solution of diethyl azodicarboxylate (5.33 mL, 11.7 mmol) at 0° C. After stirring at rt for 16 hours, the reaction mixture is diluted with EtOAc (200 mL) and washed with water (200 mL). The organic layer is dried over sodium sulfate, and concentrated under reduced pressure. The residue is purified by column chromatography on silica gel eluting with hexane/EtOAc (5:1-4:1) to give 1.30 g (37% yield) of the title compound as a pale yellow solid and 1.62 g (46% yield) of its regioisomer (4-chloro-1-((5-methyl-6-(2,2,2-trifluoroethoxy)pyridin-3-yl)methyl)-1H-pyrazolo[4,3-c]pyridine) as a pale yellow solid.

¹H-NMR (300 MHz, CDCl$_3$) delta 8.09 (1H, s), 8.06-8.04 (2H, m), 7.48-7.45 (2H, m), 5.53 (2H, s), 4.77 (2H, q, J=8.6 Hz), 2.28 (3H, s), MS (ESI) m/z: 357 (M+H)$^+$.

Representative Procedure for Method B

The following preparation of Intermediate-52a represents the Method B.

Intermediate-52a 4-chloro-2-((5-methyl-6-((2,2,2-trifluoroethoxy)methyl)pyridin-3-yl)methyl)-2H-pyrazolo[4,3-c]pyridine A mixture of 4-chloro-2H-pyrazolo[4,3-c]pyridine (457 mg, 2.97 mmol, Intermediate-B1), 5-(chloromethyl)-3-methyl-2-((2,2,2-trifluoroethoxy)methyl)pyridine (830 mg, 3.27 mmol, Intermediate-A37), and potassium carbonate (1.65 g, 11.9 mmol) in DMF (20 mL) is stirred at 60° C. for 17 hours. After cooling to rt, the mixture is poured onto water (200 mL). The aqueous layer is extracted with EtOAc (200 mL). The separated organic layer is washed with water (100 mL), dried over sodium sulfate, and concentrated in vacuo. The residue is purified by column chromatography on silica gel eluting with hexane/EtOAc (3:1 to EtOAc only) to give 242 mg (22% yield) of the title compound as a white solid and 557 mg (51% yield) of its regioisomer as a white solid.

¹H-NMR (270 MHz, DMSO-d$_6$) delta 9.00 (1H, s), 8.47 (1H, s), 7.99 (1H, d, J=5.9 Hz), 7.65 (1H, s), 7.56 (1H, d, J=5.9 Hz), 5.74 (2H, s), 4.75 (2H, s), 4.13 (2H, q, J=10.0 Hz), 2.31 (3H, s), MS (ESI) m/z: 371 (M+H)$^+$.

Representative Procedure for Method C

The following preparation of Intermediate-1a represents the Method C.

Intermediate-1a 4-chloro-2-((5-methyl-6-(2,2,2-trifluoroethoxy)pyridin-3-yl)methyl)-2H-pyrazolo[4,3-c]pyridine <Step-1>: 2-chloro-3-((((5-methyl-6-(2,2,2-trifluoroethoxy)pyridin-3-yl)methyl)imino)methyl)pyridin-4-amine To a stirred solution of 4-amino-2-chloronicotinaldehyde trifluoroacetate (1.00 g, 3.70 mmol) and (5-methyl-6-(2,2,2-trifluoroethoxy)pyridin-3-yl)methanamine hydrochloride (1.14 g, 4.43 mmol) in THF (10 mL) is added titanium tetraisopropoxide (4.33 mL, 14.8 mmol) at rt. The resulting mixture is refluxed for 2 hours. After cooling to rt, the reaction mixture is poured into a stirred solution of 2 M aqueous sodium hydroxide solution (100 mL) at rt. Then the mixture is diluted with EtOAc (100 mL) and filtered through a pad of Celite, and washed with EtOAc (100 mL). The filtrate is washed with brine (200 mL), and the organic layer is dried over sodium sulfate. Then the organic fraction is diluted with hexane (100 mL). This solution is filtered through a silica-gel-filled glass filter, and washed with hexane/EtOAc (1:1). The filtrate is concentrated under reduced pressure to give 1.29 g (97% yield) of the title compound as a pale yellow solid.

¹H-NMR (300 MHz, CDCl$_3$) delta 9.00 (1H, s), 7.93 (1H, s), 7.87 (1H, d, J=5.9 Hz), 7.39 (1H, s), 6.46 (1H, d, J=5.9 Hz), 4.81-4.72 (4H, m), 2.24 (3H, s) (signals due to NH2 are not observed), MS (ESI) m/z: 359 (M+H)$^+$.

<Step-2>: 4-chloro-2-((5-methyl-6-(2,2,2-trifluoroethoxy)pyridin-3-yl)methyl)-2H-pyrazolo[4,3-c]pyridine A mixture of 2-chloro-3-((((5-methyl-6-(2,2,2-trifluoroethoxy)pyridin-3-yl)methyl)imino)methyl)pyridin-4-amine (1.29 g, 3.59 mmol, Step-1), iodobenzene diacetate (4.63 g, 14.4 mmol), and DMF (30 mL) is stirred at 80° C. for 2 hours. After cooling to rt, the mixture is poured onto water (150 mL), and extracted with EtOAc (150 mL×2). The combined organic fraction is washed with water (200 mL), and dried over sodium sulfate. After removal of the solvent, the residue is purified by column chromatography on silica-gel eluting with n-hexane/EtOAc (3:1-1:1) to give 0.59 g (46% yield) of the title compound as a white solid.

¹H-NMR and MS data are identical with those showed in Method A.

Representative Procedure for Method D

The following preparation of Intermediate-1d represents the Method D.

Intermediate-1d 4-chloro-6-methyl-2-((5-methyl-6-(2,2,2-trifluoroethoxy)pyridin-3-yl)methyl)-2H-pyrazolo[4,3-c]pyridine To a THF (5 mL) solution of 4-chloro-6-methyl-1H-pyrazolo[4,3-c]pyridine (0.320 g, 1.91 mmol) is added (5-methyl-6-(2,2,2-trifluoroethoxy)pyridin-3-yl)methanol (0.507 g, 2.3 mmol) and (cyanomethylene)tributylphosphorane (0.80 mL, 3.05 mmol) at rt. The resulting mixture is stirred at 60° C. for 20 hours under nitrogen atmosphere. The reaction mixture is concentrated to dryness. The crude reaction product is purified by column chromatography of silica gel eluting with hexane/EtOAc (5:1-1:2) to give 284 mg (40% yield) of the title compound as a white solid.

¹H-NMR (300 MHz, CDCl$_3$) delta 8.04-8.02 (2H, m), 7.45 (1H, br s), 7.27-7.25 (1H), 5.48 (2H, s), 4.77 (2H, q, J=8.3 Hz), 2.58 (3H, s), 2.22 (3H, s), MS (ESI) m/z: 371 (M+H)$^+$.

The following intermediate compounds are prepared using the Method A, B, C, or D from starting materials shown in Table 3-1 to 3-5. Spectral data of the intermediate compounds are shown in the Table 4-1 to 4-6.

| ID | Name | Method | Starting material-1 | Starting material-2 |
| --- | --- | --- | --- | --- |
| Table 3-1 | | | | |
| Intermediate-1f | 4-chloro-7-methyl-2-((5-methyl-6-(2,2,2-trifluoroethoxy)pyridin-3-yl)methyl)-2H-pyrazolo[4,3-c]pyridine | D | Intermediate-A1 | Intermediate-B3 |
| Intermediate-1g | 4-chloro-3-methyl-2-((5-methyl-6-(2,2,2-trifluoroethoxy)pyridin-3-yl)methyl)-2H-pyrazolo[4,3-c]pyridine | D | Intermediate-A1 | Intermediate-B4 |

| ID | Name | Method | Starting material-1 | Starting material-2 |
|---|---|---|---|---|
| Intermediate-2a | 4-chloro-2-((6-(2,2-difluoroethoxy)-5-methylpyridin-3-yl)methyl)-2H-pyrazolo[4,3-c]pyridine | A | Intermediate-A2 | Intermediate-B1 |
| Intermediate-3a | 4-chloro-2-(1-(5-methyl-6-(2,2,2-trifluoroethoxy)pyridin-3-yl)ethyl)-2H-pyrazolo[4,3-c]pyridine | A | Intermediate-A48 | Intermediate-B1 |
| Intermediate-4a | 4-chloro-2-((6-(2,2,2-trifluoroethoxy)pyridin-3-yl)methyl)-2H-pyrazolo[4,3-c]pyridine | A | (6-(2,2,2-trifluoroethoxy)pyridin-3-yl)methanol | Intermediate-B1 |
| Intermediate-5a | 4-chloro-2-((5-chloro-6-(2,2,2-trifluoroethoxy)pyridin-3-yl)methyl)-2H-pyrazolo[4,3-c]pyridine | A | Intermediate-A3 | Intermediate-B1 |
| Intermediate-6a | 4-chloro-2-((5-chloro-6-(2,2-difluoroethoxy)pyridin-3-yl)methyl)-2H-pyrazolo[4,3-c]pyridine | A | Intermediate-A4 | Intermediate-B1 |
| Intermediate-7a | 4-chloro-2-((6-(2,2-difluoroethoxy)-5-fluoropyridin-3-yl)methyl)-2H-pyrazolo[4,3-c]pyridine | A | Intermediate-A8 | Intermediate-B1 |
| Intermediate-8a | 4-chloro-2-((6-(2,2,2-trifluoroethoxy)pyridazin-3-yl)methyl)-2H-pyrazolo[4,3-c]pyridine | A | (6-(2,2,2-trifluoroethoxy)pyridazin-3-yl)methanol | Intermediate-B1 |
| Intermediate-9a | 4-chloro-2-((5-(2,2,2-trifluoroethoxy)pyridin-2-yl)methyl)-2H-pyrazolo[4,3-c]pyridine | A | (5-(2,2,2-trifluoroethoxy)pyridin-2-yl)methanol | Intermediate-B1 |
| Intermediate-10a | 4-chloro-2-((6-(3,3,3-trifluoropropoxy)pyridin-3-yl)methyl)-2H-pyrazolo[4,3-c]pyridine | A | Intermediate-A6 | Intermediate-B1 |
| Intermediate-11a | 4-chloro-2-(1-(5-methyl-6-(2,2,2-trifluoroethoxy)pyridin-3-yl)ethyl)-2H-pyrazolo[4,3-c]pyridine (single enantiomer) | C | Intermediate-A7 | Intermediate-B5 |
| Intermediate-12a | 4-chloro-2-((5-fluoro-6-(2,2,2-trifluoroethoxy)pyridin-3-yl)methyl)-2H-pyrazolo[4,3-c]pyridine | A | Intermediate-A5 | Intermediate-B1 |
| Intermediate-13a | 4-chloro-2-((6-(2,2,3,3-tetrafluoropropoxy)pyridin-3-yl)methyl)-2H-pyrazolo[4,3-c]pyridine | A | Intermediate-A9 | Intermediate-B1 |
| Intermediate-14a | 4-chloro-2-(4-(2,2,2-trifluoroethoxy)benzyl)-2H-pyrazolo-[4,3-c]pyridine | A | (4-(2,2,2-trifluoroethoxy)phenyl)methanol | Intermediate-B1 |
| Intermediate-15a | 4-chloro-2-((6-(2,2,3,3,3-pentafluoropropoxy)pyridin-3-yl)methyl)-2H-pyrazolo[4,3-c]pyridine | A | Intermediate-A10 | Intermediate-B1 |
| Intermediate-16a | 4-chloro-2-(4-(trifluoromethoxy)benzyl)-2H-pyrazolo[4,3-c]pyridine | A | (4-(trifluoromethoxy)phenyl)methanol | Intermediate-B1 |

Table 3-2

| ID | Name | Method | Starting material-1 | Starting material-2 |
|---|---|---|---|---|
| Intermediate-17a | 4-chloro-2-(1-(6-(2,2-difluoroethoxy)-5-methylpyridin-3-yl)ethyl)-2H-pyrazolo[4,3-c]pyridine (single enantiomer) | C | Intermediate-A11 | Intermediate-B5 |
| Intermediate-18a | 4-chloro-2-(2-(6-(2,2,2-trifluoroethoxy)pyridin-3-yl)ethyl)-2H-pyrazolo[4,3-c]pyridine | A | 2-(6-(2,2,2-trifluoroethoxy)pyridin-3-yl)ethanol | Intermediate-B1 |
| Intermediate-19a | 4-chloro-2-((6-(4-fluorophenoxy)-5-methylpyridin-3-yl)methyl)-2H-pyrazolo[4,3-c]pyridine | A | Intermediate-A12 | Intermediate-B1 |
| Intermediate-20a | 4-chloro-2-((4-methyl-6-(2,2,2-trifluoroethoxy)pyridin-3-yl)methyl)-2H-pyrazolo[4,3-c]pyridine | A | (4-methyl-6-(2,2,2-trifluoroethoxy)pyridin-3-yl)methanol | Intermediate-B1 |
| Intermediate-21a | 4-chloro-2-((5-methyl-6-(3,3,3-trifluoropropoxy)pyridin-3-yl)methyl)-2H-pyrazolo[4,3-c]pyridine | A | Intermediate-A13 | Intermediate-B1 |
| Intermediate-22a | 4-chloro-2-((5-methyl-6-(2,2,2-trifluoroethoxy)pyridazin-3-yl)methyl)-2H-pyrazolo[4,3-c]pyridine | A | Intermediate-A14 | Intermediate-B1 |
| Intermediate-23a | 4-chloro-2-((4-methyl-5-(2,2,2-trifluoroethoxy)pyridin-2-yl)methyl)-2H-pyrazolo[4,3-c]pyridine | A | Intermediate-A15 | Intermediate-B1 |
| Intermediate-24a | 4-chloro-2-((5-methoxy-6-(2,2,2-trifluoroethoxy)pyridin-3-yl)methyl)-2H-pyrazolo[4,3-c]pyridine | A | (5-methoxy-6-(2,2,2-trifluoroethoxy)pyridin-3-yl)methanol | Intermediate-B1 |
| Intermediate-25a | 4-chloro-2-(3-methyl-4-(2,2,2-trifluoroethoxy)benzyl)-2H-pyrazolo-[4,3-c]pyridine | A | Intermediate-A16 | Intermediate-B1 |

-continued

| ID | Name | Method | Starting material-1 | Starting material-2 |
|---|---|---|---|---|
| Intermediate-26a | 4-chloro-2-(4-(2,2-difluoroethoxy)-3-methylbenzyl)-2H-pyrazolo[4,3-c]-pyridine | A | Intermediate-A17 | Intermediate-B1 |
| Intermediate-27a | 4-chloro-2-((5-methyl-6-(2,2,3,3-tetrafluoropropoxy)pyridin-3-yl)methyl)-2H-pyrazolo[4,3-c]pyridine | A | Intermediate-A18 | Intermediate-B1 |
| Intermediate-28a | 4-chloro-2-((2-methyl-6-(2,2,2-trifluoroethoxy)pyridin-4-yl)methyl)-2H-pyrazolo[4,3-c]pyridine | A | Intermediate-A19 | Intermediate-B1 |
| Intermediate-29a | 4-chloro-2-((6-methyl-5-(2,2,2-trifluoroethoxy)pyridin-2-yl)methyl)-2H-pyrazolo[4,3-c]pyridine | A | (6-methyl-5-(2,2,2-trifluoroethoxy)pyridin-2-yl)methanol | Intermediate-B1 |
| Intermediate-30a | 4-chloro-2-((1-(5-(trifluoromethyl)pyridin-2-yl)-1H-pyrazol-3-yl)methyl)-2H-pyrazolo[4,3-c]pyridine | A | Intermediate-A20 | Intermediate-B1 |
| Intermediate-31a | 4-chloro-2-((5-methyl-6-(2-(2,2,2-trifluoroethoxy)ethoxy)pyridin-3-yl)methyl)-2H-pyrazolo[4,3-c]pyridine | A | Intermediate-A28 | Intermediate-B1 |
| Intermediate-32a | 4-chloro-2-((2-methoxy-6-(2,2,2-trifluoroethoxy)pyridin-3-yl)methyl)-2H-pyrazolo[4,3-c]pyridine | A | Intermediate-A22 | Intermediate-B1 |
| Intermediate-33a | 4-chloro-2-(2-(4-(trifluoromethyl)phenoxy)ethyl)-2H-pyrazolo[4,3-c]pyridine | A | 2-(4-(trifluoromethyl)phenoxy)ethanol | Intermediate-B1 |

Table 3-3

| ID | Name | Method | Starting material-1 | Starting material-2 |
|---|---|---|---|---|
| Intermediate-34a | 4-chloro-2-((6-methyl-5-(2,2,2-trifluoroethoxy)pyrazin-2-yl)methyl)-2H-pyrazolo[4,3-c]pyridine | A | Intermediate-A23 | Intermediate-B1 |
| Intermediate-35a | 4-chloro-2-((6-(2,2-difluoropropoxy)-5-methylpyridin-3-yl)methyl)-2H-pyrazolo[4,3-c]pyridine | A | Intermediate-A24 | Intermediate-B1 |
| Intermediate-36a | 4-chloro-2-(2-((3-chloro-5-(trifluoromethyl)pyridin-2-yl)oxy)ethyl)-2H-pyrazolo[4,3-c]pyridine | A | 2-((3-chloro-5-(trifluoromethyl)pyridin-2-yl)oxy)ethanol | Intermediate-B1 |
| Intermediate-37a | 4-chloro-2-((5-cyclopropyl-6-(2,2,2-trifluoroethoxy)pyridin-3-yl)methyl)-2H-pyrazolo[4,3-c]pyridine | A | Intermediate-A25 | Intermediate-B1 |
| Intermediate-38a | 4-chloro-2-((6-(4-chloro-1H-pyrazol-1-yl)-5-methylpyridin-3-yl)methyl)-2H-pyrazolo[4,3-c]pyridine | A | Intermediate-A26 | Intermediate-B1 |
| Intermediate-39a | 4-chloro-2-(1-(5-methyl-6-(2,2,2-trifluoroethoxy)pyridin-3-yl)ethyl)-2H-pyrazolo[4,3-c]pyridine (single enantiomer) | C | Intermediate-A27 | Intermediate-B5 |
| Intermediate-40a | 4-chloro-2-((5-methyl-2-phenyl-2H-1,2,3-triazol-4-yl)methyl)-2H-pyrazolo[4,3-c]pyridine | A | (5-methyl-2-phenyl-2H-1,2,3-triazol-4-yl)methanol | Intermediate-B1 |
| Intermediate-41a | 4-chloro-2-((6-(2,2,2-trifluoroethoxy)pyridin-2-yl)methyl)-2H-pyrazolo[4,3-c]pyridine | A | (6-(2,2,2-trifluoroethoxy)pyridin-2-yl)methanol | Intermediate-B1 |
| Intermediate-42a | 4-chloro-2-((6-(cyclopropylmethoxy)-5-methylpyridin-3-yl)methyl)-2H-pyrazolo[4,3-c]pyridine | A | Intermediate-A21 | Intermediate-B1 |
| Intermediate-43a | 5-((4-chloro-2H-pyrazolo[4,3-c]pyridin-2-yl)methyl)-3-methyl-N-(2,2,2-trifluoroethyl)pyridin-2-amine | A | Intermediate-A29 | Intermediate-B1 |
| Intermediate-44a | 4-chloro-2-(3-methyl-4-(trifluoromethoxy)benzyl)-2H-pyrazolo[4,3-c]pyridine | A | Intermediate-A30 | Intermediate-B1 |
| Intermediate-45a | 4-chloro-2-((2-(2,2,2-trifluoroethoxy)pyridin-4-yl)methyl)-2H-pyrazolo[4,3-c]pyridine | A | Intermediate-A31 | Intermediate-B1 |
| Intermediate-46a | 4-chloro-2-((5-phenyl-6-(2,2,2-trifluoroethoxy)pyridin-3-yl)methyl)-2H-pyrazolo[4,3-c]pyridine | A | Intermediate-A32 | Intermediate-B1 |
| Intermediate-47a | 4-((4-chloro-2H-pyrazolo[4,3-c]pyridin-2-yl)methyl)-1-(2,2,2-trifluoroethoxy)isoquinoline | A | Intermediate-A33 | Intermediate-B1 |
| Intermediate-48a | 4-chloro-2-(4-((2,2,2-trifluoroethoxy)methyl)benzyl)-2H-pyrazolo[4,3-c]pyridine | A | (4-((2,2,2-trifluoroethoxy)methyl)phenyl)methanol | Intermediate-B1 |
| Intermediate-49a | 4-chloro-2-((5-(2,2-difluoroethoxy)-4-methylpyridin-2-yl)methyl)-2H-pyrazolo[4,3-c]pyridine | C | Intermediate-A34 | Intermediate-B5 |

-continued

| ID | Name | Method | Starting material-1 | Starting material-2 |
|---|---|---|---|---|
| Intermediate-50a | 4-chloro-2-((1-methyl-5-(trifluoromethoxy)-1H-indol-2-yl)-methyl)2H-pyrazolo[4,3-c]pyridine | A | Intermediate-A35 | Intermediate-B1 |

Table 3-4

| ID | Name | Method | Starting material-1 | Starting material-2 |
|---|---|---|---|---|
| Intermediate-51a | 4-chloro-2-(3-chloro-4-(2,2-difluoroethoxy)benzyl)-2H-pyrazolo-[4,3-c])pyridine | A | Intermediate-A36 | Intermediate-B1 |
| Intermediate-53a | 4-chloro-2-(3-(trifluoromethoxy)benzyl)-2H-pyrazolo[4,3-c]pyridine | B | 1-(bromomethyl)-3-(trifluoromethoxy)benzene | Intermediate-B1 |
| Intermediate-54a | 4-chloro-2-(2-((3-fluoro-5-(trifluoromethyl)pyridin-2-yl)oxy)ethyl)-2H-pyrazolo[4,3-c]pyridine | A | Intermediate-A38 | Intermediate-B1 |
| Intermediate-55a | 4-chloro-2-((5-(2,2,3,3,3-pentafluoropropoxy)pyridin-2-yl)methyl)-2H-pyrazolo[4,3-c]pyridine | B | Intermediate-A39 | Intermediate-B1 |
| Intermediate-56a | 4-chloro-2-(4-(1,1,2,2-tetrafluoroethoxy)benzyl)-2H-pyrazolo[4,3-c]pyridine | A | Intermediate-A40 | Intermediate-B1 |
| Intermediate-57a | 4-chloro-2-((5-(2,2,3,3-tetrafluoropropoxy)pyridin-2-yl)methyl)-2H-pyrazolo[4,3-c]pyridine | A | Intermediate-A41 | Intermediate-B1 |
| Intermediate-58a | 4-chloro-2-((5-chloro-6-(2,2,3,3-tetrafluoropropoxy)pyridin-3-yl)methyl)-2H-pyrazolo[4,3-c]pyridine | A | Intermediate-A42 | Intermediate-B1 |
| Intermediate-59a | 4-chloro-2-(3-(trifluoromethyl)benzyl)-2H-pyrazolo[4,3-c]pyridine | B | 1-(chloromethyl)-3-(trifluoromethyl)benzene | Intermediate-B1 |
| Intermediate-60a | 4-chloro-2-(1-(4-methyl-5-(2,2,2-trifluoroethoxy)pyridin-2-yl)ethyl)-2H-pyrazolo[4,3-c]pyridine (single enantiomer) | C | Intermediate-A43 | Intermediate-B5 |
| Intermediate-61a | 4-chloro-2-((5-methyl-6-(3,3,3-trifluoropropyl)pyridin-3-yl)methyl)-2H-pyrazolo[4,3-c]pyridine | A | Intermediate-A44 | Intermediate-B1 |
| Intermediate-62a | 4-chloro-2-((4-methyl-5-(3,3,3-trifluoropropoxy)pyridin-2-yl)methyl)-2H-pyrazolo[4,3-c]pyridine | A | Intermediate-A45 | Intermediate-B1 |
| Intermediate-63a | 4-chloro-2-((5-chloro-6-(2,2-difluoropropoxy)pyridin-3-yl)methyl)-2H-pyrazolo[4,3-c]pyridine | A | Intermediate-A46 | Intermediate-B1 |
| Intermediate-64a | 4-chloro-2-((5-chloro-6-(3,3,3-trifluoropropoxy)pyridin-3-yl)methyl)-2H-pyrazolo[4,3-c]pyridine | A | Intermediate-A47 | Intermediate-B1 |
| Intermediate-65a | 4-chloro-2-((1-methyl-5-(trifluoronnethyl)-1H-benzo[d]imidazol-2-yl)methyl)-2H-pyrazolo[4,3-c]pyridine | B | 2-(chloromethyl)-1-methyl-5-(trifluoromethyl)-1H-benzo[d]imidazole | Intermediate-B1 |
| Intermediate-66a | 4-chloro-2-((4-methyl-5-(2,2,3,3-tetrafluoropropoxy)pyridin-2-yl)methyl)-2H-pyrazolo[4,3-c]pyridine | C | Intermediate-A49 | Intermediate-B5 |
| Intermediate-67a | 4-chloro-2-((5-chloro-6-(cyclopropylmethoxy)pyridin-3-yl)methyl)-2H-pyrazolo[4,3-c]pyridine | C | Intermediate-A50 | Intermediate-B5 |

Table 3-5

| ID | Name | Method | Starting material-1 | Starting material-2 |
|---|---|---|---|---|
| Intermediate-68a | 4-chloro-2-(1-(4-methyl-5-(2,2,2-trifluoroethoxy)pyridin-2-yl)ethyl)-2H-pyrazolo[4,3-c]pyridine (single enantiomer, antipode of Intermediate-60a) | C | Intermediate-A51 | Intermediate-B5 |
| Intermediate-69a | 4-chloro-2-(3-chloro-4-(2,2,2-trifluoroethoxy)benzyl)-2H-pyrazolo-[4,3-c]pyridine | C | Intermediate-A52 | Intermediate-B5 |
| Intermediate-70a | 4-chloro-2((6-(4-fluorobenzyl)oxy)-5-methylpyridin-3-yl)methyl)-2H-pyrazolo[4,3-c]pyridine | C | Intermediate-A53 | Intermediate-B5 |
| Intermediate-71a | 4-chloro-2-((6-cyclobutoxy-5-methylpyridin-3-yl)methyl)-2H-pyrazolo[4,3-c]pyridine | C | Intermediate-A54 | Intermediate-B5 |
| Intermediate-72a | 4-chloro-2-((5-(cyclopropylmethoxy)-4-methylpyridin-2-yl)methyl)-2H-pyrazolo[4,3-c]pyridine | C | Intermediate-A55 | Intermediate-B5 |
| Intermediate-73a | 4-chloro-2-((5-methyl-6-(2,2,3,3-tetrafluoropropoxy)pyridazin-3-yl)methyl)-2H-pyrazolo[4,3-c]pyridine | A | Intermediate-A56 | Intermediate-B1 |

| ID | Name | Method | Starting material-1 | Starting material-2 |
|---|---|---|---|---|
| Intermediate-74a | 4-chloro-2-((5-(2,2-difluoropropoxy)-4-methylpyridin-2-yl)methyl)-2H-pyrazolo[4,3-c]pyridine | C | Intermediate-A57 | Intermediate-B5 |
| Intermediate-75a | 4-chloro-2-(4-(2,2-difluoropropoxy)-3-methylbenzyl)-2H-pyrazolo[4,3-c]pyridine | C | Intermediate-A58 | Intermediate-B5 |
| Intermediate-76a | 4-chloro-2-(1-(4-(2,2-difluoroethoxy)-3-methylphenyl)ethyl)-2H-pyrazolo-[4,3-c]pyridine (single enantiomer) | C | Intermediate-A59 | Intermediate-B5 |
| Intermediate-77a | 4-chloro-2-(4-(2,2-difluoroethoxy)-3,5-dimethylbenzyl)-2H-pyrazolo-[4,3-c]pyridine | C | (4-(2,2-difluoroethoxy)-3,5-dimethylphenyl)methanamine | Intermediate-B5 |
| Intermediate-78a | 4-chloro-2-(3-(2,2-difluoroethoxy)-4-methylbenzyl)-2H-pyrazolo-[4,3-c]pyridine | C | (3-(2,2-difluoroethoxy)-4-methylphenyl)methanamine | Intermediate-B5 |
| Intermediate-79a | 4-chloro-2-(1-(4-(2,2-difluoropropoxy)-3-methylphenyl)ethyl)-2H-pyrazolo-[4,3-c]pyridine (single enantiomer) | C | Intermediate-A60 | Intermediate-B5 |
| Intermediate-80a | 4-chloro-2-(1-(4-(2,2-difluoroethoxy)-3-methylphenyl)ethyl)-2H-pyrazolo-[4,3-c]pyridine (single enantiomer, antipode of Intermediate-76a) | C | Intermediate-A61 | Intermediate-B5 |
| Intermediate-81a | 4-chloro-2-(4-(difluoromethoxy)-3-methylbenzyl)-2H-pyrazolo-[4,3-c]pyridine | C | (4-(difluoromethoxy)-3-methylphenyl)-methanamine | Intermediate-B5 |

| ID# | data |
|---|---|
| | Table 4-1 |
| Intermediate-1f | $^1$H-NMR (300 MHz, CDCl$_3$) δ 8.04-8.01 (2H, m), 7.83 (1H, s), 7.46 (1H, br s), 5.54 (2H, s), 4.78 (2H, q, J = 8.6 Hz), 2.53 (3H, s), 2.23 (3H, s), MS (ESI) m/z: 371 (M + H)$^+$. |
| Intermediate-1g | $^1$H-NMR (300 MHz, CDCl$_3$) δ 7.98 (1H, d, J = 5.9 Hz), 7.92 (1H, br s), 7.41 (1H, d, J = 6.6 Hz), 7.36 (1H, br s), 5.49 (2H, s), 4.74 (2H, q, J = 8.6 Hz), 2.86 (3H, s), 2.19 (3H, s), MS (ESI) m/z: 371 (M + H)$^+$. |
| Intermediate-2a | $^1$H-NMR (300 MHz, DMSO-d$_6$) δ 8.96 (1H, s), 8.16 (1H, d, J = 1.8 Hz), 7.99 (1H, d, J = 6.2 Hz), 7.68 (1H, d, J = 1.8 Hz), 7.56 (1H, d, J = 6.2 Hz), 6.38 (1H, tt, J = 55.0, 3.7 Hz), 5.65 (2H, s), 4.57 (2H, td, J = 15.0, 3.7 Hz), 2.14 (3H, s), MS (ESI) m/z: 339 (M + H)$^+$. |
| Intermediate-3a | $^1$H-NMR (270 MHz, DMSO-d$_6$) δ 8.97 (1H, s), 8.13 (1H, d, J = 2.0 Hz), 7.97 (1H, d, J = 6.3 Hz), 7.77 (1H, s), 7.56 (1H, d, J = 6.3 Hz), 6.04 (1H, q, J = 7.3 Hz), 4.97 (2H, q, J = 9.2 Hz), 2.14 (3H, s), 1.97 (3H, d, J = 6.9 Hz), MS (ESI) m/z: 371 (M + H)$^+$. |
| Intermediate-4a | $^1$H-NMR (300 MHz, CDCl$_3$) δ 8.22 (1H, d, J = 2.2 Hz), 8.11 (1H, s), 8.05 (1H, d, J = 6.6 Hz), 7.67 (1H, dd, J = 8.0, 2.2 Hz), 7.46 (1H, d, J = 5.9 Hz), 6.90 (1H, d, J = 8.8 Hz), 5.56 (2H, s), 4.77 (2H, q, J = 8.6 Hz), MS (ESI) m/z: 343 (M+ H)$^+$. |
| Intermediate-5a | $^1$H-NMR (300 MHz, DMSO-d$_6$) δ 8.97 (1H, s), 8.32 (1H, d, J = 2.2 Hz), 8.14 (1H, d, J = 2.2 Hz), 8.00 (1H, d, J = 5.9 Hz), 7.57 (1H, d, J = 5.9 Hz), 5.72 (2H, s), 5.08 (2H, q, J = 8.8 Hz), MS (ESI) m/z: 377 (M + H)$^+$. |
| Intermediate-6a | $^1$H-NMR (300 MHz, DMSO-d$_6$) δ 8.96 (1H, s), 8.28 (1H, d, J = 1.8 Hz), 8.09 (1H, d, J = 2.2 Hz), 7.98 (1H, d, J = 6.2 Hz), 7.56 (1H, d, J = 6.2 Hz), 6.40 (1H, tt, J = 54.7, 3.7 Hz), 5.69 (2H, s), 4.64 (2H, td, J = 15.0, 3.7 Hz), MS (ESI) m/z: 359 (M + H)$^+$. |
| Intermediate-7a | $^1$H-NMR (300 MHz, CDCl$_3$) δ 8.23 (1H, s), 8.21 (1H, dd, J = 5.9, 1.5 Hz), 8.00 (1H, d, J = 2.2 Hz), 7.47 (1H, d, J = 6.6 Hz), 7.38 (1H, d, J = 5.1 Hz), 6.15 (1H, tt, J = 55.4, 4.4 Hz), 5.56 (2H, s), 4.61 (2H, td, J = 13.2, 4.4 Hz), MS (ESI) m/z: 343 (M + H)$^+$. |
| Intermediate-8a | $^1$H-NMR (300 MHz, DMSO-d$_6$) δ 9.02 (1H, s), 7.99 (1H, d, J = 6.2 Hz), 7.74 (1H, d, J = 8.8 Hz), 7.55 (1H, d, J = 6.2 Hz), 7.44 (1H, d, J = 8.8 Hz), 5.99 (2H, s), 5.16 (2H, q, J = 8.8 Hz), MS (ESI) m/z: 344 (M + H)$^+$. |
| Intermediate-9a | $^1$H-NMR (300 MHz, DMSO-d$_6$) δ 8.94 (1H, s), 8.33 (1H, d, J = 2.9 Hz), 7.98 (1H, dd, J = 6.2, 0.7 Hz), 7.57-7.51 (2H, m), 7.41 (1H, d, J = 8.8 Hz), 5.77 (2H, s), 4.86 (2H, q, J = 8.8 Hz), MS (ESI) m/z: 343 (M + H)$^+$. |
| Intermediate-10a | $^1$H-NMR (300 MHz, DMSO-d$_6$) δ 8.96 (1H, s), 8.31 (1H, d, J = 1.8 Hz), 7.97 (1H, d, J = 6.2 Hz), 7.78 (1H, dd, J = 8.4, 2.6 Hz), 7.55 (1H, dd, J = 6.2, 1.1 Hz), 6.82 (1H, d, J = 8.4 Hz), 5.66 (2H, s), 4.46 (2H, t, J = 5.8 Hz), 2.85-2.66 (2H, m), MS (ESI) m/z: 357 (M + H)$^+$. |
| Intermediate-11a | $^1$H-NMR (300 MHz, DMSO-d$_6$) δ 8.99 (1H, s), 8.15 (1H, d, J = 2.2 Hz), 7.99 (1H, d, J = 5.9 Hz), 7.78 (1H, d, J = 2.2 Hz), 7.58 (1H, d, J = 5.9 Hz), 6.05 (1H, q, J = 7.3 Hz), 4.99 (2H, q, J = 8.8 Hz), 2.15 (3H, s), 1.98 (3H, d, J = 7.3 Hz), MS (ESI) m/z: 371 (M + H)$^+$. |

-continued

| ID# | data |
| --- | --- |
| Intermediate-12a | $^1$H-NMR (300 MHz, CDCl$_3$) δ 8.17 (1H, s), 8.06 (1H, dd, J = 6.6, 1.5 Hz), 8.00 (1H, br s), 7.47-7.44 (2H, m), 5.57 (2H, s), 4.84 (2H, q, J = 8.3 Hz), MS (ESI) m/z: 361 (M + H)$^+$. |
| Intermediate-13a | $^1$H-NMR (300 MHz, DMSO-d$_6$) δ 8.96 (1H, s), 8.33 (1H, d, J = 2.2 Hz), 7.98 (1H, d, J = 6.2 Hz), 7.84 (1H, dd, J = 8.4, 2.2 Hz), 7.55 (1H, d, J = 6.2 Hz), 6.95 (1H, d, J = 8.4 Hz), 6.64 (1H, tt, J = 52.1, 5.5 Hz), 5.69 (2H, s), 4.84 (2H, t, J = 14.3 Hz), MS (ESI) m/z: 375 (M + H)$^+$. |

Table 4-2

| | |
| --- | --- |
| Intermediate-14a | $^1$H-NMR (300 MHz, DMSO-d$_6$) δ 8.93 (1H, s), 7.97 (1H, d, J = 6.2 Hz), 7.55 (1H, d, J = 6.2 Hz), 7.40 (2H, d, J = 8.8 Hz), 7.04 (2H, d, J = 8.8 Hz), 5.63 (2H, s), 4.73 (2H, q, J = 8.8 Hz), MS (ESI) m/z: 342 (M + H)$^+$. |
| Intermediate-15a | $^1$H-NMR (300 MHz, DMSO-d$_6$) δ 8.99 (1H, s), 8.36 (1H, d, J = 1.8 Hz), 7.99 (1H, d, J = 6.2 Hz), 7.87 (1H, dd, J = 8.4, 2.2 Hz), 7.57 (1H, dd, J = 6.2, 1.1 Hz), 6.99 (1H, d, J = 8.8 Hz), 5.71 (2H, s), 5.09 (2H, t, J = 13.9 Hz), MS (ESI) m/z: 393 (M +H)$^+$. |
| Intermediate-16a | $^1$H-NMR (300 MHz, DMSO-d$_6$) δ 9.01 (1H, s), 8.00 (1H, d, J = 6.2 Hz), 7.59-7.50 (3H, m), 7.38 (2H, d, J = 7.7 Hz), 5.76 (2H, s), MS (ESI) m/z: 328 (M + H)$^+$. |
| Intermediate-17a | $^1$H-NMR (300 MHz, CDCl$_3$) δ 8.11 (1H, s), 8.03 (1H, d, J = 6.2 Hz), 8.00 (1H, d, J = 2.2 Hz), 7.46 (1H, d, J = 6.2 Hz), 7.42 (1H, d, J = 2.2 Hz), 6.12 (1H, tt, J = 55.8, 4.4 Hz), 5.76 (1H, q, J = 7.0 Hz), 4.54 (2H, td, J = 13.6, 4.4 Hz), 2.20 (3H, s), 2.05 (3H, d, J = 7.0 Hz), MS (ESI) m/z: 353 (M + H)$^+$. |
| Intermediate-18a | $^1$H-NMR (300 MHz, DMSO-d$_6$) δ 8.71 (1H, s), 7.98 (1H, d, J = 6.2 Hz), 7.92 (1H, d, J = 2.2 Hz), 7.61-7.56 (2H, m), 6.88 (1H, d, J = 8.4 Hz), 4.90 (2H, q, J = 8.8 Hz), 4.73 (2H, t, J = 7.0 Hz), 3.26 (2H, t, J = 7.0 Hz), MS (ESI) m/z: 357 (M + H)$^+$. |
| Intermediate-19a | $^1$H-NMR (300 MHz, DMSO-d$_6$) δ 8.96 (1H, s), 8.06 (1H, d, J = 2.2 Hz), 7.99 (1H, d, J = 6.2 Hz), 7.77 (1H, d, J = 2.2 Hz), 7.57 (1H, d, J = 6.2 Hz), 7.25-7.11 (4H, m), 5.65 (2H, s), 2.28 (3H, s), MS (ESI) m/z: 369 (M + H)$^+$. |
| Intermediate-20a | $^1$H-NMR (300 MHz, DMSO-d$_6$) δ 8.89 (1H, s), 8.18 (1H, s), 7.96 (1H, d, J = 6.2 Hz), 7.54 (1H, d, J = 6.2 Hz), 6.86 (1H, s), 5.72 (2H, s), 4.95 (2H, q, J = 8.8 Hz), 2.29 (3H, s), MS (ESI) m/z: 357 (M + H)$^+$. |
| Intermediate-21a | $^1$H-NMR (300 MHz, DMSO-d$_6$) δ 8.96 (1H, s), 8.15 (1H, d, J = 1.8 Hz), 7.99 (1H, d, J = 6.2 Hz), 7.65 (1H, d, J = 1.8 Hz), 7.57 (1H, d, J = 6.2 Hz), 5.63 (2H, s), 4.49 (2H, t, J = 5.9 Hz), 2.85-2.69 (2H, m), 2.10 (3H, s), MS (ESI) m/z: 371 (M + H)$^+$. |
| Intermediate-22a | $^1$H-NMR (300 MHz, DMSO-d$_6$) δ 9.01 (1H, s), 8.00 (1H, d, J = 6.2 Hz), 7.61 (1H, s), 7.56 (1H, d, J = 6.2 Hz), 5.94 (2H, s), 5.17 (2H, q, J = 8.8 Hz), 2.20 (3H, s), MS (ESI) m/z: 358 (M + H)$^+$. |
| Intermediate-23a | $^1$H-NMR (270 MHz, DMSO-d$_6$) δ 8.93 (1H, s), 8.29 (1H, s), 7.98 (1H, d, J = 5.9 Hz), 7.54 (1H, d, J = 5.9 Hz), 7.31 (1 H, s), 5.73 (2H, s), 4.89 (2H, q, J = 8.6 Hz), 2.20 (3H, s), MS (ESI) m/z: 357 (M + H)$^+$. |
| Intermediate-24a | $^1$H-NMR (300 MHz, DMSO-d$_6$) δ 8.96 (1H, s), 7.99 (1H, d, J = 6.2 Hz), 7.85 (1H, s), 7.58-7.53 (2H, m), 5.68 (2H, s), 4.98 (2H, q, J = 9.2 Hz), 3.81 (3H, s), MS (ESI) m/z: 373 (M + H)$^+$. |
| Intermediate-25a | $^1$H-NMR (300 MHz, DMSO-d$_6$) δ 8.93 (1H, s), 7.98 (1H, d, J = 5.9 Hz), 7.56 (1H, d, J = 6.2 Hz), 7.29-7.26 (2H, m), 7.09-7.02 (1H, m), 5.60 (2H, s), 4.74 (2H, q, J = 8.8 Hz), 2.15 (3H, s), MS (ESI) m/z: 356 (M + H)$^+$. |
| Intermediate-26a | $^1$H-NMR (300 MHz, DMSO-d$_6$) δ 8.90 (1H, s), 7.96 (1H, d, J = 6.2 Hz), 7.54 (1H, d, J = 5.7 Hz) 7.26 (1H, s), 7.24 (1H, d, J = 6.2 Hz), 6.98 (1H, d, J = 8.8 Hz), 6.36 (1H, tt, J = 54.7, 3.6 Hz), 5.57 (2H, s), 4.28 (2H, td, J = 14.7, 3.6 Hz), 2.13 (3H, s), MS (ESI) m/z: 338 (M + H)$^+$. |
| Intermediate-27a | $^1$H-NMR (300 MHz, DMSO-d$_6$) δ 8.96 (1H, s), 8.17 (1H, d, J = 2.2 Hz), 7.99 (1H, d, J = 5.9 Hz), 7.71 (1H, d, J = 2.2 Hz), 7.56 (1H, d, J = 5.9 Hz), 6.67 (1H, tt, J = 52.1, 5.9 Hz), 5.66 (2H, s), 4.85 (2H, t, J = 13.2 Hz), 2.15 (3H, s), MS (ESI) m/z: 389 (M + H)$^+$. |
| Intermediate-28a | $^1$H-NMR (300 MHz, DMSO-d$_6$) δ 8.99 (1H, s), 8.00 (1H, dd, J = 6.2, 0.7 Hz), 7.57 (1H, d, J = 6.2 Hz), 6.84 (1H, s), 6.65 (1H, s), 5.70 (2H, s), 4.94 (2H, q, J = 8.8 Hz), 2.35 (3H, s), MS (ESI) m/z: 357 (M + H)$^+$. |

Table 4-3

| | |
| --- | --- |
| Intermediate-29a | $^1$H-NMR (300 MHz, DMSO-d$_6$) δ 8.99 (1H, s), 8.19 (1H, d, J = 5.9 Hz), 7.81 (1H, d, J = 5.9 Hz), 7.43 (1H, d, J = 8.1 Hz), 7.00 (1H, d, J = 8.1 Hz), 5.72 (2H, s), 4.79 (2H, q, J = 8.8 Hz), 2.31 (3H, s), MS (ESI) m/z: 357 (M + H)$^+$. |
| Intermediate-30a | $^1$H-NMR (300 MHz, DMSO-d$_6$) δ 9.00 (1H, s), 8.89 (1H, s), 8.66 (1H, d, J = 2.2 Hz), 8.39(1H, dd, J = 8.8 and 2.2 Hz), 8.05 (1H, d, J = 8.8 Hz), 8.00 (1H, d, J = 6.6 Hz), 7.58 (1H, d, J = 6.6 Hz), 6.66 (1 H, d, J = 2.2 Hz), 5.85 (2H, s), MS (ESI) m/z: 379 (M + H)$^+$. |
| Intermediate-31a | $^1$H-NMR (300 MHz, DMSO-d$_6$) δ 8.95 (1H, s), 8.14 (1H, d, J = 2.2 Hz), 7.98 (1H, d, J = 6.6 Hz), 7.63 (1H, d, J = 1.5 Hz), 7.57 (1H, d, J = 6.6 Hz), 5.63 (2H, s), 4.44-4.37 (2H, m), 4.14 (2H, q, J = 8.8 Hz), 3.95-3.90 (2H, m), 2.12 (3H, s), MS (ESI) m/z: 401 (M + H)$^+$. |
| Intermediate-32a | $^1$H-NMR (300 MHz, DMSO-d$_6$) δ 8.82 (1H, s), 7.98 (1H, d, J = 6.6 Hz), 7.70 (1H, d, J = 8.1 Hz), 7.55 (1H, d, J = 6.6 Hz), 6.55 (1H, d, J = 8.1 Hz), 5.76 (2H, s), 5.00 (2H, q, J = 8.8 Hz), 3.91 (3H, s), MS (ESI) m/z: 373 (M + H)$^+$. |
| Intermediate-33a | $^1$H-NMR (300 MHz, DMSO-d$_6$) δ 8.90 (1H, s), 7.98 (1H, d, J = 6.2 Hz), 7.66-7.53 (3H, m), 7.09 (2H, d, J = 8.8 Hz), 4.91 (2H, t, J = 5.1 Hz), 4.63 (2H, t, J = 5.1 Hz), MS (ESI) m/z: 342 (M + H)$^+$. |
| Intermediate-34a | $^1$H-NMR (300 MHz, DMSO-d$_6$) δ 8.97 (1H, s), 8.25 (1H, s), 7.99 (1H, d, J = 5.9 Hz), 7.55 (1H, d, J = 5.9 Hz), 5.79 (2H, s), 5.05 (2H, q, J = 8.8 Hz), 2.39 (3H, s), MS (ESI) m/z: 358 (M + H)$^+$. |

| ID# | data |
|---|---|
| Intermediate-35a | $^1$H-NMR (300 MHz, DMSO-$d_6$) δ 8.96 (1H, s), 8.15 (1H, d, J = 1.5 Hz), 7.99 (1H, d, J = 6.6 Hz), 7.68 (1H, d, J = 1.5 Hz), 7.56 (1H, d, J = 6.6 Hz), 5.65 (2H, s), 4.55 (2H, t, J = 13.2 Hz), 2.15 (3H, s), 1.72 (3H, t, J = 19.1 Hz), MS (ESI) m/z: 353 (M + H)$^+$. |
| Intermediate-36a | $^1$H-NMR (270 MHz, CDCl$_3$) δ 8.34 (1H, s), 8.29 (1H, s), 8.04 (1H, d, J = 5.9 Hz), 7.87(1H, d, J = 2.2 Hz), 7.45 (1H, d, J = 7.3 Hz), 4.35-4.09 (4H, m), MS (ESI) m/z: 378 (M + H)$^+$. |
| Intermediate-37a | $^1$H-NMR (300 MHz, CDCl$_3$) δ 8.07 (1H, d, J = 2.9 Hz), 8.04 (1H, s), 8.00 (1H, d, J = 2.2 Hz), 7.46 (1H, d, J = 6.6 Hz), 7.21 (1H, d, J = 2.2 Hz), 5.50 (2H, s), 4.79 (2H, q, J = 8.8 Hz), 2.10-2.01 (1H, m), 1.01-0.96 (2H, m), 0.70-0.65 (2H, m), MS (ESI) m/z: 383 (M + H)$^+$. |
| Intermediate-38a | $^1$H-NMR (300 MHz, DMSO-$d_6$) δ 9.02 (1H, s), 8.54 (1H, s), 8.47 (1H, s), 7.99 (1H, d, J = 6.2 Hz), 7.93 (1H, s), 7.90 (1H, s), 7.57 (1H, d, J = 6.2 Hz), 5.80 (2H, s), 2.41 (3H, s), MS (ESI) m/z: 360 (M + H)$^+$. |
| Intermediate-39a | $^1$H-NMR (300 MHz, CDCl$_3$) δ 8.12 (1H, s), 8.07-8.00 (2H, m), 7.50-7.43 (2H, m), 5.77 (1H, q, J = 8.8 Hz), 4.75 (2H, q, J = 8.8 Hz), 2.22 (3H, s), 2.06 (3H, d, J = 8.8 Hz), MS (ESI) m/z: 371 (M + H)$^+$. |
| Intermediate-40a | $^1$H-NMR (300 MHz, DMSO-$d_6$) δ 9.02 (1H, s), 8.00 (1H, d, J = 5.9 Hz), 7.93 (2H, d, J = 8.8 Hz), 7.58-7.51 (3H, m), 7.40 (1H, t, J = 7.3 Hz), 5.93 (2H, s), 2.35 (3H, s), MS (ESI) m/z: 325 (M + H)$^+$. |
| Intermediate-41a | $^1$H-NMR (300 MHz, DMSO-$d_6$) δ 9.00 (1H, s), 8.01 (1H, d, J = 5.9 Hz), 7.82 (1H, t, J = 7.3 Hz), 7.57 (1H, d, J = 5.9 Hz), 6.99 (1H, d, J = 7.3 Hz), 6.94 (1H, d, J = 8.1 Hz), 5.77 (2H, s), 4.91(2H, q, J = 9.5 Hz), MS (ESI) m/z: 343 (M + H)$^+$. |
| Intermediate-42a | $^1$H-NMR (300 MHz, DMSO-$d_6$) δ 8.94 (1H, s), 8.11 (1H, d, J = 2.2 Hz), 7.98 (1H, d, J = 5.9 Hz), 7.60 (1H, d, J = 2.2 Hz), 7.56 (1H, d, J = 5.9 Hz), 5.61 (2H, s), 4.10 (2H, d, J = 7.3 Hz), 2.11 (3H, s), 1.30-1.14 (1H, m), 0.55-0.48 (2H, m), 0.33-0.28 (2H, m), MS (ESI) m/z: 329 (M + H)$^+$. |

Table 4-4

| ID# | data |
|---|---|
| Intermediate-43a | $^1$H-NMR (300 MHz, DMSO-$d_6$) δ 8.91 (1H, s), 8.07 (1H, br s), 7.98 (1H, d, J = 6.2 Hz), 7.56 (1H, d, J = 6.2 Hz), 7.42 (1H, br s), 6.63 (1H, t, J = 6.8 Hz), 5.53 (2H, s), 4.25-4.11 (2H, m), 2.06(3H, s), MS (ESI) m/z: 356 (M + H)$^+$. |
| Intermediate-44a | $^1$H-NMR (300 MHz, DMSO-$d_6$) δ 9.00 (1H, s), 8.00 (1H, d, J = 6.2 Hz), 7.58 (1H, d, J = 6.2 Hz), 7.43 (1H, s), 7.32 (2H, s), 5.70 (2H, s), 2.26 (3H, s), MS (ESI) m/z: 342 (M + H)$^+$. |
| Intermediate-45a | $^1$H-NMR (300 MHz, DMSO-$d_6$) δ 9.03 (1H, s), 8.17 (1H, d, J =5.1 Hz), 8.01 (1H, dd, J = 6.2, 1.1 Hz), 7.59 (1H, d, J = 6.2 Hz), 6.99 (1H, d, J = 5.1 Hz), 6.86 (1H, s), 5.78 (2H, s), 4.98 (2H, q, J = 9.0 Hz), MS (ESI) m/z: 343 (M + H)$^+$. |
| Intermediate-46a | $^1$H-NMR (300 MHz, CDCl$_3$) δ 9.00 (2H, s), 8.33 (1H, s), 8.01 (1H, s), 7.59-7.38 (6H, m), 5.75 (2H, s), 5.02 (2H, q, J = 9.5 Hz), MS (ESI) m/z: 419 (M + H)$^+$. |
| Intermediate-47a | $^1$H-NMR (300 MHz, DMSO-$d_6$) δ 9.02 (1H, s), 8.30-8.20 (3H, m), 7.96 (1H, d, J = 6.2 Hz), 7.89 (1H, t, J = 8.0 Hz), 7.73 (1H, t, J = 8.0 Hz), 7.55 (1H, d, J = 6.2 Hz), 6.12 (2H, s), 5.25 (2H, q, J = 9.0 Hz), MS (ESI) m/z: 393 (M + H)$^+$. |
| Intermediate-48a | $^1$H-NMR (300 MHz, DMSO-$d_6$) δ 8.91 (1H, s), 7.97 (1H, d, J = 6.6 Hz), 7.54 (1H, d, J = 6.6 Hz), 7.4-7.2 (4H, m), 5.70 (2H, s), 4.62 (2H, s), 4.05 (2H, q, J = 9.3 Hz), MS (ESI) m/z: 356 (M + H)$^+$. |
| Intermediate-49a | $^1$H-NMR (300 MHz, DMSO-$d_6$) δ 8.93 (1H, s), 8.25 (1H, s), 7.99 (1H, d, J = 5.9 Hz), 7.55 (1H, d, J = 5.9 Hz), 7.29 (1H, s), 6.40 (1H, tt, J = 54.3 and 3.7 Hz), 5.72 (2H, s), 4.49-4.38 (2H, m), 2.18 (3H, s), MS (ESI) m/z: 339 (M + H)$^+$. |
| Intermediate-50a | $^1$H-NMR (300 MHz, DMSO-$d_6$) δ 8.93 (1H, s), 7.99 (1H, d, J = 6.2 Hz), 7.60-7.52 (3H, m), 7.14 (1H, d, J = 9.5 Hz), 6.66 (1H, s), 6.02 (2H, s), 3.81 (3H, s), MS (ESI) m/z: 381 (M + H)$^+$. |
| Intermediate-51a | $^1$H-NMR (300 MHz, DMSO-$d_6$) δ 8.96 (1H, s), 7.99 (1H, d, J = 6.2 Hz), 7.65-7.54 (2H, m), 7.39 (1H, dd, J = 8.6, 2.2 Hz), 7.23 (1H, d, J = 8.6 Hz), 6.40 (1H, tt, J = 54.3, 3.7 Hz), 5.65 (2H, s), 4.40 (2H, td, J = 14.7, 3.7 Hz), MS (ESI) m/z: 358 (M + H)$^+$. |
| Intermediate-53a | $^1$H-NMR (300 MHz, DMSO-$d_6$) δ 9.00 (1H, s), 8.00 (1H, d, J = 6.6 Hz), 7.58-7.31 (5H, m), 5.77 (2H, s), MS (ESI) m/z: 328 (M + H)$^+$. |
| Intermediate-54a | $^1$H-NMR (300 MHz, CDCl$_3$) δ 8.27 (1H, s), 8.19 (1H, s), 8.05 (1H, d, J = 5.9 Hz), 7.56 (1H, dd, J = 8.8, 2.2 Hz), 7.45 (1H, d, J = 5.9 Hz), 4.99-4.89 (4H, m), MS (ESI) m/z: 361 (M + H)$^+$. |
| Intermediate-55a | $^1$H-NMR (300 MHz, DMSO-$d_6$) δ 8.96 (1H, s), 8.35 (1H, d, J = 2.9 Hz), 7.99 (1H, d, J = 6.2 Hz), 7.60-7.54 (2H, m), 7.44 (1H, d, J = 8.8 Hz), 5.79 (2H, s), 4.96 (2H, t, J = 13.2 Hz), MS (ESI) m/z: 393 (M + H)$^+$. |
| Intermediate-56a | $^1$H-NMR (300 MHz, DMSO-$d_6$) δ 9.00 (1H, s), 7.98 (1H, d, J = 6.2 Hz), 7.56 (1H, d, J = 6.2 Hz), 7.47 (2H, d, J = 8.6 Hz), 7.28 (2H, d, J = 8.6 Hz), 6.78 (1H, tt, J = 51.8, 3.3 Hz), 5.73 (2H, s), MS (ESI) m/z: 360 (M + H)$^+$. |
| Intermediate-57a | $^1$H-NMR (300 MHz, DMSO-$d_6$) δ 8.96 (1H, s), 8.34 (1H, d, J = 2.9 Hz), 7.99 (1H, d, J = 6.6 Hz), 7.57-7.53 (2H, m), 7.42 (1H, d, J = 8.1 Hz), 6.68 (1H, tt, J = 52.1 and 5.9 Hz), 5.78 (2H, s), 4.70 (2H, t, J = 13.2 Hz), MS (ESI) m/z: 375 (M + H)$^+$. |
| Intermediate-58a | $^1$H-NMR (300 MHz, DMSO-$d_6$) δ 8.96 (1H, s), 8.30 (1H, d, J = 1.8 Hz), 8.11 (1H, d, J = 1.8 Hz), 7.98 (1H, d, J = 6.2 Hz), 7.56 (1H, d, J = 6.2 Hz), 6.61 (1H, tt, J = 52.0, 5.2 Hz), 5.70 (2H, s), 4.94 (2H, t, J = 14.0 Hz), MS (ESI) m/z: 409 (M + H)$^+$. |
| Intermediate-59a | $^1$H-NMR (300 MHz, DMSO-$d_6$) δ 9.02 (1H, s), 7.97 (1H, d, J = 5.9 Hz), 7.82 (1H, s), 7.71-7.55 (4H, m), 5.81 (2H, s), MS (ESI) m/z: 312 (M + H)$^+$. |

| ID# | data |
| --- | --- |
| Table 4-5 | |
| Intermediate-60a | ¹H-NMR (270 MHz, CDCl₃) δ 8.32 (1H, s), 8.13 (1H, s), 8.02 (1H, d, J = 5.9 Hz), 7.45 (1H, d, J = 5.9 Hz), 7.14 (1H, s), 5.86 (1H, q, J = 6.6 Hz), 4.44 (2H, q, J = 7.9 Hz), 2.07 (3H, d, J = 6.6 Hz), MS (ESI) m/z: 371 (M + H)⁺. |
| Intermediate-61a | ¹H-NMR (300 MHz, CDCl₃) δ 8.44 (1H, d, J = 1.5 Hz, 8.13 (1H, s), 8.06 (1H, d, J = 6.6 Hz), 7.47 (1H, d, J = 6.6 Hz), 7.43 (1H, s), 5.58 (2H, s), 3.04-3.00 (2H, m), 2.69-2.60 (2H, m), 2.32 (3H, s), MS (ESI) m/z: 355 (M + H)⁺. |
| Intermediate-62a | ¹H-NMR (300 MHz, DMSO-d₆) δ 8.92 (1H, s), 8.22 (1H, s), 7.99 (1H, d, J = 5.9 Hz), 7.55 (1H, d, J = 5.9 Hz), 7.27 (1 H, s), 5.71 (2H, s), 4.32 (2H, t, J = 5.9 Hz), 2.87-2.75 (2H, m), 2.15 (3H, s), MS (ESI) m/z: 371 (M + H)⁺. |
| Intermediate-63a | ¹H-NMR (300 MHz, DMSO-d₆) δ 8.95 (1H, s), 8.28 (1H, s), 8.08 (1H, s), 7.97 (1H, d, J = 6.6 Hz), 7.55 (1H, d, J = 5.9 Hz), 5.69 (2H, s), 4.62 (2H, t, J = 12.5 Hz), 1.71 (3H, t, J = 19.8 Hz), MS (ESI) m/z: 373 (M + H)⁺. |
| Intermediate-64a | ¹H-NMR (300 MHz, DMSO-d₆) δ 8.97 (1H, s), 8.29 (1H, d, J = 2.2 Hz), 8.07 (1H, d, J = 2.2 Hz), 7.99 (1H, d, J = 6.2 Hz), 7.57 (1H, d, J = 6.2 Hz), 5.69 (2H, s), 4.56 (2H, t, J = 5.9 Hz), 2.90-2.73 (2H, m), MS (ESI) m/z: 391 (M + H)⁺. |
| Intermediate-65a | ¹H-NMR (300 MHz, DMSO-d₆) δ 9.05 (1H, s), 8.01 (1H, d, J = 6.2 Hz), 7.98 (1H, s), 7.84 (1H, d, J = 8.4 Hz), 7.62 (1H, d, J = 8.8 Hz), 7.57 (1 H, d, J = 6.2 Hz), 6.19 (2H, s), 3.97 (3H, s), MS (ESI) m/z: 366 (M + H)⁺. |
| Intermediate-66a | ¹H-NMR (300 MHz, DMSO-d₆) δ 8.94 (1H, s), 8.28 (1H, s), 7.99 (1H, d, J = 6.2 Hz), 7.55 (1H, d, J = 6.2 Hz), 7.30 (1H, s), 6.69 (1H, tt, J = 51.6, 5.5 Hz), 5.72 (2H, s), 4.72 (2H, t, J = 13.2 Hz), 2.20 (3H, s), MS (ESI) m/z: 389 (M + H)⁺. |
| Intermediate-67a | ¹H-NMR (300 MHz, CDCl₃) δ 8.96 (1H, s), 8.25 (1H, d, J = 2.0 Hz), 8.03 (1H, d, J = 2.0 Hz), 7.99 (1H, d, J = 6.2 Hz), 7.57 (1H, d, J = 6.2 Hz), 5.67 (2H, s), 4.18 (2H, d, J = 7.0 Hz), 1.28-1.20 (1H, m), 0.61-0.50 (2H, m), 0.37-0.30 (2H, m), MS (ESI) m/z: 349 (M + H)⁺. |
| Intermediate-68a | ¹H-NMR (300 MHz, CDCl₃) δ 8.37 (1H, s), 8.15 (1H, s), 8.03 (1H, d, J = 6.6 Hz), 7.45 (1H, d, J = 5.6 Hz), 7.23 (1H, s), 5.97 (1H, q, J = 7.3 Hz), 4.45 (2H, q, J = 7.3 Hz), 2.29 (3H, s), 2.09 (3H, d, J = 8.8 Hz), MS (ESI) m/z: 371 (M + H)⁺. |
| Intermediate-69a | ¹H-NMR (300 MHz, DMSO-d₆) δ 8.97 (1H, s), 7.99 (1H, d, J = 6.2 Hz), 7.62 (1H, d, J = 2.0 Hz), 7.57 (1H, d, J = 6.2 Hz), 7.41 (1H, dd, J = 8.6, 2.0 Hz), 7.27 (1H, d, J = 8.6 Hz), 5.66 (2H, s), 4.86 (2H, q, J = 8.8 Hz), MS (ESI) m/z: 376 (M + H)⁺. |
| Intermediate-70a | ¹H-NMR (300 MHz, DMSO-d₆) δ 8.96 (1H, s), 8.15 (1H, d, J = 1.6 Hz), 7.99 (1H, d, J = 6.2 Hz), 7.64 (1H, d, J = 1.6 Hz), 7.56 (1H, d, J = 6.2 Hz), 7.53-7.44 (2H, m), 7.25-7.15 (2H, m), 5.63 (2H, s), 5.35 (2H, s), 2.14 (3H, s), MS (ESI) m/z: 383 (M + H)⁺. |
| Intermediate-71a | ¹H-NMR (300 MHz, DMSO-d₆) δ 8.95 (1H, s), 8.09 (1H, d, J = 1.8 Hz), 7.98 (1H, d, J = 6.2 Hz), 7.60 (1H, d, J = 1.8 Hz), 7.56 (1H, d, J = 6.2 Hz), 5.60 (2H, s), 5.13 (1H, quintet, J = 7.4 Hz), 2.44-2.30 (2H, m), 2.18-1.93 (2H, m), 2.10 (3H, s), 1.82-1.56 (2H, m), MS (ESI) m/z: 329 (M + H)⁺. |
| Intermediate-72a | ¹H-NMR (300 MHz, DMSO-d₆) δ 8.89 (1H, s), 8.12 (1H, s), 7.97 (1H, d, J = 6.0 Hz), 7.53(1H, d, J = 6.0 Hz), 7.24 (1H, s), 5.67 (2H, s), 3.91 (2H, d, J = 7.0 Hz), 2.16 (3H, s), 1.24-1.10 (1H, m), 0.59-0.50 (2H, m), 0.34-0.25 (2H, m), MS (ESI) m/z: 329 (M + H)⁺. |
| Table 4-6 | |
| Intermediate-73a | ¹H-NMR (300 MHz, CDCl₃) δ 8.20 (1H, s), 8.18 (1H, d, J = 5.9 Hz), 7.42 (1H, d, J = 5.9 Hz), 7.24 (1H, s), 5.98 (1H, tt, J = 52.7, 3.7 Hz), 5.79 (2H, s), 4.93 (2H, t, J = 12.5 Hz), 2.22 (3H, s), MS (ESI) m/z: 390 (M + H)⁺. |
| Intermediate-74a | ¹H-NMR (300 MHz, DMSO-d₆) δ 8.94 (1H, s), 8.23 (1H, s), 7.99 (1H, d, J = 5.9 Hz), 7.55 (1H, d, J = 5.9 Hz), 7.29 (1H, s), 5.72 (2H, s), 4.40 (2H, t, J = 12.5 Hz), 2.19 (3H, s), 1.74 (3H, t, J = 19.4 Hz), MS (ESI) m/z: 353 (M + H)⁺. |
| Intermediate-75a | ¹H-NMR (300 MHz, DMSO-d₆) δ 8.92 (1H, s), 7.98 (1H, d, J = 6.2 Hz), 7.56 (1H, d, J = 6.2 Hz), 7.31-7.23 (2H, m), 6.98 (1H, d, J = 8.8 Hz), 5.59 (2H, s), 4.25 (2H, t, J = 12.1 Hz), 2.15 (3H, s), 1.74 (3H, t, J = 19.4 Hz), MS (ESI) m/z: 352 (M + H)⁺. |
| Intermediate-76a | ¹H-NMR (300 MHz, CDCl₃) δ 8.05-8.01 (2H, m), 7.47 (1H, d, J = 6.2 Hz), 7.21-7.14 (2H, m), 6.79 (1H, d, J = 9.2 Hz), 6.11 (1 H, tt, J = 55.2 and 4.0 Hz), 5.76 (1H, q, J = 7.0 Hz), 4.19 (2H, td, J = 13.0 and 4.0 Hz), 2.24 (3H, s), 2.03 (3H, d, J = 7.0 Hz), MS (ESI) m/z: 352 (M + H)⁺. |
| Intermediate-77a | ¹H-NMR (300 MHz, CDCl₃) δ 8.07-8.03 (2H, m), 7.48 (1H, d, J = 5.9 Hz), 7.01 (2H, s), 6.08 (1H, tt, J = 55.0 and 4.4 Hz), 5.49 (2H, s), 4.00 (2H, td, J = 13.9 and 4.4 Hz), 2.28 (6H, s), MS (ESI) m/z: 352 (M + H)⁺. |
| Intermediate 78a | ¹H-NMR (300 MHz, CDCl₃) δ 8.08-8.01 (2H, m), 7.48 (1H, d, J = 6.2 Hz), 7.20 (1H, d, J = 7.3 Hz), 6.93 (1H, d, J = 7.7 Hz), 6.79 (1H, s), 6.10 (1H, tt, J = 55.0 and 4.0 Hz), 5.55 (2H, s), 4.16 (2H, td, J = 12.8 and 4.0 Hz), 2.24 (3H, s), MS (ESI) m/z: 338 (M + H)⁺. |
| Intermediate-79a | ¹H-NMR (270 MHz, CDCl₃) δ 8.06-8.00 (2H, m), 7.47 (1H, d, J = 6.3 Hz), 7.21-7.13 (2H, m), 6.78 (1H, d, J = 9.2 Hz), 5.76 (1H, q, J = 6.8 Hz), 4.10 (2H, t, J = 11.2 Hz), 2.25 (3H, s), 2.03 (3H, d, J = 6.8 Hz), 1.78 (3H, t, J = 18.8 Hz), MS (ESI) m/z: 366 (M + H)⁺. |
| Intermediate-80a | ¹H-NMR (270 MHz, CDCl₃) δ 8.07-8.00 (2H, m), 7.47 (1H, d, J = 6.2 Hz), 7.22-7.13 (2H, m), 6.79 (1H, d, J = 9.2 Hz), 6.10 (1H, tt, J = 55.3 and 3.9 Hz), 5.76 (1H, q, J = 6.9 Hz), 4.19 (2H, td, J = 12.9 and 3.9 Hz), 2.24 (3H, s), 2.03 (3H, d, J = 6.9 Hz), MS (ESI) m/z: 352 (M + H)⁺. |
| Intermediate-81a | ¹H-NMR (270 MHz, CDCl₃) δ 8.09-8.03 (2H, m), 7.48 (1H, d, J = 5.9 Hz), 7.27-7.09 (3H, m), 6.50 (1H, t, J = 73.5 Hz), 5.55 (2H, s), 2.29 (3H, s), MS (ESI) m/z: 324 (M + H)⁺. |

Representative Procedure for Method E

The following preparation of Intermediate-1b represents the Method E.

Intermediate-1b ethyl 2-((5-methyl-6-(2,2,2-trifluoroethoxy)pyridin-3-yl)methyl)-2H-pyrazolo[4,3-c]pyridine-4-carboxylate To a solution of 4-chloro-2-((5-methyl-6-(2,2,2-trifluoroethoxy)pyridin-3-yl)methyl)-2H-pyrazolo[4,3-c]pyridine (6.31 g, 17.7 mmol, Intermediate-1a) in DMF/EtOH (2:1, 180 mL), palladium(II) acetate (1.19 g, 5.31 mmol), 1,3-bis(diphenylphosphino)propane (2.19 g, 5.31 mmol) and triethylamine (7.4 mL, 53.1 mmol) are added. The mixture is heated at 80° C. for 3 hours under CO gas atmosphere. The reaction mixture is diluted with EtOAc (400 mL) and washed with water (200 mL). The organic layer is dried over sodium sulfate, filtered and concentrated under reduced pressure. The residue is purified by silica gel column chromatography eluting with hexane/EtOAc (4:1-1:4) to give 5.13 g (74% yield) of title compound as a pale yellow solid.

$^1$H-NMR (300 MHz, CDCl$_3$) delta 8.64 (1H, s), 8.48 (1H, d, J=5.9 Hz), 8.07 (1H, s), 7.75 (1H, d, J=6.6 Hz), 7.48 (1H, s), 5.58 (2H, s), 4.77 (2H, q, J=8.6 Hz), 4.54 (2H, q, J=7.3 Hz), 2.21 (3H, s), 1.49 (3H, t, J=7.3 Hz), MS (ESI) m/z: 395 (M+H)$^+$.

Intermediate-1c 2-((5-methyl-6-(2,2,2-trifluoroethoxy)pyridin-3-yl)methyl)-2H-pyrazolo[4,3-c]pyridine-4-carboxylic acid The title compound is prepared in 96% yield (183 mg, a pale yellow solid) from ethyl 2-((5-methyl-6-(2,2,2-trifluoroethoxy)pyridin-3-yl)methyl)-2H-pyrazolo[4,3-c]pyridine-4-carboxylate (205 mg, 0.52 mmol, Intermediate-1b) in a similar manner to Step-2 of Intermediate-A6.

MS (ESI) m/z: 365 (M−H)$^−$.

Intermediate-1h

N-(2-aminoethyl)-2-((5-methyl-6-(2,2,2-trifluoroethoxy)pyridin-3-yl)methyl)-2H-pyrazolo[4,3-c]pyridine-4-carboxamide hydrochloride <Step 122 tert-butyl (2-(2-((5-methyl-6-(2,2,2-trifluoroethoxy)pyridin-3-yl)methyl)-2H-pyrazolo[4,3-c]pyridine-4-carboxamido)ethyl)carbamate The title compound is prepared in >99% yield (278 mg, a colorless syrup) from 2-((5-methyl-6-(2,2,2-trifluoroethoxy)pyridin-3-yl)methyl)-2H-pyrazolo[4,3-c]pyridine-4-carboxylic acid (200 mg, 0.55 mmol, Intermediate-1c) and tert-butyl (2-aminoethyl)carbamate (131 mg, 0.82 mmol) in a similar manner to Step-1 of Intermediate-A7.

$^1$H-NMR (300 MHz, CDCl$_3$) delta 8.81 (1H, s), 8.35 (1H, br s), 8.25 (1H, d, J=5.1 Hz), 8.07 (1H, s), 8.02 (1H, s), 7.69 (1H, d, J=5.1 Hz), 7.46 (1H, s), 5.56 (2H, s), 4.76 (2H, q, J=8.8 Hz), 3.70-3.58 (2H, m), 3.50-3.38 (2H, m), 2.20 (3H, s), 1.42 (9H, s), MS (ESI) m/z: 509 (M+H)$^+$.

<Step 2> N-(2-aminoethyl)-2-((5-methyl-6-(2,2,2-trifluoroethoxy)pyridin-3-yl)methyl)-2H-pyrazolo[4,3-c]pyridine-4-carboxamide hydrochloride A mixture of tert-butyl (2-(2-((5-methyl-6-(2,2,2-trifluoroethoxy)pyridin-3-yl)methyl)-2H-pyrazolo[4,3-c]pyridine-4-carboxamido)ethyl)carbamate (278 mg, 0.55 mmol, Step-1) and 4 M hydrogen chloride in dioxane solution (10 mL) is stirred at rt for 1 hour. After removal of the solvent, the residual solid is washed with diisopropylether-hexane to give 243 mg (>99%) of the title compound as a white solid.

MS (ESI) m/z: 409 (M+H)$^+$.

Representative Procedure for Method F

The following preparation of Intermediate-36b represents the Method F.

Intermediate-36b:

phenyl 2-(2-((3-chloro-5-(trifluoromethyl)pyridin-2-yl)oxy)ethyl)-2H-pyrazolo[4,3-c]pyridine-4-carboxylate A mixture of 4-chloro-2-(2-((3-chloro-5-(trifluoromethyl)pyridin-2-yl)oxy)ethyl)-2H-pyrazolo[4,3-c]pyridine (310 mg, 0.82 mmol), phenyl formate (201 mg, 1.64 mmol), palladium(II) acetate (5 mg, 0.03 mmol), Xantphos (57 mg, 0.10 mmol), and triethylamine (0.23 mL, 1.64 mmol) in MeCN is refluxed with stirring for 12 hours. After cooling to rt, the solvent is removed in vacuo. The residue is purified by column chromatography on silica-gel eluting with n-hexane/EtOAc (1:1-1:3) to give 152 mg (40% yield) of the title compound as a yellow solid.

$^1$H-NMR (270 MHz, DMSO-d$_6$) delta 8.85 (1H, s), 8.57 (1H, d, J=5.9 Hz), 8.28 (1H, s), 7.84-7.82 (2H, m), 7.51-7.45 (2H, m), 7.35-7.29 (3H, m), 4.96 (4H, s), MS (ESI) m/z: 463 (M+H)$^+$.

The following intermediate compounds are prepared using the Method E or F from starting materials shown in Table 5-1 to 5-4. Spectral data of the intermediate compounds are shown in Table 6-1 to 6-6.

| ID | Name | Method | Starting Material |
|---|---|---|---|
| Table 5-1 | | | |
| Intermediate-1e | ethyl 6-methyl-2-((5-methyl-6-(2,2,2-trifluoroethoxy)pyridin-3-yl)methyl)-2H-pyrazolo-[4,3-c]pyridine-4-carboxylate | E | Intermediate-1d |
| Intermediate-2b | ethyl 2-((6-(2,2-difluoroethoxy)-5-methylpyridin-3-yl)methyl)-2H-pyrazolo[4,3-c]pyridine-4-carboxylate | E | Intermediate-2a |
| Intermediate-4b | ethyl 2-((6-(2,2,2-trifluoroethoxy)pyridin-3-yl)methyl-2H-pyrazolo[4,3-c]pyridine-4-carboxylate | E | Intermediate-4a |
| Intermediate-5b | ethyl 2-((5-chloro-6-(2,2,2-trifluoroethoxy)pyridin-3-yl)methyl)-2H-pyrazolo[4,3-c]pyridine-4-carboxylate | E | Intermediate-5a |

| ID | Name | Method | Starting Material |
|---|---|---|---|
| Intermediate-6b | ethyl 2-((5-chloro-6-(2,2-difluoroethoxy)pyridin-3-yl)methyl)-2H-pyrazolo[4,3-c]pyridine-4-carboxylate | E | Intermediate-6a |
| Intermediate-10b | ethyl 2-(6-(3,3,3-trifluoropropoxy)pyridin-3-yl)methyl)-2H-pyrazolo[4,3-c]pyridine-4-carboxylate | E | Intermediate-10a |
| Intermediate-11b | ethyl 2-(1-(5-methyl-6-(2,2,2-trifluoroethoxy)pyridin-3-yl)ethyl)-2H-pyrazolo[4,3-c]pyridine-4-carboxylate (single enantiomer) | E | Intermediate-11a |
| Intermediate-11c | phenyl 2-(1-(5-methyl-6-(2,2,2-trifluoroethoxy)pyridin-3-yl)ethyl)-2H-pyrazolo[4,3-c]pyridine-4-carboxylate (single enantiomer) | F | Intermediate-11a |
| Intermediate-12b | ethyl 2-((5-fluoro-6-(2,2,2-trifluoroethoxy)pyridin-3-yl)methyl)-2H-pyrazolo[4,3-c]pyridine-4-carboxylate | E | Intermediate-12a |
| Intermediate-13b | ethyl 2-((6-(2,2,3,3-tetrafluoropropoxy)pyridin-3-yl)methyl)-2H-pyrazolo[4,3-c]pyridine-4-carboxylate | E | Intermediate-13a |
| Intermediate-14b | ethyl 2-(4-(2,2,2-trifluoroethoxy)benzyl)-2H-pyrazolo[4,3-c]pyridine-4-carboxylate | E | Intermediate-14a |
| Intermediate-15b | ethyl 2-((6-(2,2,3,3,3-pentafluoropropoxy)pyridin-3-yl)methyl)-2H-pyrazolo[4,3-c]pyridine-4-carboxylate | E | Intermediate-15a |
| Intermediate-19b | ethyl 2-(6-(4-fluorophenoxy)-5-methylpyridin-3-yl)methyl)-2H-pyrazolo[4,3-c]pyridine-4-carboxylate | E | Intermediate-19a |
| Intermediate-20b | ethyl 2-((4-methyl-6-(2,2,2-trifluoroethoxy)pyridin-3-yl)methyl)-2H-pyrazolo[4,3-c]pyridine-4-carboxylate | E | Intermediate-20a |
| Intermediate-21b | ethyl 2-((5-methyl-6-(3,3,3-trifluoropropoxy)pyridin-3-yl)methyl)-2H-prazolo[4,3-c]pyridine-4-carboxylate | E | Intermediate-21a |
| Intermediate-22b | ethyl 2-(5-methyl-6-(2,2,2-trifluoroethoxy)pyridazin-3-yl)methyl)-2H-pyrazolo[4,3-c]pyridine-4-carboxylate | E | Intermediate-22a |
| Intermediate-23b | ethyl 2-((4-methyl-5-(2,2,2-trifluoroethoxy)pyridin-2-yl)methyl)-2H-pyrazolo[4,3-c]pyridine-4-carboxylate | E | Intermediate-23a |
| Intermediate-24b | ethyl 2-((5-methoxy-6-(2,2,2-trifluoroethoxy)pyridin-3-yl)methyl)-2H-pyrazolo[4,3-c]pyridine-4-carboxylate | E | Intermediate-24a |
| Intermediate-25b | ethyl 2-(3-methyl-4-(2,2,2-trifluoroethoxy)benzyl)-2H-pyrazolo[4,3-c]pyridine-4-carboxylate | E | Intermediate-25a |
| Intermediate-26b | ethyl 2-(4-(2,2-difluoroethoxy)-3-methylbenzyl)-2H-pyrazolo[4,3-c]pyridine-4-carboxylate | E | Intermediate-26a |
| Intermediate-27b | ethyl 2-((5-methyl-6-(2,2,3,3-tetrafluoropropoxy)pyridin-3-yl)methyl)-2H-pyrazolo[4,3-c]pyridine-4-carboxylate | E | Intermediate-27a |
| Intermediate-28b | ethyl 2-((2-methyl-6-(2,2,2-trifluoroethoxy)pyridin-4-yl)methyl)-2H-pyrazolo[4,3-c]pyridine-4-carboxylate | E | Intermediate-28a |
| Intermediate-30b | ethyl 2-((1-(5-(trifluoromethyl)pyridin-2-yl)-1H-pyrazol-3-yl)methyl)-2H-pyrazolo[4,3-c]pyridine-4-carboxylate | E | Intermediate-30a |

Table 5-2

| ID | Name | Method | Starting Material |
|---|---|---|---|
| Intermediate-31b | ethyl 2-((5-methyl-6-(2-(2,2,2-trifluoroethoxy)ethoxy)pyridin-3-yl)methyl)-2H-pyrazolo[4,3-c]pyridine-4-carboxylate | E | Intermediate-31a |
| Intermediate-32b | ethyl 2-(2-methoxy-642,2,2-trifluoroethoxy)pyridin-3-yl)methyl)-2H-pyrazolo[4,3-c]pyridine-4-carboxylate | E | Intermediate-32a |
| Intermediate-33b | ethyl 2-(2-(4-(trifluoromethyl)phenoxy)ethyl)-2H-pyrazolo[4,3-c]pyridine-4-carboxylate | E | Intermediate-33a |
| Intermediate-34b | ethyl 2-(6-methyl-5-(2,2,2-trifluoroethoxy)pyrazin-2-yl)methyl)-2H-pyrazolo[4,3-c]pyridine-4-carboxylate | E | Intermediate-34a |
| Intermediate-35b | ethyl 2-((6-(2,2-difluoropropoxy)-5-methylpyridin-3-yl)methyl)-2H-pyrazolo[4,3-c]pyridine-4-carboxylate | E | Intermediate-35a |
| Intermediate-37b | phenyl 2-((5-cyclopropyl-6-(2,2,2-trifluoroethoxy)pyridin-3-yl)methyl)-2H-pyrazolo-[4,3-c]pyridine-4-carboxylate | F | Intermediate-37a |
| Intermediate-38b | ethyl 2-((6-(4-chloro-1H-pyrazol-1-yl)-5-methylpyridin-3-yl)methyl)-2H-pyrazolo[4,3-c]pyridine-4-carboxylate | E | Intermediate-38a |
| Intermediate-39b | phenyl 2-(1-(5-methyl-6-(2,2,2-trifluoroethoxy)pyridin-3-yl)ethyl)-2H-pyrazolo[4,3-c]pyridine-4-carboxylate (single enantiomer) | F | Intermediate-39a |
| Intermediate-40b | ethyl 2-((5-methyl-2-phenyl-2H-1,2,3-triazol-4-yl)methyl)-2H-pyrazolo[4,3-c]pyridine-4-carboxylate | E | Intermediate-40a |
| Intermediate-41b | ethyl 2-((6-(2,2,2-trifluoroethoxy)pyridin-2-yl)methyl)-2H-pyrazolo[4,3-c]pyridine-4-carboxylate | E | Intermediate-41a |
| Intermediate-42b | ethyl 2-((6-(cyclopropylmethoxy)-5-methylpyridin-3-yl)methyl)-2H-pyrazolo[4,3-c]pyridine-4-carboxylate | E | Intermediate-42a |
| Intermediate-43b | ethyl 2-((5-methyl-6-((2,2,2-trifluoroethyl)amino)pyridin-3-yl)methyl)-2H-pyrazolo[4,3-c]pyridine-4-carboxylate | E | Intermediate-43a |
| Intermediate-44b | ethyl 2-(3-methyl-4-(trifluoromethoxy)benzyl)-2H-pyrazolo[4,3-c]pyridine-4-carboxylate | E | Intermediate-44a |
| Intermediate-45b | ethyl 2-((2-(2,2,2-trifluoroethoxy)pyridin-4-yl)methyl)-2H-pyrazolo[4,3-c]pyridine-4-carboxylate | E | Intermediate-45a |
| Intermediate-47b | ethyl 2-((1-(2,2,2-trifluoroethoxy)isoquinolin-4-yl)methyl)-2H-pyrazolo[4,3-c]pyridine-4-carboxylate | F | Intermediate-47a |

-continued

| ID | Name | Method | Starting Material |
|---|---|---|---|
| Intermediate-48b | ethyl 2-(4-((2,2,2-trifluoroethoxy)methyl)benzyl)-2H-pyrazolo[4,3-c]pyridine-4-carboxylate | E | Intermediate-48a |
| Intermediate-49b | ethyl 2-((5-(2,2-difluoroethoxy)-4-methylpyridin-2-yl)methyl)-2H-pyrazolo[4,3-c]pyridine-4-carboxylate | E | Intermediate-49a |
| Intermediate-50b | ethyl 2-((1-methyl-5-(trifluoromethoxy)-1H-indol-2-yl)methyl)-2H-pyrazolo[4,3-c]pyridine-4-carboxylate | E | Intermediate-50a |
| Intermediate-51b | ethyl 2-(3-chloro-4-(2,2-difluoroethoxy)benzyl)-2H-pyrazolo[4,3-c]pyridine-4-carboxylate | E | Intermediate-51a |
| Intermediate-52b | ethyl 2-((5-methyl-6-((2,2,2-trifluoroethoxy)methyl)pyridin-3-yl)methyl)-2H-pyrazolo[4,3-c]pyridine-4-carboxylate | E | Intermediate-52a |
| Intermediate-53b | phenyl 2-(3-(trifluoromethoxy)benzyl)-2H-pyrazolo[4,3-c]pyridine-4-carboxylate | F | Intermediate-53a |
| Intermediate-54b | phenyl 2-(2-((3-fluoro-5-(trifluoromethyl)pyridin-2-yl)oxy)ethyl)-2H-pyrazolo[4,3-c]pyridine-4-carboxylate | F | Intermediate-54a |
| Intermediate-55b | ethyl 2-((5-(2,2,3,3,3-pentafluoropropoxy)pyridin-2-yl)methyl)-2H-pyrazolo[4,3-c]pyridine-4-carboxylate | E | Intermediate-55a |

Table 5-3

| ID | Name | Method | Starting Material |
|---|---|---|---|
| Intermediate-56b | ethyl 2-(4-(1,1,2,2-tetrafluoroethoxy)benzyl)-2H-pyrazolo[4,3-c]pyridine-4-carboxylate | E | Intermediate-56a |
| Intermediate-57b | ethyl 2-((5-(2,2,3,3-tetrafluoropropoxy)pyridin-2-yl)methyl)-2H-pyrazolo[4,3-c]pyridine-4-carboxylate | E | Intermediate-57a |
| Intermediate-58b | ethyl 2-((5-chloro-6-(2,2,3,3-tetrafluoropropoxy)pyridin-3-yl)methyl)-2H-pyrazolo[4,3-c]pyridine-4-carboxylate | E | Intermediate-58a |
| Intermediate-59b | phenyl 2-(3-(trifluoromethyl)benzyl)-2H-pyrazolo[4,3-c]pyridine-4-carboxylate | F | Intermediate-59a |
| Intermediate-60b | ethyl 2-(1-(4-methyl-5-(2,2,2-trifluoroethoxy)pyridin-2-yl)ethyl)-2H-pyrazolo[4,3-c]pyridine-4-carboxylate (single enantiomer) | E | Intermediate-60a |
| Intermediate-61b | phenyl 2-((5-methyl-6-(3,3,3-trifluoropropyl)pyridin-3-yl)methyl)-2H-pyrazolo[4,3-c]pyridine-4-carboxylate | F | Intermediate-61a |
| Intermediate-62b | ethyl 2-((4-methyl-5-(3,3,3-trifluoropropoxy)pyridin-2-yl)methyl)-2H-pyrazolo[4,3-c]pyridine-4-carboxylate | E | Intermediate-62a |
| Intermediate-63b | phenyl 2-((5-chloro-6-(2,2-difluoropropoxy)pyridin-3-yl)methyl)-2H-pyrazolo[4,3-c]pyridine-4-carboxylate | F | Intermediate-63a |
| Intermediate-64b | ethyl 2-((5-chloro-6-(3,3,3-trifluoropropoxy)pyridin-3-yl)methyl)-2H-pyrazolo[4,3-c]pyridine-4-carboxylate | E | Intermediate-64a |
| Intermediate-65b | ethyl 2-((1-methyl-5-(trifluoromethyl)-1H-benzo[d]imazol-2-yl)methyl)-2H-pyrazolo[4,3-c]pyridine-4-carboxylate | E | Intermediate-65a |
| Intermediate-66b | ethyl 2-((4-methyl-5-(2,2,3,3-tetrafluoropropoxy)pyridin-2-yl)methyl)-2H-pyrazolo[4,3-c]pyridine-4-carboxylate | E | Intermediate-66a |
| Intermediate-67b | ethyl 2-((5-chloro-6-(cyclopropylmethoxy)pyridin-3-yl)methyl)-2H-pyrazolo[4,3-c]pyridine-4-carboxylate | E | Intermediate-67a |
| Intermediate-68b | ethyl 2-(1-(4-methyl-5-(2,2,2-trifluoroethoxy)pyridin-2-yl)ethyl)-2H-pyrazolo[4,3-c]pyridine-4-carboxylate (single enantiomer, antipode of Intermediate-60b) | E | Intermediate-68a |
| Intermediate-69b | ethyl 2-(3-chloro-4-(2,2,2-trifluoroethoxy)benzyl)-2H-pyrazolo[4,3-c]pyridine-4-carboxylate | E | Intermediate-69a |
| Intermediate-70b | ethyl 2-((6-((4-fluorobenzyl)oxy)-5-methylpyridin-3-yl)methyl)-2H-pyrazolo[4,3-c]pyridine-4-carboxylate | E | Intermediate-70a |
| Intermediate-71b | ethyl 2-((6-cyclobutoxy-5-methylpyridin-3-yl)methyl)-2H-pyrazolo[4,3-c]pyridine-4-carboxylate | E | Intermediate-71a |
| Intermediate-72b | ethyl 2-((5-(cyclopropylmethoxy)-4-methylpyridin-2-yl)methyl)-2H-pyrazolo[4,3-c]pyridine-4-carboxylate | E | Intermediate-72a |
| Intermediate-73b | ethyl 2-((5-methyl-6-(2,2,3,3-tetrafluoropropoxy)pyridazin-3-yl)methyl)-2H-pyrazolo[4,3-c]pyridine-4-carboxylate | E | Intermediate-73a |
| Intermediate-74b | ethyl 2-((5-(2,2-difluoropropoxy)-4-methylpyridin-2-yl)methyl)-2H-pyrazolo[4,3-c]pyridine-4-carboxylate | E | Intermediate-74a |
| Intermediate-75b | ethyl 2-(4-(2,2-difluoropropoxy)-3-methylbenzyl)-2H-pyrazolo[4,3-c]pyridine-4-carboxylate | E | Intermediate-75a |
| Intermediate-76b | ethyl 2-(1-(4-(2,2-difluoroethoxy)-3-methylphenyl)ethyl)-2H-pyrazolo[4,3-c]pyridine-4-carboxylate (single enantiomer) | E | Intermediate-76a |
| Intermediate-77b | ethyl 2-(4-(2,2-difluoroethoxy)-3,5-dimethylbenzyl)-2H-pyrazolo[4,3-c]pyridine-4-carboxylate | E | Intermediate-77a |

Table 5-4

| ID | Name | Method | Starting Material |
|---|---|---|---|
| Intermediate-78b | ethyl 2-(3-(2,2-difluoroethoxy)-4-methylbenzyl)-2H-pyrazolo[4,3-c]pyridine-4-carboxylate | E | Intermediate-78a |
| Intermediate-79b | ethyl 2-(1-(4-(2,2-difluoropropoxy)-3-methylphenyl)ethyl)-2H-pyrazolo[4,3-c]pyridine-4-carboxylate (single enantiomer) | E | Intermediate-79a |

-continued

| ID | Name | Method | Starting Material |
|---|---|---|---|
| Intermediate-80b | ethyl 2-(1-(4-(2,2-difluoroethoxy)-3-methylphenyl)ethyl)-2H-pyrazolo[4,3-c]pyridine-4-carboxylate (single enantiomer, antipode of Intermediate-76b) | E | Intermediate-80a |
| Intermediate-81b | ethyl 2-(4-(difluoromethoxy)-3-methylbenzyl)-2H-pyrazolo[4,3-c]pyridine-4-carboxylate | E | Intermediate-81a |

| ID# | data |
|---|---|
| | Table 6-1 |
| Intermediate-1e | $^1$H-NMR (300 MHz, CDCl$_3$) δ 8.54 (1H, s), 8.05 (1H, s), 7.55 (1H, s), 7.46 (1H, s), 5.54 (2H, s), 4.76 (2H, q, J = 8.6 Hz), 4.54 (2H, q, J = 7.1 Hz), 2.73 (3H, s), 2.21 (3H, s), 1.48 (3H, t, 7.0 Hz), MS (ESI) m/z: 409 (M + H)$^+$. |
| Intermediate-2b | $^1$H-NMR (300 MHz, CDCl$_3$) δ 8.64 (1H, s), 8.48 (1H, d, J = 6.2 Hz), 8.06 (1H, d, J = 2.2 Hz), 7.75 (1H, dd, J = 6.2, 1.1 Hz), 7.45 (1H, d, J =1.1 Hz), 6.14 (1H, tt, J = 55.4, 4.0 Hz), 5.57 (2H, s), 4.60-4.50 (4H, m), 2.19 (3H, s), 1.49 (3H, t, J = 7.0 Hz), MS (ESI) m/z: 377 (M + H)$^+$. |
| Intermediate-4b | $^1$H-NMR (300 MHz, CDCl$_3$) δ 8.66 (1H, s), 8.48 (1H, d, J = 6.2 Hz), 8.24 (1H, d, J = 2.2 Hz), 7.75 (1H, d, J = 6.2 Hz), 7.68 (1H, dd, J = 8.4, 2.2 Hz), 6.89 (1H, d, J = 8.4 Hz), 5.61 (2H, s), 4.76 (2H, q, J = 8.4 Hz), 4.54 (2H, q, J = 7.0 Hz), 1.49 (3H, t, J = 7.0 Hz), MS (ESI) m/z: 381 (M + H)$^+$. |
| Intermediate-5b | $^1$H-NMR (300 MHz, DMSO-d$_6$) δ 9.10 (1H, s), 8.35 (1H, d, J = 6.6 Hz), 8.32 (1H, d, J = 2.2 Hz), 8.13 (1H, d, J = 2.2 Hz), 7.81 (1H, d, J = 6.6 Hz), 5.78 (2H, s), 5.07 (2H, q, J = 8.8 Hz), 4.42 (2H, q, J = 7.3 Hz), 1.38 (3H, t, J = 7.3 Hz), MS (ESI) m/z: 415 (M + H)$^+$. |
| Intermediate-6b | $^1$H-NMR (300 MHz, DMSO-d$_6$) δ 9.10 (1H, s), 8.34 (1H, d, J = 6.2 Hz), 8.30 (1H, d, J = 1.8 Hz), 8.09 (1H, d, J = 1.8 Hz), 7.80 (1H, d, J = 6.2 Hz), 6.39 (1H, tt, J = 54.7, 3.3 Hz), 5.77 (2H, s), 4.64 (2H, td, J = 15.0, 3.3 Hz), 4.42 (2H, q, J = 7.0 Hz), 1.38 (3H, t, J = 7.0 Hz), MS (ESI) m/z: 397 (M + H)$^+$. |
| Intermediate-10b | $^1$H-NMR (300 MHz, CDCl$_3$) δ 8.64 (1H, s), 8.48 (1H, d, J = 6.2 Hz), 8.24 (1H, d, J = 2.6 Hz), 7.75 (1H, d, J = 6.2 Hz), 7.62 (1H, dd, J = 8.4, 2.6 Hz), 6.77 (1H, d, J = 8.4 Hz), 5.60 (2H, s), 4.58-4.50 (4H, m), 2.68-2.54 (2H, m), 1.49 (3H, t, J = 7.0 Hz), MS (ESI) m/z: 395 (M + H)$^+$. |
| Intermediate-11b | $^1$H-NMR (300 MHz, CDCl$_3$) δ 8.68 (1H, s), 8.47 (1H, d, J = 6.6 Hz), 8.03 (1H, d, J = 2.2 Hz), 7.76 (1H, d, J = 6.6 Hz), 7.46 (1H, d, J = 2.2 Hz), 5.83 (1H, q, J = 6.6 Hz), 4.76 (2H, q, J = 8.8 Hz), 4.54 (2H, q, J = 7.3 Hz), 2.21 (3H, s), 2.07 (3H, d, J = 6.6 Hz), 1.50 (3H, t, J = 7.3 Hz), MS (ESI) m/z: 409 (M + H)$^+$. |
| Intermediate-11c | 1H-NMR (300 MHz, CDCl$_3$) δ 8.66 (1H, s), 8.56 (1H, d, J = 5.9 Hz), 8.02 (1H, s), 7.84 (1H, d, J = 6.6 Hz), 7.50-7.42 (3H, m), 7.35-7.25 (3H, m), 5.84 (1H, q, J = 6.6 Hz), 4.75 (2H, q, J = 8.8 Hz), 2.21 (3H, s), 2.08 (3H, d, J = 6.6 Hz), MS (ESI) m/z: 457 (M + H)+. |
| Intermediate-12b | $^1$H-NMR (300 MHz, CDCl$_3$) δ 8.70 (1H, s), 8.49 (1H, d, J = 6.2 Hz), 8.02 (1H, s), 7.75 (1H, d, J = 6.2 Hz), 7.46 (1H, dd, J = 9.9, 2.2 Hz), 5.62 (2H, s), 4.83 (2H, q, J = 8.4 Hz), 4.55 (2H, q, J = 7.3 Hz), 1.50 (3H, t, J = 7.3 Hz), MS (ESI) m/z: 399 (M + H)$^+$. |
| Intermediate-13b | $^1$H-NMR (300 MHz, DMSO-d$_6$) δ 9.08 (1H, s), 8.35 (1H, s), 8.34 (1H, d, J = 6.2 Hz), 7.86 (1H, dd, J = 8.4, 2.2 Hz), 7.80 (1H, d, J = 5.9 Hz), 6.95 (1H, d, J = 8.4 Hz), 6.64 (1H, tt, J = 51.7, 5.1 Hz), 5.77 (2H, s), 4.84 (2H, t, J = 13.9 Hz), 4.42 (2H, q, J = 7.0 Hz), 1.39 (3H, t, J = 7.0 Hz), MS (ESI) m/z: 413 (M + H)$^+$. |
| Intermediate-14b | $^1$H-NMR (300 MHz, DMSO-d$_6$) δ 9.03 (1H, s), 8.35 (1H, d, J = 5.9 Hz), 7.81 (1H, d, J = 5.9 Hz), 7.43 (2H, d, J = 8.8 Hz), 7.06 (2H, d, J = 8.8 Hz), 5.73 (2H, s), 4.75 (2H, q, J = 8.8 Hz), 4.43 (2H, q, J = 7.3 Hz), 1.39 (3H, t, J = 7.3 Hz), MS (ESI) m/z: 380 (M + H)$^+$. |
| Intermediate-15b | $^1$H-NMR (300 MHz, CDCl$_3$) δ 8.66 (1H, s), 8.48 (1H, d, J = 6.2 Hz), 8.24 (1H, d, J = 2.2 Hz), 7.75 (1H, d, J = 6.2 Hz), 7.68 (1H, dd, J = 8.8, 2.2 Hz), 6.88 (1H, d, J = 8.8 Hz), 5.62 (2H, s), 4.92-4.74 (2H, m), 4.55 (2H, q, J = 7.0 Hz), 1.49 (3H, t, J = 7.0 Hz), MS (ESI) m/z: 431 (M + H)$^+$. |
| | Table 6-2 |
| Intermediate-19b | $^1$H-NMR (300 MHz, CDCl$_3$) δ 8.64 (1H, s), 8.48 (1H, d, J = 6.2 Hz), 8.03 (1H, d, J = 1.8 Hz), 7.76 (1H, d, J = 6.2 Hz), 7.54 (1H, d, J = 1.8 Hz), 7.08 (4H, d, J = 6.6 Hz), 5.58 (2H, s), 4.54 (2H, q, J = 7.0 Hz), 2.33 (3H, s), 1.50 (3H, t, J = 7.0 Hz), MS (ESI) m/z: 407 (M + H)$^+$. |
| Intermediate-20b | $^1$H-NMR (300 MHz, CDCl$_3$) δ 8.50-8.46 (2H, m), 8.11 (1H, s), 7.75 (1H, dd, J = 6.2, 0.7 Hz), 6.77 (1H, s), 5.64 (2H, s), 4.77 (2H, q, J = 8.4 Hz), 4.52 (2H, q, J = 7.3 Hz), 2.26 (3H, s), 1.48 (3H, t, J = 7.3 Hz), MS (ESI) m/z: 395 (M + H)$^+$. |
| Intermediate-21b | $^1$H-NMR (300 MHz, CDCl$_3$) δ 8.63 (1H, s), 8.48 (1H, d, J = 5.9 Hz), 8.07 (1H, d, J = 2.2 Hz), 7.75 (1H, d, J = 5.9 Hz), 7.43 (1H, d, J = 2.2 Hz), 5.56 (2H, s), 4.59-4.50 (4H, m), 2.71-2.54 (2H, m), 2.16 (3H, s), 1.49 (3H, t, J = 7.0 Hz), MS (ESI) m/z: 409 (M + H)$^+$. |
| Intermediate-22b | $^1$H-NMR (300 MHz, CDCl$_3$) δ 8.81 (1H, s), 8.49 (1H, d, J = 6.2 Hz), 7.75 (1H, d, J= 6.2 Hz), 7.34 (1H, s), 5.89 (2H, s), 4.94 (2H, q, J = 8.4 Hz), 4.55 (2H, q, J = 7.0 Hz), 2.26 (3H, s), 1.50 (3H, t, J = 7.0 Hz), MS (ESI) m/z: 396 (M + H)$^+$. |

-continued

| ID# | data |
| --- | --- |
| Intermediate-23b | ¹H-NMR (300 MHz, CDCl₃) δ 8.78 (1H, s), 8.47 (1H, d, J = 6.6 Hz), 8.13 (1H, s), 7.75 (1H, d, J = 6.6 Hz), 7.15 (1H, s), 5.70 (2H, s), 4.55 (2H, q, J = 7.3 Hz), 4.44 (2H, q, J = 8.1 Hz), 2.26 (3H, s), 1.50 (3H, t, J = 7.3 Hz), MS (ESI) m/z: 395 (M + H)⁺. |
| Intermediate-24b | ¹H-NMR (300 MHz, CDCl₃) δ 8.66 (1H, s), 8.49 (1H, d, J = 5.9 Hz), 7.80-7.74 (2H, m), 7.12 (1H, d, J = 1.8 Hz), 5.60 (2H, s), 4.83 (2H, q, J = 8.4 Hz), 4.54 (2H, q, J = 7.3 Hz), 3.84 (3H, s), 1.49 (3H, t, J = 7.3 Hz), MS (ESI) m/z: 411 (M + H)⁺. |
| Intermediate-25b | ¹H-NMR (300 MHz, CDCl₃) δ 8.60 (1H, s), 8.46 (1H, d, J = 5.9 Hz), 7.75 (1H, d, J = 6.2 Hz), 7.24-7.19 (2H, m), 6.81-6.77 (1H, m), 5.57 (2H, s), 4.53 (2H, q, J = 7.0 Hz), 4.35 (2H, q, J = 8.1 Hz), 2.25 (3H, s), 1.49 (3H, t, J = 7.0 Hz), MS (ESI) m/z: 394 (M + H)⁺. |
| Intermediate-26b | ¹H-NMR (300 MHz, DMSO-d₆) δ 8.99 (1H, s), 8.33 (1H, d, J = 5.9 Hz), 7.80 (1H, d, J = 5.9 Hz), 7.27 (1H, s), 7.25 (1H, d, J = 5.9 Hz), 6.99 (1H, d, J = 8.8 Hz), 6.36 (1H, tt, J = 54.7, 3.3 Hz), 5.66 (2H, s), 4.41 (2H, q, J = 7.3 Hz), 4.28 (2H, td, J = 14.7, 3.3 Hz), 2.13 (3H, s), 1.38 (3H, t, J = 7.3 Hz), MS (ESI) m/z: 376 (M + H)⁺. |
| Intermediate-27b | ¹H-NMR (300 MHz, DMSO-d₆) δ 9.08 (1H, s), 8.35 (1H, d, J = 5.9 Hz), 8.19 (1H, d, J = 2.2 Hz), 7.82 (1H, d, J = 6.6 Hz), 7.71 (1H, s), 6.66 (1H, tt, J = 52.1, 5.1 Hz), 5.74 (2H, s), 4.85 (2H, t, J = 13.9 Hz), 4.43 (2H, q, J = 7.3 Hz), 2.15 (3H, s), 1.40 (3H, t, J = 7.3 Hz), MS (ESI) m/z: 427 (M + H)⁺. |
| Intermediate-28b | ¹H-NMR (300 MHz, CDCl₃) δ 8.71 (1H, s), 8.50 (1H, d, J = 6.2 Hz), 7.77 (1H, d, J = 6.2 Hz), 6.67 (1H, s), 6.50 (1H, s), 5.59 (2H, s), 4.74 (2H, q, J = 8.8 Hz), 4.56 (2H, q, J = 7.0 Hz), 2.41 (3H, s), 1.50 (3H, t, J = 7.0 Hz), MS (ESI) m/z: 395 (M + H)⁺. |
| Intermediate-30b | ¹H-NMR (300 MHz, DMSO-d₆) δ 9.11 (1H, s), 8.89 (1H, s), 8.66 (1H, d, J = 2.2 Hz), 8.40-8.30 (2H, m), 8.05 (1H, d, J = 8.8 Hz), 7.84 (1H, d, J = 5.9 Hz), 6.65 (1H, d, J = 2.2 Hz), 5.94 (2H, s), 4.44 (2H, q, J = 6.6 Hz), 1.40 (3H, t, J = 6.6 Hz), MS (ESI) m/z: 417 (M + H)⁺. |
| Intermediate-31b | ¹H-NMR (300 MHz, DMSO-d₆) δ 9.06 (1H, s), 8.35 (1H, d, J =5.9 Hz), 8.15 (1H, s), 7.81 (1H, d, J = 5.9 Hz), 7.49 (1H, s), 5.71 (2H, s), 4.47-4.37 (4H, m), 4.13 (2H, q, J = 9.5 Hz), 3.95-3.90 (2H, m), 2.11 (3H, s), 1.40 (3H, t, J = 6.6 Hz), MS (ESI) m/z: 439 (M + H)⁺. |
| Intermediate-32b | ¹H-NMR (300 MHz, DMSO-d₆) δ 8.90 (1H, s), 8.35 (1H, d, J = 5.9 Hz), 7.80 (1H, d, J = 6.6 Hz), 7.70 (1H, d, J = 8.0 Hz), 6.56 (1H, d, J = 8.1 Hz), 5.69 (2H, s), 5.02 (2H, q, J = 8.8 Hz), 4.43 (2H, q, J = 7.3 Hz), 3.91 (3H, s), 1.40 (3H, t, J = 6.6 Hz), MS (ESI) m/z: 411 (M + H)⁺. |

Table 6-3

| ID# | data |
| --- | --- |
| Intermediate-33b | ¹H-NMR (300 MHz, CDCl₃) δ 8.81 (1H, s), 8.48 (1H, d, J = 6.2 Hz), 7.74 (1H, d, J = 6.2 Hz), 7.52 (2H, d, J = 8.8 Hz), 6.94 (2H, d, J = 8.8 Hz), 4.91 (2H, t, J = 5.1 Hz), 4.60-4.53 (4H, m), 1.52 (3H, t, J = 7.0 Hz), MS (ESI) m/z: 380 (M + H)⁺. |
| Intermediate-34b | ¹H-NMR (300 MHz, DMSO-d₆) δ 9.09 (1H, s), 8.36 (1H, d, J = 5.9 Hz), 8.25 (1H, s), 7.80 (1H, d, J = 5.9 Hz), 5.88 (2H, s), 5.05 (2H, q, J = 9.5 Hz), 4.45 (2H, q, J = 7.3 Hz), 2.38 (3H, s), 1.39 (3H, t, J = 7.3 Hz), MS (ESI) m/z: 396 (M + H)⁺. |
| Intermediate-35b | ¹H-NMR (300 MHz, DMSO-d₆) δ 9.07 (1H, s), 8.35 (1H, d, J = 5.9 Hz), 8.18 (1H, d, J = 2.2 Hz), 7.82 (1H, d, J = 5.9 Hz), 7.69 (1H, d, J = 2.2 Hz), 5.74 (2H, s), 4.56 (2H, t, J = 12.5 Hz), 4.44 (2H, q, J = 7.3 Hz), 2.15 (3H, s), 1.73 (3H, t, J = 19.1 Hz), 1.40 (3H, t, J = 7.3 Hz), MS (ESI) m/z: 391 (M + H)⁺. |
| Intermediate-37b | ¹H-NMR (300 MHz, CDCl₃) δ 8.60-8.56 (2H, m), 8.00 (1H, s), 7.84 (1H, d, J = 6.6 Hz), 7.46 (2H, t, J = 8.0 Hz), 7.34-7.26 (3H, m), 7.22 (1H, s), 5.56 (2H, s), 4.77 (2H, q, J = 8.0 Hz), 2.18-2.01 (1H, m), 1.00-0.95 (2H, m), 0.69-0.65 (2H, m), MS (ESI) m/z: 469 (M + H)⁺. |
| Intermediate-38b | ¹H-NMR (300 MHz, CDCl₃) δ 8.73 (1H, s), 8.49 (1H, d, J = 6.2 Hz), 8.36 (1H, s), 8.27 (1H, s), 7.77 (1H, d, J = 6.2 Hz), 7.64 (2H, s), 5.69 (2H, s), 4.55 (2H, q, J = 7.0 Hz), 2.57 (3H, s), 1.50 (3H, t, J = 7.0 Hz), MS (ESI) m/z: 397 (M + H)⁺. |
| Intermediate-39b | ¹H-NMR (300 MHz, CDCl₃) δ 8.66 (1H, s), 8.56 (1H, d, J = 5.9 Hz), 8.02 (1H, d, J = 2.2 Hz), 7.84 (1H, d, J = 5.9 Hz), 7.50-7.43 (3H, m), 7.35-7.25 (3H, m), 5.84 (1H, q, J = 6.6 Hz), 4.75 (2H, q, J = 8.8 Hz), 2.21 (3H, s), 2.08 (3H, d, J = 6.6 Hz), MS (ESI) m/z: 457 (M + H)⁺. |
| Intermediate-40b | ¹H-NMR (300 MHz, DMSO-d₆) δ 9.13 (1H, s), 8.37 (1H, d, J = 5.9 Hz), 7.93 (2H, d, J = 8.1 Hz), 7.82 (1H, d, J = 5.9 Hz), 7.54 (2H, t, J = 8.1 Hz), 7.39 (1H, t, J = 7.3 Hz), 6.03 (2H, s), 4.45 (2H, q, J = 6.6 Hz), 2.35 (3H, s), 1.41 (3H, t, J = 7.3 Hz), MS (ESI) m/z: 363 (M + H)⁺. |
| Intermediate-41b | ¹H-NMR (300 MHz, DMSO-d₆) δ 9.11 (1H, s), 8.37 (1H, d, J = 5.9 Hz), 7.84-7.79 (2H, m), 6.98-6.93 (2H, m), 5.86 (2H, s), 4.89 (2H, q, J = 9.5 Hz), 4.45 (2H, q, J = 7.3 Hz), 1.41 (3H, t, J = 7.3 Hz), MS (ESI) m/z: 381 (M + H)⁺. |
| Intermediate-42b | ¹H-NMR (300 MHz, DMSO-d₆) δ 9.05 (1H, s), 8.35 (1H, d, J = 5.9 Hz), 8.13 (1H, d, J = 2.2 Hz), 7.81 (1H, d, J = 5.9 Hz), 7.61 (1H, d, J = 2.2 Hz), 5.69 (2H, s), 4.43 (2H, q, J = 7.3 Hz), 4.10 (2H, d, J =6.6 Hz), 2.11 (3H, s), 1.39 (3H, t, J = 7.3 Hz), 1.28-1.15 (1H m), 0.55-0.48 (2H, m), 0.32-0.28 (2H, m), MS (ESI) m/z: 367 (M + H)⁺. |
| Intermediate-43b | ¹H-NMR (300 MHz, CDCl₃) δ 8.60 (1H, s), 8.47 (1H, d, J = 6.2 Hz), 8.12 (1H, s), 7.75 (1H d, J = 6.2 Hz), 7.32 (2H, s), 5.52 (2H, s), 4.53 (2H, q, J = 7.0 Hz), 4.51-4.45 (1H, m), 4.32-4.20 (2H, m), 2.12 (3H, s), 1.49 (3H, t, J = 7.0 Hz), MS (ESI) m/z: 394 (M + H)⁺. |

| ID# | data |
| --- | --- |
| Intermediate-44b | ¹H-NMR (300 MHz, CDCl₃) δ 8.67 (1H, s), 8.48 (1H, d, J = 6.2 Hz), 7.76 (1H, d, J = 6.2 Hz), 7.26-7.21 (3H, m), 5.62 (2H, s), 4.54 (2H, q, J = 7.0 Hz), 2.30 (3H, s), 1.49 (3H, t, J = 7.0 Hz), MS (ESI) m/z: 380 (M + H)⁺. |
| Intermediate-45b | ¹H-NMR (300 MHz, CDCl₃) δ 8.73 (1H, s), 8.51 (1H, d, J = 6.2 Hz), 8.13 (1H, d, J = 5.1 Hz), 7.77 (1H, d, J = 6.2 Hz), 6.84 (1H, d, J = 5.1 Hz), 6.68 (1H, s), 5.65 (2H, s), 4.75 (2H, q, J = 8.4 Hz), 4.55 (2H, q, J = 7.0 Hz), 1.50 (3H, t, J = 7.0 Hz), MS (ESI) m/z: 381 (M + H)⁺. |
| Intermediate-47b | ¹H-NMR (300 MHz, CDCl₃) δ 8.55-8.45 (2H, m), 8.36 (1H, d, J = 7.7 Hz), 8.15 (1H, s), 7.88-7.76 (2H, m), 7.73-7.61 (2H, m), 5.99 (2H, s), 5.00 (2H, q, J = 8.4 Hz), 4.46 (2H, q, J = 7.0 Hz), 1.42 (3H, t, J = 7.0 Hz), MS (ESI) m/z: 431 (M + H)⁺. |

Table 6-4

| ID# | data |
| --- | --- |
| Intermediate-48b | ¹H-NMR (300 MHz, DMSO-d₆) δ 9.08 (1H, s), 8.36 (1H, d, J = 5.9 Hz), 7.83 (1H, d, J = 5.9 Hz), 7.42 (2H, d, J = 8.1 Hz), 7.35 (2H, d, J = 8.1 Hz), 5.80 (2H, s), 4.64 (2H, s), 4.44 (2H, q, J = 7.3 Hz), 4.08 (2H, q, J =9.5 Hz), 1.40 (3H, t, J = 7.3 Hz), MS (ESI) m/z: 394 (M + H)⁺. |
| Intermediate-49b | MS (ESI) m/z: 377 (M + H)⁺. |
| Intermediate-50b | ¹H-NMR (300 MHz, CDCl₃) δ 8.56 (1H, s), 8.48 (1H, d, J = 6.2 Hz), 7.76 (1H, d, J = 6.2 Hz), 7.51 (1H, s), 7.35-7.26 (1H, m), 7.20-7.11 (1H, m), 6.77 (1H, s), 5.87 (2H, s), 4.49 (2H, q, J = 7.0 Hz), 3.68 (3H, s), 1.45 (3H, t, J = 7.0 Hz), MS (ESI) m/z: 419 (M + H)⁺. |
| Intermediate-51b | ¹H-NMR (300 MHz, CDCl₃) δ 8.64 (1H, s), 8.48 (1H, d, J = 6.2 Hz), 7.76 (1H, dd, J = 6.2, 0.9 Hz), 7.42 (1H, d, J = 2.2 Hz), 7.35-7.22 (1H, m), 6.94 (1H, d, J = 8.4 Hz), 6.14 (1H, tt, J = 55.0, 4.0 Hz), 5.58 (2H, s), 4.54 (2H, q, J = 7.3 Hz), 4.24 (2H, td, J = 12.8, 4.0 Hz), 1.49 (3H, t, J = 7.3 Hz), MS (ESI) m/z: 396 (M + H)⁺. |
| Intermediate-52b | ¹H-NMR (300 MHz, CDCl₃) δ 8.70 (1H, s), 8.50-8.46 (2H, m), 7.76 (1H, d, J = 5.5 Hz), 7.49 (1H, s), 5.66 (2H, s), 4.81 (2H, s), 4.55 (2H, q, J = 7.0 Hz), 3.88 (2H, q, J = 8.8 Hz), 2.38 (3H, s), 1.50 (3H, t, J = 6.9 Hz), MS (ESI) m/z: 409 (M + H)⁺. |
| Intermediate-53b | ¹H-NMR (300 MHz, CDCl₃) δ 8.68 (1H, s), 8.58 (1H, d, J = 5.9 Hz), 7.85 (1H, d, J = 5.9 Hz), 7.49-7.39 (3H, m), 7.34-7.21 (6H, m), 5.69 (2H, s), 4.44 (2H, q, J = 8.1 Hz), 2.26 (3H, s), 1.50 (3H, t, J = 7.3 Hz), MS (ESI) m/z: 414 (M + H)⁺. |
| Intermediate-54b | ¹H-NMR (300 MHz, CDCl₃) δ 8.78 (1H, s), 8.57 (1H, d, J = 6.6 Hz), 8.18 (1H, s), 7.83 (1H, d, J = 6.6 Hz), 7.55-7.45 (3H, m), 7.35-7.27 (3H, m), 5.02-4.96 (4H, m), MS (ESI) m/z: 447 (M + H)⁺. |
| Intermediate-55b | ¹H-NMR (300 MHz, CDCl₃) δ 8.80 (1H, s), 8.47 (1H, d, J = 5.9 Hz), 8.35 (1H, d, J = 2.2 Hz), 7.75 (1H, d, J = 6.2 Hz), 7.32-7.23 (2H, m), 5.75 (2H, s), 4.55 (2H, q, J = 7.0 Hz), 4.47 (2H, t, J = 12.8 Hz), 1.50 (3H, t, J = 7.0 Hz), MS (ESI) m/z: 431 (M + H)⁺. |
| Intermediate-56b | ¹H-NMR (300 MHz, CDCl₃) δ 8.66 (1H, s), 8.49 (1H, d, J = 6.2 Hz), 7.76 (1H, d, J = 6.2 Hz), 7.38 (2H, d, J = 8.8 Hz), 7.24 (2H, d, J = 8.8 Hz), 5.91 (1H, tt, J = 52.7, 2.6 Hz), 5.67 (2H, s), 4.54 (2H, q, J = 7.0 Hz), 1.49 (3H, t, J = 7.0 Hz), MS (ESI) m/z: 398 (M + H)⁺. |
| Intermediate-57b | ¹H-NMR (300 MHz, DMSO-d₆) δ 9.05 (1H, s), 8.37-8.33 (2H, m), 7.84-7.77 (1H, m), 7.57-7.40 (2H, m), 6.68 (1H, tt, J = 52.1 and 5.1 Hz), 5.86 (2H, s), 4.70 (2H, t, J = 13.9 Hz), 4.45 (2H, q, J = 6.6 Hz), 1.41 (3H, t, J = 6.6 Hz), MS (ESI) m/z: 413 (M + H)⁺. |
| Intermediate-58b | ¹H-NMR (300 MHz, CDCl₃) δ 8.70 (1H, s), 8.49 (1H, d, J = 6.2 Hz), 8.14 (1H, d, J = 2.2 Hz), 7.76-7.74 (2H, m), 6.05 (1H, tt, J = 52.7, 4.7 Hz), 5.60 (2H, s), 4.78 (2H, t, J = 12.1 Hz), 4.55 (2H, q, J = 7.0 Hz), 1.50 (3H, t, J = 7.0 Hz), MS (ESI) m/z: 447 (M + H)⁺. |
| Intermediate-59b | ¹H-NMR (300 MHz, CDCl₃) δ 8.69 (1H, s), 8.58 (1H, d, J = 5.9 Hz), 7.85 (1H, d, J = 6.2 Hz), 7.62 (2H, s), 7.53-7.44 (4H, m), 7.34-7.27 (3H, m), 5.73 (2H, s), MS (ESI) m/z: 398 (M + H)⁺. |
| Intermediate-60b | ¹H-NMR (300 MHz, CDCl₃) δ 8.82 (1H, s), 8.46 (1H, d, J = 6.6 Hz), 8.12 (1H, s), 7.74 (1H, d, J = 6.6 Hz), 7.12 (1H, s), 5.92 (1H, q, J = 7.4 Hz), 4.55 (2H, q, J = 7.3 Hz), 4.43 (2H, q, J = 8.0 Hz), 2.24 (3H, s), 2.10 (3H, d, J = 7.4 Hz), 1.50 (3H, t, J = 7.3 Hz), MS (ESI) m/z: 409 (M + H)⁺. |
| Intermediate-61b | ¹H-NMR (300 MHz, CDCl₃) δ 8.66 (1H, s), 8.57 (1H, d, J = 5.9 Hz), 8.44 (1H, d, J = 2.2 Hz), 7.84 (1 H, d, J = 5.9 Hz), 7.49-7.43 (3H, m), 7.34-7.27 (3H, m), 5.64 (2H, s), 3.03-2.98 (2H, m), 2.71-2.57 (2H, m), 2.23 (3H, s), MS (ESI) m/z: 441 (M + H)⁺. |
| Intermediate-62b | MS (ESI) m/z: 409 (M + H)⁺. |

Table 6-5

| ID# | data |
| --- | --- |
| Intermediate-63b | ¹H-NMR (300 MHz, CDCl₃) δ 8.67 (1H, s), 8.58 (1H, d, J = 6.6 Hz), 8.12 (1H, s), 7.84 (1H d, J = 6.6 Hz), 7.72 (1H, d, J = 2.2 Hz), 7.47 (2H, t, J = 7.3 Hz), 7.35-7.26 (3H, m), 5.60 (2H, s), 4.54 (2H, t, J = 11.7 Hz), 1.76 (3H, t, J = 18.3 Hz), MS (ESI) m/z: 459 (M + H)⁺. |
| Intermediate-64b | ¹H-NMR (300 MHz, CDCl₃) δ 8.68 (1H, s), 8.49 (1H, d, J = 6.2 Hz), 8.13 (1H, d, J = 2.2 Hz), 7.75 (1H, d, J = 5.9 Hz), 7.70 (1H, d, J = 1.8 Hz), 5.58 (2H, s), 4.62 (2H, t, J = 6.6 Hz), 4.55 (2H, q, J = 7.0 Hz), 2.74-2.58 (2H m), 1.50 (3H, t, J = 7.3 Hz), MS (ESI) m/z: 429 (M + H)⁺. |
| Intermediate-65b | ¹H-NMR (300 MHz, CDCl₃) δ 8.85 (1H, s), 8.48 (1H, d, J = 5.9 Hz), 8.08 (1H, s), 7.72 (1H, d, J = 6.2 Hz), 7.59 (1H, d, J = 7.3 Hz), 7.46 (1H, d, J = 8.8 Hz), 6.02 (2H, s), 4.53 (2H, q, J = 7.3 Hz), 3.96 (3H, s), 1.48 (3H, t, J = 6.9 Hz), MS (ESI) m/z: 404 (M + H)⁺. |
| Intermediate-66b | ¹H-NMR (300 MHz, CDCl₃) δ 8.78 (1H, s), 8.47 (1H, d, J = 6.0 Hz), 8.14 (1H, s), 7.75 (1H, d, J = 6.0 Hz), 7.14 (1H, s), 6.02 (1H, tt, J = 52.9, 4.0 Hz), 5.70 (2H, s), 4.55 (2H, q, J = 7.3 Hz), 4.45 (2H, t, J = 11.7 Hz), 2.23 (3H, s), 1.50 (3H, t, J = 7.3 Hz), MS (ESI) m/z: 427 (M + H)⁺. |

-continued

| ID# | data |
| --- | --- |
| Intermediate-67b | $^1$H-NMR (300 MHz, DMSO-d$_6$) δ 8.66 (1H, s), 8.49 (1H, d, J = 5.9 Hz), 8.11 (1H, d, J = 2.2 Hz), . 7 75 (1H, d, J = 5.9 Hz), 7.67 (1H, d, J = 2.2 Hz), 5.57 (2H, s), 4.55 (2H, q, J = 7.0 Hz), 4.23 (2H, d, J = 7.4 Hz), 1.50 (3H, t, J = 7.0 Hz), 1.38-1.20 (1H, m), 0.66-0.56 (2H, m), 0.42-0.32 (2H, m), MS (ESI) m/z: 387 (M + H)$^+$. |
| Intermediate-68b | $^1$H-NMR (300 MHz, CDCl$_3$) δ 8.83 (1H, s), 8.46 (1H, d, J = 6.6 Hz), 8.12 (1H, s), 7.75 (1H, d, J = 5.9 Hz), 7.12 (1H, s), 5.93 (1H, q, J = 6.6 Hz), 4.55 (2H, q, J = 7.3 Hz), 4.43 (2H, q, J = 7.3 Hz), 2.25 (3H, s), 2.10 (3H, d, J = 7.3 Hz), 1.50 (3H, t, J = 6.6 Hz), MS (ESI) m/z: 409 (M + H)$^+$. |
| Intermediate-69b | $^1$H-NMR (300 MHz, CDCl$_3$) δ 8.65 (1H, s), 8.49 (1H, d, J = 6.2 Hz), 7.76 (1H, d, J = 6.2 Hz), 7.43 (1H, d, J = 2.2 Hz), 7.25 (1H, dd, J = 8.4, 2.2 Hz), 6.97 (1H, d, J = 8.4 Hz), 5.59 (2H, s), 4.54 (2H, q, J = 7.1 Hz), 4.40 (2H, q, J = 8.0 Hz), 1.50 (3H, t, J = 7.1 Hz), MS (ESI) m/z: 414 (M + H)$^+$. |
| Intermediate-70b | $^1$H-NMR (300 MHz, CDCl$_3$) δ 8.63 (1H, s), 8.48 (1H, d, J = 6.2 Hz), 8.09 (1H, d, J = 2.2 Hz), 7.76 (1H, d, J = 6.2 Hz), 7.49-7.37 (3H, m), 7.10-6.98 (2H, m), 5.56 (2H, s), 5.37 (2H, s), 4.54 (2H, q, J = 6.9 Hz), 2.20 (3H, s), 1.49 (3H, t, J = 6.9 Hz), MS (ESI) m/z: 421 (M + H)$^+$. |
| Intermediate-71b | $^1$H-NMR (300 MHz, CDCl$_3$) δ 8.62 (1H, s), 8.47 (1H, d, J = 6.2 Hz), 8.04 (1H, d, J = 2.0 Hz), 7.76 (1H, d, J = 6.2 Hz), 7.38 (1H, d, J = 2.0 Hz), 5.54 (2H, s), 5.21 (1H, quintet, J = 7.0 Hz), 4.53 (2H, q, J = 7.0 Hz), 2.53-2.38 (2H, m), 2.20-2.07 (2H, m), 2.16 (3H, s), 1.94-1.60 (2H, m), 1.49 (3H, t, J = 7.0 Hz), MS (ESI) m/z: 367 (M + H)$^+$. |
| Intermediate-72b | $^1$H-NMR (300 MHz, CDCl$_3$) δ 8.75 (1H, s), 8.46 (1H, d, J = 5.9 Hz), 8.09 (1H, s), 7.75 (1H, d, J = 5.9 Hz), 7.11 (1H, s), 5.68 (2H, s), 4.54 (2H, q, J = 7.0 Hz), 3.90 (2H, d, J = 6.6 Hz), 2.22 (3H, s), 1.49 (3H, t, J = 7.0 Hz), 1.34-1.20 (1H, m), 0.69-0.58 (2H, m), 0.40-0.30 (2H, m), MS (ESI) m/z: 367 (M + H)$^+$. |
| Intermediate-73b | $^1$H-NMR (300 MHz, CDCl$_3$) δ 8.81 (1H, s), 8.49 (1H, d, J = 5.9 Hz), 7.75 (1H, d, J = 5.9 Hz), 7.34 (1H, s), 5.99 (1H, tt, J = 53.4, 4.3 Hz), 5.89 (2H, s), 4.95 (2H, t, J = 12.5 Hz), 4.55 (2H, q, J = 7.3 Hz), 2.24 (3H, s), 1.50 (3H, t, J = 7.3 Hz), MS (ESI) m/z: 428 (M + H)$^+$. |

Table 6-6

| | |
| --- | --- |
| Intermediate-74b | $^1$H-NMR (300 MHz, CDCl$_3$) δ 8.77 (1H, s), 8.47 (1H, d, J = 6.0 Hz), 8.11 (1H, s), 7.75 (1H, d, J = 6.0 Hz), 7.14 (1H, s), 5.70 (2H, s), 4.55 (2H, q, J = 7.0 Hz), 4.19 (2H, t, J = 11.0 Hz), 2.24 (3H, s), 1.78 (3H, t, J = 18.7 Hz), 1.50 (3H, t, J = 7.0 Hz), MS (ESI) m/z: 391 (M + H)$^+$. |
| Intermediate-75b | $^1$H-NMR (300 MHz, CDCl$_3$) δ 8.59 (1H, s), 8.47 (1H, d, J = 6.2 Hz), 7.76 (1H, d, J = 6.2 Hz), 7.24-7.18 (2H, m), 6.78 (1H, d, J = 8.8 Hz), 5.57 (2H, s), 4.53 (2H, q, J = 7.3 Hz), 4.10 (2H, t, J = 11.0 Hz), 2.24 (3H, s), 1.79 (3H, t, J = 18.7 Hz), 1.49 (3H, t, J = 7.3 Hz), MS (ESI) m/z: 390 (M + H)$^+$. |
| Intermediate-76b | $^1$H-NMR (300 MHz, CDCl$_3$) δ 8.61 (1H, s), 8.46 (1H, d, J = 6.0 Hz), 7.76 (1H, d, J = 6.0 Hz), 7.21-7.13 (2H, m), 6.77 (1H, d, J = 9.2 Hz), 6.09 (1H, tt, J = 55.0 and 4.0 Hz), 5.82 (1H, q, J = 6.9 Hz), 4.53 (2H, q, J = 7.3 Hz), 4.17 (2H, td, J = 13.0 and 4.0 Hz), 2.22 (3H, s), 2.06 (3H, d, J = 6.9 Hz), 1.49 (3H, t, J = 7.3 Hz), MS (ESI) m/z: 390 (M + H)$^+$. |
| Intermediate-77b | $^1$H-NMR (300 MHz, CDCl$_3$) δ 8.64 (1H, s), 8.48 (1H, d, J = 5.9 Hz), 7.77 (1H, d, J = 5.9 Hz), 7.02 (2H, s), 6.07 (1H, tt, J = 55.0 and 4.4 Hz), 5.54 (2H, s), 4.54 (2H, q, J = 6.6 Hz), 3.99 (2H, td, J = 13.9 and 4.4 Hz), 2.27 (6H, s), 1.49 (3H, t, J = 6.6 Hz), MS (ESI) m/z: 390 (M + H)$^+$. |
| Intermediate-78b | $^1$H-NMR (300 MHz, CDCl$_3$) δ 8.62 (1H, s), 8.48 (1H, d, J = 6.2 Hz), 7.76 (1H, d, J = 5.9 Hz), 7.18 (1H, d, J = 7.3 Hz), 6.94 (1H, d, J = 7.7 Hz), 6.79 (1H, s), 6.09 (1H, tt, J = 54.9 and 4.0 Hz), 5.60 (2H, s), 4.53 (2H, q, J = 7.0 Hz), 4.14 (2H, td, J = 12.8 and 4.0 Hz), 2.23 (3H, s), 1.49 (3H, t, J = 7.0 Hz), MS (ESI) m/z: 376 (M + H)$^+$. |
| Intermediate-79b | $^1$H-NMR (270 MHz, CDCl$_3$) δ 8.60 (1H, s), 8.46 (1H, d, J = 6.3 Hz), 7.76 (1H, d, J = 6.3 Hz), 7.22-7.14 (2H, m), 6.77 (1H, d, J = 8.9 Hz), 5.82 (1H, q, J = 6.9 Hz), 4.53 (2H, q, J = 7.2 Hz), 4.09 (2H, t, J = 11.3 Hz), 2.23 (3H, s), 2.06 (3H, d, J = 6.9 Hz), 1.78 (3H, t, J = 18.8 Hz), 1.48 (3H, t, J = 7.2 Hz), MS (ESI) m/z: 404 (M + H)$^+$. |
| Intermediate-80b | $^1$H-NMR (270 MHz, CDCl$_3$) δ 8.62 (1H, s), 8.46 (1H, d, J = 6.0 Hz), 7.76 (1H, d, J = 6.0 Hz), 7.22-7.13 (2H, m), 6.77 (1H, d, J = 9.2 Hz), 6.09 (1H, tt, J = 55.3 and 4.0 Hz), 5.82 (1H, q, J = 6.9 Hz), 4.53 (2H, q, J = 7.3 Hz), 4.17 (2H, td, J = 12.9 and 4.0 Hz), 2.22 (3H, s), 2.06 (3H, d, J = 6.9 Hz), 1.49 (3H, t, J = 7.3 Hz), MS (ESI) m/z: 390 (M + H)$^+$. |
| Intermediate-81b | $^1$H-NMR (270 MHz, CDCl$_3$) δ 8.64 (1H, s), 8.48 (1H, d, J = 5.9 Hz), 7.76 (1H, d, J = 5.9 Hz), 7.26-7.18 (2H, m), 7.08 (1H, d, J = 7.9 Hz), 6.49 (1H, t, J = 73.8 Hz), 5.60 (2H, s), 4.54 (2H, q, J = 6.6 Hz), 2.28 (3H, s), 1.49 (3H, t, J = 6.6 Hz), MS (ESI) m/z: 362 (M + H)$^+$. |

EXAMPLE SYNTHESIS PART

Example compounds (Example-1 to 649) are prepared as follows.

Representative Procedure for Method G

The following preparation of Example 1 represents the Method G.

Example 1

N-(2-((5-methyl-6-(2,2,2-trifluoroethoxy)pyridin-3-yl)methyl)-2H-pyrazolo[4,3-c]pyridin-4-yl)isobutyramide

[Chem. 14]

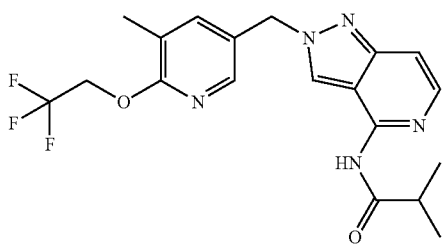

A mixture of 4-chloro-2-((5-methyl-6-(2,2,2-trifluoroethoxy)pyridin-3-yl)methyl)-2H-pyrazolo[4,3-c]pyridine (20 mg, 0.056 mmol, Intermediate-1a), isopbutyramide (15 mg, 0.17 mmol), tirs(dibenzylideneacetone)dipalladium(0) (1 mg, 1 micromol), 4,5-bis(diphenylphosphino)-9,9-dimethylxanthene (2 mg, 3 micromol), and tripotassium phosphate (18 mg, 0.084 mmol) in dioxane (2 mL) is stirred at 170° C. for 20 minutes under microwave irradiation. After cooling to rt, the resulting mixture is filtered through a short column of NH-gel eluting with EtOAc, and the filtrate is concentrated. The residue is purified by a strong cation exchange cartridge (BondElute(registered trademark) SCX, 1 g/6 mL, Varian Inc.) and then by preparative LC-MS to give 9.3 mg (40% yield) of the title compound.

Representative Procedure for Method H

The following preparation of Example 33 represents the Method H.

Example 33

N-isopropyl-2-((5-methyl-6-(2,2,2-trifluoroethoxy)pyridin-3-yl)methyl)-2H-pyrazolo[4,3-c]pyridine-4-carboxamide

[Chem. 15]

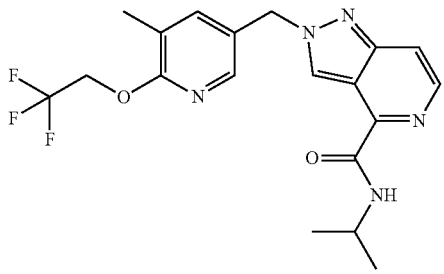

To a mixture of 2-((5-methyl-6-(2,2,2-trifluoroethoxy)pyridin-3-yl)methyl)-2H-pyrazolo[4,3-c]pyridine-4-carboxylic acid (16 mg, 0.044 mmol, Intermediate-1c) and triethylamine (0.06 mL, 0.4 mmol) in DMF (1 mL) is added HBTU (33 mg, 0.087 mmol). After stirring at rt for 10 minutes, isopropylamine (0.022 mL, 0.26 mmol) is added to the mixture. After stirring at 60° C. for 1 hour, the mixture is diluted with EtOAc (3 mL). The organic layer is washed with water (3 mL), dried over sodium sulfate, and concentrated in vacuo. The residue is filtered through NH-gel eluting with EtOAc, and the filtrate is concentrated in vacuo. The residue is purified by preparative LC-MS to give 4.6 mg (26% yield) of the title compound.

Representative Procedure for Method J

The following preparation of Example 289 represents the Method J.

Example 289

2-(2-((3-chloro-5-(trifluoromethyl)pyridin-2-yl)oxy)ethyl)-N-methyl-2H-pyrazolo[4,3-c]pyridine-4-carboxamide

[Chem. 16]

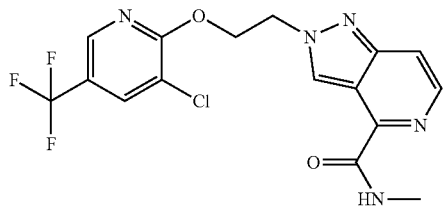

A mixture of phenyl 2-(2-((3-chloro-5-(trifluoromethyl)pyridin-2-yl)oxy)ethyl)-2H-pyrazolo[4,3-c]pyridine-4-carboxylate (15 mg, 0.032 mmol, Intermediate-36b) and 40% aqueous methylamine solution (0.1 mL) in THF (1 mL) is stirred at 80° C. for 2 hours. After removing the solvent, the residue is purified by preparative LC-MS to give 8.6 mg (66% yield) of the title compound.

Representative Procedure for Method K

The following preparation of Example 143 represents the Method K.

Example 143

N-methyl-2-((4-methyl-6-(2,2,2-trifluoroethoxy)pyridin-3-yl)methyl)-2H-pyrazolo[4.3-c]pyridine-4-carboxamide

[Chem. 17]

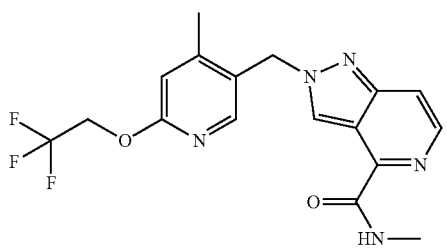

A mixture of ethyl 2-((4-methyl-6-(2,2,2-trifluoroethoxy)pyridin-3-yl)methyl)-2H-pyrazolo[4,3-c]pyridine-4-carboxylate (15 mg, 0.038 mmol, Intermediate-20b) and 40% aqueous methylamine solution (2 mL) is stirred at 60° C. for 30 minutes. After cooling to rt, the mixture is diluted with EtOAc (2 mL) and washed with water (2 mL). The organic layer is dried over sodium sulfate and concentrated. The residue is purified by a strong cation exchange cartridge (BondElute(registered trademark) SCX, 1 g/6 mL, Varian Inc.) and then by preparative LC-MS to give 6.0 mg (42% yield) of the title compound.

Representative Procedure for Method L

The following preparation of Example 141 represents the Method L.

Example 141

N-(2-hydroxyethyl)-2-((5-methyl-6-(2,2,2-trifluoroethoxy)pyridin-3-yl)methyl)-2H-pyrazolo[4,3-c]pyridine-4-carboxamide

[Chem. 18]

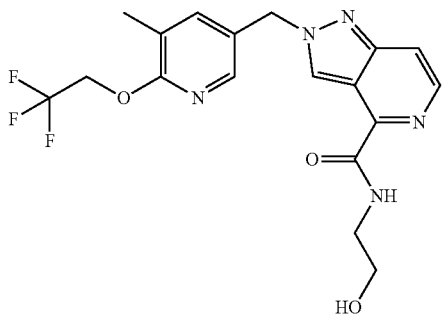

A mixture of ethyl 2-((5-methyl-6-(2,2,2-trifluoroethoxy)pyridin-3-yl)methyl)-2H-pyrazolo[4,3-c]pyridine-4-carboxylate (1.10 g, 2.79 mmol, Intermediate-1b) and 2-aminoethanol (3.41 g, 55.8 mmol) in EtOH (20 mL) is stirred at 60° C. for 3 hours. After evaporation of the solvent, the residue is diluted with EtOAc (200 mL) and washed with water (100 mL) and brine (100 mL). The organic layer is dried over sodium sulfate and concentrated in vacuo. The residual solid is washed with diisopropyl ether-EtOAc to give 1.13 g (99% yield) of the title compound as a white powder.

Representative Procedure for Method M

The following preparation of Example 30 represents the Method M.

Example 30

4-methoxy-2-((5-methyl-6-(2,2,2-trifluoroethoxy)pyridin-3-yl)methyl)-2H-pyrazolo[4,3-c]pyridine

[Chem. 19]

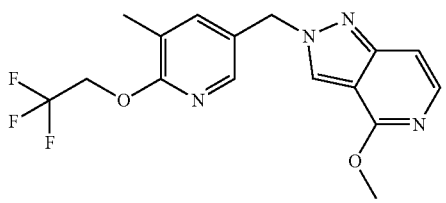

The title compound is prepared in 41% yield (72 mg, a yellow oil) from 4-chloro-2-((5-methyl-6-(2,2,2-trifluoroethoxy)pyridin-3-yl)methyl)-2H-pyrazolo[4,3-c]pyridine (180 mg, 0.51 mmol, Intermediate-1a) using MeOH as a solvent in a similar manner to Step-2 of Intermediate-A14.

Representative Procedure for Method N

The following preparation of Example 55 represents the Method N.

Example 55

4-(2-((5-methyl-6-(2,2,2-trifluoroethoxy)pyridin-3-yl)methyl)-2H-pyrazolo[4,3-c]pyridin-4-yl)morpholine

[Chem. 20]

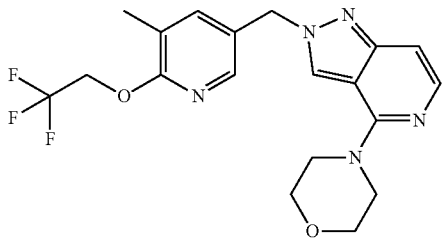

A mixture of 4-chloro-2-((5-methyl-6-(2,2,2-trifluoroethoxy)pyridin-3-yl)methyl)-2H-pyrazolo[4,3-c]pyridine (20 mg, 0.056 mmol, Intermediate-1a), morpholine (49 mg, 0.56 mmol), and potassium carbonate (47 mg, 0.34 mmol) in DMA (1.5 mL) is stirred at 120° C. for 3 hours. After cooling to rt, the mixture is diluted with EtOAc (5 mL) and washed with water (5 mL). The organic layer is dried over sodium sulfate and concentrated. The residue is purified by a strong cation exchange cartridge (BondElute(registered trademark) SCX, 1 g/6 mL, Varian Inc.) and then by preparative LC-MS to give 8.5 mg (37% yield) of the title compound.

Representative Procedure for Method P

The following preparation of Example 64 represents the Method P.

Example 64

2-((5-methyl-6-(2,2,2-trifluoroethoxy)pyridin-3-yl)methyl)-4-(1H-pyrazol-5-yl)-2H-pyrazolo[4,3-c]pyridine

[Chem. 21]

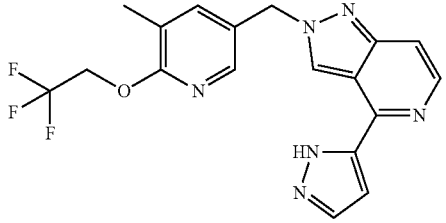

A mixture of 4-chloro-2-((5-methyl-6-(2,2,2-trifluoroethoxy)pyridin-3-yl)methyl)-2H-pyrazolo[4,3-c]pyridine (25 mg, 0.070 mmol, Intermediate-1a), (1H-pyrazol-5-yl)boronic acid hydrate (27 mg, 0.21 mmol), tris(dibenzylideneacetone)dipalladium(0) (13 mg, 0.014 mmol), 2-dicyclohexylphosphino-2',6'-dimethoxybiphenyl (12 mg, 0.028 mmol), and potassium phosphate (45 mg, 0.21 mmol) in DMF (1 mL) is stirred at 100° C. for 16 hours. After cooling to rt, the mixture is diluted with EtOAc (5 mL) and washed with water (5 mL). The organic layer is dried over sodium sulfate and concentrated. The residue is purified by a strong cation exchange cartridge (BondElute(registered trademark) SCX, 1 g/6 mL, Varian Inc.) and then by preparative LC-MS to give 2.9 mg (11% yield) of the title compound.

The following examples are prepared using the Method G, H, J, K, L, M, or N from starting materials and reagents shown in Table 7-1 to 7-55 and Table 8-1 to 8-15. The retention time and observed MS (positive or negative mode) by LC-MS of all examples are described in Table 9-1 to 9-5. $^1$H-NMR data of Example 1, 2, 69, 141, 149, 158, 166, 172, 174, 179, 183, 199, 220, 222, 223, 288, 301, 343, 462, and 518 are described in Table 10-1 to 10-2.

TABLE 7

| Ex | Structure | Name |
|---|---|---|
| 2 | 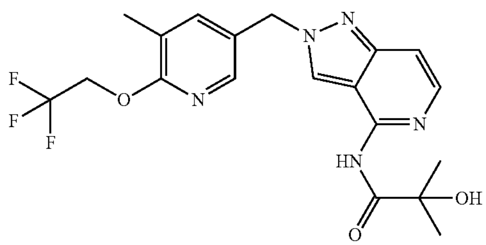 | 2-hydroxy-2-methyl-N-(2-((5-methyl-6-(2,2,2-trifluoroethoxy)pyridin-3-yl)methyl)-2H-pyrazolo[4,3-c]pyridin-4-yl)propanamide |
| 3 | 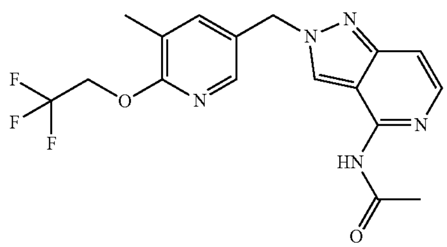 [SMILES: CC(=O)Nc1nccc2nn(Cc3cnc(OCC(F)(F)F)c(C)c3)cc12] | N-(2-((5-methyl-6-(2,2,2-trifluoroethoxy)pyridin-3-yl)methyl)-2H-pyrazolo[4,3-c]pyridin-4-yl)acetamide |
| 4 | 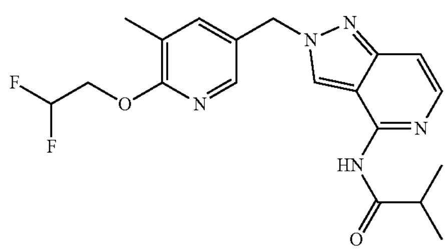 | N-(2-((6-(2,2-difluoroethoxy)-5-methylpyridin-3-yl)methyl)-2H-pyrazolo[4,3-c]pyridin-4-yl)isobutyramide |
| 5 | 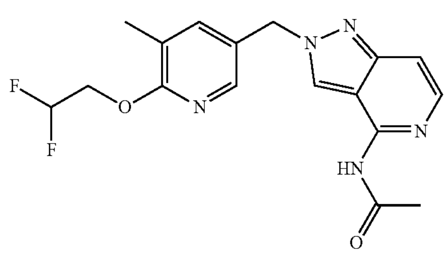 [SMILES: CC(=O)Nc1nccc2nn(Cc3cnc(OCC(F)F)c(C)c3)cc12] | N-(2-((6-(2,2-difluoroethoxy)-5-methylpyridin-3-yl)methyl-2H-pyrazolo[4,3-c]pyridin-4-yl)acetamide |
| 6 | 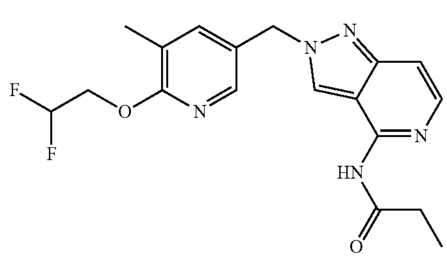 [SMILES: CCC(=O)Nc1nccc2nn(Cc3cnc(OCC(F)F)c(C)c3)cc12] | N-(2-((6-(2,2-difluoroethoxy)-5-methylpyridin-3-yl)methyl)-2H-pyrazolo[4,3-c]pyridin-4-yl)propionamide |

TABLE 7-continued

| Ex | Structure | Name |
|---|---|---|
| 7 | 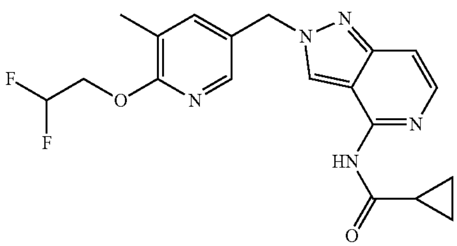 | N-(2-((6-(2,2-difluoroethoxy)-5-methylpyridin-3-yl)methyl)-2H-pyrazolo[4,3-c]pyridin-4-yl)cyclopropanecarboxamide |
| 8 | 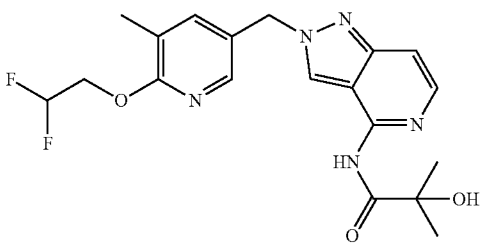 | N-(2-((6-(2,2-difluoroethoxy)-5-methylpyridin-3-yl)methyl-2H-pyrazolo[4,3-c]pyridin-4-yl)-2-hydroxy-2-methylpropanamide |
| 9 | 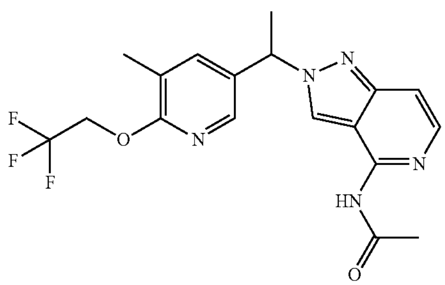 [SMILES: CC(=O)Nc1nccc2nn(C(C)c3cnc(OCC(F)(F)F)c(C)c3)cc12] | N-(2-(1-(5-methyl-6-(2,2,2-trifluoroethoxy)pyridin-3-yl)ethyl)-2H-pyrazolo[4,3-c]pyridin-4-yl)acetamide |
| 10 | 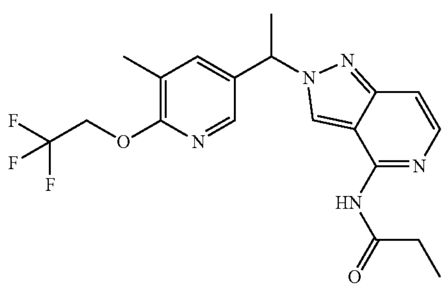 [SMILES: CCC(=O)Nc1nccc2nn(C(C)c3cnc(OCC(F)(F)F)c(C)c3)cc12] | N-(2-(1-(5-methyl-6-(2,2,2-trifluoroethoxy)pyridin-3-yl)ethyl)-2H-pyrazolo[4,3-c]pyridin-4-yl)propionamide |
| 11 | 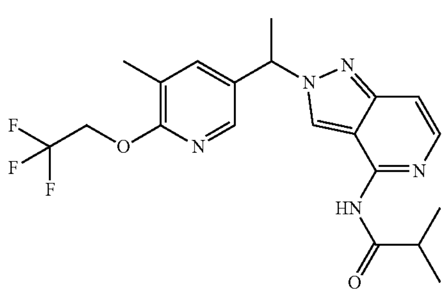 [SMILES: Cc1cc(C(C)n2cc3c(NC(=O)C(C)C)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)isobutyramide |

TABLE 7-continued

| Ex | Structure | Name |
|---|---|---|
| 12 | 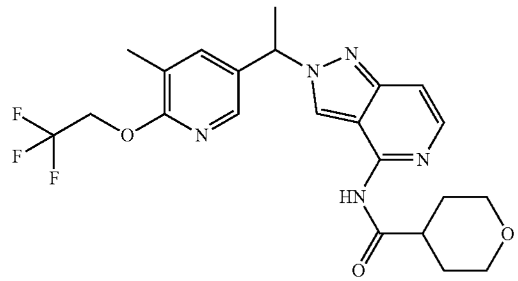 [SMILES: Cc1cc(C(C)n2cc3c(NC(=O)C4CCOCC4)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)tetrahydro-2H-pyran-4-carboxamide |
| 13 | 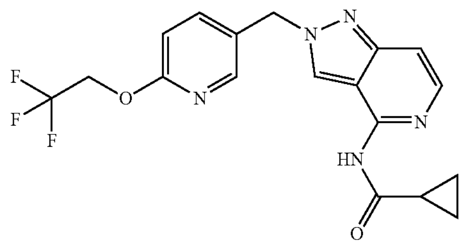 | N-(2-((6-(2,2,2-trifluoroethoxy)pyridin-3-yl)methyl)-2H-pyrazolo[4,3-c]pyridin-4-yl)cyclopropanecarboxamide |
| 14 | 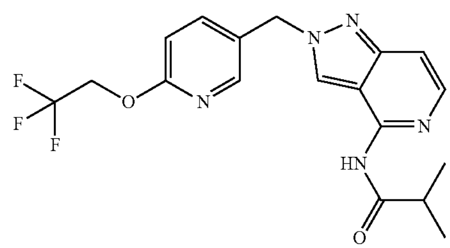 | N-(2-((6-(2,2,2-trifluoroethoxy)pyridin-3-yl)methyl)-2H-pyrazolo[4,3-c]pyridin-4-yl)isobutyramide |
| 15 | 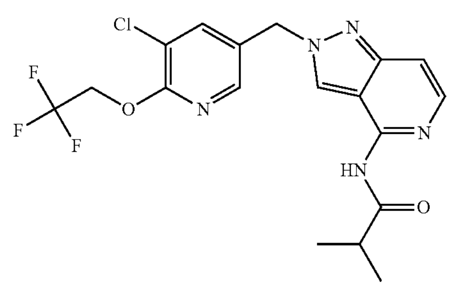 [SMILES: CC(C)C(=O)Nc1nccc2nn(Cc3cnc(OCC(F)(F)F)c(Cl)c3)cc12] | N-(2-((5-chloro-6-(2,2,2-trifluoroethoxy)pyridin-3-yl)methyl)-2H-pyrazolo[4,3-c]pyridin-4-yl)isobutyramide |
| 16 | 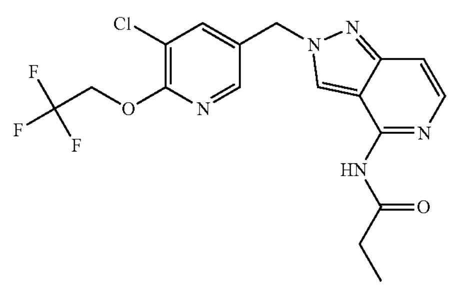 [SMILES: CCC(=O)Nc1nccc2nn(Cc3cnc(OCC(F)(F)F)c(Cl)c3)cc12] | N-(2-((5-chloro-6-(2,2,2-trifluoroethoxy)pyridin-3-yl)methyl)-2H-pyrazolo[4,3-c]pyridin-4-yl)propionamide |

TABLE 7-continued

| Ex | Structure | Name |
|---|---|---|
| 17 | 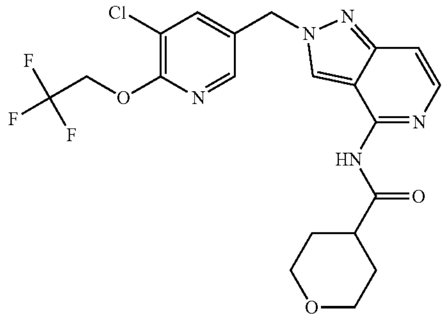 [SMILES: O=C(Nc1nccc2nn(Cc3cnc(OCC(F)(F)F)c(Cl)c3)cc12)C1CCOCC1] | N-(2-((5-chloro-6-(2,2,2-trifluoroethoxy)pyridin-3-yl)methyl)-2H-pyrazolo[4,3-c]pyridin-4-yl)tetrahydro-2H-pyran-4-carboxamide |
| 18 | 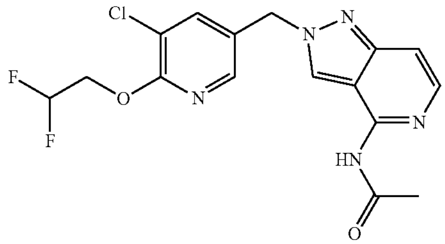 [SMILES: CC(=O)Nc1nccc2nn(Cc3cnc(OCC(F)F)c(Cl)c3)cc12] | N-(2-((5-chloro-6-(2,2-difluoroethoxy)pyridin-3-yl)methyl)-2H-pyrazolo[4,3-c]pyridin-4-yl)acetamide |
| 19 | 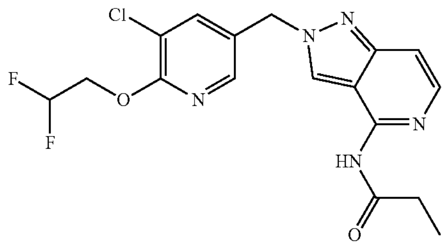 [SMILES: CCC(=O)Nc1nccc2nn(Cc3cnc(OCC(F)F)c(Cl)c3)cc12] | N-(2-((5-chloro-6-(2,2-difluoroethoxy)pyridin-3-yl)methyl)-2H-pyrazolo[4,3-c]pyridin-4-yl)propionamide |
| 20 | 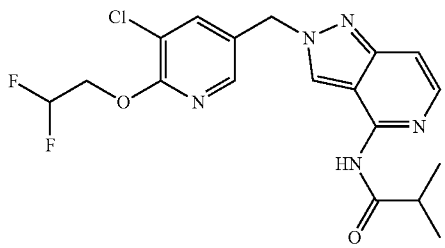 [SMILES: CC(C)C(=O)Nc1nccc2nn(Cc3cnc(OCC(F)F)c(Cl)c3)cc12] | N-(2-((5-chloro-6-(2,2-difluoroethoxy)pyridin-3-yl)methyl)-2H-pyrazolo[4,3-c]pyridin-4-yl)isobutyramide |
| 21 | 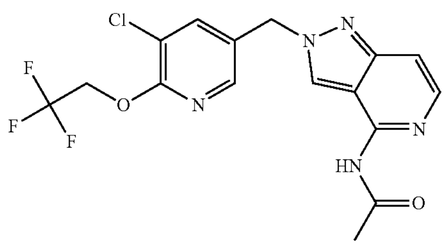 [SMILES: CC(=O)Nc1nccc2nn(Cc3cnc(OCC(F)(F)F)c(Cl)c3)cc12] | N-(2-((5-chloro-6-(2,2,2-trifluoroethoxy)pyridin-3-yl)methyl)-2H-pyrazolo[4,3-c]pyridin-4-yl)acetamide |
| 22 | 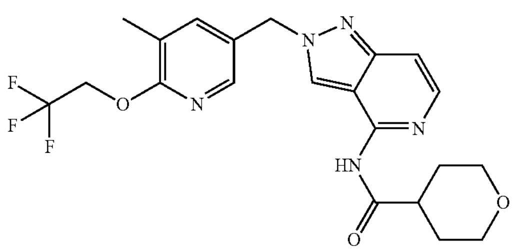 [SMILES: Cc1cc(Cn2cc3c(NC(=O)C4CCOCC4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)tetrahydro-2H-pyran-4-carboxamide |

| Ex | Structure | Name |
|---|---|---|
| 23 | 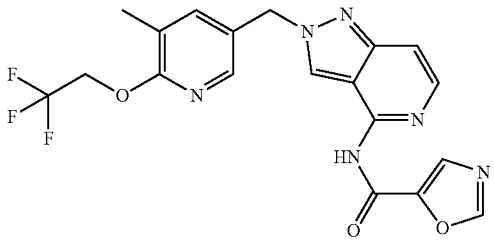 [SMILES: Cc1cc(Cn2cc3c(NC(=O)c4cnco4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)oxazole-5-carboxamide |
| 24 | 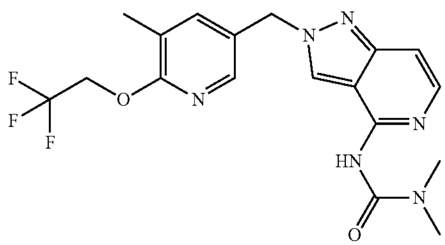 [SMILES: Cc1cc(Cn2cc3c(NC(=O)N(C)C)nccc3n2)cnc1OCC(F)(F)F] | 1,1-dimethyl-3-(2-((5-methyl-6-(2,2,2-trifluoroethoxy)pyridin-3-yl)methyl)-2H-pyrazolo[4,3-c]pyridin-4-yl)urea |
| 25 | 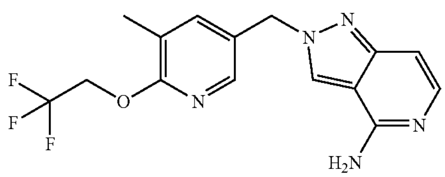 [SMILES: Cc1cc(Cn2cc3c(N)nccc3n2)cnc1OCC(F)(F)F] | 2-((5-methyl-6-(2,2,2-trifluoroethoxy)pyridin-3-yl)methyl)-2H-pyrazolo[4,3-c]pyridin-4-amine |
| 26 | 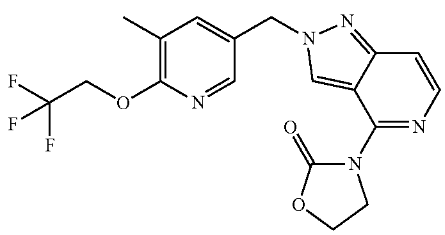 [SMILES: Cc1cc(Cn2cc3c(N4CCOC4=O)nccc3n2)cnc1OCC(F)(F)F] | 3-(2-((5-methyl-6-(2,2,2-trifluoroethoxy)pyridin-3-yl)methyl)-2H-pyrazolo[4,3-c]pyridin-4-yl)oxazolidin-2-one |
| 27 | 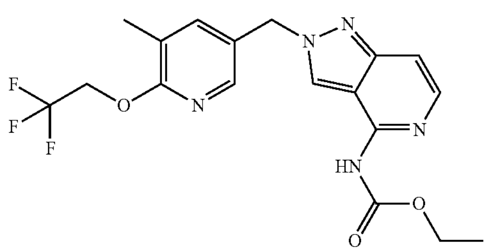 [SMILES: CCOC(=O)Nc1nccc2nn(Cc3cnc(OCC(F)(F)F)c(C)c3)cc12] | ethyl (2-((5-methyl-6-(2,2,2-trifluoroethoxy)pyridin-3-yl)methyl)-2H-pyrazolo[4,3-c]pyridin-4-yl)carbamate |
| 28 | 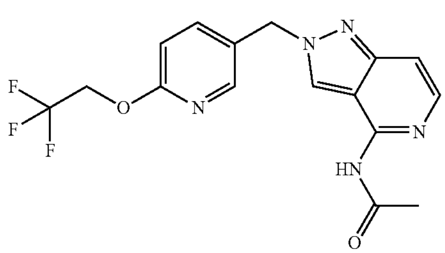 [SMILES: CC(=O)Nc1nccc2nn(Cc3ccc(OCC(F)(F)F)nc3)cc12] | N-(2-((6-(2,2,2-trifluoroethoxy)pyridin-3-yl)methyl)-2H-pyrazolo[4,3-c]pyridin-4-yl)acetamide |

TABLE 7-continued

| Ex | Structure | Name |
|---|---|---|
| 29 | 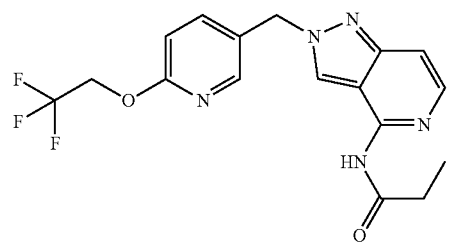 [SMILES: CCC(=O)Nc1nccc2nn(Cc3ccc(OCC(F)(F)F)nc3)cc12] | N-(2-((6-(2,2,2-trifluoroethoxy)pyridin-3-yl)methyl)-2H-pyrazolo[4,3-c]pyridin-4-yl)propionamide |
| 31 | 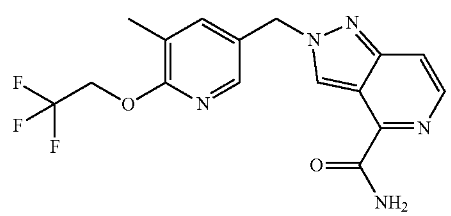 [SMILES: Cc1cc(Cn2cc3c(C(N)=O)nccc3n2)cnc1OCC(F)(F)F] | 2-((5-methyl-6-(2,2,2-trifluoroethoxy)pyridin-3-yl)methyl)-2H-pyrazolo[4,3-c]pyridine-4-carboxamide |
| 32 | 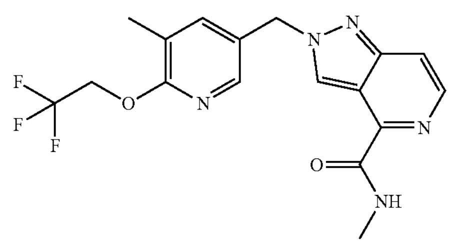 [SMILES: CNC(=O)c1nccc2nn(Cc3cnc(OCC(F)(F)F)c(C)c3)cc12] | N-methyl-2-((5-methyl-6-(2,2,2-trifluoroethoxy)pyridin-3-yl)methyl)-2H-pyrazolo[4,3-c]pyridine-4-carboxamide |
| 34 | 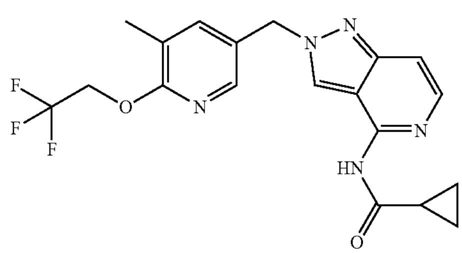 [SMILES: Cc1cc(Cn2cc3c(NC(=O)C4CC4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)cyclopropanecarboxamide |
| 35 | 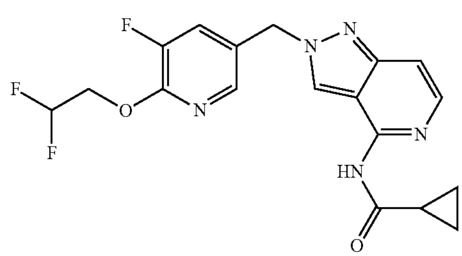 [SMILES: O=C(Nc1nccc2nn(Cc3cnc(OCC(F)F)c(F)c3)cc12)C1CC1] | N-(2-((6-(2,2-difluoroethoxy)-5-fluoropyridin-3-yl)methyl)-2H-pyrazolo[4,3-c]pyridin-4-yl)cyclopropanecarboxamide |
| 36 | 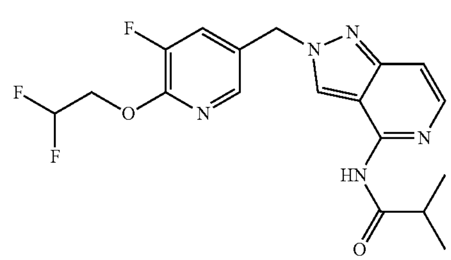 [SMILES: CC(C)C(=O)Nc1nccc2nn(Cc3cnc(OCC(F)F)c(F)c3)cc12] | N-(2-((6-(2,2-difluoroethoxy)-5-fluoropyridin-3-yl)methyl)-2H-pyrazolo[4,3-c]pyridin-4-yl)isobutyramide |

| Ex | Structure | Name |
|---|---|---|
| 37 | 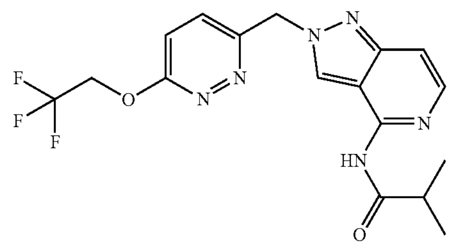 | N-(2-((6-(2,2,2-trifluoroethoxy)pyridazin-3-yl)methyl)-2H-pyrazolo[4,3-c]pyridin-4-yl)isobutyramide |
| 38 | 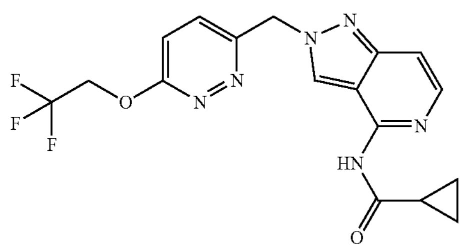 | N-(2-((6-(2,2,2-trifluoroethoxy)pyridazin-3-yl)methyl)-2H-pyrazolo[4,3-c]pyridin-4-yl)cyclopropanecarboxamide |
| 39 | 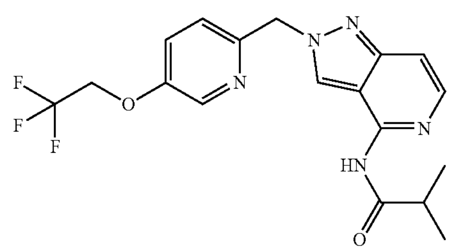 [SMILES: CC(C)C(=O)Nc1nccc2nn(Cc3ccc(OCC(F)(F)F)cn3)cc12] | N-(2-((5-(2,2,2-trifluoroethoxy)pyridin-2-yl)methyl)-2H-pyrazolo[4,3-c]pyridin-4-yl)isobutyramide |
| 40 | 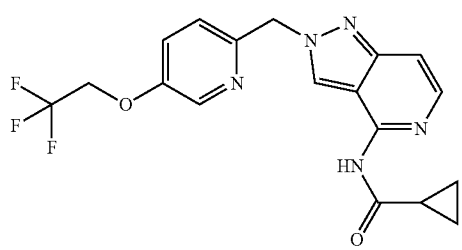 | N-(2-((5-(2,2,2-trifluoroethoxy)pyridin-2-yl)methyl)-2H-pyrazolo[4,3-c]pyridin-4-yl)cyclopropanecarboxamide |
| 41 | 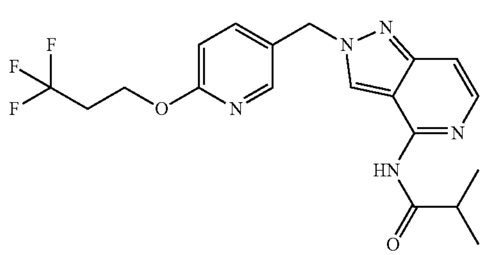 [SMILES: CC(C)C(=O)Nc1nccc2nn(Cc3ccc(OCCC(F)(F)F)nc3)cc12] | N-(2-((6-(3,3,3-trifluoropropoxy)pyridin-3-yl)methyl)-2H-pyrazolo[4,3-c]pyridin-4-yl)isobutyramide |
| 42 | 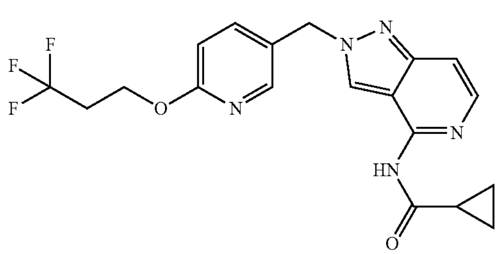 [SMILES: O=C(Nc1nccc2nn(Cc3ccc(OCCC(F)(F)F)nc3)cc12)C1CC1] | N-(2-((6-(3,3,3-trifluoropropoxy)pyridin-3-yl)methyl)-2H-pyrazolo[4,3-c]pyridin-4-yl)cyclopropanecarboxamide |

TABLE 7-continued

| Ex | Structure | Name |
|---|---|---|
| 43 | 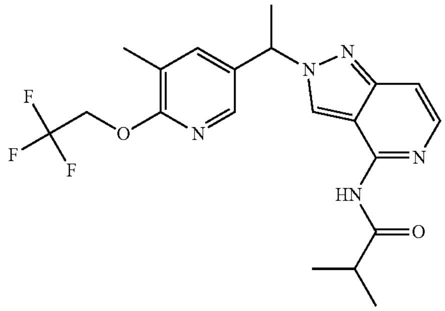 [SMILES: Cc1cc(C(C)n2cc3c(NC(=O)C(C)C)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)isobutyramide (single enantiomer) |
| 44 | 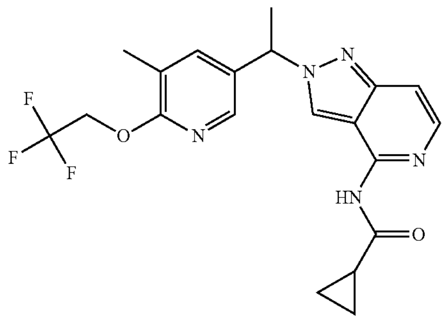 [SMILES: Cc1cc(C(C)n2cc3c(NC(=O)C4CC4)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)cyclopropanecarboxamide (single enantiomer) |
| 45 | 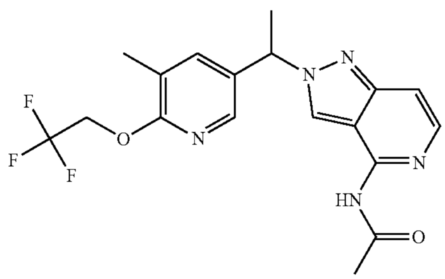 [SMILES: CC(=O)Nc1nccc2nn(C(C)c3cnc(OCC(F)(F)F)c(C)c3)cc12] | N-(2-(1-(5-methyl-6-(2,2,2-trifluoroethoxy)pyridin-3-yl)ethyl)-2H-pyrazolo[4,3-c]pyridin-4-yl)acetamide (single enantiomer) |
| 46 | 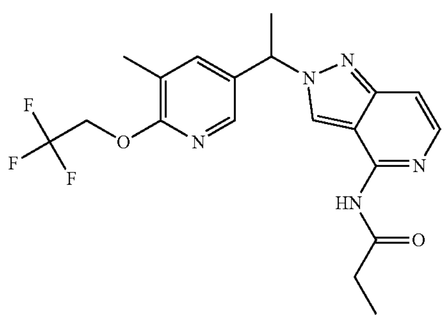 [SMILES: CCC(=O)Nc1nccc2nn(C(C)c3cnc(OCC(F)(F)F)c(C)c3)cc12] | N-(2-(1-(5-methyl-6-(2,2,2-trifluoroethoxy)pyridin-3-yl)ethyl)-2H-pyrazolo[4,3-c]pyridin-4-yl)propionamide (single enantiomer) |
| 47 | 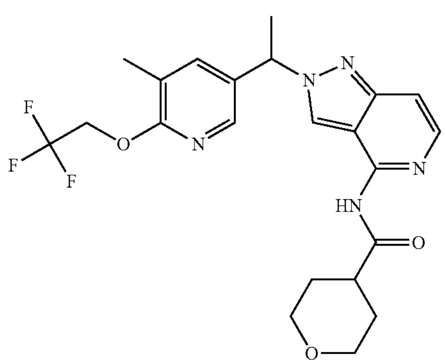 [SMILES: Cc1cc(C(C)n2cc3c(NC(=O)C4CCOCC4)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)tetrahydro-2H-pyran-4-carboxamide (single enantiomer) |

TABLE 7-continued

| Ex | Structure | Name |
|---|---|---|
| 48 | 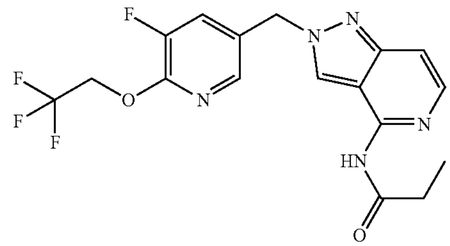 [SMILES: CCC(=O)Nc1nccc2nn(Cc3cnc(OCC(F)(F)F)c(F)c3)cc12] | N-(2-((5-fluoro-6-(2,2,2-trifluoroethoxy)pyridin-3-yl)methyl)-2H-pyrazolo[4,3-c]pyridin-4-yl)propionamide |
| 49 | 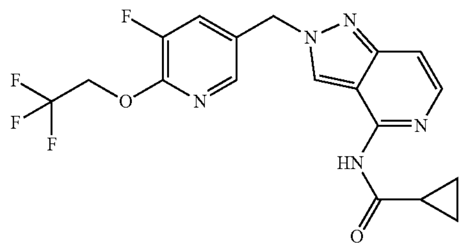 [SMILES: O=C(Nc1nccc2nn(Cc3cnc(OCC(F)(F)F)c(F)c3)cc12)C1CC1] | N-(2-((5-fluoro-6-(2,2,2-trifluoroethoxy)pyridin-3-yl)methyl)-2H-pyrazolo[4,3-c]pyridin-4-yl)cyclopropanecarboxamide |
| 50 | 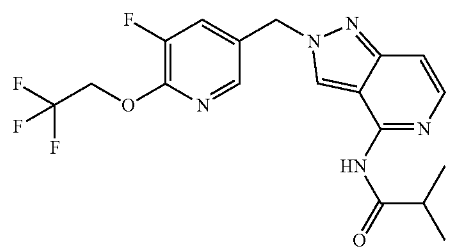 | N-(2-((5-fluoro-6-(2,2,2-trifluoroethoxy)pyridin-3-yl)methyl)-2H-pyrazolo[4,3-c]pyridin-4-yl)isobutyramide |
| 51 | 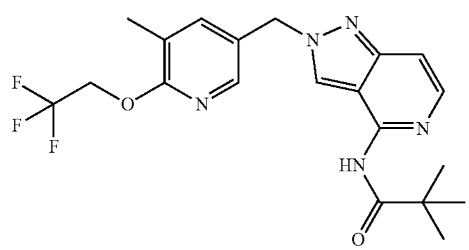 [SMILES: Cc1cc(Cn2cc3c(NC(=O)C(C)(C)C)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)pivalamide |
| 52 | 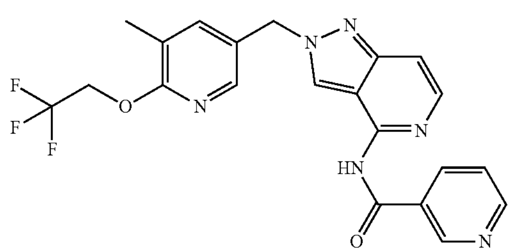 [SMILES: Cc1cc(Cn2cc3c(NC(=O)c4cccnc4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)nicotinamide |
| 53 | 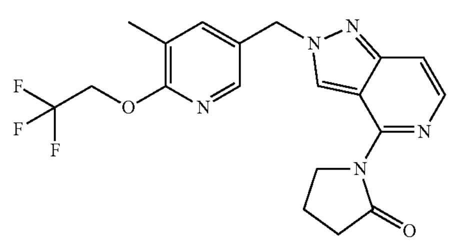 [SMILES: Cc1cc(Cn2cc3c(N4CCCC4=O)nccc3n2)cnc1OCC(F)(F)F] | 1-(2-((5-methyl-6-(2,2,2-trifluoroethoxy)pyridin-3-yl)methyl)-2H-pyrazolo[4,3-c]pyridin-4-yl)pyrrolidin-2-one |

TABLE 7-continued

| Ex | Structure | Name |
|---|---|---|
| 54 | 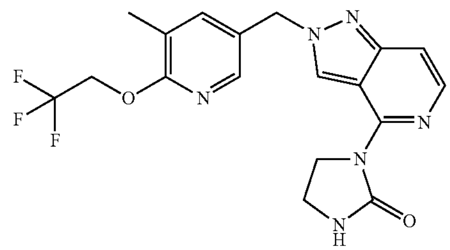 [SMILES: Cc1cc(Cn2cc3c(N4CCNC4=O)nccc3n2)cnc1OCC(F)(F)F] | 1-(2-((5-methyl-6-(2,2,2-trifluoroethoxy)pyridin-3-yl)methyl)-2H-pyrazolo[4,3-c]pyridin-4-yl)imidazolidin-2-one |
| 56 | 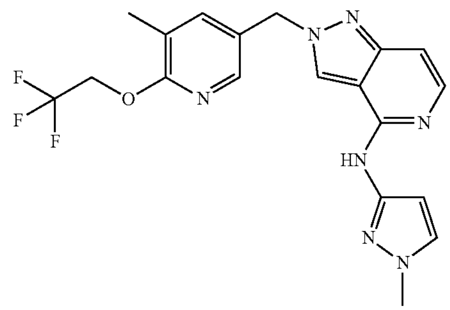 [SMILES: Cc1cc(Cn2cc3c(Nc4ccn(C)n4)nccc3n2)cnc1OCC(F)(F)F] | N-(1-methyl-1H-pyrazol-3-yl)-2-((5-methyl-6-(2,2,2-trifluoroethoxy)pyridin-3-yl)methyl)-2H-pyrazolo[4,3-c]pyridin-4-amine |
| 57 | 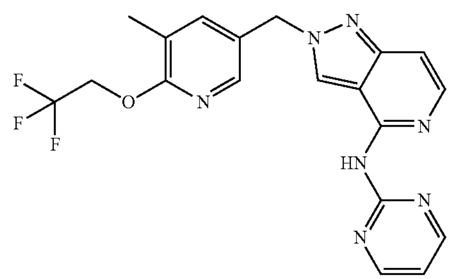 [SMILES: Cc1cc(Cn2cc3c(Nc4ncccn4)nccc3n2)cnc1OCC(F)(F)F] | 2-((5-methyl-6-(2,2,2-trifluoroethoxy)pyridin-3-yl)methyl)-N-(pyrimidin-2-yl)-2H-pyrazolo[4,3-c]pyridin-4-amine |
| 58 | 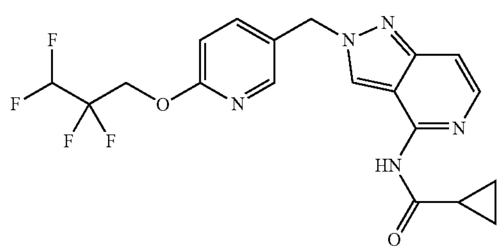 [SMILES: O=C(Nc1nccc2nn(Cc3ccc(OCC(F)(F)C(F)F)nc3)cc12)C1CC1] | N-(2-((6-(2,2,3,3-tetrahydropropoxy)pyridin-3-yl)methyl-2H-pyrazolo[4,3-c]pyridin-4-yl)cyclopropanecarboxamide |
| 59 | 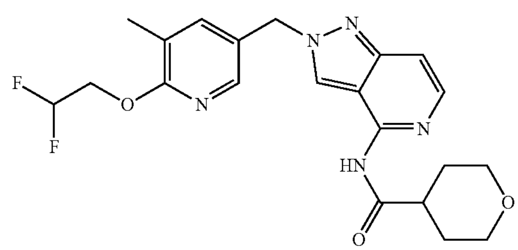 [SMILES: Cc1cc(Cn2cc3c(NC(=O)C4CCOCC4)nccc3n2)cnc1OCC(F)F] | N-(2-((6-(2,2-difluoroethoxy)-5-methylpyridin-3-yl)methyl)-2H-pyrazolo[4,3-c]pyridin-4-yl)tetrahydro-2H-pyran-4-carboxamide |
| 60 | 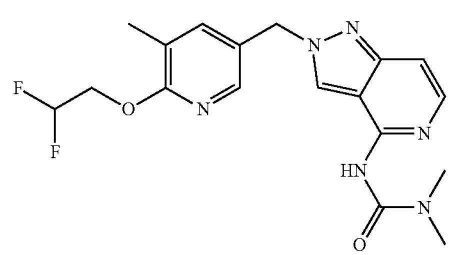 [SMILES: Cc1cc(Cn2cc3c(NC(=O)N(C)C)nccc3n2)cnc1OCC(F)F] | 3-(2-((6-(2,2-difluoroethoxy)-5-methylpyridin-3-yl)methyl)-2H-pyrazolo[4,3-c]pyridin-4-yl)-1,1-dimethylurea |

TABLE 7-continued

| Ex | Structure | Name |
|---|---|---|
| 61 | 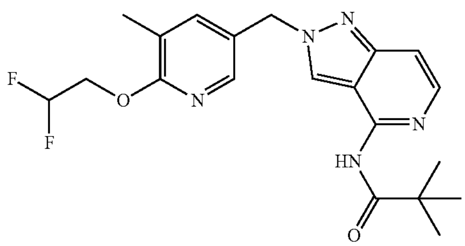 [SMILES: Cc1cc(Cn2cc3c(NC(=O)C(C)(C)C)nccc3n2)cnc1OCC(F)F] | N-(2-((6-(2,2-difluoroethoxy)-5-methylpyridin-3-yl)methyl)-2H-pyrazolo[4,3-c]pyridin-4-yl)pivalamide |
| 62 | 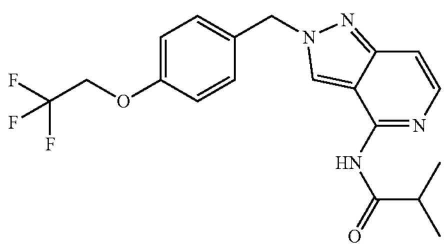 [SMILES: CC(C)C(=O)Nc1nccc2nn(Cc3ccc(OCC(F)(F)F)cc3)cc12] | N-(2-(4-(2,2,2-trifluoroethoxy)benzyl)-2H-pyrazolo[4,3-c]pyridin-4-yl)isobutyramide |
| 63 | 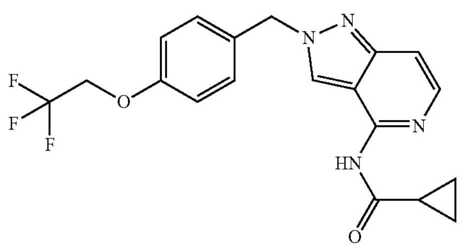 [SMILES: O=C(Nc1nccc2nn(Cc3ccc(OCC(F)(F)F)cc3)cc12)C1CC1] | N-(2-(4-(2,2,2-trifluoroethoxy)benzyl)-2H-pyrazolo[4,3-c]pyridin-4-yl)cyclopropanecarboxamide |
| 65 | 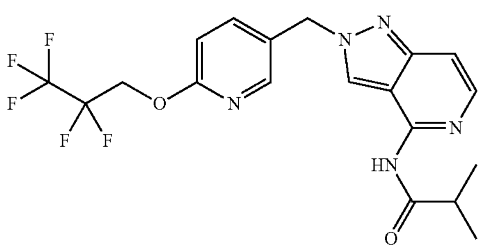 [SMILES: CC(C)C(=O)Nc1nccc2nn(Cc3ccc(OCC(F)(F)C(F)(F)F)nc3)cc12] | N-(2-((6-(2,2,3,3,3-pentafluoropropoxy)pyridin-3-yl)methyl)-2H-pyrazolo[4,3-c]pyridin-4-yl)isobutyramide |
| 66 | 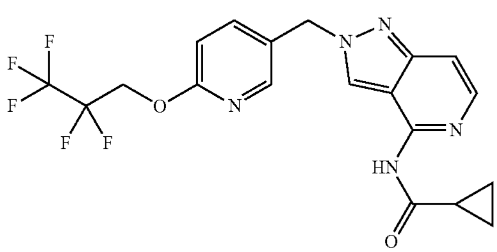 [SMILES: O=C(Nc1nccc2nn(Cc3ccc(OCC(F)(F)C(F)(F)F)nc3)cc12)C1CC1] | N-(2-((6-(2,2,3,3,3-pentafluoropropoxy)pyridin-3-yl)methyl)-2H-pyrazolo[4,3-c]pyridin-4-yl)cyclopropanecarboxamide |
| 67 | 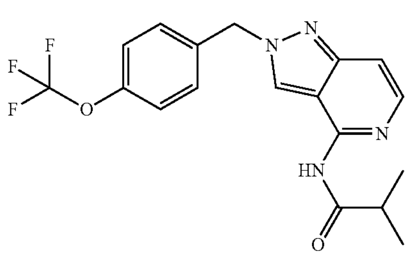 [SMILES: CC(C)C(=O)Nc1nccc2nn(Cc3ccc(OC(F)(F)F)cc3)cc12] | N-(2-(4-(trifluoromethoxy)benzyl)-2H-pyrazolo[4,3-c]pyridin-4-yl)isobutyramide |

| Ex | Structure | Name |
|---|---|---|
| 68 | 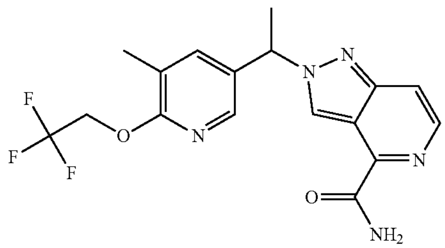 [SMILES: Cc1cc(C(C)n2cc3c(C(N)=O)nccc3n2)cnc1OCC(F)(F)F] | 2-(1-(5-methyl-6-(2,2,2-trifluoroethoxy)pyridin-3-yl)ethyl)-2H-pyrazolo[4,3-c]pyridine-4-carboxamide (single enantiomer) |
| 69 | 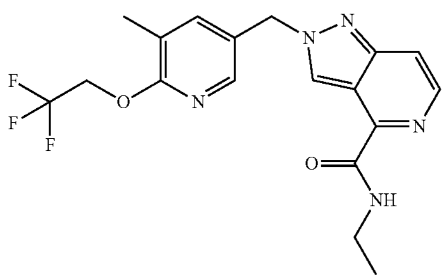 | N-ethyl-2-((5-methyl-6-(2,2,2-trifluoroethoxy)pyridin-3-yl)methyl)-2H-pyrazolo[4,3-c]pyridine-4-carboxamide |
| 70 | 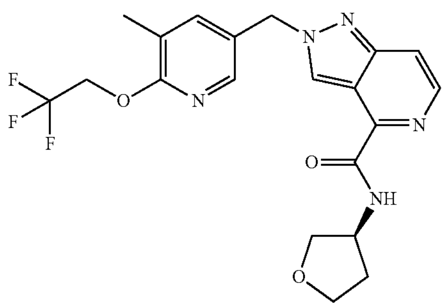 [SMILES: Cc1cc(Cn2cc3c(C(=O)N[C@H]4CCOC4)nccc3n2)cnc1OCC(F)(F)F] | (S)-2-((5-methyl-6-(2,2,2-trifluoroethoxy)pyridin-3-yl)methyl)-N-(tetrahydrofuran-3-yl)-2H-pyrazolo[4,3-c]pyridine-4-carboxamide |
| 71 | 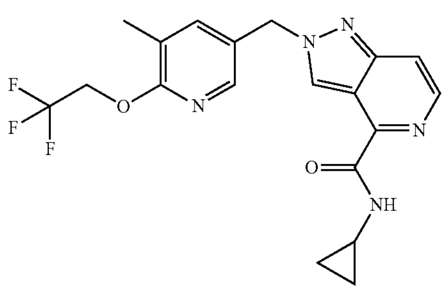 [SMILES: Cc1cc(Cn2cc3c(C(=O)NC4CC4)nccc3n2)cnc1OCC(F)(F)F] | N-cyclopropyl-2-((5-methyl-6-(2,2,2-trifluoroethoxy)pyridin-3-yl)methyl)-2H-pyrazolo[4,3-c]pyridine-4-carboxamide |
| 72 | 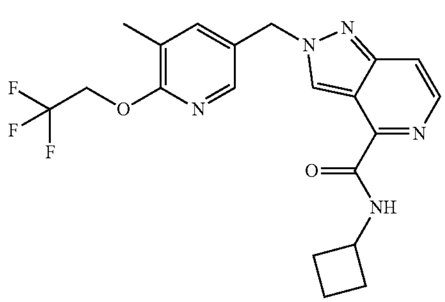 [SMILES: Cc1cc(Cn2cc3c(C(=O)NC4CCC4)nccc3n2)cnc1OCC(F)(F)F] | N-cyclobutyl-2-((5-methoxy-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 73 | 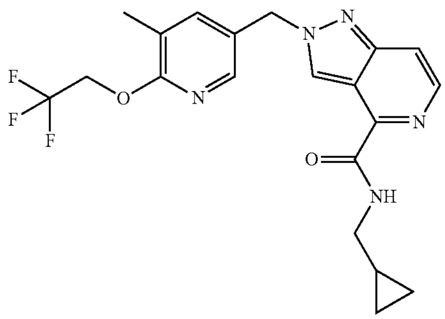 [SMILES: Cc1cc(Cn2cc3c(C(=O)NCC4CC4)nccc3n2)cnc1OCC(F)(F)F] | N-(cyclopropylmethyl)-2-((5-methyl-6-(2,2,2-trifluoroethoxy)pyridin-3-yl)methyl)-2H-pyrazolo[4,3-c]pyridine-4-carboxamide |
| 74 | 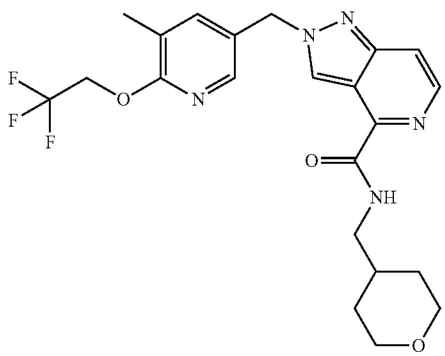 [SMILES: Cc1cc(Cn2cc3c(C(=O)NCC4CCOCC4)nccc3n2)cnc1OCC(F)(F)F] | 2-((5-methyl-6-(2,2,2-trifluoroethoxy)pyridin-3-yl)methyl)-N-((tetrahydro-2H-pyran-4-yl)methyl)-2H-pyrazolo[4,3-c]pyridine-4-carboxamide |
| 75 | 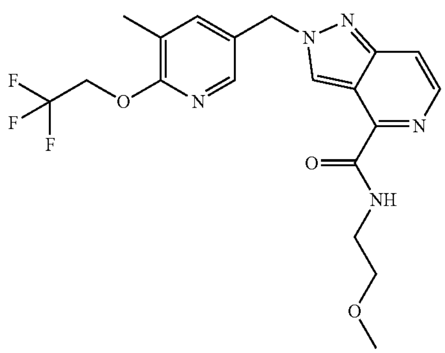 [SMILES: COCCNC(=O)c1nccc2nn(Cc3cnc(OCC(F)(F)F)c(C)c3)cc12] | N-(2-methoxyethyl)-2-((5-methyl-6-(2,2,2-trifluoroethoxy)pyridin-3-yl)methyl)-2H-pyrazolo[4,3-c]pyridine-4-carboxamide |
| 76 | 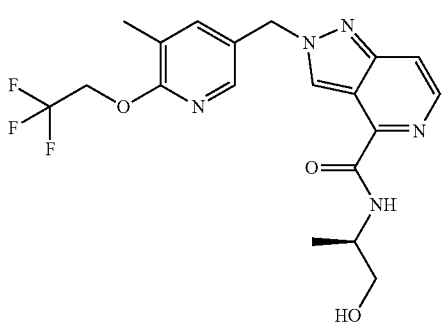 [SMILES: Cc1cc(Cn2cc3c(C(=O)N[C@H](C)CO)nccc3n2)cnc1OCC(F)(F)F] | (R)-N-(1-hydroxypropan-2-yl)-2-((5-methyl-6-(2,2,2-trifluoroethoxy)pyridin-3-yl)methyl)-2H-pyrazolo[4,3-c]pyridine-4-carboxamide |
| 77 | 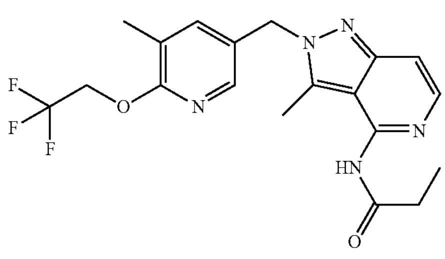 [SMILES: CCC(=O)Nc1nccc2nn(Cc3cnc(OCC(F)(F)F)c(C)c3)c(C)c12] | N-(3-methyl-2-((5-methyl-6-(2,2,2-trifluoroethoxy)pyridin-3-yl)methyl)-2H-pyrazolo[4,3-c]pyridin-4-yl)propionamide |

TABLE 7-continued

| Ex | Structure | Name |
|---|---|---|
| 78 | 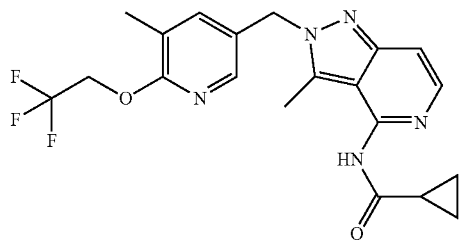 [SMILES: Cc1cc(Cn2nc3ccnc(NC(=O)C4CC4)c3c2C)cnc1OCC(F)(F)F] | N-(3-methyl-2-((5-methyl-6-(2,2,2-trifluoroethoxy)pyridin-3-yl)methyl)-2H-pyrazolo[4,3-c]pyridin-4-yl)cyclopropanecarboxamide |
| 79 | 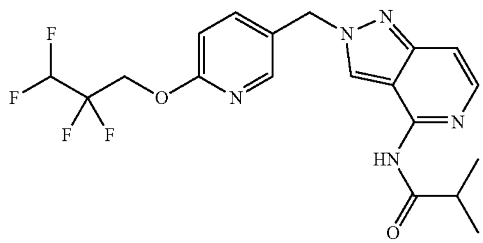 [SMILES: CC(C)C(=O)Nc1nccc2nn(Cc3ccc(OCC(F)(F)C(F)F)nc3)cc12] | N-(2-((6-(2,2,3,3-tetrafluoropropoxy)pyridin-3-yl)methyl)-2H-pyrazolo[4,3-c]pyridin-4-yl)isobutyramide |
| 80 | 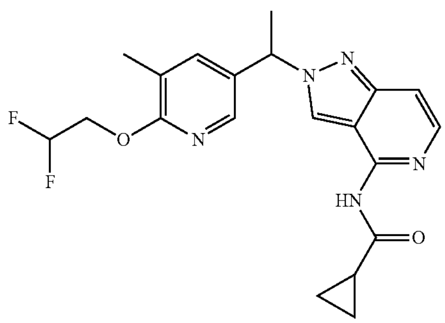 [SMILES: Cc1cc(C(C)n2cc3c(NC(=O)C4CC4)nccc3n2)cnc1OCC(F)F] | N-(2-(1-(6-(2,2-difluoroethoxy)-5-methylpyridin-3-yl)ethyl)-2H-pyrazolo[4,3-c]pyridin-4-yl)cyclopropanecarboxamide (single enantiomer) |
| 81 | 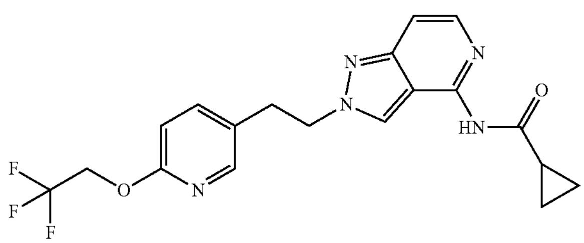 [SMILES: O=C(Nc1nccc2nn(CCc3ccc(OCC(F)(F)F)nc3)cc12)C1CC1] | N-(2-(2-(6-(2,2,2-trifluoroethoxy)pyridin-3-yl)ethyl)-2H-pyrazolo[4,3-c]pyridin-4-yl)cyclopropanecarboxamide |
| 82 | 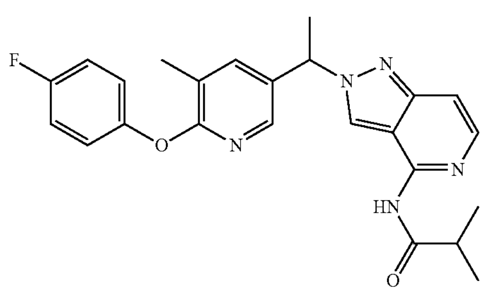 [SMILES: Cc1cc(C(C)n2cc3c(NC(=O)C(C)C)nccc3n2)cnc1Oc1ccc(F)cc1] | N-(2-((6-(4-fluorophenoxy)-5-methylpyridin-3-yl)methyl)-2H-pyrazolo[4,3-c]pyridin-4-yl)isobutyramide |
| 83 | 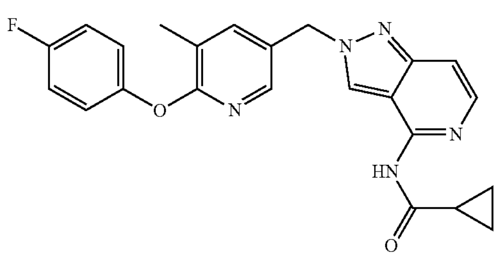 [SMILES: Cc1cc(Cn2cc3c(NC(=O)C4CC4)nccc3n2)cnc1Oc1ccc(F)cc1] | N-(2-((6-(4-fluorophenoxy)-5-methylpyridin-3-yl)methyl)-2H-pyrazolo[4,3-c]pyridin-4-yl)cyclopropanecarboxamide |

TABLE 7-continued

| Ex | Structure | Name |
|---|---|---|
| 84 | 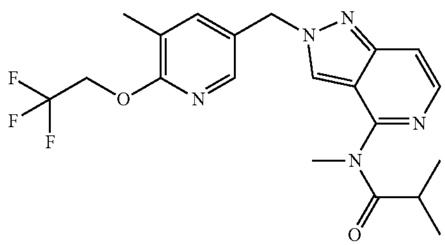 [SMILES: Cc1cc(Cn2cc3c(N(C)C(=O)C(C)C)nccc3n2)cnc1OCC(F)(F)F] | N-methyl-N-(2-((5-methyl-6-(2,2,2-trifluoroethoxy)pyridin-3-yl)methyl)-2H-pyrazolo[4,3-c]pyridin-4-yl)isobutyramide |
| 85 | 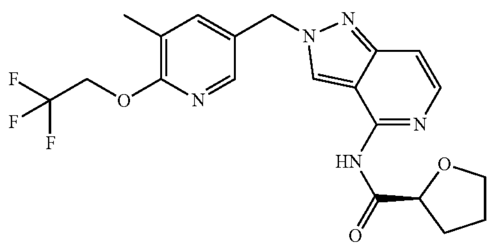 [SMILES: Cc1cc(Cn2cc3c(NC(=O)[C@@H]4CCCO4)nccc3n2)cnc1OCC(F)(F)F] | (S)-N-(2-((5-methyl-6-(2,2,2-trifluoroethoxy)pyridin-3-yl)methyl)-2H-pyrazolo[4,3-c]pyridin-4-yl)tetrahydrofuran-2-carboxamide |
| 86 | 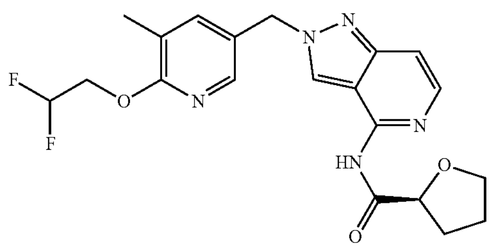 [SMILES: Cc1cc(Cn2cc3c(NC(=O)[C@@H]4CCCO4)nccc3n2)cnc1OCC(F)F] | (S)-N-(2-((6-(2,2-difluoroethoxy)-5-methylpyridin-3-yl)methyl)-2H-pyrazolo[4,3-c]pyridin-4-yl)tetrahydrofuran-2-carboxamide |
| 87 | 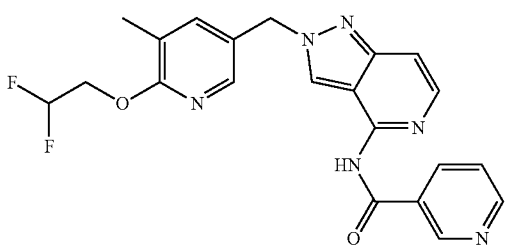 [SMILES: Cc1cc(Cn2cc3c(NC(=O)c4cccnc4)nccc3n2)cnc1OCC(F)F] | N-(2-((6-(2,2-difluoroethoxy)-5-methylpyridin-3-yl)methyl)-2H-pyrazolo[4,3-c]pyridin-4-yl)nicotinamide |
| 88 | 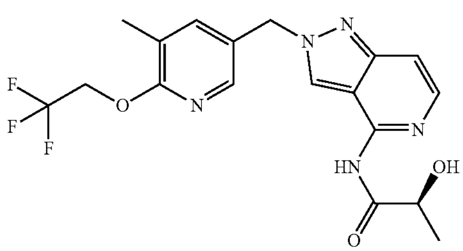 [SMILES: Cc1cc(Cn2cc3c(NC(=O)[C@H](C)O)nccc3n2)cnc1OCC(F)(F)F] | (R)-2-hydroxy-N-(2-((5-methyl-6-(2,2,2-trifluoroethoxy)pyridin-3-yl)methyl)-2H-pyrazolo[4,3-c]pyridin-4-yl)propanamide |
| 89 | 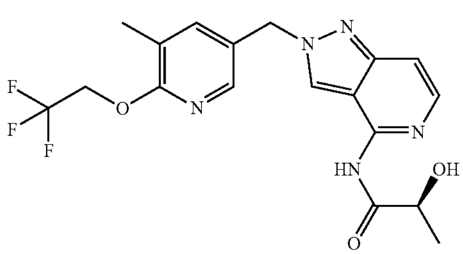 [SMILES: Cc1cc(Cn2cc3c(NC(=O)[C@H](C)O)nccc3n2)cnc1OCC(F)(F)F] | (S)-2-hydroxy-N-(2-((5-methyl-6-(2,2,2-trifluoroethoxy)pyridin-3-yl)methyl)-2H-pyrazolo[4,3-c]pyridin-4-yl)propanamide |

TABLE 7-continued

| Ex | Structure | Name |
|---|---|---|
| 90 | 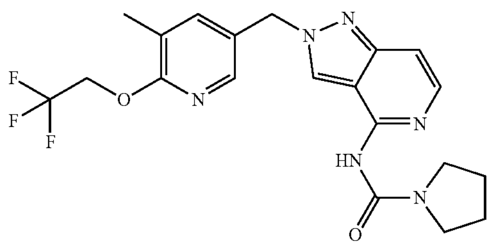 [SMILES: Cc1cc(Cn2cc3c(NC(=O)N4CCCC4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)pyrrolidine-1-carboxamide |
| 91 | 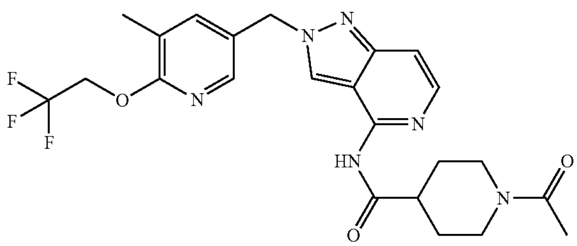 [SMILES: CC(=O)N1CCC(C(=O)Nc2nccc3nn(Cc4cnc(OCC(F)(F)F)c(C)c4)cc23)CC1] | 1-acetyl-N-(2-((5-methyl-6-(2,2,2-trifluoroethoxy)pyridin-3-yl)methyl)-2H-pyrazolo[4,3-c]pyridin-4-yl)piperidine-4-carboxamide |
| 92 | 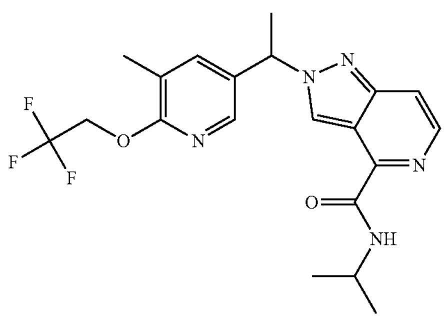 [SMILES: Cc1cc(C(C)n2cc3c(C(=O)NC(C)C)nccc3n2)cnc1OCC(F)(F)F] | N-isopropyl-2-(1-(5-methyl-6-(2,2,2-trifluoroethoxy)pyridin-3-yl)ethyl)-2H-pyrazolo[4,3-c]pyridine-4-carboxamide (single enantiomer) |
| 93 | 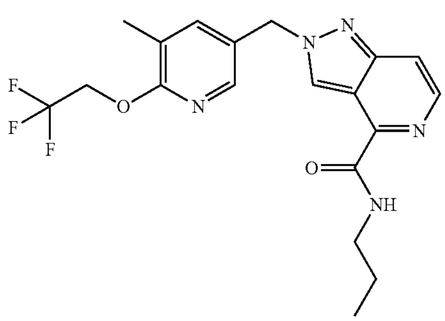 [SMILES: CCCNC(=O)c1nccc2nn(Cc3cnc(OCC(F)(F)F)c(C)c3)cc12] | 2-((5-methyl-6-(2,2,2-trifluoroethoxy)pyridin-3-yl)methyl)-N-propyl-2H-pyrazolo[4,3-c]pyridine-4-carboxamide |
| 94 | 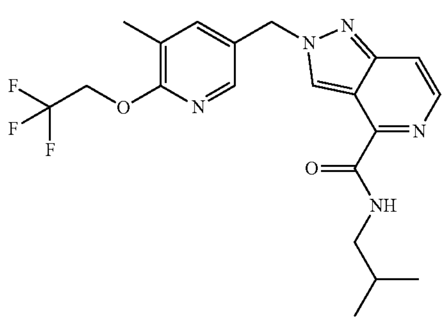 [SMILES: Cc1cc(Cn2cc3c(C(=O)NCC(C)C)nccc3n2)cnc1OCC(F)(F)F] | N-isobutyl-2-((5-methyl-6-(2,2,2-trifluoroethoxy)pyridin-3-yl)methyl)-2H-pyrazolo[4,3-c]pyridine-4-carboxamide |

| Ex | Structure | Name |
|---|---|---|
| 95 | 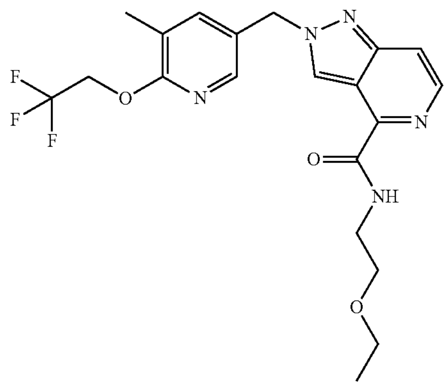 [SMILES: CCOCCNC(=O)c1nccc2nn(Cc3cnc(OCC(F)(F)F)c(C)c3)cc12] | N-(2-ethoxyethyl)-2-((5-methyl-6-(2,2,2-trifluoroethoxy)pyridin-3-yl)methyl)-2H-pyrazolo[4,3-c]pyridine-4-carboxamide |
| 96 | 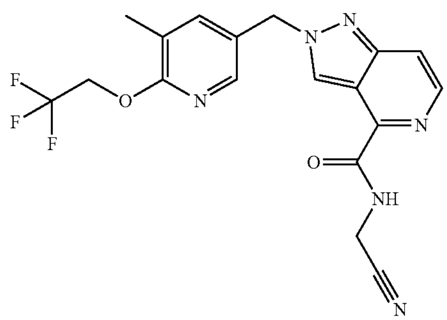 [SMILES: Cc1cc(Cn2cc3c(C(=O)NCC#N)nccc3n2)cnc1OCC(F)(F)F] | N-(cyanomethyl)-2-((5-methyl)-6-(2,2,2-trifluoroethoxy)pyridin-3-yl)methyl)-2H-pyrazolo[4,3-c]pyridine-4-carboxamide |
| 97 | 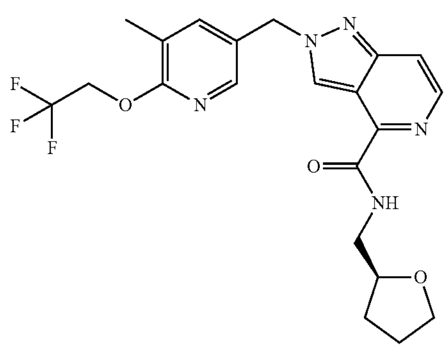 [SMILES: Cc1cc(Cn2cc3c(C(=O)NC[C@@H]4CCCO4)nccc3n2)cnc1OCC(F)(F)F] | (S)-2-((5-methyl-6-(2,2,2-trifluoroethoxy)pyridin-3-yl)methyl)-N-((tetrahydrofuran-2-yl)methyl)-2H-pyrazolo[4,3-c]pyridine-4-carboxamide |
| 98 | 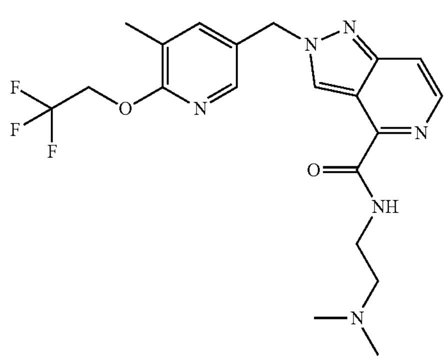 [SMILES: Cc1cc(Cn2cc3c(C(=O)NCCN(C)C)nccc3n2)cnc1OCC(F)(F)F] | N-(2-(dimethylamino)ethyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 99 | 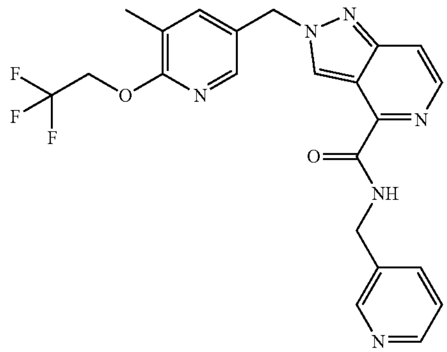 [SMILES: Cc1cc(Cn2cc3c(C(=O)NCc4cccnc4)nccc3n2)cnc1OCC(F)(F)F] | 2-((5-methyl-6-(2,2,2-trifluoroethoxy)pyridin-3-yl)methyl)-N-(pyridin-3-ylmethyl)-2H-pyrazolo[4,3-c]pyridine-4-carboxamide |
| 100 | 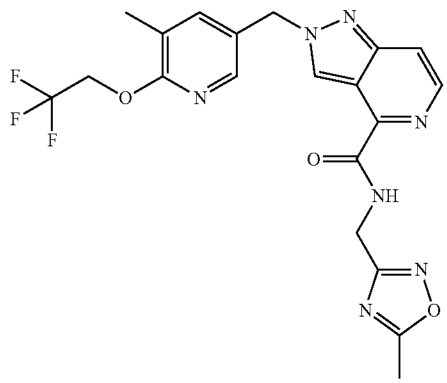 [SMILES: Cc1nc(CNC(=O)c2nccc3nn(Cc4cnc(OCC(F)(F)F)c(C)c4)cc23)no1] | N-((5-methyl-1,2,4-oxadiazol-3-yl)methyl)-2-((5-methyl-6-(2,2,2-trifluoroethoxy)pyridin-3-yl)methyl)-2H-pyrazolo[4,3-c]pyridine-4-carboxamide |
| 101 | 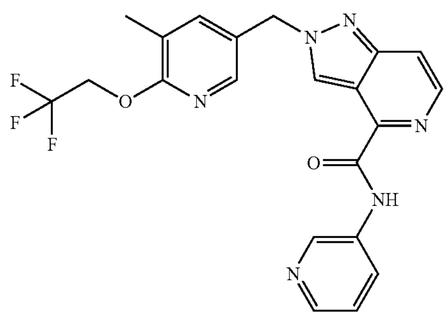 [SMILES: Cc1cc(Cn2cc3c(C(=O)Nc4cccnc4)nccc3n2)cnc1OCC(F)(F)F] | 2-((5-methyl-6-(2,2,2-trifluoroethoxy)pyridin-3-yl)methyl)-N-(pyridin-3-yl)-2H-pyrazolo[4,3-c]pyridine-4-carboxamide |
| 102 | 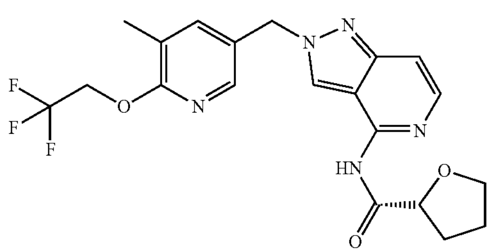 | (R)-N-(2-((5-methyl-6-(2,2,2-trifluoroethoxy)pyridin-3-yl)methyl)-2H-pyrazolo[4,3-c]pyridin-4-yl)tetrahydrofuran-2-carboxamide |
| 103 | 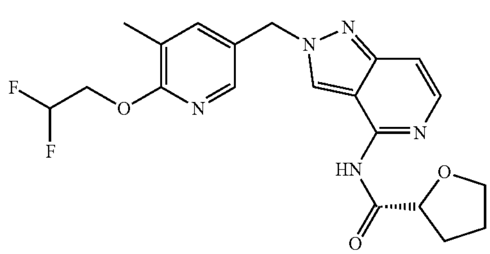 | (R)-N-(2-((6-(2,2-difluoroethoxy)-5-methylpyridin-3-yl)methyl)-2H-pyrazolo[4,3-c]pyridin-4-yl)tetrahydrofuran-2-carboxamide |

TABLE 7-continued

| Ex | Structure | Name |
|---|---|---|
| 104 | 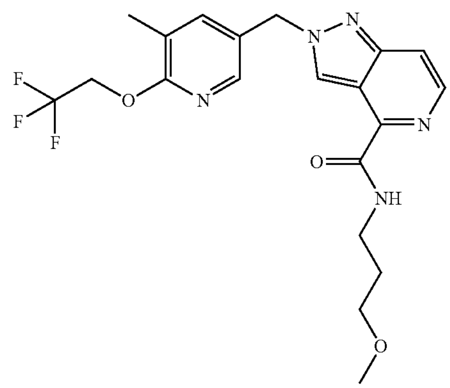 [SMILES: COCCCNC(=O)c1nccc2nn(Cc3cnc(OCC(F)(F)F)c(C)c3)cc12] | N-(3-methoxypropyl)-2-((5-methyl-6-(2,2,2-trifluoroethoxy)pyridin-3-yl)methyl)-2H-pyrazolo[4,3-c]pyridine-4-carboxamide |
| 105 | 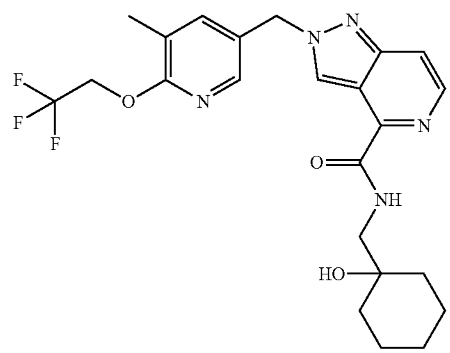 [SMILES: Cc1cc(Cn2cc3c(C(=O)NCC4(O)CCCCC4)nccc3n2)cnc1OCC(F)(F)F] | N-((1-hydroxycyclohexyl)methyl)-2-((5-methyl-6-(2,2,2-trifluoroethoxy)pyridin-3-yl)methyl)-2H-pyrazolo[4,3-c]pyridine-4-carboxamide |
| 106 | 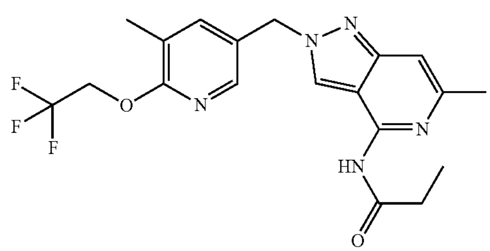 [SMILES: CCC(=O)Nc1nc(C)cc2nn(Cc3cnc(OCC(F)(F)F)c(C)c3)cc12] | N-(6-methyl-2-((5-methyl-6-(2,2,2-trifluoroethoxy)pyridin-3-yl)methyl)-2H-pyrazolo[4,3-c]pyridin-4-yl)propionamide |
| 107 | 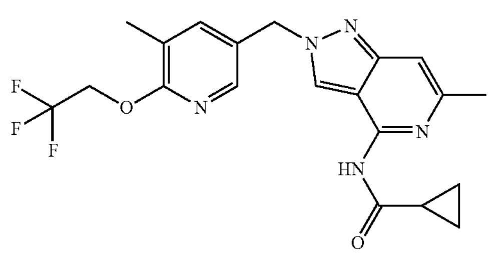 [SMILES: Cc1cc2nn(Cc3cnc(OCC(F)(F)F)c(C)c3)cc2c(NC(=O)C2CC2)n1] | N-(6-methyl-2-((5-methyl-6-(2,2,2-trifluoroethoxy)pyridin-3-yl)methyl)-2H-pyrazolo[4,3-c]pyridin-4-yl)cyclopropanecarboxamide |
| 108 | 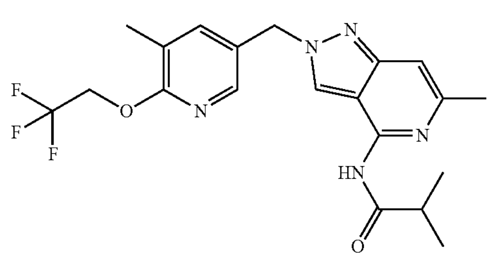 [SMILES: Cc1cc2nn(Cc3cnc(OCC(F)(F)F)c(C)c3)cc2c(NC(=O)C(C)C)n1] | N-(6-methyl-2-((5-methyl-6-(2,2,2-trifluoroethoxy)pyridin-3-yl)methyl)-2H-pyrazolo[4,3-c]pyridin-4-yl)isobutyramide |

TABLE 7-continued

| Ex | Structure | Name |
| --- | --- | --- |
| 109 | 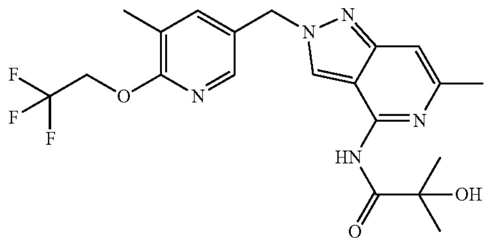 [SMILES: Cc1cc2nn(Cc3cnc(OCC(F)(F)F)c(C)c3)cc2c(NC(=O)C(C)(C)O)n1] | 2-hydroxy-2-methyl-N-(6-methyl-2-((5-methyl-6-(2,2,2-trifluoroethoxy)pyridin-3-yl)methyl)-2H-pyrazolo[4,3-c]pyridin-4-yl)propanamide |
| 110 | 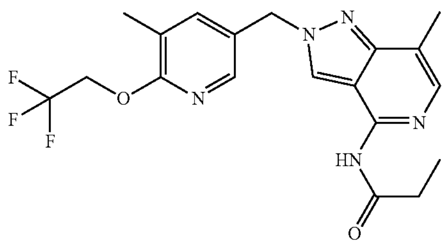 [SMILES: CCC(=O)Nc1ncc(C)c2nn(Cc3cnc(OCC(F)(F)F)c(C)c3)cc12] | N-(7-methyl-2-((5-methyl-6-(2,2,2-trifluoroethoxy)pyridin-3-yl)methyl)-2H-pyrazolo[4,3-c]pyridin-4-yl)propionamide |
| 111 | 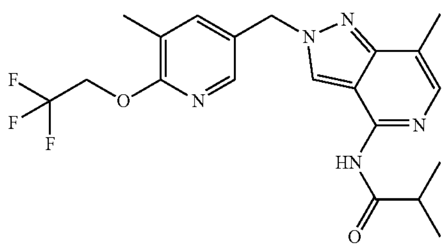 [SMILES: Cc1cc(Cn2cc3c(NC(=O)C(C)C)ncc(C)c3n2)cnc1OCC(F)(F)F] | N-(7-methyl-2-((5-methyl-6-(2,2,2-trifluoroethoxy)pyridin-3-yl)methyl)-2H-pyrazolo[4,3-c]pyridin-4-yl)isobutyramide |
| 112 | 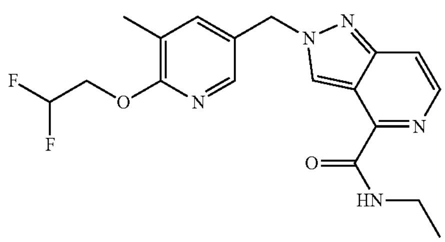 [SMILES: CCNC(=O)c1nccc2nn(Cc3cnc(OCC(F)F)c(C)c3)cc12] | 2-((6-(2,2-difluoroethoxy)-5-methylpyridin-3-yl)methyl)-N-ethyl-2H-pyrazolo[4,3-c]pyridine-4-carboxamide |
| 113 | 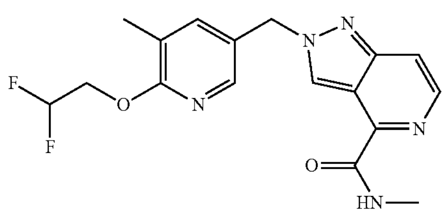 [SMILES: CNC(=O)c1nccc2nn(Cc3cnc(OCC(F)F)c(C)c3)cc12] | 2-((6-(2,2-difluoroethoxy)-5-methylpyridin-3-yl)methyl)-N-methyl-2H-pyrazolo[4,3-c]pyridine-4-carboxamide |
| 114 | 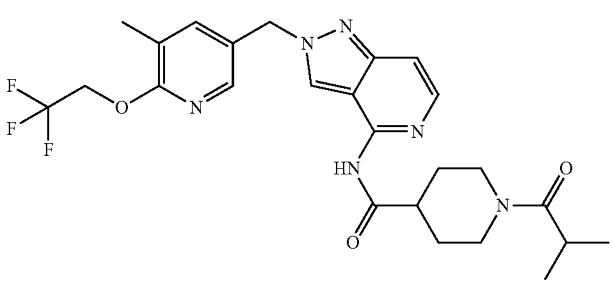 [SMILES: Cc1cc(Cn2cc3c(NC(=O)C4CCN(C(=O)C(C)C)CC4)nccc3n2)cnc1OCC(F)(F)F] | 1-isobutyryl-N-(2-((5-methyl-6-(2,2,2-trifluoroethoxy)pyridin-3-yl)methyl)-2H-pyrazolo[4,3-c]pyridin-4-yl)piperidine-4-carboxamide |

| Ex | Structure | Name |
|---|---|---|
| 115 | 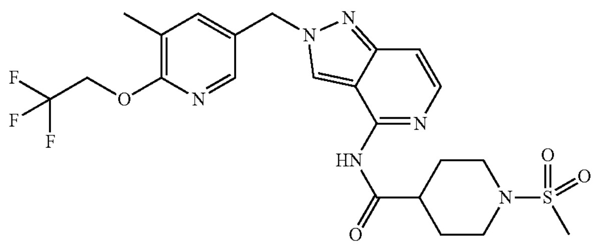 [SMILES: Cc1cc(Cn2cc3c(NC(=O)C4CCN(S(C)(=O)=O)CC4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)-1-(methylsulfonyl)piperidine-4-carboxamide |
| 116 | 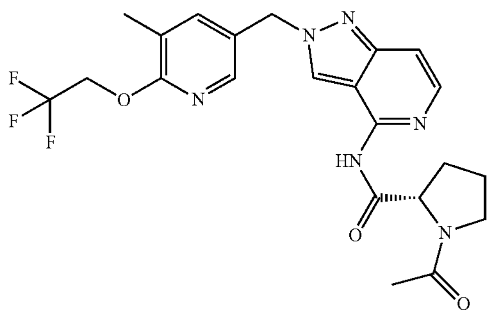 [SMILES: CC(=O)N1CCC[C@H]1C(=O)Nc1nccc2nn(Cc3cnc(OCC(F)(F)F)c(C)c3)cc12] | (S)-1-acetyl-N-(2-((5-methyl-6-(2,2,2-trifluoroethoxy)pyridin-3-yl)methyl)-2H-pyrazolo[4,3-c]pyridin-4-yl)-1-(methylsulfonyl)piperidine-4-carboxamide |
| 117 | 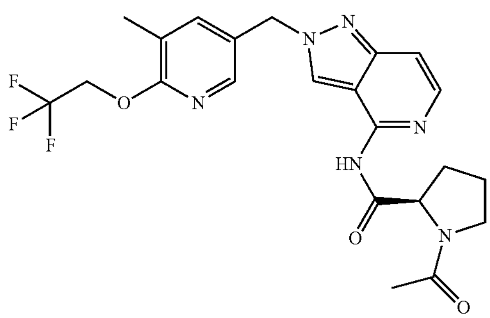 [SMILES: CC(=O)N1CCC[C@@H]1C(=O)Nc1nccc2nn(Cc3cnc(OCC(F)(F)F)c(C)c3)cc12] | (R)-1-acetyl-N-(2-((5-methyl-6-(2,2,2-trifluoroethoxy)pyridin-3-yl)methyl)-2H-pyrazolo[4,3-c]pyridin-4-yl)pyrrolidine-2-carboxamide |
| 118 | 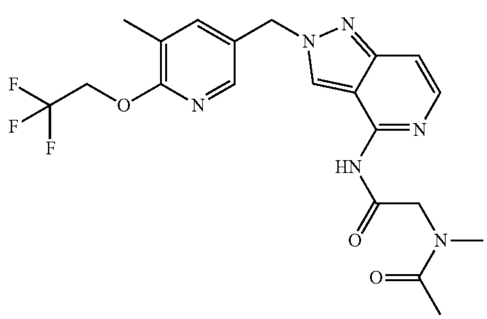 [SMILES: CC(=O)N(C)CC(=O)Nc1nccc2nn(Cc3cnc(OCC(F)(F)F)c(C)c3)cc12] | N-methyl-N-(2-((2-((5-methyl-6-(2,2,2-trifluoroethoxy)pyridin-3-yl)methyl)-2H-pyrazolo[4,3-c]pyridin-4-yl)amino)-2-oxoethyl)acetamide |
| 119 | 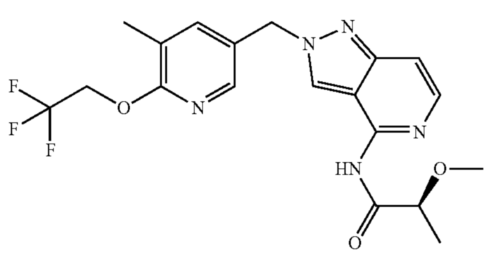 [SMILES: CO[C@@H](C)C(=O)Nc1nccc2nn(Cc3cnc(OCC(F)(F)F)c(C)c3)cc12] | (S)-2-methoxy-N-(2-((5-methyl-6-(2,2,2-trifluoroethoxy)pyridin-3-yl)methyl)-2H-pyrazolo[4,3-c]pyridin-4-yl)propanamide |

TABLE 7-continued

| Ex | Structure | Name |
|---|---|---|
| 120 | 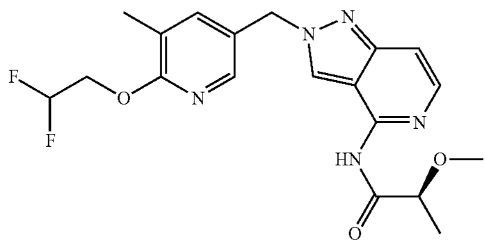 [SMILES: CO[C@@H](C)C(=O)Nc1nccc2nn(Cc3cnc(OCC(F)F)c(C)c3)cc12] | (S)-N-(2-((6-(2,2-difluoroethoxy)-5-methylpyridin-3-yl)methyl)-2H-pyrazolo[4,3-c]pyridin-4-yl)-2-methoxypropanamide |
| 121 | 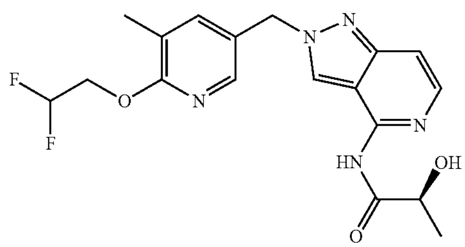 [SMILES: Cc1cc(Cn2cc3c(NC(=O)[C@H](C)O)nccc3n2)cnc1OCC(F)F] | (R)-N-(2-((6-(2,2-difluoroethoxy)-5-methylpyridin-3-yl)methyl)-2H-pyrazolo[4,3-c]pyridin-4-yl)-2-hydroxypropanamide |
| 122 | 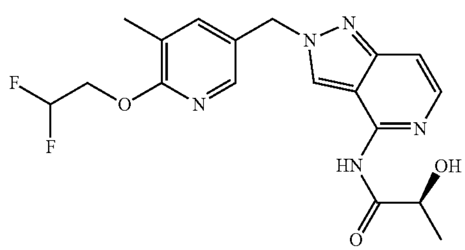 [SMILES: Cc1cc(Cn2cc3c(NC(=O)[C@H](C)O)nccc3n2)cnc1OCC(F)F] | (S)-N-(2-((6-(2,2-difluoroethoxy)-5-methylpyridin-3-yl)methyl)-2H-pyrazolo[4,3-c]pyridin-4-yl)-2-hydroxypropanamide |
| 123 | 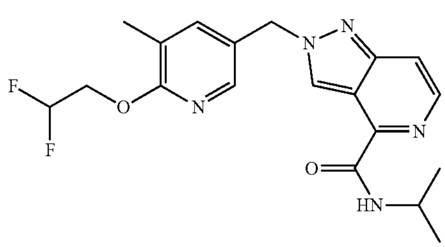 [SMILES: Cc1cc(Cn2cc3c(C(=O)NC(C)C)nccc3n2)cnc1OCC(F)F] | 2-((6-(2,2-difluoroethoxy)-5-methylpyridin-3-yl)methyl)-N-isopropyl-2H-pyrazolo[4,3-c]pyridine-4-carboxamide |
| 124 | 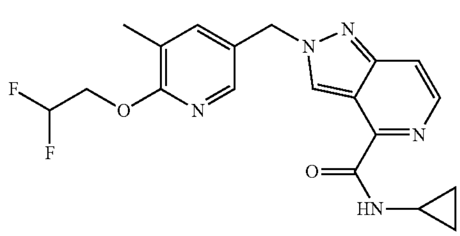 [SMILES: Cc1cc(Cn2cc3c(C(=O)NC4CC4)nccc3n2)cnc1OCC(F)F] | N-cyclopropyl-2-((6-(2,2-difluoroethoxy)-5-methylpyridin-3-yl)methyl)-2H-pyrazolo[4,3-c]pyridine-4-carboxamide |
| 125 | 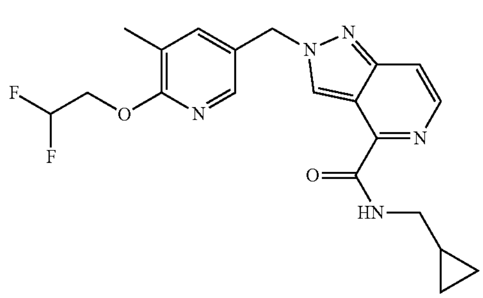 [SMILES: Cc1cc(Cn2cc3c(C(=O)NCC4CC4)nccc3n2)cnc1OCC(F)F] | N-(cyclopropylmethyl)-2-((6-(2,2-difluoroethoxy)-5-methylpyridin-3-yl)methyl)-2H-pyrazolo[4,3-c]pyridine-4-carboxamide |

TABLE 7-continued

| Ex | Structure | Name |
|---|---|---|
| 126 | 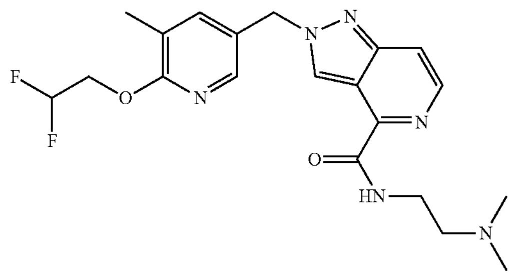 [SMILES: Cc1cc(Cn2cc3c(C(=O)NCCN(C)C)nccc3n2)cnc1OCC(F)F] | 2-((6-(2,2-difluoroethoxy)-5-methylpyridin-3-yl)methyl)-N-(2-(dimethylamino)ethyl)-2H-pyrazolo[4,3-c]pyridine-4-carboxamide |
| 127 | 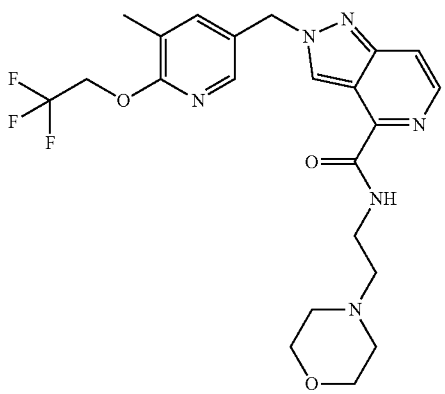 [SMILES: Cc1cc(Cn2cc3c(C(=O)NCCN4CCOCC4)nccc3n2)cnc1OCC(F)(F)F] | 2-((5-methyl-6-(2,2,2-trifluoroethoxy)pyridin-3-yl)methyl)-N-(2-morpholinoethyl)-2H-pyrazolo[4,3-c]pyridine-4-carboxamide |
| 128 | 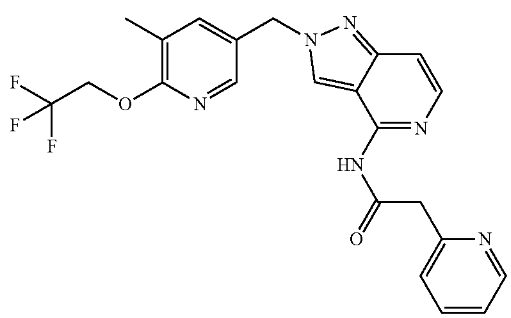 [SMILES: Cc1cc(Cn2cc3c(NC(=O)Cc4ccccn4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)-2-(pyridin-2-yl)acetamide |
| 129 | 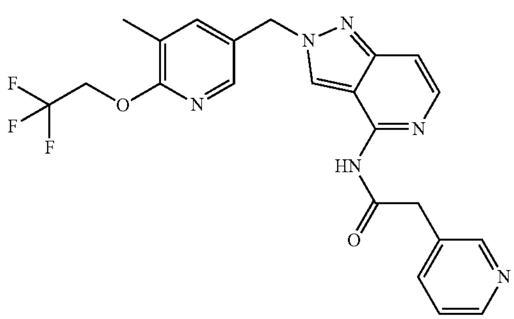 [SMILES: Cc1cc(Cn2cc3c(NC(=O)Cc4cccnc4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)-2-(pyridin-3-yl)acetamide |
| 130 | 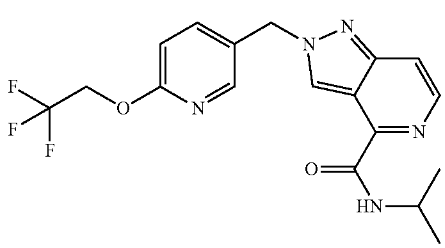 [SMILES: CC(C)NC(=O)c1nccc2nn(Cc3ccc(OCC(F)(F)F)nc3)cc12] | N-isopropyl-2-((6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 131 | 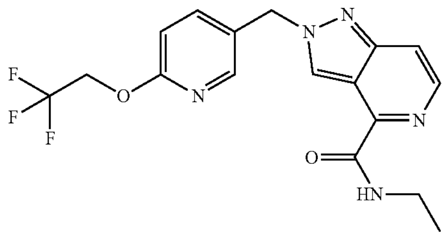 [SMILES: CCNC(=O)c1nccc2nn(Cc3ccc(OCC(F)(F)F)nc3)cc12] | N-ethyl-2-((6-(2,2,2-trifluoroethoxy)pyridin-3-yl)methyl)-2H-pyrazolo[4,3-c]pyridine-4-carboxamide |
| 132 | 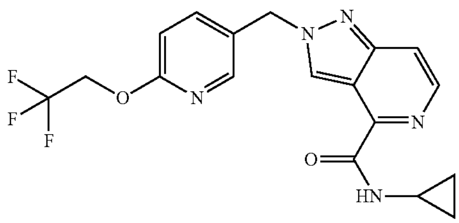 [SMILES: O=C(NC1CC1)c1nccc2nn(Cc3ccc(OCC(F)(F)F)nc3)cc12] | N-cyclopropyl-2-((6-(2,2,2-trifluoroethoxy)pyridin-3-yl)methyl)-2H-pyrazolo[4,3-c]pyridine-4-carboxamide |
| 133 | 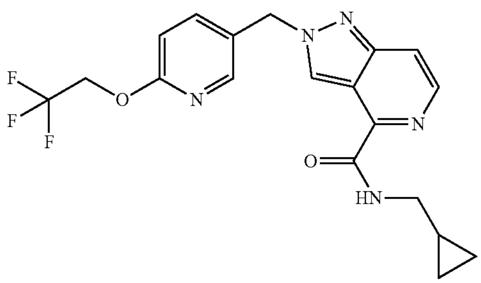 [SMILES: O=C(NCC1CC1)c1nccc2nn(Cc3ccc(OCC(F)(F)F)nc3)cc12] | N-(cyclopropylmethyl)-2-((6-(2,2,2-trifluoroethoxy)pyridin-3-yl)methyl)-2H-pyrazolo[4,3-c]pyridine-4-carboxamide |
| 134 | 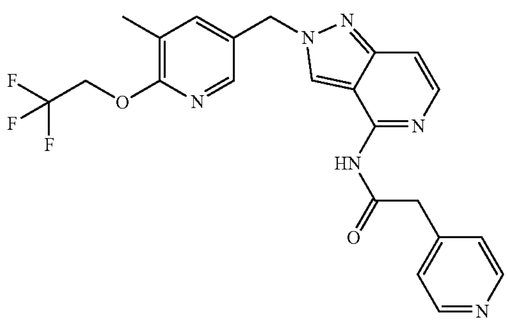 [SMILES: Cc1cc(Cn2cc3c(NC(=O)Cc4ccncc4)nccc3n2)cnc1OCC(F)(F)F] | N-(2-((5-methyl-6-(2,2,2-trifluoroethoxy)pyridin-3-yl)methyl)-2H-pyrazolo[4,3-c]pyridin-4-yl)-2-(pyridin-4-yl)acetamide |
| 135 | 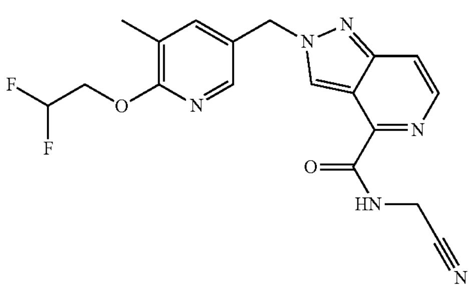 [SMILES: Cc1cc(Cn2cc3c(C(=O)NCC#N)nccc3n2)cnc1OCC(F)F] | N-(cyanomethyl)-2-((6-(2,2-difluoroethoxy)-5-methylpyridin-3-yl)methyl)-2H-pyrazolo[4,3-c]pyridine-4-carboxamide |
| 136 | 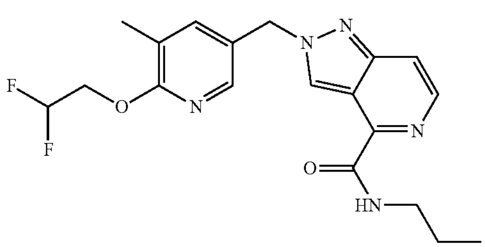 [SMILES: CCCNC(=O)c1nccc2nn(Cc3cnc(OCC(F)F)c(C)c3)cc12] | 2-((6-(2,2-difluoroethoxy)-5-methylpyridin-3-yl)methyl)-N-propyl-2H-pyrazolo[4,3-c]pyridine-4-carboxamide |

TABLE 7-continued

| Ex | Structure | Name |
|---|---|---|
| 137 | 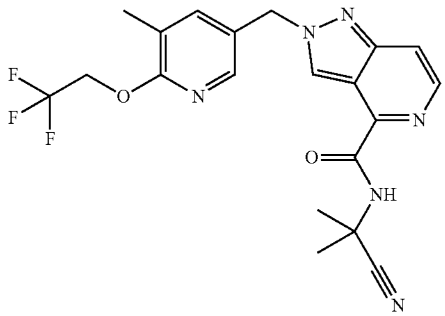 [SMILES: Cc1cc(Cn2cc3c(C(=O)NC(C)(C)C#N)nccc3n2)cnc1OCC(F)(F)F] | N-(2-cyanopropan-2-yl)-2-((5-methyl-6-(2,2,2-trifluoroethoxy)pyridin-3-yl)methyl)-2H-pyrazolo[4,3-c]pyridine-4-carboxamide |
| 138 | 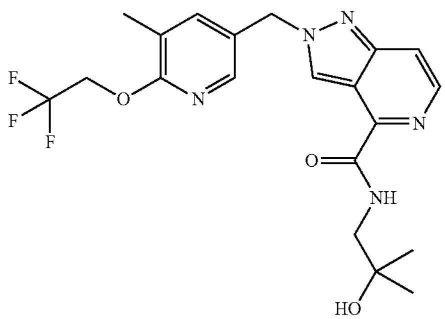 [SMILES: Cc1cc(Cn2cc3c(C(=O)NCC(C)(C)O)nccc3n2)cnc1OCC(F)(F)F] | N-(2-hydroxy-2-methylpropyl)-2-((5-methyl-6-(2,2,2-trifluoroethoxy)pyridin-3-yl)methyl)-2H-pyrazolo[4,3-c]pyridine-4-carboxamide |
| 139 | 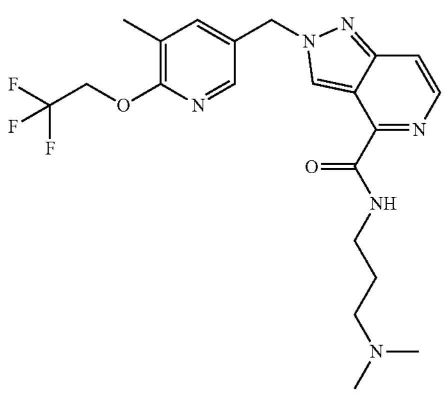 [SMILES: Cc1cc(Cn2cc3c(C(=O)NCCCN(C)C)nccc3n2)cnc1OCC(F)(F)F] | N-(3-(dimethylamino)propyl)-2-((5-methyl-6-(2,2,2-trifluoroethoxy)pyridin-3-yl)methyl)-2H-pyrazolo[4,3-c]pyridine-4-carboxamide |
| 140 | 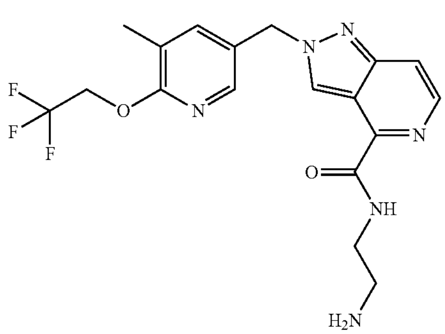 [SMILES: Cc1cc(Cn2cc3c(C(=O)NCCN)nccc3n2)cnc1OCC(F)(F)F] | N-(2-aminoethyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 142 | 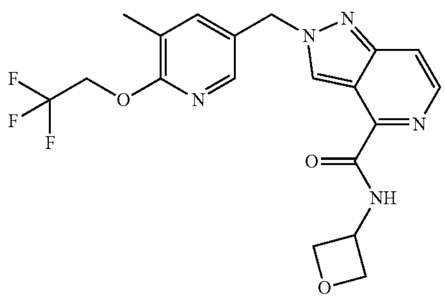 [SMILES: Cc1cc(Cn2cc3c(C(=O)NC4COC4)nccc3n2)cnc1OCC(F)(F)F] | 2-((5-methyl-6-(2,2,2-trifluoroethoxy)pyridin-3-yl)methyl)-N-(oxetan-3-yl)-2H-pyrazolo[4,3-c]pyridine-4-carboxamide |
| 144 | 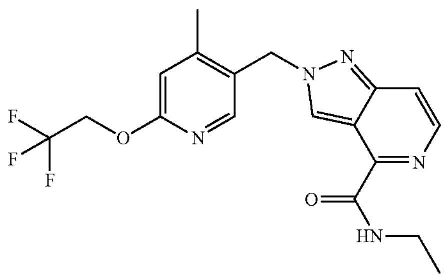 [SMILES: CCNC(=O)c1nccc2nn(Cc3cnc(OCC(F)(F)F)cc3C)cc12] | N-ethyl-2-((4-methyl-6-(2,2,2-trifluoroethoxy)pyridin-3-yl)methyl)-2H-pyrazolo[4,3-c]pyridine-4-carboxamide |
| 145 | 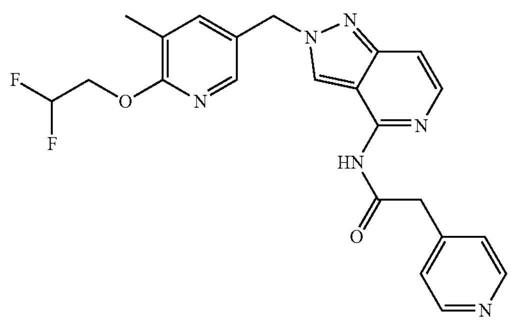 [SMILES: Cc1cc(Cn2cc3c(NC(=O)Cc4ccncc4)nccc3n2)cnc1OCC(F)F] | N-(2-((6-(2,2-difluoroethoxy)-5-methylpyridin-3-yl)methyl)-2H-pyrazolo[4,3-c]pyridin-4-yl)-2-(pyridin-4-yl)acetamide |
| 146 | 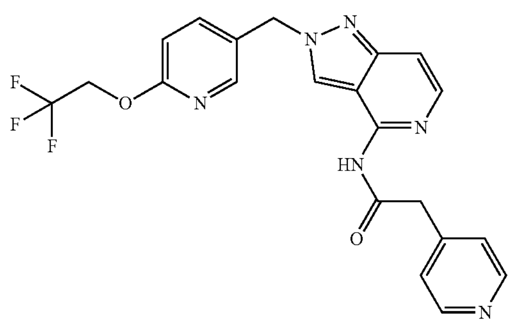 [SMILES: O=C(Cc1ccncc1)Nc1nccc2nn(Cc3ccc(OCC(F)(F)F)nc3)cc12] | 2-(pyridin-4-yl)-N-(2-((6-(2,2,2-trifluoroethoxy)pyridin-3-yl)methyl)-2H-pyrazolo[4,3-c]pyridin-4-yl)acetamide |
| 147 | 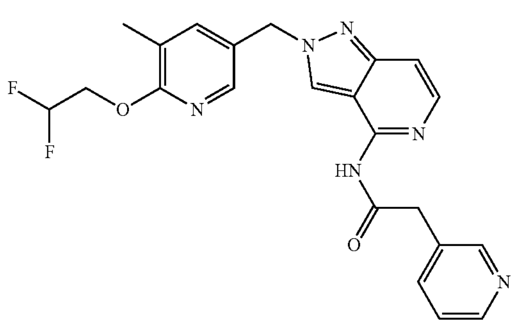 [SMILES: Cc1cc(Cn2cc3c(NC(=O)Cc4cccnc4)nccc3n2)cnc1OCC(F)F] | N-(2-((6-(2,2-difluoroethoxy)-5-methylpyridin-3-yl)methyl)-2H-pyrazolo[4,3-c]pyridin-4-yl)-2-(pyridin-3-yl)acetamide |

TABLE 7-continued

| Ex | Structure | Name |
|---|---|---|
| 148 | 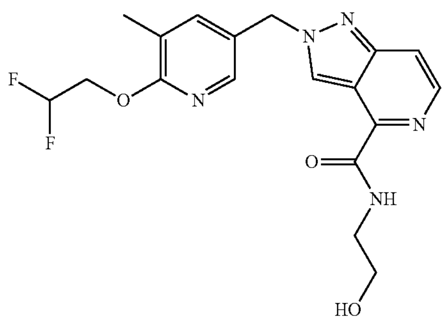 [SMILES: Cc1cc(Cn2cc3c(C(=O)NCCO)nccc3n2)cnc1OCC(F)F] | 2-((6-(2,2-difluoroethoxy)-5-methylpyridin-3-yl)methyl)-N-(2-hydroxyethyl)-2H-pyrazolo[4,3-c]pyridine-4-carboxamide |
| 149 | 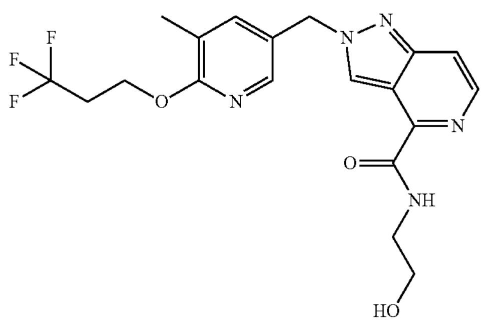 | N-(2-hydroxyethyl)-2-((5-methyl-6-(3,3,3-trifluoropropoxy)pyridin-3-yl)methyl)-2H-pyrazolo[4,3-c]pyridine-4-carboxamide |
| 150 | 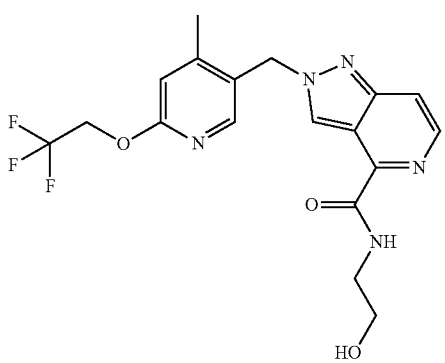 [SMILES: Cc1cc(OCC(F)(F)F)ncc1Cn1cc2c(C(=O)NCCO)nccc2n1] | N-(2-hydroxyethyl)-2-((4-methyl-6-(2,2,2-trifluoroethoxy)pyridin-3-yl)methyl)-2H-pyrazolo[4,3-c]pyridine-4-carboxamide |
| 151 | 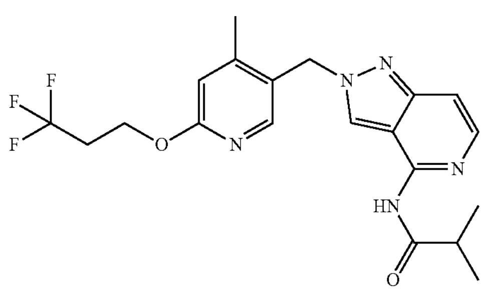 [SMILES: Cc1cc(OCCC(F)(F)F)ncc1Cn1cc2c(NC(=O)C(C)C)nccc2n1] | N-(2-((5-methyl-6-(3,3,3-trifluoropropoxy)pyridin-3-yl)methyl)-2H-pyrazolo[4,3-c]pyridin-4-yl)isobutyramide |
| 152 | 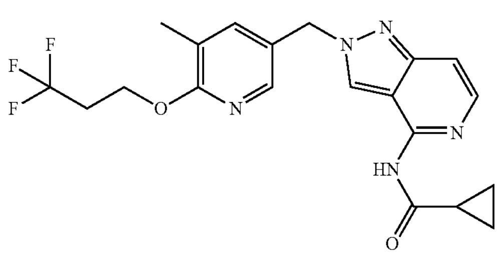 [SMILES: Cc1cc(Cn2cc3c(NC(=O)C4CC4)nccc3n2)cnc1OCCC(F)(F)F] | N-(2-((5-methyl-6-(3,3,3-trifluoropropoxy)pyridin-3-yl)methyl)-2H-pyrazolo[4,3-c]pyridin-4-yl)cyclopropanecarboxamide |

TABLE 7-continued

| Ex | Structure | Name |
| --- | --- | --- |
| 153 | 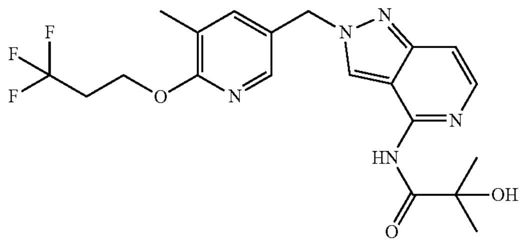 [SMILES: Cc1cc(Cn2cc3c(NC(=O)C(C)(C)O)nccc3n2)cnc1OCCC(F)(F)F] | 2-hydroxy-2-methyl-N-(2-((5-methyl-6-(3,3,3-trifluoropropoxy)pyridin-3-yl)methyl)-2H-pyrazolo[4,3-c]pyridin-4-yl)propanamide |
| 154 | 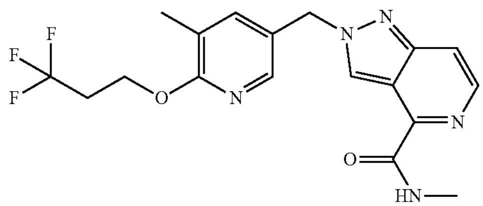 [SMILES: CNC(=O)c1nccc2nn(Cc3cnc(OCCC(F)(F)F)c(C)c3)cc12] | N-methyl-2-((5-methyl-6-(3,3,3-trifluoropropoxy)pyridin-3-yl)methyl)-2H-pyrazolo[4,3-c]pyridine-4-carboxamide |
| 155 | 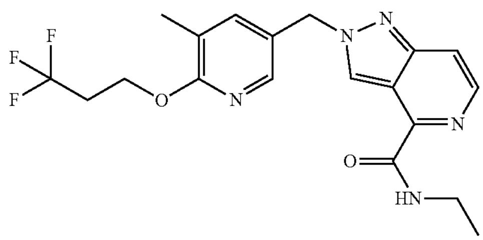 [SMILES: CCNC(=O)c1nccc2nn(Cc3cnc(OCCC(F)(F)F)c(C)c3)cc12] | N-ethyl-2-((5-methyl-6-(3,3,3-trifluoropropoxy)pyridin-3-yl)methyl)-2H-pyrazolo[4,3-c]pyridine-4-carboxamide |
| 156 | 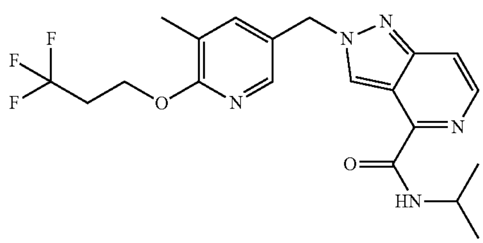 [SMILES: Cc1cc(Cn2cc3c(C(=O)NC(C)C)nccc3n2)cnc1OCCC(F)(F)F] | N-isopropyl-2-((5-methyl-6-(3,3,3-trifluoropropoxy)pyridin-3-yl)methyl)-2H-pyrazolo[4,3-c]pyridine-4-carboxamide |
| 157 | 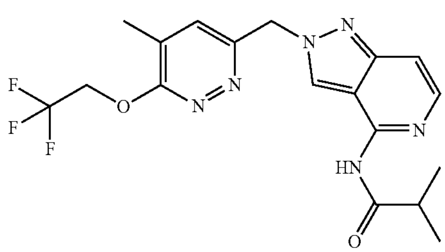 [SMILES: Cc1cc(Cn2cc3c(NC(=O)C(C)C)nccc3n2)nnc1OCC(F)(F)F] | N-(2-((5-methyl-6-(2,2,2-trifluoroethoxy)pyridazin-3-yl)methyl)-2H-pyrazolo[4,3-c]pyridin-4-yl)isobutyramide |
| 158 | 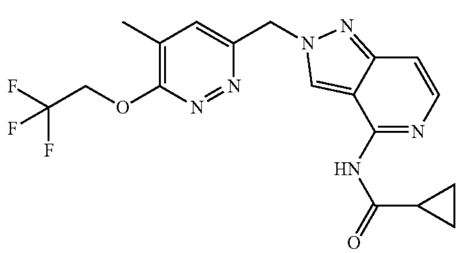 [SMILES: Cc1cc(Cn2cc3c(NC(=O)C4CC4)nccc3n2)nnc1OCC(F)(F)F] | N-(2-((5-methyl-6-(2,2,2-trifluoroethoxy)pyridazin-3-yl)methyl)-2H-pyrazolo[4,3-c]pyridin-4-yl)cyclopropanecarboxamide |

TABLE 7-continued

| Ex | Structure | Name |
|---|---|---|
| 159 | 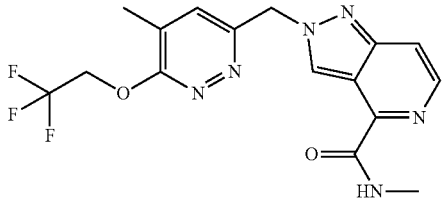 [SMILES: CNC(=O)c1nccc2nn(Cc3cc(C)c(OCC(F)(F)F)nn3)cc12] | N-methyl-2-((5-methyl-6-(2,2,2-trifluoroethoxy)pyridazin-3-yl)methyl)-2H-pyrazolo[4,3-c]pyridine-4-carboxamide |
| 160 | 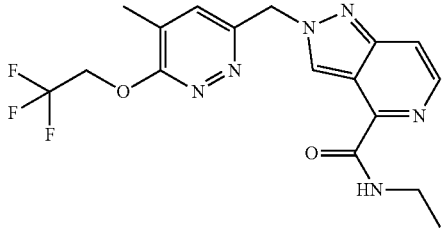 [SMILES: CCNC(=O)c1nccc2nn(Cc3cc(C)c(OCC(F)(F)F)nn3)cc12] | N-ethyl-2-((5-methyl-6-(2,2,2-trifluoroethoxy)pyridazin-3-yl)methyl)-2H-pyrazolo[4,3-c]pyridine-4-carboxamide |
| 161 | 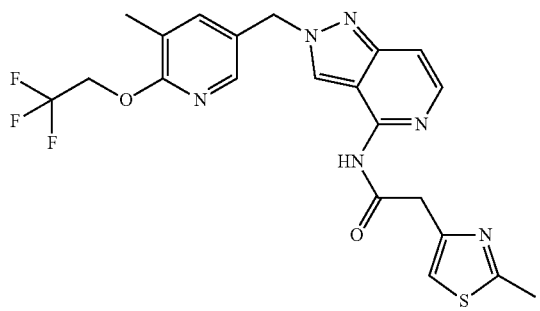 [SMILES: Cc1nc(CC(=O)Nc2nccc3nn(Cc4cnc(OCC(F)(F)F)c(C)c4)cc23)cs1] | N-(2-((5-methyl-6-(2,2,2-trifluoroethoxy)pyridin-3-yl)methyl)-2H-pyrazolo[4,3-c]pyridin-4-yl)-2-(2-methylthiazol-4-yl)acetamide |
| 162 | 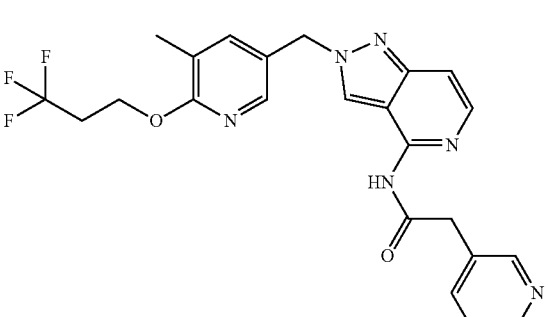 | N-(2-((5-methyl-6-(3,3,3-trifluoropropoxy)pyridin-3-yl)methyl)-2H-pyrazolo[4,3-c]pyridin-4-yl)-2-(pyridin-3-yl)acetamide |
| 163 | 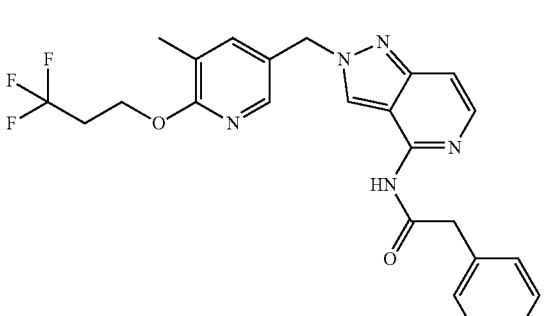 | N-(2-((5-methyl-6-(3,3,3-trifluoropropoxy)pyridin-3-yl)methyl)-2H-pyrazolo[4,3-c]pyridin-4-yl)-2-(pyridin-4-yl)acetamide |

TABLE 7-continued

| Ex | Structure | Name |
|---|---|---|
| 164 | 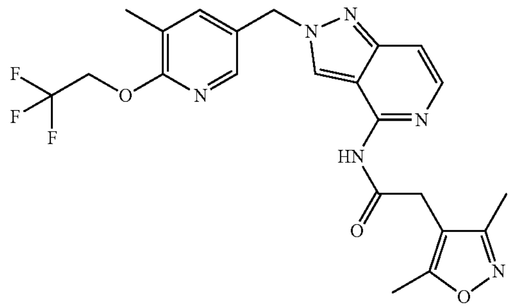 [SMILES: Cc1cc(Cn2cc3c(NC(=O)Cc4c(C)noc4C)nccc3n2)cnc1OCC(F)(F)F] | 2-(3,5-dimethylisoxazol-4-yl)-N-(2-((5-methyl-6-(2,2,2-trifluoroethoxy)pyridin-3-yl)methyl)-2H-pyrazolo[4,3-c]pyridin-4-yl)acetamide |
| 165 | 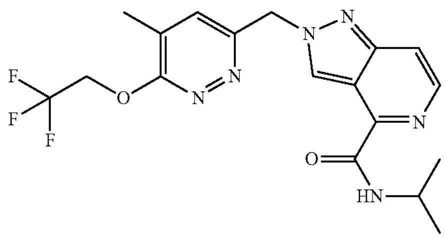 [SMILES: Cc1cc(Cn2cc3c(C(=O)NC(C)C)nccc3n2)nnc1OCC(F)(F)F] | N-isopropyl-2-((5-methyl-6-(2,2,2-trifluoroethoxy)pyridazin-3-yl)methyl)-2H-pyrazolo[4,3-c]pyridine-4-carboxamide |
| 166 | 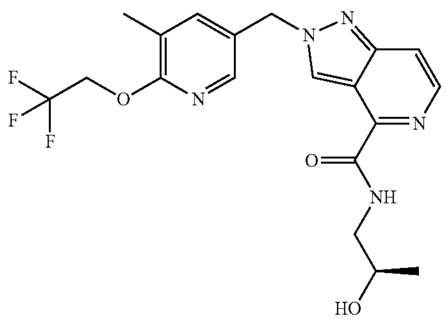 [SMILES: Cc1cc(Cn2cc3c(C(=O)NC[C@@H](C)O)nccc3n2)cnc1OCC(F)(F)F] | (R)-N-(2-hydroxypropyl)-2-((5-methyl-6-(2,2,2-trifluoroethoxy)pyridin-3-yl)methyl)-2H-pyrazolo[4,3-c]pyridine-4-carboxamide |
| 167 | 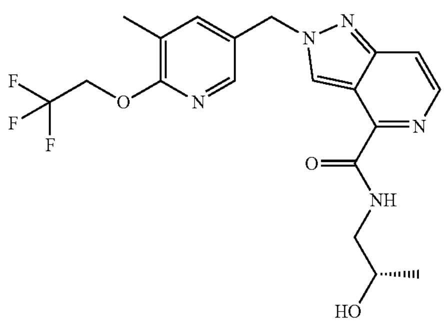 [SMILES: Cc1cc(Cn2cc3c(C(=O)NC[C@H](C)O)nccc3n2)cnc1OCC(F)(F)F] | (S)-N-(2-hydroxypropyl)-2-((5-methyl-6-(2,2,2-trifluoroethoxy)pyridin-3-yl)methyl)-2H-pyrazolo[4,3-c]pyridine-4-carboxamide |
| 168 | 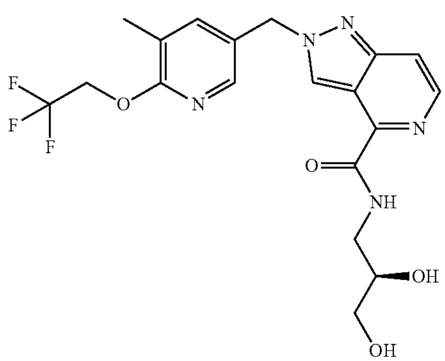 [SMILES: Cc1cc(Cn2cc3c(C(=O)NC[C@@H](O)CO)nccc3n2)cnc1OCC(F)(F)F] | (S)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 169 | 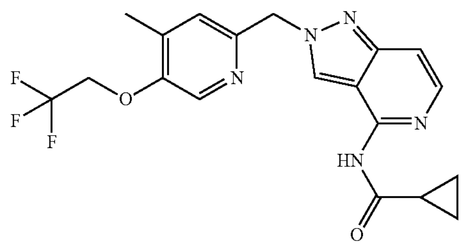 | N-(2-((4-methyl-5-(2,2,2-trifluoroethoxy)pyridin-2-yl)methyl)-2H-pyrazolo[4,3-c]pyridin-4-yl)cyclopropanecarboxamide |
| 170 | 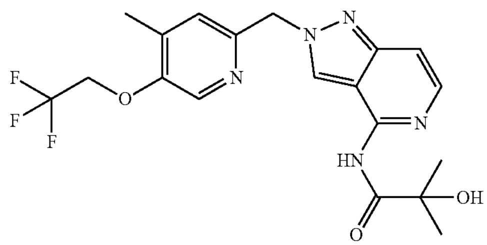 | 2-hydroxy-2-methyl-N-(2-((4-methyl-5-(2,2,2-trifluoroethoxy)pyridin-2-yl)methyl)-2H-pyrazolo[4,3-c]pyridin-4-yl)propanamide |
| 171 | 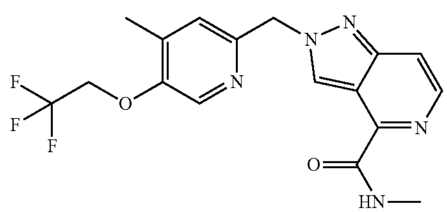 [SMILES: CNC(=O)c1nccc2nn(Cc3cc(C)c(OCC(F)(F)F)cn3)cc12] | N-methyl-2-((4-methyl-5-(2,2,2-trifluoroethoxy)pyridin-2-yl)methyl)-2H-pyrazolo[4,3-c]pyridine-4-carboxamide |
| 172 | 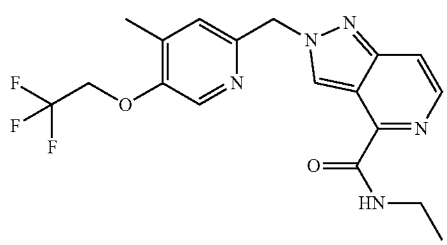 [SMILES: CCNC(=O)c1nccc2nn(Cc3cc(C)c(OCC(F)(F)F)cn3)cc12] | N-ethyl-2-((4-methyl-5-(2,2,2-trifluoroethoxy)pyridin-2-yl)methyl)-2H-pyrazolo[4,3-c]pyridine-4-carboxamide |
| 173 | 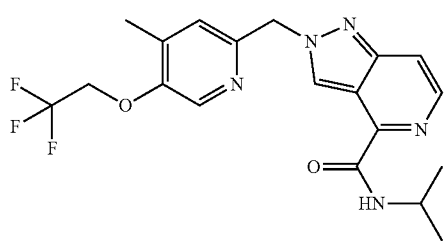 [SMILES: Cc1cc(Cn2cc3c(C(=O)NC(C)C)nccc3n2)ncc1OCC(F)(F)F] | N-isopropyl-2-((4-methyl-5-(2,2,2-trifluoroethoxy)pyridin-2-yl)methyl)-2H-pyrazolo[4,3-c]pyridine-4-carboxamide |
| 174 | 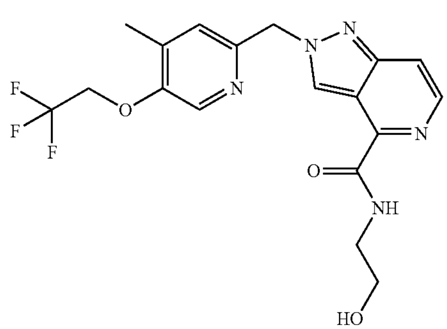 [SMILES: Cc1cc(Cn2cc3c(C(=O)NCCO)nccc3n2)ncc1OCC(F)(F)F] | N-(2-hydroxyethyl)-2-((4-methyl-5-(2,2,2-trifluoroethoxy)pyridin-2-yl)methyl)-2H-pyrazolo[4,3-c]pyridine-4-carboxamide |

TABLE 7-continued

| Ex | Structure | Name |
|---|---|---|
| 175 | 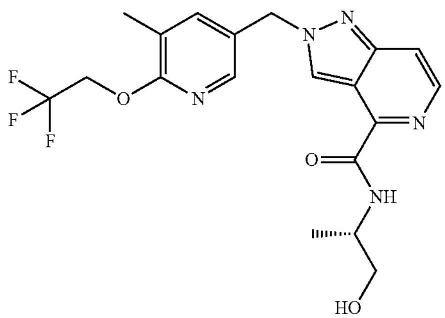 [SMILES: Cc1cc(Cn2cc3c(C(=O)N[C@@H](C)CO)nccc3n2)cnc1OCC(F)(F)F] | (S)-N-(1-hydroxypropan-2-yl)-2-((5-methyl-6-(2,2,2-trifluoroethoxy)pyridin-3-yl)methyl)-2H-pyrazolo[4,3-c]pyridine-4-carboxamide |
| 176 | 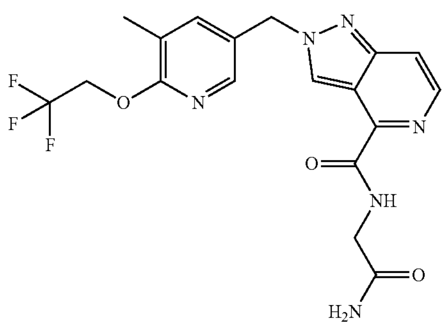 [SMILES: Cc1cc(Cn2cc3c(C(=O)NCC(N)=O)nccc3n2)cnc1OCC(F)(F)F] | N-(2-amino-2-oxoethyl)-2-((5-methyl-6-(2,2,2-trifluoroethoxy)pyridin-3-yl)methyl)-2H-pyrazolo[4,3-c]pyridine-4-carboxamide |
| 177 | 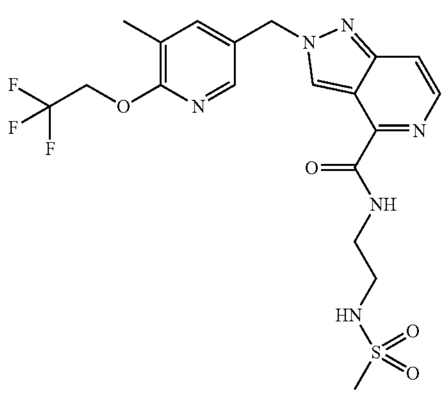 [SMILES: Cc1cc(Cn2cc3c(C(=O)NCCNS(C)(=O)=O)nccc3n2)cnc1OCC(F)(F)F] | 2-((5-methyl-6-(2,2,2-trifluoroethoxy)pyridin-3-yl)methyl)-N-(2-(methylsulfonamido)ethyl)-2H-pyrazolo[4,3-c]pyridine-4-carboxamide |
| 178 | 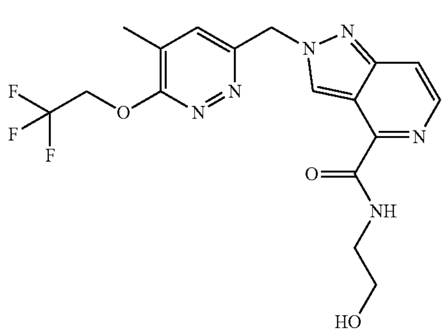 [SMILES: Cc1cc(Cn2cc3c(C(=O)NCCO)nccc3n2)nnc1OCC(F)(F)F] | N-(2-hydroxyethyl)-2-((5-methyl-6-(2,2,2-trifluoroethoxy)pyridazin-3-yl)methyl)-2H-pyrazolo[4,3-c]pyridine-4-carboxamide |

TABLE 7-continued

| Ex | Structure | Name |
|----|-----------|------|
| 179 | 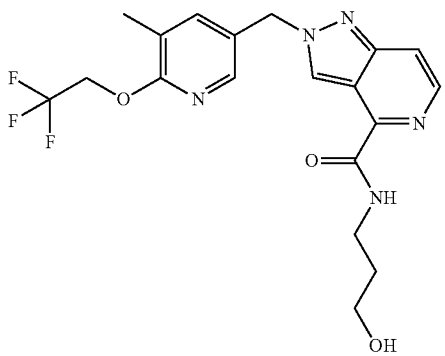 [SMILES: Cc1cc(Cn2cc3c(C(=O)NCCCO)nccc3n2)cnc1OCC(F)(F)F] | N-(3-hydroxypropyl)-2-((5-methyl-6-(2,2,2-trifluoroethoxy)pyridin-3-yl)methyl)-2H-pyrazolo[4,3-c]pyridine-4-carboxamide |
| 180 | 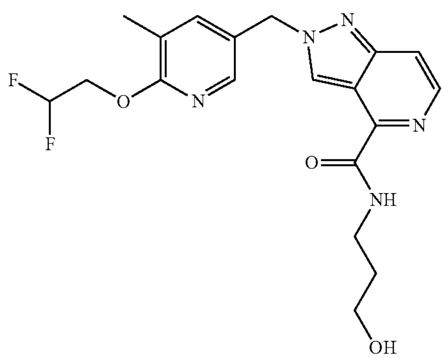 [SMILES: Cc1cc(Cn2cc3c(C(=O)NCCCO)nccc3n2)cnc1OCC(F)F] | 2-((6-(2,2-difluoroethoxy)-5-methylpyridin-3-yl)methyl)-N-(3-hydroxypropyl)-2H-pyrazolo[4,3-c]pyridine-4-carboxamide |
| 181 | 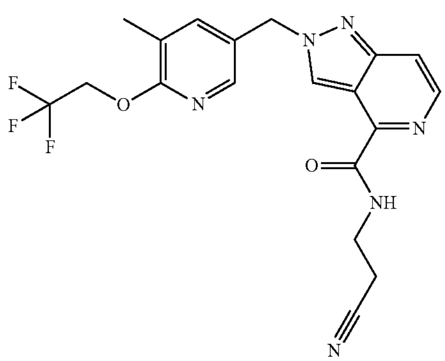 [SMILES: Cc1cc(Cn2cc3c(C(=O)NCCC#N)nccc3n2)cnc1OCC(F)(F)F] | N-(2-cyanoethyl)-2-((5-methyl-6-(2,2,2-trifluoroethoxy)pyridin-3-yl)methyl)-2H-pyrazolo[4,3-c]pyridine-4-carboxamide |
| 182 | 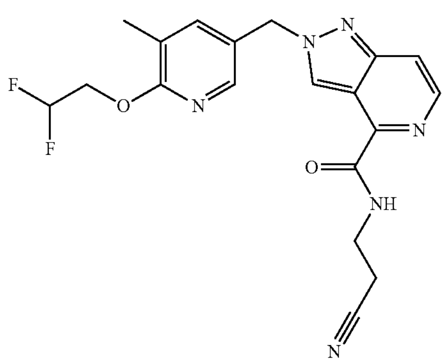 [SMILES: Cc1cc(Cn2cc3c(C(=O)NCCC#N)nccc3n2)cnc1OCC(F)F] | N-(2-cyanoethyl)-2-((6-(2,2-difluoroethoxy)-5-methylpyridin-2-yl)methyl)-2H-pyrazolo[4,3-c]pyridine-4-carboxamide |

TABLE 7-continued

| Ex | Structure | Name |
|---|---|---|
| 183 | 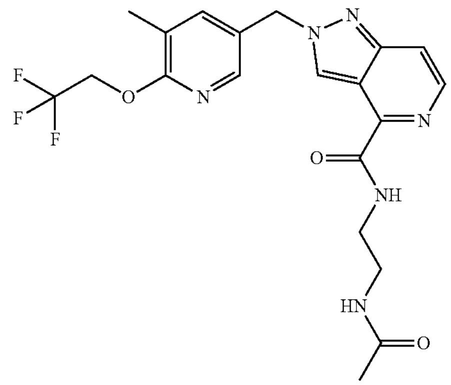 [SMILES: CC(=O)NCCNC(=O)c1nccc2nn(Cc3cnc(OCC(F)(F)F)c(C)c3)cc12] | N-(2-acetamidoethyl)-2-((5-methyl-6-(2,2,2-trifluoroethoxy)pyridin-3-yl)methyl)-2H-pyrazolo[4,3-c]pyridine-4-carboxamide |
| 184 | 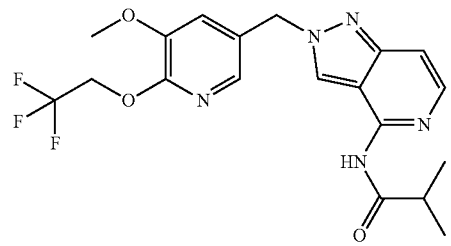 [SMILES: COc1cc(Cn2cc3c(NC(=O)C(C)C)nccc3n2)cnc1OCC(F)(F)F] | N-(2-((5-methoxy-6-(2,2,2-trifluoroethoxy)pyridin-3-yl)methyl)-2H-pyrazolo[4,3-c]pyridin-4-yl)isobutyramide |
| 185 | 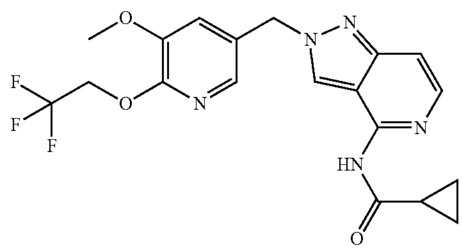 [SMILES: COc1cc(Cn2cc3c(NC(=O)C4CC4)nccc3n2)cnc1OCC(F)(F)F] | N-(2-((5-methoxy-6-(2,2,2-trifluoroethoxy)pyridin-3-yl)methyl)-2H-pyrazolo[4,3-c]pyridin-4-yl)cyclopropanecarboxamide |
| 186 | 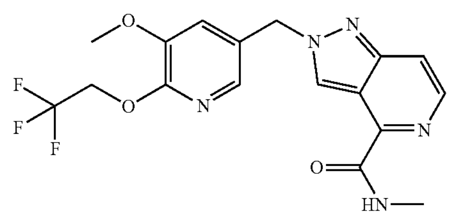 [SMILES: CNC(=O)c1nccc2nn(Cc3cnc(OCC(F)(F)F)c(OC)c3)cc12] | 2-((5-methoxy-6-(2,2,2-trifluoroethoxy)pyridin-3-yl)methyl)-N-methyl-2H-pyrazolo[4,3-c]pyridine-4-carboxamide |
| 187 | 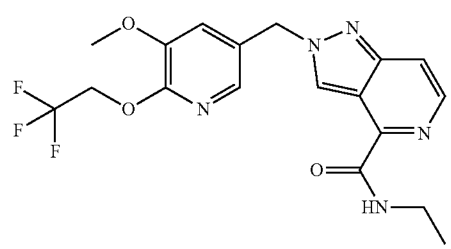 [SMILES: CCNC(=O)c1nccc2nn(Cc3cnc(OCC(F)(F)F)c(OC)c3)cc12] | N-ethyl-2-((5-methoxy-6-(2,2,2-trifluoroethoxy)pyridin-3-yl)methyl)-2H-pyrazolo[4,3-c]pyridine-4-carboxamide |
| 188 | 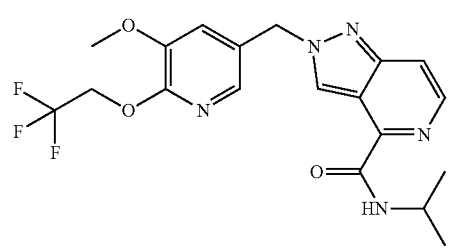 [SMILES: COc1cc(Cn2cc3c(C(=O)NC(C)C)nccc3n2)cnc1OCC(F)(F)F] | N-isopropyl-2-((5-methoxy-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 189 | 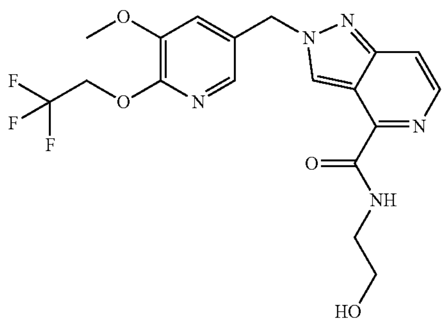 [SMILES: COc1cc(Cn2cc3c(C(=O)NCCO)nccc3n2)cnc1OCC(F)(F)F] | N-(2-hydroxyethyl)-2-((5-methoxy-6-(2,2,2-trifluoroethoxy)pyridin-3-yl)methyl)-2H-pyrazolo[4,3-c]pyridine-4-carboxamide |
| 190 | 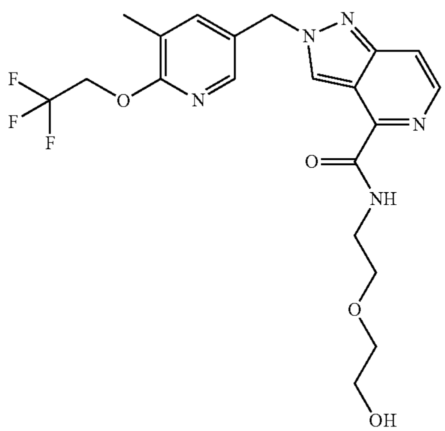 [SMILES: Cc1cc(Cn2cc3c(C(=O)NCCOCCO)nccc3n2)cnc1OCC(F)(F)F] | N-(2-(2-hydroxyethoxy)ethyl)-2-((5-methyl-6-(2,2,2-trifluoroethoxy)pyridin-3-yl)methyl)-2H-pyrazolo[4,3-c]pyridine-4-carboxamide |
| 191 | 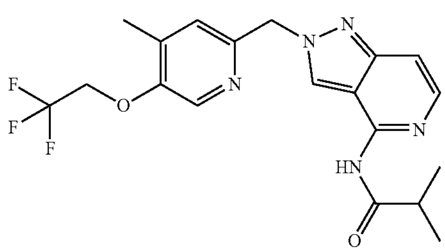 [SMILES: Cc1cc(Cn2cc3c(NC(=O)C(C)C)nccc3n2)ncc1OCC(F)(F)F] | N-(2-((4-methyl-5-(2,2,2-trifluoroethoxy)pyridin-2-yl)methyl)-2H-pyrazolo[4,3-c]pyridin-4-yl)isobutyramide |
| 192 | 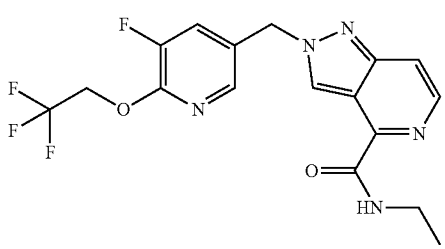 [SMILES: CCNC(=O)c1nccc2nn(Cc3cnc(OCC(F)(F)F)c(F)c3)cc12] | N-ethyl-2-((5-fluoro-6-(2,2,2-trifluoroethoxy)pyridin-3-yl)methyl)-2H-pyrazolo[4,3-c]pyridine-4-carboxamide |
| 193 | 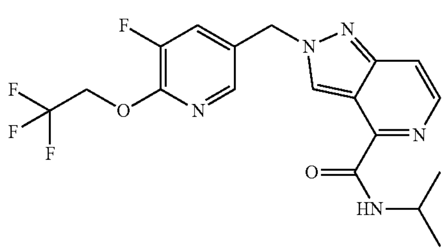 [SMILES: CC(C)NC(=O)c1nccc2nn(Cc3cnc(OCC(F)(F)F)c(F)c3)cc12] | 2-((5-fluoro-6-(2,2,2-trifluoroethoxy)pyridin-3-yl)methyl)-N-isopropyl-2H-pyrazolo[4,3-c]pyridine-4-carboxamide |

TABLE 7-continued

| Ex | Structure | Name |
|---|---|---|
| 194 | 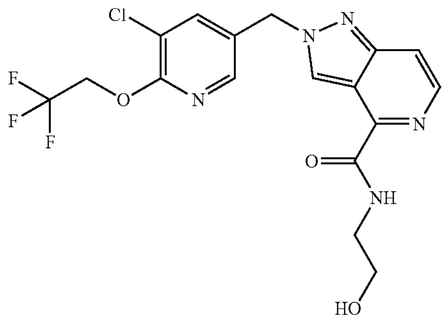 [SMILES: O=C(NCCO)c1nccc2nn(Cc3cnc(OCC(F)(F)F)c(Cl)c3)cc12] | 2-((5-chloro-6-(2,2,2-trifluoroethoxy)pyridin-3-yl)methyl)-N-(2-hydroxyethyl)-2H-pyrazolo[4,3-c]pyridine-4-carboxamide |
| 195 | 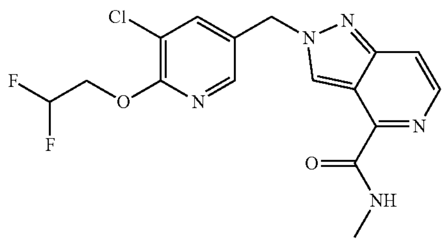 | 2-((5-chloro-6-(2,2-difluoroethoxy)pyridin-3-yl)methyl)-N-methyl-2H-pyrazolo[4,3-c]pyridine-4-carboxamide |
| 196 | 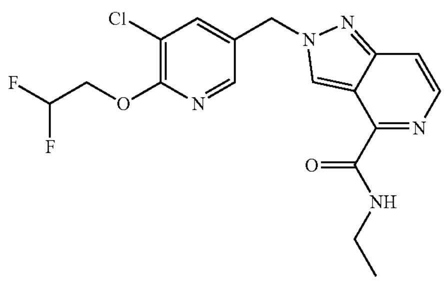 | 2-((5-chloro-6-(2,2-difluoroethoxy)pyridin-3-yl)methyl)-N-ethyl-2H-pyrazolo[4,3-c]pyridine-4-carboxamide |
| 197 | 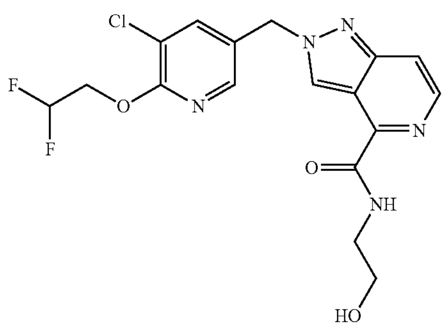 | 2-((5-chloro-6-(2,2-difluoroethoxy)pyridin-3-yl)methyl)-N-(2-hydroxyethyl)-2H-pyrazolo[4,3-c]pyridine-4-carboxamide |
| 198 | 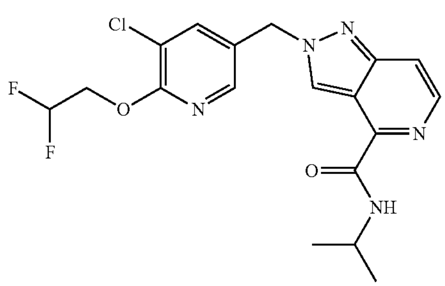 [SMILES: CC(C)NC(=O)c1nccc2nn(Cc3cnc(OCC(F)F)c(Cl)c3)cc12] | 2-((5-chloro-6-(2,2-difluoroethoxy)pyridin-3-yl)methyl)-N-isopropyl-2H-pyrazolo[4,3-c]pyridine-4-carboxamide |

TABLE 7-continued

| Ex | Structure | Name |
|---|---|---|
| 199 | 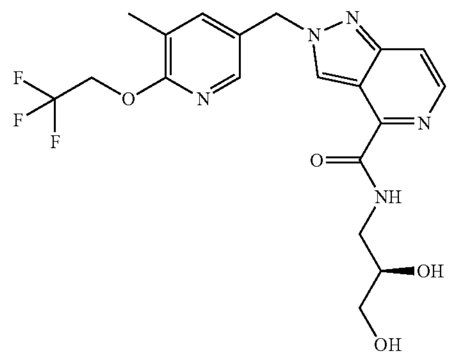 [SMILES: Cc1cc(Cn2cc3c(C(=O)NC[C@@H](O)CO)nccc3n2)cnc1OCC(F)(F)F] | (R)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide |
| 200 | 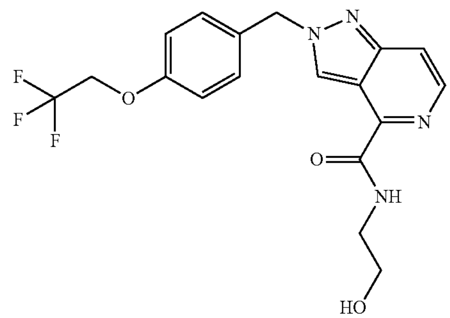 [SMILES: O=C(NCCO)c1nccc2nn(Cc3ccc(OCC(F)(F)F)cc3)cc12] | N-(2-hydroxyethyl)-2-(4-(2,2,2-trifluoroethoxy)benzyl)-2H-pyrazolo[4,3-c]pyridine-4-carboxamide |
| 201 | 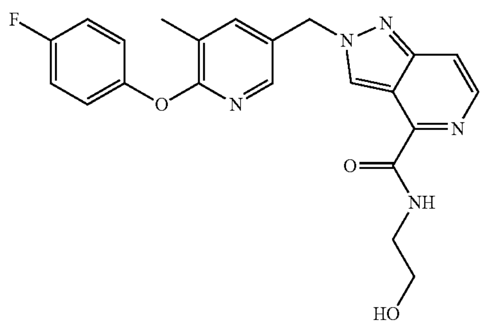 [SMILES: Cc1cc(Cn2cc3c(C(=O)NCCO)nccc3n2)cnc1Oc1ccc(F)cc1] | 2-((6-(4-fluorophenoxy)-5-methylpyridin-3-yl)methyl)-N-(2-hydroxyethyl)-2H-pyrazolo[4,3-c]pyridine-4-carboxamide |
| 202 | 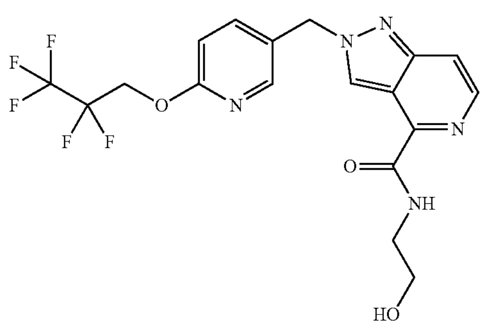 [SMILES: O=C(NCCO)c1nccc2nn(Cc3ccc(OCC(F)(F)C(F)(F)F)nc3)cc12] | N-(2-hydroxyethyl)-2-((6-(2,2,3,3,3-pentafluoropropoxy)pyridin-3-yl)methyl)-2H-pyrazolo[4,3-c]pyridine-4-carboxamide |
| 203 | 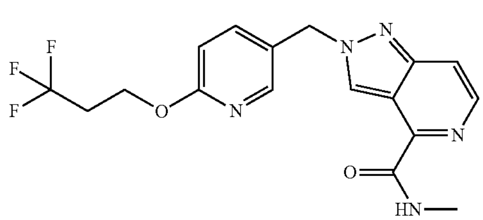 [SMILES: CNC(=O)c1nccc2nn(Cc3ccc(OCCC(F)(F)F)nc3)cc12] | N-methyl-2-((6-(3,3,3-trifluoropropoxy)pyridin-3-yl)methyl)-2H-pyrazolo[4,3-c]pyridine-4-carboxamide |

TABLE 7-continued

| Ex | Structure | Name |
|---|---|---|
| 204 | 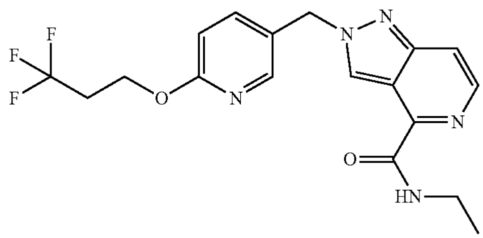 [SMILES: CCNC(=O)c1nccc2nn(Cc3ccc(OCCC(F)(F)F)nc3)cc12] | N-ethyl-2-((6-(3,3,3-trifluoropropoxy)pyridin-3-yl)methyl)-2H-pyrazolo[4,3-c]pyridine-4-carboxamide |
| 205 | 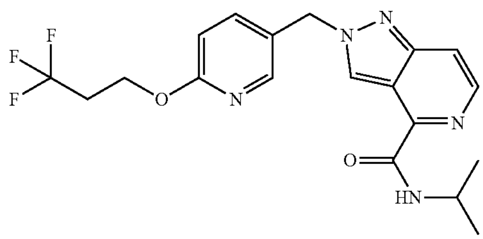 [SMILES: CC(C)NC(=O)c1nccc2nn(Cc3ccc(OCCC(F)(F)F)nc3)cc12] | N-isopropyl-2-((6-(3,3,3-trifluoropropoxy)pyridin-3-yl)methyl)-2H-pyrazolo[4,3-c]pyridine-4-carboxamide |
| 206 | 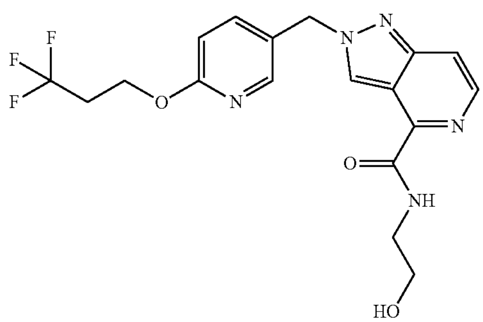 [SMILES: O=C(NCCO)c1nccc2nn(Cc3ccc(OCCC(F)(F)F)nc3)cc12] | N-(2-hydroxyethyl)-2-((6-(3,3,3-trifluoropropoxy)pyridin-3-yl)methyl)-2H-pyrazolo[4,3-c]pyridine-4-carboxamide |
| 207 | 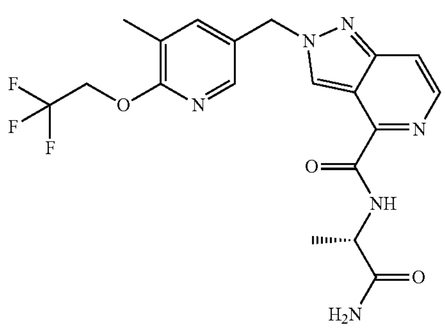 [SMILES: Cc1cc(Cn2cc3c(C(=O)N[C@@H](C)C(N)=O)nccc3n2)cnc1OCC(F)(F)F] | (S)-N-(1-amino-1-oxopropan-2-yl)-2-((5-methyl-6-(2,2,2-trifluoroethoxy)pyridin-3-yl)methyl)-2H-pyrazolo[4,3-c]pyridine-4-carboxamide |
| 208 | 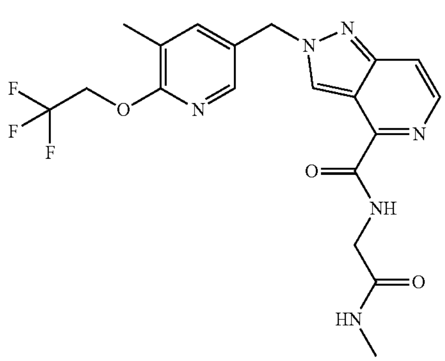 [SMILES: CNC(=O)CNC(=O)c1nccc2nn(Cc3cnc(OCC(F)(F)F)c(C)c3)cc12] | 2-((5-methyl-6-(2,2,2-trifluoroethoxy)pyridin-3-yl)methyl)-N-(2-(methylamino)-2-oxoethyl)-2H-pyrazolo[4,3-c]pyridine-4-carboxamide |

TABLE 7-continued

| Ex | Structure | Name |
|---|---|---|
| 209 | 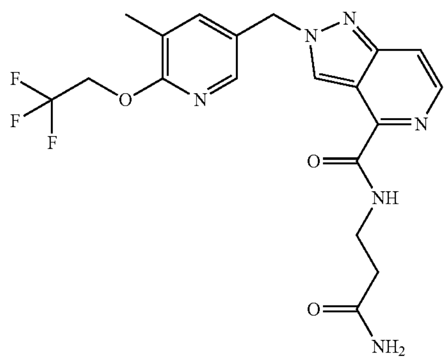 [SMILES: Cc1cc(Cn2cc3c(C(=O)NCCC(N)=O)nccc3n2)cnc1OCC(F)(F)F] | N-(3-amino-3-oxopropyl)-2-((5-methyl-6-(2,2,2-trifluoroethoxy)pyridin-3-yl)methyl)-2H-pyrazolo[4,3-c]pyridine-4-carboxamide |
| 210 | 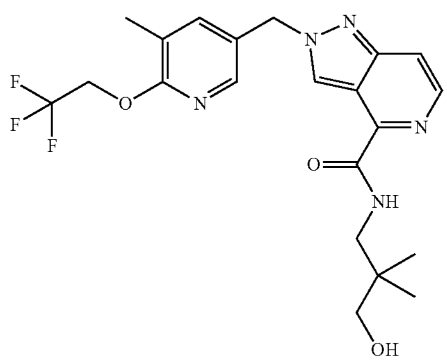 [SMILES: Cc1cc(Cn2cc3c(C(=O)NCC(C)(C)CO)nccc3n2)cnc1OCC(F)(F)F] | N-(3-hydroxy-2,2-dimethylpropyl)-2-((5-methyl-6-(2,2,2-trifluoroethoxy)pyridin-3-yl)methyl)-2H-pyrazolo[4,3-c]pyridine-4-carboxamide |
| 211 | 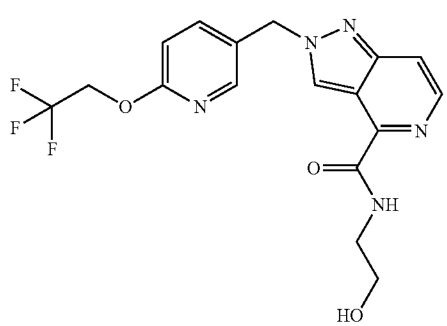 [SMILES: O=C(NCCO)c1nccc2nn(Cc3ccc(OCC(F)(F)F)nc3)cc12] | N-(2-hydroxyethyl)-2-((6-(2,2,2-trifluoroethoxy)pyridin-3-yl)methyl)-2H-pyrazolo[4,3-c]pyridine-4-carboxamide |
| 212 | 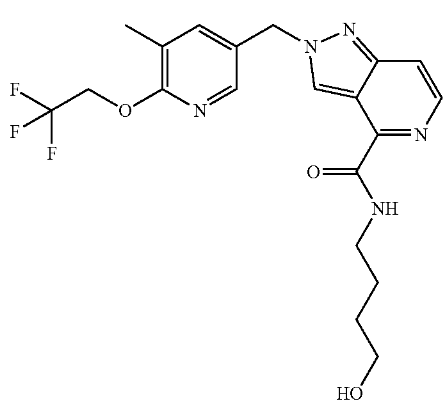 [SMILES: Cc1cc(Cn2cc3c(C(=O)NCCCCO)nccc3n2)cnc1OCC(F)(F)F] | N-(4-hydroxybutyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 213 | 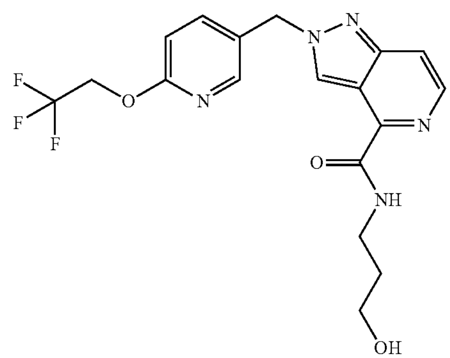 [SMILES: O=C(NCCCO)c1nccc2nn(Cc3ccc(OCC(F)(F)F)nc3)cc12] | N-(3-hydroxypropyl)-2-((6-(2,2,2-trifluoroethoxy)pyridin-3-yl)methyl)-2H-pyrazolo[4,3-c]pyridine-4-carboxamide |
| 214 | 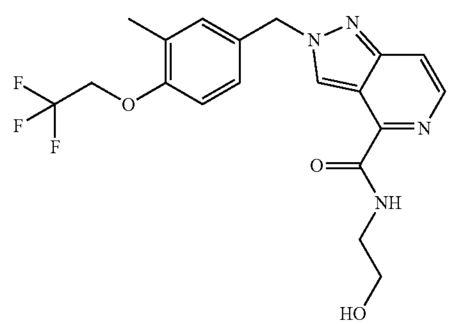 | N-(2-hydroxyethyl)-2-(3-methyl-4-(2,2,2-trifluoroethoxy)benzyl)-2H-pyrazolo[4,3-c]pyridine-4-carboxamide |
| 215 | 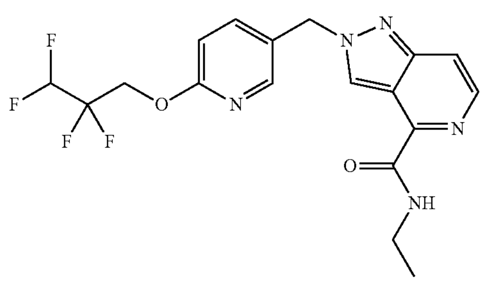 [SMILES: CCNC(=O)c1nccc2nn(Cc3ccc(OCC(F)(F)C(F)F)nc3)cc12] | N-ethyl-2-((6-(2,2,3,3-tetrafluoropropoxy)pyridin-3-yl)methyl)-2H-pyrazolo[4,3-c]pyridine-4-carboxamide |
| 216 | 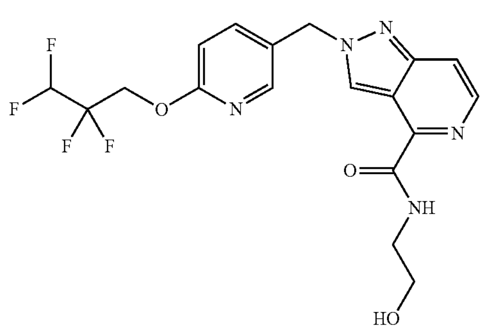 [SMILES: O=C(NCCO)c1nccc2nn(Cc3ccc(OCC(F)(F)C(F)F)nc3)cc12] | N-(2-hydroxyethyl)-2-((6-(2,2,3,3-tetrafluoropropoxy)pyridin-3-yl)methyl)-2H-pyrazolo[4,3-c]pyridine-4-carboxamide |

TABLE 7-continued

| Ex | Structure | Name |
|---|---|---|
| 217 | 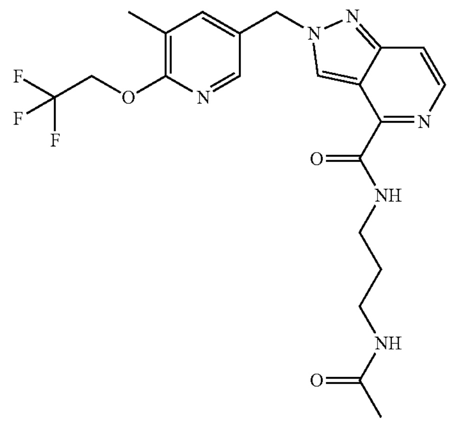 [SMILES: CC(=O)NCCCNC(=O)c1nccc2nn(Cc3cnc(OCC(F)(F)F)c(C)c3)cc12] | N-(3-acetamidopropyl)-2-((5-methyl-6-(2,2,2-trifluoroethoxy)pyridin-3-yl)methyl)-2H-pyrazolo[4,3-c]pyridine-4-carboxamide |
| 218 | 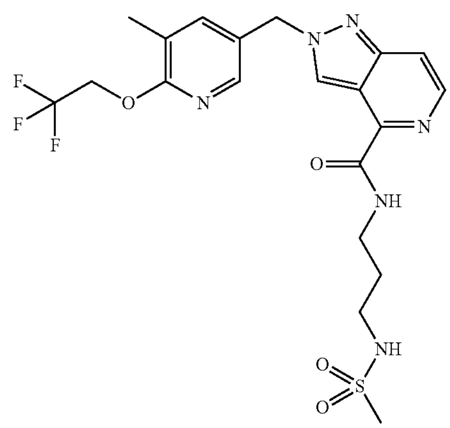 [SMILES: Cc1cc(Cn2cc3c(C(=O)NCCCNS(C)(=O)=O)nccc3n2)cnc1OCC(F)(F)F] | 2-((5-methyl-6-(2,2,2-trifluoroethoxy)pyridin-3-yl)methyl)-N-(3-(methylsulfonamido)propyl)-2H-pyrazolo[4,3-c]pyridine-4-carboxamide |
| 219 | 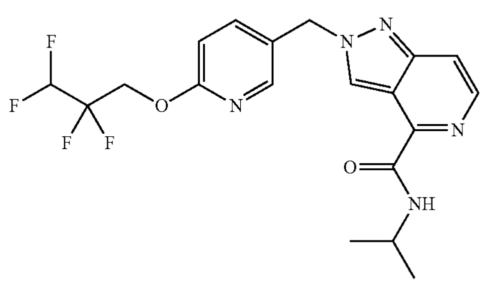 [SMILES: CC(C)NC(=O)c1nccc2nn(Cc3ccc(OCC(F)(F)C(F)F)nc3)cc12] | N-isopropyl-2-((6-(2,2,3,3-tetrafluoropropoxy)pyridin-3-yl)methyl)-2H-pyrazolo[4,3-c]pyridine-4-carboxamide |
| 220 | 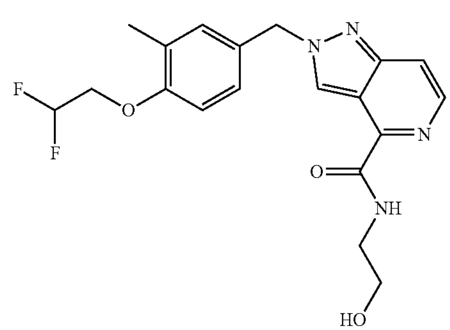 [SMILES: Cc1cc(Cn2cc3c(C(=O)NCCO)nccc3n2)ccc1OCC(F)F] | 2-(4-(2,2-difluoroethoxy)-3-methylbenzyl)-N-(2-hydroxyethyl)-2H-pyrazolo[4,3-c]pyridine-4-carboxamide |

TABLE 7-continued

| Ex | Structure | Name |
|---|---|---|
| 221 | 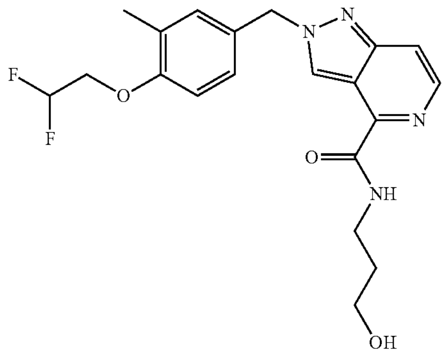 | 2-(4-(2,2-difluoroethoxy)-3-methylbenzyl)-N-(3-hydroxypropyl)-2H-pyrazolo[4,3-c]pyridine-4-carboxamide |
| 222 | 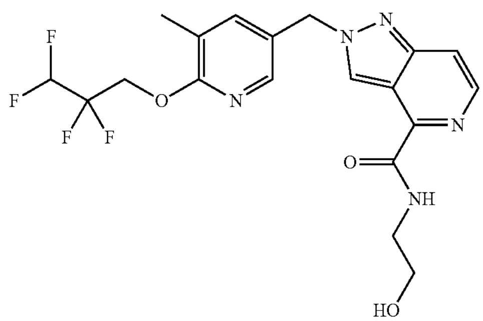 [SMILES: Cc1cc(Cn2cc3c(C(=O)NCCO)nccc3n2)cnc1OCC(F)(F)C(F)F] | N-(2-hydroxyethyl)-2-((5-methyl-6-(2,2,3,3-tetrafluoropropoxy)pyridin-3-yl)methyl)-2H-pyrazolo[4,3-c]pyridine-4-carboxamide |
| 223 | 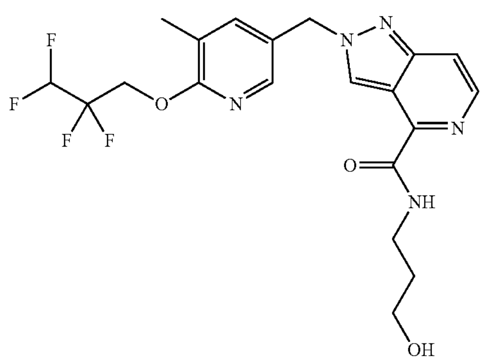 [SMILES: Cc1cc(Cn2cc3c(C(=O)NCCCO)nccc3n2)cnc1OCC(F)(F)C(F)F] | N-(3-hydroxypropyl)-2-((5-methyl-6-(2,2,3,3-tetrafluoropropoxy)pyridin-3-yl)methyl)-2H-pyrazolo[4,3-c]pyridine-4-carboxamide |
| 224 | 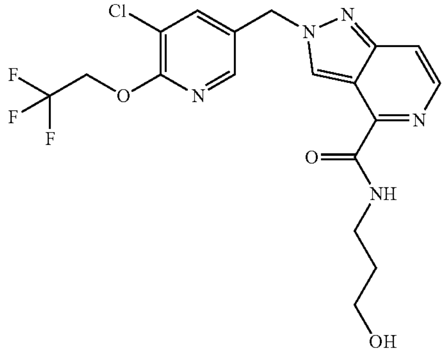 [SMILES: O=C(NCCCO)c1nccc2nn(Cc3cnc(OCC(F)(F)F)c(Cl)c3)cc12] | 2-((5-chloro-6-(2,2,2-trifluoroethoxy)pyridin-3-yl)methyl)-N-(3-hydroxypropyl)-2H-pyrazolo[4,3-c]pyridine-4-carboxamide |

TABLE 7-continued

| Ex | Structure | Name |
|---|---|---|
| 225 | 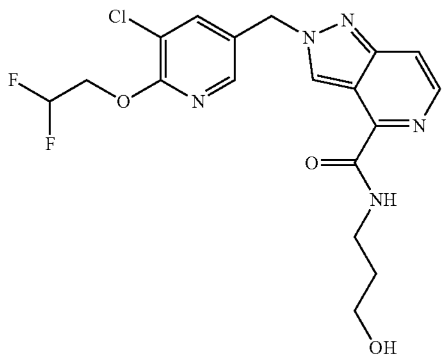 | 2-((5-chloro-6-(2,2-difluoroethoxy)pyridin-3-yl)methyl)-N-(3-hydroxypropyl)-2H-pyrazolo[4,3-c]pyridine-4-carboxamide |
| 226 | 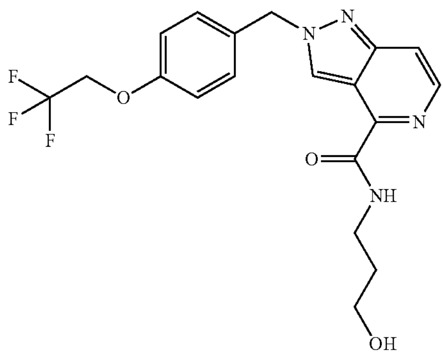 [SMILES: O=C(NCCCO)c1nccc2nn(Cc3ccc(OCC(F)(F)F)cc3)cc12] | N-(3-hydroxypropyl)-2-(4-(2,2,2-trifluoroethoxy)benzyl)-2H-pyrazolo[4,3-c]pyridine-4-carboxamide |
| 227 | 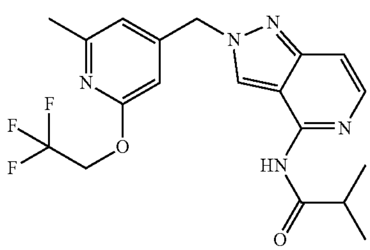 [SMILES: Cc1cc(Cn2cc3c(NC(=O)C(C)C)nccc3n2)cc(OCC(F)(F)F)n1] | N-(2-((2-methyl-6-(2,2,2-trifluoroethoxy)pyridin-4-yl)methyl)-2H-pyrazolo[4,3-c]pyridin-4-yl)isobutyramide |
| 228 | 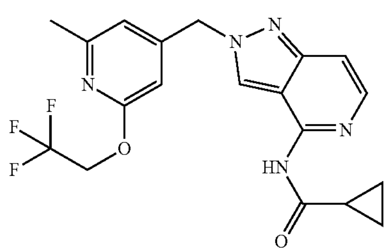 [SMILES: Cc1cc(Cn2cc3c(NC(=O)C4CC4)nccc3n2)cc(OCC(F)(F)F)n1] | N-(2-((2-methyl-6-(2,2,2-trifluoroethoxy)pyridin-4-yl)methyl)-2H-pyrazolo[4,3-c]pyridin-4-yl)cyclopropanecarboxamide |
| 229 | 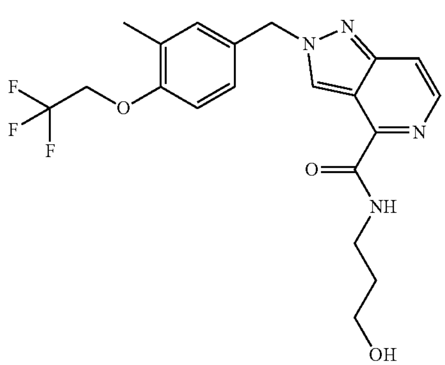 | N-(3-hydroxypropyl)-2-(3-methyl-4-(2,2,2-trifluoroethoxy)benzyl)-2H-pyrazolo[4,3-c]pyridine-4-carboxamide |

TABLE 7-continued

| Ex | Structure | Name |
|---|---|---|
| 230 | 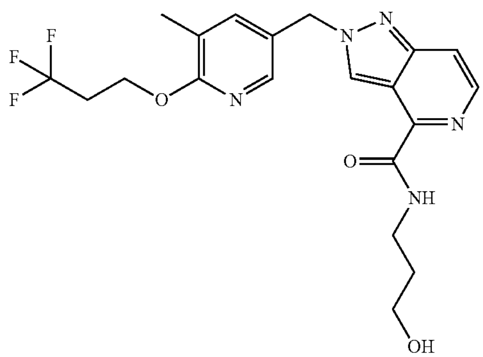 [SMILES: Cc1cc(Cn2cc3c(C(=O)NCCCO)nccc3n2)cnc1OCCC(F)(F)F] | N-(3-hydroxypropyl)-2-((5-methyl-6-(3,3,3-trifluoropropoxy)pyridin-3-yl)methyl)-2H-pyrazolo[4,3-c]pyridine-4-carboxamide |
| 231 | 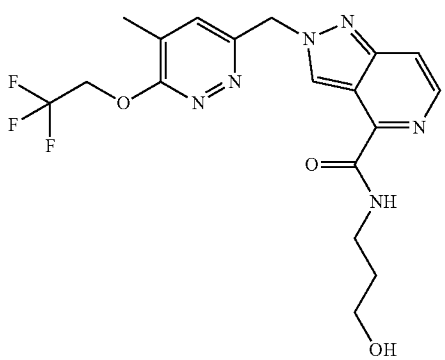 | N-(3-hydroxypropyl)-2-((5-methyl-6-(2,2,2-trifluoroethoxy)pyridazin-3-yl)methyl)-2H-pyrazolo[4,3-c]pyridine-4-carboxamide |
| 232 | 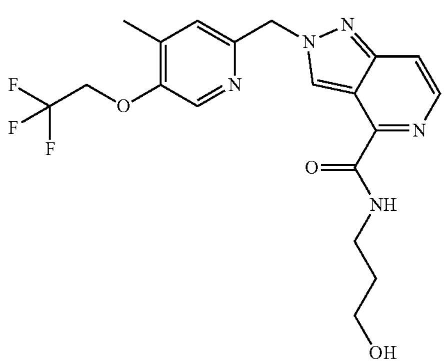 [SMILES: Cc1cc(Cn2cc3c(C(=O)NCCCO)nccc3n2)ncc1OCC(F)(F)F] | N-(3-hydroxypropyl)-2-((4-methyl-5-(2,2,2-trifluoroethoxy)pyridin-2-yl)methyl)-2H-pyrazolo[4,3-c]pyridine-4-carboxamide |
| 233 | 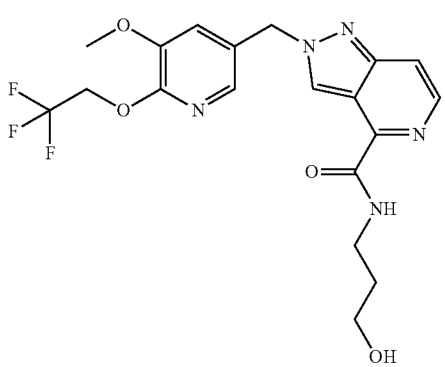 [SMILES: COc1cc(Cn2cc3c(C(=O)NCCCO)nccc3n2)cnc1OCC(F)(F)F] | N-(3-hydroxypropyl)-2-((5-methoxy-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 234 | 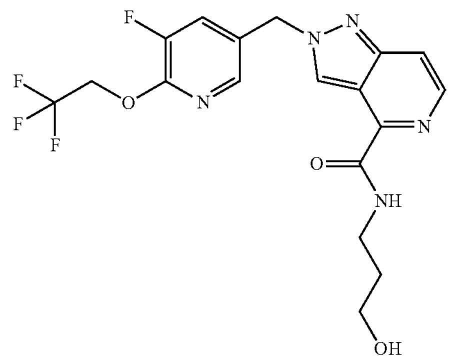 | 2-((5-fluoro-6-(2,2,2-trifluoroethoxy)pyridin-3-yl)methyl)-N-(3-hydroxypropyl)-2H-pyrazolo[4,3-c]pyridine-4-carboxamide |
| 235 | 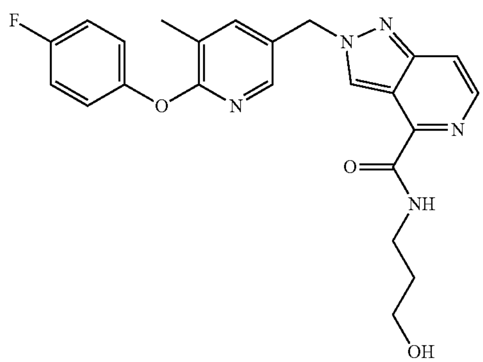 [SMILES: Cc1cc(Cn2cc3c(C(=O)NCCCO)nccc3n2)cnc1Oc1ccc(F)cc1] | 2-((6-(4-fluorophenoxy)-5-methylpyridin-3-yl)methyl)-N-(3-hydroxypropyl)-2H-pyrazolo[4,3-c]pyridine-4-carboxamide |
| 236 | 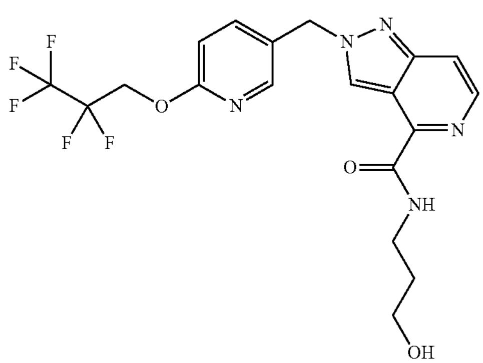 | N-(3-hydroxypropyl)-2-((6-(2,2,3,3,3-pentafluoropropoxy)pyridin-3-yl)methyl)-2H-pyrazolo[4,3-c]pyridine-4-carboxamide |
| 237 | 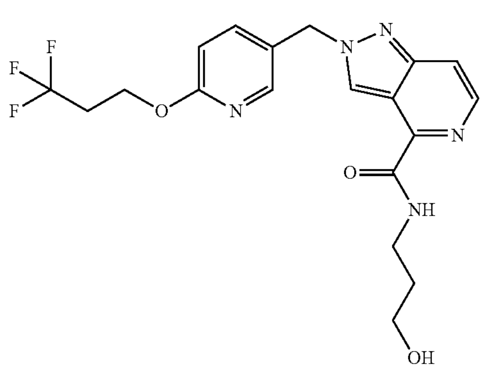 [SMILES: O=C(NCCCO)c1nccc2nn(Cc3ccc(OCCC(F)(F)F)nc3)cc12] | N-(3-hydroxypropyl)-2-((6-(3,3,3-trifluoropropoxy)pyridin-3-yl)methyl)-2H-pyrazolo[4,3-c]pyridine-4-carboxamide |

TABLE 7-continued

| Ex | Structure | Name |
|---|---|---|
| 238 | 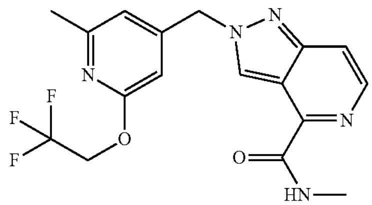 [SMILES: CNC(=O)c1nccc2nn(Cc3cc(C)nc(OCC(F)(F)F)c3)cc12] | N-methyl-2-((2-methyl-6-(2,2,2-trifluoroethoxy)pyridin-4-yl)methyl)-2H-pyrazolo[4,3-c]pyridine-4-carboxamide |
| 239 | 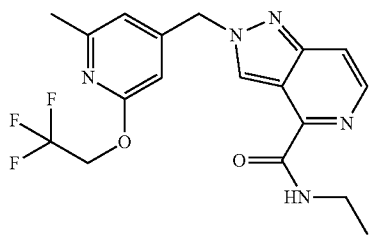 [SMILES: CCNC(=O)c1nccc2nn(Cc3cc(C)nc(OCC(F)(F)F)c3)cc12] | N-ethyl-2-((2-methyl-6-(2,2,2-trifluoroethoxy)pyridin-4-yl)methyl)-2H-pyrazolo[4,3-c]pyridine-4-carboxamide |
| 240 | 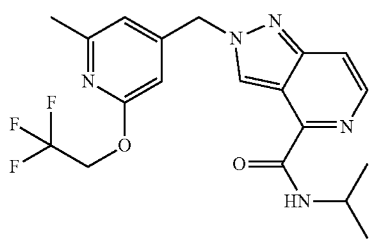 [SMILES: Cc1cc(Cn2cc3c(C(=O)NC(C)C)nccc3n2)cc(OCC(F)(F)F)n1] | N-isopropyl-2-((2-methyl-6-(2,2,2-trifluoroethoxy)pyridin-4-yl)methyl)-2H-pyrazolo[4,3-c]pyridine-4-carboxamide |
| 241 | 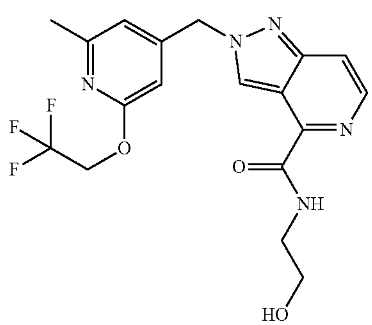 [SMILES: Cc1cc(Cn2cc3c(C(=O)NCCO)nccc3n2)cc(OCC(F)(F)F)n1] | N-(2-hydroxyethyl)-2-((2-methyl-6-(2,2,2-trifluoroethoxy)pyridin-4-yl)methyl)-2H-pyrazolo[4,3-c]pyridine-4-carboxamide |
| 242 | 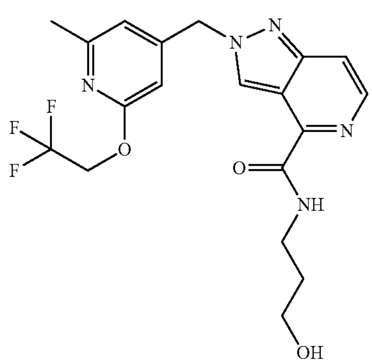 [SMILES: Cc1cc(Cn2cc3c(C(=O)NCCCO)nccc3n2)cc(OCC(F)(F)F)n1] | N-(3-hydroxypropyl)-2-((2-methyl-6-(2,2,2-trifluoroethoxy)pyridin-4-yl)methyl)-2H-pyrazolo[4,3-c]pyridine-4-carboxamide |

| Ex | Structure | Name |
|---|---|---|
| 243 | 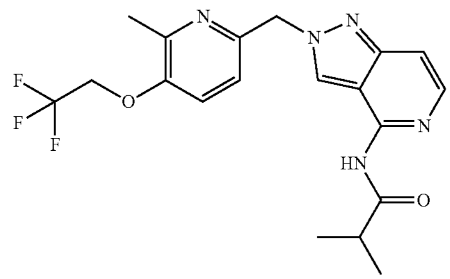 | N-(2-((6-methyl-5-(2,2,2-trifluoroethoxy)pyridin-2-yl)methyl)-2H-pyrazolo[4,3-c]pyridin-4-yl)isobutyramide |
| 244 | 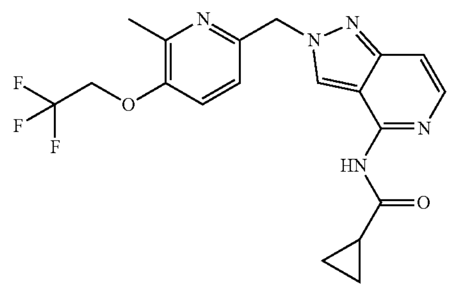 | N-(2-((6-methyl-5-(2,2,2-trifluoroethoxy)pyridin-2-yl)methyl)-2H-pyrazolo[4,3-c]pyridin-4-yl)cyclopropanecarboxamide |
| 245 | 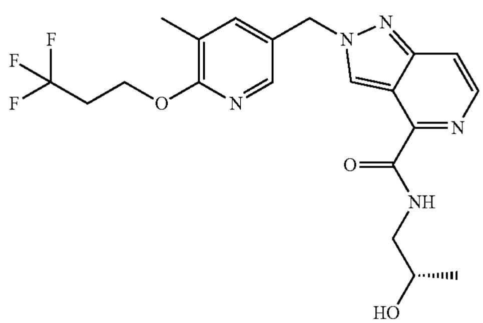 [SMILES: Cc1cc(Cn2cc3c(C(=O)NC[C@H](C)O)nccc3n2)cnc1OCCC(F)(F)F] | (S)-N-(2-hydroxypropyl)-2-((5-methyl-6-(3,3,3-trifluoropropoxy)pyridin-3-yl)methyl)-2H-pyrazolo[4,3-c]pyridine-4-carboxamide |
| 246 | 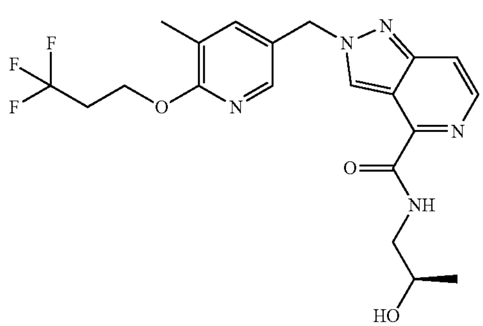 [SMILES: Cc1cc(Cn2cc3c(C(=O)NC[C@@H](C)O)nccc3n2)cnc1OCCC(F)(F)F] | (R)-N-(2-hydroxypropyl)-2-((5-methyl-6-(3,3,3-trifluoropropoxy)pyridin-3-yl)methyl)-2H-pyrazolo[4,3-c]pyridine-4-carboxamide |
| 247 | 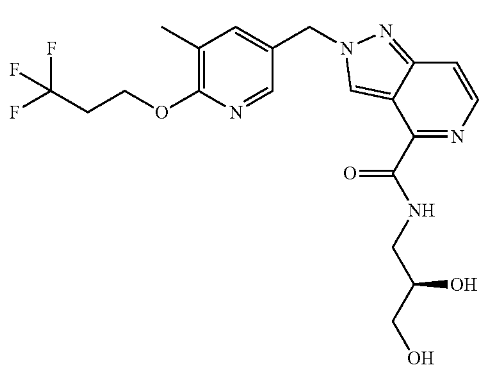 [SMILES: Cc1cc(Cn2cc3c(C(=O)NC[C@@H](O)CO)nccc3n2)cnc1OCCC(F)(F)F] | (S)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide |

TABLE 7-continued

| Ex | Structure | Name |
|---|---|---|
| 248 | 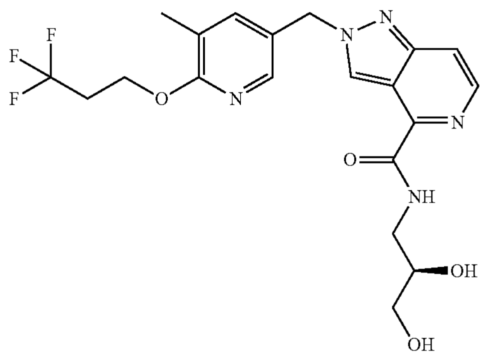 [SMILES: Cc1cc(Cn2cc3c(C(=O)NC[C@@H](O)CO)nccc3n2)cnc1OCCC(F)(F)F] | (R)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide |
| 249 | 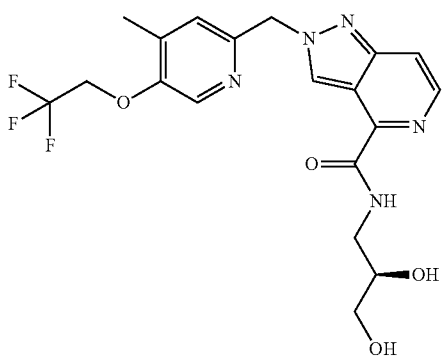 [SMILES: Cc1cc(Cn2cc3c(C(=O)NC[C@@H](O)CO)nccc3n2)ncc1OCC(F)(F)F] | (S)-N-(2,3-dihydroxypropyl)-2-((4-methyl-5-(2,2,2-trifluoroethoxy)pyridin-2-yl)methyl)-2H-pyrazolo[4,3-c]pyridine-4-carboxamide |
| 250 | 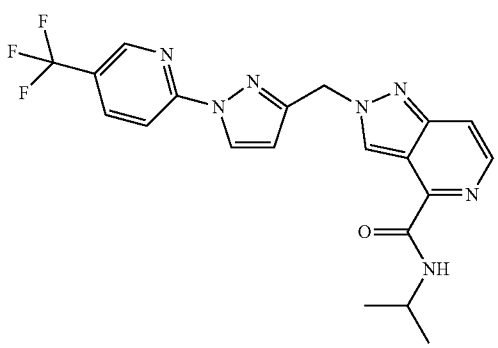 [SMILES: CC(C)NC(=O)c1nccc2nn(Cc3ccn(-c4ccc(C(F)(F)F)cn4)n3)cc12] | N-isopropyl-2-((1-(5-(trifluoromethyl)pyridin-2-yl)-1H-pyrazol-3-yl)methyl)-2H-pyrazolo[4,3-c]pyridine-4-carboxamide |
| 251 | 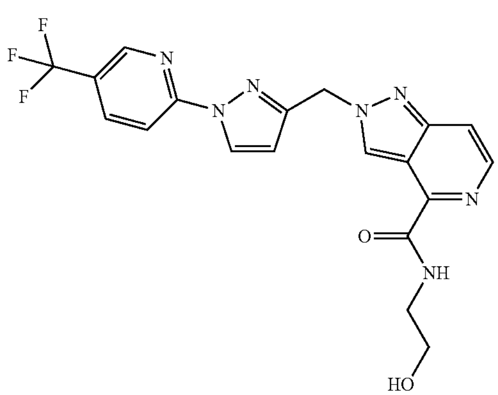 [SMILES: O=C(NCCO)c1nccc2nn(Cc3ccn(-c4ccc(C(F)(F)F)cn4)n3)cc12] | N-(2-hydroxyethyl)-2-((1-(5-(trifluoromethyl)pyridin-2-yl)-1H-pyrazol-3-yl)methyl)-2H-pyrazolo[4,3-c]pyridine-4-carboxamide |

TABLE 7-continued

| Ex | Structure | Name |
|---|---|---|
| 252 | 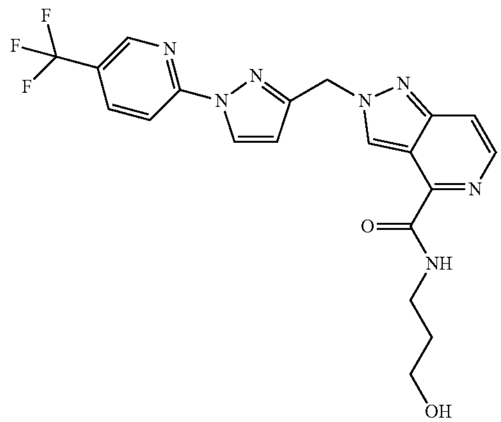 [SMILES: O=C(NCCCO)c1nccc2nn(Cc3ccn(-c4ccc(C(F)(F)F)cn4)n3)cc12] | N-(3-hydroxypropyl)-2-((1-(5-(trifluoromethyl)pyridin-2-yl)-1H-pyrazol-3-yl)methyl)-2H-pyrazolo[4,3-c]pyridine-4-carboxamide |
| 253 | 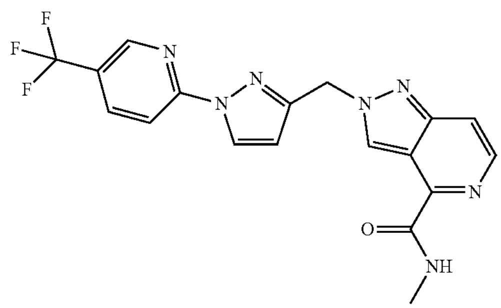 [SMILES: CNC(=O)c1nccc2nn(Cc3ccn(-c4ccc(C(F)(F)F)cn4)n3)cc12] | N-methyl-2-((1-(5-(trifluoromethyl)pyridin-2-yl)-1H-pyrazol-3-yl)methyl)-2H-pyrazolo[4,3-c]pyridine-4-carboxamide |
| 254 | 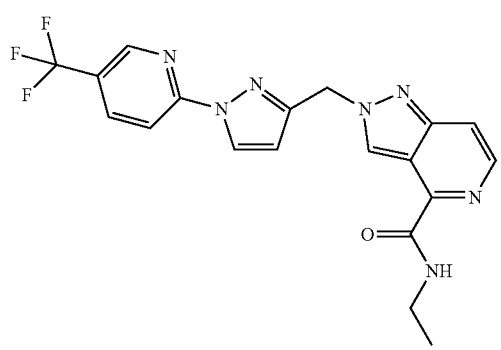 [SMILES: CCNC(=O)c1nccc2nn(Cc3ccn(-c4ccc(C(F)(F)F)cn4)n3)cc12] | N-ethyl-2-((1-(5-(trifluoromethyl)pyridin-2-yl)-1H-pyrazol-3-yl)methyl)-2H-pyrazolo[4,3-c]pyridine-4-carboxamide |
| 255 | 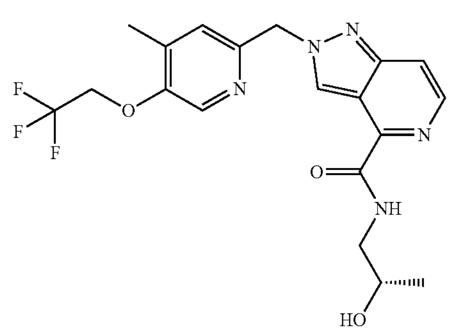 [SMILES: Cc1cc(Cn2cc3c(C(=O)NC[C@H](C)O)nccc3n2)ncc1OCC(F)(F)F] | (S)-N-(2-hydroxypropyl)-2-((4-methyl-5-(2,2,2-trifluoroethoxy)pyridin-2-yl)methyl)-2H-pyrazolo[4,3-c]pyridine-4-carboxamide |

TABLE 7-continued

| Ex | Structure | Name |
|---|---|---|
| 256 | 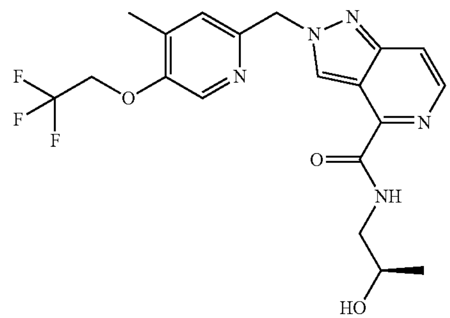 [SMILES: Cc1cc(Cn2cc3c(C(=O)NC[C@@H](C)O)nccc3n2)ncc1OCC(F)(F)F] | (R)-N-(2-hydroxypropyl)-2-((4-methyl-5-(2,2,2-trifluoroethoxy)pyridin-2-yl)methyl)-2H-pyrazolo[4,3-c]pyridine-4-carboxamide |
| 257 | 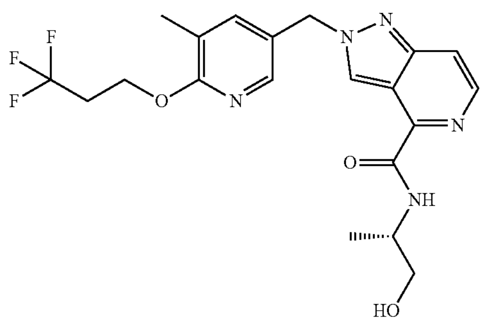 [SMILES: Cc1cc(Cn2cc3c(C(=O)N[C@@H](C)CO)nccc3n2)cnc1OCCC(F)(F)F] | (S)-N-(1-hydroxypropan-2-yl)-2-((5-methyl-6-(3,3,3-trifluoropropoxy)pyridin-3-yl)methyl)-2H-pyrazolo[4,3-c]pyridine-4-carboxamide |
| 258 | 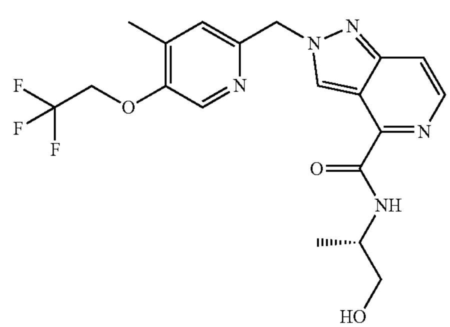 [SMILES: Cc1cc(Cn2cc3c(C(=O)N[C@@H](C)CO)nccc3n2)ncc1OCC(F)(F)F] | (S)-N-(1-hydroxypropan-2-yl)-2-((4-methyl-5-(2,2,2-trifluoroethoxy)pyridin-2-yl)methyl)-2H-pyrazolo[4,3-c]pyridine-4-carboxamide |
| 259 | 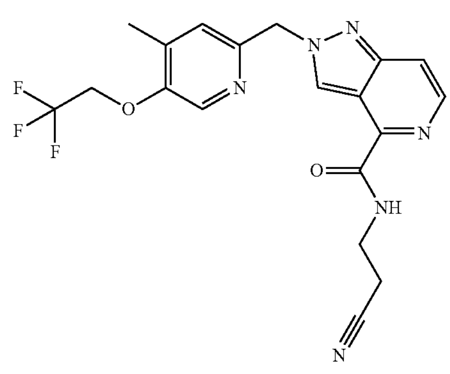 [SMILES: Cc1cc(Cn2cc3c(C(=O)NCCC#N)nccc3n2)ncc1OCC(F)(F)F] | N-(2-cyanoethyl)-2-((4-methyl-5-(2,2,2-trifluoroethoxy)pyridin-2-yl)methyl)-2H-pyrazolo[4,3-c]pyridine-4-carboxamide |

TABLE 7-continued

| Ex | Structure | Name |
|---|---|---|
| 260 | 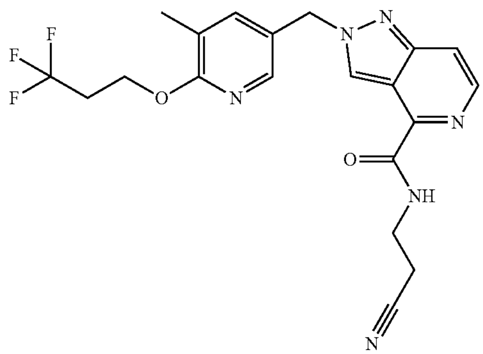 [SMILES: Cc1cc(Cn2cc3c(C(=O)NCCC#N)nccc3n2)cnc1OCCC(F)(F)F] | N-(2-cyanoethyl)-2-((5-methyl-6-(3,3,3-trifluoropropoxy)pyridin-3-yl)methyl)-2H-pyrazolo[4,3-c]pyridine-4-carboxamide |
| 261 | 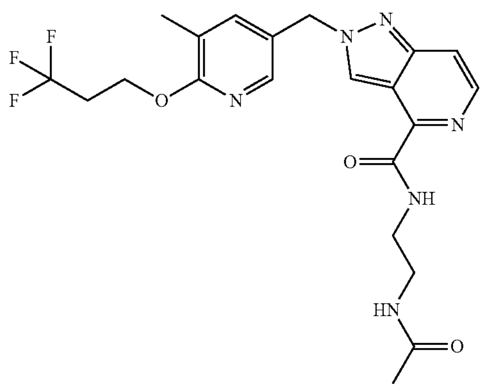 [SMILES: CC(=O)NCCNC(=O)c1nccc2nn(Cc3cnc(OCCC(F)(F)F)c(C)c3)cc12] | N-(2-acetamidoethyl)-2-((5-methyl-6-(3,3,3-trifluoropropoxy)pyridin-3-yl)methyl)-2H-pyrazolo[4,3-c]pyridine-4-carboxamide |
| 262 | 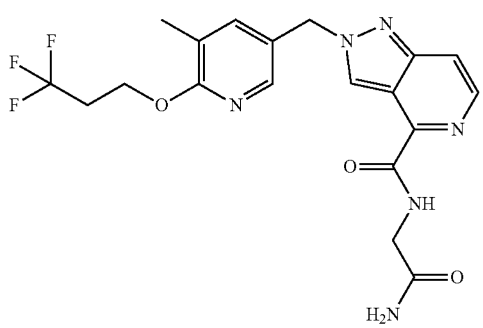 [SMILES: Cc1cc(Cn2cc3c(C(=O)NCC(N)=O)nccc3n2)cnc1OCCC(F)(F)F] | N-(2-amino-2-oxoethyl)-2-((5-methyl-6-(3,3,3-trifluoropropoxy)pyridin-3-yl)methyl)-2H-pyrazolo[4,3-c]pyridine-4-carboxamide |
| 263 | 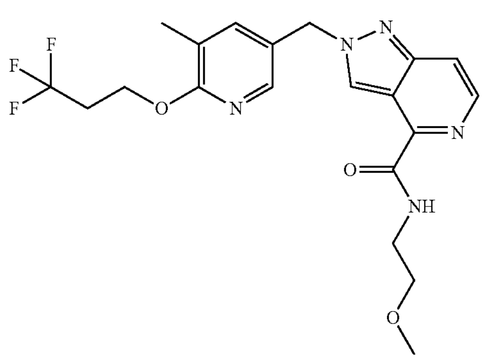 [SMILES: COCCNC(=O)c1nccc2nn(Cc3cnc(OCCC(F)(F)F)c(C)c3)cc12] | N-(2-methoxyethyl)-2-((5-methyl-6-(3,3,3-trifluoropropoxy)pyridin-3-yl)methyl)-2H-pyrazolo[4,3-c]pyridine-4-carboxamide |

TABLE 7-continued

| Ex | Structure | Name |
|---|---|---|
| 264 | 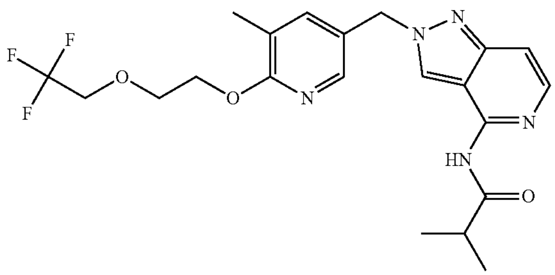 [SMILES: Cc1cc(Cn2cc3c(NC(=O)C(C)C)nccc3n2)cnc1OCCOCC(F)(F)F] | N-(2-((5-methyl-6-(2,2,2-trifluoroethoxy)ethoxy)pyridin-3-yl)methyl)-2H-pyrazolo[4,3-c]pyridin-4-yl)isobutyramide |
| 265 | 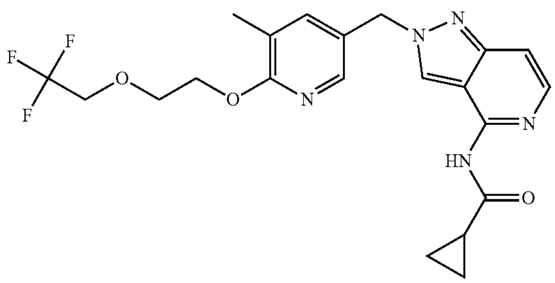 [SMILES: Cc1cc(Cn2cc3c(NC(=O)C4CC4)nccc3n2)cnc1OCCOCC(F)(F)F] | N-(2-((5-methyl-6-(2,2,2-trifluoroethoxy)ethoxy)pyridin-3-yl)methyl)-2H-pyrazolo[4,3-c]pyridin-4-yl)cyclopropanecarboxamide |
| 266 | 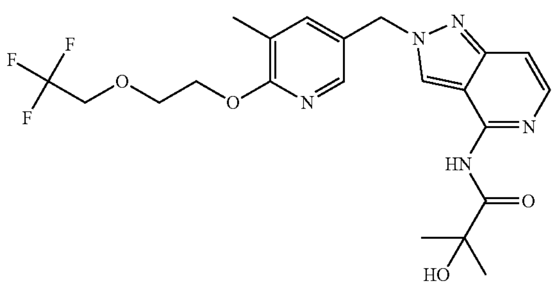 [SMILES: Cc1cc(Cn2cc3c(NC(=O)C(C)(C)O)nccc3n2)cnc1OCCOCC(F)(F)F] | 2-hydroxy-2-methyl-N-(2-((5-methyl-6-(2-(2,2,2-trifluoroethoxy)ethoxy)pyridin-3-yl)methyl)-2H-pyrazolo[4,3-c]pyridin-4-yl)propanamide |
| 267 | 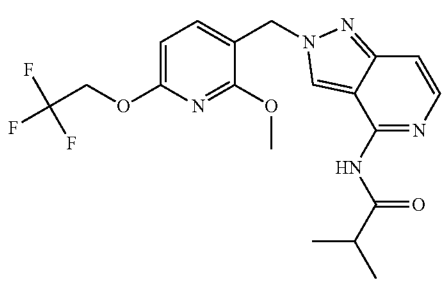 [SMILES: COc1nc(OCC(F)(F)F)ccc1Cn1cc2c(NC(=O)C(C)C)nccc2n1] | N-(2-((2-methoxy-6-(2,2,2-trifluoroethoxy)pyridin-3-yl)methyl)-2H-pyrazolo[4,3-c]pyridin-4-yl)isobutyramide |
| 268 | 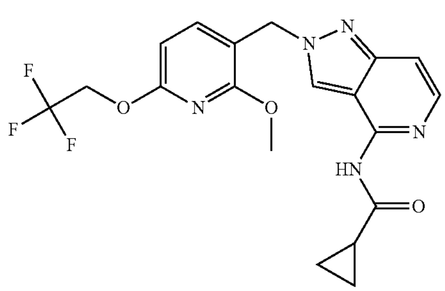 [SMILES: COc1nc(OCC(F)(F)F)ccc1Cn1cc2c(NC(=O)C3CC3)nccc2n1] | N-(2-((2-methoxy-6-(2,2,2-trifluoroethoxy)pyridin-3-yl)methyl)-2H-pyrazolo[4,3-c]pyridin-4-yl)cyclopropanecarboxamide |

TABLE 7-continued

| Ex | Structure | Name |
|---|---|---|
| 269 | 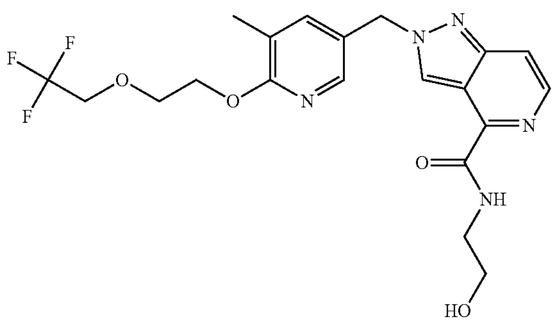 [SMILES: Cc1cc(Cn2cc3c(C(=O)NCCO)nccc3n2)cnc1OCCOCC(F)(F)F] | N-(2-hydroxyethyl)-2-((5-methyl-6-(2-(2,2,2-trifluoroethoxy)ethoxy)pyridin-3-yl)methyl)-2H-pyrazolo[4,3-c]pyridine-4-carboxamide |
| 270 | 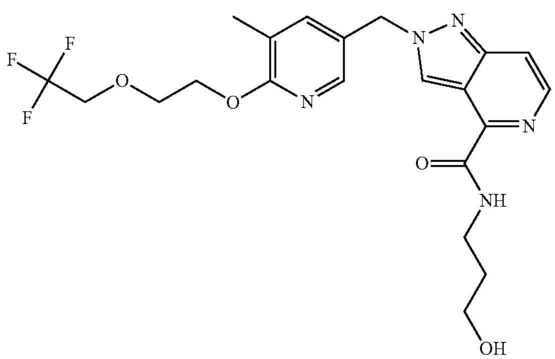 [SMILES: Cc1cc(Cn2cc3c(C(=O)NCCCO)nccc3n2)cnc1OCCOCC(F)(F)F] | N-(3-hydroxypropyl)-2-((5-methyl-6-(2-(2,2,2-trifluoroethoxy)ethoxy)pyridin-3-yl)methyl)-2H-pyrazolo[4,3-c]pyridine-4-carboxamide |
| 271 | 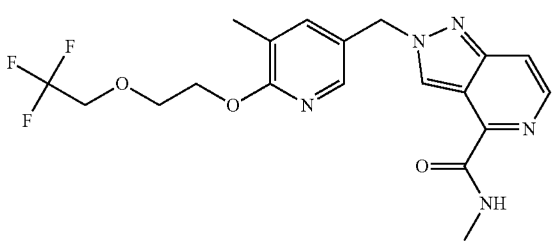 [SMILES: CNC(=O)c1nccc2nn(Cc3cnc(OCCOCC(F)(F)F)c(C)c3)cc12] | N-methyl-2-((5-methyl-6-(2-(2,2,2-trifluoroethoxy)ethoxy)pyridin-3-yl)methyl)-2H-pyrazolo[4,3-c]pyridine-4-carboxamide |
| 272 | 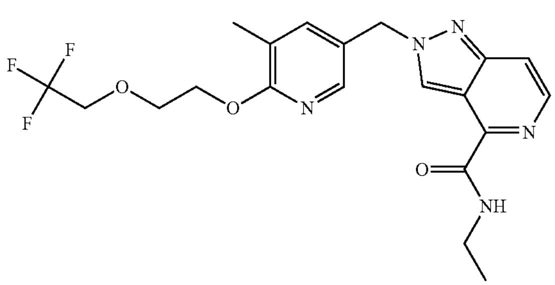 [SMILES: CCNC(=O)c1nccc2nn(Cc3cnc(OCCOCC(F)(F)F)c(C)c3)cc12] | N-ethyl-2-((5-methyl-6-(2-(2,2,2-trifluoroethoxy)ethoxy)pyridin-3-yl)methyl)-2H-pyrazolo[4,3-c]pyridine-4-carboxamide |
| 273 | 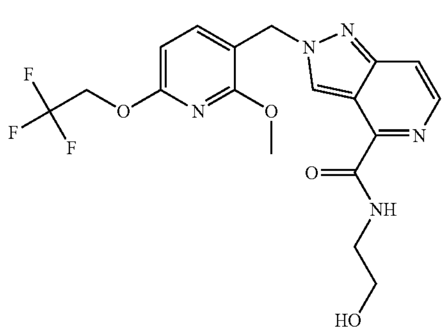 [SMILES: COc1nc(OCC(F)(F)F)ccc1Cn1cc2c(C(=O)NCCO)nccc2n1] | N-(2-hydroxyethyl)-2-((2-methoxy-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 274 | 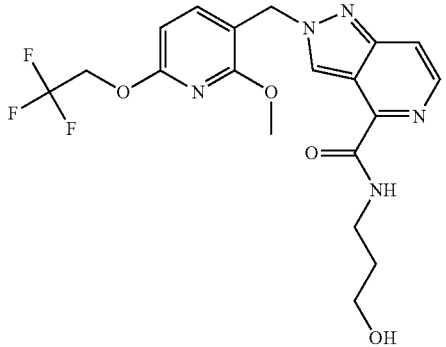 [SMILES: COc1nc(OCC(F)(F)F)ccc1Cn1cc2c(C(=O)NCCCO)nccc2n1] | N-(3-hydroxypropyl)-2-((2-methoxy-6-(2,2,2-trifluoroethoxy)pyridin-3-yl)methyl)-2H-pyrazolo[4,3-c]pyridine-4-carboxamide |
| 275 | 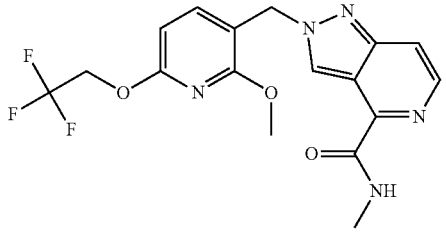 [SMILES: CNC(=O)c1nccc2nn(Cc3ccc(OCC(F)(F)F)nc3OC)cc12] | 2-((2-methoxy-6-(2,2,2-trifluoroethoxy)pyridin-3-yl)methyl)-N-methyl-2H-pyrazolo[4,3-c]pyridine-4-carboxamide |
| 276 | 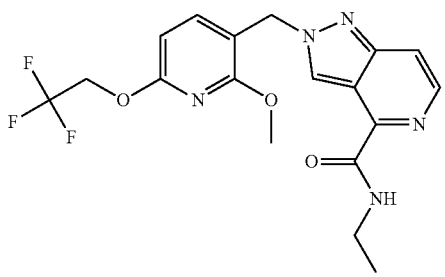 [SMILES: CCNC(=O)c1nccc2nn(Cc3ccc(OCC(F)(F)F)nc3OC)cc12] | N-ethyl-2-((2-methoxy-6-(2,2,2-trifluoroethoxy)pyridin-3-yl)methyl)-2H-pyrazolo[4,3-c]pyridine-4-carboxamide |
| 277 | 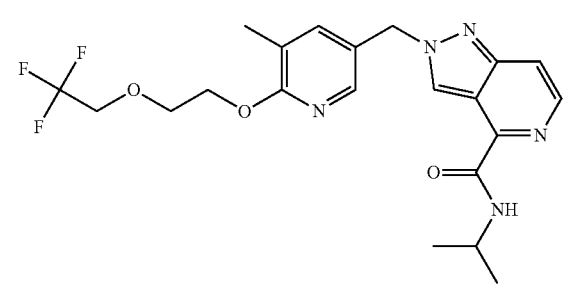 [SMILES: Cc1cc(Cn2cc3c(C(=O)NC(C)C)nccc3n2)cnc1OCCOCC(F)(F)F] | N-isopropyl-2-((5-methyl-6-(2-(2,2,2-trifluoroethoxy)ethoxy)pyridin-3-yl)methyl)-2H-pyrazolo[4,3-c]pyridine-4-carboxamide |
| 278 | 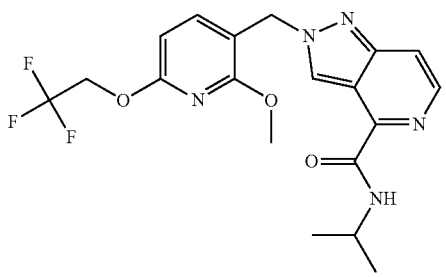 [SMILES: COc1nc(OCC(F)(F)F)ccc1Cn1cc2c(C(=O)NC(C)C)nccc2n1] | N-isopropyl-2-((2-methoxy-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 279 | 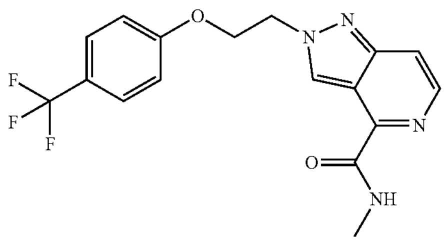 [SMILES: CNC(=O)c1nccc2nn(CCOc3ccc(C(F)(F)F)cc3)cc12] | N-methyl-2-(2-(4-(trifluoromethyl)phenoxy)ethyl)-2H-pyrazolo[4,3-c]pyridine-4-carboxamide |
| 280 | 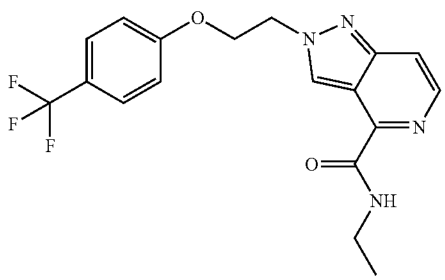 [SMILES: CCNC(=O)c1nccc2nn(CCOc3ccc(C(F)(F)F)cc3)cc12] | N-ethyl-2-(2-(4-(trifluoromethyl)phenoxy)ethyl)-2H-pyrazolo[4,3-c]pyridine-4-carboxamide |
| 281 | 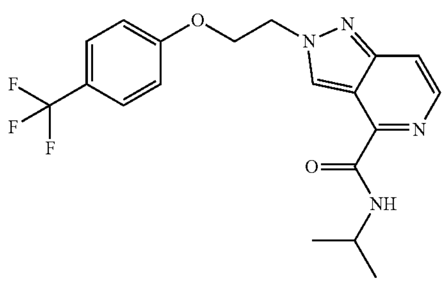 [SMILES: CC(C)NC(=O)c1nccc2nn(CCOc3ccc(C(F)(F)F)cc3)cc12] | N-isopropyl-2-(2-(4-(trifluoromethyl)phenoxy)ethyl)-2H-pyrazolo[4,3-c]pyridine-4-carboxamide |
| 282 | 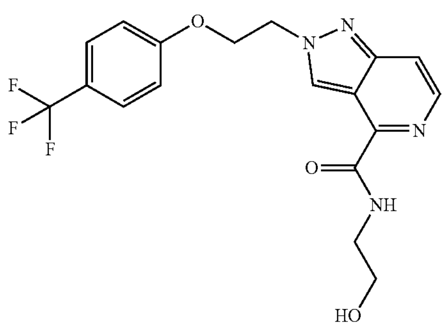 [SMILES: O=C(NCCO)c1nccc2nn(CCOc3ccc(C(F)(F)F)cc3)cc12] | N-(2-hydroxyethyl)-2-(2-(4-(tifluoromethyl)phenoxy)ethyl)-2H-pyrazolo[4,3-c]pyridine-4-carboxamide |
| 283 | 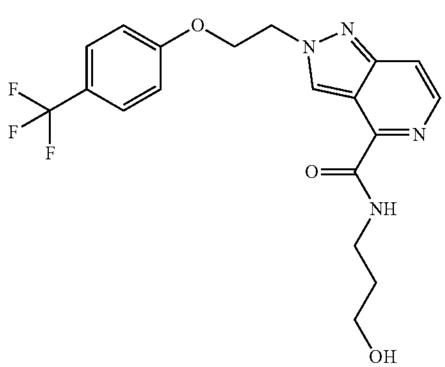 [SMILES: O=C(NCCCO)c1nccc2nn(CCOc3ccc(C(F)(F)F)cc3)cc12] | N-(3-hydroxypropyl)-2-(2-(4-(trifluoromethyl)phenoxy)ethyl)-2H-pyrazolo[4,3-c]pyridine-4-carboxamide |

TABLE 7-continued

| Ex | Structure | Name |
|---|---|---|
| 284 | 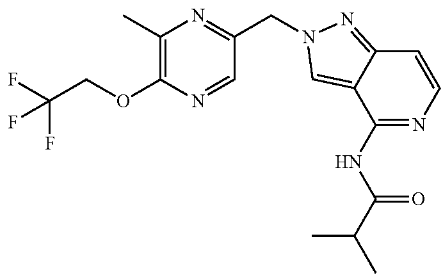 [SMILES: Cc1nc(Cn2cc3c(NC(=O)C(C)C)nccc3n2)cnc1OCC(F)(F)F] | N-(2-((6-methyl-5-(2,2,2-trifluoroethoxy)pyrazin-2-yl)methyl)-2H-pyrazolo[4,3-c]pyridin-4-yl)isobutyramide |
| 285 | 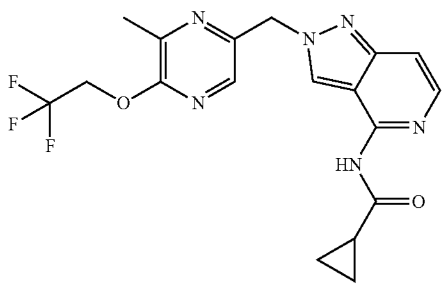 [SMILES: Cc1nc(Cn2cc3c(NC(=O)C4CC4)nccc3n2)cnc1OCC(F)(F)F] | N-(2-((6-methyl-5-(2,2,2-trifluoroethoxy)pyrazin-2-yl)methyl)-2H-pyrazolo[4,3-c]pyridin-4-yl)cyclopropanecarboxamide |
| 286 | 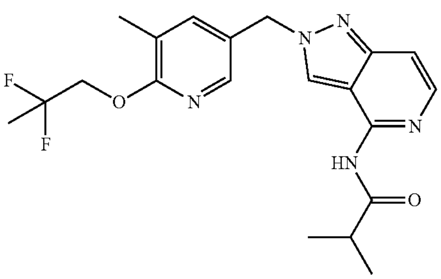 [SMILES: Cc1cc(Cn2cc3c(NC(=O)C(C)C)nccc3n2)cnc1OCC(C)(F)F] | N-(2-((6-(2,2-difluoropropoxy)-5-methylpyridin-3-yl)methyl)-2H-pyrazolo[4,3-c]pyridin-4-yl)isobutyramide |
| 287 | 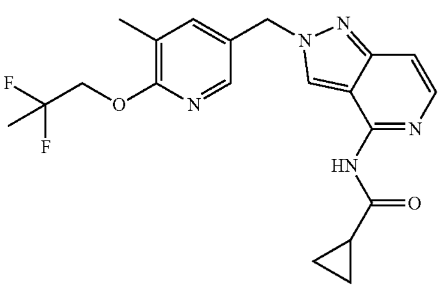 [SMILES: Cc1cc(Cn2cc3c(NC(=O)C4CC4)nccc3n2)cnc1OCC(C)(F)F] | N-(2-((6-(2,2-difluoropropoxy)-5-methylpyridin-3-yl)methyl)-2H-pyrazolo[4,3-c]pyridin-4-yl)cyclopropanecarboxamide |
| 288 | 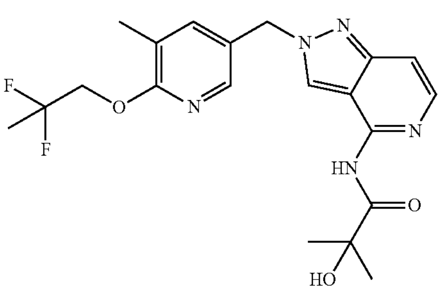 [SMILES: Cc1cc(Cn2cc3c(NC(=O)C(C)(C)O)nccc3n2)cnc1OCC(C)(F)F] | N-(2-((6-(2,2-difluoropropoxy)-5-methylpyridin-3-yl)methyl)-2H-pyrazolo[4,3-c]pyridin-4-yl)-2-hydroxy-2-methylpropanamide |
| 290 | 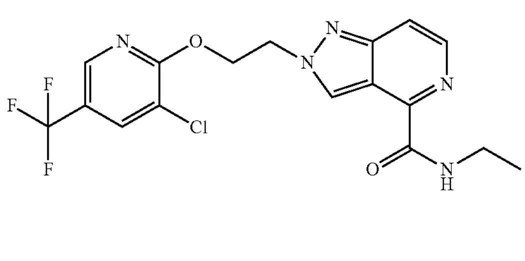 [SMILES: CCNC(=O)c1nccc2nn(CCOc3ncc(C(F)(F)F)cc3Cl)cc12] | 2-(2-((3-chloro-5-(trifluoromethyl)pyridin-2-yl)oxy)ethyl)-N-ethyl-2H-pyrazolo[4,3-c]pyridine-4-carboxamide |

TABLE 7-continued

| Ex | Structure | Name |
|---|---|---|
| 291 | 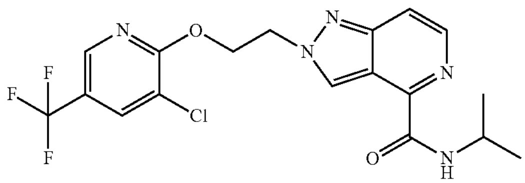 [SMILES: CC(C)NC(=O)c1nccc2nn(CCOc3ncc(C(F)(F)F)cc3Cl)cc12] | 2-(2-((3-chloro-5-(trifluoromethyl)pyridin-2-yl)oxy)ethyl)-N-isopropyl-2H-pyrazolo[4,3-c]pyridine-4-carboxamide |
| 292 | 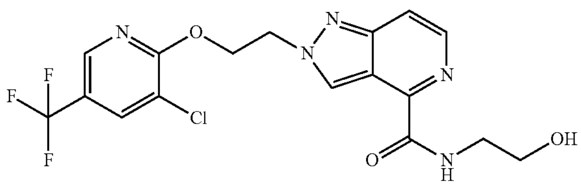 [SMILES: O=C(NCCO)c1nccc2nn(CCOc3ncc(C(F)(F)F)cc3Cl)cc12] | 2-(2-((3-chloro-5-(trifluoromethyl)pyridin-2-yl)oxy)ethyl)-N-(2-hydroxyethyl)-2H-pyrazolo[4,3-c]pyridine-4-carboxamide |
| 293 | 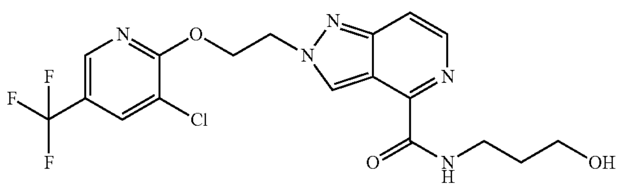 [SMILES: O=C(NCCCO)c1nccc2nn(CCOc3ncc(C(F)(F)F)cc3Cl)cc12] | 2-(2-((3-chloro-5-(trifluoromethyl)pyridin-2-yl)oxy)ethyl)-N-(3-hydroxypropyl)-2H-pyrazolo[4,3-c]pyridine-4-carboxamide |
| 294 | 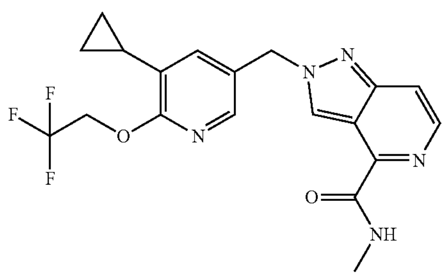 [SMILES: CNC(=O)c1nccc2nn(Cc3cnc(OCC(F)(F)F)c(C4CC4)c3)cc12] | 2-((5-cyclopropyl-6-(2,2,2-trifluoroethoxy)pyridin-3-yl)methyl)-N-methyl-2H-pyrazolo[4,3-c]pyridine-4-carboxamide |
| 295 | 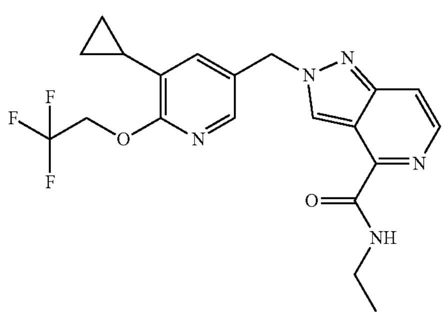 [SMILES: CCNC(=O)c1nccc2nn(Cc3cnc(OCC(F)(F)F)c(C4CC4)c3)cc12] | 2-((5-cyclopropyl-6-(2,2,2-trifluoroethoxy)pyridin-3-yl)methyl)-N-ethyl-2H-pyrazolo[4,3-c]pyridine-4-carboxamide |
| 296 | 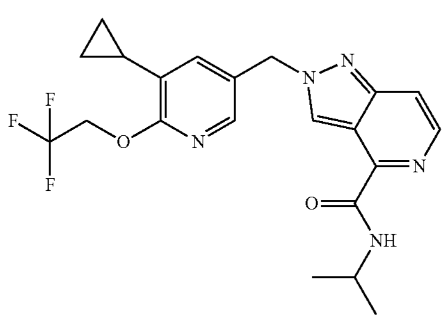 [SMILES: CC(C)NC(=O)c1nccc2nn(Cc3cnc(OCC(F)(F)F)c(C4CC4)c3)cc12] | 2-((5-cyclopropyl-6-(2,2,2-trifluoroethoxy)pyridin-3-yl)methyl)-N-isopropyl-2H-pyrazolo[4,3-c]pyridine-4-carboxamide |

TABLE 7-continued

| Ex | Structure | Name |
|---|---|---|
| 297 | 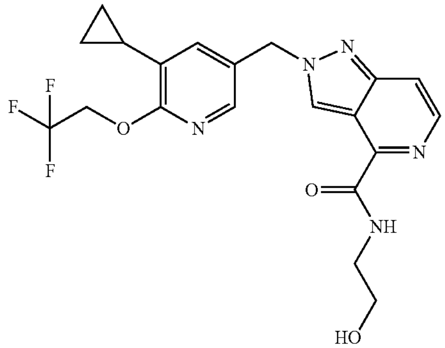 [SMILES: O=C(NCCO)c1nccc2nn(Cc3cnc(OCC(F)(F)F)c(C4CC4)c3)cc12] | 2-((5-cyclopropyl-6-(2,2,2-trifluoroethoxy)pyridin-3-yl)methyl)-N-(2-hydroxyethyl)-2H-pyrazolo[4,3-c]pyridine-4-carboxamide |
| 298 | 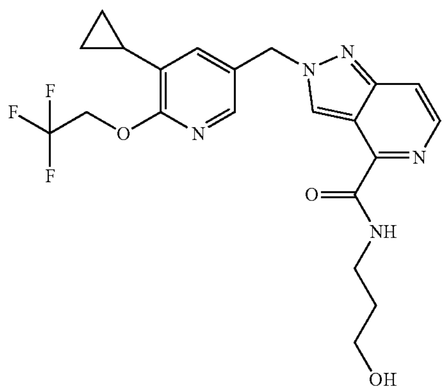 [SMILES: O=C(NCCCO)c1nccc2nn(Cc3cnc(OCC(F)(F)F)c(C4CC4)c3)cc12] | 2-((5-cyclopropyl-6-(2,2,2-trifluoroethoxy)pyridin-3-yl)methyl)-N-(3-hydroxypropyl)-2H-pyrazolo[4,3-c]pyridine-4-carboxamide |
| 299 | 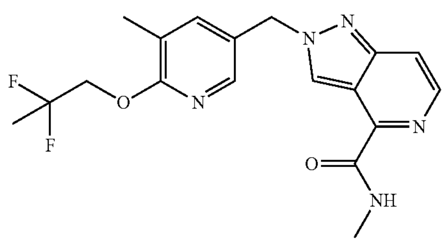 [SMILES: CNC(=O)c1nccc2nn(Cc3cnc(OCC(C)(F)F)c(C)c3)cc12] | 2-((6-(2,2-difluoropropoxy)-5-methylpyridin-3-yl)methyl)-N-methyl-2-pyrazolo[4,3-c]pyridine-4-carboxamide |
| 300 | 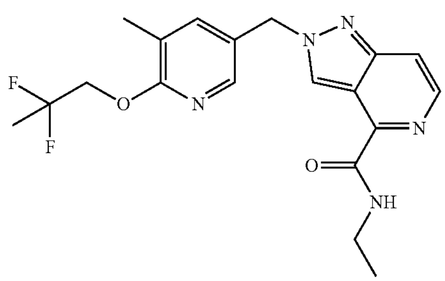 [SMILES: CCNC(=O)c1nccc2nn(Cc3cnc(OCC(C)(F)F)c(C)c3)cc12] | 2-((6-(2,2-difluoropropoxy)-5-methylpyridin-3-yl)methyl)-N-ethyl-2H-pyrazolo[4,3-c]pyridine-4-carboxamide |
| 301 | 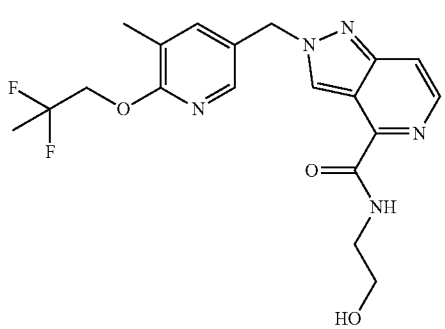 [SMILES: Cc1cc(Cn2cc3c(C(=O)NCCO)nccc3n2)cnc1OCC(C)(F)F] | 2-((6-(2,2-difluoropropoxy)-5-methylpyridin-3-yl)methyl)-N-(2-hydroxyethyl)-2H-pyrazolo[4,3-c]pyridine-4-carboxamide |

TABLE 7-continued

| Ex | Structure | Name |
|---|---|---|
| 302 | 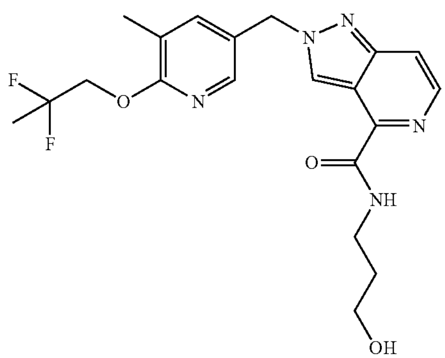 [SMILES: Cc1cc(Cn2cc3c(C(=O)NCCCO)nccc3n2)cnc1OCC(C)(F)F] | 2-((6-(2,2-difluoropropoxy)-5-methylpyridin-3-yl)methyl)-N-(3-hydroxypropyl)-2H-pyrazolo[4,3-c]4-carboxamide |
| 303 | 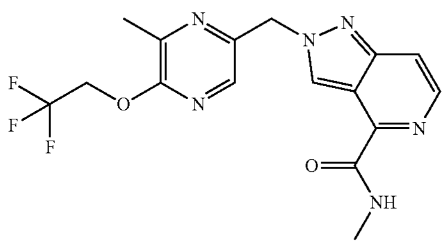 [SMILES: CNC(=O)c1nccc2nn(Cc3cnc(OCC(F)(F)F)c(C)n3)cc12] | N-methyl-2-((6-methyl-5-(2,2,2-trifluoroethoxy)pyrazin-2-yl)methyl)-2H-pyrazolo[4,3-c]pyridine-4-carboxamide |
| 304 | 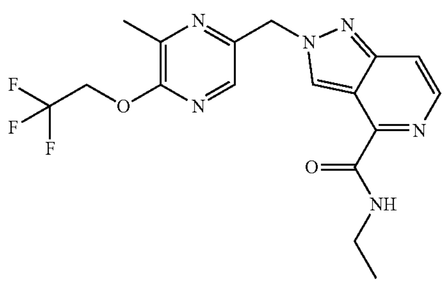 [SMILES: CCNC(=O)c1nccc2nn(Cc3cnc(OCC(F)(F)F)c(C)n3)cc12] | N-ethyl-2-((6-methyl-5-(2,2,2-trifluoroethoxy)pyrazin-2-yl)methyl)-2H-pyrazolo[4,3-c]pyridine-4-carboxamide |
| 305 | 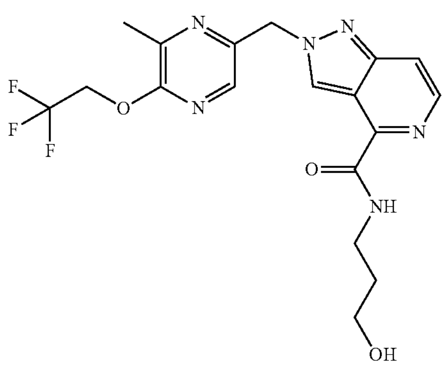 [SMILES: Cc1nc(Cn2cc3c(C(=O)NCCCO)nccc3n2)cnc1OCC(F)(F)F] | N-(3-hydroxypropyl)-2-((6-methyl-5-(2,2,2-trifluoroethoxy)pyrazin-2-yl)methyl)-2H-pyrazolo[4,3-c]pyridine-4-carboxamide |
| 306 | 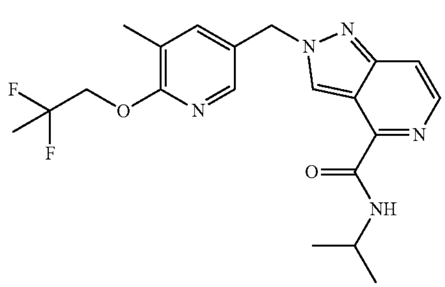 [SMILES: Cc1cc(Cn2cc3c(C(=O)NC(C)C)nccc3n2)cnc1OCC(C)(F)F] | 2-((6-(2,2-difluoropropoxy)-5-methylpyridin-3-yl)methyl)-N-isopropyl-2H-pyrazolo[4,3-c]pyridine-4-carboxamide |

TABLE 7-continued

| Ex | Structure | Name |
|---|---|---|
| 307 | 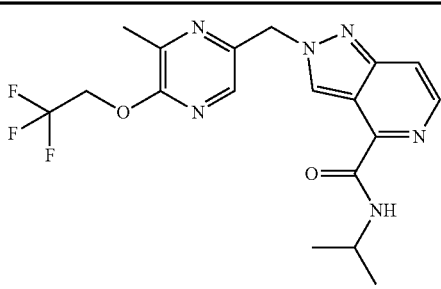 | N-isopropyl-2-((6-methyl-5-(2,2,2-trifluoroethoxy)pyrazin-2-yl)methyl)-2H-pyrazolo[4,3-c]pyridine-4-carboxamide |
| 308 | 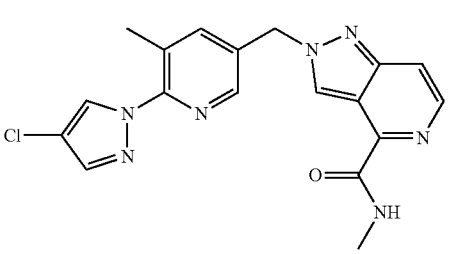 [SMILES: CNC(=O)c1nccc2nn(Cc3cnc(-n4cc(Cl)cn4)c(C)c3)cc12] | 2-((6-(4-chloro-1H-pyrazol-1-yl)-5-methylpyridin-3-yl)methyl)-N-methyl-2H-pyrazolo[4,3-c]pyridine-4-carboxamide |
| 309 | 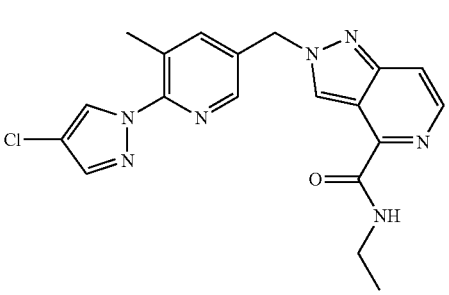 [SMILES: CCNC(=O)c1nccc2nn(Cc3cnc(-n4cc(Cl)cn4)c(C)c3)cc12] | 2-((6-(4-chloro-1H-pyrazol-1-yl)-5-methylpyridin-3-yl)methyl)-N-ethyl-2H-pyrazolo[4,3-c]pyridine-4-carboxamide |
| 310 | 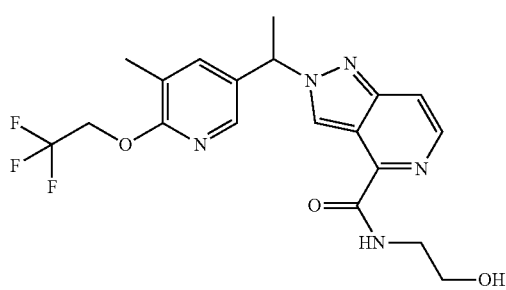 [SMILES: Cc1cc(C(C)n2cc3c(C(=O)NCCO)nccc3n2)cnc1OCC(F)(F)F] | N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide (single enantiomer) |
| 311 | 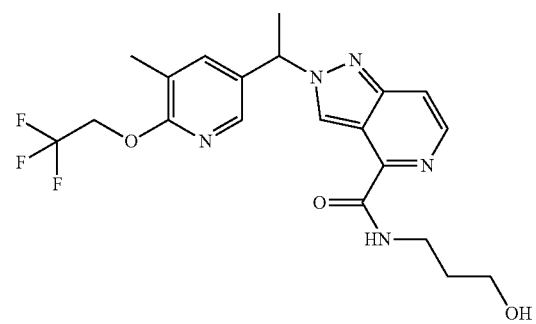 [SMILES: Cc1cc(C(C)n2cc3c(C(=O)NCCCO)nccc3n2)cnc1OCC(F)(F)F] | N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide (single enantiomer) |

TABLE 7-continued

| Ex | Structure | Name |
|---|---|---|
| 312 | 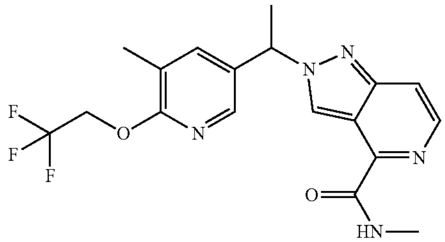 [SMILES: CNC(=O)c1nccc2nn(C(C)c3cnc(OCC(F)(F)F)c(C)c3)cc12] | N-methyl-2-(1-(5-methyl-6-(2,2,2-trifluoroethoxy)pyridin-3-yl)ethyl)-2H-pyrazolo[4,3-c]pyridine-4-carboxamide (single enantiomer) |
| 313 | 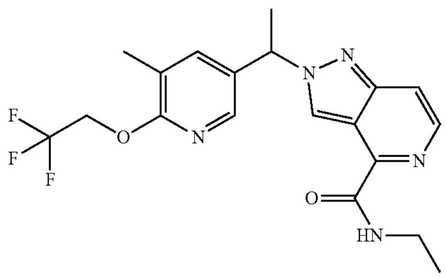 [SMILES: CCNC(=O)c1nccc2nn(C(C)c3cnc(OCC(F)(F)F)c(C)c3)cc12] | N-ethyl-2-(1-(5-methyl-6-(2,2,2-trifluoroethoxy)pyridin-3-yl)ethyl)-2H-pyrazolo[4,3-c]pyridine-4-carboxamide (single enantiomer) |
| 314 | 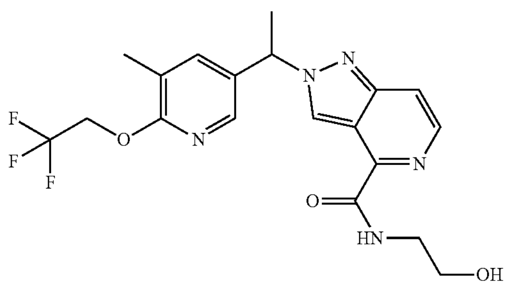 [SMILES: Cc1cc(C(C)n2cc3c(C(=O)NCCO)nccc3n2)cnc1OCC(F)(F)F] | N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide (single enantiomer) |
| 315 | 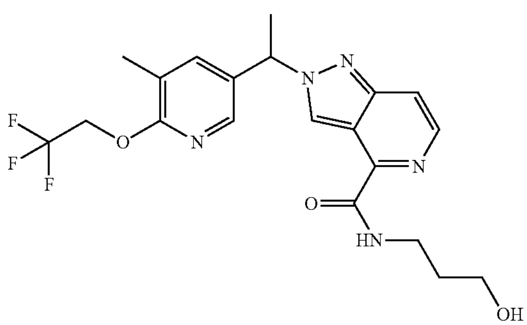 [SMILES: Cc1cc(C(C)n2cc3c(C(=O)NCCCO)nccc3n2)cnc1OCC(F)(F)F] | N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide (single enantiomer) |
| 316 | 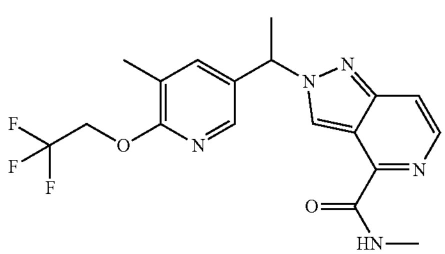 [SMILES: CNC(=O)c1nccc2nn(C(C)c3cnc(OCC(F)(F)F)c(C)c3)cc12] | N-methyl-2-(1-(5-methyl-6-(2,2,2-trifluoroethoxy)pyridin-3-yl)ethyl)-2H-pyrazolo[4,3-c]pyridine-4-carboxamide (single enantiomer) |

TABLE 7-continued

| Ex | Structure | Name |
|---|---|---|
| 317 | 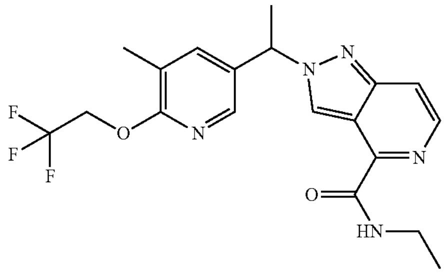 [SMILES: CCNC(=O)c1nccc2nn(C(C)c3cnc(OCC(F)(F)F)c(C)c3)cc12] | N-ethyl-2-(1-(5-methyl-6-(2,2,2-trifluoroethoxy)pyridin-3-yl)ethyl)-2H-pyrazolo[4,3-c]pyridine-4-carboxamide (single enantiomer) |
| 318 | 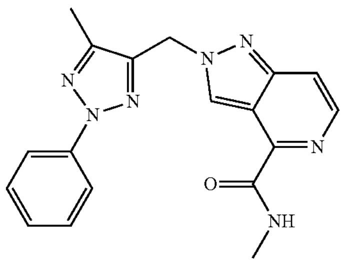 [SMILES: CNC(=O)c1nccc2nn(Cc3nn(-c4ccccc4)nc3C)cc12] | N-methyl-2-((5-methyl-2-phenyl-2H-1,2,3-triazol-4-yl)methyl)-2H-pyrazolo[4,3-c]pyridine-4-carboxamide |
| 319 | 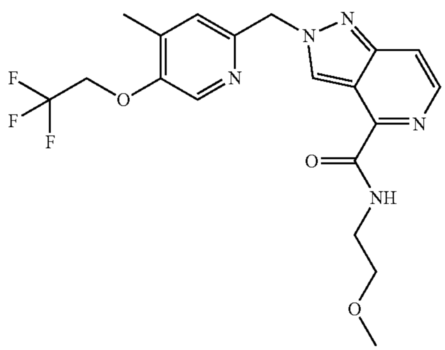 [SMILES: COCCNC(=O)c1nccc2nn(Cc3cc(C)c(OCC(F)(F)F)cn3)cc12] | N-(2-methoxyethyl)-2-((4-methyl-5-(2,2,2-trifluoroethoxy)pyridin-2-yl)methyl)-2H-pyrazolo[4,3-c]pyridine-4-carboxamide |
| 320 | 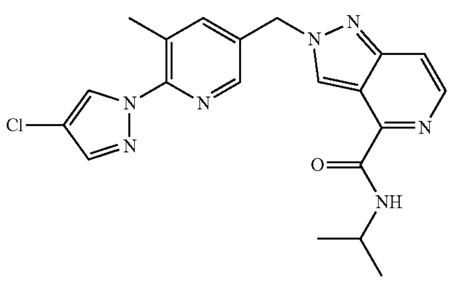 [SMILES: Cc1cc(Cn2cc3c(C(=O)NC(C)C)nccc3n2)cnc1-n1cc(Cl)cn1] | 2-((6-(4-chloro-1H-pyrazol-1-yl)-5-methylpyridin-3-yl)methyl)-N-isopropyl-2H-pyrazolo[4,3-c]pyridine-4-carboxamide |
| 321 | 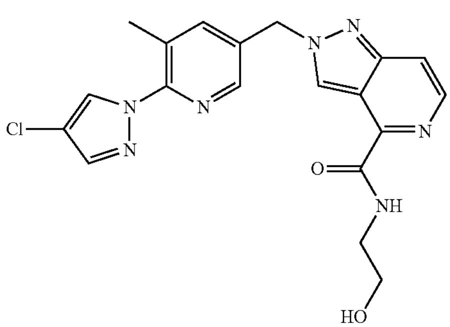 [SMILES: Cc1cc(Cn2cc3c(C(=O)NCCO)nccc3n2)cnc1-n1cc(Cl)cn1] | 2-((6-(4-chloro-1H-pyrazol-1-yl)-5-methylpyridin-3-yl)methyl)-N-(2-hydroxyethyl)-2H-pyrazolo[4,3-c]pyridine-4-carboxamide |

TABLE 7-continued

| Ex | Structure | Name |
|---|---|---|
| 322 | 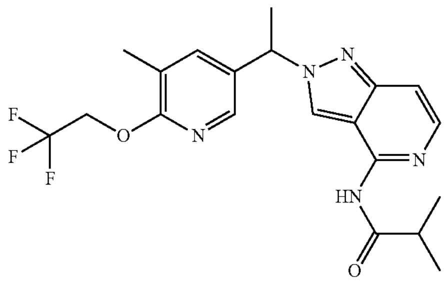 [SMILES: Cc1cc(C(C)n2cc3c(NC(=O)C(C)C)nccc3n2)cnc1OCC(F)(F)F] | N-(2-(1-(5-methyl-6-(2,2,2-trifluoroethoxy)pyridin-3-yl)ethyl)-2H-pyrazolo[4,3-c]pyridin-4-yl)isobutyramide (single enantiomer) |
| 323 | 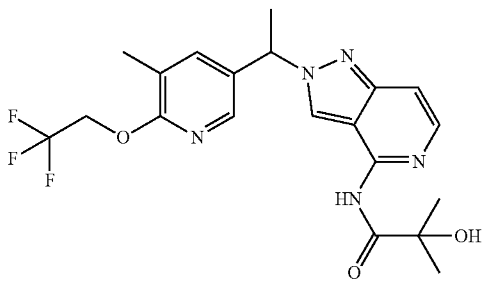 [SMILES: Cc1cc(C(C)n2cc3c(NC(=O)C(C)(C)O)nccc3n2)cnc1OCC(F)(F)F] | 2-hydroxy-2-methyl-N-(2-(1-(5-methyl-6-(2,2,2-trifluoroethoxy)pyridin-3-yl)ethyl)-2H-pyrazolo[4,3-c]pyridin-4-yl)propanamide (single enantiomer) |
| 324 | 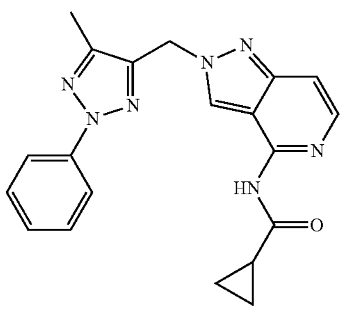 [SMILES: Cc1nn(-c2ccccc2)nc1Cn1cc2c(NC(=O)C3CC3)nccc2n1] | N-(2-((5-methyl-2-phenyl-2H-1,2,3-triazol-4-yl)methyl)-2H-pyrazolo[4,3-c]pyridin-4-yl)cyclopropanecarboxamide |
| 325 | 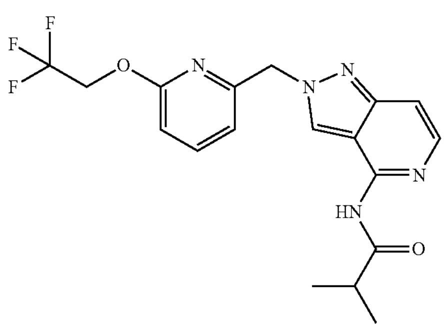 [SMILES: CC(C)C(=O)Nc1nccc2nn(Cc3cccc(OCC(F)(F)F)n3)cc12] | N-(2-((6-(2,2,2-trifluoroethoxy)pyridin-2-yl)methyl)-2H-pyrazolo[4,3-c]pyridin-4-yl)isobutyramide |
| 326 | 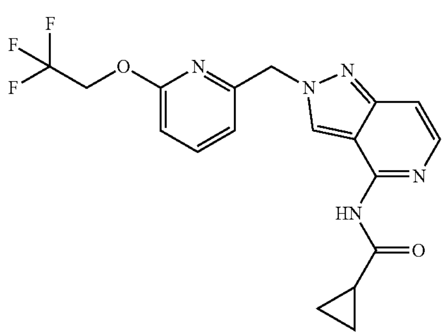 [SMILES: O=C(Nc1nccc2nn(Cc3cccc(OCC(F)(F)F)n3)cc12)C1CC1] | N-(2-((6-(2,2,2-trifluoroethoxy)pyridin-2-yl)methyl)-2H-pyrazolo[4,3-c]pyridin-4-yl)cyclopropanecarboxamide |

TABLE 7-continued

| Ex | Structure | Name |
|---|---|---|
| 327 | 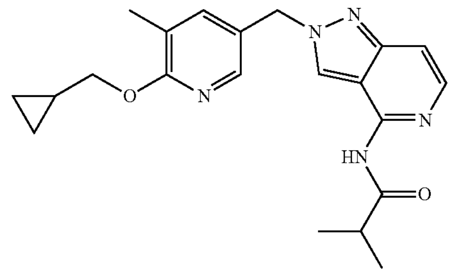 [SMILES: Cc1cc(Cn2cc3c(NC(=O)C(C)C)nccc3n2)cnc1OCC1CC1] | N-(2-((6-(cyclopropylmethoxy)-5-methylpyridin-3-yl)methyl)-2H-pyrazolo[4,3-c]pyridin-4-yl)isobutyramide |
| 328 | 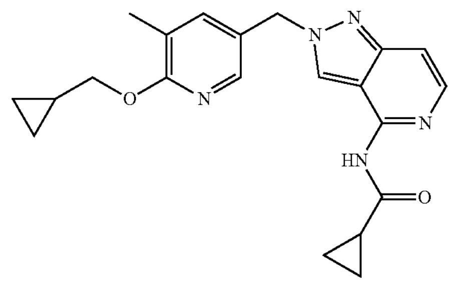 [SMILES: Cc1cc(Cn2cc3c(NC(=O)C4CC4)nccc3n2)cnc1OCC1CC1] | N-(2-((6-(cyclopropylmethoxy)-5-methylpyridin-3-yl)methyl)-2H-pyrazolo[4,3-c]pyridin-4-yl)cyclopropanecarboxamide |
| 329 | 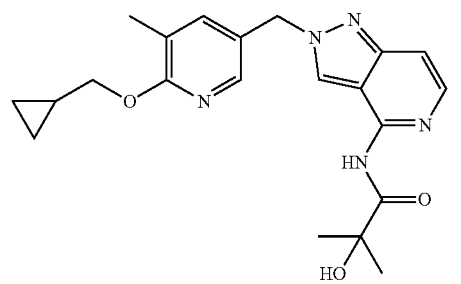 [SMILES: Cc1cc(Cn2cc3c(NC(=O)C(C)(C)O)nccc3n2)cnc1OCC1CC1] | N-(2-((6-(cyclopropylmethoxy)-5-methylpyridin-3-yl)methyl)-2H-pyrazolo[4,3-c]pyridin-4-yl)-2-hydroxy-2-methylpropanamide |
| 330 | 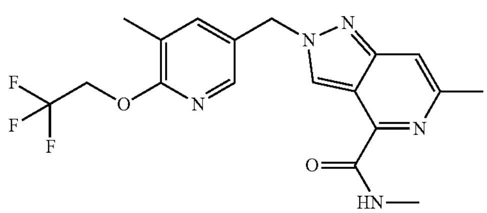 [SMILES: CNC(=O)c1nc(C)cc2nn(Cc3cnc(OCC(F)(F)F)c(C)c3)cc12] | N,6-dimethyl-2-((5-methyl-6-(2,2,2-trifluoroethoxy)pyridin-3-yl)methyl)-2H-pyrazolo[4,3-c]pyridine-4-carboxamide |
| 331 | 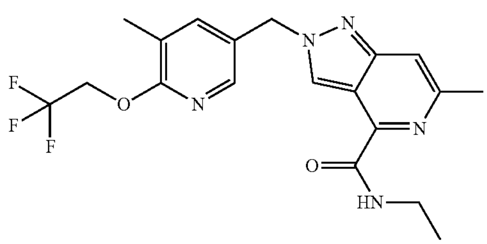 [SMILES: CCNC(=O)c1nc(C)cc2nn(Cc3cnc(OCC(F)(F)F)c(C)c3)cc12] | N-ethyl-6-methyl-2-((5-methyl-6-(2,2,2-trifluoroethoxy)pyridin-3-yl)methyl)-2H-pyrazolo[4,3-c]pyridine-4-carboxamide |
| 332 | 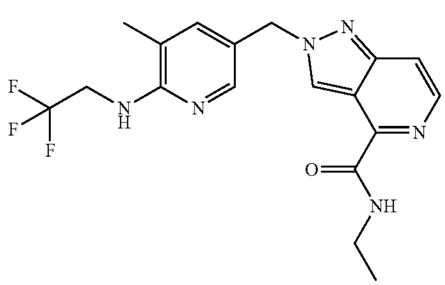 [SMILES: CCNC(=O)c1nccc2nn(Cc3cnc(NCC(F)(F)F)c(C)c3)cc12] | N-ethyl-2-((5-methyl-6-(2,2,2-trifluoroethyl)amino)pyridin-3-yl)methyl)-2H-pyrazolo[4,3-c]pyridine-4-carboxamide |

TABLE 7-continued

| Ex | Structure | Name |
|---|---|---|
| 333 | 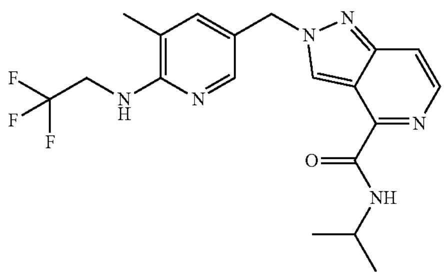 [SMILES: Cc1cc(Cn2cc3c(C(=O)NC(C)C)nccc3n2)cnc1NCC(F)(F)F] | N-isopropyl-2-((5-methyl-6-((2,2,2-trifluoroethyl)amino)pyridin-3-yl)methyl)-2H-pyrazolo[4,3-c]pyridine-4-carboxamide |
| 334 | 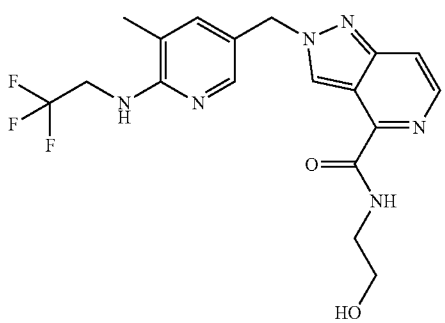 [SMILES: Cc1cc(Cn2cc3c(C(=O)NCCO)nccc3n2)cnc1NCC(F)(F)F] | N-(2-hydroxyethyl)-2-((5-methyl-6-((2,2,2-trifluoroethyl)amino)pyridin-3-yl)methyl)-2H-pyrazolo[4,3-c]pyridine-4-carboxamide |
| 335 | 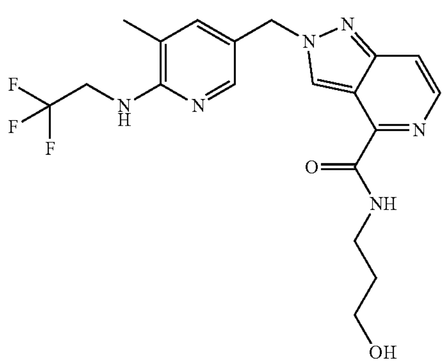 [SMILES: Cc1cc(Cn2cc3c(C(=O)NCCCO)nccc3n2)cnc1NCC(F)(F)F] | N-(3-hydroxypropyl)-2-((5-methyl-6-((2,2,2-trifluoroethyl)amino)pyridin-3-yl)methyl)-2H-pyrazolo[4,3-c]pyridine-4-carboxamide |
| 336 | 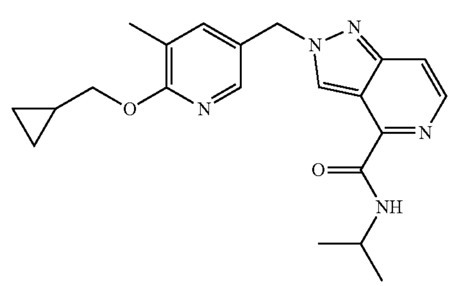 [SMILES: Cc1cc(Cn2cc3c(C(=O)NC(C)C)nccc3n2)cnc1OCC1CC1] | 2-((6-(cyclopropylmethoxy)-5-methylpyridin-3-yl)methyl)-N-isopropyl-2H-pyrazolo[4,3-c]pyridine-4-carboxamide |
| 337 | 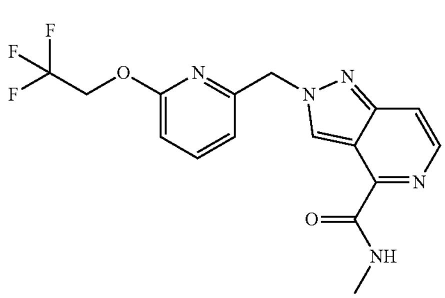 [SMILES: CNC(=O)c1nccc2nn(Cc3cccc(OCC(F)(F)F)n3)cc12] | N-methyl-2-((6-(2,2,2-trifluoroethoxy)pyridin-2-yl)methyl)-2H-pyrazolo[4,3-c]pyridine-4-carboxamide |

TABLE 7-continued

| Ex | Structure | Name |
|---|---|---|
| 338 | 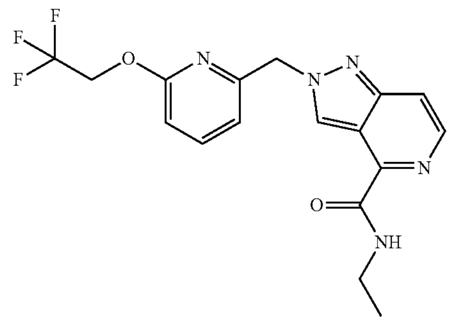 | N-ethyl-2-((6-(2,2,2-trifluoroethoxy)pyridin-2-yl)methyl)-2H-pyrazolo[4,3-c]pyridine-4-carboxamide |
| 339 | 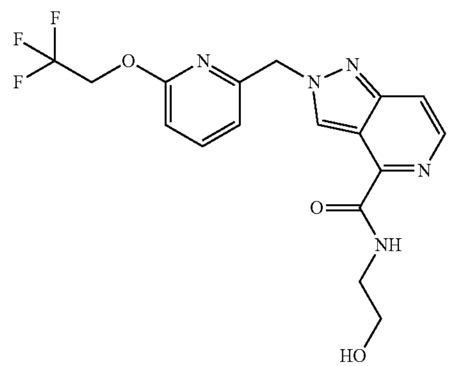 [SMILES: O=C(NCCO)c1nccc2nn(Cc3cccc(OCC(F)(F)F)n3)cc12] | N-(2-hydroxyethyl)-2-((6-(2,2,2-trifluoroethoxy)pyridin-2-yl)methyl)-2H-pyrazolo[4,3-c]pyridine-4-carboxamide |
| 340 | 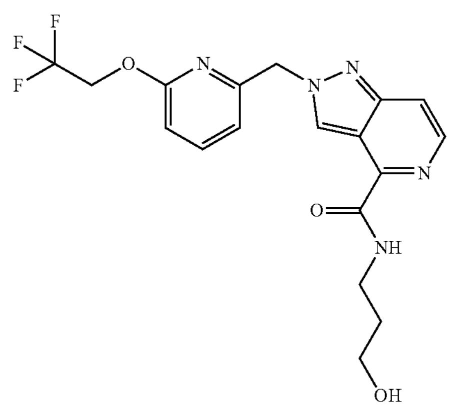 [SMILES: O=C(NCCCO)c1nccc2nn(Cc3cccc(OCC(F)(F)F)n3)cc12] | N-(3-hydroxypropyl)-2-((6-(2,2,2-trifluoroethoxy)pyridin-2-yl)methyl)-2H-pyrazolo[4,3-c]pyridine-4-carboxamide |
| 341 | 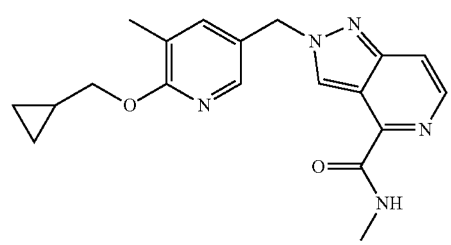 [SMILES: CNC(=O)c1nccc2nn(Cc3cnc(OCC4CC4)c(C)c3)cc12] | 2-((6-(cyclopropylmethoxy)-5-methylpyridin-3-yl)methyl)-N-methyl-2H-pyrazolo[4,3-c]pyridine-4-carboxamide |
| 342 | 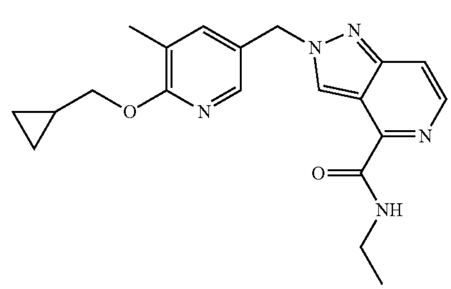 [SMILES: CCNC(=O)c1nccc2nn(Cc3cnc(OCC4CC4)c(C)c3)cc12] | 2-((6-(cyclopropylmethoxy)-5-methylpyridin-3-yl)methyl)-N-ethyl-2H-pyrazolo[4,3-c]pyridine-4-carboxamide |

TABLE 7-continued

| Ex | Structure | Name |
|---|---|---|
| 343 | 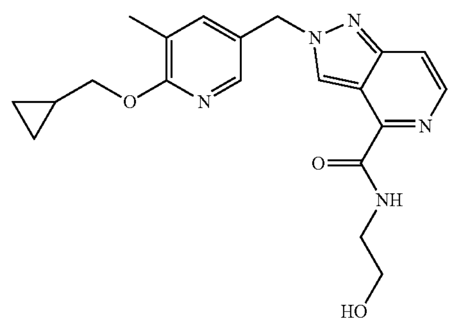 [SMILES: Cc1cc(Cn2cc3c(C(=O)NCCO)nccc3n2)cnc1OCC1CC1] | 2-((6-(cyclopropylmethoxy)-5-methylpyridin-3-yl)methyl)-N-(2-hydroxyethyl)-2H-pyrazolo[4,3-c]pyridine-4-carboxamide |
| 344 | 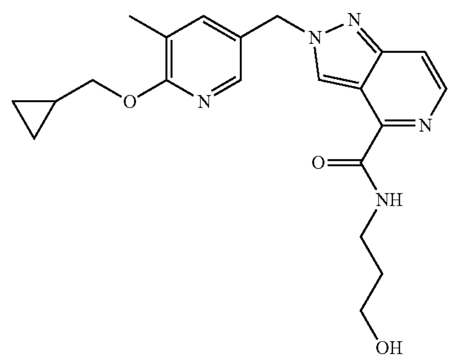 [SMILES: Cc1cc(Cn2cc3c(C(=O)NCCCO)nccc3n2)cnc1OCC1CC1] | 2-((6-(cyclopropylmethoxy)-5-methylpyridin-3-yl)methyl)-N-(3-hydroxypropyl)-2H-pyrazolo[4,3-c]pyridine-4-carboxamide |
| 345 | 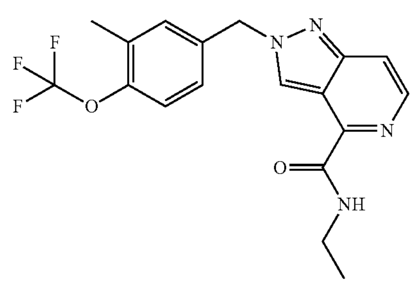 | N-ethyl-2-(3-methyl-4-(trifluoromethoxy)benzyl)-2H-pyrazolo[4,3-c]pyridine-4-carboxamide |
| 346 | 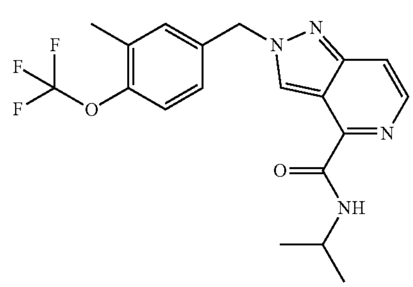 [SMILES: Cc1cc(Cn2cc3c(C(=O)NC(C)C)nccc3n2)ccc1OC(F)(F)F] | N-isopropyl-2-(3-methyl-4-(trifluoromethoxy)benzyl)-2H-pyrazolo[4,3-c]pyridine-4-carboxamide |
| 347 | 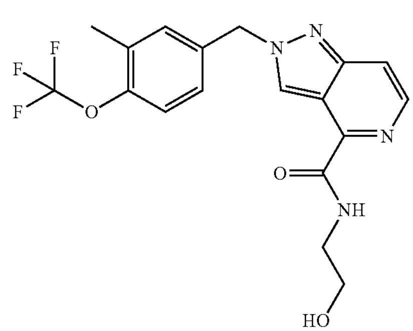 [SMILES: Cc1cc(Cn2cc3c(C(=O)NCCO)nccc3n2)ccc1OC(F)(F)F] | N-(2-hydroxyethyl)-2-(3-methyl-4-(trifluoromethoxy)benzyl)-2H-pyrazolo[4,3-c]pyridine-4-carboxamide |

TABLE 7-continued

| Ex | Structure | Name |
|---|---|---|
| 348 | 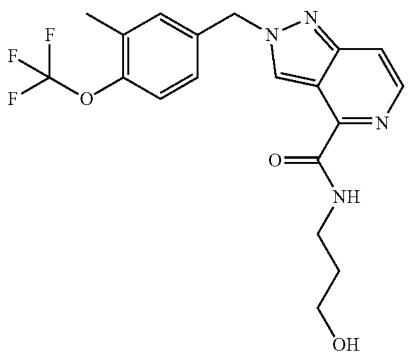 [SMILES: Cc1cc(Cn2cc3c(C(=O)NCCCO)nccc3n2)ccc1OC(F)(F)F] | N-(3-hydroxypropyl)-2-(3-methyl-4-(trifluoromethoxy)benzyl)-2H-pyrazolo[4,3-c]pyridine-4-carboxamide |
| 349 | 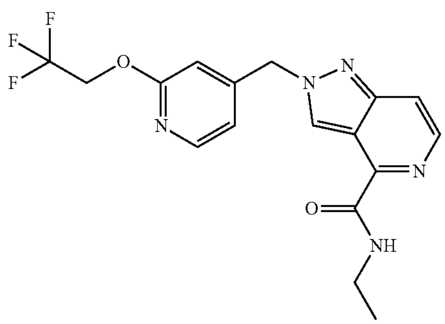 [SMILES: CCNC(=O)c1nccc2nn(Cc3ccnc(OCC(F)(F)F)c3)cc12] | N-ethyl-2-((2-(2,2,2-trifluoroethoxy)pyridin-4-yl)methyl)-2H-pyrazolo[4,3-c]pyridine-4-carboxamide |
| 350 | 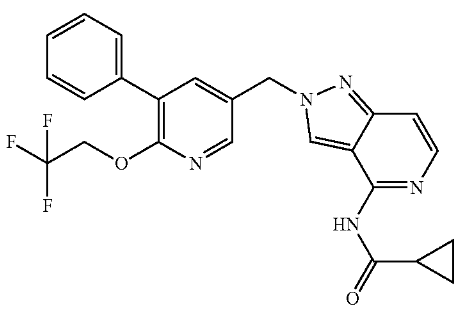 [SMILES: O=C(Nc1nccc2nn(Cc3cnc(OCC(F)(F)F)c(-c4ccccc4)c3)cc12)C1CC1] | N-(2-((5-phenyl-6-(2,2,2-trifluoroethoxy)pyridin-3-yl)methyl)-2H-pyrazolo[4,3-c]pyridin-4-yl)cyclopropanecarboxamide |
| 351 | 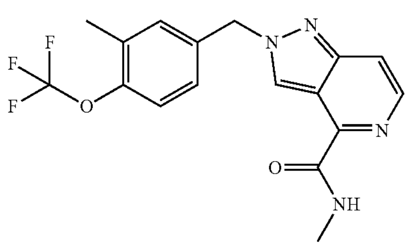 | N-methyl-2-(3-methyl-4-(trifluoromethoxy)benzyl)-2H-pyrazolo[4,3-c]pyridine-4-carboxamide |
| 352 | 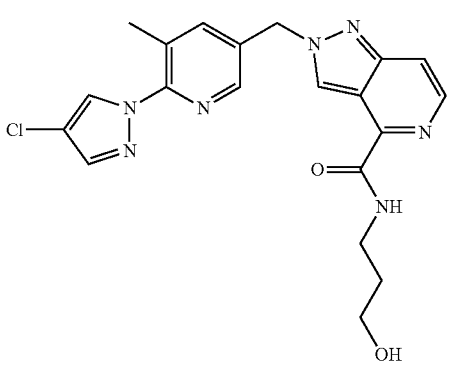 [SMILES: Cc1cc(Cn2cc3c(C(=O)NCCCO)nccc3n2)cnc1-n1cc(Cl)cn1] | 2-((6-(4-chloro-1H-pyrazol-1-yl)-5-methylpyridin-3-yl)methyl)-N-(3-hydroxypropyl)-2H-pyrazolo[4,3-c]pyridine-4-carboxamide |

TABLE 7-continued

| Ex | Structure | Name |
|---|---|---|
| 353 | 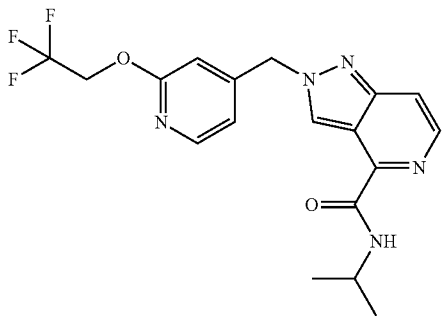 [SMILES: CC(C)NC(=O)c1nccc2nn(Cc3ccnc(OCC(F)(F)F)c3)cc12] | N-isopropyl-2-((2-(2,2,2-trifluoroethoxy)pyridin-4-yl)methyl)-2H-pyrazolo[4,3-c]pyridine-4-carboxamide |
| 354 | 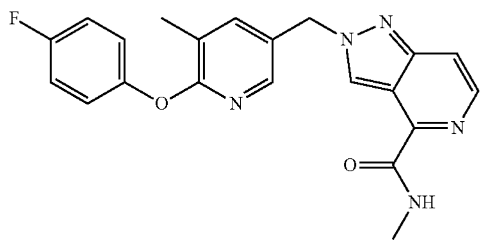 [SMILES: CNC(=O)c1nccc2nn(Cc3cnc(Oc4ccc(F)cc4)c(C)c3)cc12] | 2-((6-(4-fluorophenoxy)-5-methylpyridin-3-yl)methyl)-N-methyl-2H-pyrazolo[4,3-c]pyridine-4-carboxamide |
| 355 | 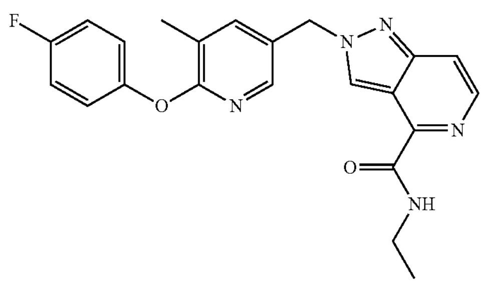 [SMILES: CCNC(=O)c1nccc2nn(Cc3cnc(Oc4ccc(F)cc4)c(C)c3)cc12] | N-ethyl-2-((6-(4-fluorophenoxy)-5-methylpyridin-3-yl)methyl)-2H-pyrazolo[4,3-c]pyridine-4-carboxamide |
| 356 | 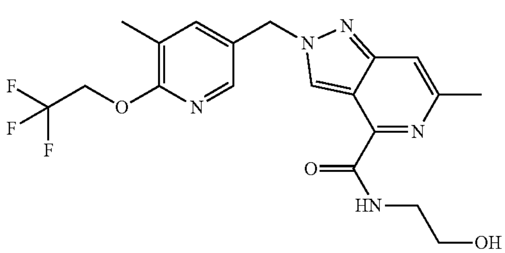 [SMILES: Cc1cc2nn(Cc3cnc(OCC(F)(F)F)c(C)c3)cc2c(C(=O)NCCO)n1] | N-(2-hydroxyethyl)-6-methyl-2-((5-methyl-6-(2,2,2-trifluoroethoxy)pyridin-3-yl)methyl)-2H-pyrazolo[4,3-c]pyridine-4-carboxamide |
| 357 | 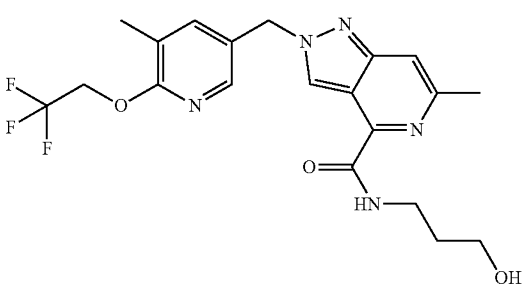 [SMILES: Cc1cc2nn(Cc3cnc(OCC(F)(F)F)c(C)c3)cc2c(C(=O)NCCCO)n1] | N-(3-hydroxypropyl)-6-methyl-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 358 | 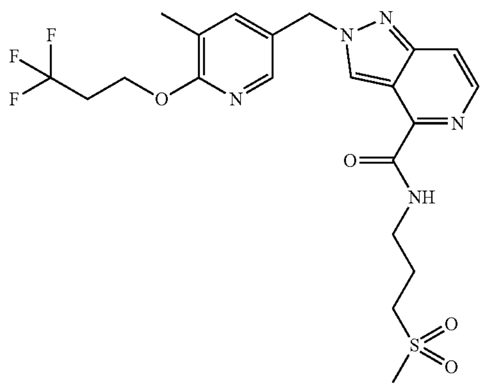 [SMILES: Cc1cc(Cn2cc3c(C(=O)NCCCS(C)(=O)=O)nccc3n2)cnc1OCCC(F)(F)F] | 2-((5-methyl-6-(3,3,3-trifluoropropoxy)pyridin-3-yl)methyl)-N-(3-(methylsulfonyl)propyl)-2H-pyrazolo[4,3-c]pyridine-4-carboxamide |
| 359 | 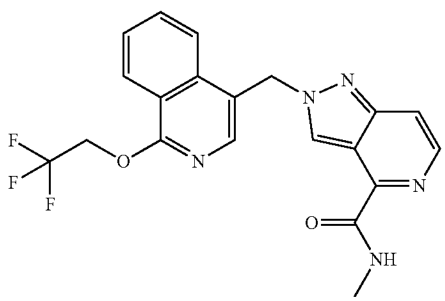 [SMILES: CNC(=O)c1nccc2nn(Cc3cnc(OCC(F)(F)F)c4ccccc34)cc12] | N-methyl-2-((1-(2,2,2-trifluoroethoxy)isoquinolin-4-yl)methyl)-2H-pyrazolo[4,3-c]pyridine-4-carboxamide |
| 360 | 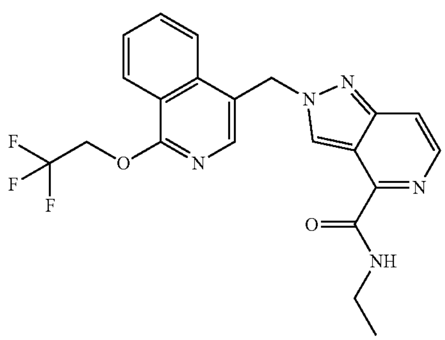 [SMILES: CCNC(=O)c1nccc2nn(Cc3cnc(OCC(F)(F)F)c4ccccc34)cc12] | N-ethyl-2-((1-(2,2,2-trifluoroethoxy)isoquinolin-4-yl)methyl)-2H-pyrazolo[4,3-c]pyridine-4-carboxamide |
| 361 | 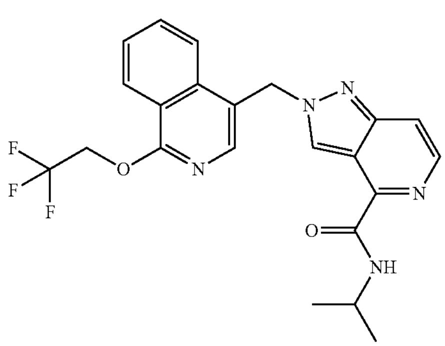 [SMILES: CC(C)NC(=O)c1nccc2nn(Cc3cnc(OCC(F)(F)F)c4ccccc34)cc12] | N-isopropyl-2-((1-(2,2,2-trifluoroethoxy)isoquinolin-4-yl)methyl)-2H-pyrazolo[4,3-c]pyridine-4-carboxamide |

TABLE 7-continued

| Ex | Structure | Name |
|---|---|---|
| 362 | 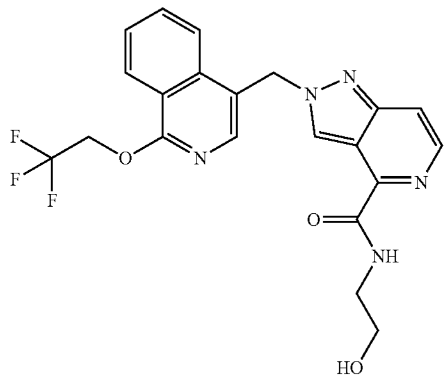 [SMILES: O=C(NCCO)c1nccc2nn(Cc3cnc(OCC(F)(F)F)c4ccccc34)cc12] | N-(2-hydroxyethyl)-2-((1-(2,2,2-trifluoroethoxy)isoquinolin-4-yl)methyl)-2H-pyrazolo[4,3-c]pyridine-4-carboxamide |
| 363 | 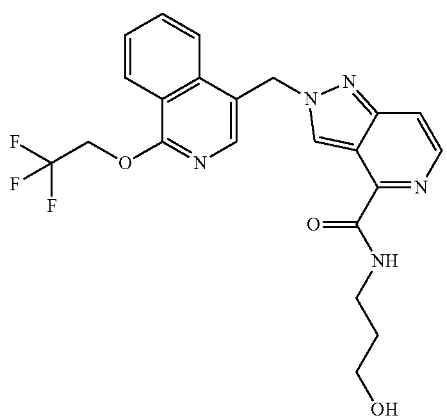 [SMILES: O=C(NCCCO)c1nccc2nn(Cc3cnc(OCC(F)(F)F)c4ccccc34)cc12] | N-(3-hydroxypropyl)-2-((1-(2,2,2-trifluoroethoxy)isoquinolin-4-yl)methyl)-2H-pyrazolo[4,3-c]pyridine-4-carboxamide |
| 364 | 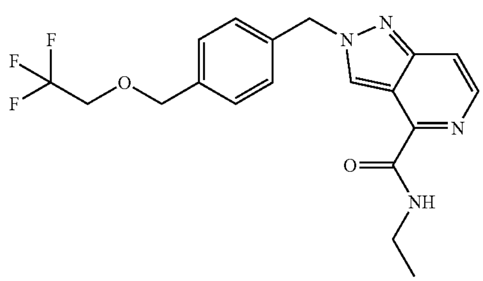 [SMILES: CCNC(=O)c1nccc2nn(Cc3ccc(COCC(F)(F)F)cc3)cc12] | N-ethyl-2-(4-((2,2,2-trifluoroethoxy)methyl)benzyl)-2H-pyrazolo[4,3-c]pyridine-4-carboxamide |
| 365 | 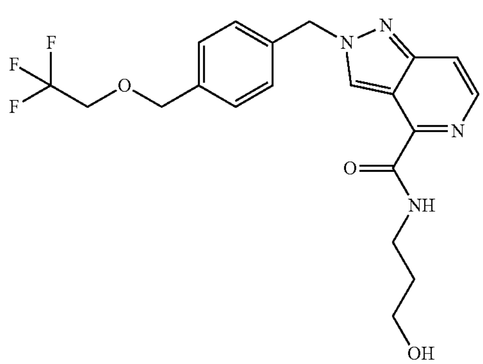 [SMILES: O=C(NCCCO)c1nccc2nn(Cc3ccc(COCC(F)(F)F)cc3)cc12] | N-(3-hydroxypropyl)-2-(4-((2,2,2-trifluoroethoxy)methyl)benzyl)-2H-pyrazolo[4,3-c]pyridine-4-carboxamide |

TABLE 7-continued

| Ex | Structure | Name |
|---|---|---|
| 366 | 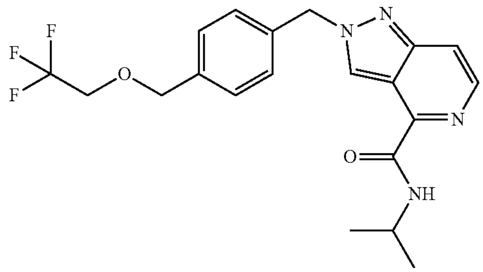 [SMILES: CC(C)NC(=O)c1nccc2nn(Cc3ccc(COCC(F)(F)F)cc3)cc12] | N-isopropyl-2-(4-((2,2,2-trifluoroethoxy)methyl)benzyl)-2H-pyrazolo[4,3-c]pyridine-4-carboxamide |
| 367 | 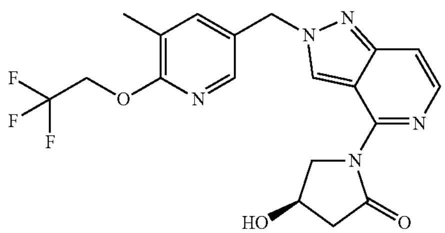 [SMILES: Cc1cc(Cn2cc3c(N4C[C@H](O)CC4=O)nccc3n2)cnc1OCC(F)(F)F] | (S)-4-hydroxy-1-(2-((5-methyl-6-(2,2,2-trifluoroethoxy)pyridin-3-yl)methyl)-2H-pyrazolo[4,3-c]pyridin-4-yl)pyrrolidin-2-one |
| 368 | 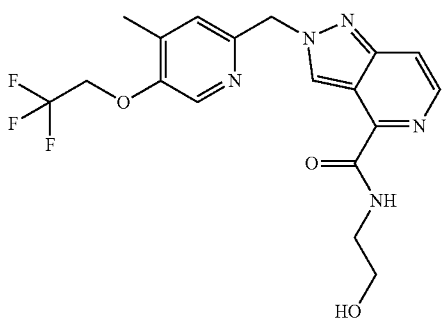 [SMILES: Cc1cc(Cn2cc3c(C(=O)NCCO)nccc3n2)ncc1OCC(F)(F)F] | 2-((5-(2,2-difluoroethoxy)-4-methylpyridin-2-yl)methyl)-N-(2-hydroxyethyl)-2H-pyrazolo[4,3-c]pyridine-4-carboxamide |
| 369 | 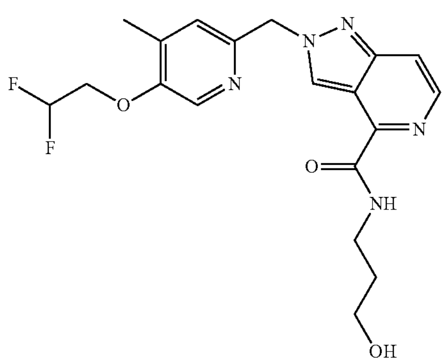 [SMILES: Cc1cc(Cn2cc3c(C(=O)NCCCO)nccc3n2)ncc1OCC(F)F] | 2-((5-(2,2-difluoroethoxy)-4-methylpyridin-2-yl)methyl)-N-(3-hydroxypropyl)-2H-pyrazolo[4,3-c]pyridine-4-carboxamide |
| 370 | 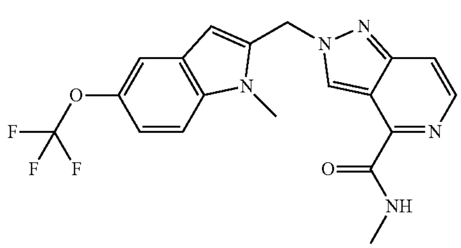 [SMILES: CNC(=O)c1nccc2nn(Cc3cc4cc(OC(F)(F)F)ccc4n3C)cc12] | N-methyl-2-((1-methyl-5-(trifluoromethoxy)-1H-indol-2-yl)methyl)-2H-pyrazolo[4,3-c]pyridine-4-carboxamide |

TABLE 7-continued

| Ex | Structure | Name |
|---|---|---|
| 371 | 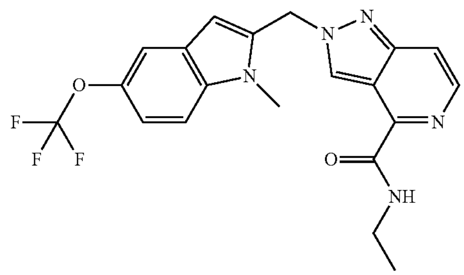 [SMILES: CCNC(=O)c1nccc2nn(Cc3cc4cc(OC(F)(F)F)ccc4n3C)cc12] | N-ethyl-2-((1-methyl-5-(trifluoromethoxy)-1H-indol-2-yl)methyl)-2H-pyrazolo[4,3-c]pyridine-4-carboxamide |
| 372 | 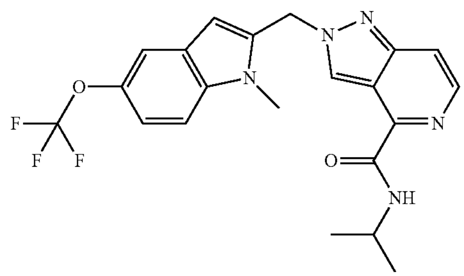 [SMILES: CC(C)NC(=O)c1nccc2nn(Cc3cc4cc(OC(F)(F)F)ccc4n3C)cc12] | N-isopropyl-2-((1-methyl-5-(trifluoromethoxy)-1H-indol-2-yl)methyl)-2H-pyrazolo[4,3-c]pyridine-4-carboxamide |
| 373 | 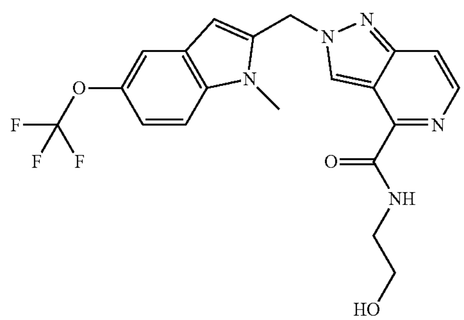 [SMILES: Cn1c(Cn2cc3c(C(=O)NCCO)nccc3n2)cc2cc(OC(F)(F)F)ccc21] | N-(2-hydroxyethyl)-2-((1-methyl-5-(trifluoromethoxy)-1H-indol-2-yl)methyl)-2H-pyrazolo[4,3-c]pyridine-4-carboxamide |
| 374 | 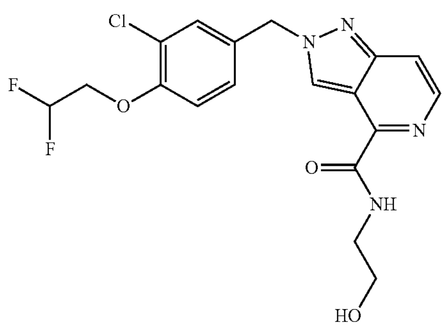 [SMILES: O=C(NCCO)c1nccc2nn(Cc3ccc(OCC(F)F)c(Cl)c3)cc12] | 2-(3-chloro-4-(2,2-difluoroethoxy)benzyl)-N-(2-hydroxyethyl)-2H-pyrazolo[4,3-c]pyridine-4-carboxamide |
| 375 | 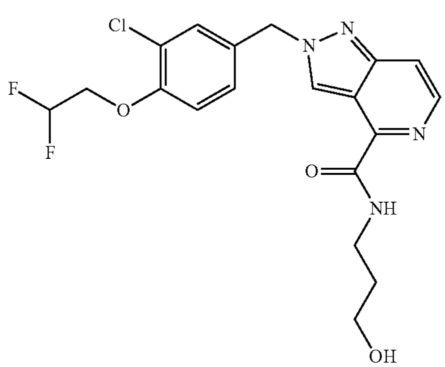 [SMILES: O=C(NCCCO)c1nccc2nn(Cc3ccc(OCC(F)F)c(Cl)c3)cc12] | 2-(3-chloro-4-(2,2-difluoroethoxy)benzyl)-N-(3-hydroxypropyl)-2H-pyrazolo[4,3-c]pyridine-4-carboxamide |

TABLE 7-continued

| Ex | Structure | Name |
|----|-----------|------|
| 376 | 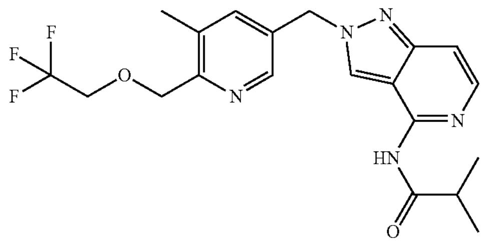 [SMILES: Cc1cc(Cn2cc3c(NC(=O)C(C)C)nccc3n2)cnc1COCC(F)(F)F] | N-(2-((5-methyl-6-((2,2,2-trifluoroethoxy)methyl)pyridin-3-yl)methyl)-2H-pyrazolo[4,3-c]pyridin-4-yl)isobutyramide |
| 377 | 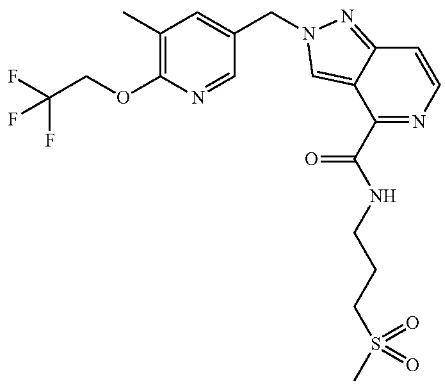 [SMILES: Cc1cc(Cn2cc3c(C(=O)NCCCS(C)(=O)=O)nccc3n2)cnc1OCC(F)(F)F] | 2-((5-methyl-6-(2,2,2-trifluoroethoxy)pyridin-3-yl)methyl)-N-(3-(methysulfonyl)propyl)-2H-pyrazolo[4,3-c]pyridine-4-carboxamide |
| 378 | 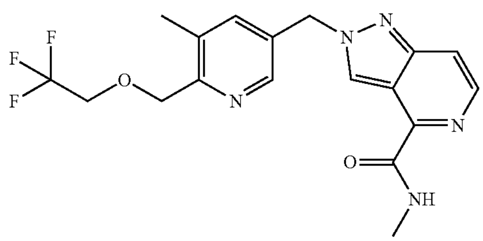 [SMILES: CNC(=O)c1nccc2nn(Cc3cnc(COCC(F)(F)F)c(C)c3)cc12] | N-ethyl-2-((5-methyl-6-((2,2,2-trifluoroethoxy)methyl)pyridin-3-yl)methyl)-2H-pyrazolo[4,3-c]pyridine-4-carboxamide |
| 379 | 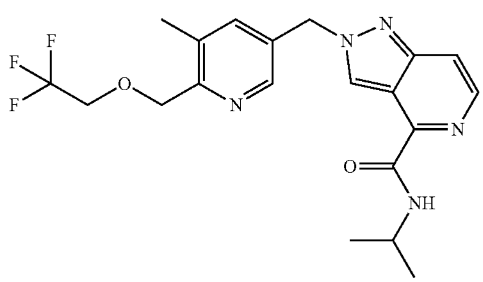 [SMILES: Cc1cc(Cn2cc3c(C(=O)NC(C)C)nccc3n2)cnc1COCC(F)(F)F] | N-isopropyl-2-((5-methyl-6-((2,2,2-trifluoroethoxy)methyl)pyridin-3-yl)methyl)-2H-pyrazolo[4,3-c]pyridine-4-carboxamide |
| 380 | 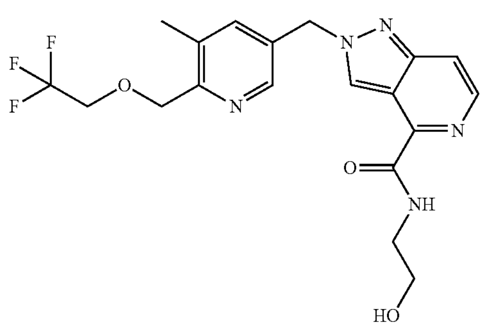 [SMILES: Cc1cc(Cn2cc3c(C(=O)NCCO)nccc3n2)cnc1COCC(F)(F)F] | N-(2-hydroxyethyl)-2-((5-methyl-6-((2,2,2-trifluoroethoxy)methyl)pyridin-3-yl)methyl)-2H-pyrazolo[4,3-c]pyridine-4-carboxamide |

TABLE 7-continued

| Ex | Structure | Name |
|---|---|---|
| 381 | 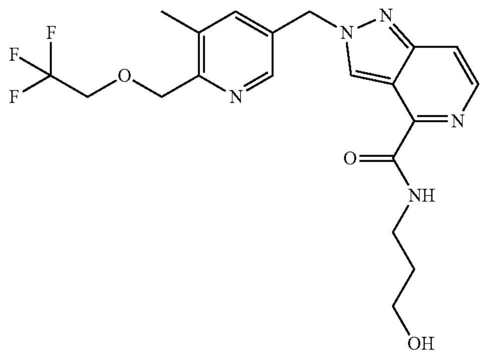 [SMILES: Cc1cc(Cn2cc3c(C(=O)NCCCO)nccc3n2)cnc1COCC(F)(F)F] | N-(3-hydroxypropyl)-2-((5-methyl-6-((2,2,2-trifluoroethoxy)methyl)pyridin-3-yl)methyl)-2H-pyrazolo[4,3-c]pyridine-4-carboxamide |
| 382 | 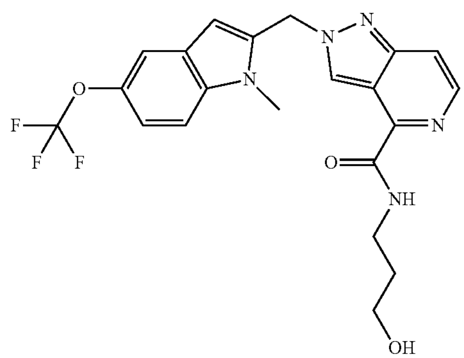 [SMILES: Cn1c(Cn2cc3c(C(=O)NCCCO)nccc3n2)cc2cc(OC(F)(F)F)ccc21] | N-(3-hydroxypropyl)-2-((1-methyl-5-(trifluoromethoxy)-1H-indol-2-yl)methyl)-2H-pyrazolo[4,3-c]pyridine-4-carboxamide |
| 383 | 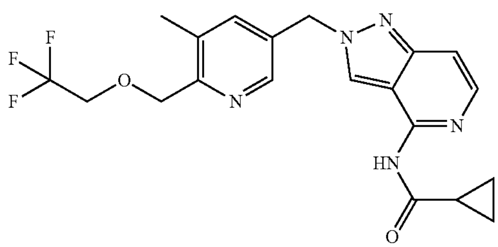 [SMILES: Cc1cc(Cn2cc3c(NC(=O)C4CC4)nccc3n2)cnc1COCC(F)(F)F] | N-(2-((5-methyl-6-((2,2,2-trifluoroethoxy)methyl)pyridin-3-yl)methyl)-2H-pyrazolo[4,3-c]pyridine-4-yl)cyclopropanecarboxamide |
| 384 | 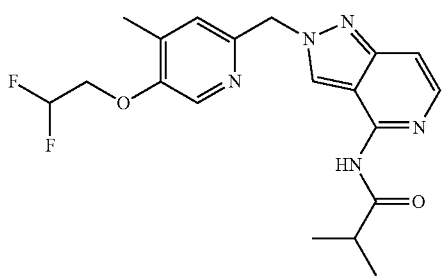 [SMILES: Cc1cc(Cn2cc3c(NC(=O)C(C)C)nccc3n2)ncc1OCC(F)F] | N-(2-((5-(2,2-difluoroethoxy)-4-methylpyridin-2-yl)methyl)-2H-pyrazolo[4,3-c]pyridin-4-yl)isobutyramide |
| 385 | 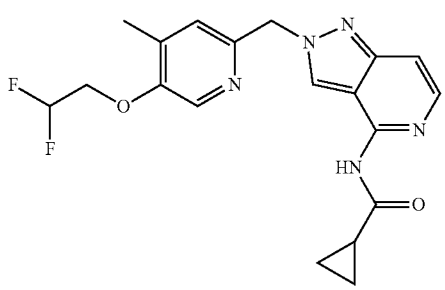 [SMILES: Cc1cc(Cn2cc3c(NC(=O)C4CC4)nccc3n2)ncc1OCC(F)F] | N-(2-((5-(2,2-difluoroethoxy)-4-methylpyridin-2-yl)methyl)-2H-pyrazolo[4,3-c]pyridin-4-yl)cyclopropanecarboxamide |

TABLE 7-continued

| Ex | Structure | Name |
|---|---|---|
| 386 | 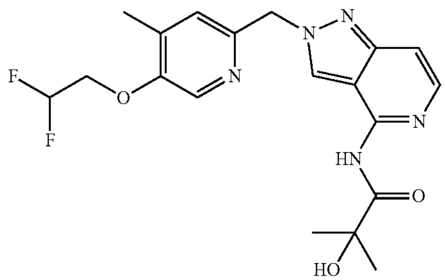 [SMILES: Cc1cc(Cn2cc3c(NC(=O)C(C)(C)O)nccc3n2)ncc1OCC(F)F] | N-(2-((5-(2,2-difluoroethoxy)-4-methylpyridin-2-yl)methyl)-2H-pyrazolo[4,3-c]pyridin-4-yl)-2-hydroxy-2-methylpropanamide |
| 387 | 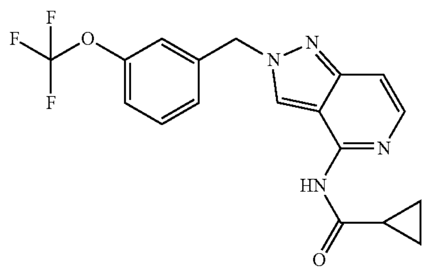 [SMILES: O=C(Nc1nccc2nn(Cc3cccc(OC(F)(F)F)c3)cc12)C1CC1] | N-(2-(3-(trifluoromethoxy)benzyl)-2H-pyrazolo[4,3-c]pyridin-4-yl)cyclopropanecarboxamide |
| 388 | 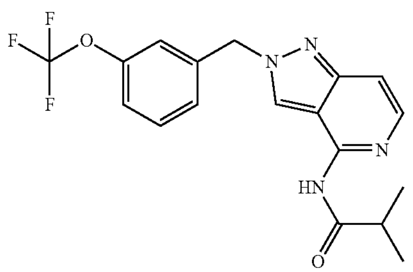 [SMILES: CC(C)C(=O)Nc1nccc2nn(Cc3cccc(OC(F)(F)F)c3)cc12] | N-(2-(3-(trifluoromethoxy)benzyl)-2H-pyrazolo[4,3-c]pyridin-4-yl)isobutyramide |
| 389 | 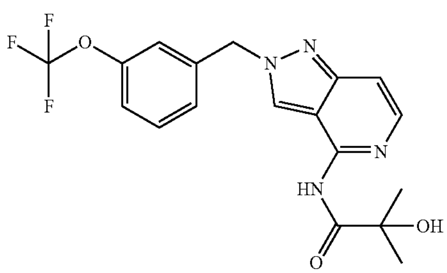 [SMILES: CC(C)(O)C(=O)Nc1nccc2nn(Cc3cccc(OC(F)(F)F)c3)cc12] | 2-hydroxy-2-methyl-N-(2-(3-(trifluoromethoxy)benzyl)-2H-pyrazolo[4,3-c]pyridin-4-yl)propanamide |
| 390 | 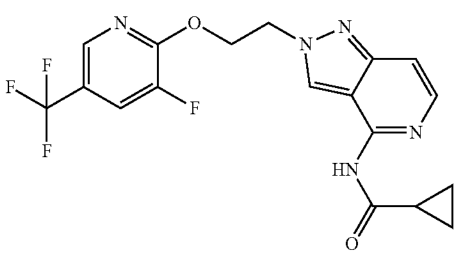 [SMILES: O=C(Nc1nccc2nn(CCOc3ncc(C(F)(F)F)cc3F)cc12)C1CC1] | N-(2-(2-((3-fluoro-5-(trifluoromethyl)pyridin-2-yl)oxy)ethyl)-2H-pyrazolo[4,3-c]pyridin-4-yl)cyclopropanecarboxamide |
| 391 | 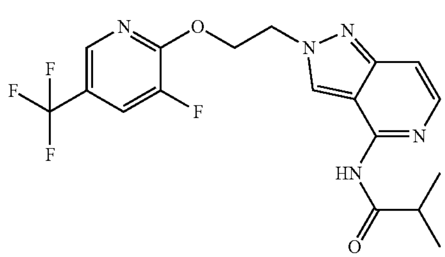 [SMILES: CC(C)C(=O)Nc1nccc2nn(CCOc3ncc(C(F)(F)F)cc3F)cc12] | N-(2-(2-((3-fluoro-5-(trifluoromethyl)pyridin-2-yl)oxy)ethyl)-2H-pyrazolo[4,3-c]pyridin-4-yl)isobutyramide |

TABLE 7-continued

| Ex | Structure | Name |
|---|---|---|
| 392 | 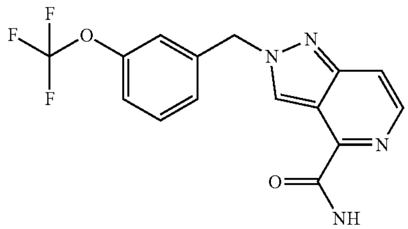 [SMILES: NC(=O)c1nccc2nn(Cc3cccc(OC(F)(F)F)c3)cc12] | N-methyl-2-(3-(trifluoromethoxy)benzyl)-2H-pyrazolo[4,3-c]pyridine-4-carboxamide |
| 393 | 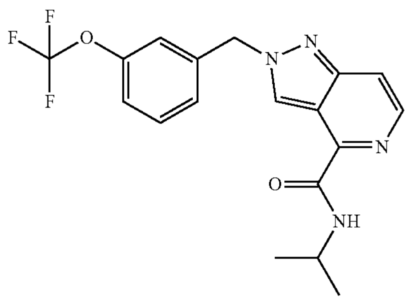 [SMILES: CC(C)NC(=O)c1nccc2nn(Cc3cccc(OC(F)(F)F)c3)cc12] | N-isopropyl-2-(3-(trifluoromethoxy)benzyl)-2H-pyrazolo[4,3-c]pyridine-4-carboxamide |
| 394 | 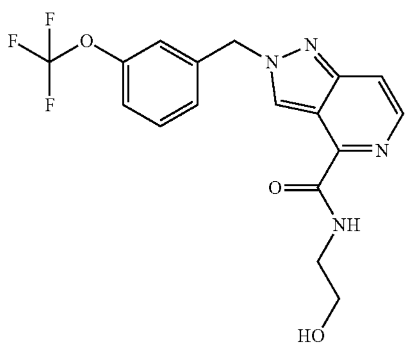 [SMILES: O=C(NCCO)c1nccc2nn(Cc3cccc(OC(F)(F)F)c3)cc12] | N-(2-hydroxyethyl)-2-(3-(trifluoromethoxy)benzyl)-2H-pyrazolo[4,3-c]pyridine-4-carboxamide |
| 395 | 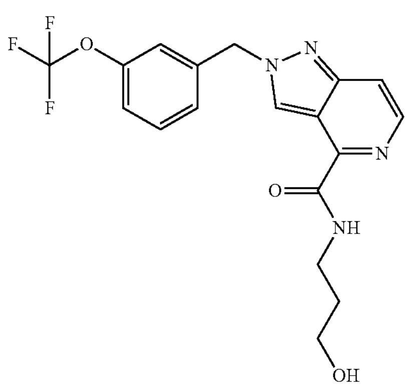 [SMILES: O=C(NCCCO)c1nccc2nn(Cc3cccc(OC(F)(F)F)c3)cc12] | N-(3-hydroxypropyl)-2-(3-(trifluoromethoxy)benzyl)-2H-pyrazolo[4,3-c]pyridine-4-carboxamide |
| 396 | 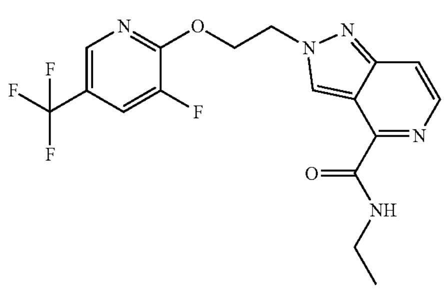 [SMILES: CCNC(=O)c1nccc2nn(CCOc3ncc(C(F)(F)F)cc3F)cc12] | N-ethyl-2-(2-((3-fluoro-5-(trifluoromethyl)pyridin-2-yl)oxy)ethyl)-2H-pyrazolo[4,3-c]pyridine-4-carboxamide |

TABLE 7-continued

| Ex | Structure | Name |
|---|---|---|
| 397 | 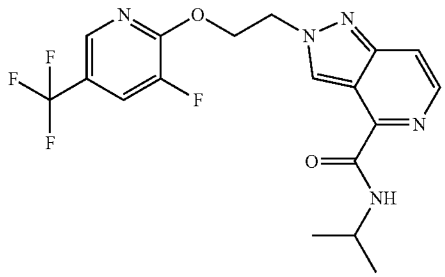 [SMILES: CC(C)NC(=O)c1nccc2nn(CCOc3ncc(C(F)(F)F)cc3F)cc12] | 2-(2-((3-fluoro-5-(trifluoromethyl)pyridin-2-yl)oxy)ethyl)-N-isopropyl-2H-pyrazolo[4,3-c]pyridine-4-carboxamide |
| 398 | 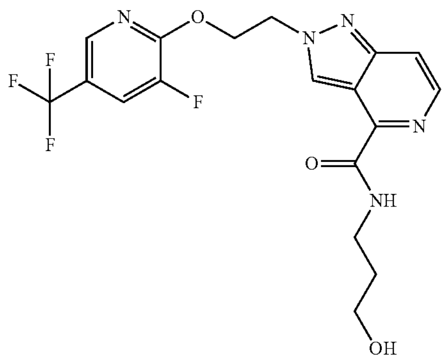 [SMILES: O=C(NCCCO)c1nccc2nn(CCOc3ncc(C(F)(F)F)cc3F)cc12] | 2-(2-((3-fluoro-5-(trifluoromethyl)pyridin-2-yl)oxy)ethyl)-N-(3-hydroxypropyl)-2H-pyrazolo[4,3-c]pyridine-4-carboxamide |
| 399 | 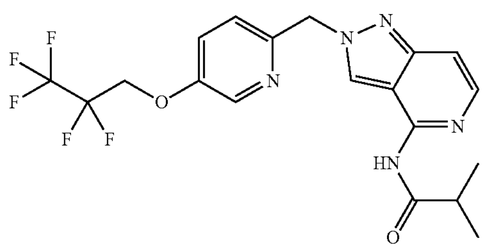 [SMILES: CC(C)C(=O)Nc1nccc2nn(Cc3ccc(OCC(F)(F)C(F)(F)F)cn3)cc12] | N-(2-((5-(2,2,3,3,3-pentafluoropropoxy)pyridin-2-yl)methyl)-2H-pyrazolo[4,3-c]pyridin-4-yl)isobutyramide |
| 400 | 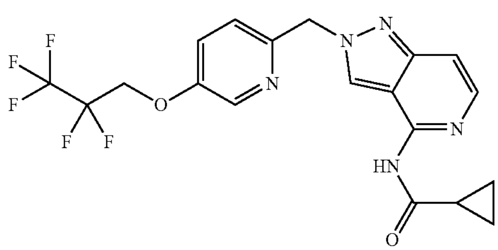 [SMILES: O=C(Nc1nccc2nn(Cc3ccc(OCC(F)(F)C(F)(F)F)cn3)cc12)C1CC1] | N-(2-((5-(2,2,3,3,3-pentafluoropropoxy)pyridin-2-yl)methyl)-2H-pyrazolo[4,3-c]pyridin-4-yl)cyclopropanecarboxamide |
| 401 | 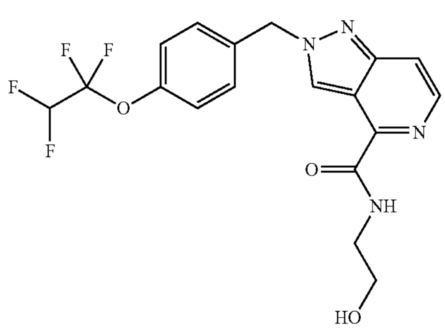 [SMILES: O=C(NCCO)c1nccc2nn(Cc3ccc(OC(F)(F)C(F)F)cc3)cc12] | N-(2-hydroxyethyl)-2-(4-(1,1,2,2-tetrafluoroethoxy)benzyl)-2H-pyrazolo[4,3-c]pyridine-4-carboxamide |

TABLE 7-continued

| Ex | Structure | Name |
|---|---|---|
| 402 | 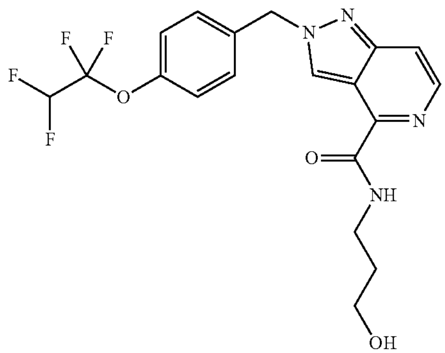 [SMILES: O=C(NCCCO)c1nccc2nn(Cc3ccc(OC(F)(F)C(F)F)cc3)cc12] | N-(3-hydroxypropyl)-2-(4-(1,1,2,2-tetrafluoroethoxy)benzyl)-2H-pyrazolo[4,3-c]pyridine-4-carboxamide |
| 403 | 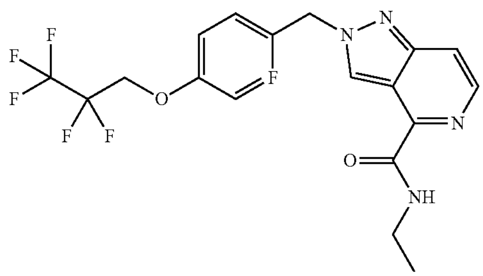 | N-ethyl-2-((5-(2,2,3,3,3-pentafluoropropoxy)pyridin-2-yl)methyl)-2H-pyrazolo[4,3-c]pyridine-4-carboxamide |
| 404 | 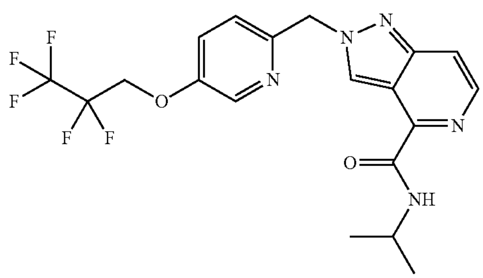 [SMILES: CC(C)NC(=O)c1nccc2nn(Cc3ccc(OCC(F)(F)C(F)(F)F)cn3)cc12] | N-isopropyl-2-((5-(2,2,3,3,3-pentafluoropropoxy)pyridin-2-yl)methyl)-2H-pyrazolo[4,3-c]pyridine-4-carboxamide |
| 405 | 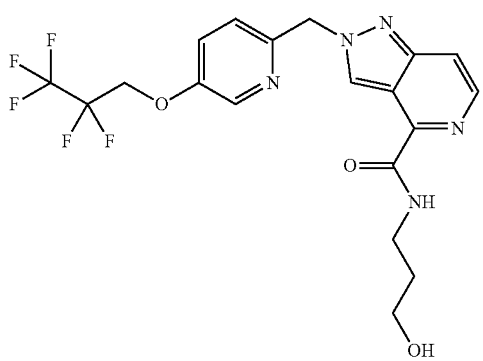 [SMILES: O=C(NCCCO)c1nccc2nn(Cc3ccc(OCC(F)(F)C(F)(F)F)cn3)cc12] | N-(3-hydroxypropyl)-2-((5-(2,2,3,3,3-pentafluoropropoxy)pyridin-2-yl)methyl)-2H-pyrazolo[4,3-c]pyridine-4-carboxamide |
| 406 | 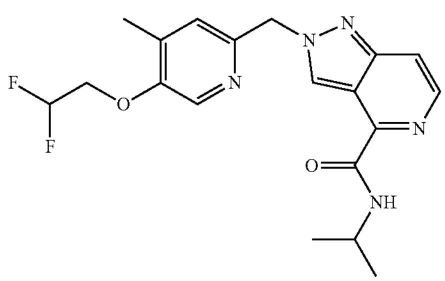 [SMILES: Cc1cc(Cn2cc3c(C(=O)NC(C)C)nccc3n2)ncc1OCC(F)F] | 2-((5-(2,2-difluoroethoxy)-4-methylpyridin-2-yl)methyl)-N-isopropyl-2H-pyrazolo[4,3-c]pyridine-4-carboxamide |

| Ex | Structure | Name |
|---|---|---|
| 407 | 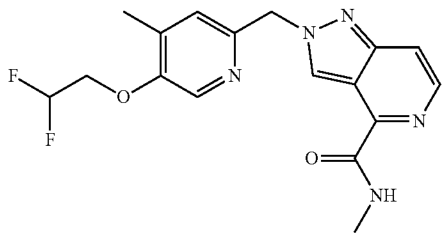 [SMILES: CNC(=O)c1nccc2nn(Cc3cc(C)c(OCC(F)F)cn3)cc12] | 2-((5-(2,2-difluoroethoxy)-4-methylpyridin-2-yl)methyl)-N-methyl-2H-pyrazolo[4,3-c]pyridine-4-carboxamide |
| 408 | 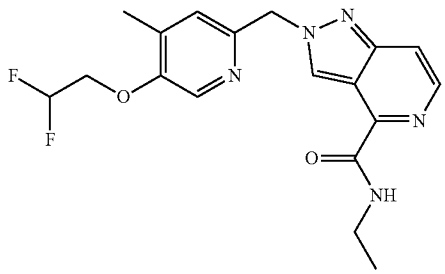 [SMILES: CCNC(=O)c1nccc2nn(Cc3cc(C)c(OCC(F)F)cn3)cc12] | 2-((5-(2,2-difluoroethoxy)-4-methylpyridin-2-yl)methyl)-N-ethyl-2H-pyrazolo[4,3-c]pyridine-4-carboxamide |
| 409 | 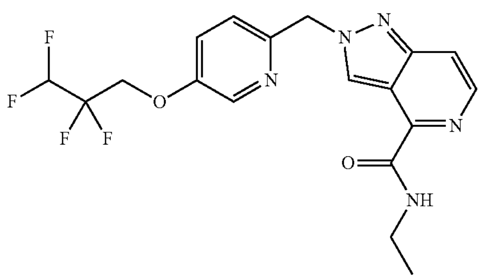 [SMILES: CCNC(=O)c1nccc2nn(Cc3ccc(OCC(F)(F)C(F)F)cn3)cc12] | N-ethyl-2-((5-(2,2,3,3-tetrafluoropropoxy)pyridin-2-yl)methyl)-2-pyrazolo[4,3-c]pyridine-4-carboxamide |
| 410 | 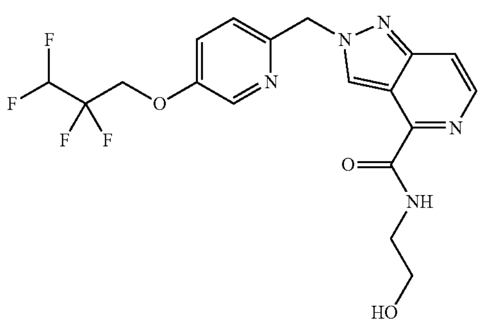 [SMILES: O=C(NCCO)c1nccc2nn(Cc3ccc(OCC(F)(F)C(F)F)cn3)cc12] | N-(2-hydroxyethyl)-2-((5-(2,2,3,3-tetrafluoropropoxy)pyridin-2-yl)methyl)-2H-pyrazolo[4,3-c]pyridine-4-carboxamide |
| 411 | 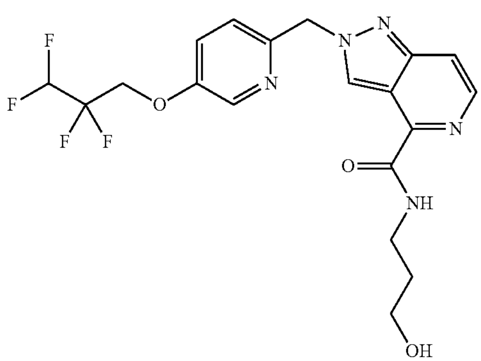 [SMILES: O=C(NCCCO)c1nccc2nn(Cc3ccc(OCC(F)(F)C(F)F)cn3)cc12] | N-(3-hydroxypropyl)-2-((5-(2,2,3,3-tetrafluoropropoxy)pyridin-2-yl)methyl)-2H-pyrazolo[4,3-c]pyridine-4-carboxamide |

TABLE 7-continued

| Ex | Structure | Name |
|---|---|---|
| 412 | 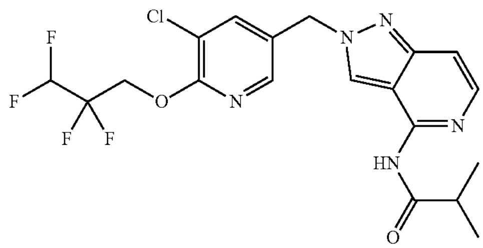 [SMILES: CC(C)C(=O)Nc1nccc2nn(Cc3cnc(OCC(F)(F)C(F)F)c(Cl)c3)cc12] | N-(2-((5-chloro-6-(2,2,3,3-tetrafluoropropoxy)pyridin-3-yl)methyl)-2H-pyrazolo[4,3-c]pyridin-4-yl)isobutyramide |
| 413 | 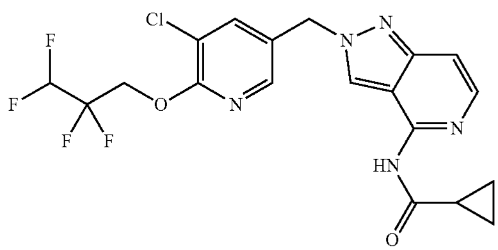 [SMILES: O=C(Nc1nccc2nn(Cc3cnc(OCC(F)(F)C(F)F)c(Cl)c3)cc12)C1CC1] | N-(2-((5-chloro-6-(2,2,3,3-tetrafluoropropoxy)pyridin-3-yl)methyl)-2H-pyrazolo[4,3-c]pyridin-4-yl)cyclopropanecarboxamide |
| 414 | 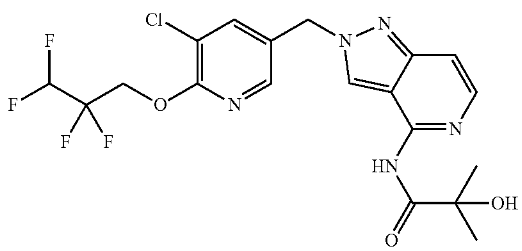 [SMILES: CC(C)(O)C(=O)Nc1nccc2nn(Cc3cnc(OCC(F)(F)C(F)F)c(Cl)c3)cc12] | N-(2-((5-chloro-6-(2,2,3,3-tetrafluoropropoxy)pyridin-3-yl)methyl)-2H-pyrazolo[4,3-c]pyridin-4-yl)-2-hydroxy-2-methylpropanamide |
| 415 | 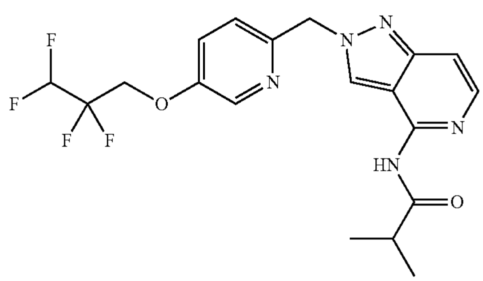 [SMILES: CC(C)C(=O)Nc1nccc2nn(Cc3ccc(OCC(F)(F)C(F)F)cn3)cc12] | N-(2-((5-(2,2,3,3-tetrafluoropropoxy)pyridin-2-yl)methyl)-2H-pyrazolo[4,3-c]pyridin-4-yl)isobutyramide |
| 416 | 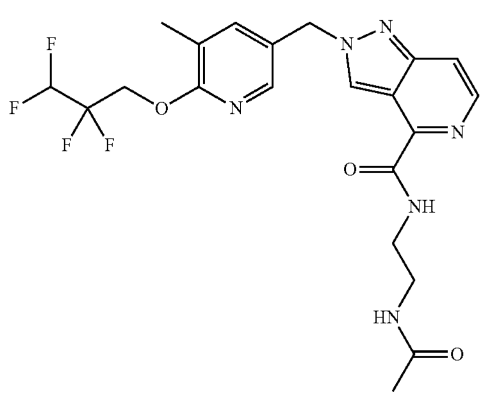 [SMILES: CC(=O)NCCNC(=O)c1nccc2nn(Cc3cnc(OCC(F)(F)C(F)F)c(C)c3)cc12] | N-(2-acetamidoethyl)-2-((5-methyl-6-(2,2,3,3-tetrafluoropropoxy)pyridin-3-yl)methyl)-2H-pyrazolo[4,3-c]pyridine-4-carboxamide |

TABLE 7-continued

| Ex | Structure | Name |
|---|---|---|
| 417 | 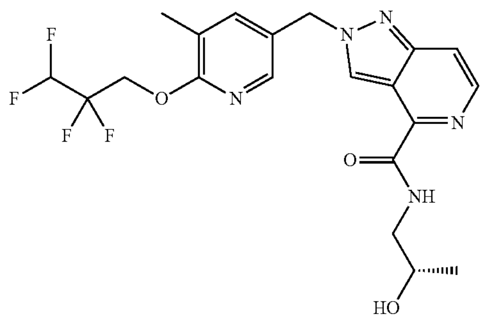 [SMILES: Cc1cc(Cn2cc3c(C(=O)NC[C@H](C)O)nccc3n2)cnc1OCC(F)(F)C(F)F] | (S)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide |
| 418 | 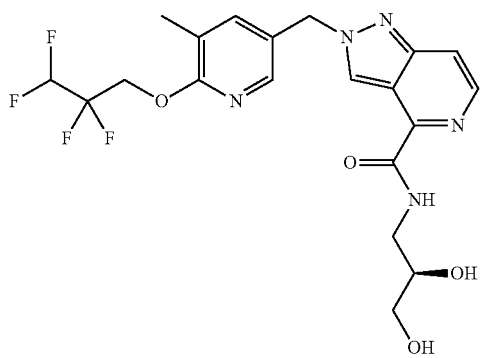 [SMILES: Cc1cc(Cn2cc3c(C(=O)NC[C@@H](O)CO)nccc3n2)cnc1OCC(F)(F)C(F)F] | (S)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide |
| 419 | 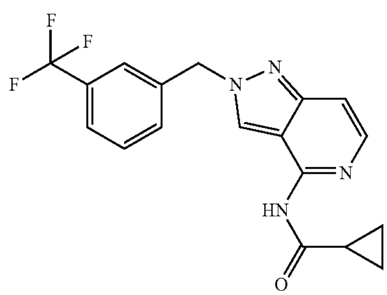 [SMILES: O=C(Nc1nccc2nn(Cc3cccc(C(F)(F)F)c3)cc12)C1CC1] | N-(2-(3-(trifluoromethyl)benzyl)-2H-pyrazolo[4,3-c]pyridin-4-yl)cyclopropanecarboxamide |
| 420 | 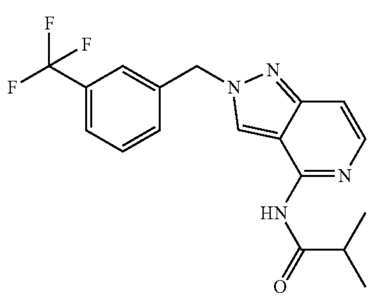 [SMILES: CC(C)C(=O)Nc1nccc2nn(Cc3cccc(C(F)(F)F)c3)cc12] | N-(2-(3-(trifluoromethyl)benzyl)-2H-pyrazolo[4,3-c]pyridin-4-yl)isobutyramide |
| 421 | 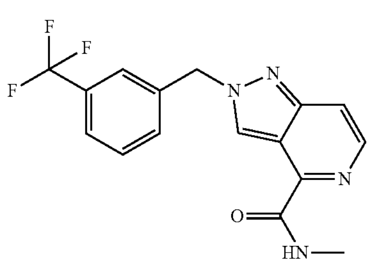 [SMILES: CNC(=O)c1nccc2nn(Cc3cccc(C(F)(F)F)c3)cc12] | N-methyl-2-(3-(trifluoromethyl)benzyl)-2H-pyrazolo[4,3-c]pyridine-4-carboxamide |

| Ex | Structure | Name |
|---|---|---|
| 422 | 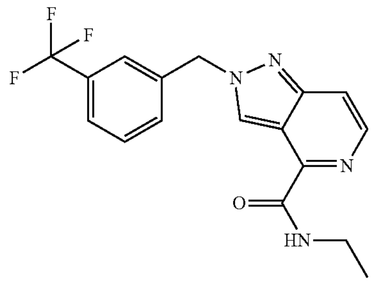 [SMILES: CCNC(=O)c1nccc2nn(Cc3cccc(C(F)(F)F)c3)cc12] | N-ethyl-2-(3-(trifluoromethyl)benzyl)-2H-pyrazolo[4,3-c]pyridine-4-carboxamide |
| 423 | 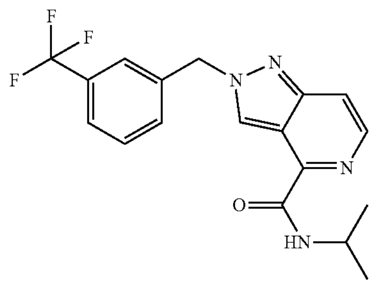 [SMILES: CC(C)NC(=O)c1nccc2nn(Cc3cccc(C(F)(F)F)c3)cc12] | N-isopropyl-2-(3-(trifluoromethyl)benzyl)-2H-pyrazolo[4,3-c]pyridine-4-carboxamide |
| 424 | 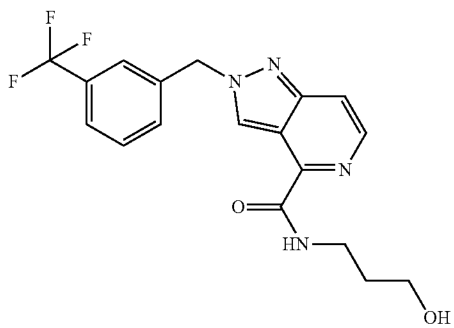 [SMILES: O=C(NCCCO)c1nccc2nn(Cc3cccc(C(F)(F)F)c3)cc12] | N-(3-hydroxypropyl)-2-(3-(trifluoromethyl)benzyl)-2H-pyrazolo[4,3-c]pyridine-4-carboxamide |
| 425 | 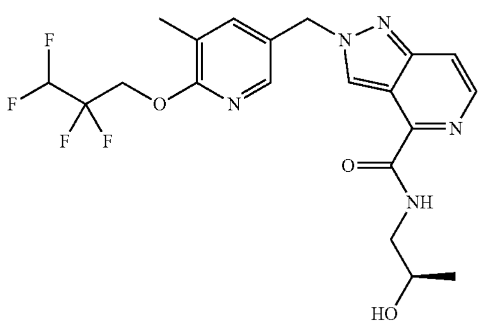 [SMILES: Cc1cc(Cn2cc3c(C(=O)NC[C@@H](C)O)nccc3n2)cnc1OCC(F)(F)C(F)F] | (R)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide |
| 426 | 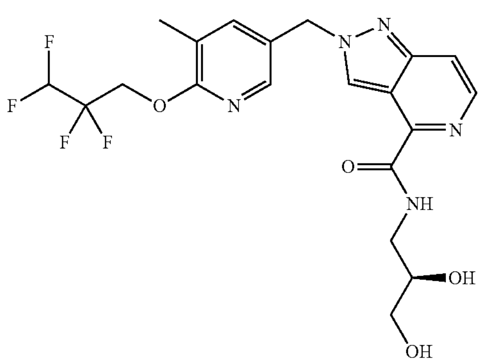 [SMILES: Cc1cc(Cn2cc3c(C(=O)NC[C@@H](O)CO)nccc3n2)cnc1OCC(F)(F)C(F)F] | (R)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide |

TABLE 7-continued

| Ex | Structure | Name |
|---|---|---|
| 427 | 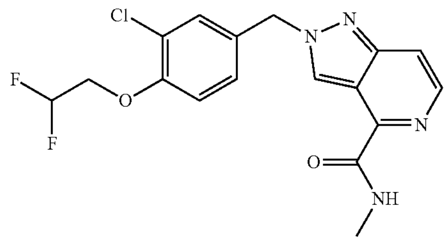 [SMILES: CNC(=O)c1nccc2nn(Cc3ccc(OCC(F)F)c(Cl)c3)cc12] | 2-(3-chloro-4-(2,2-difluoroethoxy)benzyl)-N-methyl-2H-pyrazolo[4,3-c]pyridine-4-carboxamide |
| 428 | 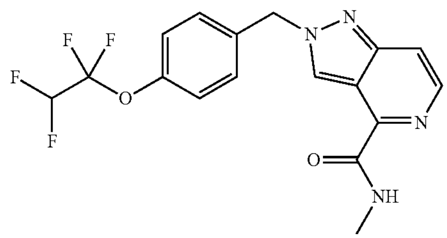 [SMILES: CNC(=O)c1nccc2nn(Cc3ccc(OC(F)(F)C(F)F)cc3)cc12] | N-methyl-2-(4-(1,1,2,2-tetrafluoroethoxy)benzyl)-2H-pyrazolo[4,3-c]pyridine-4-carboxamide |
| 429 | 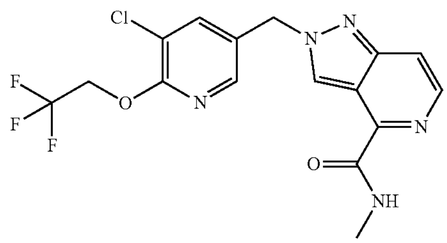 [SMILES: CNC(=O)c1nccc2nn(Cc3cnc(OCC(F)(F)F)c(Cl)c3)cc12] | 2-((5-chloro-6-(2,2,2-trifluoroethoxy)pyridin-3-yl)methyl)-N-methyl-2H-pyrazolo[4,3-c]pyridine-4-carboxamide |
| 430 | 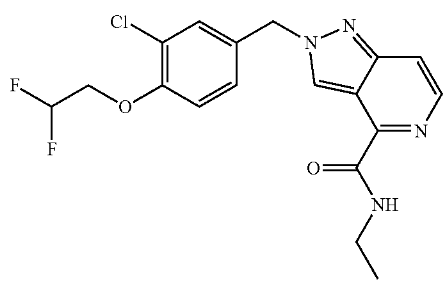 [SMILES: CCNC(=O)c1nccc2nn(Cc3ccc(OCC(F)F)c(Cl)c3)cc12] | 2-(3-chloro-4-(2,2-difluoroethoxy)benzyl)-N-ethyl-2H-pyrazolo[4,3-c]pyridine-4-carboxamide |
| 431 | 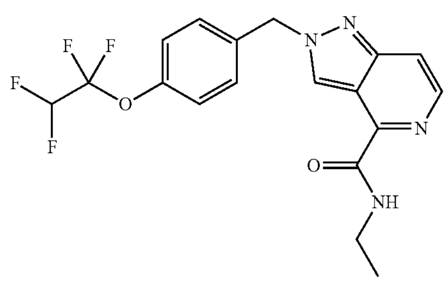 [SMILES: CCNC(=O)c1nccc2nn(Cc3ccc(OC(F)(F)C(F)F)cc3)cc12] | N-ethyl-2-(4-(1,1,2,2-tetrafluoroethoxy)benzyl)-2H-pyrazolo[4,3-c]pyridine-4-carboxamide |
| 432 | 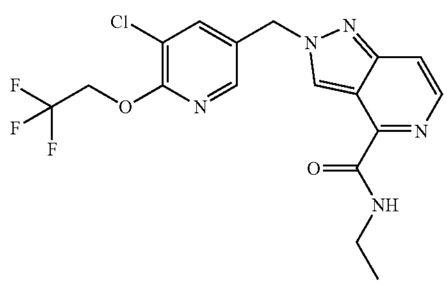 [SMILES: CCNC(=O)c1nccc2nn(Cc3cnc(OCC(F)(F)F)c(Cl)c3)cc12] | 2-((5-chloro-6-(2,2,2-trifluoroethoxy)pyridin-3-yl)methyl)-N-ethyl-2H-pyrazolo[4,3-c]pyridine-4-carboxamide |

US 9,944,634 B2

TABLE 7-continued

| Ex | Structure | Name |
|---|---|---|
| 433 | 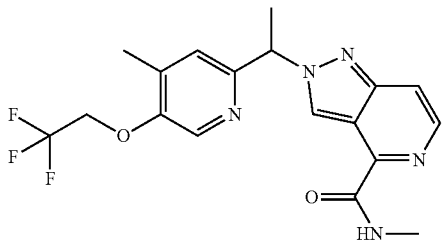 [SMILES: CNC(=O)c1nccc2nn(C(C)c3cc(C)c(OCC(F)(F)F)cn3)cc12] | N-methyl-2-(1-(4-methyl-5-(2,2,2-trifluoroethoxy)pyridin-2-yl)ethyl)-2H-pyrazolo[4,3-c]pyridine-4-carboxamide (single enantiomer) |
| 434 | 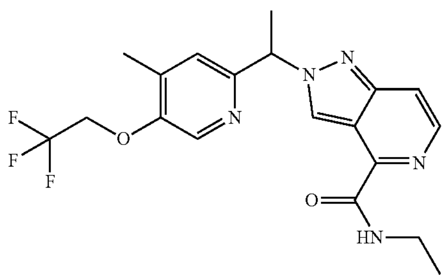 [SMILES: CCNC(=O)c1nccc2nn(C(C)c3cc(C)c(OCC(F)(F)F)cn3)cc12] | N-ethyl-2-(1-(4-methyl-5-(2,2,2-trifluoroethoxy)pyridin-2-yl)ethyl)-2H-pyrazolo[4,3-c]pyridine-4-carboxamide (single enantiomer) |
| 435 | 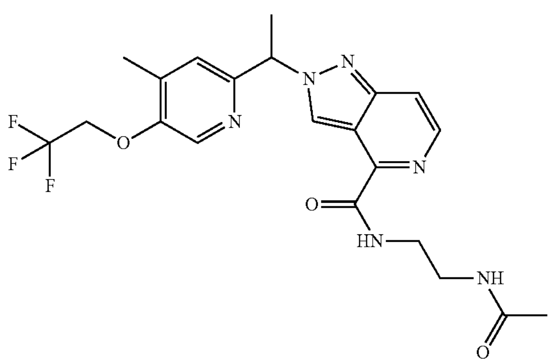 [SMILES: CC(=O)NCCNC(=O)c1nccc2nn(C(C)c3cc(C)c(OCC(F)(F)F)cn3)cc12] | N-(2-acetamidoethyl)-2-(1-(4-methyl-5-(2,2,2-trifluoroethoxy)pyridin-2-yl)ethyl)-2H-pyrazolo[4,3-c]pyridine-4-carboxamide (single enantiomer) |
| 436 | 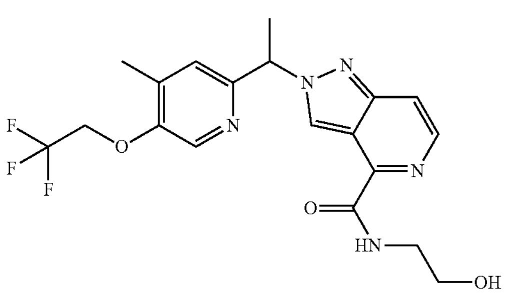 [SMILES: Cc1cc(C(C)n2cc3c(C(=O)NCCO)nccc3n2)ncc1OCC(F)(F)F] | N-(2-hydroxyethyl)-2-(1-(4-methyl-5-(2,2,2-trifluoroethoxy)pyridin-2-yl)ethyl)-2H-pyrazolo[4,3-c]pyridine-4-carboxamide (single enantiomer) |
| 437 | 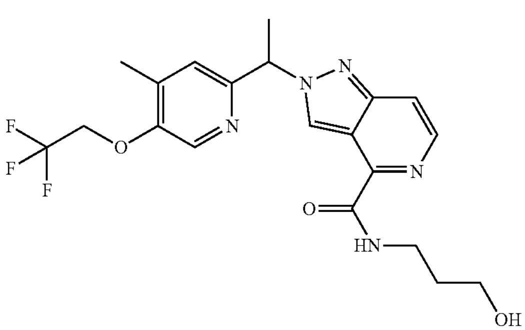 [SMILES: Cc1cc(C(C)n2cc3c(C(=O)NCCCO)nccc3n2)ncc1OCC(F)(F)F] | N-(3-hydroxypropyl)-2-(1-(4-methyl-5-(2,2,2-trifluoroethoxy)pyridin-2-yl)ethyl)-2H-pyrazolo[4,3-c]pyridine-4-carboxamide (single enantiomer) |

TABLE 7-continued

| Ex | Structure | Name |
|---|---|---|
| 438 | 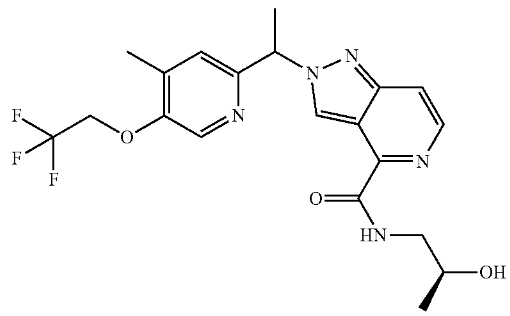 [SMILES: Cc1cc(C(C)n2cc3c(C(=O)NC[C@H](C)O)nccc3n2)ncc1OCC(F)(F)F] | N-((S)-2-hydroxypropyl)-2-(1-(4-methyl-5-(2,2,2-trifluoroethoxy)pyridin-2-yl)ethyl)-2H-pyrazolo[4,3-c]pyridine-4-carboxamide (single enantiomer) |
| 439 | 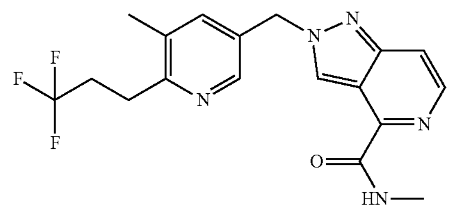 [SMILES: CNC(=O)c1nccc2nn(Cc3cnc(CCC(F)(F)F)c(C)c3)cc12] | N-methyl-2-((5-methyl-6-(3,3,3-trifluoropropyl)pyridin-3-yl)methyl)-2H-pyrazolo[4,3-c]pyridine-4-carboxamide |
| 440 | 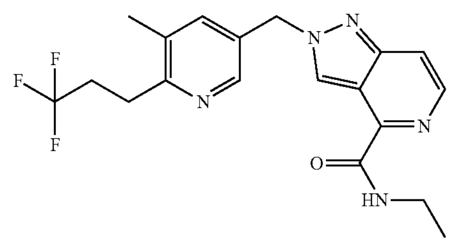 [SMILES: CCNC(=O)c1nccc2nn(Cc3cnc(CCC(F)(F)F)c(C)c3)cc12] | N-ethyl-2-((5-methyl-6-(3,3,3-trifluoropropyl)pyridin-3-yl)methyl)-2H-pyrazolo[4,3-c]pyridine-4-carboxamide |
| 441 | 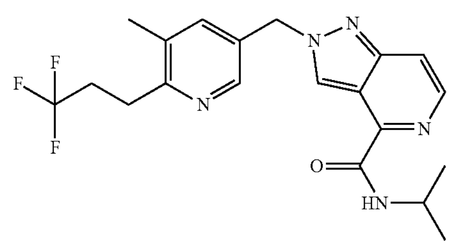 [SMILES: Cc1cc(Cn2cc3c(C(=O)NC(C)C)nccc3n2)cnc1CCC(F)(F)F] | N-isopropyl-2-((5-methyl-6-(3,3,3-trifluoropropyl)pyridin-3-yl)methyl)-2H-pyrazolo[4,3-c]pyridine-4-carboxamide |
| 442 | 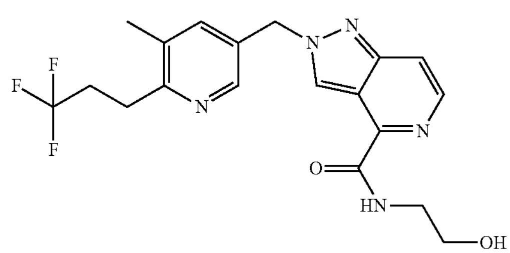 [SMILES: Cc1cc(Cn2cc3c(C(=O)NCCO)nccc3n2)cnc1CCC(F)(F)F] | N-(2-hydroxyethyl)-2-((5-methyl-6-(3,3,3-trifluoropropyl)pyridin-3-yl)methyl)-2H-pyrazolo[4,3-c]pyridine-4-carboxamide |
| 443 | 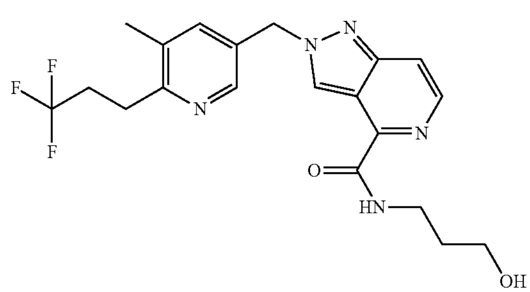 [SMILES: Cc1cc(Cn2cc3c(C(=O)NCCCO)nccc3n2)cnc1CCC(F)(F)F] | N-(3-hydroxypropyl)-2-((5-methyl-6-(3,3,3-trifluoropropyl)pyridin-3-yl)methyl)-2H-pyrazolo[4,3-c]pyridine-4-carboxamide |

TABLE 7-continued

| Ex | Structure | Name |
|---|---|---|
| 444 | 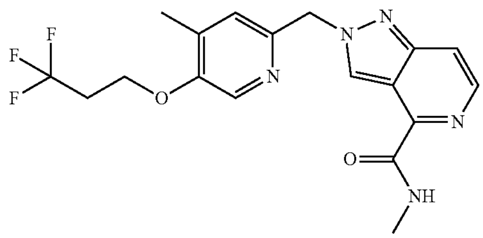 [SMILES: CNC(=O)c1nccc2nn(Cc3cc(C)c(OCCC(F)(F)F)cn3)cc12] | N-methyl-2-((4-methyl-5-(3,3,3-trifluoropropoxy)pyridin-2-yl)methyl)-2H-pyrazolo[4,3-c]pyridine-4-carboxamide |
| 445 | 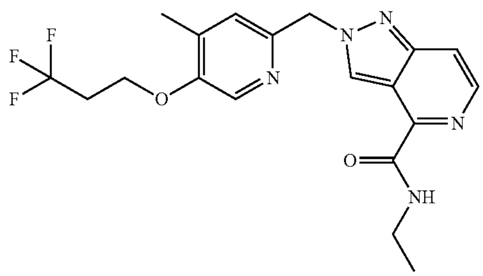 [SMILES: CCNC(=O)c1nccc2nn(Cc3cc(C)c(OCCC(F)(F)F)cn3)cc12] | N-ethyl-2-((4-methyl-5-(3,3,3-trifluoropropoxy)pyridin-2-yl)methyl)-2H-pyrazolo[4,3-c]pyridine-4-carboxamide |
| 446 | 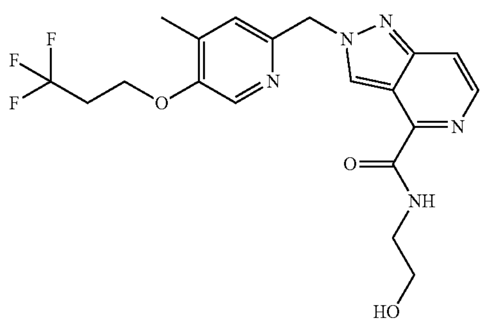 [SMILES: Cc1cc(Cn2cc3c(C(=O)NCCO)nccc3n2)ncc1OCCC(F)(F)F] | N-(2-hydroxyethyl)-2-((4-methyl-5-(3,3,3-trifluoropropoxy)pyridin-2-yl)methyl)-2H-pyrazolo[4,3-c]pyridine-4-carboxamide |
| 447 | 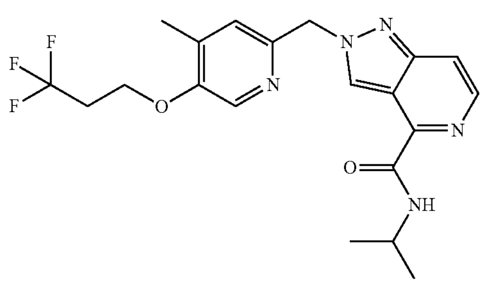 [SMILES: Cc1cc(Cn2cc3c(C(=O)NC(C)C)nccc3n2)ncc1OCCC(F)(F)F] | N-isopropyl-2-((4-methyl-5-(3,3,3-trifluoropropoxy)pyridin-2-yl)methyl)-2H-pyrazolo[4,3-c]pyridine-4-carboxamide |
| 448 | 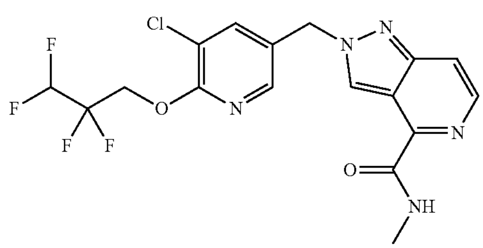 [SMILES: CNC(=O)c1nccc2nn(Cc3cnc(OCC(F)(F)C(F)F)c(Cl)c3)cc12] | 2-((5-chloro-6-(2,2,3,3-tetrafluoropropoxy)pyridin-3-yl)methyl)-N-methyl-2H-pyrazolo[4,3-c]pyridine-4-carboxamide |

TABLE 7-continued

| Ex | Structure | Name |
|---|---|---|
| 449 | 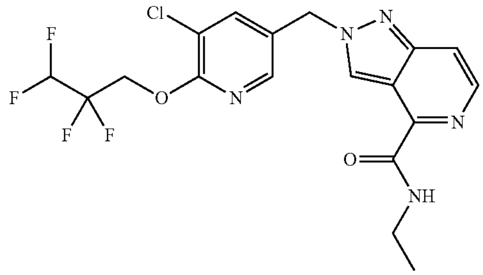 [SMILES: CCNC(=O)c1nccc2nn(Cc3cnc(OCC(F)(F)C(F)F)c(Cl)c3)cc12] | 2-((5-chloro-6-(2,2,3,3-tetrafluoropropoxy)pyridin-3-yl)methyl)-N-ethyl-2H-pyrazolo[4,3-c]pyridine-4-carboxamide |
| 450 | 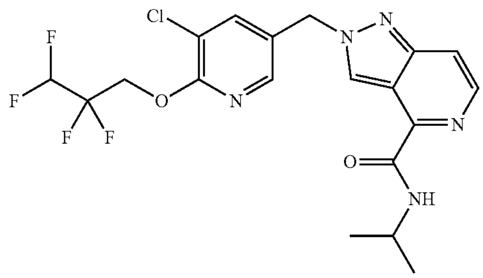 [SMILES: CC(C)NC(=O)c1nccc2nn(Cc3cnc(OCC(F)(F)C(F)F)c(Cl)c3)cc12] | 2-((5-chloro-6-(2,2,3,3-tetrafluoropropoxy)pyridin-3-yl)methyl)-N-isopropyl-2H-pyrazolo[4,3-c]pyridine-4-carboxamide |
| 451 | 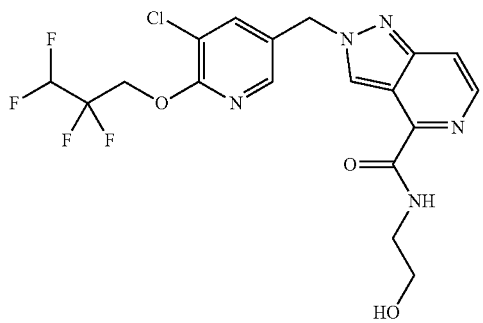 [SMILES: O=C(NCCO)c1nccc2nn(Cc3cnc(OCC(F)(F)C(F)F)c(Cl)c3)cc12] | 2-((5-chloro-6-(2,2,3,3-tetrafluoropropoxy)pyridin-3-yl)methyl)-N-(2-hydroxyethyl)-2H-pyrazolo[4,3-c]pyridine-4-carboxamide |
| 452 | 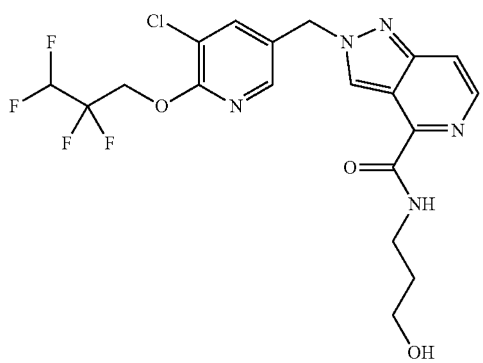 [SMILES: O=C(NCCCO)c1nccc2nn(Cc3cnc(OCC(F)(F)C(F)F)c(Cl)c3)cc12] | 2-((5-chloro-6-(2,2,3,3-tetrafluoropropoxy)pyridin-3-yl)methyl)-N-(3-hydroxypropyl)-2H-pyrazolo[4,3-c]pyridine-4-carboxamide |
| 453 | 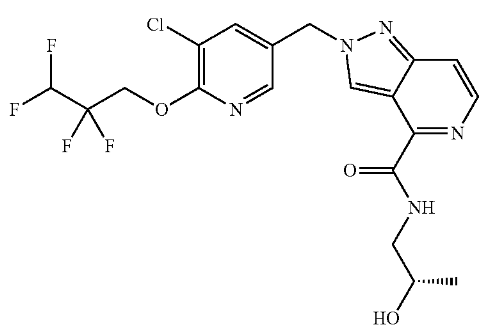 [SMILES: C[C@H](O)CNC(=O)c1nccc2nn(Cc3cnc(OCC(F)(F)C(F)F)c(Cl)c3)cc12] | (S)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide |

TABLE 7-continued

| Ex | Structure | Name |
|---|---|---|
| 454 | 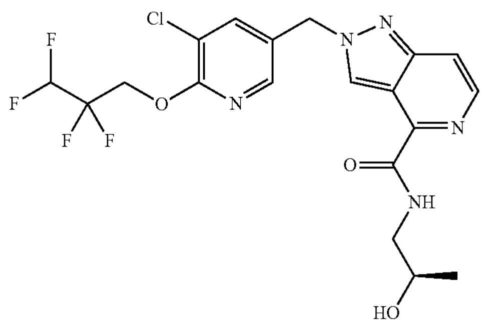 [SMILES: C[C@@H](O)CNC(=O)c1nccc2nn(Cc3cnc(OCC(F)(F)C(F)F)c(Cl)c3)cc12] | (R)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide |
| 455 | 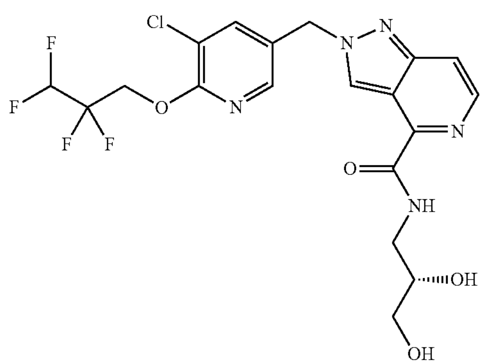 [SMILES: O=C(NC[C@H](O)CO)c1nccc2nn(Cc3cnc(OCC(F)(F)C(F)F)c(Cl)c3)cc12] | (S)-2-((5-chloro-6-(2,2,3,3-tetrafluoropropoxy)pyridin-3-yl)methyl)-N-(2,3-dihydroxypropyl)-2H-pyrazolo[4,3-c]pyridine-4-carboxamide |
| 456 | 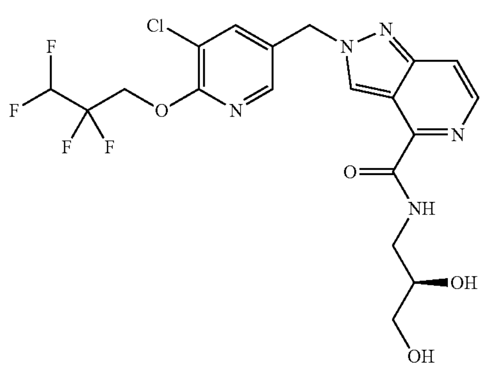 [SMILES: O=C(NC[C@@H](O)CO)c1nccc2nn(Cc3cnc(OCC(F)(F)C(F)F)c(Cl)c3)cc12] | (R)-2-((5-chloro-6-(2,2,3,3-tetrafluoropropoxy)pyridin-3-yl)methyl)-N-(2,3-dihydroxypropyl)-2H-pyrazolo[4,3-c]pyridine-4-carboxamide |
| 457 | 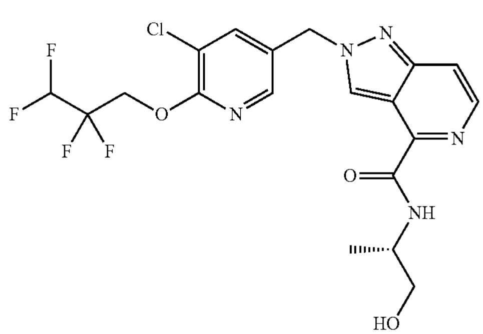 [SMILES: C[C@@H](CO)NC(=O)c1nccc2nn(Cc3cnc(OCC(F)(F)C(F)F)c(Cl)c3)cc12] | (S)-2-((5-chloro-6-(2,2,3,3-tetrafluoropropoxy)pyridin-3-yl)methyl)-N-(1-hydroxypropan-2-yl)-2H-pyrazolo[4,3-c]pyridine-4-carboxamide |

TABLE 7-continued

| Ex | Structure | Name |
|---|---|---|
| 458 | 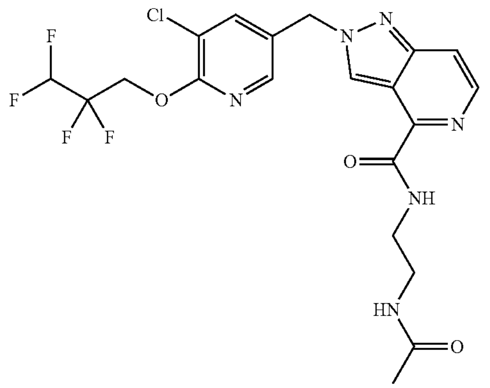 [SMILES: CC(=O)NCCNC(=O)c1nccc2nn(Cc3cnc(OCC(F)(F)C(F)F)c(Cl)c3)cc12] | N-(2-acetamidoethyl)-2-((5-chloro-6-(2,2,3,3-tetrafluoropropoxy)pyridin-3-yl)methyl)-2H-pyrazolo[4,3-c]pyridine-4-carboxamide |
| 459 | 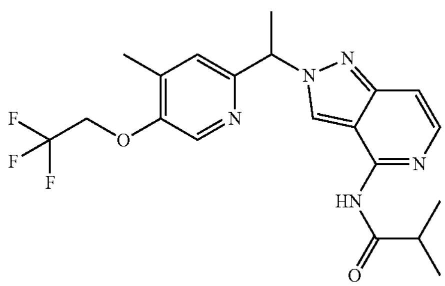 [SMILES: Cc1cc(C(C)n2cc3c(NC(=O)C(C)C)nccc3n2)ncc1OCC(F)(F)F] | N-(2-(1-(4-methyl-5-(2,2,2-trifluoroethoxy)pyridin-2-yl)ethyl)-2H-pyrazolo[4,3-c]pyridin-4-yl)isobutyramide (single enantiomer) |
| 460 | 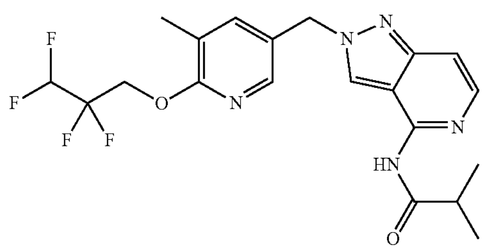 [SMILES: Cc1cc(Cn2cc3c(NC(=O)C(C)C)nccc3n2)cnc1OCC(F)(F)C(F)F] | N-(2-((5-methyl-6-(2,2,3,3-tetrafluoropropoxy)pyridin-3-yl)methyl)-2H-pyrazolo[4,3-c]pyridin-4-yl)isobutyramide |
| 461 | 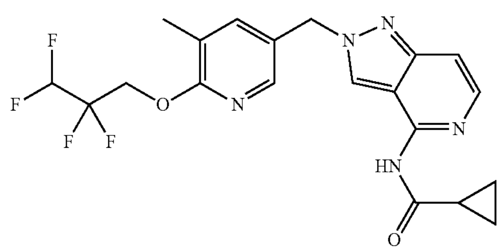 [SMILES: Cc1cc(Cn2cc3c(NC(=O)C4CC4)nccc3n2)cnc1OCC(F)(F)C(F)F] | N-(2-((5-methyl-6-(2,2,3,3-tetrafluoropropoxy)pyridin-3-yl)methyl)-2H-pyrazolo[4,3-c]pyridin-4-yl)cyclopropanecarboxamide |
| 462 | 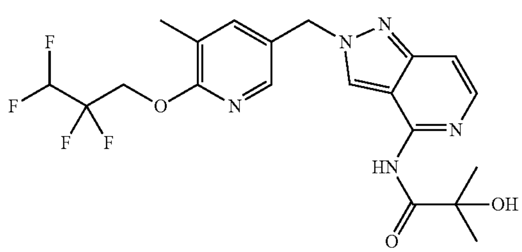 [SMILES: Cc1cc(Cn2cc3c(NC(=O)C(C)(C)O)nccc3n2)cnc1OCC(F)(F)C(F)F] | 2-hydroxy-2-methyl-N-(2-((5-methyl-6-(2,2,3,3-tetrafluoropropoxy)pyridin-3-yl)methyl)-2H-pyrazolo[4,3-c]pyridin-4-yl)propanamide |

| Ex | Structure | Name |
|---|---|---|
| 463 | 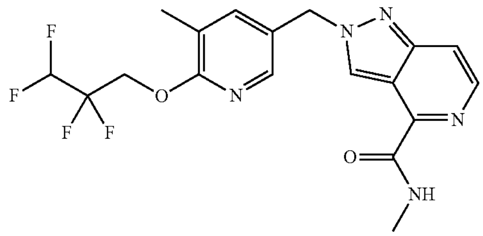 [SMILES: CNC(=O)c1nccc2nn(Cc3cnc(OCC(F)(F)C(F)F)c(C)c3)cc12] | N-methyl-2-((5-methyl-6-(2,2,3,3-tetrafluoropropoxy)pyridin-3-yl)methyl)-2H-pyrazolo[4,3-c]pyridine-4-carboxamide |
| 464 | 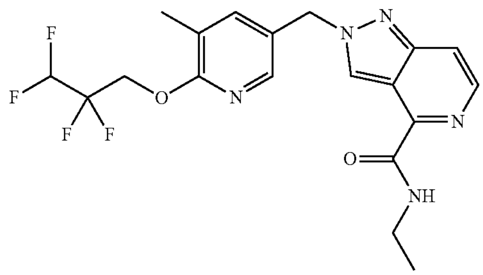 [SMILES: CCNC(=O)c1nccc2nn(Cc3cnc(OCC(F)(F)C(F)F)c(C)c3)cc12] | N-ethyl-2-((5-methyl-6-(2,2,3,3-tetrafluoropropoxy)pyridin-3-yl)methyl)-2H-pyrazolo[4,3-c]pyridine-4-carboxamide |
| 465 | 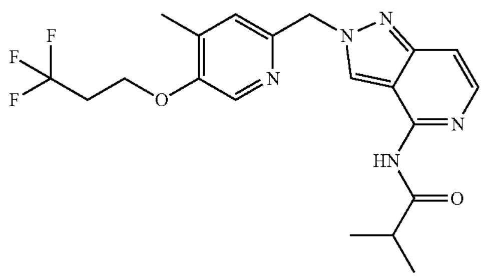 [SMILES: Cc1cc(Cn2cc3c(NC(=O)C(C)C)nccc3n2)ncc1OCCC(F)(F)F] | N-(2-((4-methyl-5-(3,3,3-trifluoropropoxy)pyridin-2-yl)methyl)-2H-pyrazolo[4,3-c]pyridin-4-yl)isobutyramide |
| 466 | 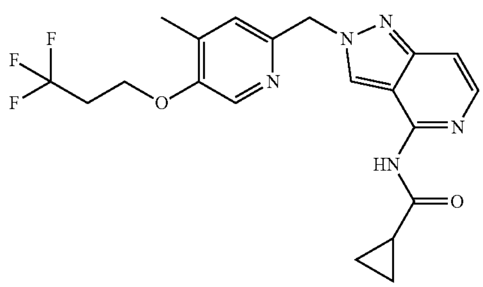 [SMILES: Cc1cc(Cn2cc3c(NC(=O)C4CC4)nccc3n2)ncc1OCCC(F)(F)F] | N-(2-((4-methyl-5-(3,3,3-trifluoropropoxy)pyridin-2-yl)methyl)-2H-pyrazolo[4,3-c]pyridin-4-yl)cyclopropanecarboxamide |
| 467 | 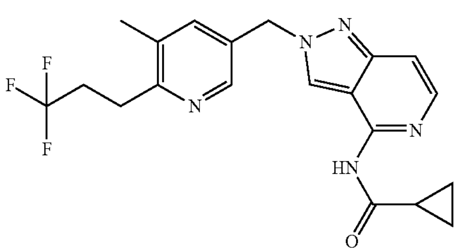 [SMILES: Cc1cc(Cn2cc3c(NC(=O)C4CC4)nccc3n2)cnc1CCC(F)(F)F] | N-(2-((5-methyl-6-(3,3,3-trifluoropropyl)pyridin-3-yl)methyl)-2H-pyrazolo[4,3-c]pyridin-4-yl)cyclopropanecarboxamide |
| 468 | 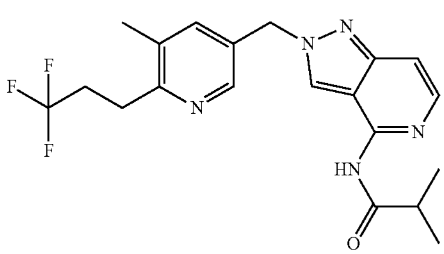 [SMILES: Cc1cc(Cn2cc3c(NC(=O)C(C)C)nccc3n2)cnc1CCC(F)(F)F] | N-(2-((5-methyl-6-(3,3,3-trifluoropropyl)pyridin-3-yl)methyl)-2H-pyrazolo[4,3-c]pyridin-4-yl)isobutyramide |

| Ex | Structure | Name |
|---|---|---|
| 469 | 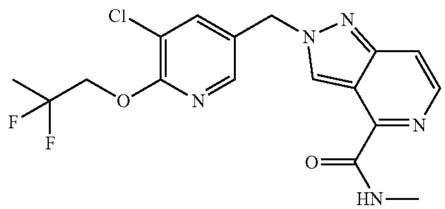 [SMILES: CNC(=O)c1nccc2nn(Cc3cnc(OCC(C)(F)F)c(Cl)c3)cc12] | 2-((5-chloro-6-(2,2-difluoropropoxy)pyridin-3-yl)methyl)-N-methyl-2H-pyrazolo[4,3-c]pyridine-4-carboxamide |
| 470 | 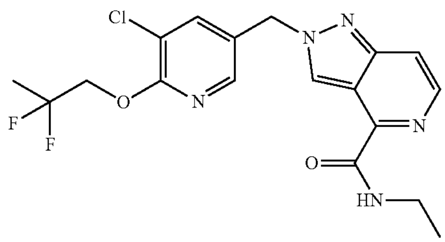 | 2-((5-chloro-6-(2,2-difluoropropoxy)pyridin-3-yl)methyl)-N-ethyl-2H-pyrazolo[4,3-c]pyridine-4-carboxamide |
| 471 | 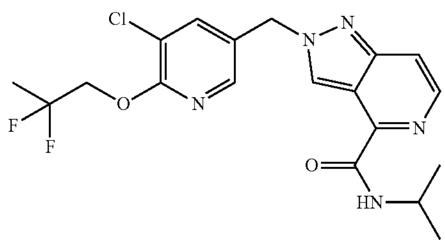 [SMILES: CC(C)NC(=O)c1nccc2nn(Cc3cnc(OCC(C)(F)F)c(Cl)c3)cc12] | 2-((5-chloro-6-(2,2-difluoropropoxy)pyridin-3-yl)methyl)-N-isopropyl-2H-pyrazolo[4,3-c]pyridine-4-carboxamide |
| 472 | 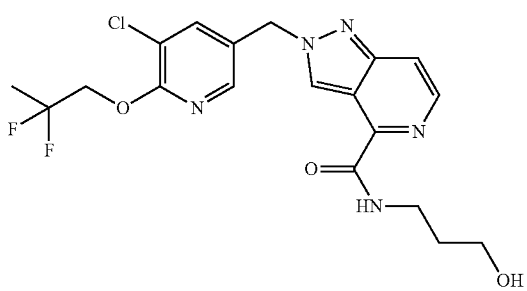 [SMILES: CC(F)(F)COc1ncc(Cn2cc3c(C(=O)NCCCO)nccc3n2)cc1Cl] | 2-((5-chloro-6-(2,2-difluoropropoxy)pyridin-3-yl)methyl)-N-(3-hydroxypropyl)-2H-pyrazolo[4,3-c]pyridine-4-carboxamide |
| 473 | 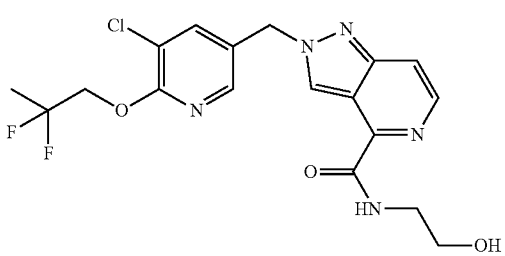 [SMILES: CC(F)(F)COc1ncc(Cn2cc3c(C(=O)NCCO)nccc3n2)cc1Cl] | 2-((5-chloro-6-(2,2-difluoropropoxy)pyridin-3-yl)methyl)-N-(2-hydroxyethyl)-2H-pyrazolo[4,3-c]pyridine-4-carboxamide |
| 474 | 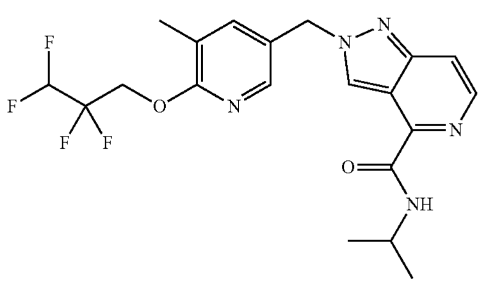 [SMILES: Cc1cc(Cn2cc3c(C(=O)NC(C)C)nccc3n2)cnc1OCC(F)(F)C(F)F] | N-isopropyl-2-((5-methyl-6-(2,2,3,3-tetrafluoropropoxy)pyridin-3-yl)methyl)-2H-pyrazolo[4,3-c]pyridine-4-carboxamide |

TABLE 7-continued

| Ex | Structure | Name |
|---|---|---|
| 475 | 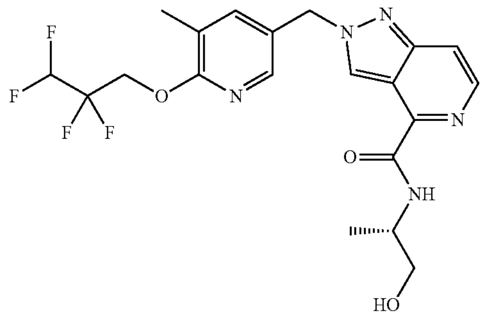 [SMILES: Cc1cc(Cn2cc3c(C(=O)N[C@@H](C)CO)nccc3n2)cnc1OCC(F)(F)C(F)F] | (S)-N-(1-hydroxypropan-2-yl)-2-((5-methyl-6-(2,2,3,3-tetrafluoropropoxy)pyridin-3-yl)methyl)-2H-pyrazolo[4,3-c]pyridine-4-carboxamide |
| 476 | 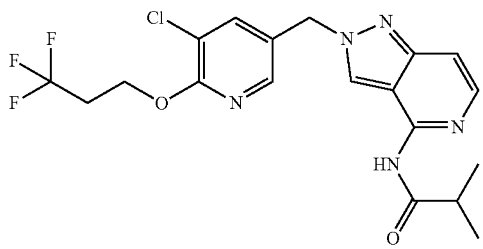 [SMILES: CC(C)C(=O)Nc1nccc2nn(Cc3cnc(OCCC(F)(F)F)c(Cl)c3)cc12] | N-(2-((5-chloro-6-(3,3,3-trifluoropropoxy)pyridin-3-yl)methyl)-2H-pyrazolo[4,3-c]pyridin-4-yl)isobutyramide |
| 477 | 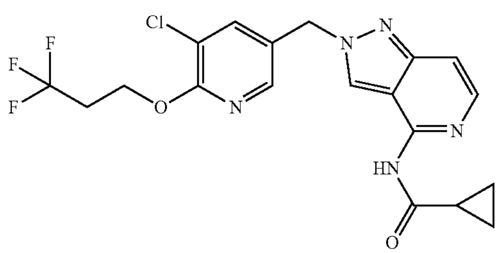 [SMILES: O=C(Nc1nccc2nn(Cc3cnc(OCCC(F)(F)F)c(Cl)c3)cc12)C1CC1] | N-(2-((5-chloro-6-(3,3,3-trifluoropropoxy)pyridin-3-yl)methyl)-2H-pyrazolo[4,3-c]pyridin-4-yl)cyclopropanecarboxamide |
| 478 | 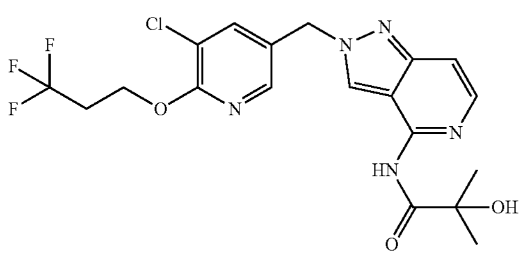 [SMILES: CC(C)(O)C(=O)Nc1nccc2nn(Cc3cnc(OCCC(F)(F)F)c(Cl)c3)cc12] | N-(2-((5-chloro-6-(3,3,3-trifluoropropoxy)pyridin-3-yl)methyl)-2H-pyrazolo[4,3-c]pyridin-4-yl)-2-hydroxy-2-methylpropanamide |
| 479 | 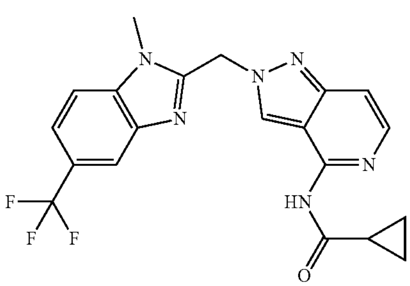 [SMILES: Cn1c(Cn2cc3c(NC(=O)C4CC4)nccc3n2)nc2cc(C(F)(F)F)ccc21] | N-(2-((1-methyl-5-(trifluoromethyl)-1H-benzo[d]imidazol-2-yl)methyl)-2H-pyrazolo[4,3-c]pyridin-4-yl)cyclopropanecarboxamide |

TABLE 7-continued

| Ex | Structure | Name |
|---|---|---|
| 480 | 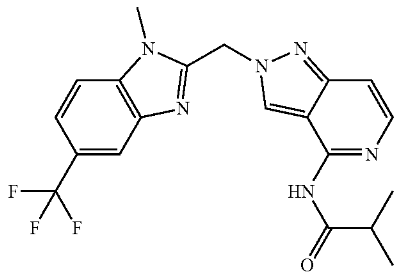 [SMILES: CC(C)C(=O)Nc1nccc2nn(Cc3nc4cc(C(F)(F)F)ccc4n3C)cc12] | N-(2-((1-methyl-5-(trifluoromethyl)-1H-benzo[d]imidazol-2-yl)methyl)-2H-pyrazolo[4,3-c]pyridin-4-yl)isobutyramide |
| 481 | 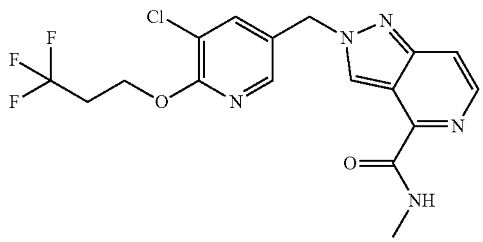 [SMILES: CNC(=O)c1nccc2nn(Cc3cnc(OCCC(F)(F)F)c(Cl)c3)cc12] | 2-((5-chloro-6-(3,3,3-trifluoropropoxy)pyridin-3-yl)methyl)-N-methyl-2H-pyrazolo[4,3-c]pyridine-4-carboxamide |
| 482 | 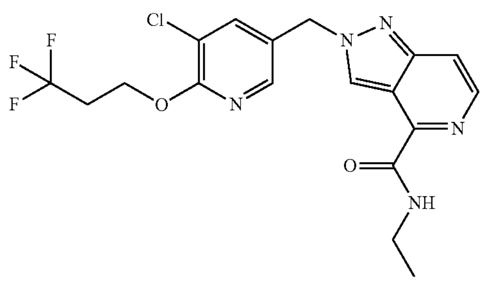 [SMILES: CCNC(=O)c1nccc2nn(Cc3cnc(OCCC(F)(F)F)c(Cl)c3)cc12] | 2-((5-chloro-6-(3,3,3-trifluoropropoxy)pyridin-3-yl)methyl)-N-ethyl-2H-pyrazolo[4,3-c]pyridine-4-carboxamide |
| 483 | 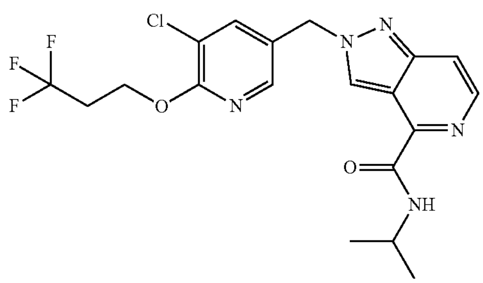 [SMILES: CC(C)NC(=O)c1nccc2nn(Cc3cnc(OCCC(F)(F)F)c(Cl)c3)cc12] | 2-((5-chloro-6-(3,3,3-trifluoropropoxy)pyridin-3-yl)methyl)-N-isopropyl-2H-pyrazolo[4,3-c]pyridine-4-carboxamide |
| 484 | 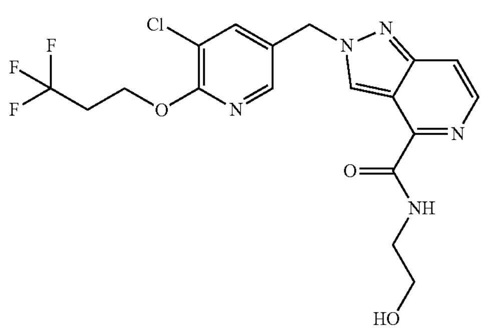 [SMILES: O=C(NCCO)c1nccc2nn(Cc3cnc(OCCC(F)(F)F)c(Cl)c3)cc12] | 2-((5-chloro-6-(3,3,3-trifluoropropoxy)pyridin-3-yl)methyl)-N-(2-hydroxyethyl)-2H-pyrazolo[4,3-c]pyridine-4-carboxamide |

TABLE 7-continued

| Ex | Structure | Name |
|---|---|---|
| 485 | 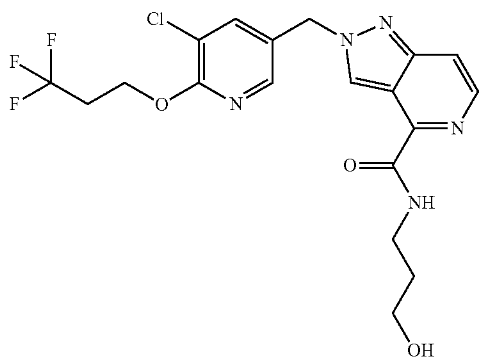 [SMILES: O=C(NCCCO)c1nccc2nn(Cc3cnc(OCCC(F)(F)F)c(Cl)c3)cc12] | 2-((5-chloro-6-(3,3,3-trifluoropropoxy)pyridin-3-yl)methyl)-N-(3-hydroxypropyl)-2H-pyrazolo[4,3-c]pyridine-4-carboxamide |
| 486 | 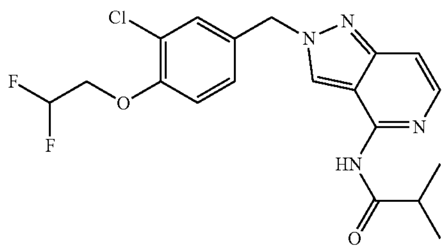 [SMILES: CC(C)C(=O)Nc1nccc2nn(Cc3ccc(OCC(F)F)c(Cl)c3)cc12] | N-(2-(3-chloro-4-(2,2-difluoroethoxy)benzyl)-2H-pyrazolo[4,3-c]pyridin-4-yl)isobutyramide |
| 487 | 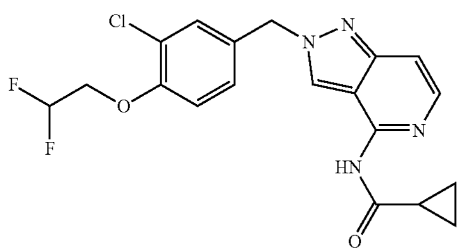 [SMILES: O=C(Nc1nccc2nn(Cc3ccc(OCC(F)F)c(Cl)c3)cc12)C1CC1] | N-(2-(3-chloro-4-(2,2-difluoroethoxy)benzyl)-2H-pyrazolo[4,3-c]pyridin-4-yl)cyclopropanecarboxamide |
| 488 | 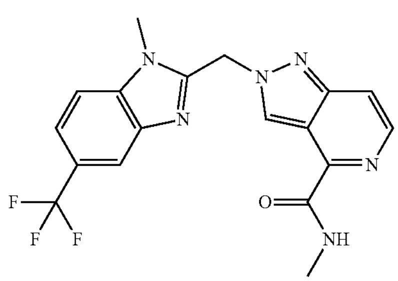 [SMILES: CNC(=O)c1nccc2nn(Cc3nc4cc(C(F)(F)F)ccc4n3C)cc12] | N-methyl-2-((1-methyl-5-(trifluoromethyl)-1H-benzo[d]imidazol-2-yl)methyl)-2H-pyrazolo[4,3-c]pyridine-4-carboxamide |
| 489 | 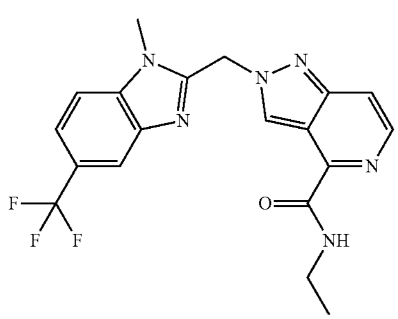 [SMILES: CCNC(=O)c1nccc2nn(Cc3nc4cc(C(F)(F)F)ccc4n3C)cc12] | N-ethyl-2-((1-methyl-5-(trifluoromethyl)-1H-benzo[d]imidazol-2-yl)methyl)-2H-pyrazolo[4,3-c]pyridine-4-carboxamide |

TABLE 7-continued

| Ex | Structure | Name |
|---|---|---|
| 490 | 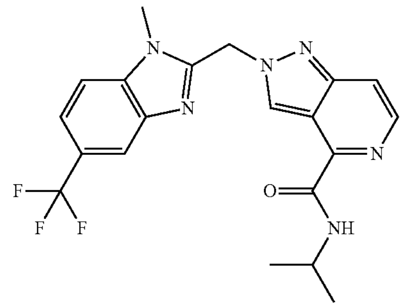 [SMILES: CC(C)NC(=O)c1nccc2nn(Cc3nc4cc(C(F)(F)F)ccc4n3C)cc12] | N-isopropyl-2-((1-methyl-5-(trifluoromethyl)-1H-benzo[d]imidazol-2-yl)methyl)-2H-pyrazolo[4,3-c]pyridine-4-carboxamide |
| 491 | 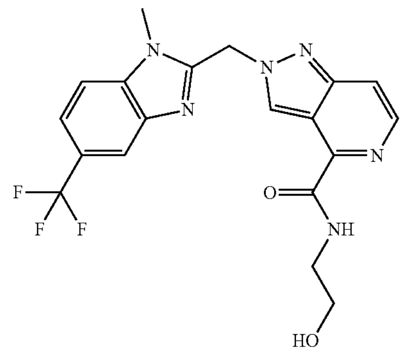 [SMILES: Cn1c(Cn2cc3c(C(=O)NCCO)nccc3n2)nc2cc(C(F)(F)F)ccc21] | N-(2-hydroxyethyl)-2-((1-methyl-5-(trifluoromethyl)-1H-benzo[d]imidazol-2-yl)methyl)-2H-pyrazolo[4,3-c]pyridine-4-carboxamide |
| 492 | 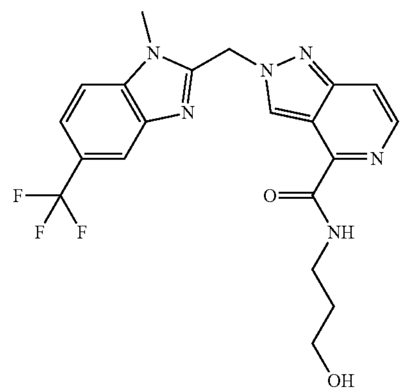 [SMILES: Cn1c(Cn2cc3c(C(=O)NCCCO)nccc3n2)nc2cc(C(F)(F)F)ccc21] | N-(3-hydroxypropyl)-2-((1-methyl-5-(trifluoromethyl)-1H-benzo[d]imidazol-2-yl)methyl)-2H-pyrazolo[4,3-c]pyridine-4-carboxamide |
| 493 | 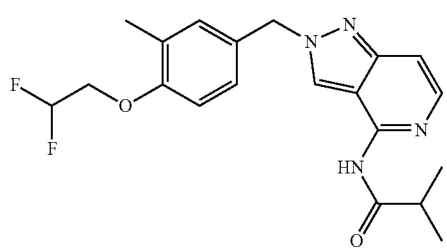 [SMILES: Cc1cc(Cn2cc3c(NC(=O)C(C)C)nccc3n2)ccc1OCC(F)F] | N-(2-(4-(2,2-difluoroethoxy)-3-methylbenzyl)-2H-pyrazolo[4,3-c]pyridin-4-yl)isobutyramide |
| 494 | 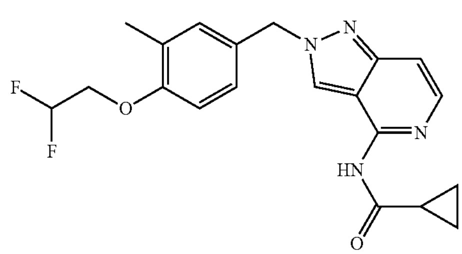 [SMILES: Cc1cc(Cn2cc3c(NC(=O)C4CC4)nccc3n2)ccc1OCC(F)F] | N-(2-(4-(2,2-difluoroethoxy)-3-methylbenzyl)-2H-pyrazolo[4,3-c]pyridin-4-yl)cyclopropanecarboxamide |

TABLE 7-continued

| Ex | Structure | Name |
|---|---|---|
| 495 | 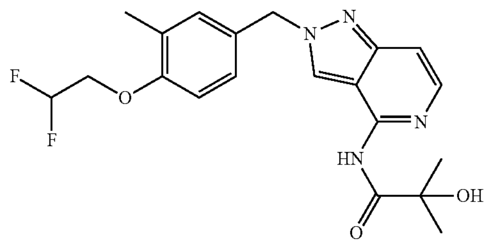 [SMILES: Cc1cc(Cn2cc3c(NC(=O)C(C)(C)O)nccc3n2)ccc1OCC(F)F] | N-(2-(4-(2,2-difluoroethoxy)-3-methylbenzyl)-2H-pyrazolo[4,3-c]pyridin-4-yl)-2-hydroxy-2-methylpropanamide |
| 496 | 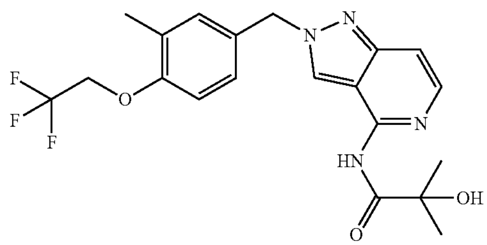 [SMILES: Cc1cc(Cn2cc3c(NC(=O)C(C)(C)O)nccc3n2)ccc1OCC(F)(F)F] | 2-hydroxy-2-methyl-N-(2-(3-methyl-4-(2,2,2-trifluoroethoxy)benzyl)-2H-pyrazolo[4,3-c]pyridin-4-yl)propanamide |
| 497 | 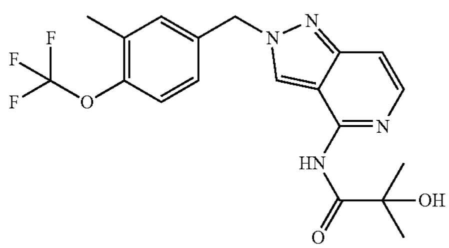 [SMILES: Cc1cc(Cn2cc3c(NC(=O)C(C)(C)O)nccc3n2)ccc1OC(F)(F)F] | 2-hydroxy-2-methyl-N-(2-(3-methyl-4-(trifluoromethoxy)benzyl)-2H-pyrazolo[4,3-c]pyridin-4-yl)propanamide |
| 498 | 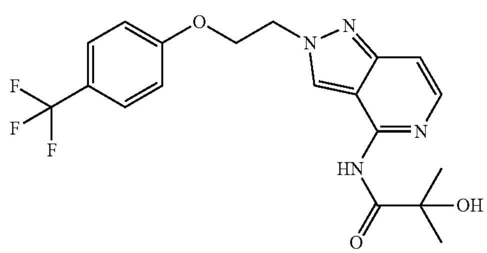 [SMILES: CC(C)(O)C(=O)Nc1nccc2nn(CCOc3ccc(C(F)(F)F)cc3)cc12] | 2-hydroxy-2-methyl-N-(2-(2-(4-(trifluoromethyl)phenoxy)ethyl)-2H-pyrazolo[4,3-c]pyridin-4-yl)propanamide |
| 499 | 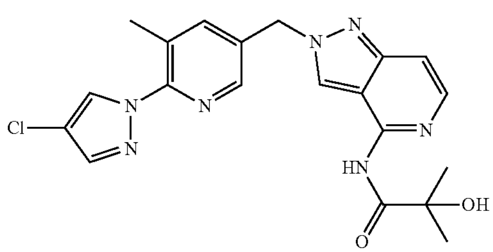 [SMILES: Cc1cc(Cn2cc3c(NC(=O)C(C)(C)O)nccc3n2)cnc1-n1cc(Cl)cn1] | N-(2-((6-(4-chloro-1H-pyrazol-1-yl)-5-methylpyridin-3-yl)methyl)-2H-pyrazolo[4,3-c]pyridin-4-yl)-2-hydroxy-2-methylpropanamide |
| 500 | 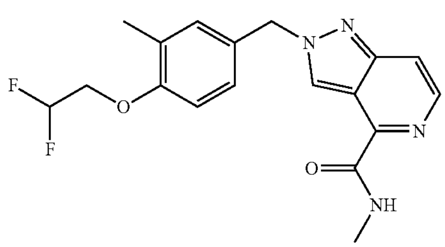 [SMILES: CNC(=O)c1nccc2nn(Cc3ccc(OCC(F)F)c(C)c3)cc12] | 2-(4-(2,2-difluoroethoxy)-3-methylbenzyl)-N-methyl-2H-pyrazolo[4,3-c]pyridine-4-carboxamide |

TABLE 7-continued

| Ex | Structure | Name |
|---|---|---|
| 501 | 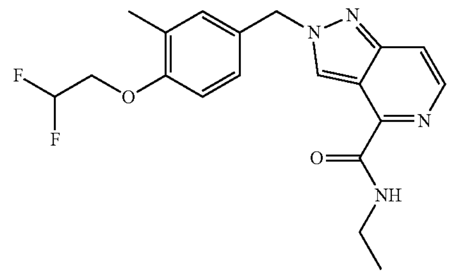 [SMILES: CCNC(=O)c1nccc2nn(Cc3ccc(OCC(F)F)c(C)c3)cc12] | 2-(4-(2,2-difluoroethoxy)-3-methylbenzyl)-N-ethyl-2H-pyrazolo[4,3-c]pyridine-4-carboxamide |
| 502 | 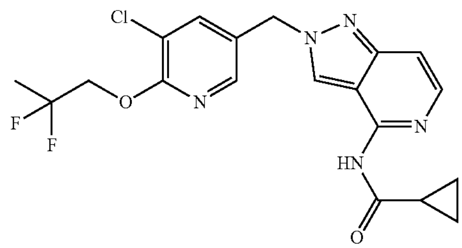 [SMILES: CC(F)(F)COc1ncc(Cn2cc3c(NC(=O)C4CC4)nccc3n2)cc1Cl] | N-(2-((5-chloro-6-(2,2-difluoropropoxy)pyridin-3-yl)methyl)-2H-pyrazolo[4,3-c]pyridin-4-yl)cyclopropanecarboxamide |
| 503 | 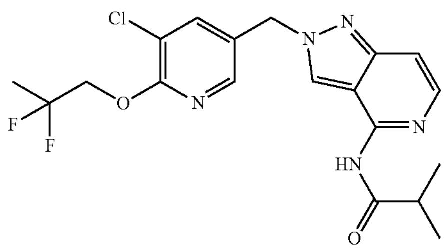 | N-(2-((5-chloro-6-(2,2-difluoropropoxy)pyridin-3-yl)methyl)-2H-pyrazolo[4,3-c]pyridin-4-yl)isobutyramide |
| 504 | 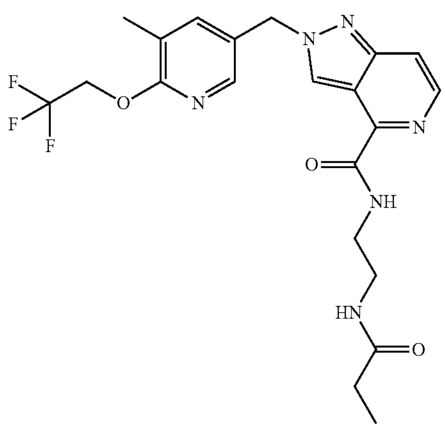 [SMILES: CCC(=O)NCCNC(=O)c1nccc2nn(Cc3cnc(OCC(F)(F)F)c(C)c3)cc12] | 2-((5-methyl-6-(2,2,2-trifluoroethoxy)pyridin-3-yl)methyl)-N-(2-propionamidoethyl)-2H-pyrazolo[4,3-c]pyridine-4-carboxamide |
| 505 | 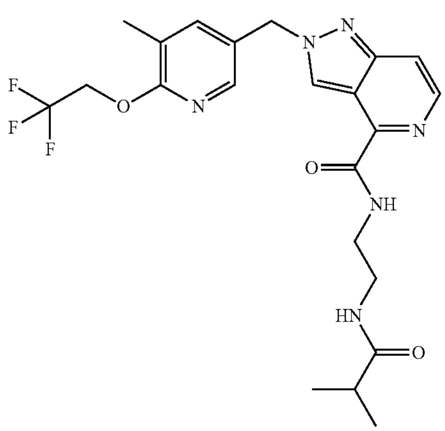 [SMILES: Cc1cc(Cn2cc3c(C(=O)NCCNC(=O)C(C)C)nccc3n2)cnc1OCC(F)(F)F] | N-(2-isobutyramidoethyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 506 | 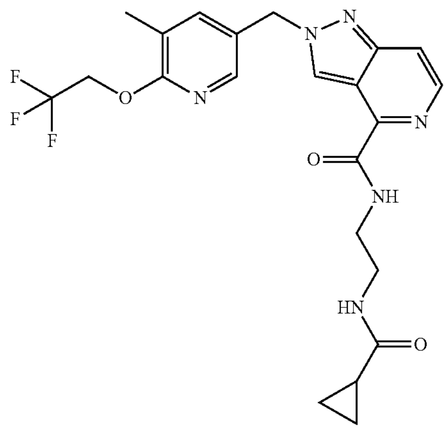 [SMILES: Cc1cc(Cn2cc3c(C(=O)NCCNC(=O)C4CC4)nccc3n2)cnc1OCC(F)(F)F] | N-(2-(cyclopropanecarboxamido)ethyl)-2-((5-methyl-6-(2,2,2-trifluoroethoxy)pyridin-3-yl)methyl)-2H-pyrazolo[4,3-c]pyridine-4-carboxamide |
| 507 | 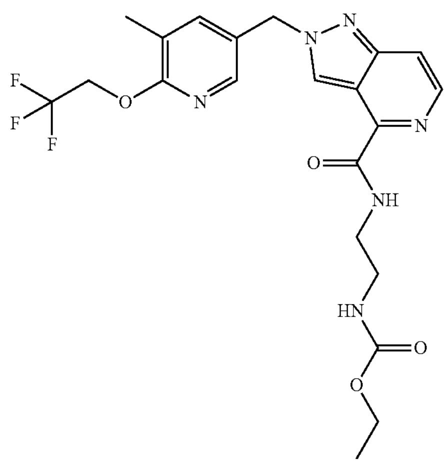 [SMILES: CCOC(=O)NCCNC(=O)c1nccc2nn(Cc3cnc(OCC(F)(F)F)c(C)c3)cc12] | ethyl 2-(2-((5-methyl-6-(2,2,2-trifluoroethoxy)pyridin-3-yl)methyl)-2H-pyrazolo[4,3-c]pyridine-4-carboxamido)ethyl)carbamate |
| 508 | 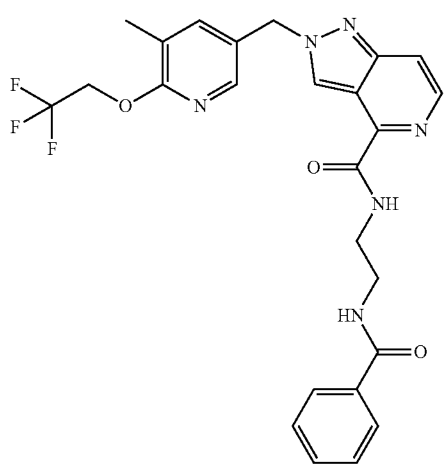 [SMILES: Cc1cc(Cn2cc3c(C(=O)NCCNC(=O)c4ccccc4)nccc3n2)cnc1OCC(F)(F)F] | N-(2-benzamidoethyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 509 | 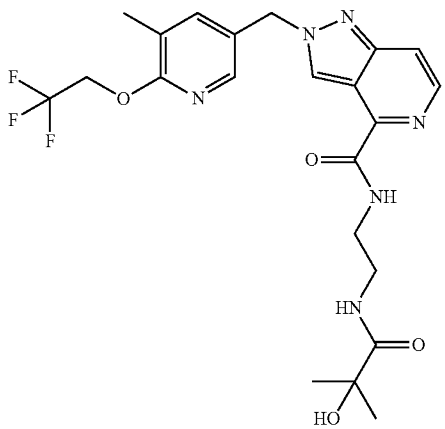 [SMILES: Cc1cc(Cn2cc3c(C(=O)NCCNC(=O)C(C)(C)O)nccc3n2)cnc1OCC(F)(F)F] | N-(2-(2-hydroxy-2-methylpropanamido)ethyl)-2-((5-methyl-6-(2,2,2-trifluoroethoxy)pyridin-3-yl)methyl)-2H-pyrazolo[4,3-c]pyridine-4-carboxamide |
| 510 | 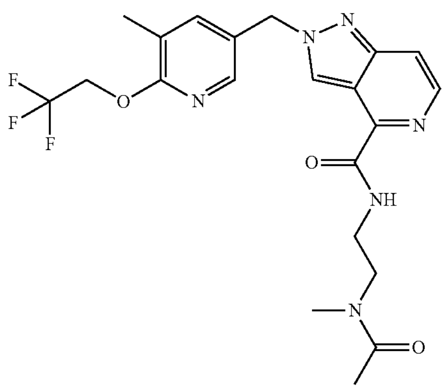 [SMILES: CC(=O)N(C)CCNC(=O)c1nccc2nn(Cc3cnc(OCC(F)(F)F)c(C)c3)cc12] | 2-((5-methyl-6-(2,2,2-trifluoroethoxy)pyridin-3-yl)methyl)-N-(2-(N-methylacetamido)ethyl)-2H-pyrazolo[4,3-c]pyridine-4-carboxamide |
| 511 | 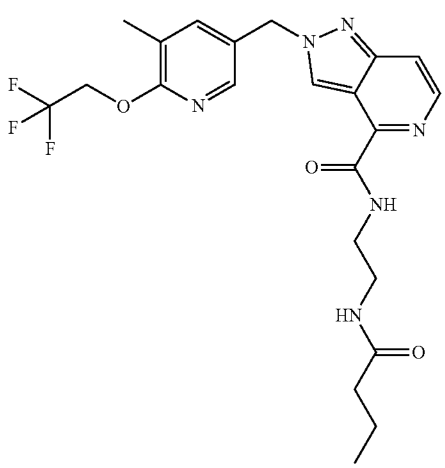 [SMILES: CCCC(=O)NCCNC(=O)c1nccc2nn(Cc3cnc(OCC(F)(F)F)c(C)c3)cc12] | N-(2-butyramidoethyl)-2-((5-methyl-6-(2,2,2-trifluoroethoxy)pyridin-3-yl)methyl)-2H-pyrazolo[4,3-c]pyridine-4-carboxamide |

TABLE 7-continued
| Ex | Structure | Name |
|---|---|---|
| 512 | 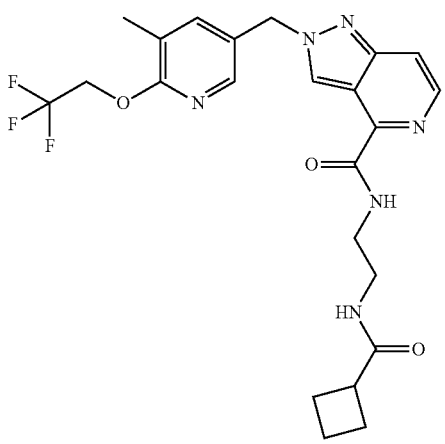 [SMILES: Cc1cc(Cn2cc3c(C(=O)NCCNC(=O)C4CCC4)nccc3n2)cnc1OCC(F)(F)F] | N-(2-(cyclobutanecarboxamido)ethyl)-2-((5-methyl-6-(2,2,2-trifluoroethoxy)pyridin-3-yl)methyl)-2H-pyrazolo[4,3-c]pyridine-4-carboxamide |
| 513 | 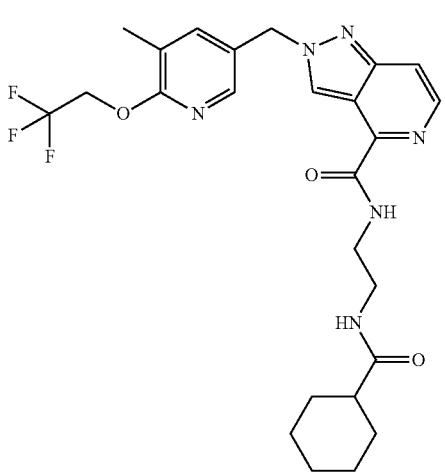 [SMILES: Cc1cc(Cn2cc3c(C(=O)NCCNC(=O)C4CCCCC4)nccc3n2)cnc1OCC(F)(F)F] | N-(2-(cyclohexanecarboxamido)ethyl)-2-((5-methyl-6-(2,2,2-trifluoroethoxy)pyridin-3-yl)methyl)-2H-pyrazolo[4,3-c]pyridine-4-carboxamide |
| 514 | 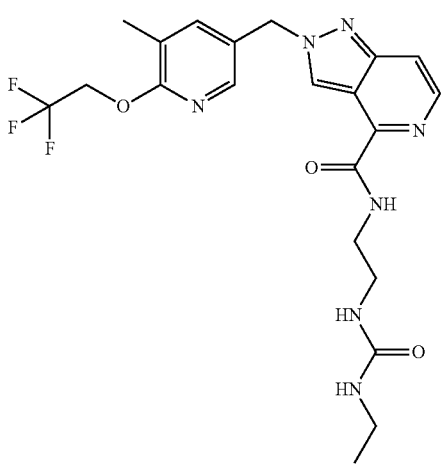 [SMILES: CCNC(=O)NCCNC(=O)c1nccc2nn(Cc3cnc(OCC(F)(F)F)c(C)c3)cc12] | N-(2-(3-ethylureido)ethyl)-2-((5-methyl-6-(2,2,2-trifluoroethoxy)pyridin-3-yl)methyl)-2H-pyrazolo[4,3-c]pyridine-4-carboxamide |

TABLE 7-continued

| Ex | Structure | Name |
|---|---|---|
| 515 | 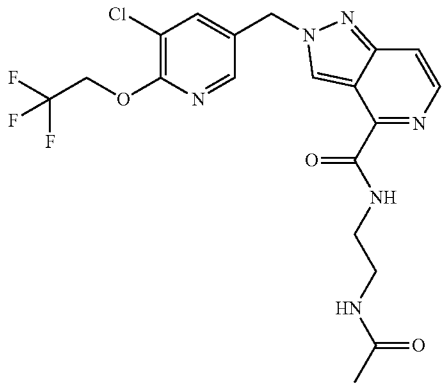 [SMILES: CC(=O)NCCNC(=O)c1nccc2nn(Cc3cnc(OCC(F)(F)F)c(Cl)c3)cc12] | N-(2-acetamidoethyl)-2-((5-chloro-6-(2,2,2-trifluoroethoxy)pyridin-3-yl)methyl)-2H-pyrazolo[4,3-c]pyridine-4-carboxamide |
| 516 | 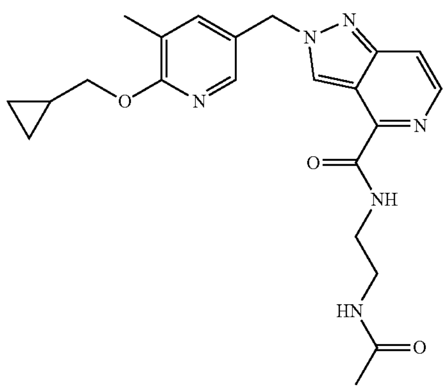 [SMILES: CC(=O)NCCNC(=O)c1nccc2nn(Cc3cnc(OCC4CC4)c(C)c3)cc12] | N-(2-acetamidoethyl)-2-((6-(cyclopropylmethoxy)-5-methylpyridin-3-yl)methyl)-2H-pyrazolo[4,3-c]pyridine-4-carboxamide |
| 517 | 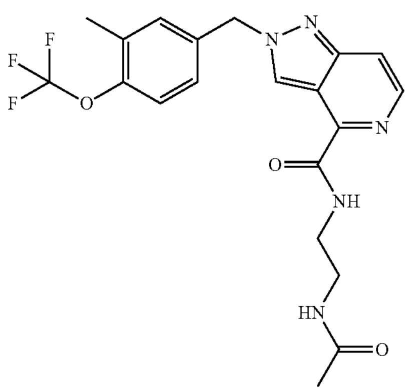 [SMILES: CC(=O)NCCNC(=O)c1nccc2nn(Cc3ccc(OC(F)(F)F)c(C)c3)cc12] | N-(2-acetamidoethyl)-2-(3-methyl-4-(trifluoromethoxy)benzyl)-2H-pyrazolo[4,3-c]pyridine-4-carboxamide |
| 518 | 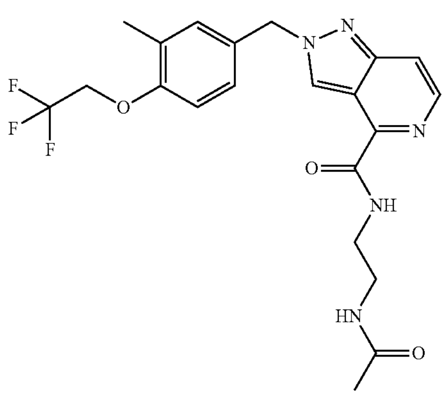 [SMILES: CC(=O)NCCNC(=O)c1nccc2nn(Cc3ccc(OCC(F)(F)F)c(C)c3)cc12] | N-(2-acetamidoethyl)-2-(3-methyl-4-(2,2,2-trifluoroethoxy)benzyl)-2H-pyrazolo[4,3-c]pyridine-4-carboxamide |

TABLE 7-continued

| Ex | Structure | Name |
|---|---|---|
| 519 | 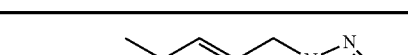 | N-(2-acetamidoethyl)-2-(4-(2,2-difluoroethoxy)-3-methylbenzyl)-2H-pyrazolo[4,3-c]pyridine-4-carboxamide |
| 520 | 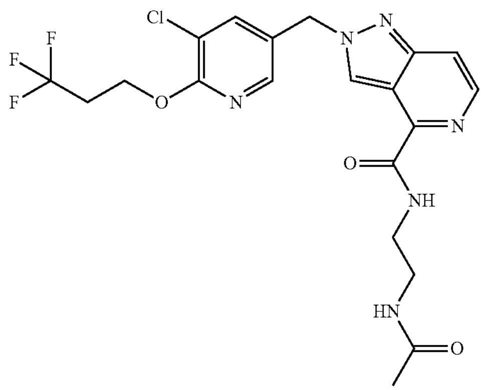 [SMILES: CC(=O)NCCNC(=O)c1nccc2nn(Cc3cnc(OCCC(F)(F)F)c(Cl)c3)cc12] | N-(2-acetamidoethyl)-2-((5-chloro-6-(3,3,3-trifluoropropoxy)pyridin-3-yl)methyl)-2H-pyrazolo[4,3-c]pyridine-4-carboxamide |
| 521 | 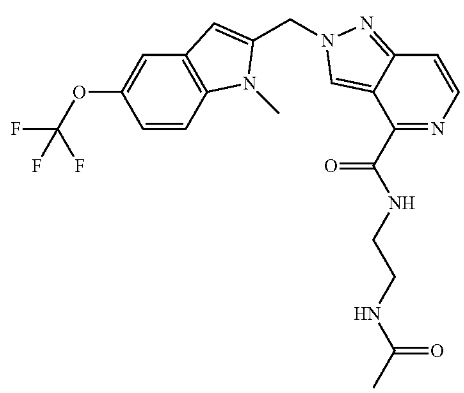 [SMILES: CC(=O)NCCNC(=O)c1nccc2nn(Cc3cc4cc(OC(F)(F)F)ccc4n3C)cc12] | N-(2-acetamidoethyl)-2-((1-methyl-5-(trifluoromethoxy)-1H-indol-2-yl)methyl)-2H-pyrazolo[4,3-c]pyridine-4-carboxamide |

| Ex | Starting Material | Reagent | method |
|---|---|---|---|
| 2 | 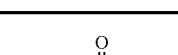

Intermediate-1a | | G |

TABLE 7-continued
| Ex | Structure | | Name | |
|----|-----------|---|------|---|
| 3 | 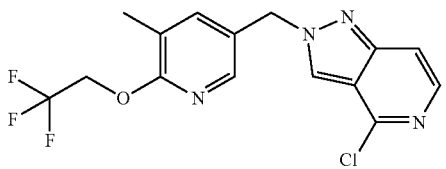<br>Intermediate-1a | | 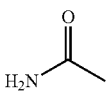 | G |
| 4 | 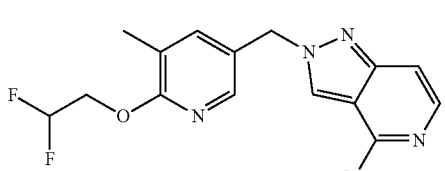<br>Intermediate-2a | | 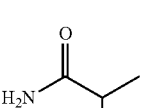 | G |
| 5 | 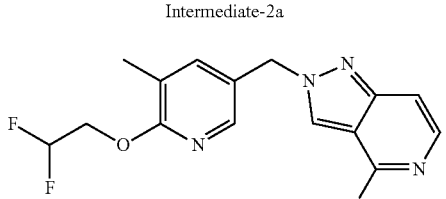<br>Intermediate-2a | |  | G |
| 6 | 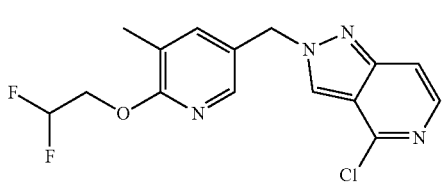<br>Intermediate-2a | | 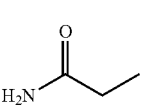 | G |
| 7 | 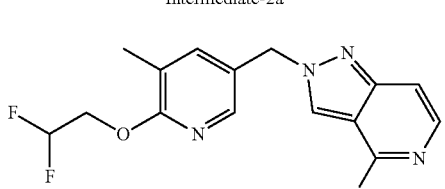<br>Intermediate-2a | | 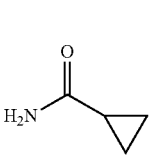 | G |
| 8 | 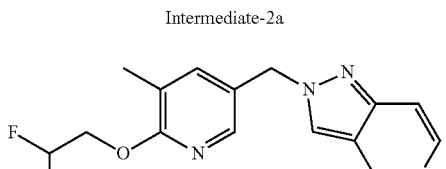<br>Intermediate-2a | | 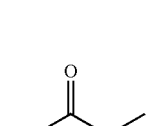 | G |
| 9 | 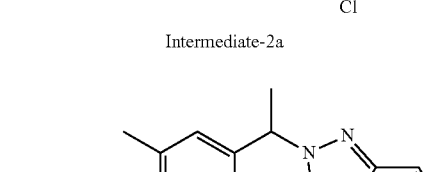<br>Intermediate-3a | |  | G |

TABLE 7-continued
| Ex | Structure | Name | |
|---|---|---|---|
| 10 | 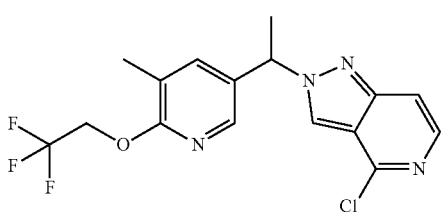 Intermediate-3a | 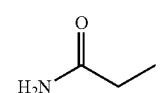 | G |
| 11 | 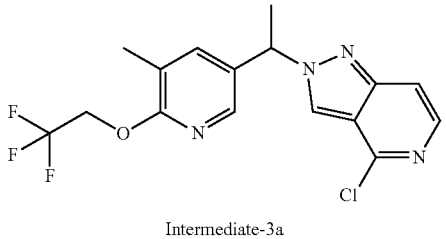 Intermediate-3a | 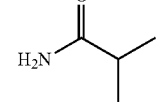 | G |
| 12 | 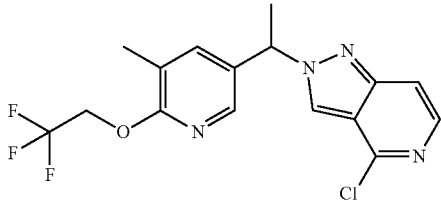 Intermediate-3a | 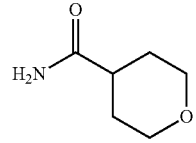 | G |
| 13 | 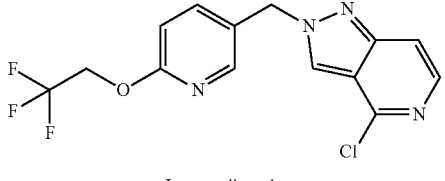 Intermediate-4a | 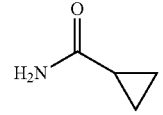 | G |
| 14 | 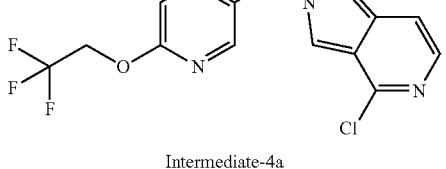 Intermediate-4a | 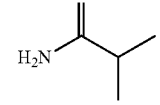 | G |
| 15 | 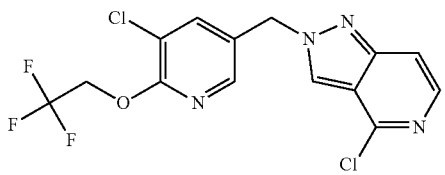 Intermediate-5a | 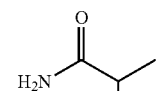 | G |

TABLE 7-continued
| Ex | Structure | | Name | |
|---|---|---|---|---|
| 16 | 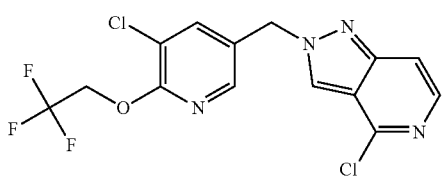<br>Intermediate-5a | | 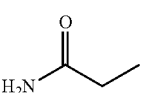 | G |
| 17 | 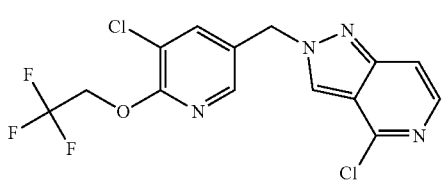<br>Intermediate-5a | | 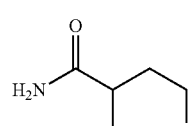 | G |
| 18 | 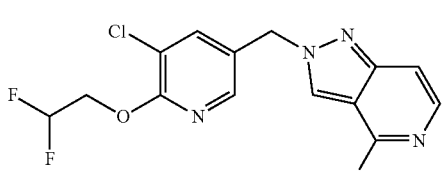<br>Intermediate-6a | | 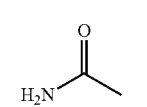 | G |
| 19 | 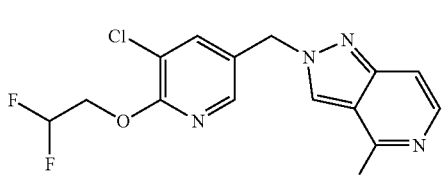<br>Intermediate-6a | | 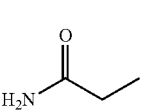 | G |
| 20 | 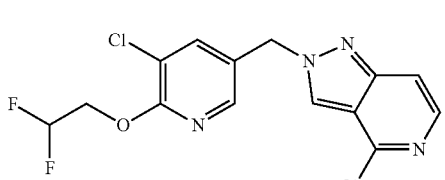<br>Intermediate-6a | | 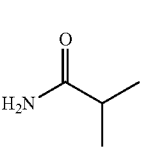 | G |
| 21 | 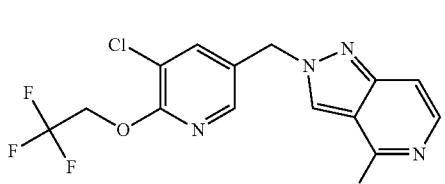<br>Intermediate-5a | | 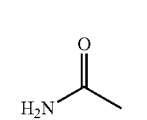 | G |
| 22 | 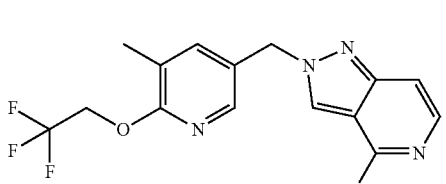<br>Intermediate-1a | | 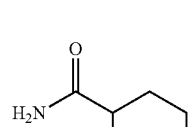 | G |

TABLE 7-continued

| Ex | Structure | Name | |
|---|---|---|---|
| 23 | Intermediate-1a | oxazole-5-carboxamide | G |
| 24 | Intermediate-1a | 1,1-dimethylurea | G |
| 25 | Intermediate-1a | methyl carbamate | G |
| 26 | Intermediate-1a | oxazolidin-2-one | G |
| 27 | Intermediate-1a | ethyl carbamate | G |
| 28 | Intermediate-4a | acetamide | G |
| 29 | Intermediate-4a | propionamide | G |

TABLE 7-continued

| Ex | Structure | | Name | |
|---|---|---|---|---|
| 31 | (Intermediate-1c) | NH₃ | | H |
| 32 | (Intermediate-1c) | H₂N–CH₃ | | H |
| 34 | (Intermediate-1a) | cyclopropanecarboxamide | | G |
| 35 | (Intermediate-7a) | cyclopropanecarboxamide | | G |
| 36 | (Intermediate-7a) | isobutyramide | | G |
| 37 | (Intermediate-8a) | isobutyramide | | G |
| 38 | (Intermediate-8a) | cyclopropanecarboxamide | | G |

| Ex | Structure | | Name | |
|---|---|---|---|---|
| 39 | (Intermediate-9a) | | isobutyramide | G |
| 40 | (Intermediate-9a) | | cyclopropanecarboxamide | G |
| 41 | (Intermediate-10a) | | isobutyramide | G |
| 42 | (Intermediate-10a) | | cyclopropanecarboxamide | G |
| 43 | (Intermediate-11a) | | isobutyramide | G |
| 44 | (Intermediate-11a) | | cyclopropanecarboxamide | G |
| 45 | (Intermediate-11a) | | acetamide | G |

TABLE 7-continued

| Ex | Structure | Name | |
|---|---|---|---|
| 46 | Intermediate-11a | propionamide | G |
| 47 | Intermediate-11a | tetrahydro-2H-pyran-4-carboxamide | G |
| 48 | Intermediate-12a | propionamide | G |
| 49 | Intermediate-12a | cyclopropanecarboxamide | G |
| 50 | Intermediate-12a | isobutyramide | G |
| 51 | Intermediate-1a | pivalamide | G |
| 52 | Intermediate-1a | nicotinamide | G |

TABLE 7-continued
| Ex | Structure | | Name | |
|---|---|---|---|---|
| 53 | 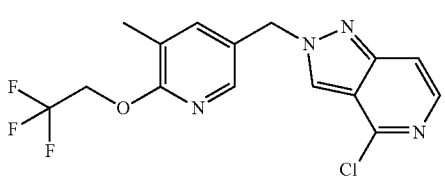 Intermediate-1a | | 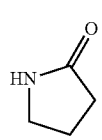 | G |
| 54 | 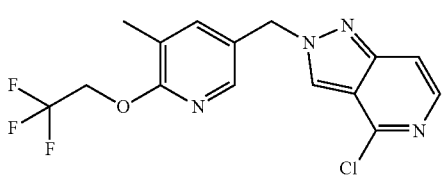 Intermediate-1a | | 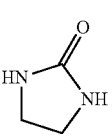 | G |
| 56 | 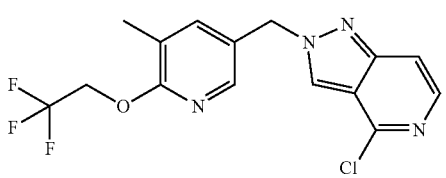 Intermediate-1a | | 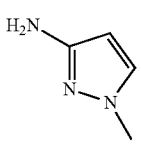 | G |
| 57 | 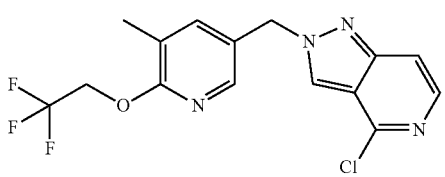 Intermediate-1a | | 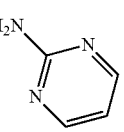 | G |
| 58 | 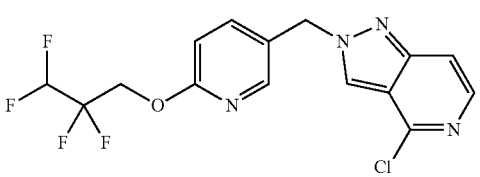 Intermediate-13a | | 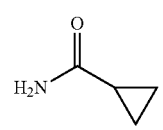 | G |
| 59 | 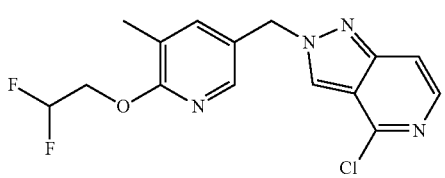 Intermediate-2a | | 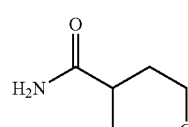 | G |
| 60 | 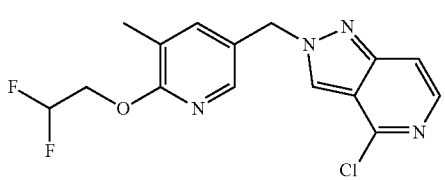 Intermediate-2a | | 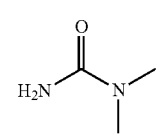 | G |

TABLE 7-continued

| Ex | Structure | Name | |
|---|---|---|---|
| 61 | Intermediate-2a | pivalamide | G |
| 62 | Intermediate-14a | isobutyramide | G |
| 63 | Intermediate-14a | cyclopropanecarboxamide | G |
| 65 | Intermediate-15a | isobutyramide | G |
| 66 | Intermediate-15a | cyclopropanecarboxamide | G |
| 67 | Intermediate-16a | isobutyramide | G |
| 68 | Intermediate-11c | NH$_3$ | J |

| Ex | Structure | | Name | |
|---|---|---|---|---|
| 69 | (Intermediate-1c) | H₂N–CH₂CH₃ | | H |
| 70 | (Intermediate-1c) | (S)-3-aminotetrahydrofuran | | H |
| 71 | (Intermediate-1c) | cyclopropylamine | | H |
| 72 | (Intermediate-1c) | cyclobutylamine | | H |
| 73 | (Intermediate-1c) | cyclopropylmethylamine | | H |
| 74 | (Intermediate-1c) | (tetrahydro-2H-pyran-4-yl)methanamine | | H |

TABLE 7-continued

| Ex | Structure | | Name | |
|---|---|---|---|---|
| 75 | (structure) Intermediate-1c | | H₂N-CH₂CH₂-O-CH₃ | H |
| 76 | (structure) Intermediate-1c | | (S)-H₂N-CH(CH₃)-CH₂OH | H |
| 77 | (structure) Intermediate-1g | | H₂N-C(O)-CH₂CH₃ | G |
| 78 | (structure) Intermediate-1g | | H₂N-C(O)-cyclopropyl | G |
| 79 | (structure) Intermediate-13a | | H₂N-C(O)-CH(CH₃)₂ | G |
| 80 | (structure) Intermediate-17a | | H₂N-C(O)-cyclopropyl | G |

TABLE 7-continued
| Ex | Structure | | Name | |
|---|---|---|---|---|
| 81 | 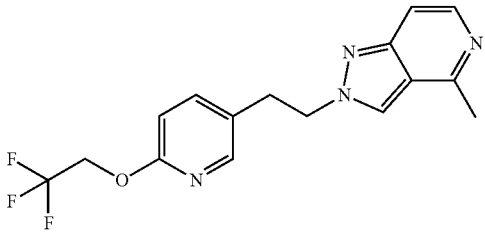<br>Intermediate-18a | | 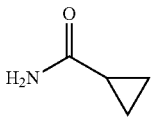 | G |
| 82 | 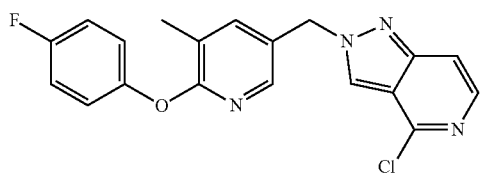<br>Intermediate-19a | | 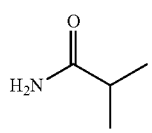 | G |
| 83 | 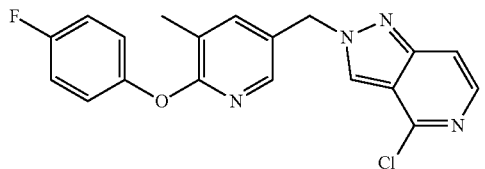<br>Intermediate-19a | | 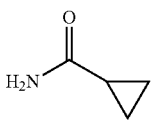 | G |
| 84 | 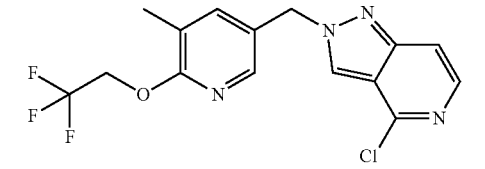<br>Intermediate-1a | | 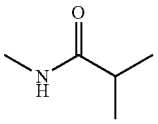 | G |
| 85 | 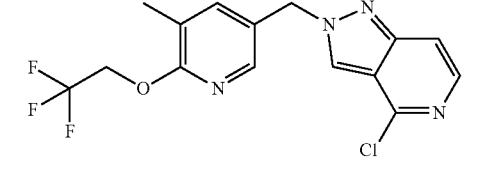<br>Intermediate-1a | | 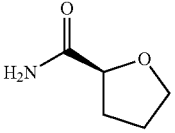 | G |
| 86 | 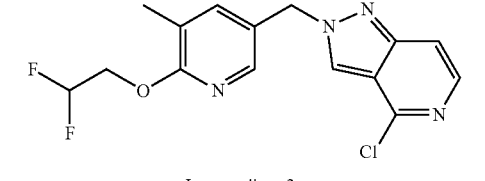<br>Intermediate-2a | | 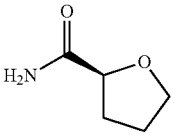 | G |
| 87 | 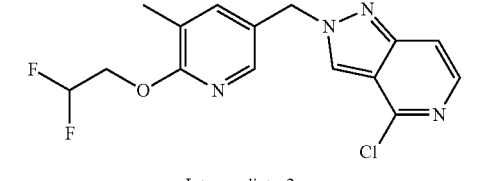<br>Intermediate-2a | | 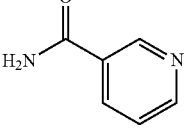 | G |

TABLE 7-continued
| Ex | Structure | Name | |
|---|---|---|---|
| 88 | 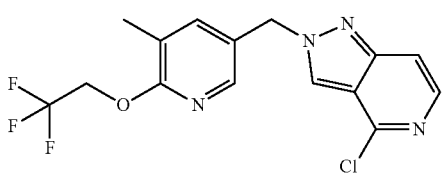<br>Intermediate-1a | 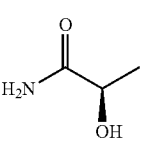 | G |
| 89 | 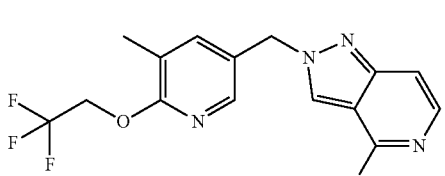<br>Intermediate-1a | 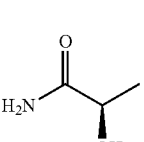 | G |
| 90 | 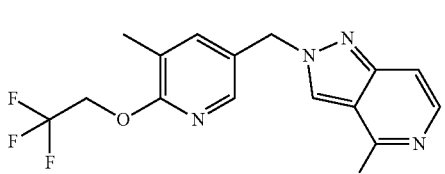<br>Intermediate-1a | 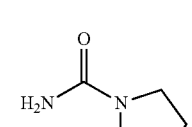 | G |
| 91 | 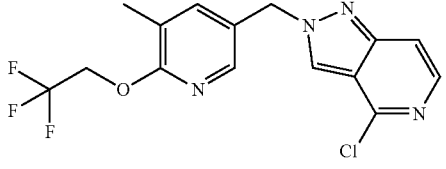<br>Intermediate-1a | 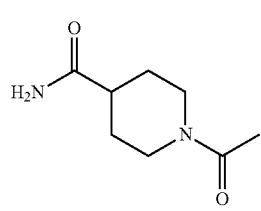 | G |
| 92 | 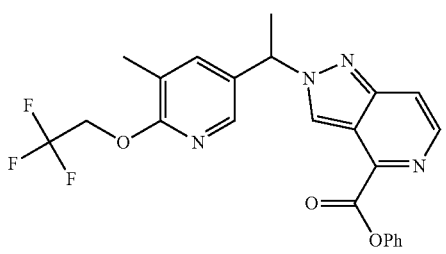<br>Intermediate-11c | 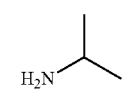 | J |
| 93 | 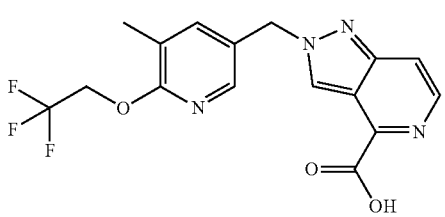<br>Intermediate-1c | 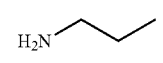 | H |

TABLE 7-continued

| Ex | Structure | Name | |
|---|---|---|---|
| 94 | Intermediate-1c | H₂N-CH(CH₃)₂ (isobutylamine structure) | H |
| 95 | Intermediate-1c | H₂N-CH₂CH₂-O-CH₂CH₃ | H |
| 96 | Intermediate-1c | H₂N-CH₂-CN | H |
| 97 | Intermediate-1c | H₂N-CH₂-(tetrahydrofuran-2-yl) | H |
| 98 | Intermediate-1c | H₂N-CH₂CH₂-N(CH₃)₂ | H |
| 99 | Intermediate-1c | H₂N-CH₂-(pyridin-3-yl) | H |

TABLE 7-continued

| Ex | Structure | | Name | |
|---|---|---|---|---|
| 100 | (Intermediate-1c) | | H₂N-CH₂-(5-methyl-1,2,4-oxadiazol-3-yl) | H |
| 101 | (Intermediate-1c) | | 3-aminopyridine | H |
| 102 | (Intermediate-1a) | | (S)-tetrahydrofuran-2-carboxamide | G |
| 103 | (Intermediate-2a) | | (S)-tetrahydrofuran-2-carboxamide | G |
| 104 | (Intermediate-1c) | | H₂N-(CH₂)₃-OCH₃ | H |
| 105 | (Intermediate-1c) | | 1-(aminomethyl)cyclohexan-1-ol | H |

TABLE 7-continued

| Ex | Structure | | Name | |
|---|---|---|---|---|
| 106 | Intermediate-1d | | propanamide | G |
| 107 | Intermediate-1d | | cyclopropanecarboxamide | G |
| 108 | Intermediate-1d | | isobutyramide | G |
| 109 | Intermediate-1d | | 2-hydroxy-2-methylpropanamide | G |
| 110 | Intermediate-1f | | propanamide | G |
| 111 | Intermediate-1f | | isobutyramide | G |
| 112 | Intermediate-2b | | ethylamine | K |

TABLE 7-continued

| Ex | Structure | | Name |
|---|---|---|---|
| 113 | Intermediate-2b | H₂N—\ | K |
| 114 | Intermediate-1a | 1-isobutyryl piperidine-4-carboxamide | G |
| 115 | Intermediate-1a | 1-(methylsulfonyl)piperidine-4-carboxamide | G |
| 116 | Intermediate-1a | 1-acetylpyrrolidine-2-carboxamide | G |
| 117 | Intermediate-1a | 1-acetylpyrrolidine-2-carboxamide | G |
| 118 | Intermediate-1a | 2-(N-methylacetamido)acetamide | G |
| 119 | Intermediate-1a | (S)-2-methoxypropanamide | G |

TABLE 7-continued
| Ex | Structure | | Name | |
|---|---|---|---|---|
| 120 | 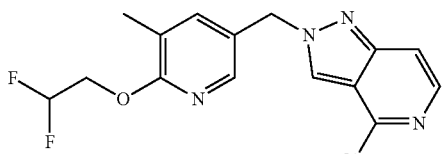 Intermediate-2a | | 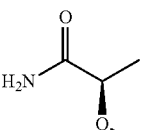 | G |
| 121 | 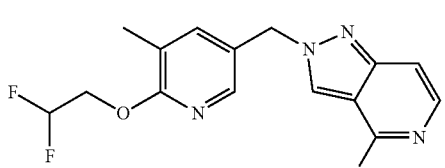 Intermediate-2a | | 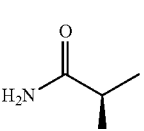 | G |
| 122 | 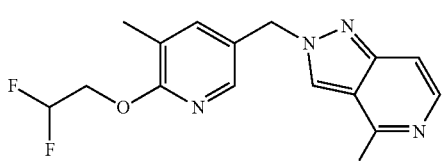 Intermediate-2a | | 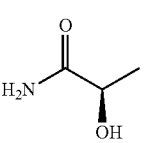 | G |
| 123 | 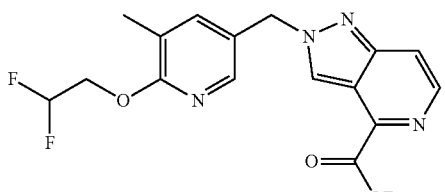 Intermediate-2b | |  | L |
| 124 | 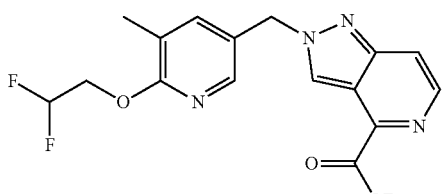 Intermediate-2b | |  | L |
| 125 | 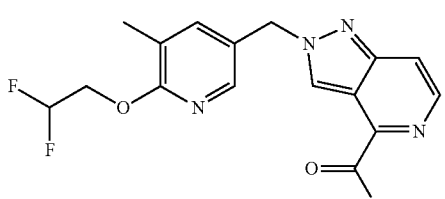 Intermediate-2b | | 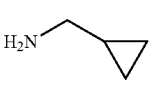 | L |

TABLE 7-continued

| Ex | Structure | Name | |
|---|---|---|---|
| 126 | Intermediate-2b | H₂N─\─N(CH₃)₂ | L |
| 127 | Intermediate-1c | H₂N─\─N(morpholine) | H |
| 128 | Intermediate-1a | H₂N-C(O)-CH₂-(2-pyridyl) | G |
| 129 | Intermediate-1a | H₂N-C(O)-CH₂-(3-pyridyl) | G |
| 130 | Intermediate-4b | H₂N-CH(CH₃)₂ | L |
| 131 | Intermediate-4b | H₂N-Et | K |

TABLE 7-continued
| Ex | Structure | | Name | |
|---|---|---|---|---|
| 132 | 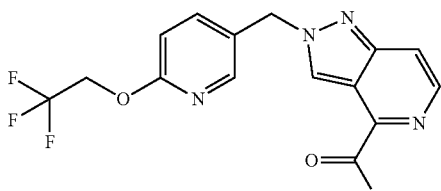 Intermediate-4b | 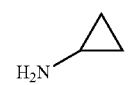 | | L |
| 133 | 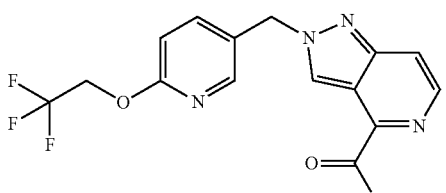 Intermediate-4b | 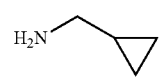 | | L |
| 134 | 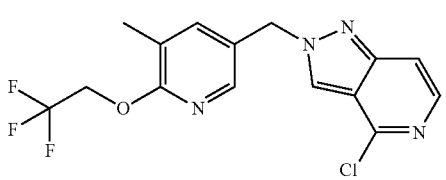 Intermediate-1a |  | | G |
| 135 | 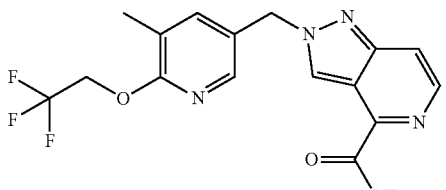 Intermediate-1c | 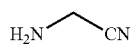 | | H |
| 136 | 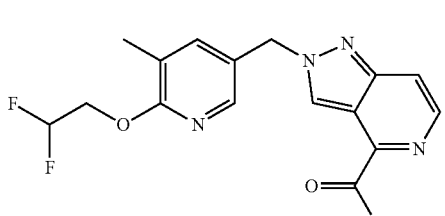 Intermediate-2b |  | | L |
| 137 | 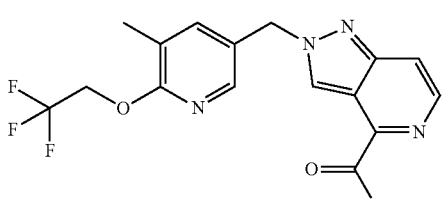 Intermediate-1c |  | | H |

TABLE 7-continued

| Ex | Structure | | Name | |
|---|---|---|---|---|
| 138 | [pyrazolo-pyridine carboxylic acid with methylpyridine-OCH2CF3 substituent], Intermediate-1c | | H2N-CH2-C(CH3)2-OH | H |
| 139 | [same core structure], Intermediate-1c | | H2N-(CH2)3-N(CH3)2 | H |
| 140 | [same core structure], Intermediate-1c | | H2N-CH2CH2-NH2 | H |
| 142 | [same core structure], Intermediate-1c | | 3-aminooxetane | H |
| 144 | [ethyl ester analog], Intermediate-20b | | H2N-CH2CH3 | K |
| 145 | [4-chloro analog with CHF2 instead of CF3], Intermediate-2a | | 2-(pyridin-4-yl)acetamide | G |

TABLE 7-continued
| Ex | Structure | Name | |
|---|---|---|---|
| 146 | 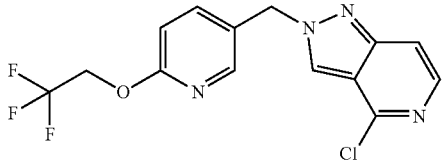 Intermediate-4a | 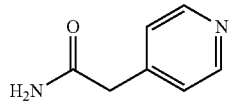 | G |
| 147 | 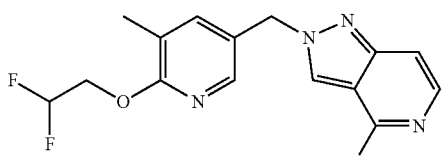 Intermediate-2a | 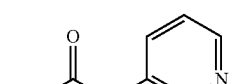 | G |
| 148 | 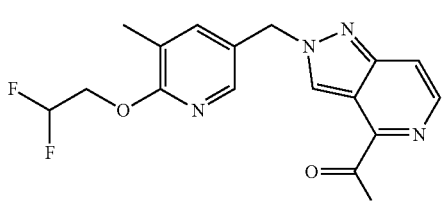 Intermediate-2b | 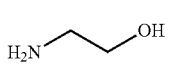 | L |
| 149 | 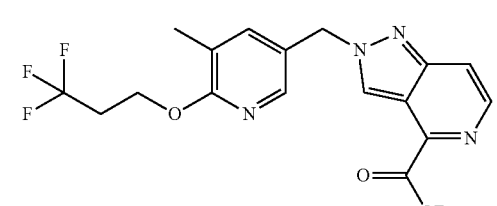 Intermediate-21b | 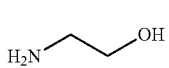 | L |
| 150 | 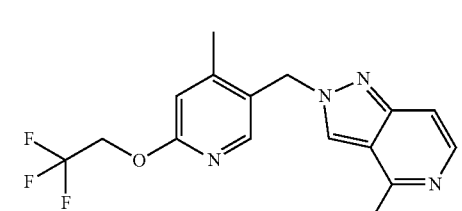 Intermediate-20b |  | L |
| 151 | 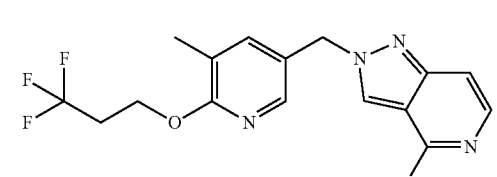 Intermediate-21a |  | G |

TABLE 7-continued
| Ex | Structure | | Name | |
|---|---|---|---|---|
| 152 |  Intermediate-21a | |  | G |
| 153 | 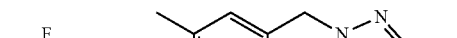 Intermediate-21a | | 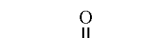 | G |
| 154 | 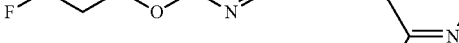 Intermediate-21b | |  | K |
| 155 |  Intermediate-21b | |  | K |
| 156 |  Intermediate-21b | | 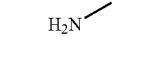 | L |
| 157 |  Intermediate-22a | |  | G |
| 158 | 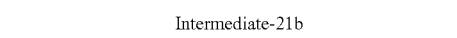 Intermediate-22a | |  | G |

TABLE 7-continued

| Ex | Structure | Name | |
|---|---|---|---|
| 159 | Intermediate-22b | H₂N–CH₃ | K |
| 160 | Intermediate-22b | H₂N–Et | K |
| 161 | Intermediate-1a | 2-(2-methylthiazol-4-yl)acetamide | G |
| 162 | Intermediate-21a | 2-(pyridin-3-yl)acetamide | G |
| 163 | Intermediate-21a | 2-(pyridin-4-yl)acetamide | G |
| 164 | Intermediate-1a | 2-(3,5-dimethylisoxazol-4-yl)acetamide | G |

| Ex | Structure | Name | |
|---|---|---|---|
| 165 | Intermediate-22b | H₂N-CH(CH₃)₂ (isopropylamine) | L |
| 166 | Intermediate-1b | H₂N-CH₂-CH(OH)-CH₃ (S) | L |
| 167 | Intermediate-1b | H₂N-CH₂-CH(OH)-CH₃ (R) | L |
| 168 | Intermediate-1b | H₂N-CH₂-CH(OH)-CH₂OH (S) | L |
| 169 | Intermediate-23a | cyclopropanecarboxamide | G |
| 170 | Intermediate-23a | 2-hydroxy-2-methylpropanamide | G |

TABLE 7-continued

| Ex | Structure | | Name |
|---|---|---|---|
| 171 | Intermediate-23b | H₂N—CH₃ | K |
| 172 | Intermediate-23b | H₂N—Et | K |
| 173 | Intermediate-23b | H₂N—CH(CH₃)₂ | L |
| 174 | Intermediate-23b | H₂N—CH₂CH₂OH | L |
| 175 | Intermediate-1b | (S)-H₂N—CH(CH₃)CH₂OH | L |
| 176 | Intermediate-1b | H₂N—CH₂C(O)NH₂ | L |

TABLE 7-continued

| Ex | Structure | | Name | |
|---|---|---|---|---|
| 177 | [pyridine with methyl, OCH2CF3, linked via CH2 to pyrazolo[4,3-c]pyridine-4-carboxylate ethyl ester] Intermediate-1b | | H2N-CH2CH2-NH-S(O2)-CH3 | L |
| 178 | [pyridazine with methyl, OCH2CF3, linked via CH2 to pyrazolo[4,3-c]pyridine-4-carboxylate ethyl ester] Intermediate-22b | | H2N-CH2CH2-OH | L |
| 179 | [pyridine with methyl, OCH2CF3, linked via CH2 to pyrazolo[4,3-c]pyridine-4-carboxylate ethyl ester] Intermediate-1b | | H2N-CH2CH2CH2-OH | L |
| 180 | [pyridine with methyl, OCH2CHF2, linked via CH2 to pyrazolo[4,3-c]pyridine-4-carboxylate ethyl ester] Intermediate-2b | | H2N-CH2CH2CH2-OH | L |
| 181 | [pyridine with methyl, OCH2CF3, linked via CH2 to pyrazolo[4,3-c]pyridine-4-carboxylate ethyl ester] Intermediate-1b | | H2N-CH2CH2-CN | L |
| 182 | [pyridine with methyl, OCH2CHF2, linked via CH2 to pyrazolo[4,3-c]pyridine-4-carboxylate ethyl ester] Intermediate-2b | | H2N-CH2CH2-CN | L |

TABLE 7-continued

| Ex | Structure | Name | |
|---|---|---|---|
| 183 | Intermediate-1b | H₂N-CH₂CH₂-NH-C(O)CH₃ | L |
| 184 | Intermediate-24a | isobutyramide (H₂N-C(O)-CH(CH₃)₂) | G |
| 185 | Intermediate-24a | cyclopropanecarboxamide (H₂N-C(O)-cyclopropyl) | G |
| 186 | Intermediate-24b | H₂N-CH₃ | K |
| 187 | Intermediate-24b | H₂N-CH₂CH₃ | K |
| 188 | Intermediate-24b | H₂N-CH(CH₃)₂ | L |

TABLE 7-continued

| Ex | Structure | Name | |
|---|---|---|---|
| 189 | Intermediate-24b | H₂N⁓OH | L |
| 190 | Intermediate-1b | H₂N⌒O⌒OH | L |
| 191 | Intermediate-23a | isobutyramide (H₂N-C(=O)-CH(CH₃)₂) | G |
| 192 | Intermediate-12b | H₂N-Et | K |
| 193 | Intermediate-12b | isopropylamine (H₂N-CH(CH₃)₂) | L |
| 194 | Intermediate-5b | H₂N⁓OH | L |

TABLE 7-continued
| Ex | Structure | Name | |
|---|---|---|---|
| 195 | 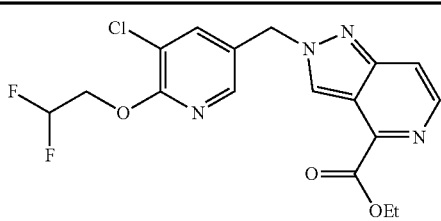<br>Intermediate-6b | 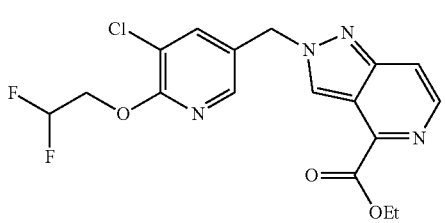 | K |
| 196 | 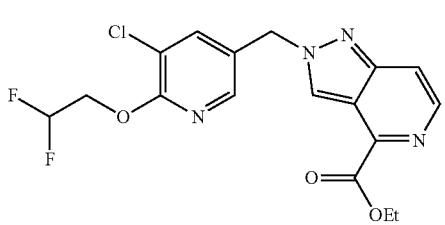<br>Intermediate-6b | 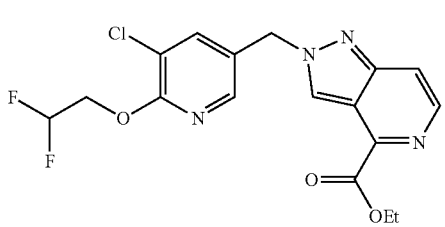 | K |
| 197 | 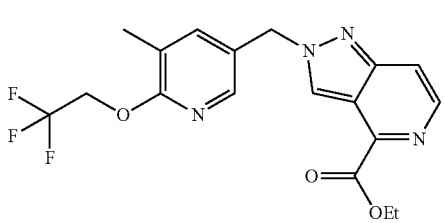<br>Intermediate-6b | H₂N⏜OH | L |
| 198 | 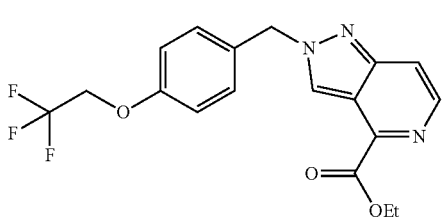<br>Intermediate-6b | H₂N⏜ | L |
| 199 | Intermediate-1b | H₂N⏜⏜OH, OH | L |
| 200 | Intermediate-14b | H₂N⏜OH | L |

TABLE 7-continued

| Ex | Structure | | Name | |
|---|---|---|---|---|
| 201 | [4-fluorophenoxy-methylpyridine-methyl-pyrazolo[4,3-c]pyridine-4-carboxylic acid ethyl ester]<br>Intermediate-19b | | H₂N∼OH (ethanolamine) | L |
| 202 | [2,2,3,3,3-pentafluoropropoxy-pyridine-methyl-pyrazolo[4,3-c]pyridine-4-carboxylic acid ethyl ester]<br>Intermediate-15b | | H₂N∼OH | L |
| 203 | [3,3,3-trifluoropropoxy-pyridine-methyl-pyrazolo[4,3-c]pyridine-4-carboxylic acid ethyl ester]<br>Intermediate-10b | | H₂N∼ (methylamine) | K |
| 204 | [3,3,3-trifluoropropoxy-pyridine-methyl-pyrazolo[4,3-c]pyridine-4-carboxylic acid ethyl ester]<br>Intermediate-10b | | H₂N∼ (ethylamine) | K |
| 205 | [3,3,3-trifluoropropoxy-pyridine-methyl-pyrazolo[4,3-c]pyridine-4-carboxylic acid ethyl ester]<br>Intermediate-10b | | H₂N-iPr (isopropylamine) | L |
| 206 | [3,3,3-trifluoropropoxy-pyridine-methyl-pyrazolo[4,3-c]pyridine-4-carboxylic acid ethyl ester]<br>Intermediate-10b | | H₂N∼OH | L |

TABLE 7-continued

| Ex | Structure | | Name | |
|---|---|---|---|---|
| 207 | [Structure: ethyl 2-((6-(2,2,2-trifluoroethoxy)-5-methylpyridin-3-yl)methyl)-2H-pyrazolo[3,4-c]pyridine-4-carboxylate] Intermediate-1b | | [Structure: (S)-2-aminopropanamide] | L |
| 208 | [Structure: ethyl 2-((6-(2,2,2-trifluoroethoxy)-5-methylpyridin-3-yl)methyl)-2H-pyrazolo[3,4-c]pyridine-4-carboxylate] Intermediate-1b | | [Structure: 2-amino-N-methylacetamide] | L |
| 209 | [Structure: ethyl 2-((6-(2,2,2-trifluoroethoxy)-5-methylpyridin-3-yl)methyl)-2H-pyrazolo[3,4-c]pyridine-4-carboxylate] Intermediate-1b | | [Structure: 3-aminopropanamide] | L |
| 210 | [Structure: ethyl 2-((6-(2,2,2-trifluoroethoxy)-5-methylpyridin-3-yl)methyl)-2H-pyrazolo[3,4-c]pyridine-4-carboxylate] Intermediate-1b | | [Structure: 3-amino-2,2-dimethylpropan-1-ol] | L |
| 211 | [Structure: ethyl 2-((6-(2,2,2-trifluoroethoxy)pyridin-3-yl)methyl)-2H-pyrazolo[3,4-c]pyridine-4-carboxylate] Intermediate-4b | | [Structure: 2-aminoethanol] | L |
| 212 | [Structure: ethyl 2-((6-(2,2,2-trifluoroethoxy)-5-methylpyridin-3-yl)methyl)-2H-pyrazolo[3,4-c]pyridine-4-carboxylate] Intermediate-1b | | [Structure: 4-aminobutan-1-ol] | L |

TABLE 7-continued
| Ex | Structure | Name | |
|---|---|---|---|
| 213 | 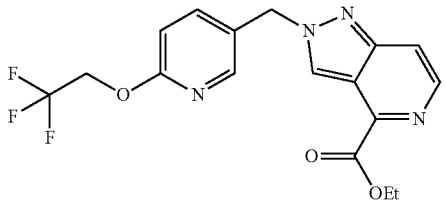<br>Intermediate-4b | H₂N⌒⌒OH | L |
| 214 | 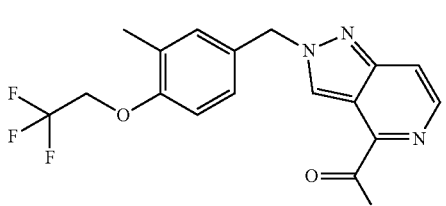<br>Intermediate-25b | H₂N⌒OH | L |
| 215 | 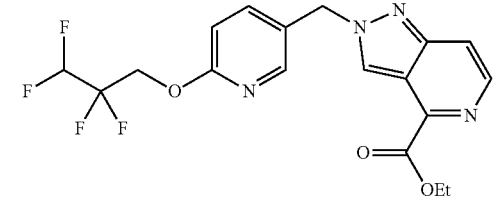<br>Intermediate-13b | H₂N⌒ | K |
| 216 | 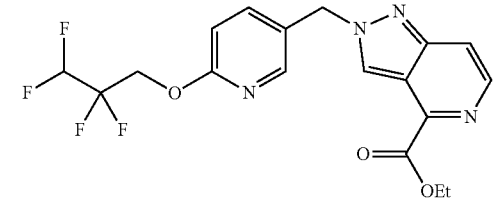<br>Intermediate-13b | H₂N⌒OH | L |
| 217 | 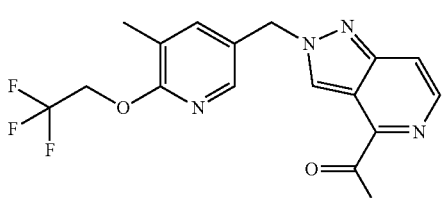<br>Intermediate-1b | H₂N⌒⌒NHAc | L |
| 218 | 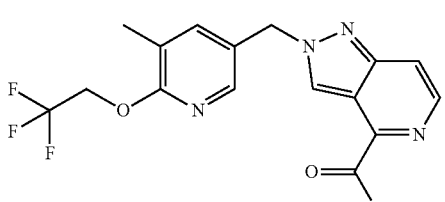<br>Intermediate-1b | H₂N⌒⌒NHS(O₂)Me | L |

TABLE 7-continued

| Ex | Structure | Name | |
|---|---|---|---|
| 219 | Intermediate-13b | H₂N⟶CH(CH₃)₂ | L |
| 220 | Intermediate-26b | H₂N–CH₂CH₂–OH | L |
| 221 | Intermediate-26b | H₂N–CH₂CH₂CH₂–OH | L |
| 222 | Intermediate-27b | H₂N–CH₂CH₂–OH | L |
| 223 | Intermediate-27b | H₂N–CH₂CH₂CH₂–OH | L |
| 224 | Intermediate-5b | H₂N–CH₂CH₂CH₂–OH | L |

TABLE 7-continued
| Ex | Structure | Name | |
|---|---|---|---|
| 225 | 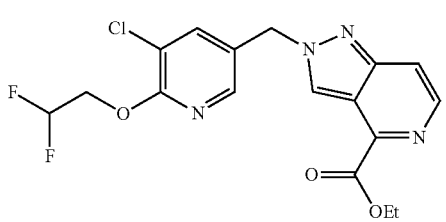<br>Intermediate-6b | H₂N⌒⌒OH | L |
| 226 | 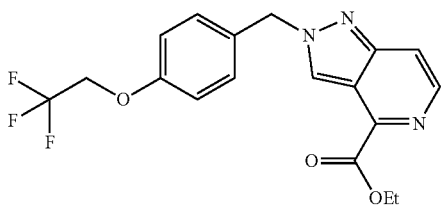<br>Intermediate-14b | H₂N⌒⌒OH | L |
| 227 | 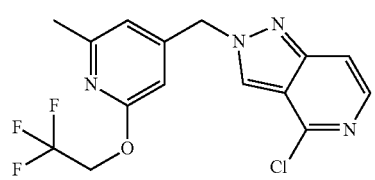<br>Intermediate-28a | isobutyramide | G |
| 228 | 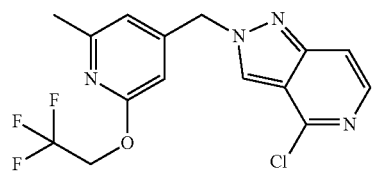<br>Intermediate-28a | cyclopropanecarboxamide | G |
| 229 | 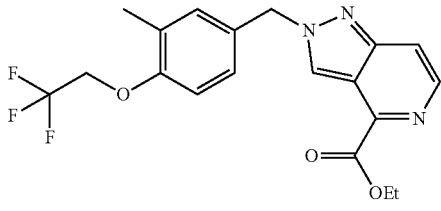<br>Intermediate-25b | H₂N⌒⌒OH | L |
| 230 | 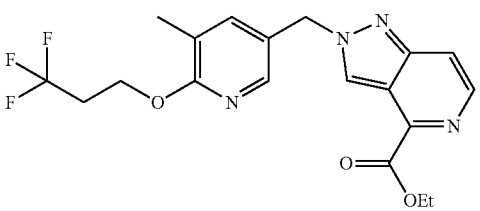<br>Intermediate-21b | H₂N⌒⌒OH | L |

US 9,944,634 B2
TABLE 7-continued
| Ex | Structure | Name | |
|---|---|---|---|
| 231 | 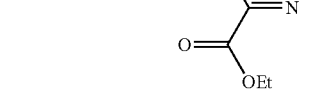<br>Intermediate-22b | H₂N⁓⁓OH | L |
| 232 | 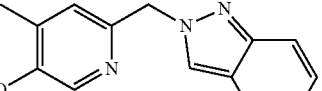<br>Intermediate-23b | H₂N⁓⁓OH | L |
| 233 | 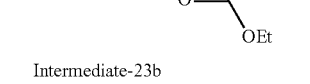<br>Intermediate-24b | H₂N⁓⁓OH | L |
| 234 | 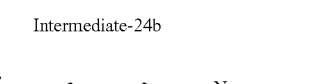<br>Intermediate-12b | H₂N⁓⁓OH | L |
| 235 | 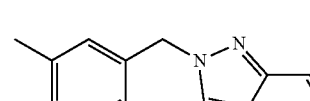<br>Intermediate-19b | H₂N⁓⁓OH | L |
| 236 | 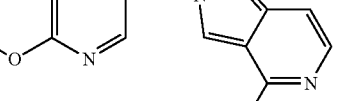<br>Intermediate-15b | H₂N⁓⁓OH | L |

TABLE 7-continued
| Ex | Structure | | Name | |
|---|---|---|---|---|
| 237 | 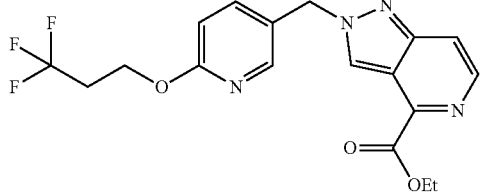 Intermediate-10b | H₂N⌒⌒OH | | L |
| 238 | 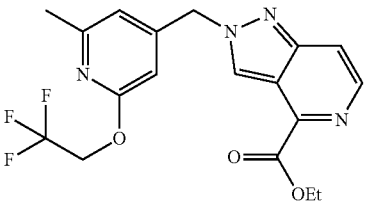 Intermediate-28b | H₂N— | | K |
| 239 | 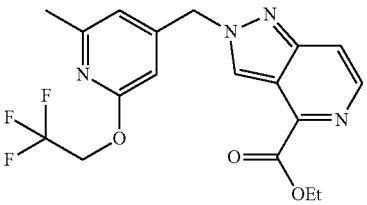 Intermediate-28b | H₂N⌒ | | K |
| 240 | 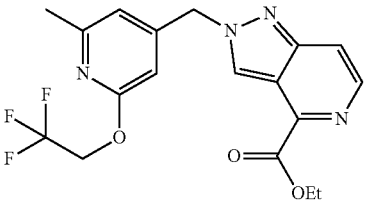 Intermediate-28b | H₂N⇃ | | L |
| 241 | 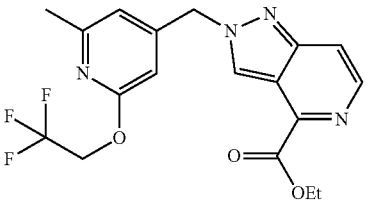 Intermediate-28b | H₂N⌒OH | | L |
| 242 | 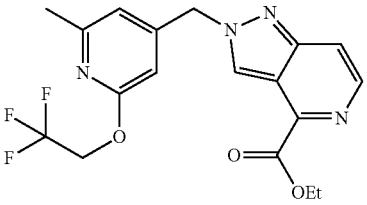 Intermediate-28b | H₂N⌒⌒OH | | L |

TABLE 7-continued

| Ex | Structure | Name | |
|---|---|---|---|
| 243 | Intermediate-29a | isobutyramide | G |
| 244 | Intermediate-29a | cyclopropanecarboxamide | G |
| 245 | Intermediate-21b | (S)-1-aminopropan-2-ol | L |
| 246 | Intermediate-21b | (R)-1-aminopropan-2-ol | L |
| 247 | Intermediate-21b | (S)-3-aminopropane-1,2-diol | L |
| 248 | Intermediate-21b | (R)-3-aminopropane-1,2-diol | L |

TABLE 7-continued

| Ex | Structure | Name | |
|---|---|---|---|
| 249 | Intermediate-23b | H₂N-CH₂-CH(OH)-CH₂-OH | L |
| 250 | Intermediate-30b | H₂N-CH(CH₃)₂ | L |
| 251 | Intermediate-30b | H₂N-CH₂-CH₂-OH | L |
| 252 | Intermediate-30b | H₂N-CH₂-CH₂-CH₂-OH | L |
| 253 | Intermediate-30b | H₂N-CH₃ (ethylamine) | K |

TABLE 7-continued

| Ex | Structure | Name | |
|---|---|---|---|
| 254 | Intermediate-30b | H₂N─⁄⁄ | K |
| 255 | Intermediate-23b | H₂N⌒OH (R) | L |
| 256 | Intermediate-23b | H₂N⌒OH (S) | L |
| 257 | Intermediate-21b | H₂N⌒OH | L |
| 258 | Intermediate-23b | H₂N⌒OH | L |
| 259 | Intermediate-23b | H₂N⌒CN | L |

TABLE 7-continued

| Ex | Structure | Name | |
|---|---|---|---|
| 260 | Intermediate-21b | H₂N−CH₂−CN | L |
| 261 | Intermediate-21b | H₂N−CH₂CH₂−NH−C(O)CH₃ | L |
| 262 | Intermediate-21b | H₂N−CH₂−C(O)NH₂ | L |
| 263 | Intermediate-21b | H₂N−CH₂CH₂−OCH₃ | L |
| 264 | Intermediate-31a | isobutyramide (H₂N−C(O)−CH(CH₃)₂) | G |
| 265 | Intermediate-31a | cyclopropanecarboxamide (H₂N−C(O)−cyclopropyl) | G |

TABLE 7-continued

| Ex | Structure | Name | |
|---|---|---|---|
| 266 | Intermediate-31a | 2-hydroxy-2-methylpropanamide | G |
| 267 | Intermediate-32a | isobutyramide | G |
| 268 | Intermediate-32a | cyclopropanecarboxamide | G |
| 269 | Intermediate-31b | 2-aminoethanol | L |
| 270 | Intermediate-31b | 3-aminopropan-1-ol | L |
| 271 | Intermediate-31b | methylamine | K |

TABLE 7-continued

| Ex | Structure | Name | |
|---|---|---|---|
| 272 | Intermediate-31b | H₂N–Et | K |
| 273 | Intermediate-32b | H₂N–CH₂CH₂OH | L |
| 274 | Intermediate-32b | H₂N–CH₂CH₂CH₂OH | L |
| 275 | Intermediate-32b | H₂N–CH₃ | K |
| 276 | Intermediate-32b | H₂N–Et | K |
| 277 | Intermediate-31b | H₂N–CH(CH₃)₂ | L |

TABLE 7-continued
| Ex | Structure | | Name | |
|---|---|---|---|---|
| 278 | 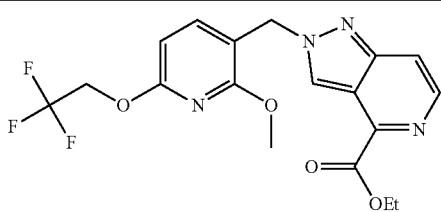<br>Intermediate-32b | |  | L |
| 279 | 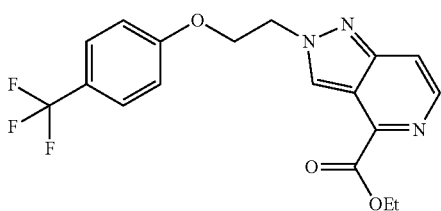<br>Intermediate-33b | |  | K |
| 280 | 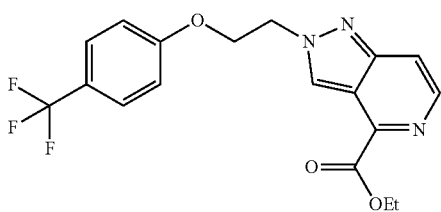<br>Intermediate-33b | |  | K |
| 281 | 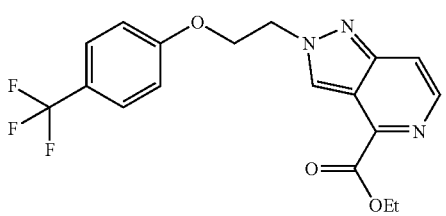<br>Intermediate-33b | |  | L |
| 282 | 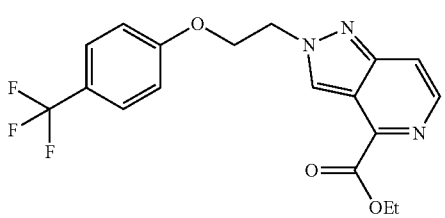<br>Intermediate-33b | | 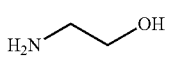 | L |
| 283 | 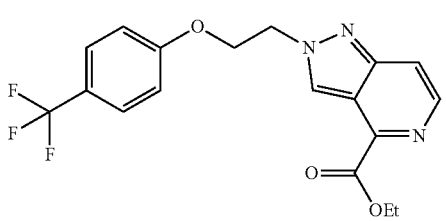<br>Intermediate-33b | | 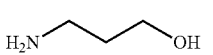 | L |

| Ex | Structure | Name | |
|---|---|---|---|
| 284 | Intermediate-34a | H₂N-C(=O)-CH(CH₃)₂ (isobutyramide) | G |
| 285 | Intermediate-34a | H₂N-C(=O)-cyclopropyl (cyclopropanecarboxamide) | G |
| 286 | Intermediate-35a | H₂N-C(=O)-CH(CH₃)₂ (isobutyramide) | G |
| 287 | Intermediate-35a | H₂N-C(=O)-cyclopropyl (cyclopropanecarboxamide) | G |
| 288 | Intermediate-35a | H₂N-C(=O)-C(CH₃)₂-OH (2-hydroxy-2-methylpropanamide) | G |
| 290 | Intermediate-36b | H₂N-CH₂CH₃ (ethylamine) | J |
| 291 | Intermediate-36b | H₂N-CH(CH₃)₂ (isopropylamine) | J |

US 9,944,634 B2
453                                                                                         454
TABLE 7-continued
| Ex | Structure | | Name | |
|----|-----------|--|------|--|
| 292 | 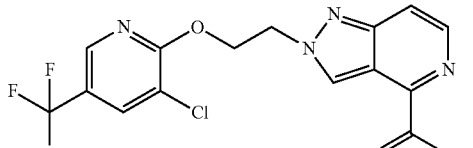<br>Intermediate-36b | H₂N⌒⌒OH | | J |
| 293 | 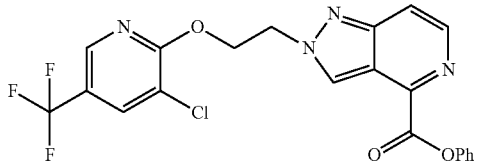<br>Intermediate-36b | H₂N⌒⌒⌒OH | | J |
| 294 | 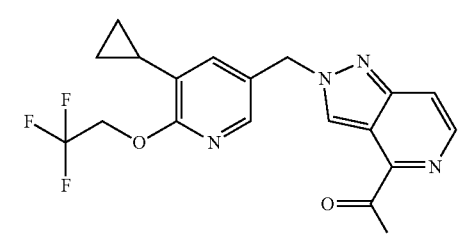<br>Intermediate-37b | H₂N⌒ | | J |
| 295 | 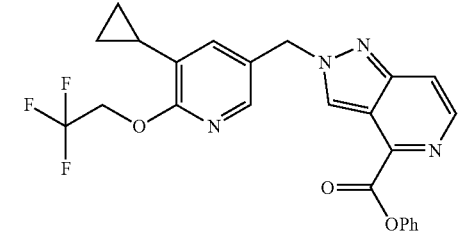<br>Intermediate-37b | H₂N⌒⌒ | | J |
| 296 | 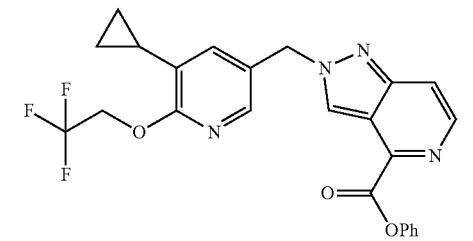<br>Intermediate-37b | H₂N⋋ | | J |
| 297 | 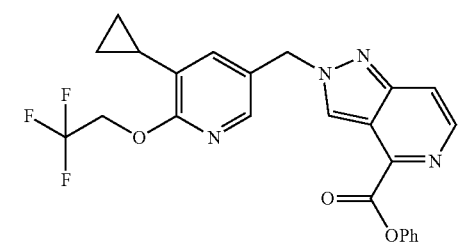<br>Intermediate-37b | H₂N⌒⌒OH | | J |

TABLE 7-continued

| Ex | Structure | Name | |
|---|---|---|---|
| 298 | Intermediate-37b | H₂N⁓⁓OH | J |
| 299 | Intermediate-35b | H₂N⁓ | K |
| 300 | Intermediate-35b | H₂N⁓ | K |
| 301 | Intermediate-35b | H₂N⁓OH | L |
| 302 | Intermediate-35b | H₂N⁓⁓OH | L |
| 303 | Intermediate-34b | H₂N⁓ | K |

TABLE 7-continued

| Ex | Structure | | Name | |
|---|---|---|---|---|
| 304 | Intermediate-34b | | H₂N─ethyl | K |
| 305 | Intermediate-34b | | H₂N─CH₂CH₂CH₂─OH | L |
| 306 | Intermediate-35b | | H₂N─isopropyl | L |
| 307 | Intermediate-34b | | H₂N─isopropyl | L |
| 308 | Intermediate-38b | | H₂N─methyl | K |
| 309 | Intermediate-38b | | H₂N─ethyl | K |

TABLE 7-continued

| Ex | Structure | | Name | |
|---|---|---|---|---|
| 310 | Intermediate-11b | | H₂N−CH₂CH₂−OH | L |
| 311 | Intermediate-11b | | H₂N−CH₂CH₂CH₂−OH | K |
| 312 | Intermediate-11b | | H₂N−CH₃ | K |
| 313 | Intermediate-11b | | H₂N−CH₂CH₃ | K |
| 314 | Intermediate-39b | | H₂N−CH₂CH₂−OH | J |

TABLE 7-continued

| Ex | Structure | Name | |
|---|---|---|---|
| 315 | Intermediate-39b | H₂N⁀⁀OH | J |
| 316 | Intermediate-39b | H₂N⁀ | J |
| 317 | Intermediate-39b | H₂N⁀⁀ | J |
| 318 | Intermediate-40b | H₂N⁀ | K |
| 319 | Intermediate-23b | H₂N⁀⁀O⁀ | L |

TABLE 7-continued

| Ex | Structure | Name | |
|---|---|---|---|
| 320 | Intermediate-38b | H₂N-CH(CH₃)₂ | L |
| 321 | Intermediate-38b | H₂N-CH₂CH₂OH | L |
| 322 | Intermediate-39a | isobutyramide | G |
| 323 | Intermediate-39a | 2-hydroxy-2-methylpropanamide | G |
| 324 | Intermediate-40a | cyclopropanecarboxamide | G |
| 325 | Intermediate-41a | isobutyramide | G |

TABLE 7-continued

| Ex | Structure | Name | |
|---|---|---|---|
| 326 | Intermediate-41a | cyclopropanecarboxamide | G |
| 327 | Intermediate-42a | isobutyramide | G |
| 328 | Intermediate-42a | cyclopropanecarboxamide | G |
| 329 | Intermediate-42a | 2-hydroxy-2-methylpropanamide | G |
| 330 | Intermediate-1e | methylamine | K |
| 331 | Intermediate-1e | ethylamine | K |

TABLE 7-continued

| Ex | Structure | | Name | |
|---|---|---|---|---|
| 332 | Intermediate-43b | | H₂N–CH₂CH₃ | K |
| 333 | Intermediate-43b | | H₂N–CH(CH₃)₂ | L |
| 334 | Intermediate-43b | | H₂N–CH₂CH₂OH | L |
| 335 | Intermediate-43b | | H₂N–CH₂CH₂CH₂OH | L |
| 336 | Intermediate-42b | | H₂N–CH(CH₃)₂ | L |
| 337 | Intermediate-41b | | H₂N–CH₂CH₃ | K |

TABLE 7-continued

| Ex | Structure | Name | |
|---|---|---|---|
| 338 | Intermediate-41b | H₂N⁀ | K |
| 339 | Intermediate-41b | H₂N⁀⁀OH | L |
| 340 | Intermediate-41b | H₂N⁀⁀⁀OH | L |
| 341 | Intermediate-42b | H₂N⁀ | K |
| 342 | Intermediate-42b | H₂N⁀⁀ | K |

TABLE 7-continued

| Ex | Structure | Name | |
|---|---|---|---|
| 343 | Intermediate-42b | H₂N−CH₂CH₂−OH | L |
| 344 | Intermediate-42b | H₂N−(CH₂)₃−OH | L |
| 345 | Intermediate-44b | H₂N−Et | K |
| 346 | Intermediate-44b | H₂N−iPr | L |
| 347 | Intermediate-44b | H₂N−CH₂CH₂−OH | L |
| 348 | Intermediate-44b | H₂N−(CH₂)₃−OH | L |

TABLE 7-continued

| Ex | Structure | Name | |
|---|---|---|---|
| 349 | Intermediate-45b | H$_2$N-CH$_2$CH$_3$ | G |
| 350 | Intermediate-46a | cyclopropanecarboxamide (H$_2$N-C(=O)-cyclopropyl) | G |
| 351 | Intermediate-44b | H$_2$N-CH$_3$ | K |
| 352 | Intermediate-38b | H$_2$N-CH$_2$CH$_2$CH$_2$-OH | L |
| 353 | Intermediate-45b | H$_2$N-CH(CH$_3$)$_2$ | L |
| 354 | Intermediate-19b | H$_2$N-CH$_3$ | K |

TABLE 7-continued

| Ex | Structure | Name | |
|---|---|---|---|
| 355 | Intermediate-19b | H₂N-Et | K |
| 356 | Intermediate-1e | H₂N-CH₂CH₂-OH | L |
| 357 | Intermediate-1e | H₂N-CH₂CH₂CH₂-OH | L |
| 358 | Intermediate-21b | H₂N-CH₂CH₂CH₂-S(O₂)-CH₃ | L |
| 359 | Intermediate-47b | H₂N-Et | K |

TABLE 7-continued

| Ex | Structure | Name | |
|---|---|---|---|
| 360 | Intermediate-47b | H₂N⁓ | K |
| 361 | Intermediate-47b | H₂N–iPr | L |
| 362 | Intermediate-47b | H₂N⁓OH | L |
| 363 | Intermediate-47b | H₂N⁓⁓OH | L |
| 364 | Intermediate-48b | H₂N⁓ | K |

TABLE 7-continued
| Ex | Structure | Name | |
|---|---|---|---|
| 365 | \nIntermediate-48b | 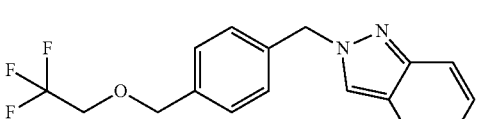 H$_2$N⁀⁀OH | L |
| 366 | 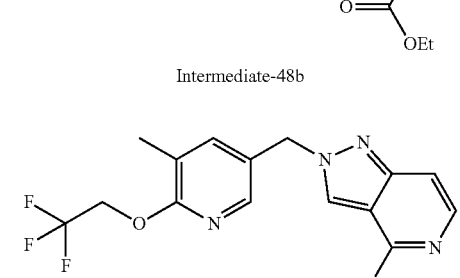\nIntermediate-48b | H$_2$N⁀< | L |
| 367 | 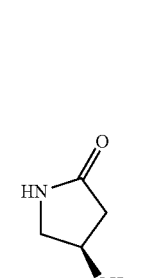\nIntermediate-1a | 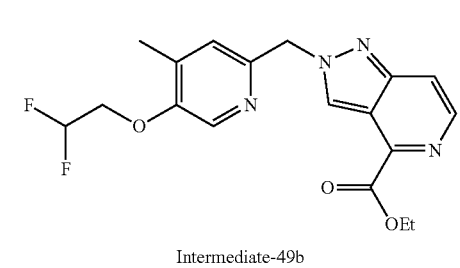 | G |
| 368 | 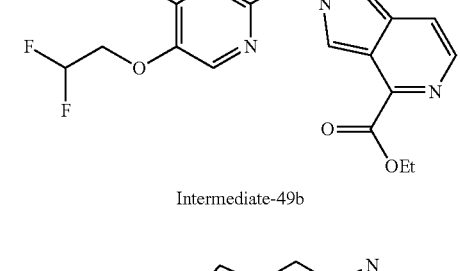\nIntermediate-49b | H$_2$N⁀OH | L |
| 369 | 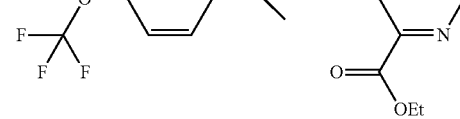\nIntermediate-49b | H$_2$N⁀⁀OH | L |
| 370 | Intermediate-50b | H$_2$N⁀ | K |

TABLE 7-continued
| Ex | Structure | | Name | |
|---|---|---|---|---|
| 371 | 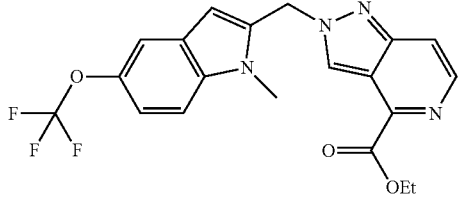 Intermediate-50b | |  | K |
| 372 | 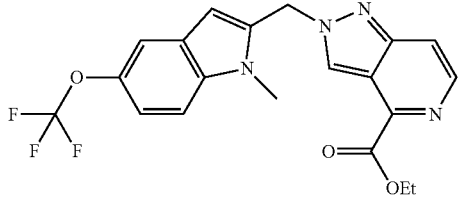 Intermediate-50b | |  | L |
| 373 | 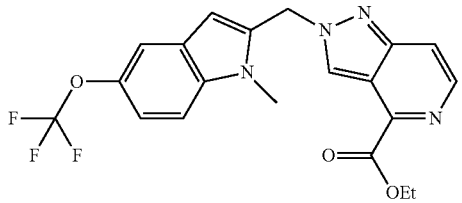 Intermediate-50b | | 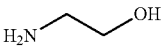 | L |
| 374 | 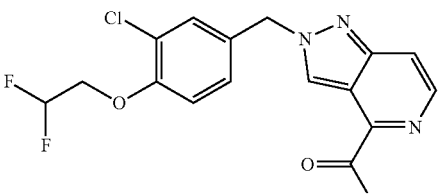 Intermediate-51b | | 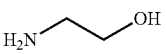 | L |
| 375 | 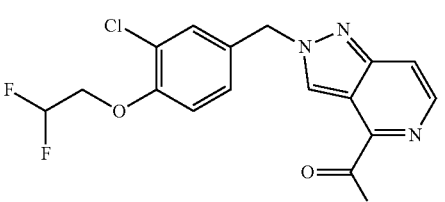 Intermediate-51b | | 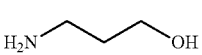 | L |
| 376 | 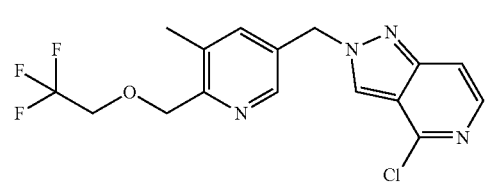 Intermediate-52a | | 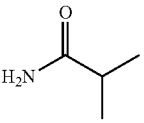 | G |

TABLE 7-continued

| Ex | Structure | | Name | |
|---|---|---|---|---|
| 377 | [Structure with methylpyridine bearing OCH2CF3, linked via CH2 to pyrazolo[4,3-c]pyridine with CO2Et]  Intermediate-1b | H2N~S(O2)~CH3 (3-(methylsulfonyl)propan-1-amine) | | L |
| 378 | [Structure with methylpyridine bearing CH2OCH2CF3, linked via CH2 to pyrazolo[4,3-c]pyridine with CO2Et]  Intermediate-52b | H2N-Et (ethylamine) | | K |
| 379 | [Structure with methylpyridine bearing CH2OCH2CF3, linked via CH2 to pyrazolo[4,3-c]pyridine with CO2Et]  Intermediate-52b | H2N-iPr (isopropylamine) | | L |
| 380 | [Structure with methylpyridine bearing CH2OCH2CF3, linked via CH2 to pyrazolo[4,3-c]pyridine with CO2Et]  Intermediate-52b | H2N-CH2CH2-OH (ethanolamine) | | L |
| 381 | [Structure with methylpyridine bearing CH2OCH2CF3, linked via CH2 to pyrazolo[4,3-c]pyridine with CO2Et]  Intermediate-52b | H2N-CH2CH2CH2-OH (3-aminopropan-1-ol) | | L |
| 382 | [Structure with 5-(trifluoromethoxy)-1-methylindole linked via CH2 to pyrazolo[4,3-c]pyridine with CO2Et]  Intermediate-50b | H2N-CH2CH2CH2-OH (3-aminopropan-1-ol) | | L |

TABLE 7-continued

| Ex | Structure | Name | |
|---|---|---|---|
| 383 | Intermediate-52a | cyclopropanecarboxamide | G |
| 384 | Intermediate-49a | isobutyramide | G |
| 385 | Intermediate-49a | cyclopropanecarboxamide | G |
| 386 | Intermediate-49a | 2-hydroxy-2-methylpropanamide | G |
| 387 | Intermediate-53a | cyclopropanecarboxamide | G |
| 388 | Intermediate-53a | isobutyramide | G |
| 389 | Intermediate-53a | 2-hydroxy-2-methylpropanamide | G |

TABLE 7-continued
| Ex | Structure | Name | |
|---|---|---|---|
| 390 | 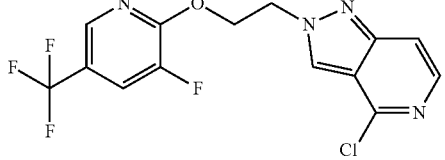<br>Intermediate-54a | 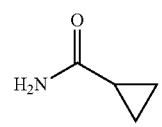 | G |
| 391 | 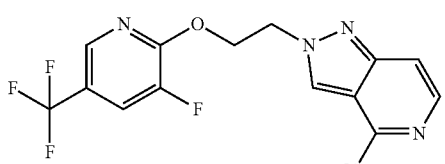<br>Intermediate-54a | 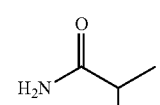 | G |
| 392 | 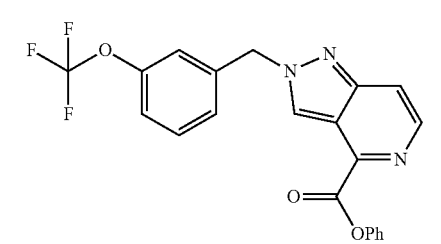<br>Intermediate-53b |  | J |
| 393 | 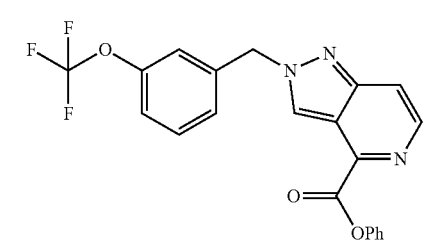<br>Intermediate-53b |  | J |
| 394 | 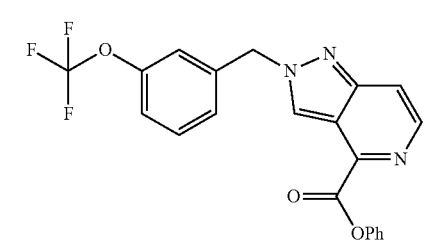<br>Intermediate-53b | 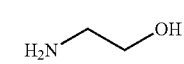 | J |
| 395 | 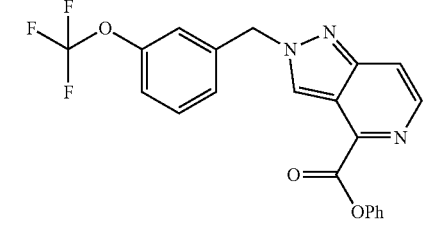<br>Intermediate-53b | 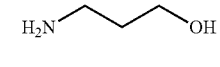 | J |

TABLE 7-continued

| Ex | Structure | | Name | |
|---|---|---|---|---|
| 396 | Intermediate-54b | | H₂N-Et | J |
| 397 | Intermediate-54b | | H₂N-iPr | J |
| 398 | Intermediate-54b | | H₂N~~OH | J |
| 399 | Intermediate-55a | | isobutyramide | G |
| 400 | Intermediate-55a | | cyclopropanecarboxamide | G |
| 401 | Intermediate-56b | | H₂N~OH | L |

| Ex | Structure | | Name | |
|---|---|---|---|---|
| 402 | Intermediate-56b | H₂N⌒⌒OH | | L |
| 403 | Intermediate-55b | H₂N⌒ | | K |
| 404 | Intermediate-55b | H₂N⋀ | | L |
| 405 | Intermediate-55b | H₂N⌒⌒OH | | L |
| 406 | Intermediate-49b | H₂N⋀ | | L |
| 407 | Intermediate-49b | H₂N⌒ | | K |

TABLE 7-continued

| Ex | Structure | Name | |
|---|---|---|---|
| 408 | Intermediate-49b | H₂N—CH₂CH₃ | K |
| 409 | Intermediate-57b | H₂N—CH₂CH₃ | K |
| 410 | Intermediate-57b | H₂N—CH₂CH₂OH | L |
| 411 | Intermediate-57b | H₂N—CH₂CH₂CH₂OH | L |
| 412 | Intermediate-58a | isobutyramide | G |
| 413 | Intermediate-58a | cyclopropanecarboxamide | G |

US 9,944,634 B2
TABLE 7-continued
| Ex | Structure | Name | |
|---|---|---|---|
| 414 | 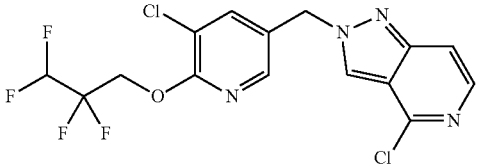<br>Intermediate-58a | 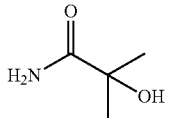 | G |
| 415 | 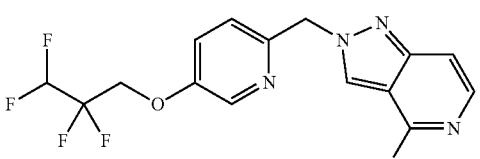<br>Intermediate-57a | 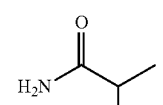 | G |
| 416 | 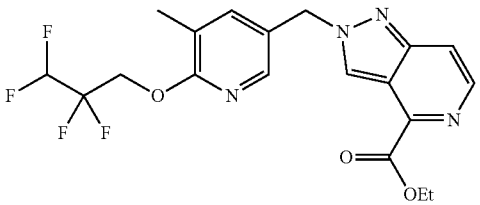<br>Intermediate-27b | 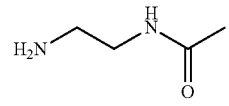 | L |
| 417 | 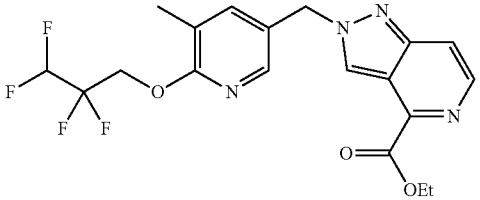<br>Intermediate-27b | 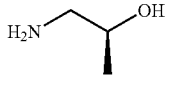 | L |
| 418 | 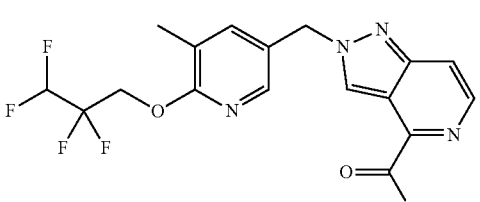<br>Intermediate-27b | 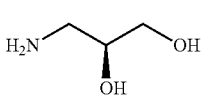 | L |
| 419 | 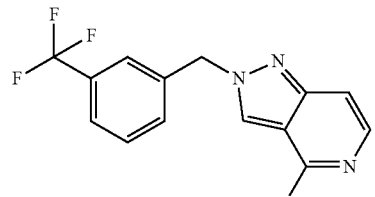<br>Intermediate-59a | 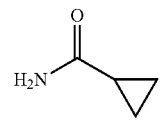 | G |

TABLE 7-continued
| Ex | Structure | Name | |
|---|---|---|---|
| 420 | 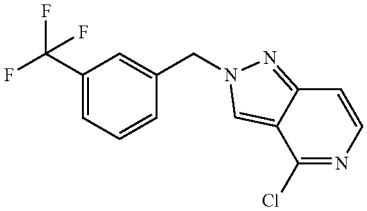<br>Intermediate-59a | 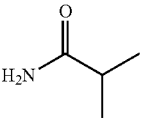 | G |
| 421 | 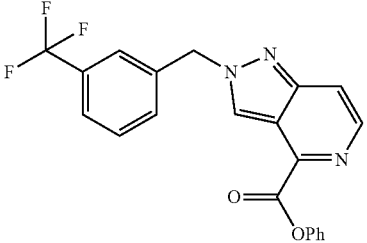<br>Intermediate-59b |  | J |
| 422 | 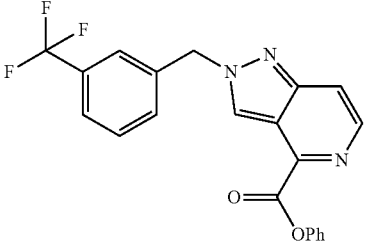<br>Intermediate-59b |  | J |
| 423 | 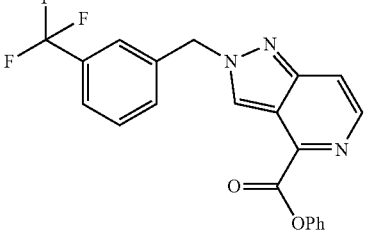<br>Intermediate-59b | 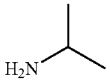 | J |
| 424 | 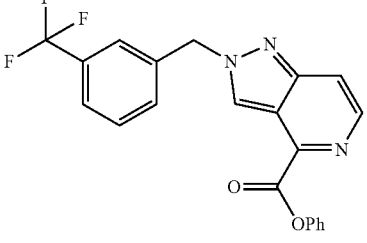<br>Intermediate-59b | 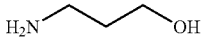 | J |

TABLE 7-continued

| Ex | Structure | | Name |
|---|---|---|---|
| 425 | Intermediate-27b | H₂N-CH₂-CH(OH)-CH₃ (S) | L |
| 426 | Intermediate-27b | H₂N-CH₂-CH(OH)-CH₂OH (S) | L |
| 427 | Intermediate-51b | H₂N-CH₃ | K |
| 428 | Intermediate-56b | H₂N-CH₃ | K |
| 429 | Intermediate-5b | H₂N-CH₃ | K |
| 430 | Intermediate-51b | H₂N-C₂H₅ | K |

TABLE 7-continued
| Ex | Structure | | Name | |
|---|---|---|---|---|
| 431 | 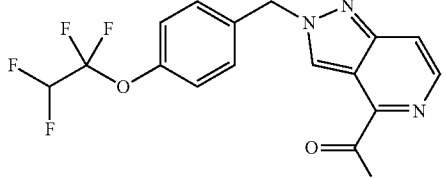 Intermediate-56b | |  | K |
| 432 | 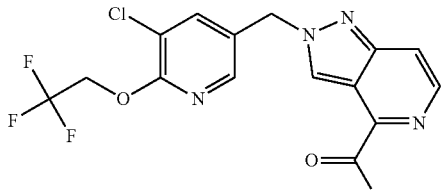 Intermediate-5b | |  | K |
| 433 | 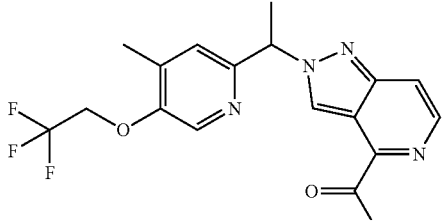 Intermediate-60b | |  | K |
| 434 | 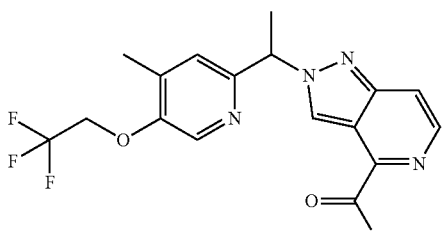 Intermediate-60b | |  | K |
| 435 | 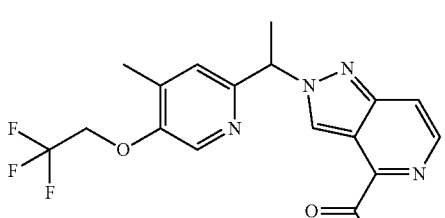 Intermediate-60b | | 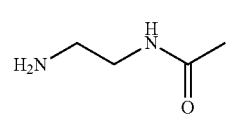 | L |

TABLE 7-continued

| Ex | Structure | Name | |
|---|---|---|---|
| 436 | Intermediate-60b | H₂N⌒OH | L |
| 437 | Intermediate-60b | H₂N⌒⌒OH | L |
| 438 | Intermediate-60b | H₂N−CH₂−CH(OH)−CH₃ (R) | L |
| 439 | Intermediate-61b | H₂N−CH₃ | J |
| 440 | Intermediate-61b | H₂N−Et | J |
| 441 | Intermediate-61b | H₂N−iPr | J |

TABLE 7-continued

| Ex | Structure | Name | |
|---|---|---|---|
| 442 | Intermediate-61b | H₂N–CH₂CH₂–OH | J |
| 443 | Intermediate-61b | H₂N–CH₂CH₂CH₂–OH | J |
| 444 | Intermediate-62b | H₂N–CH₂CH₃ | K |
| 445 | Intermediate-62b | H₂N–CH₂CH₃ | K |
| 446 | Intermediate-62b | H₂N–CH₂CH₂–OH | L |
| 447 | Intermediate-62b | H₂N–CH(CH₃)₂ | L |

TABLE 7-continued

| Ex | Structure | | Name | |
|---|---|---|---|---|
| 448 | [Intermediate-58b structure: 3-chloro-2-(2,2,3,3-tetrafluoropropoxy)pyridin-5-yl-methyl linked to 2H-pyrazolo[4,3-c]pyridine-4-carboxylic acid ethyl ester] Intermediate-58b | | H₂N–CH₃ (methylamine) | K |
| 449 | [Intermediate-58b] Intermediate-58b | | H₂N–CH₂CH₃ (ethylamine) | K |
| 450 | [Intermediate-58b] Intermediate-58b | | H₂N–CH(CH₃)₂ (isopropylamine) | L |
| 451 | [Intermediate-58b] Intermediate-58b | | H₂N–CH₂CH₂OH | L |
| 452 | [Intermediate-58b] Intermediate-58b | | H₂N–CH₂CH₂CH₂OH | L |
| 453 | [Intermediate-58b] Intermediate-58b | | H₂N–CH₂–CH(OH)–CH₃ (chiral) | L |

TABLE 7-continued

| Ex | Structure | Name | |
|---|---|---|---|
| 454 | Intermediate-58b | H₂N⟋⟍OH (with CH₃, stereo) | L |
| 455 | Intermediate-58b | H₂N⟋⟍OH, OH (stereo) | L |
| 456 | Intermediate-58b | H₂N⟋⟍OH, OH (stereo) | L |
| 457 | Intermediate-58b | H₂N⟋⟍OH (with CH₃, stereo) | L |
| 458 | Intermediate-58b | H₂N⟋⟍NHAc | L |
| 459 | Intermediate-60a | H₂N-C(O)-CH(CH₃)₂ | G |

TABLE 7-continued

| Ex | Structure | | Name | |
|---|---|---|---|---|
| 460 | [Intermediate-27a: 4-chloro-pyrazolopyridine linked via CH2 to methylpyridine with OCH2CF2CHF2 group] | Intermediate-27a | isobutyramide (H2N-C(=O)-CH(CH3)2) | G |
| 461 | [Intermediate-27a structure] | Intermediate-27a | cyclopropanecarboxamide | G |
| 462 | [Intermediate-27a structure] | Intermediate-27a | 2-hydroxy-2-methylpropanamide | G |
| 463 | [Intermediate-27b: pyrazolopyridine with CO2Et group linked via CH2 to methylpyridine with OCH2CF2CHF2] | Intermediate-27b | H2N-CH3 (methylamine) | K |
| 464 | [Intermediate-27b structure] | Intermediate-27b | H2N-CH2CH3 (ethylamine) | K |
| 465 | [Intermediate-62a: 4-chloro-pyrazolopyridine linked via CH2 to methylpyridine with OCH2CH2CF3] | Intermediate-62a | isobutyramide | G |
| 466 | [Intermediate-62a structure] | Intermediate-62a | cyclopropanecarboxamide | G |

TABLE 7-continued

| Ex | Structure | Name | |
|---|---|---|---|
| 467 | Intermediate-61a | cyclopropanecarboxamide (H2N-C(=O)-cyclopropyl) | G |
| 468 | Intermediate-61a | isobutyramide (H2N-C(=O)-CH(CH3)2) | G |
| 469 | Intermediate-63b | methylamine (H2N-CH3) | J |
| 470 | Intermediate-63b | ethylamine (H2N-CH2CH3) | J |
| 471 | Intermediate-63b | isopropylamine (H2N-CH(CH3)2) | J |
| 472 | Intermediate-63b | 3-aminopropan-1-ol (H2N-CH2CH2CH2-OH) | J |

TABLE 7-continued
| Ex | Structure | Name | |
|---|---|---|---|
| 473 | 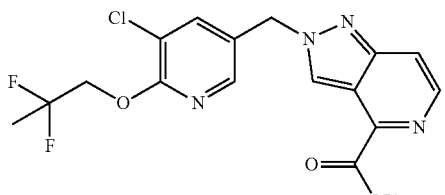<br>Intermediate-63b | 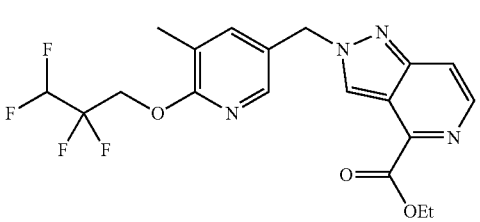 | J |
| 474 | 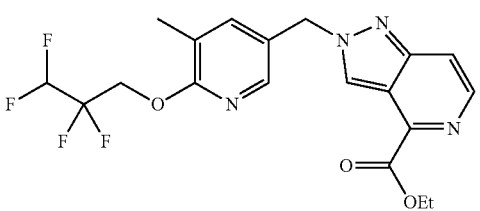<br>Intermediate-27b | 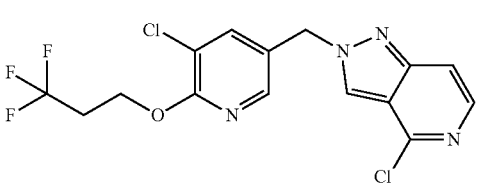 | L |
| 475 | 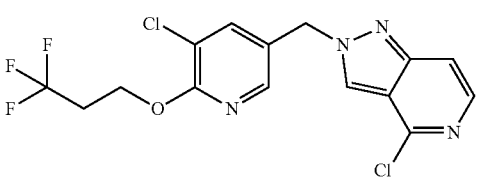<br>Intermediate-27b | 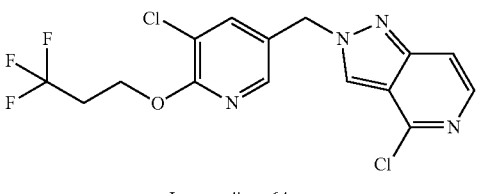 | L |
| 476 | Intermediate-64a | | G |
| 477 | Intermediate-64a | | G |
| 478 | Intermediate-64a | | G |

TABLE 7-continued

| Ex | Structure | | Name | |
|---|---|---|---|---|
| 479 | Intermediate-65a | | cyclopropanecarboxamide (H2N-C(=O)-cyclopropyl) | G |
| 480 | Intermediate-65a | | isobutyramide (H2N-C(=O)-CH(CH3)2) | G |
| 481 | Intermediate-64b | | H2N-CH3 (methylamine) | K |
| 482 | Intermediate-64b | | H2N-CH2CH3 (ethylamine) | K |
| 483 | Intermediate-64b | | H2N-CH(CH3)2 (isopropylamine) | L |
| 484 | Intermediate-64b | | H2N-CH2CH2OH (ethanolamine) | L |

TABLE 7-continued

| Ex | Structure | Name | |
|---|---|---|---|
| 485 | Intermediate-64b | H₂N~~~OH | L |
| 486 | Intermediate-51a | isobutyramide (H₂N-C(=O)-CH(CH₃)₂) | G |
| 487 | Intermediate-51a | cyclopropanecarboxamide (H₂N-C(=O)-cyclopropyl) | G |
| 488 | Intermediate-65b | H₂N-CH₃ | K |
| 489 | Intermediate-65b | H₂N-CH₂CH₃ | K |
| 490 | Intermediate-65b | H₂N-CH(CH₃)₂ | L |

TABLE 7-continued

| Ex | Structure | Name | |
|---|---|---|---|
| 491 | Intermediate-65b | H₂N⟋⟍OH | L |
| 492 | Intermediate-65b | H₂N⟋⟍⟋OH | L |
| 493 | Intermediate-26a | isobutyramide | G |
| 494 | Intermediate-26a | cyclopropanecarboxamide | G |
| 495 | Intermediate-26a | 2-hydroxy-2-methylpropanamide | G |
| 496 | Intermediate-25a | 2-hydroxy-2-methylpropanamide | G |

TABLE 7-continued

| Ex | Structure | Name | |
|---|---|---|---|
| 497 | Intermediate-44a | H₂N-C(=O)-C(CH₃)₂-OH | G |
| 498 | Intermediate-33a | H₂N-C(=O)-C(CH₃)₂-OH | |
| 499 | Intermediate-38a | H₂N-C(=O)-C(CH₃)₂-OH | G |
| 500 | Intermediate-26b | H₂N-CH₃ | K |
| 501 | Intermediate-26b | H₂N-CH₂CH₃ | K |
| 502 | Intermediate-63a | cyclopropanecarboxamide | G |
| 503 | Intermediate-63a | isobutyramide | G |

TABLE 7-continued
| Ex | Structure | | Name | |
|---|---|---|---|---|
| 504 | 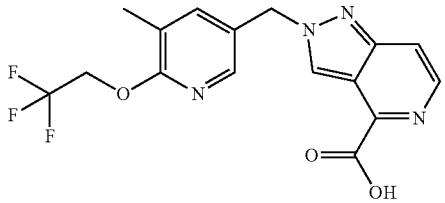<br>Intermediate-1c | | 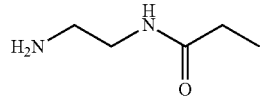 | H |
| 505 | 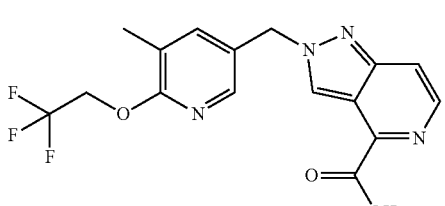<br>Intermediate-1c | | 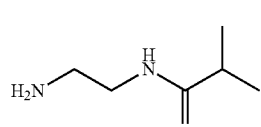 | H |
| 506 | 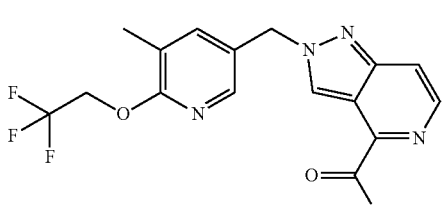<br>Intermediate-1c | | 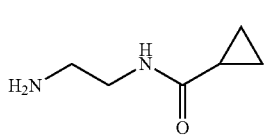 | H |
| 507 | 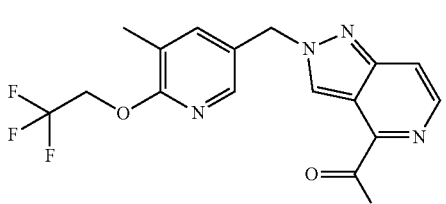<br>Intermediate-1c | | 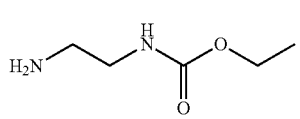 | H |
| 508 | 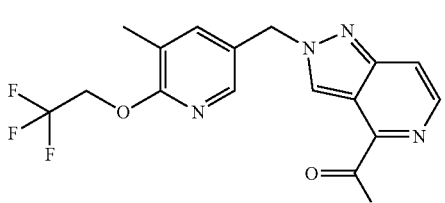<br>Intermediate-1c | | 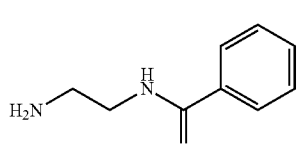 | H |
| 509 | 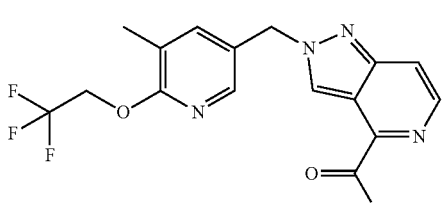<br>Intermediate-1c | | 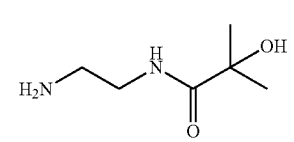 | H |

TABLE 7-continued

| Ex | Structure | Name | |
|---|---|---|---|
| 510 | (pyridine with CH₃, OCH₂CF₃, linked via CH₂ to pyrazolo[4,3-c]pyridine-4-COOH) Intermediate-1c | H₂N–CH₂CH₂–N(CH₃)–C(=O)–CH₃ | H |
| 511 | (same core) Intermediate-1c | H₂N–CH₂CH₂–NH–C(=O)–CH₂CH₃ | H |
| 512 | (same core) Intermediate-1c | H₂N–CH₂CH₂–NH–C(=O)–cyclobutyl | H |
| 513 | (same core) Intermediate-1c | H₂N–CH₂CH₂–NH–C(=O)–cyclohexyl | H |
| 514 | (same core) Intermediate-1c | H₂N–CH₂CH₂–NH–C(=O)–NH–CH₂CH₃ | H |
| 515 | (Cl-substituted pyridine with OCH₂CF₃, linked via CH₂ to pyrazolo[4,3-c]pyridine-4-COOEt) Intermediate-5b | H₂N–CH₂CH₂–NH–C(=O)–CH₃ | L |

TABLE 7-continued

| Ex | Structure | Name | |
|---|---|---|---|
| 516 | Intermediate-42b | H₂N–CH₂CH₂–NH–C(O)–CH₃ | L |
| 517 | Intermediate-44b | H₂N–CH₂CH₂–NH–C(O)–CH₃ | L |
| 518 | Intermediate-25b | H₂N–CH₂CH₂–NH–C(O)–CH₃ | L |
| 519 | Intermediate-26b | H₂N–CH₂CH₂–NH–C(O)–CH₃ | L |
| 520 | Intermediate-64b | H₂N–CH₂CH₂–NH–C(O)–CH₃ | L |
| 521 | Intermediate-50b | H₂N–CH₂CH₂–NH–C(O)–CH₃ | L |

TABLE 8

| Ex | Structure | Name |
|---|---|---|
| 522 | 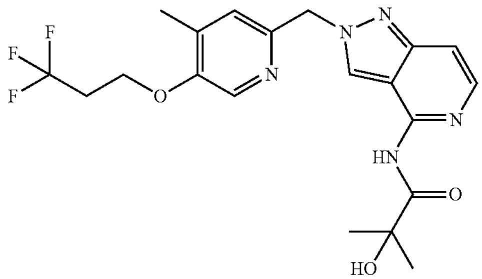 [SMILES: Cc1cc(Cn2cc3c(NC(=O)C(C)(C)O)nccc3n2)ncc1OCCC(F)(F)F] | 2-hydroxy-2-methyl-N-(2-((4-methyl-5-(3,3,3-trifluoropropoxy)pyridin-2-yl)methyl)-2H-pyrazolo[4,3-c]pyridin-4-yl)propanamide |
| 523 | 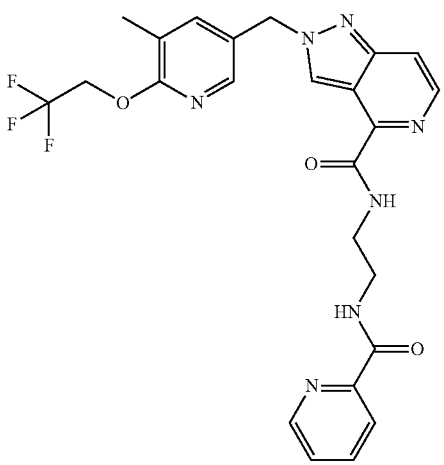 | 2-((5-methyl-6-(2,2,2-trifluoroethoxy)pyridin-3-yl)methyl)-N-(2-(picolinamido)ethyl)-2H-pyrazolo[4,3-c]pyridine-4-carboxamide |
| 524 | 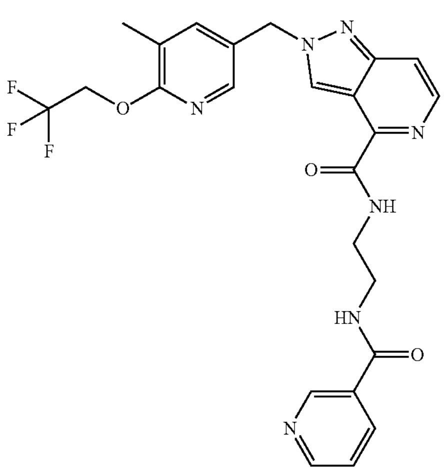 | 2-((5-methyl-6-(2,2,2-trifluoroethoxy)pyridin-3-yl)methyl)-N-(2-(nicotinamido)ethyl)-2H-pyrazolo[4,3-c]pyridine-4-carboxamide |

TABLE 8-continued

| | | |
|---|---|---|
| 525 | 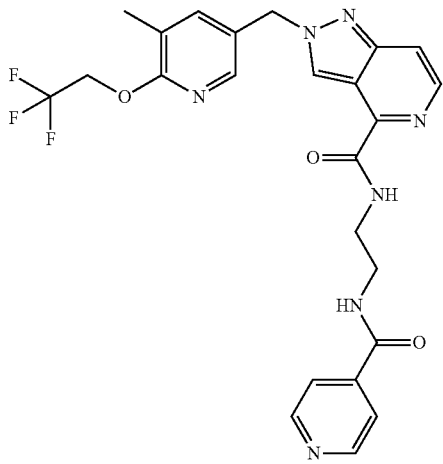 [SMILES: Cc1cc(Cn2cc3c(C(=O)NCCNC(=O)c4ccncc4)nccc3n2)cnc1OCC(F)(F)F] | N-(2-(isonicotinamido)ethyl)-2-((5-methyl-6-(2,2,2-trifluoroethoxy)pyridin-3-yl)methyl)-2H-pyrazolo[4,3-c]pyridine-4-carboxamide |
| 526 | 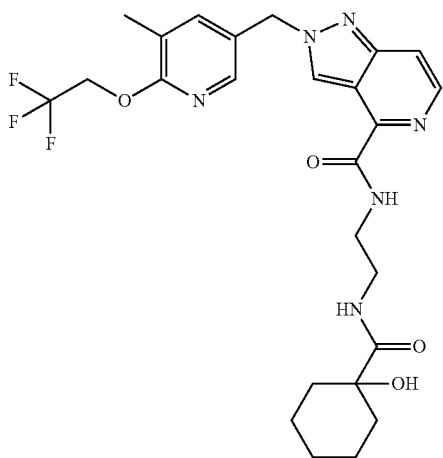 [SMILES: Cc1cc(Cn2cc3c(C(=O)NCCNC(=O)C4(O)CCCCC4)nccc3n2)cnc1OCC(F)(F)F] | N-(2-(1-hydroxycyclohexanecarboxamido)ethyl)-2-((5-methyl-6-(2,2,2-trifluoroethoxy)pyridin-3-yl)methyl)-2H-pyrazolo[4,3-c]pyridine-4-carboxamide |
| 527 | 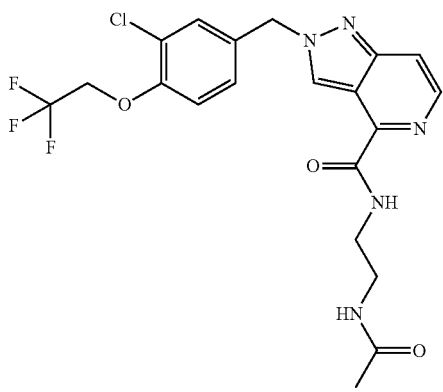 | N-(2-acetamidoethyl)-2-(3-chloro-4-(2,2,2-trifluoroethoxy)benzyl)-2H-pyrazolo[4,3-c]pyridine-4-carboxamide |
| 528 | 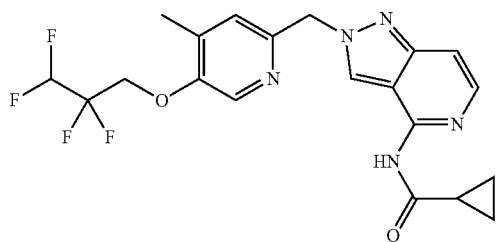 | N-(2-((4-methyl-5-(2,2,3,3-tetrafluoropropoxy)pyridin-2-yl)methyl)-2H-pyrazolo[4,3-c]pyridin-4-yl)cyclopropanecarboxamide |

TABLE 8-continued

| # | Structure | Name |
|---|---|---|
| 529 | 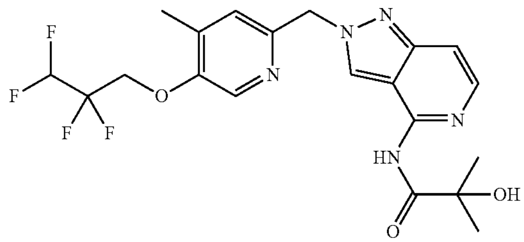 [SMILES: Cc1cc(Cn2cc3c(NC(=O)C(C)(C)O)nccc3n2)ncc1OCC(F)(F)C(F)F] | 2-hydroxy-2-methyl-N-(2-((4-methyl-5-(2,2,3,3-tetrafluoropropoxy)pyridin-2-yl)methyl)-2H-pyrazolo[4,3-c]pyridin-4-yl)propanamide |
| 530 | 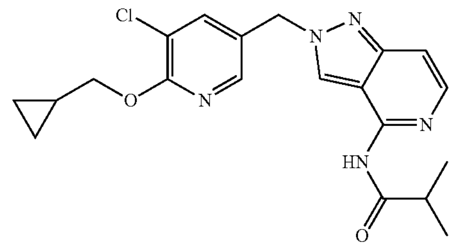 [SMILES: CC(C)C(=O)Nc1nccc2nn(Cc3cnc(OCC4CC4)c(Cl)c3)cc12] | N-(2-((5-chloro-6-(cyclopropylmethoxy)pyridin-3-yl)methyl)-2H-pyrazolo[4,3-c]pyridin-4-yl)isobutyramide |
| 531 | 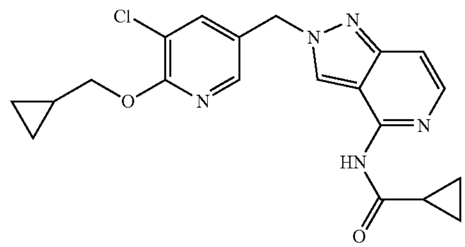 [SMILES: O=C(Nc1nccc2nn(Cc3cnc(OCC4CC4)c(Cl)c3)cc12)C1CC1] | N-(2-((5-chloro-6-(cyclopropylmethoxy)pyridin-3-yl)methyl)-2H-pyrazolo[4,3-c]pyridin-4-yl)cyclopropanecarboxamide |
| 532 | 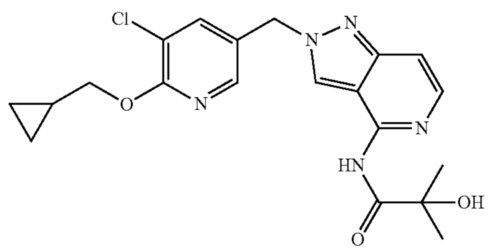 [SMILES: CC(C)(O)C(=O)Nc1nccc2nn(Cc3cnc(OCC4CC4)c(Cl)c3)cc12] | N-(2-((5-chloro-6-(cyclopropylmethoxy)pyridin-3-yl)methyl)-2H-pyrazolo[4,3-c]pyridin-4-yl)-2-hydroxy-2-methylpropanamide |
| 533 | 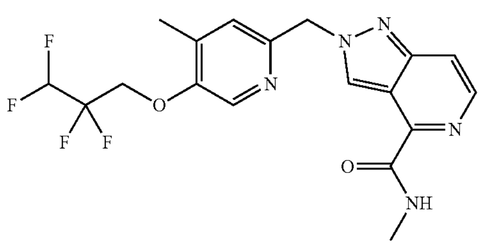 [SMILES: CNC(=O)c1nccc2nn(Cc3cc(C)c(OCC(F)(F)C(F)F)cn3)cc12] | N-methyl-2-((4-methyl-5-(2,2,3,3-tetrafluoropropoxy)pyridin-2-yl)methyl)-2H-pyrazolo[4,3-c]pyridine-4-carboxamide |
| 534 | 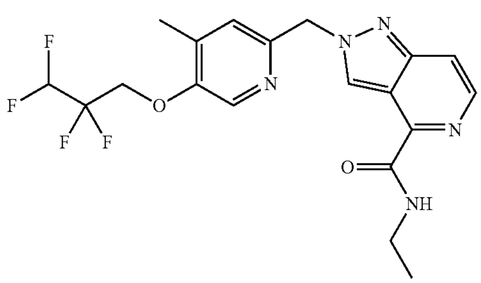 [SMILES: CCNC(=O)c1nccc2nn(Cc3cc(C)c(OCC(F)(F)C(F)F)cn3)cc12] | N-ethyl-2-((4-methyl-5-(2,2,3,3-tetrafluoropropoxy)pyridin-2-yl)methyl)-2H-pyrazolo[4,3-c]pyridine-4-carboxamide |

TABLE 8-continued

| 535 | 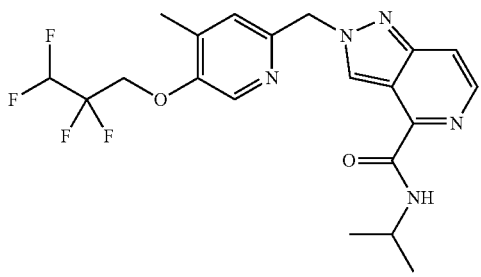 [SMILES: Cc1cc(Cn2cc3c(C(=O)NC(C)C)nccc3n2)ncc1OCC(F)(F)C(F)F] | N-isopropyl-2-((4-methyl-5-(2,2,3,3-tetrafluoropropoxy)pyridin-2-yl)methyl)-2H-pyrazolo[4,3-c]pyridine-4-carboxamide |
| 536 | 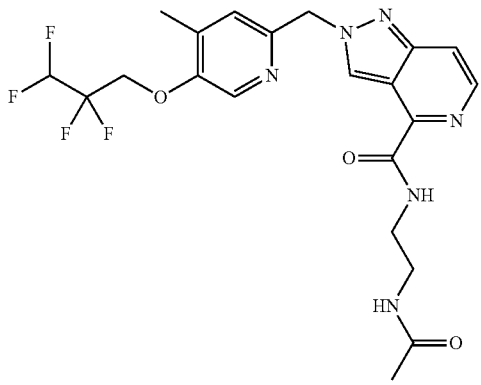 [SMILES: CC(=O)NCCNC(=O)c1nccc2nn(Cc3cc(C)c(OCC(F)(F)C(F)F)cn3)cc12] | N-(2-acetamidoethyl)-2-((4-methyl-5-(2,2,3,3-tetrafluoropropoxy)pyridin-2-yl)methyl)-2H-pyrazolo[4,3-c]pyridine-4-carboxamide |
| 537 | 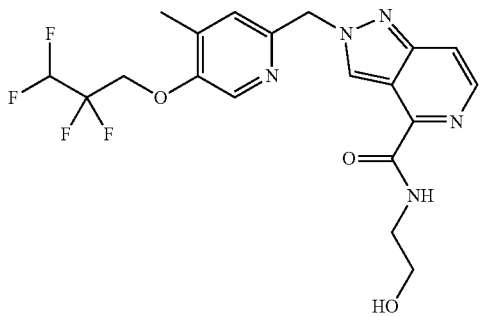 [SMILES: Cc1cc(Cn2cc3c(C(=O)NCCO)nccc3n2)ncc1OCC(F)(F)C(F)F] | N-(2-hydroxyethyl)-2-((4-methyl-5-(2,2,3,3-tetrafluoropropoxy)pyridin-2-yl)methyl)-2H-pyrazolo[4,3-c]pyridine-4-carboxamide |
| 538 | 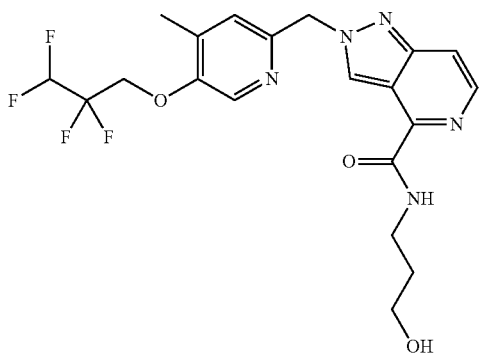 [SMILES: Cc1cc(Cn2cc3c(C(=O)NCCCO)nccc3n2)ncc1OCC(F)(F)C(F)F] | N-(3-hydroxypropyl)-2-((4-methyl-5-(2,2,3,3-tetrafluoropropoxy)pyridin-2-yl)methyl)-2H-pyrazolo[4,3-c]pyridine-4-carboxamide |
| 539 | 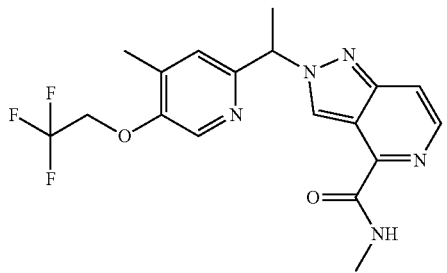 [SMILES: CNC(=O)c1nccc2nn(C(C)c3cc(C)c(OCC(F)(F)F)cn3)cc12] | N-methyl-2-(1-(4-methyl-5-(2,2,2-trifluoroethoxy)pyridin-2-yl)ethyl)-2H-pyrazolo[4,3-c]pyridine-4-carboxamide (single enantiomer) |

TABLE 8-continued

| | | |
|---|---|---|
| 540 | 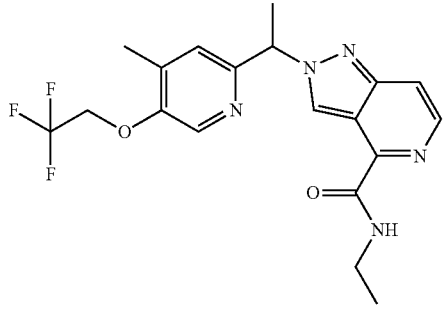 [SMILES: CCNC(=O)c1nccc2nn(C(C)c3cc(C)c(OCC(F)(F)F)cn3)cc12] | N-ethyl-2-(1-(4-methyl-5-(2,2,2-trifluoroethoxy)pyridin-2-yl)ethyl)-2H-pyrazolo[4,3-c]pyridine-4-carboxamide (single enantiomer) |
| 541 | 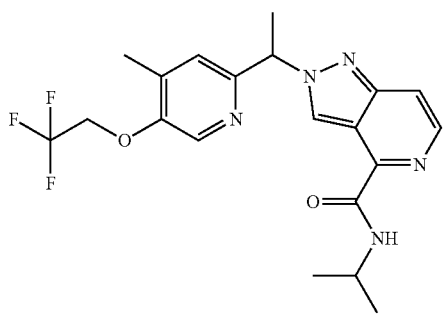 [SMILES: Cc1cc(C(C)n2cc3c(C(=O)NC(C)C)nccc3n2)ncc1OCC(F)(F)F] | N-isopropyl 2-(1-(4-methyl-5-(2,2,2-trifluoroethoxy)pyridin-2-yl)ethyl)-2H-pyrazolo[4,3-c]pyridine-4-carboxamide (single enantiomer) |
| 542 | 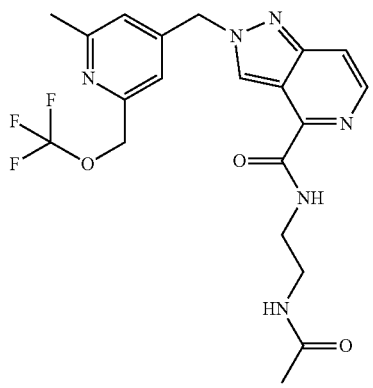 [SMILES: CC(=O)NCCNC(=O)c1nccc2nn(Cc3cc(C)nc(COC(F)(F)F)c3)cc12] | N-(2-acetamidoethyl)-2-((2-methyl-6-(2,2,2-trifluoroethoxy)pyridin-4-yl)methyl)-2H-pyrazolo[4,3-c]pyridine-4-carboxamide |
| 543 | 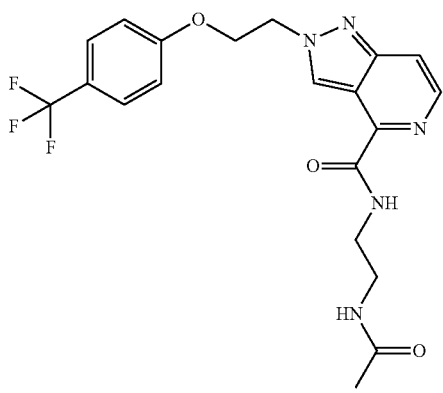 [SMILES: CC(=O)NCCNC(=O)c1nccc2nn(CCOc3ccc(C(F)(F)F)cc3)cc12] | N-(2-acetamidoethyl)-2-(2-(4-(trifluoromethyl)phenoxy)ethyl)-2H-pyrazolo[4,3-c]pyridine-4-carboxamide |

TABLE 8-continued

| | | |
|---|---|---|
| 544 | 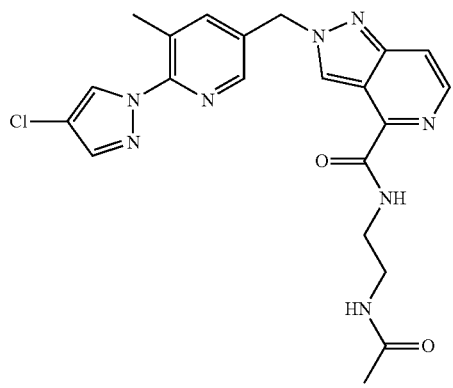 [SMILES: CC(=O)NCCNC(=O)c1nccc2nn(Cc3cnc(-n4cc(Cl)cn4)c(C)c3)cc12] | N-(2-acetamidoethyl)-2-((6-(4-chloro-1H-pyrazol-1-yl)-5-methylpyridin-3-yl)methyl)-2H-pyrazolo[4,3-c]pyridine-4-carboxamide |
| 545 | 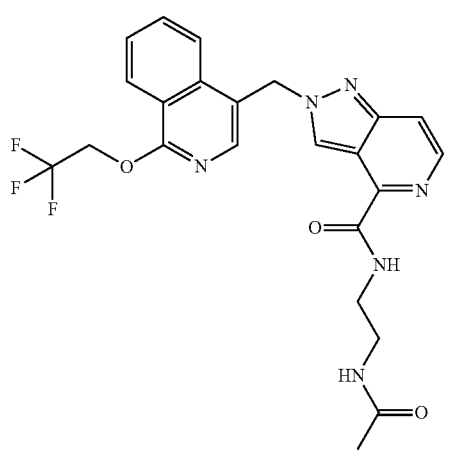 [SMILES: CC(=O)NCCNC(=O)c1nccc2nn(Cc3cnc(OCC(F)(F)F)c4ccccc34)cc12] | N-(2-acetamidoethyl)-2-((1-(2,2,2-trifluoroethoxy)isoquinolin-4-yl)methyl)-2H-pyrazolo[4,3-c]pyridine-4-carboxamide |
| 546 | 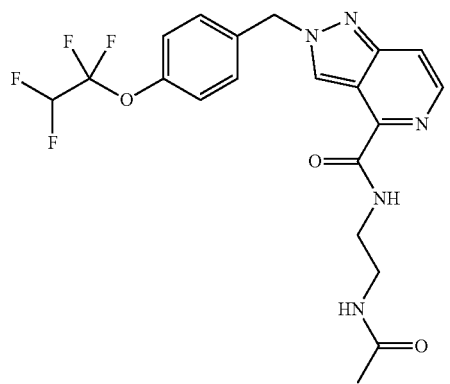 [SMILES: CC(=O)NCCNC(=O)c1nccc2nn(Cc3ccc(OC(F)(F)C(F)F)cc3)cc12] | N-(2-acetamidoethyl)-2-(4-(1,1,2,2-tetrafluoroethoxy)benzyl)-2H-pyrazolo[4,3-c]pyridine-4-carboxamide |
| 547 | 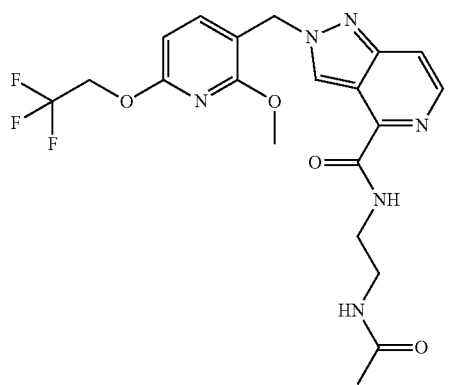 [SMILES: COc1nc(OCC(F)(F)F)ccc1Cn1cc2c(C(=O)NCCNC(C)=O)nccc2n1] | N-(2-acetamidoethyl)-2-((2-methoxy-6-(2,2,2-trifluoroethoxy)pyridin-3-yl)methyl)-2H-pyrazolo[4,3-c]pyridine-4-carboxamide |

TABLE 8-continued

| | | |
|---|---|---|
| 548 | 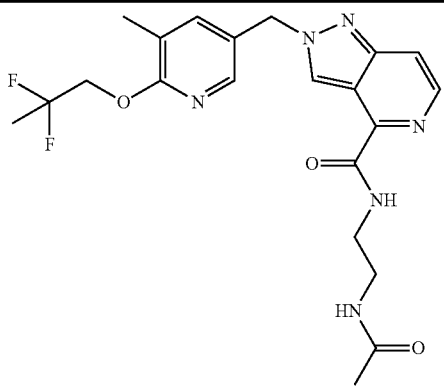 | N-(2-acetamidoethyl)-2-((6-(2,2-difluoropropoxy)-5-methylpyridin-3-yl)methyl)-2H-pyrazolo[4,3-c]pyridine-4-carboxamide |
| 549 | 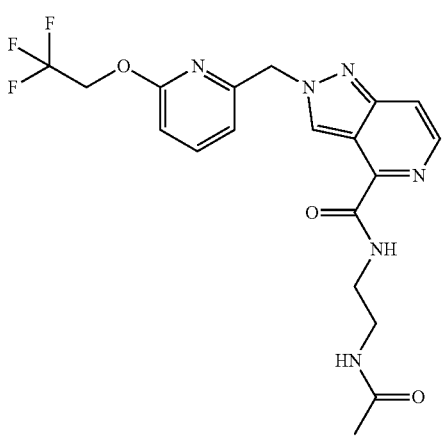 [SMILES: CC(=O)NCCNC(=O)c1nccc2nn(Cc3cccc(OCC(F)(F)F)n3)cc12] | N-(2-acetamidoethyl)-2-((6-(2,2,2-trifluoroethoxy)pyridin-2-yl)methyl)-2H-pyrazolo[4,3-c]pyridine-4-carboxamide |
| 550 | 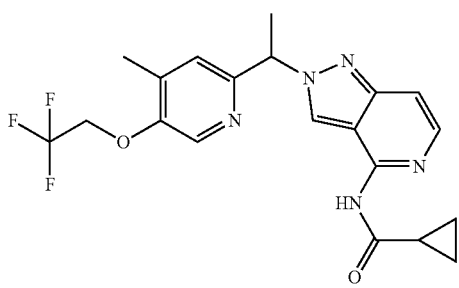 [SMILES: Cc1cc(C(C)n2cc3c(NC(=O)C4CC4)nccc3n2)ncc1OCC(F)(F)F] | N-(2-(1-(4-methyl-5-(2,2,2-trifluoroethoxy)pyridin-2-yl)ethyl)-2H-pyrazolo[4,3-c]pyridin-4-yl)cyclopropanecarboxamide (single enantiomer) |
| 551 | 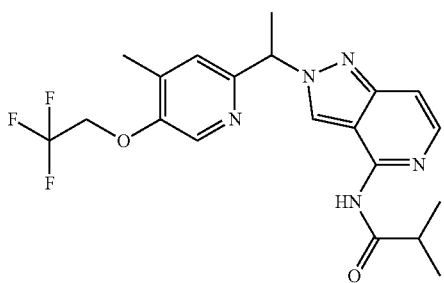 [SMILES: Cc1cc(C(C)n2cc3c(NC(=O)C(C)C)nccc3n2)ncc1OCC(F)(F)F] | N-(2-(1-(4-methyl-5-(2,2,2-trifluoroethoxy)pyridin-2-yl)ethyl)-2H-pyrazolo[4,3-c]pyridin-4-yl)isobutyramide (single enantiomer) |
| 552 | 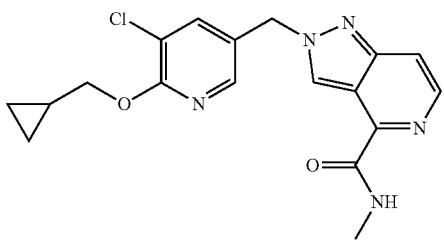 [SMILES: CNC(=O)c1nccc2nn(Cc3cnc(OCC4CC4)c(Cl)c3)cc12] | 2-((5-chloro-6-(cyclopropylmethoxy)pyridin-3-yl)methyl)-N-methyl-2H-pyrazolo[4,3-c]pyridine-4-carboxamide |

TABLE 8-continued

| | | |
|---|---|---|
| 553 | 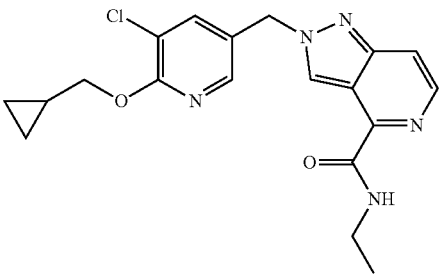 [SMILES: CCNC(=O)c1nccc2nn(Cc3cnc(OCC4CC4)c(Cl)c3)cc12] | 2-((5-chloro-6-(cyclopropylmethoxy)pyridin-3-yl)methyl)-N-ethyl-2H-pyrazolo(4,3-c]pyridine-4-carboxamide |
| 554 | 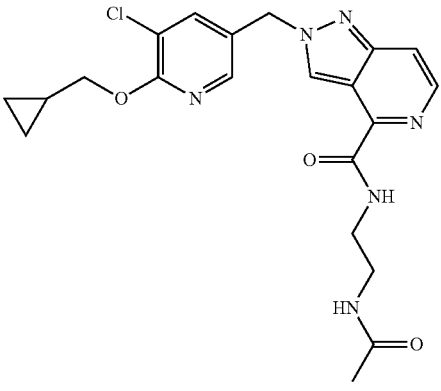 [SMILES: CC(=O)NCCNC(=O)c1nccc2nn(Cc3cnc(OCC4CC4)c(Cl)c3)cc12] | N-(2-acetamidoethyl)-2-((5-chloro-6-(cyclopropylmethoxy)pyridin-3-yl)methyl)-2H-pyrazolo[4,3-c]pyridine-4-carboxamide |
| 555 | 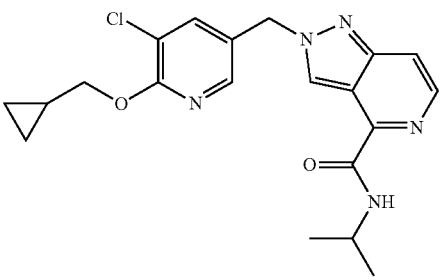 [SMILES: CC(C)NC(=O)c1nccc2nn(Cc3cnc(OCC4CC4)c(Cl)c3)cc12] | 2-((5-chloro-6-(cyclopropylmethoxy)pyridin-3-yl)methyl)-N-isopropyl-2H-pyrazolo[4,3-c]pyridine-4-carboxamide |
| 556 | 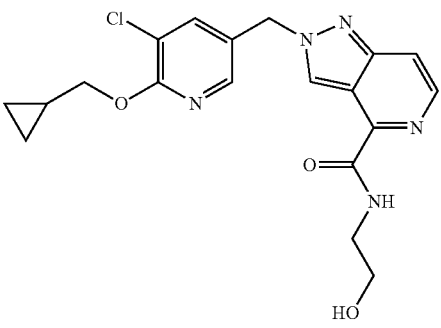 [SMILES: O=C(NCCO)c1nccc2nn(Cc3cnc(OCC4CC4)c(Cl)c3)cc12] | 2-((5-chloro-6-(cyclopropylmethoxy)pyridin-3-yl)methyl)-N-(2-hydroxyethyl)-2H-pyrazolo[4,3-c]pyridine-4-carboxamide |
| 557 | 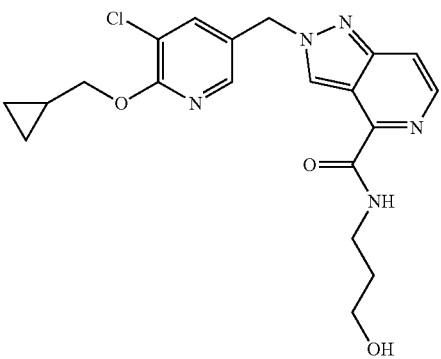 [SMILES: O=C(NCCCO)c1nccc2nn(Cc3cnc(OCC4CC4)c(Cl)c3)cc12] | 2-((5-chloro-6-(cyclopropylmethoxy)pyridin-3-yl)methyl)-N-(3-hydroxypropyl)-2H-pyrazolo[4,3-c]pyridine-4-carboxamide |

TABLE 8-continued

| | | |
|---|---|---|
| 558 | | N-(2-((6-((4-fluorobenzyl)oxy)-5-methylpyridin-3-yl)methyl)-2H-pyrazolo[4,3-c]pyridin-4-yl)isobutyramide |
| 559 | | N-(2-((6-((4-fluorobenzyl)oxy)-5-methylpyridin-3-yl)methyl)-2H-pyrazolo[4,3-c]pyridin-4-yl)cyclopropanecarboxamide |
| 560 | | N-(2-((6-((4-fluorobenzyl)oxy)-5-methylpyridin-3-yl)methyl)-2H-pyrazolo[4,3-c]pyridin-4-yl)-2-hydroxy-2-methylpropanamide |
| 561 | | 2-((6-((4-fluorobenzyl)oxy)-5-methylpyridin-3-yl)methyl)-N-methyl-2H-pyrazolo[4,3-c]pyridine-4-carboxamide |
| 562 | | N-ethyl-2-((6-((4-fluorobenzyl)oxy)-5-methylpyridin-3-yl)methyl)-2H-pyrazolo[4,3-c]pyridine-4-carboxamide |
| 563 | | N-(2-acetamidoethyl)-2-((6-((4-fluorobenzyl)oxy)-5-methylpyridin-3-yl)methyl)-2H-pyrazolo[4,3-c]pyridine-4-carboxamide |

TABLE 8-continued

| | | |
|---|---|---|
| 564 | 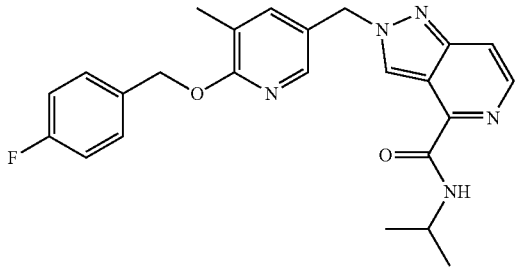 [SMILES: Cc1cc(Cn2cc3c(C(=O)NC(C)C)nccc3n2)cnc1OCc1ccc(F)cc1] | 2-((6-((4-fluorobenzyl)oxy)-5-methylpyridin-3-yl)methyl)-N-isopropyl-2H-pyrazolo[4,3-c]pyridine-4-carboxamide |
| 565 | 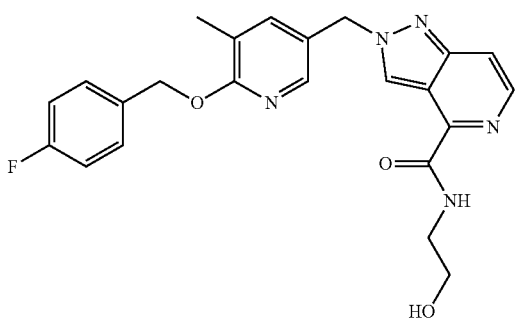 [SMILES: Cc1cc(Cn2cc3c(C(=O)NCCO)nccc3n2)cnc1OCc1ccc(F)cc1] | 2-((6-((4-fluorobenzyl)oxy)-5-methylpyridin-3-yl)methyl)-N-(2-hydroxyethyl)-2H-pyrazolo[4,3-c]pyridine-4-carboxamide |
| 566 | 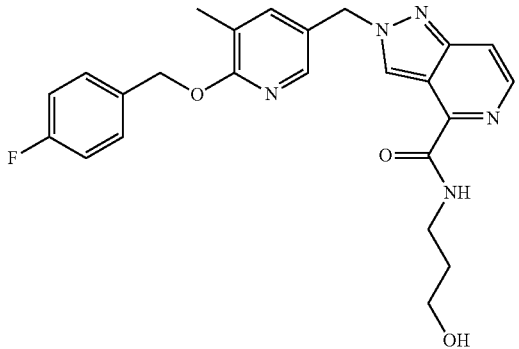 [SMILES: Cc1cc(Cn2cc3c(C(=O)NCCCO)nccc3n2)cnc1OCc1ccc(F)cc1] | 2-((6-((4-fluorobenzyl)oxy)-5-methylpyridin-3-yl)methyl)-N-(3-hydroxypropyl)-2H-pyrazolo[4,3-c]pyridine-4-carboxamide |
| 567 | 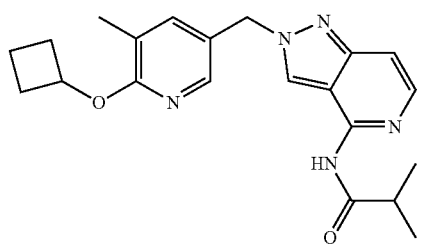 [SMILES: Cc1cc(Cn2cc3c(NC(=O)C(C)C)nccc3n2)cnc1OC1CCC1] | N-(2-((6-cyclobutoxy-5-methylpyridin-3-yl)methyl)-2H-pyrazolo[4,3-c]pyridin-4-yl)-isobutyramide |
| 568 | 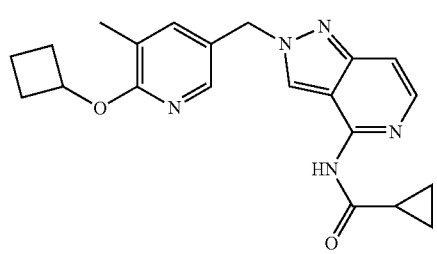 [SMILES: Cc1cc(Cn2cc3c(NC(=O)C4CC4)nccc3n2)cnc1OC1CCC1] | N-(2-((6-cyclobutoxy-5-methylpyridin-3-yl)methyl)-2H-pyrazolo[4,3-c]pyridin-4-yl)cyclopropanecarboxamide |

TABLE 8-continued

| | | |
|---|---|---|
| 569 | 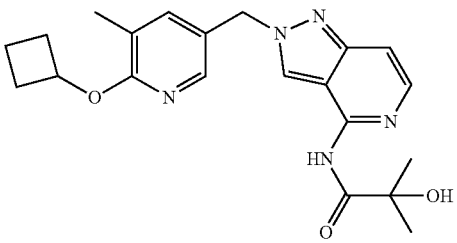 [SMILES: Cc1cc(Cn2cc3c(NC(=O)C(C)(C)O)nccc3n2)cnc1OC1CCC1] | N-(2-((6-cyclobutoxy-5-methylpyridin-3-yl)methyl)-2H-pyrazolo[4,3-c]pyridin-4-yl)-2-hydroxy-2-methylpropanamide |
| 570 | 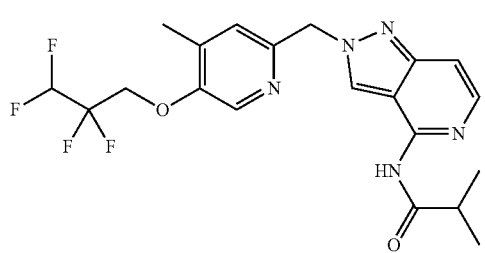 | N-(2-((4-methyl-5-(2,2,3,3-tetrafluoropropoxy)pyridin-2-yl)methyl)-2H-pyrazolo[4,3-c]pyridin-4-yl)isobutyramide |
| 571 | 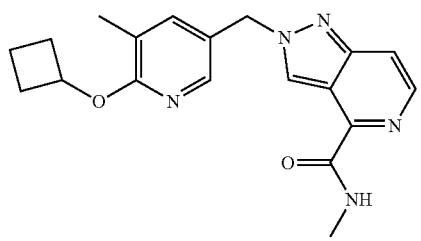 [SMILES: CNC(=O)c1nccc2nn(Cc3cnc(OC4CCC4)c(C)c3)cc12] | 2-((6-cyclobutoxy-5-methylpyridin-3-yl)methyl)-N-methyl-2H-pyrazolo[4,3-c]pyridine-4-carboxamide |
| 572 | 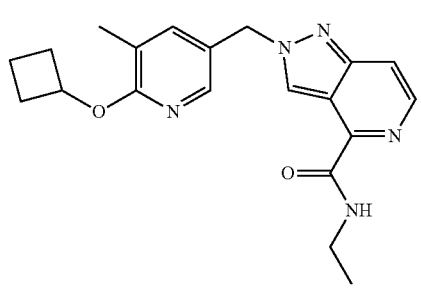 [SMILES: CCNC(=O)c1nccc2nn(Cc3cnc(OC4CCC4)c(C)c3)cc12] | 2-((6-cyclobutoxy-5-methylpyridin-3-yl)methyl)-N-ethyl-2H-pyrazolo[4,3-c]pyridine-4-carboxamide |
| 573 | 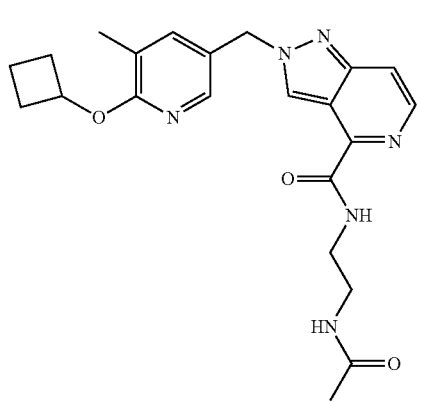 [SMILES: CC(=O)NCCNC(=O)c1nccc2nn(Cc3cnc(OC4CCC4)c(C)c3)cc12] | N-(2-acetamidoethyl)-2-((6-cyclobutoxy-5-methylpyridin-3-yl)methyl)-2H-pyrazolo[4,3-c]pyridine-4-carboxamide |

TABLE 8-continued

| 574 | 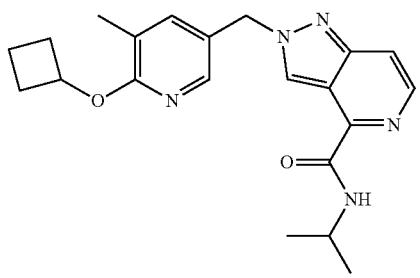 | 2-((6-cyclobutoxy-5-methylpyridin-3-yl)methyl)-N-isopropyl-2H-pyrazolo[4,3-c]pyridine-4-carboxamide |
| --- | --- | --- |
| 575 | 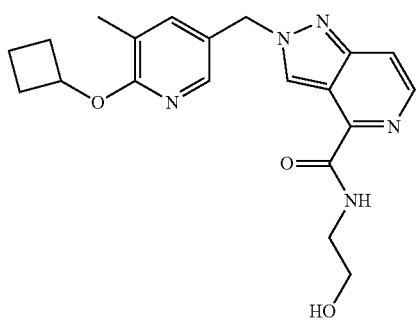 [SMILES: Cc1cc(Cn2cc3c(C(=O)NCCO)nccc3n2)cnc1OC1CCC1] | 2-((6-cyclobutoxy-5-methylpyridin-3-yl)methyl)-N-(2-hydroxyethyl)-2H-pyrazolo[4,3-c]pyridine-4-carboxamide |
| 576 | 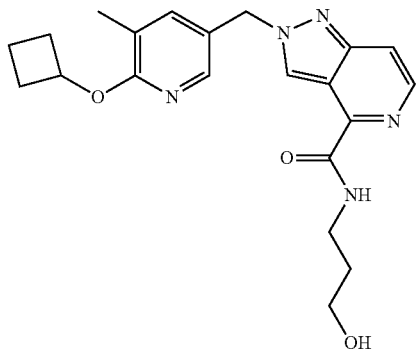 [SMILES: Cc1cc(Cn2cc3c(C(=O)NCCCO)nccc3n2)cnc1OC1CCC1] | 2-((6-cyclobutoxy-5-methylpyridin-3-yl)methyl)-N-(3-hydroxypropyl)-2H-pyrazolo[4,3-c]pyridine-4-carboxamide |
| 577 | 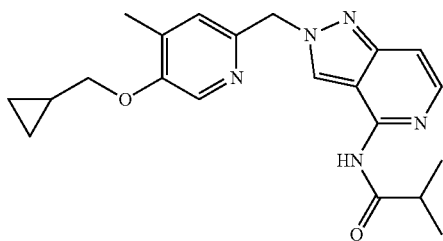 [SMILES: Cc1cc(Cn2cc3c(NC(=O)C(C)C)nccc3n2)ncc1OCC1CC1] | N-(2-((5-(cyclopropylmethoxy)-4-methylpyridin-2-yl)methyl)-2H-pyrazolo[4,3-c]pyridin-4-yl)isobutyramide |
| 578 | 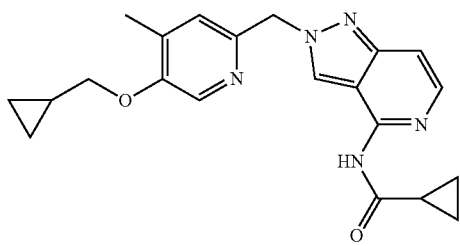 [SMILES: Cc1cc(Cn2cc3c(NC(=O)C4CC4)nccc3n2)ncc1OCC1CC1] | N-(2-((5-(cyclopropylmethoxy)-4-methylpyridin-2-yl)methyl)-2H-pyrazolo[4,3-c]pyridin-4-yl)cyclopropanecarboxamide |

| | | |
|---|---|---|
| 579 | 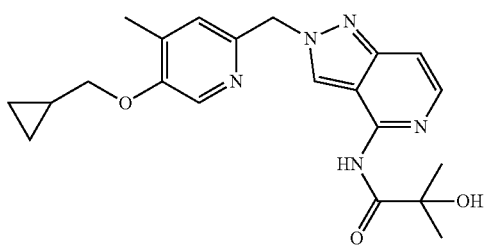 [SMILES: Cc1cc(Cn2cc3c(NC(=O)C(C)(C)O)nccc3n2)ncc1OCC1CC1] | N-(2-((5-(cyclopropylmethoxy)-4-methylpyridin-2-yl)methyl)-2H-pyrazolo[4,3-c]pyridin-4-yl)-2-hydroxy-2-methylpropanamide |
| 580 | 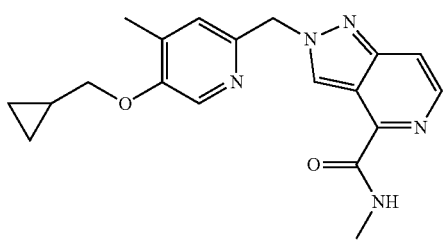 [SMILES: CNC(=O)c1nccc2nn(Cc3cc(C)c(OCC4CC4)cn3)cc12] | 2-((5-(cyclopropylmethoxy)-4-methylpyridin-2-yl)methyl)-N-methyl-2H-pyrazolo[4,3-c]pyridine-4-carboxamide |
| 581 | 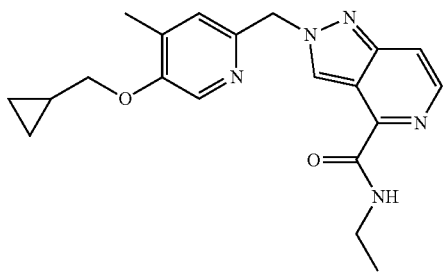 [SMILES: CCNC(=O)c1nccc2nn(Cc3cc(C)c(OCC4CC4)cn3)cc12] | 2-((5-(cyclopropylmethoxy)-4-methylpyridin-2-yl)methyl)-N-ethyl-2H-pyrazolo[4,3-c]pyridine-4-carboxamide |
| 582 | 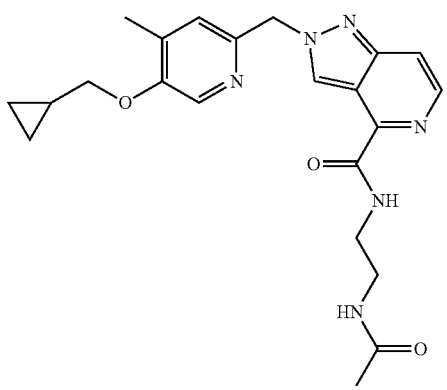 [SMILES: CC(=O)NCCNC(=O)c1nccc2nn(Cc3cc(C)c(OCC4CC4)cn3)cc12] | N-(2-acetamidoethyl)-2-((5-(cyclopropylmethoxy)-4-methylpyridin-2-yl)methyl)-2H-pyrazolo[4,3-c]pyridine-4-carboxamide |
| 583 | 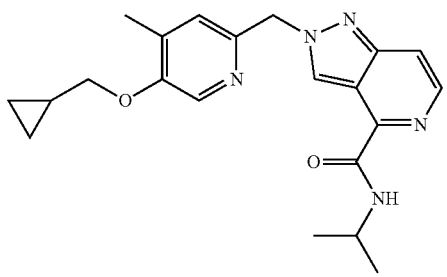 [SMILES: Cc1cc(Cn2cc3c(C(=O)NC(C)C)nccc3n2)ncc1OCC1CC1] | 2-((5-(cyclopropylmethoxy)-4-methylpyridin-2-yl)methyl)-N-isopropyl-2H-pyrazolo[4,3-c]pyridine-4-carboxamide |

TABLE 8-continued

| 584 | 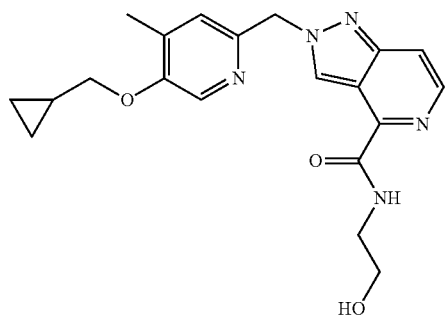 [SMILES: Cc1cc(Cn2cc3c(C(=O)NCCO)nccc3n2)ncc1OCC1CC1] | 2-((5-(cyclopropylmethoxy)-4-methylpyridin-2-yl)methyl)-N-(2-hydroxyethyl)-2H-pyrazolo[4,3-c]pyridine-4-carboxamide |
| 585 | 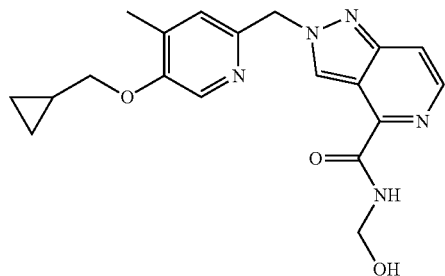 [SMILES: Cc1cc(Cn2cc3c(C(=O)NCO)nccc3n2)ncc1OCC1CC1] | 2-((5-(cyclopropylmethoxy)-4-methylpyridin-2-yl)methyl)-N-(3-hydroxypropyl)-2H-pyrazolo[4,3-c]pyridine-4-carboxamide |
| 586 | 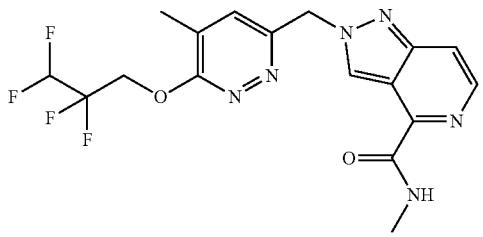 [SMILES: CNC(=O)c1nccc2nn(Cc3cc(C)c(OCC(F)(F)C(F)F)nn3)cc12] | N-methyl-2-((5-methyl-6-(2,2,3,3-tetrafluoropropoxy)pyridazin-3-yl)methyl)-2H-pyrazolo[4,3-c]pyridine-4-carboxamide |
| 587 | 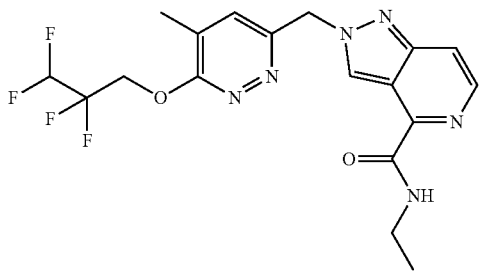 [SMILES: CCNC(=O)c1nccc2nn(Cc3cc(C)c(OCC(F)(F)C(F)F)nn3)cc12] | N-ethyl-2-((5-methyl-6-(2,2,3,3-tetrafluoropropoxy)pyridazin-3-yl)methyl)-2H-pyrazolo[4,3-c]pyridine-4-carboxamide |
| 588 | 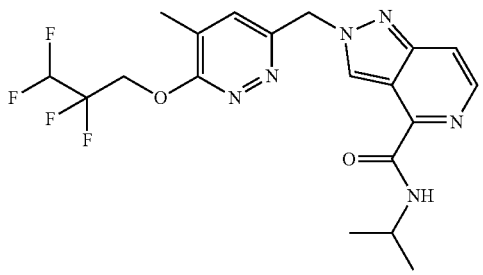 [SMILES: Cc1cc(Cn2cc3c(C(=O)NC(C)C)nccc3n2)nnc1OCC(F)(F)C(F)F] | N-isopropyl-2-((5-methyl-6-(2,2,3,3-tetrafluoropropoxy)pyridazin-3-yl)methyl)-2H-pyrazolo[4,3-c]pyridine-4-carboxamide |

TABLE 8-continued

| | | |
|---|---|---|
| 589 | 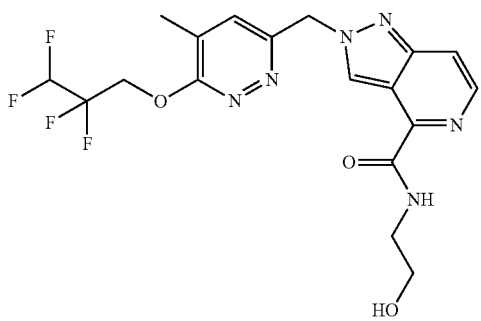 [SMILES: Cc1cc(Cn2cc3c(C(=O)NCCO)nccc3n2)nnc1OCC(F)(F)C(F)F] | N-(2-hydroxyethyl)-2-((5-methyl-6-(2,2,3,3-tetrafluoropropoxy)pyridazin-3-yl)methyl)-2H-pyrazolo[4,3-c]pyridine-4-carboxamide |
| 590 | 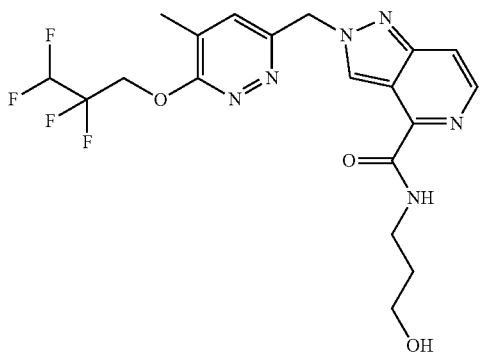 [SMILES: Cc1cc(Cn2cc3c(C(=O)NCCCO)nccc3n2)nnc1OCC(F)(F)C(F)F] | N-(3-hydroxypropyl)-2-((5-methyl-6-(2,2,3,3-tetrafluoropropoxy)pyridazin-3-yl)methyl)-2H-pyrazolo[4,3-c]pyridine-4-carboxamide |
| 591 | 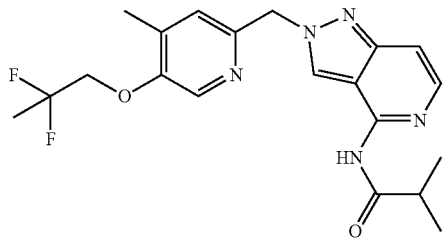 | N-(2-((5-(2,2-difluoropropoxy)-4-methylpyridin-2-yl)methyl)-2H-pyrazolo[4,3-c]pyridin-4-yl)isobutyramide |
| 592 | 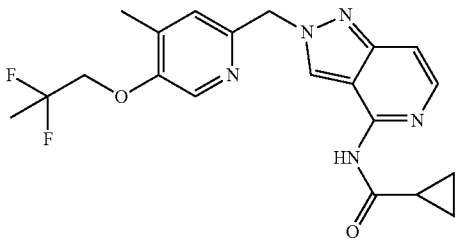 | N-(2-((5-(2,2-difluoropropoxy)-4-methylpyridin-2-yl)methyl)-2H-pyrazolo[4,3-c]pyridin-4-yl)cyclopropanecarboxamide |
| 593 | 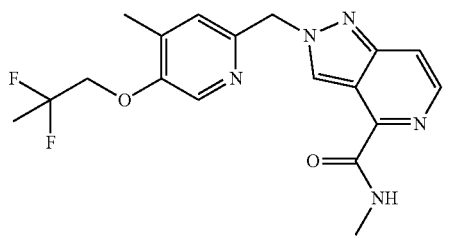 | 2-((5-(2,2-difluoropropoxy)-4-methylpyridin-2-yl)methyl)-N-methyl-2H-pyrazolo[4,3-c]pyridine-4-carboxamide |

TABLE 8-continued

| 594 | 2-((5-(2,2-difluoropropoxy)-4-methylpyridin-2-yl)methyl)-N-ethyl-2H-pyrazolo[4,3-c]pyridine-4-carboxamide |
| 595 | N-{2-acetamidoethyl)-2-((5-(2,2-difluoropropoxy)-4-methylpyridin-2-yl)methyl)-2H-pyrazolo[4,3-c]pyridine-4-carboxamide |
| 596 | 2-((5-(2,2-difluoropropoxy)-4-methylpyridin-2-yl)methyl)-N-isopropyl-2H-pyrazolo[4,3-c]pyridine-4-carboxamide |
| 597 | 2-((5-(2,2-difluoropropoxy)-4-methylpyridin-2-yl)methyl)-N-(2-hydroxyethyl)-2H-pyrazolo[4,3-c]pyridine-4-carboxamide |
| 598 | 2-((5-(2,2-difluoropropoxy)-4-methylpyridin-2-yl)methyl)-N-(3-hydroxypropyl)-2H-pyrazolo[4,3-c]pyridine-4-carboxamide |

TABLE 8-continued

| | | |
|---|---|---|
| 599 | 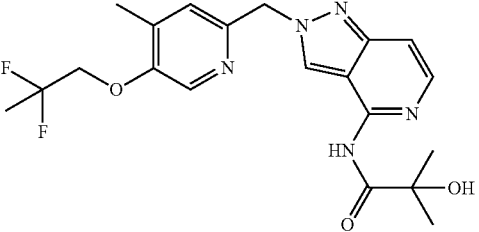 [SMILES: Cc1cc(Cn2cc3c(NC(=O)C(C)(C)O)nccc3n2)ncc1OCC(C)(F)F] | N-(2-((5-(2,2-difluoropropoxy)-4-methylpyridin-2-yl)methyl)-2H-pyrazolo[4,3-c]pyridin-4-yl)-2-hydroxy-2-methylpropanamide |
| 600 | 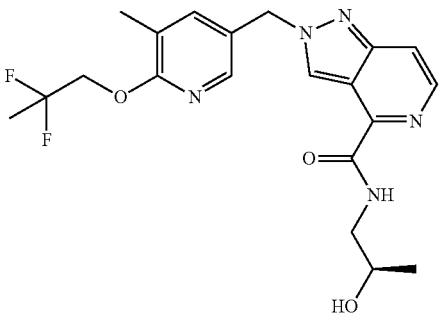 | (R)-2-((6-(2,2-difluoropropoxy)-5-methylpyridin-3-yl)methyl)-N-(2-hydroxypropyl)-2H-pyrazolo[4,3-c]pyridine-4-carboxamide |
| 601 | 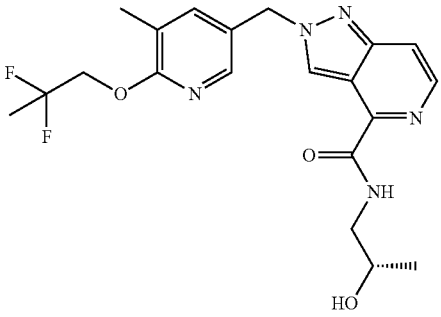 | (S)-2-((6-(2,2-difluoropropoxy)-5-methylpyridin-3-yl)methyl)-N-(2-hydroxypropyl)-2H-pyrazolo[4,3-c]pyridine-4-carboxamide |
| 602 | 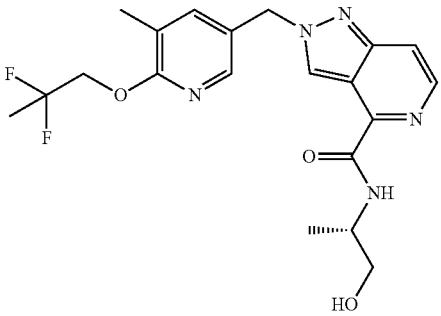 | (S)-2-((6-(2,2-difluoropropoxy)-5-methylpyridin-3-yl)methyl)-N-(1-hydroxypropan-2-yl)-2H-pyrazolo[4,3-c]pyridine-4-carboxamide |
| 603 | 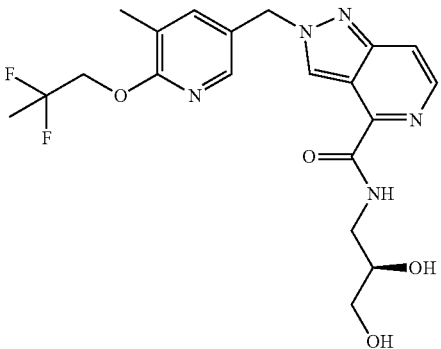 | (S)-2-((6-(2,2-difluoropropoxy)-5-methylpyridin-3-yl)methyl)-N-(2,3-dihydroxypropyl)-2H-pyrazolo[4,3-c]pyridine-4-carboxamide |

TABLE 8-continued

| 604 | 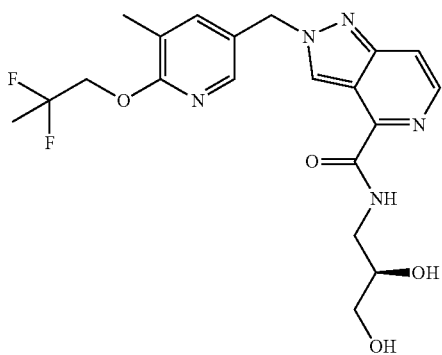 | (R)-2-((6-(2,2-difluoropropoxy)-5-methylpyridin-3-yl)methyl)-N-(2,3-dihydroxypropyl)-2H-pyrazolo[4,3-c]pyridine-4-carboxamide |
| 605 | 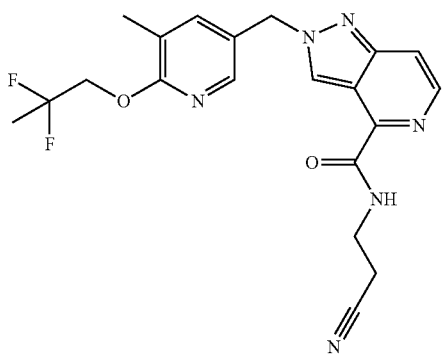 | N-(2-cyanoethyl)-2-((6-(2,2-difluoropropoxy)-5-methylpyridin-3-yl)methyl)-2H-pyrazolo[4,3-c]pyridine-4-carboxamide |
| 606 | 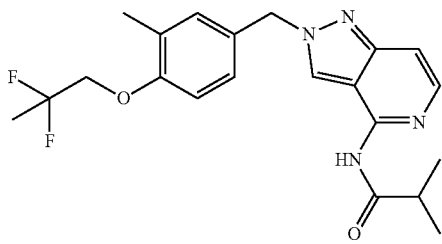 | N-(2-(4-(2,2-difluoropropoxy)-3-methylbenzyl)-2H-pyrazolo[4,3-c]pyridin-4-yl)isobutyramide |
| 607 | 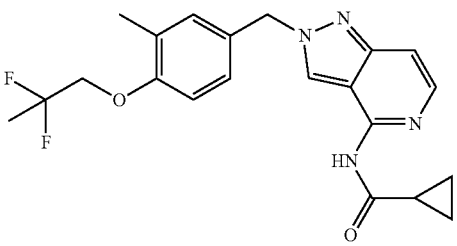 | N-(2-(4-(2,2-difluoropropoxy)-3-methylbenzyl)-2H-pyrazolo[4,3-c]pyridin-4-yl)cyclopropanecarboxamide |
| 608 | 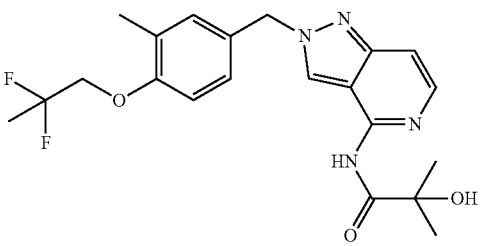 | N-(2-(4-(2,2-difluoropropoxy)-3-methylbenzyl)-2H-pyrazolo[4,3-c]pyridin-4-yl)-2-hydroxy-2-methylpropanamide |

TABLE 8-continued

| 609 | 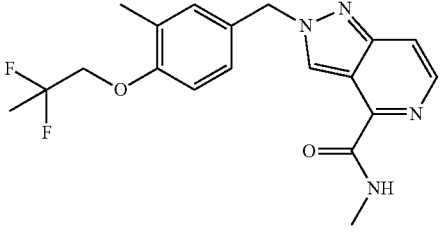 | 2-(4-(2,2-difluoropropoxy)-3-methylbenzyl)-N-methyl-2H-pyrazolo[4,3-c]pyridine-4-carboxamide |
| 610 | 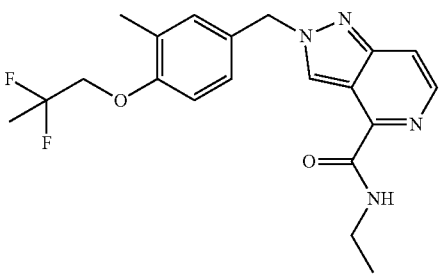 | 2-(4-(2,2-difluoropropoxy)-3-methylbenzyl)-N-ethyl-2H-pyrazolo[4,3-c]pyridine-4-carboxamide |
| 611 | 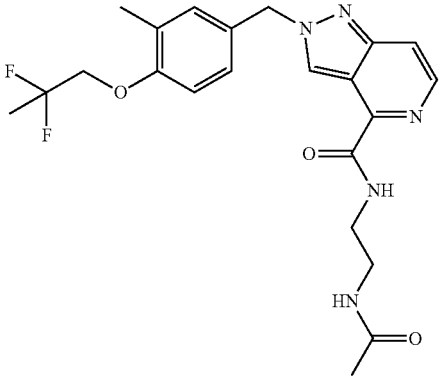 | N-(2-acetamidoethyl)-2-(4-(2,2-difluoropropoxy)-3-methylbenzyl)-2H-pyrazolo[4,3-c]pyridine-4-carboxamide |
| 612 | 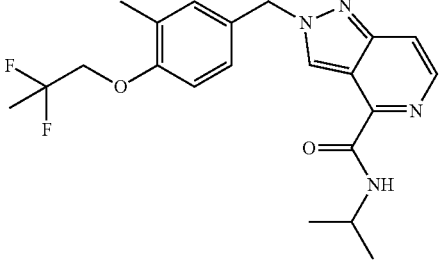 | 2-(4-(2,2-difluoropropoxy)-3-methylbenzyl)-N-isopropyl-2H-pyrazolo[4,3-c]pyridine-4-carboxamide |
| 613 | 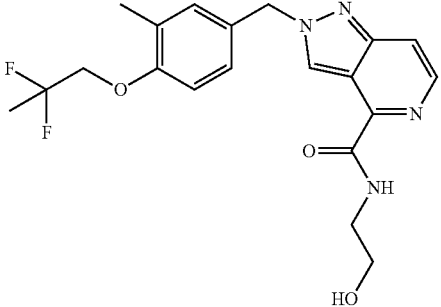 | 2-(4-(2,2-difluoropropoxy)-3-methylbenzyl)-N-(2-hydroxyethyl)-2H-pyrazolo[4,3-c]pyridine-4-carboxamide |

TABLE 8-continued

| | | |
|---|---|---|
| 614 | | 2-(4-(2,2-difluoropropoxy)-3-methylbenzyl)-N-(3-hydroxypropyl)-2H-pyrazolo[4,3-c]pyridine-4-carboxamide |
| 615 | | N-(2-(1-(5-methyl-6-(2,2,2-trifluoroethoxy)pyridin-3-yl)ethyl)-2H-pyrazolo[4,3-c]pyridin-4-yl)oxazole-5-carboxamide (single enantiomer) |
| 616 | | 2-hydroxy-2-methyl-N-(2-(1-(5-methyl-6-(2,2,2-trifluoroethoxy)pyridin-3-yl)ethyl)-2H-pyrazolo[4,3-c]pyridin-4-yl)propanamide (single enantiomer) |
| 617 | | (S)-2-(4-(2,2-difluoroethoxy)-3-methylbenzyl)-N-(2-hydroxypropyl)-2H-pyrazolo[4,3-c]pyridine-4-carboxamide |
| 618 | | (R)-2-(4-(2,2-difluoroethoxy)-3-methylbenzyl)-N-(2-hydroxypropyl)-2H-pyrazolo[4,3-c]pyridine-4-carboxamide |

TABLE 8-continued

| 619 | 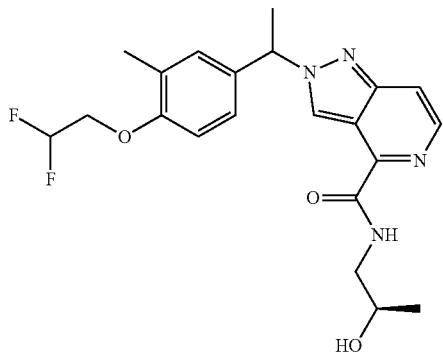 [SMILES: Cc1cc(C(C)n2cc3c(C(=O)NC[C@@H](C)O)nccc3n2)ccc1OCC(F)F] | 2-(1-(4-(2,2-difluoroethoxy)-3-methylphenyl)ethyl)-N-((R)-2-hydroxypropyl)-2H-pyrazolo[4,3-c]pyridine-4-carboxamide (single enantiomer) |
| --- | --- | --- |
| 620 | 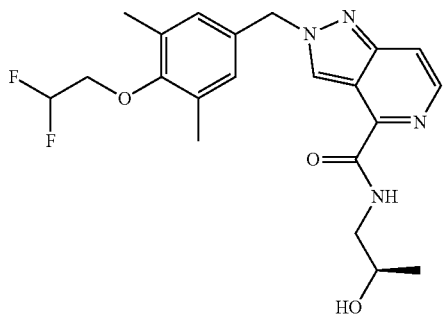 [SMILES: Cc1cc(Cn2cc3c(C(=O)NC[C@@H](C)O)nccc3n2)cc(C)c1OCC(F)F] | (R)-2-(4-(2,2-difluoroethoxy)-3,5-dimethylbenzyl)-N-(2-hydroxypropyl)-2H-pyrazolo[4,3-c]pyridine-4-carboxamide |
| 621 | 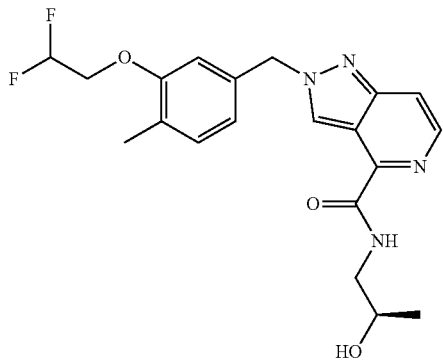 [SMILES: Cc1ccc(Cn2cc3c(C(=O)NC[C@@H](C)O)nccc3n2)cc1OCC(F)F] | (R)-2-(3-(2,2-difluoroethoxy)-4-methylbenzyl)-N-(2-hydroxypropyl)-2H-pyrazolo[4,3-c]pyridine-4-carboxamide |
| 622 | 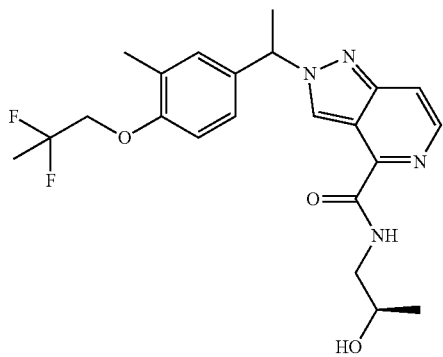 [SMILES: Cc1cc(C(C)n2cc3c(C(=O)NC[C@@H](C)O)nccc3n2)ccc1OCC(C)(F)F] | 2-(1-(4-(2,2-difluoropropoxy)-3-methylphenyl)ethyl)-N-((R)-2-hydroxypropyl)-2H-pyrazolo[4,3-c]pyridine-4-carboxamide (single enantiomer) |

TABLE 8-continued

| 623 | 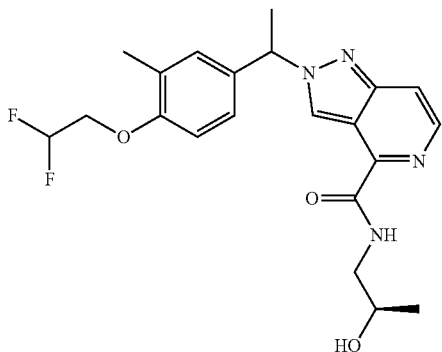 [SMILES: Cc1cc(C(C)n2cc3c(C(=O)NC[C@@H](C)O)nccc3n2)ccc1OCC(F)F] | 2-(1-(4-(2,2-difluoroethoxy)-3-methylphenyl)ethyl)-N-((R)-2-hydroxypropyl)-2H-pyrazolo[4,3-c]pyridine-4-carboxamide (single enantiomer) |
| --- | --- | --- |
| 624 | 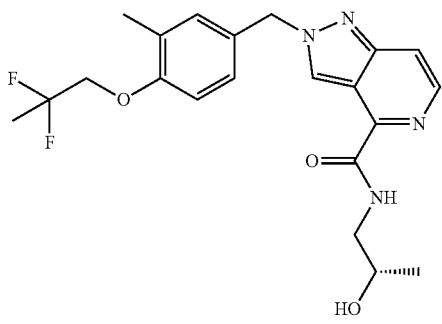 | (S)-2-(4-(2,2-difluoropropoxy)-3-methylbenzyl)-N-(2-hydroxypropyl)-2H-pyrazolo[4,3-c]pyridine-4-carboxamide |
| 625 | 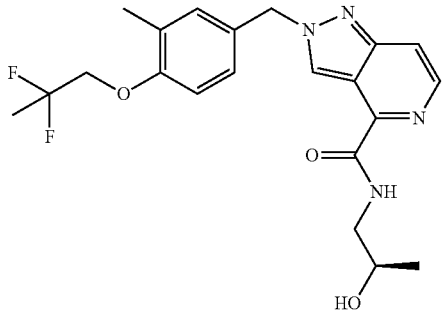 | (R)-2-(4-(2,2-difluoropropoxy)-3-methylbenzyl)-N-(2-hydroxypropyl)-2H-pyrazolo[4,3-c]pyridine-4-carboxamide |
| 626 | 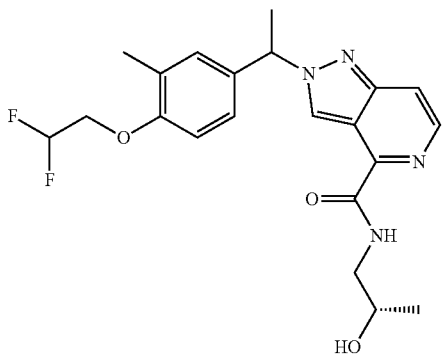 [SMILES: Cc1cc(C(C)n2cc3c(C(=O)NC[C@H](C)O)nccc3n2)ccc1OCC(F)F] | 2-(1-(4-(2,2-difluoroethoxy)-3-methylphenyl)ethyl)-N-((S)-2-hydroxypropyl)-2H-pyrazolo[4,3-c]pyridine-4-carboxamide (single enantiomer) |

TABLE 8-continued

| 627 | 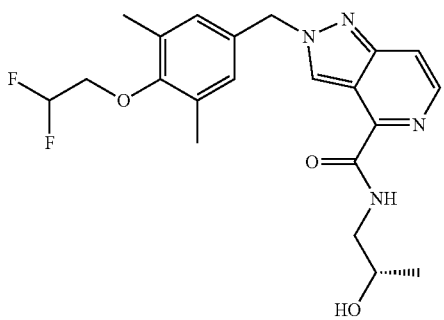 [SMILES: Cc1cc(Cn2cc3c(C(=O)NC[C@H](C)O)nccc3n2)cc(C)c1OCC(F)F] | (S)-2-(4-(2,2-difluoroethoxy)-3,5-dimethylbenzyl)-N-(2-hydroxypropyl)-2H-pyrazolo[4,3-c]pyridine-4-carboxamide |
| 628 | 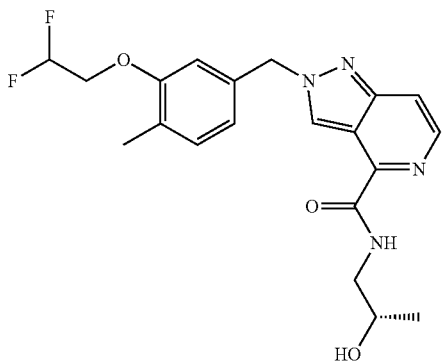 [SMILES: Cc1ccc(Cn2cc3c(C(=O)NC[C@H](C)O)nccc3n2)cc1OCC(F)F] | (S)-2-(3-(2,2-difluoroethoxy)-4-methylbenzyl)-N-(2-hydroxypropyl)-2H-pyrazolo[4,3-c]pyridine-4-carboxamide |
| 629 | 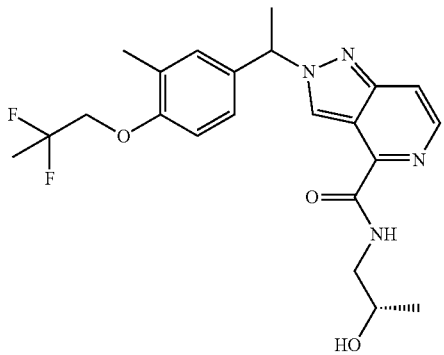 [SMILES: Cc1cc(C(C)n2cc3c(C(=O)NC[C@H](C)O)nccc3n2)ccc1OCC(C)(F)F] | 2-(1-(4-(2,2-difluoropropoxy)-3-methylphenyl)ethyl)-N-((S)-2-hydroxypropyl)-2H-pyrazolo[4,3-c]pyridine-4-carboxamide (single enantiomer) |
| 630 | 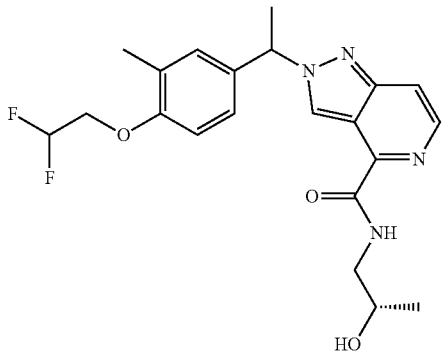 [SMILES: Cc1cc(C(C)n2cc3c(C(=O)NC[C@H](C)O)nccc3n2)ccc1OCC(F)F] | 2-(1-(4-(2,2-difluoroethoxy)-3-methylphenyl)ethyl)-N-((S)-2-hydroxypropyl)-2H-pyrazolo[4,3-c]pyridine-4-carboxamide (single enantiomer) |

TABLE 8-continued

| | | |
|---|---|---|
| 631 | 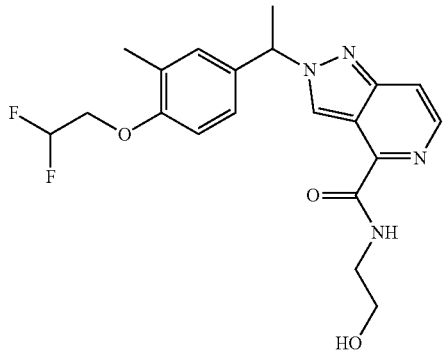 [SMILES: Cc1cc(C(C)n2cc3c(C(=O)NCCO)nccc3n2)ccc1OCC(F)F] | (R)-2-(1-(4-(2,2-difluoroethoxy)-3-methylphenyl)ethyl)-N-(2-hydroxyethyl)-2H-pyrazolo[4,3-c]pyridine-4-carboxamide |
| 632 | 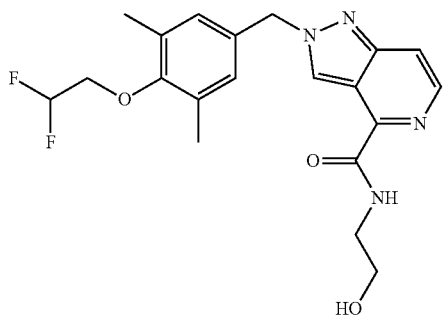 | 2-(4-(2,2-difluoroethoxy)-3,5-dimethylbenzyl)-N-(2-hydroxyethyl)-2H-pyrazolo[4,3-c]pyridine-4-carboxamide |
| 633 | 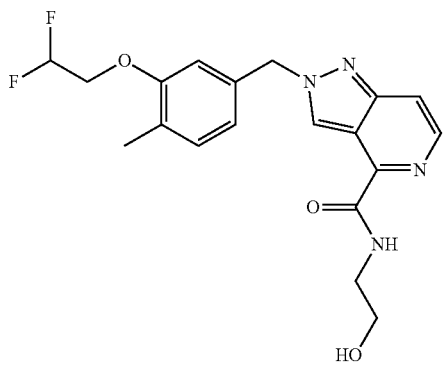 [SMILES: Cc1ccc(Cn2cc3c(C(=O)NCCO)nccc3n2)cc1OCC(F)F] | 2-(3-(2,2-difluoroethoxy)-4-methylbenzyl)-N-(2-hydroxyethyl)-2H-pyrazolo[4,3-c]pyridine-4-carboxamide |
| 634 | 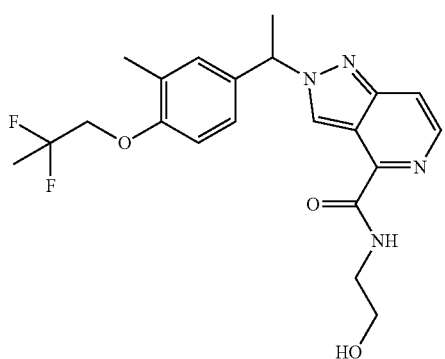 [SMILES: Cc1cc(C(C)n2cc3c(C(=O)NCCO)nccc3n2)ccc1OCC(C)(F)F] | 2-(1-(4-(2,2-difluoropropoxy)-3-methylphenyl)ethyl)-N-(2-hydroxyethyl)-2H-pyrazolo[4,3-c]pyridine-4-carboxamide (single enantiomer) |

| | | |
|---|---|---|
| 635 | 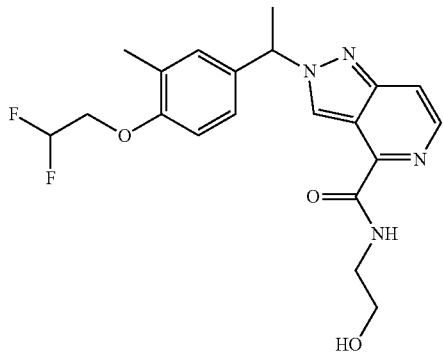 [SMILES: Cc1cc(C(C)n2cc3c(C(=O)NCCO)nccc3n2)ccc1OCC(F)F] | 2-(1-(4-(2,2-difluoroethoxy)-3-methylphenyl)ethyl)-N-(2-hydroxyethyl)-2H-pyrazolo[4,3-c]pyridine-4-carboxamide (single enantiomer) |
| 636 | 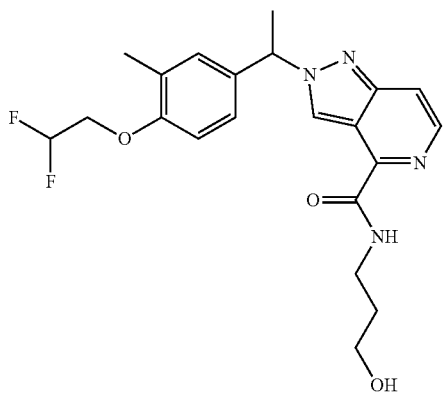 [SMILES: Cc1cc(C(C)n2cc3c(C(=O)NCCCO)nccc3n2)ccc1OCC(F)F] | 2-(1-(4-(2,2-difluoroethoxy)-3-methylphenyl)ethyl)-N-(3-hydroxypropyl)-2H-pyrazolo[4,3-c]pyridine-4-carboxamide (single enantiomer) |
| 637 | 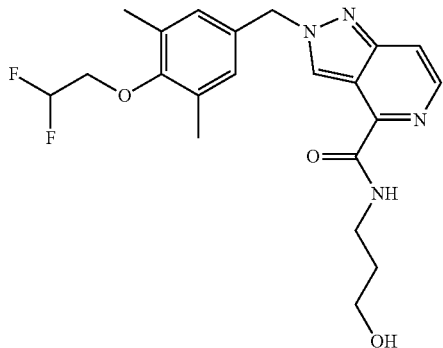 | 2-(4-(2,2-difluoroethoxy)-3,5-dimethylbenzyl)-N-(3-hydroxypropyl)-2H-pyrazolo[4,3-c]pyridine-4-carboxamide |
| 638 | 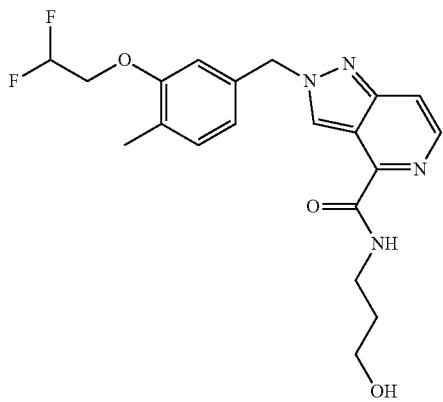 [SMILES: Cc1ccc(Cn2cc3c(C(=O)NCCCO)nccc3n2)cc1OCC(F)F] | 2-(3-(2,2-difluoroethoxy)-4-methylbenzyl)-N-(3-hydroxypropyl)-2H-pyrazolo[4,3-c]pyridine-4-carboxamide |

TABLE 8-continued

| | | |
|---|---|---|
| 639 | 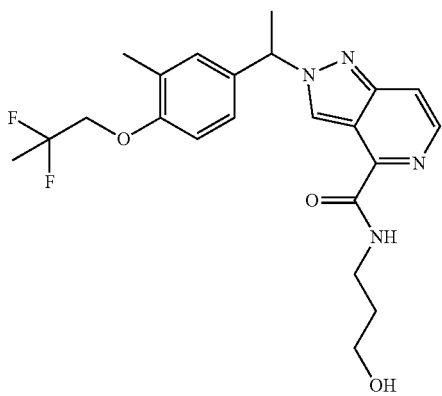 [SMILES: Cc1cc(C(C)n2cc3c(C(=O)NCCCO)nccc3n2)ccc1OCC(C)(F)F] | 2-(1-(4-(2,2-difluoropropoxy)-3-methylphenyl)ethyl)-N-(3-hydroxypropyl)-2H-pyrazolo[4,3-c]pyridine-4-carboxamide (single enantiomer) |
| 640 | 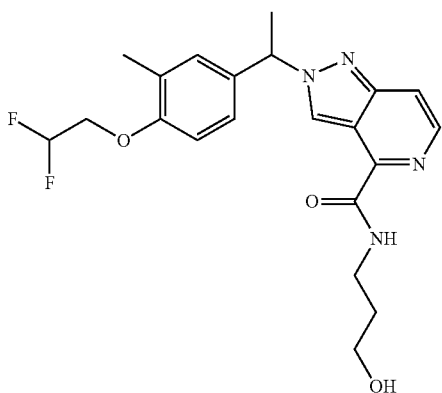 [SMILES: Cc1cc(C(C)n2cc3c(C(=O)NCCCO)nccc3n2)ccc1OCC(F)F] | 2-(1-(4-(2,2-difluoroethoxy)-3-methylphenyl)ethyl)-N-(3-hydroxypropyl)-2H-pyrazolo[4,3-c]pyridine-4-carboxamide (single enantiomer) |
| 641 | 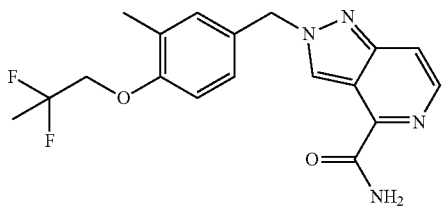 | 2-(4-(2,2-difluoropropoxy)-3-methylbenzyl)-2H-pyrazolo[4,3-c]pyridine-4-carboxamide |
| 642 | 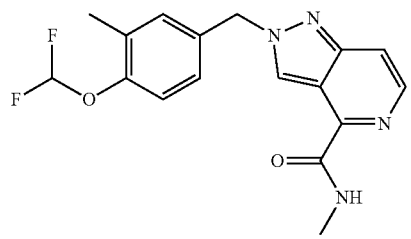 [SMILES: CNC(=O)c1nccc2nn(Cc3ccc(OC(F)F)c(C)c3)cc12] | 2-(4-(difluoromethoxy)-3-methylbenzyl)-N-methyl-2H-pyrazolo[4,3-c]pyridine-4-carboxamide |
| 643 | 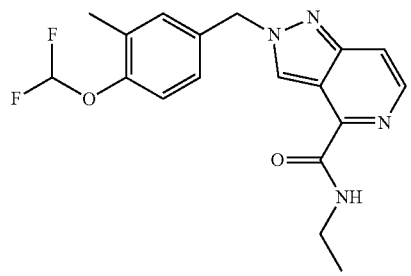 [SMILES: CCNC(=O)c1nccc2nn(Cc3ccc(OC(F)F)c(C)c3)cc12] | 2-(4-(difluoromethoxy)-3-methylbenzyl)-N-ethyl-2H-pyrazolo[4,3-c]pyridine-4-carboxamide |

| | | |
|---|---|---|
| 644 | 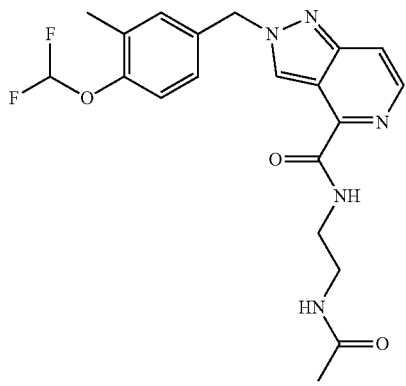 [SMILES: CC(=O)NCCNC(=O)c1nccc2nn(Cc3ccc(OC(F)F)c(C)c3)cc12] | N-(2-acetamidoethyl)-2-(4-(difluoromethoxy)-3-methylbenzyl)-2H-pyrazolo[4,3-c]pyridine-4-carboxamide |
| 645 | 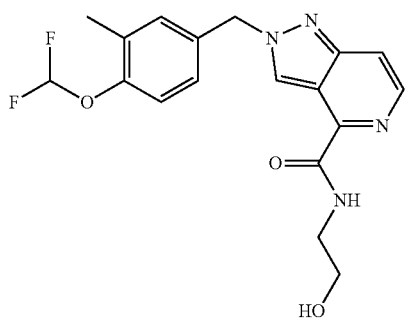 [SMILES: Cc1cc(Cn2cc3c(C(=O)NCCO)nccc3n2)ccc1OC(F)F] | 2-(4-(difluoromethoxy)-3-methylbenzyl)-N-(2-hydroxyethyl)-2H-pyrazolo[4,3-c]pyridine-4-carboxamide |
| 646 | 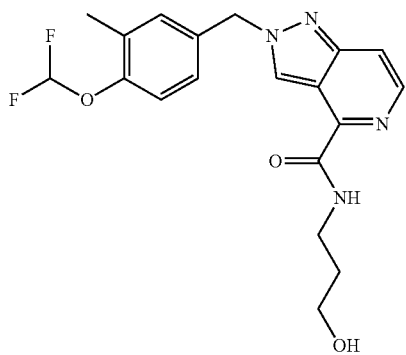 [SMILES: Cc1cc(Cn2cc3c(C(=O)NCCCO)nccc3n2)ccc1OC(F)F] | 2-(4-(difluoromethoxy)-3-methylbenzyl)-N-(3-hydroxypropyl)-2H-pyrazolo[4,3-c]pyridine-4-carboxamide |
| 647 | 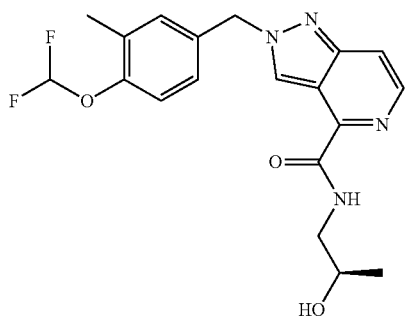 [SMILES: Cc1cc(Cn2cc3c(C(=O)NC[C@@H](C)O)nccc3n2)ccc1OC(F)F] | (R)-2-(4-(difluoromethoxy)-3-methylbenzyl)-N-(2-hydroxypropyl)-2H-pyrazolo[4,3-c]pyridine-4-carboxamide |

TABLE 8-continued

| | | |
|---|---|---|
| 648 | [structure] | (S)-2-(4-(difluoromethoxy)-3-methylbenzyl)-N-(2-hydroxypropyl)-2H-pyrazolo[4,3-c]pyridine-4-carboxamide |
| 649 | [structure] | 2-(4-(difluoromethoxy)-3-methylbenzyl)-N-isopropyl-2H-pyrazolo[4,3-c]pyridine-4-carboxamide |

| Ex | Starting Material | Reagent | method |
|---|---|---|---|
| 522 | Intermediate-62a | [2-hydroxyisobutyramide] | G |
| 523 | Intermediate-1h | picolinic acid | H |
| 524 | Intermediate-1h | nicotinic acid | H |
| 525 | Intermediate-1h | isonicotinic acid | H |

TABLE 8-continued
| 526 | 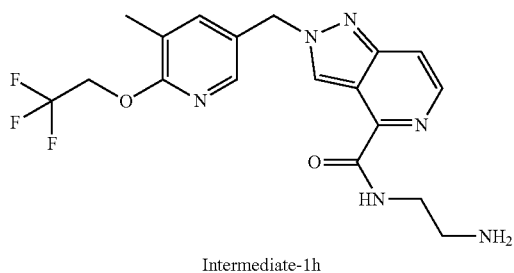<br>Intermediate-1h | 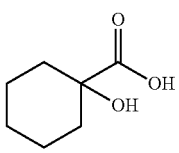 | H |
| 527 | 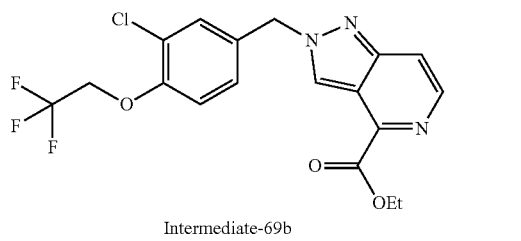<br>Intermediate-69b | 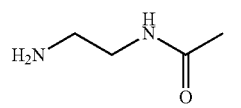 | L |
| 528 | 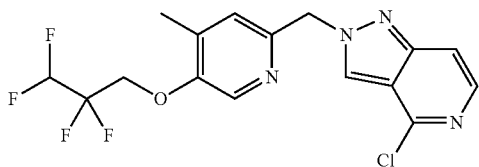 [SMILES: Cc1cc(Cn2cc3c(Cl)nccc3n2)ncc1OCC(F)(F)C(F)F]<br>Intermediate-66a | 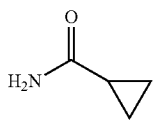 | G |
| 529 | <br>Intermediate-66a | 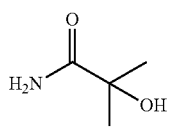 | G |
| 530 | 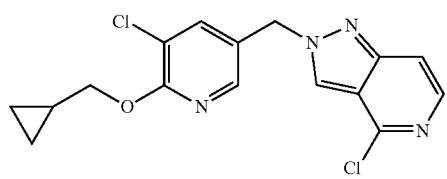 [SMILES: Clc1cc(Cn2cc3c(Cl)nccc3n2)cnc1OCC1CC1]<br>Intermediate-67a | 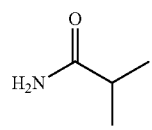 | G |
| 531 | 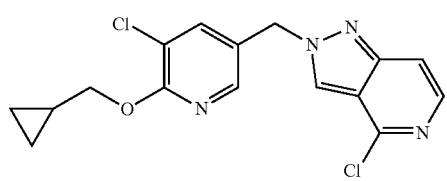 [SMILES: Clc1cc(Cn2cc3c(Cl)nccc3n2)cnc1OCC1CC1]<br>Intermediate-67a | 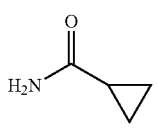 | G |
| 532 | 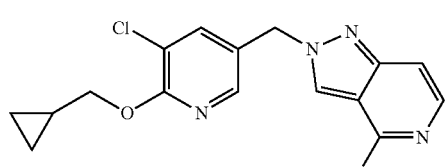<br>Intermediate-67a | 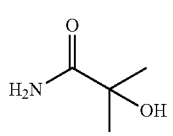 | G |

TABLE 8-continued
| 533 | 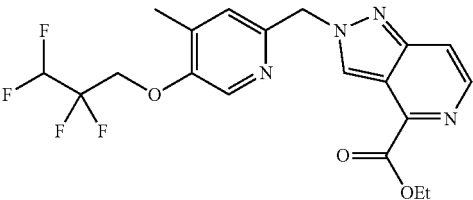 [SMILES: CCOC(=O)c1nccc2nn(Cc3cc(C)c(OCC(F)(F)C(F)F)cn3)cc12] Intermediate-66b |  | K |
| --- | --- | --- | --- |
| 534 | 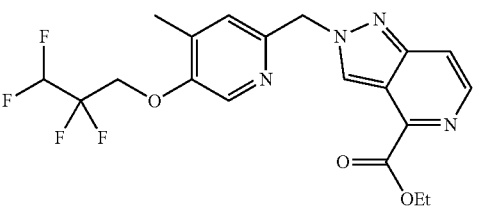 [SMILES: CCOC(=O)c1nccc2nn(Cc3cc(C)c(OCC(F)(F)C(F)F)cn3)cc12] Intermediate-66b |  | K |
| 535 | 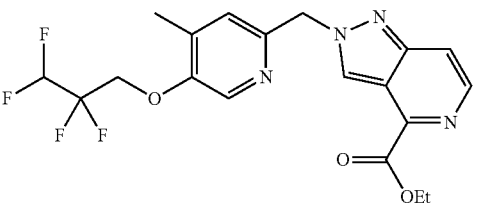 Intermediate-66b |  | L |
| 536 | 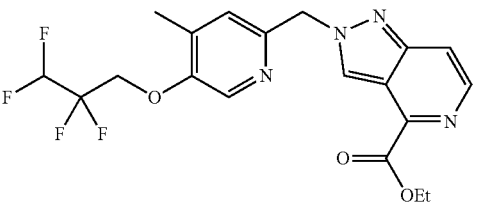 Intermediate-66b | 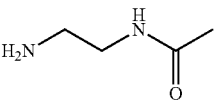 | L |
| 537 | 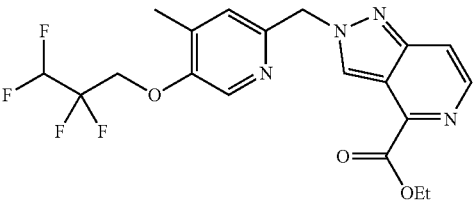 Intermediate-66b | 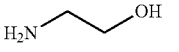 | L |
| 538 | 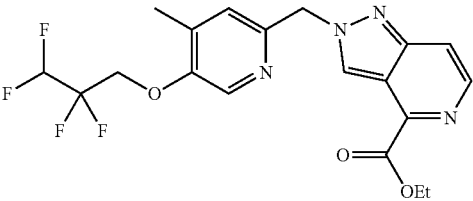 [SMILES: CCOC(=O)c1nccc2nn(Cc3cc(C)c(OCC(F)(F)C(F)F)cn3)cc12] Intermediate-66b | 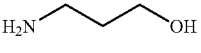 | L |

TABLE 8-continued
| 539 | 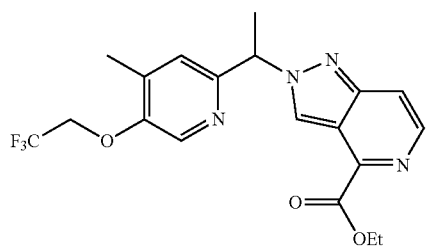 [SMILES: CCOC(=O)c1nccc2nn(C(C)c3cc(C)c(OCC(F)(F)F)cn3)cc12]
Intermediate-68b | H₂N— | K |
| 540 | 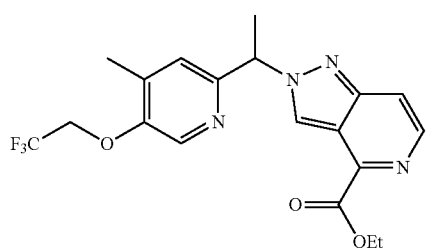 [SMILES: CCOC(=O)c1nccc2nn(C(C)c3cc(C)c(OCC(F)(F)F)cn3)cc12]
Intermediate-68b | H₂N— | K |
| 541 | 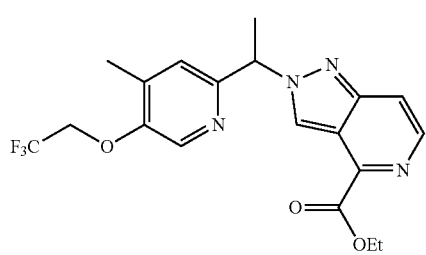 [SMILES: CCOC(=O)c1nccc2nn(C(C)c3cc(C)c(OCC(F)(F)F)cn3)cc12]
Intermediate-68b | H₂N— | L |
| 542 | 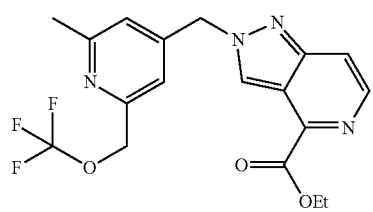 [SMILES: CCOC(=O)c1nccc2nn(Cc3cc(C)nc(COC(F)(F)F)c3)cc12]
Intermediate-28b | H₂N—NH—C(O)CH₃ | L |
| 543 | 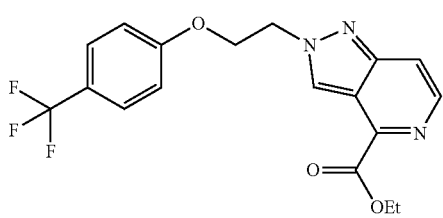 [SMILES: CCOC(=O)c1nccc2nn(CCOc3ccc(C(F)(F)F)cc3)cc12]
Intermediate-33b | H₂N—NH—C(O)CH₃ | L |
| 544 | 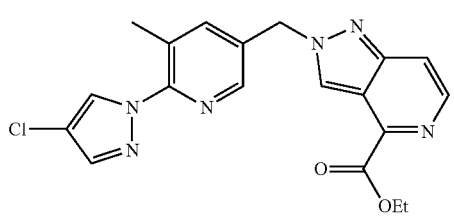 [SMILES: CCOC(=O)c1nccc2nn(Cc3cnc(-n4cc(Cl)cn4)c(C)c3)cc12]
Intermediate-38b | H₂N—NH—C(O)CH₃ | L |

TABLE 8-continued
| 545 | 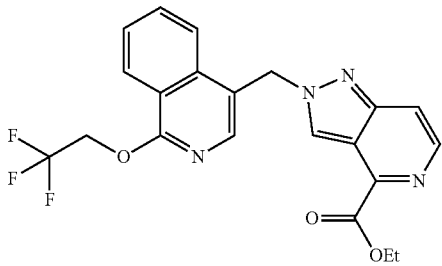 [SMILES: CCOC(=O)c1nccc2nn(Cc3cnc(OCC(F)(F)F)c4ccccc34)cc12] Intermediate-47b | 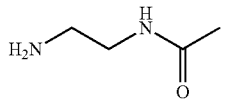 | L |
| 546 | 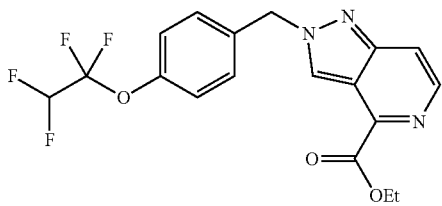 [SMILES: CCOC(=O)c1nccc2nn(Cc3ccc(OC(F)(F)C(F)F)cc3)cc12] Intermediate-56b | 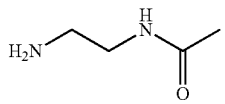 | L |
| 547 | 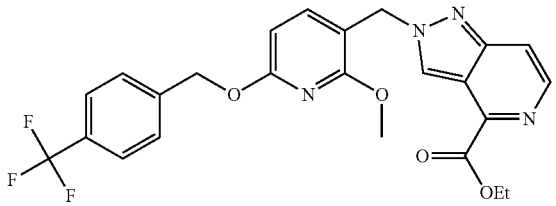 [SMILES: CCOC(=O)c1nccc2nn(Cc3ccc(OCc4ccc(C(F)(F)F)cc4)nc3OC)cc12] Intermediate-32b | 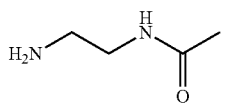 | L |
| 548 | 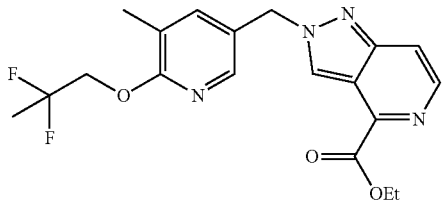 [SMILES: CCOC(=O)c1nccc2nn(Cc3cnc(OCC(C)(F)F)c(C)c3)cc12] Intermediate-35b | 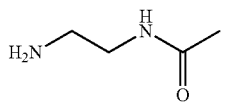 | L |
| 549 | 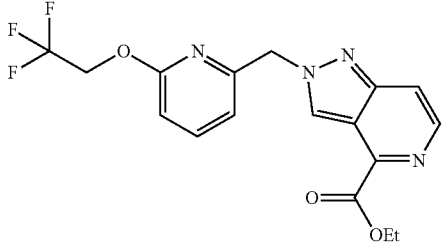 [SMILES: CCOC(=O)c1nccc2nn(Cc3cccc(OCC(F)(F)F)n3)cc12] Intermediate-41b | 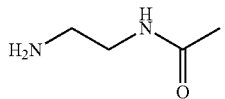 | L |
| 550 | 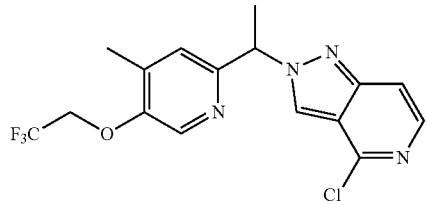 [SMILES: Cc1cc(C(C)n2cc3c(Cl)nccc3n2)ncc1OCC(F)(F)F] Intermediate-68a | 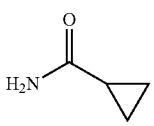 | G |

TABLE 8-continued

| | | | |
|---|---|---|---|
| 551 | Intermediate-68a (pyridine with F3C-CH2-O, methyl, linked via CH(CH3) to pyrazolo[4,3-c]pyridine with Cl) | H2N-C(=O)-CH(CH3)2 (isobutyramide) | G |
| 552 | Intermediate-67b (5-chloro-6-(cyclopropylmethoxy)pyridin-3-yl)methyl-pyrazolo[4,3-c]pyridine-4-carboxylic acid ethyl ester | H2N-CH2-CH3 (? methylamine shown as H2N—) | K |
| 553 | Intermediate-67b | H2N-CH2CH3 (ethylamine) | K |
| 554 | Intermediate-67b | H2N-CH2CH2-NH-C(=O)-CH3 | L |
| 555 | Intermediate-67b | H2N-CH(CH3)2 (isopropylamine) | L |
| 556 | Intermediate-67b | H2N-CH2CH2-OH (ethanolamine) | L |

TABLE 8-continued

| | | | |
|---|---|---|---|
| 557 | Intermediate-67b | H₂N⌒⌒OH | L |
| 558 | Intermediate-70a | isobutyramide | G |
| 559 | Intermediate-70a | cyclopropanecarboxamide | G |
| 560 | Intermediate-70a | 2-hydroxy-2-methylpropanamide | G |
| 561 | Intermediate-70b | H₂N-iPr | K |
| 562 | Intermediate-70b | H₂N-Et | K |
| 563 | Intermediate-70b | H₂N-CH₂CH₂-NHAc | L |

TABLE 8-continued
| | | | |
|---|---|---|---|
| 564 | 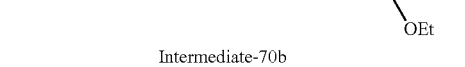 Intermediate-70b |  | L |
| 565 | 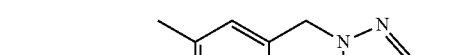 Intermediate-70b | 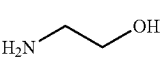 | L |
| 566 | 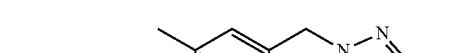 Intermediate-70b | 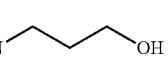 | L |
| 567 | 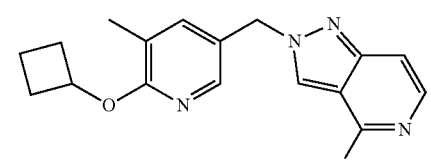 Intermediate-71a | 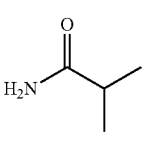 | G |
| 568 | 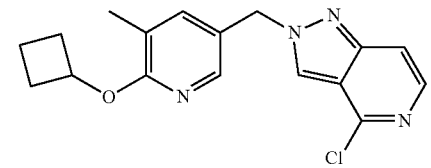 [SMILES: Cc1cc(Cn2cc3c(Cl)nccc3n2)cnc1OC1CCC1] Intermediate-71a | 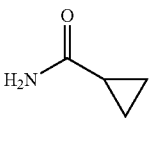 | G |
| 569 | 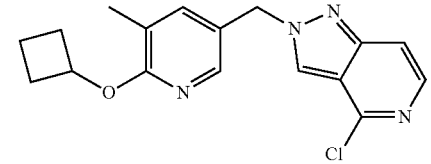 [SMILES: Cc1cc(Cn2cc3c(Cl)nccc3n2)cnc1OC1CCC1] Intermediate-71a | 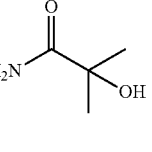 | G |
| 570 | 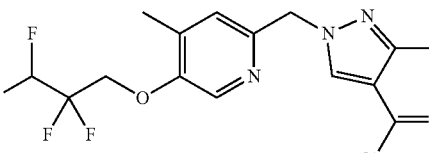 Intermediate-66a | 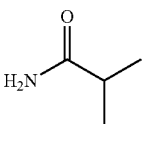 | G |

TABLE 8-continued

| | | | |
|---|---|---|---|
| 571 | Intermediate-71b | H₂N–CH₃ | K |
| 572 | Intermediate-71b | H₂N–Et | K |
| 573 | Intermediate-71b | H₂N–CH₂CH₂–NH–C(O)CH₃ | L |
| 574 | Intermediate-71b | H₂N–iPr | L |
| 575 | Intermediate-71b | H₂N–CH₂CH₂OH | L |
| 576 | Intermediate-71b | H₂N–CH₂CH₂CH₂OH | L |
| 577 | Intermediate-72a | isobutyramide (H₂N–C(O)–CH(CH₃)₂) | G |

TABLE 8-continued
| | | | |
|---|---|---|---|
| 578 | 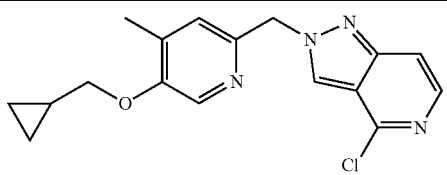 Intermediate-72a | 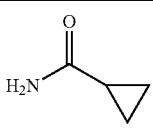 | G |
| 579 | 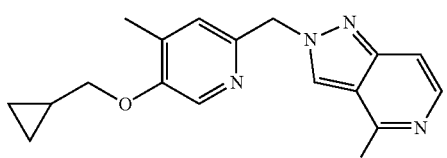 Intermediate-72a | 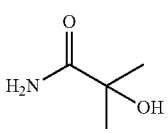 | G |
| 580 | 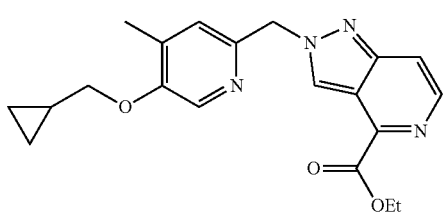 [SMILES: CCOC(=O)c1nccc2nn(Cc3cc(C)c(OCC4CC4)cn3)cc12] Intermediate-72b |  | K |
| 581 | 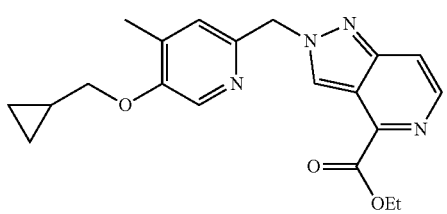 [SMILES: CCOC(=O)c1nccc2nn(Cc3cc(C)c(OCC4CC4)cn3)cc12] Intermediate-72b | 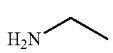 | K |
| 582 | 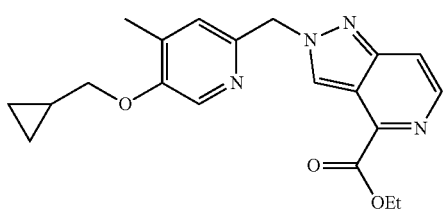 [SMILES: CCOC(=O)c1nccc2nn(Cc3cc(C)c(OCC4CC4)cn3)cc12] Intermediate-72b | 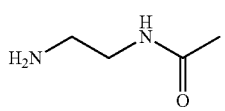 | L |
| 583 | 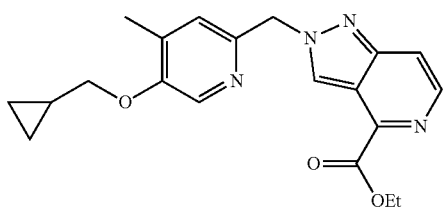 [SMILES: CCOC(=O)c1nccc2nn(Cc3cc(C)c(OCC4CC4)cn3)cc12] Intermediate-72b | 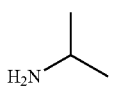 | L |
| 584 | 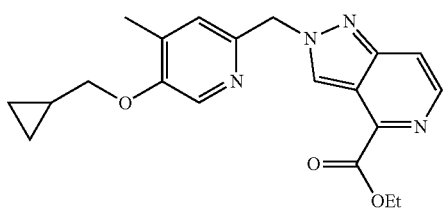 [SMILES: CCOC(=O)c1nccc2nn(Cc3cc(C)c(OCC4CC4)cn3)cc12] Intermediate-72b | 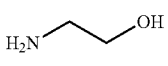 | L |

TABLE 8-continued

| 585 | Intermediate-72b | H₂N∼∼OH | L |
| 586 | Intermediate-73b | H₂N∼ | K |
| 587 | Intermediate-73b | H₂N∼ | K |
| 588 | Intermediate-73b | H₂N⟨ | L |
| 589 | Intermediate-73b | H₂N∼OH | L |
| 590 | Intermediate-73b | H₂N∼∼OH | L |
| 591 | Intermediate-74a | isobutyramide | G |

TABLE 8-continued

| | | | |
|---|---|---|---|
| 592 | Intermediate-74a (4-chloro variant) | cyclopropanecarboxamide (H₂N-C(=O)-cyclopropyl) | G |
| 593 | Intermediate-74b | H₂N-CH₃ | K |
| 594 | Intermediate-74b | H₂N-CH₂CH₃ | K |
| 595 | Intermediate-74b | H₂N-CH₂CH₂-NH-C(=O)-CH₃ | L |
| 596 | Intermediate-74b | H₂N-CH(CH₃)₂ | L |
| 597 | Intermediate-74b | H₂N-CH₂CH₂-OH | L |
| 598 | Intermediate-74b | H₂N-CH₂CH₂CH₂-OH | L |

TABLE 8-continued

| | | | |
|---|---|---|---|
| 599 | Intermediate-74a | H₂N-C(=O)-C(CH₃)₂-OH | G |
| 600 | Intermediate-35b | H₂N-CH₂-CH(OH)-CH₃ (S) | L |
| 601 | Intermediate-35b | H₂N-CH₂-CH(OH)-CH₃ (R) | L |
| 602 | Intermediate-35b | H₂N-CH(CH₃)-CH₂OH | L |
| 603 | Intermediate-35b | H₂N-CH₂-CH(OH)-CH₂OH | L |
| 604 | Intermediate-35b | H₂N-CH₂-CH(OH)-CH₂OH | L |
| 605 | Intermediate-35b | H₂N-CH₂-CH₂-CN | L |

TABLE 8-continued

| 606 | Intermediate-75a | isobutyramide | G |
| 607 | Intermediate-75a | cyclopropanecarboxamide | G |
| 608 | Intermediate-75a | 2-hydroxy-2-methylpropanamide | G |
| 609 | Intermediate-75b | methylamine | K |
| 610 | Intermediate-75b | ethylamine | K |
| 611 | Intermediate-75b | N-(2-aminoethyl)acetamide | L |
| 612 | Intermediate-75b | isopropylamine | L |

TABLE 8-continued

| | | | |
|---|---|---|---|
| 613 | Intermediate-75b | H₂N⌒⌒OH | L |
| 614 | Intermediate-75b | H₂N⌒⌒⌒OH | L |
| 615 | Intermediate-11a | oxazole-5-carboxamide | G |
| 616 | Intermediate-11a | 2-hydroxy-2-methylpropanamide | G |
| 617 | Intermediate-26b | (R)-1-amino-2-propanol | L |
| 618 | Intermediate-26b | (S)-1-amino-2-propanol | L |

TABLE 8-continued

| | | | |
|---|---|---|---|
| 619 | Intermediate-76b | H₂N⟋⟍OH | L |
| 620 | Intermediate-77b | H₂N⟋⟍OH | L |
| 621 | Intermediate-78b | H₂N⟋⟍OH | L |
| 622 | Intermediate-79b | H₂N⟋⟍OH | L |
| 623 | Intermediate-80b | H₂N⟋⟍OH | L |
| 624 | Intermediate-75b | H₂N⟋⟍OH | L |

TABLE 8-continued
| 625 | 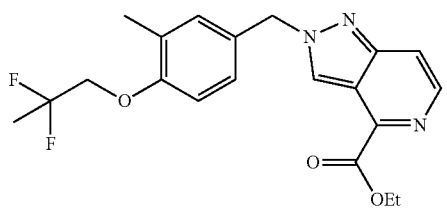 [SMILES: CCOC(=O)c1nccc2nn(Cc3ccc(OCC(C)(F)F)c(C)c3)cc12] Intermediate-75b | 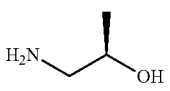 | L |
| 626 | 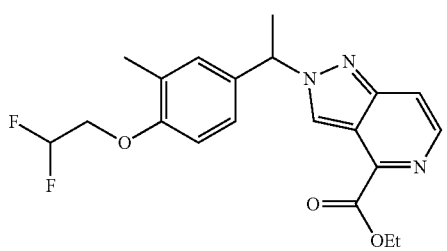 [SMILES: CCOC(=O)c1nccc2nn(C(C)c3ccc(OCC(F)F)c(C)c3)cc12] Intermediate-76b | 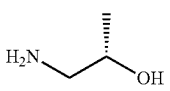 | L |
| 627 | 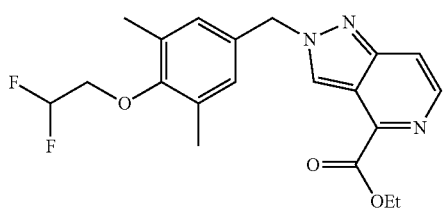 [SMILES: CCOC(=O)c1nccc2nn(Cc3cc(C)c(OCC(F)F)c(C)c3)cc12] Intermediate-77b | 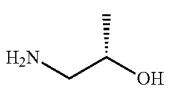 | L |
| 628 | 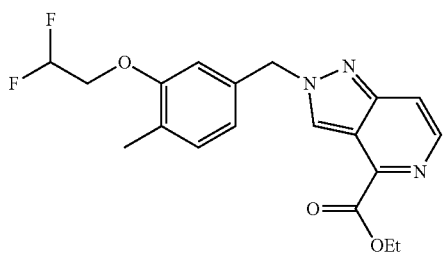 [SMILES: CCOC(=O)c1nccc2nn(Cc3ccc(C)c(OCC(F)F)c3)cc12] Intermediate-78b | 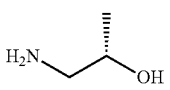 | L |
| 629 | 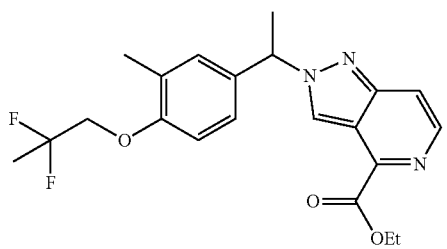 [SMILES: CCOC(=O)c1nccc2nn(C(C)c3ccc(OCC(C)(F)F)c(C)c3)cc12] Intermediate-79b | 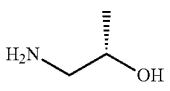 | L |
| 630 | 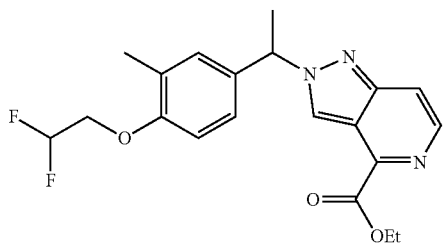 [SMILES: CCOC(=O)c1nccc2nn(C(C)c3ccc(OCC(F)F)c(C)c3)cc12] Intermediate-80b | 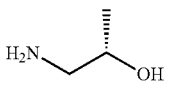 | L |

TABLE 8-continued

| | | | |
|---|---|---|---|
| 631 | Intermediate-76b | H₂N–CH₂–CH₂–OH | L |
| 632 | Intermediate-77b | H₂N–CH₂–CH₂–OH | L |
| 633 | Intermediate-78b | H₂N–CH₂–CH₂–OH | L |
| 634 | Intermediate-79b | H₂N–CH₂–CH₂–OH | L |
| 635 | Intermediate-80b | H₂N–CH₂–CH₂–OH | L |
| 636 | Intermediate-76b | H₂N–CH₂–CH₂–CH₂–OH | L |

| | | | | |
|---|---|---|---|---|
| 637 | Intermediate-77b | | H₂N⌒⌒OH | L |
| 638 | Intermediate-78b | | H₂N⌒⌒OH | L |
| 639 | Intermediate-79b | | H₂N⌒⌒OH | L |
| 640 | Intermediate-80b | | H₂N⌒⌒OH | L |
| 641 | Intermediate-75b | | NH₃ | K |
| 642 | Intermediate-81b | | H₂N⌒ | K |

TABLE 8-continued

| | | | |
|---|---|---|---|
| 643 | Intermediate-81b | H₂N-Et | K |
| 644 | Intermediate-81b | H₂N-CH₂CH₂-NHC(O)CH₃ | L |
| 645 | Intermediate-81b | H₂N-CH₂CH₂-OH | L |
| 646 | Intermediate-81b | H₂N-CH₂CH₂CH₂-OH | L |
| 647 | Intermediate-81b | H₂N-CH₂-(R)-CH(OH)CH₃ | L |
| 648 | Intermediate-81b | H₂N-CH₂-(S)-CH(OH)CH₃ | L |
| 649 | Intermediate-81b | H₂N-CH(CH₃)₂ | L |

TABLE 9

| Ex. | tR (min) | m/z | Method |
|---|---|---|---|
| 1 | 1.74 | 408.1 | QC1 |
| 2 | 1.65 | 424.1 | QC1 |
| 3 | 1.54 | 380.1 | QC1 |
| 4 | 1.60 | 390.2 | QC1 |
| 5 | 1.42 | 362.1 | QC1 |
| 6 | 1.51 | 376.2 | QC1 |
| 7 | 1.56 | 388.1 | QC1 |
| 8 | 1.50 | 406.2 | QC1 |
| 9 | 1.61 | 392.3 | QC1 |
| 10 | 1.71 | 406.4 | QC1 |
| 11 | 1.80 | 420.4 | QC1 |
| 12 | 1.67 | 462.4 | QC1 |
| 13 | 1.57 | 392.1 | QC1 |
| 14 | 1.62 | 394.1 | QC1 |
| 15 | 1.73 | 428.0 | QC1 |
| 16 | 1.65 | 414.0 | QC1 |
| 17 | 1.61 | 470.0 | QC1 |
| 18 | 1.44 | 382.0 | QC1 |
| 19 | 1.53 | 396.1 | QC1 |
| 20 | 1.62 | 410.0 | QC1 |
| 21 | 1.55 | 400.0 | QC1 |
| 22 | 1.60 | 450.1 | QC1 |
| 23 | 1.57 | 433.0 | QC1 |
| 24 | 1.67 | 409.1 | QC1 |
| 25 | 1.40 | 338.1 | QC1 |
| 26 | 1.69 | 408.1 | QC1 |
| 27 | 1.69 | 410.1 | QC1 |
| 28 | 1.44 | 366.1 | QC1 |
| 29 | 1.53 | 380.1 | QC1 |
| 30 | 1.76 | 353.1 | QC1 |
| 31 | 1.58 | 366.1 | QC1 |
| 32 | 1.67 | 380.1 | QC1 |
| 33 | 1.88 | 408.1 | QC1 |
| 34 | 1.67 | 406.1 | QC1 |
| 35 | 1.50 | 392.0 | QC1 |
| 36 | 1.54 | 394.1 | QC1 |
| 37 | 1.45 | 395.1 | QC1 |
| 38 | 1.41 | 393.1 | QC1 |
| 39 | 1.47 | 394.1 | QC1 |
| 40 | 1.43 | 392.1 | QC1 |
| 41 | 1.61 | 408.1 | QC1 |
| 42 | 1.56 | 406.1 | QC1 |
| 43 | 1.79 | 422.0 | QC1 |
| 44 | 1.74 | 420.1 | QC1 |
| 45 | 1.61 | 394.1 | QC1 |
| 46 | 1.71 | 408.1 | QC1 |
| 47 | 1.67 | 464.1 | QC1 |
| 48 | 1.57 | 398.1 | QC1 |
| 49 | 1.60 | 410.0 | QC1 |
| 50 | 1.64 | 412.0 | QC1 |
| 51 | 1.83 | 422.0 | QC1 |
| 52 | 1.64 | 443.0 | QC1 |
| 53 | 1.68 | 406.1 | QC1 |
| 54 | 1.55 | 407.0 | QC1 |
| 55 | 1.65 | 408.1 | QC1 |
| 56 | 1.59 | 418.1 | QC1 |
| 57 | 1.56 | 416.0 | QC1 |
| 58 | 1.57 | 424.0 | QC1 |
| 59 | 1.48 | 432.1 | QC1 |
| 60 | 1.54 | 391.1 | QC1 |
| 61 | 1.71 | 404.1 | QC1 |
| 62 | 1.64 | 393.1 | QC1 |
| 63 | 1.59 | 391.1 | QC1 |
| 64 | 1.92 | 389.2 | QC1 |
| 65 | 1.75 | 444.1 | QC1 |
| 66 | 1.71 | 442.0 | QC1 |
| 67 | 1.70 | 379.1 | QC1 |
| 68 | 1.66 | 380.1 | QC1 |
| 69 | 1.77 | 394.0 | QC1 |
| 70 | 1.69 | 436.0 | QC1 |
| 71 | 1.78 | 406.0 | QC1 |
| 72 | 1.92 | 420.0 | QC1 |
| 73 | 1.89 | 420.0 | QC1 |
| 74 | 1.76 | 464.0 | QC1 |
| 75 | 1.73 | 424.0 | QC1 |
| 76 | 1.60 | 424.0 | QC1 |
| 77 | 1.67 | 408.0 | QC1 |
| 78 | 1.77 | 420.0 | QC1 |
| 79 | 1.62 | 426.0 | QC1 |
| 80 | 1.63 | 402.1 | QC1 |
| 81 | 1.59 | 406.2 | QC1 |
| 82 | 1.72 | 420.2 | QC1 |
| 83 | 1.68 | 418.2 | QC1 |
| 84 | 1.72 | 422.1 | QC1 |
| 85 | 1.69 | 436.1 | QC1 |
| 86 | 1.57 | 418.1 | QC1 |
| 87 | 1.53 | 425.0 | QC1 |
| 88 | 1.54 | 410.0 | QC1 |
| 89 | 1.54 | 410.0 | QC1 |
| 90 | 1.71 | 435.0 | QC1 |
| 91 | 1.51 | 491.1 | QC1 |
| 92 | 1.94 | 422.1 | QC1 |
| 93 | 1.87 | 408.1 | QC1 |
| 94 | 1.96 | 422.0 | QC1 |
| 95 | 1.81 | 438.1 | QC1 |
| 96 | 1.68 | 405.1 | QC1 |
| 97 | 1.79 | 450.0 | QC1 |
| 98 | 1.51 | 437.1 | QC1 |
| 99 | 1.66 | 457.1 | QC1 |
| 100 | 1.70 | 462.1 | QC1 |
| 101 | 1.75 | 443.1 | QC1 |
| 102 | 1.69 | 436.0 | QC1 |
| 103 | 1.57 | 418.1 | QC1 |
| 104 | 1.76 | 438.1 | QC1 |
| 105 | 1.84 | 478.1 | QC1 |
| 106 | 1.71 | 408.1 | QC1 |
| 107 | 1.75 | 420.1 | QC1 |
| 108 | 1.79 | 422.1 | QC1 |
| 109 | 1.68 | 438.1 | QC1 |
| 110 | 1.69 | 408.1 | QC1 |
| 111 | 1.77 | 422.1 | QC1 |
| 112 | 1.66 | 376.1 | QC1 |
| 113 | 1.55 | 362.2 | QC1 |
| 114 | 1.64 | 519.2 | QC1 |
| 115 | 1.60 | 527.2 | QC1 |
| 116 | 1.53 | 477.2 | QC1 |
| 117 | 1.53 | 477.2 | QC1 |
| 118 | 1.48 | 451.1 | QC1 |
| 119 | 1.69 | 424.0 | QC1 |
| 120 | 1.56 | 406.1 | QC1 |
| 121 | 1.42 | 392.1 | QC1 |
| 122 | 1.42 | 392.1 | QC1 |
| 123 | 1.76 | 390.2 | QC1 |
| 124 | 1.67 | 388.0 | QC1 |
| 125 | 1.78 | 402.1 | QC1 |
| 126 | 1.98 | 417.0 | QC2 |
| 127 | 2.14 | 477.2 | QC2 |
| 128 | 2.09 | 455.1 | QC2 |
| 129 | 2.04 | 455.1 | QC2 |
| 130 | 1.76 | 394.1 | QC1 |
| 131 | 1.65 | 380.1 | QC1 |
| 132 | 1.67 | 392.0 | QC1 |
| 133 | 1.78 | 406.0 | QC1 |
| 134 | 1.53 | 457.1 | QC1 |
| 135 | 1.55 | 387.1 | QC1 |
| 136 | 1.75 | 390.1 | QC1 |
| 137 | 1.80 | 433.1 | QC1 |
| 138 | 1.63 | 438.1 | QC1 |
| 139 | 1.44 | 451.1 | QC1 |
| 140 | 1.37 | 409.1 | QC1 |
| 141 | 1.51 | 410.1 | QC1 |
| 142 | 1.61 | 422.1 | QC1 |
| 143 | 1.62 | 380.1 | QC1 |
| 144 | 1.72 | 394.2 | QC1 |
| 145 | 1.42 | 439.1 | QC1 |
| 146 | 1.43 | 443.1 | QC1 |
| 147 | 1.43 | 439.1 | QC1 |
| 148 | 1.39 | 392.2 | QC1 |
| 149 | 1.51 | 423.8 | QC1 |
| 150 | 1.48 | 410.1 | QC1 |
| 151 | 1.70 | 422.2 | QC1 |
| 152 | 1.65 | 420.2 | QC1 |
| 153 | 1.60 | 438.2 | QC1 |
| 154 | 1.66 | 394.2 | QC1 |
| 155 | 1.76 | 408.1 | QC1 |
| 156 | 1.86 | 422.2 | QC1 |

TABLE 9-continued

| Ex. | tR (min) | m/z | Method |
|---|---|---|---|
| 157 | 1.51 | 409.2 | QC1 |
| 158 | 1.47 | 407.2 | QC1 |
| 159 | 1.46 | 381.0 | QC1 |
| 160 | 1.56 | 395.1 | QC1 |
| 161 | 1.64 | 477.1 | QC1 |
| 162 | 1.54 | 471.1 | QC1 |
| 163 | 1.53 | 471.1 | QC1 |
| 164 | 1.64 | 475.1 | QC1 |
| 165 | 1.67 | 408.8 | QC1 |
| 166 | 1.57 | 424.1 | QC1 |
| 167 | 1.57 | 424.1 | QC1 |
| 168 | 1.44 | 440.1 | QC1 |
| 169 | 1.50 | 406.1 | QC1 |
| 170 | 1.45 | 424.1 | QC1 |
| 171 | 1.50 | 380.0 | QC1 |
| 172 | 1.59 | 394.1 | QC1 |
| 173 | 1.70 | 408.1 | QC1 |
| 174 | 1.38 | 410.1 | QC1 |
| 175 | 1.58 | 424.1 | QC1 |
| 176 | 1.46 | 423.1 | QC1 |
| 177 | 1.56 | 487.1 | QC1 |
| 178 | 1.34 | 411.1 | QC1 |
| 179 | 1.54 | 424.0 | QC1 |
| 180 | 1.43 | 406.1 | QC1 |
| 181 | 1.65 | 419.1 | QC1 |
| 182 | 1.53 | 401.1 | QC1 |
| 183 | 1.48 | 450.8 | QC1 |
| 184 | 1.58 | 424.2 | QC1 |
| 185 | 1.53 | 422.1 | QC1 |
| 186 | 1.53 | 396.1 | QC1 |
| 187 | 1.63 | 410.1 | QC1 |
| 188 | 1.74 | 424.2 | QC1 |
| 189 | 1.40 | 426.1 | QC1 |
| 190 | 1.52 | 454.1 | QC1 |
| 191 | 1.54 | 408.1 | QC1 |
| 192 | 1.69 | 398.1 | QC1 |
| 193 | 1.79 | 412.1 | QC1 |
| 194 | 1.53 | 430.0 | QC1 |
| 195 | 1.56 | 382.1 | QC1 |
| 196 | 1.66 | 396.1 | QC1 |
| 197 | 1.42 | 412.1 | QC1 |
| 198 | 1.77 | 410.0 | QC1 |
| 199 | 1.44 | 440.1 | QC1 |
| 200 | 1.44 | 395.1 | QC1 |
| 201 | 1.52 | 422.1 | QC1 |
| 202 | 1.56 | 446.1 | QC1 |
| 203 | 1.54 | 380.1 | QC1 |
| 204 | 1.65 | 394.1 | QC1 |
| 205 | 1.75 | 408.1 | QC1 |
| 206 | 1.41 | 410.1 | QC1 |
| 207 | 1.51 | 437.1 | QC1 |
| 208 | 1.50 | 437.1 | QC1 |
| 209 | 1.46 | 437.1 | QC1 |
| 210 | 1.75 | 452.1 | QC1 |
| 211 | 1.41 | 396.0 | QC1 |
| 212 | 1.57 | 438.1 | QC1 |
| 213 | 1.44 | 410.1 | QC1 |
| 214 | 1.54 | 409.1 | QC1 |
| 215 | 1.65 | 412.1 | QC1 |
| 216 | 1.43 | 428.0 | QC1 |
| 217 | 1.51 | 465.2 | QC1 |
| 218 | 1.58 | 501.1 | QC1 |
| 219 | 1.75 | 426.1 | QC1 |
| 220 | 1.44 | 391.1 | QC1 |
| 221 | 1.47 | 405.2 | QC1 |
| 222 | 1.51 | 442.1 | QC1 |
| 223 | 1.54 | 456.1 | QC1 |
| 224 | 1.56 | 444.1 | QC1 |
| 225 | 1.45 | 426.0 | QC1 |
| 226 | 1.47 | 409.1 | QC1 |
| 227 | 1.72 | 408.2 | QC1 |
| 228 | 1.67 | 406.1 | QC1 |
| 229 | 1.57 | 423.1 | QC1 |
| 230 | 1.54 | 438.1 | QC1 |
| 231 | 1.37 | 425.1 | QC1 |
| 232 | 1.40 | 424.1 | QC1 |
| 233 | 1.43 | 440.1 | QC1 |
| 234 | 1.48 | 428.1 | QC1 |
| 235 | 1.56 | 436.1 | QC1 |
| 236 | 1.59 | 460.1 | QC1 |
| 237 | 1.44 | 424.1 | QC1 |
| 238 | 1.66 | 380.1 | QC1 |
| 239 | 1.77 | 394.1 | QC1 |
| 240 | 1.87 | 408.2 | QC1 |
| 241 | 1.52 | 410.1 | QC1 |
| 242 | 1.55 | 424.1 | QC1 |
| 243 | 1.57 | 408.2 | QC1 |
| 244 | 1.53 | 406.2 | QC1 |
| 245 | 1.57 | 438.1 | QC1 |
| 246 | 1.57 | 437.7 | QC1 |
| 247 | 1.44 | 454.2 | QC1 |
| 248 | 1.44 | 454.2 | QC1 |
| 249 | 1.32 | 440.1 | QC1 |
| 250 | 1.85 | 430.1 | QC1 |
| 251 | 1.51 | 432.1 | QC1 |
| 252 | 1.54 | 446.2 | QC1 |
| 253 | 1.65 | 402.1 | QC1 |
| 254 | 1.75 | 416.2 | QC1 |
| 255 | 1.43 | 424.1 | QC1 |
| 256 | 1.43 | 424.0 | QC1 |
| 257 | 1.58 | 438.1 | QC1 |
| 258 | 1.44 | 424.2 | QC1 |
| 259 | 1.50 | 419.1 | QC1 |
| 260 | 1.65 | 433.1 | QC1 |
| 261 | 1.48 | 465.1 | QC1 |
| 262 | 1.45 | 437.1 | QC1 |
| 263 | 1.71 | 438.2 | QC1 |
| 264 | 1.65 | 452.1 | QC1 |
| 265 | 1.61 | 450.1 | QC1 |
| 266 | 1.55 | 468.0 | QC1 |
| 267 | 1.72 | 424.1 | QC1 |
| 268 | 1.68 | 422.1 | QC1 |
| 269 | 1.47 | 454.1 | QC1 |
| 270 | 1.50 | 468.1 | QC1 |
| 271 | 1.61 | 424.1 | QC1 |
| 272 | 1.71 | 438.1 | QC1 |
| 273 | 1.53 | 426.1 | QC1 |
| 274 | 1.56 | 440.0 | QC1 |
| 275 | 1.67 | 396.1 | QC1 |
| 276 | 1.77 | 409.7 | QC1 |
| 277 | 1.81 | 452.1 | QC1 |
| 278 | 1.87 | 424.1 | QC1 |
| 279 | 1.63 | 364.8 | QC1 |
| 280 | 1.73 | 379.1 | QC1 |
| 281 | 1.83 | 393.1 | QC1 |
| 282 | 1.48 | 395.1 | QC1 |
| 283 | 1.51 | 409.1 | QC1 |
| 284 | 1.60 | 409.1 | QC1 |
| 285 | 1.56 | 407.0 | QC1 |
| 286 | 1.65 | 404.1 | QC1 |
| 287 | 1.60 | 402.1 | QC1 |
| 288 | 1.55 | 420.1 | QC1 |
| 289 | 1.66 | 400.0 | QC1 |
| 290 | 1.77 | 413.9 | QC1 |
| 291 | 1.88 | 428.0 | QC1 |
| 292 | 1.51 | 430.0 | QC1 |
| 293 | 1.54 | 443.7 | QC1 |
| 294 | 1.74 | 406.1 | QC1 |
| 295 | 1.84 | 420.1 | QC1 |
| 296 | 1.94 | 434.1 | QC1 |
| 297 | 1.60 | 436.1 | QC1 |
| 298 | 1.63 | 450.0 | QC1 |
| 299 | 1.60 | 376.0 | QC1 |
| 300 | 1.71 | 390.1 | QC1 |
| 301 | 1.46 | 406.1 | QC1 |
| 302 | 1.49 | 420.1 | QC1 |
| 303 | 1.54 | 381.1 | QC1 |
| 304 | 1.65 | 395.1 | QC1 |
| 305 | 1.44 | 425.0 | QC1 |
| 306 | 1.81 | 404.1 | QC1 |
| 307 | 1.76 | 409.1 | QC1 |
| 308 | 1.57 | 382.1 | QC1 |
| 309 | 1.69 | 396.1 | QC1 |
| 310 | 1.59 | 424.1 | QC1 |
| 311 | 1.62 | 438.1 | QC1 |
| 312 | 1.74 | 394.1 | QC1 |

TABLE 9-continued

| Ex. | tR (min) | m/z | Method |
|---|---|---|---|
| 313 | 1.84 | 408.1 | QC1 |
| 314 | 1.59 | 424.0 | QC1 |
| 315 | 1.62 | 438.0 | QC1 |
| 316 | 1.74 | 394.0 | QC1 |
| 317 | 1.84 | 408.1 | QC1 |
| 318 | 1.61 | 348.2 | QC1 |
| 319 | 1.55 | 424.0 | QC1 |
| 320 | 1.80 | 410.1 | QC1 |
| 321 | 1.43 | 412.1 | QC1 |
| 322 | 1.78 | 422.1 | QC1 |
| 323 | 1.68 | 438.0 | QC1 |
| 324 | 1.62 | 374.1 | QC1 |
| 325 | 1.63 | 394.1 | QC1 |
| 326 | 1.59 | 392.0 | QC1 |
| 327 | 1.72 | 380.1 | QC1 |
| 328 | 1.67 | 378.1 | QC1 |
| 329 | 1.61 | 396.1 | QC1 |
| 330 | 1.74 | 394.1 | QC1 |
| 331 | 1.84 | 408.1 | QC1 |
| 332 | 1.54 | 393.1 | QC1 |
| 333 | 1.65 | 407.1 | QC1 |
| 334 | 1.30 | 409.1 | QC1 |
| 335 | 1.33 | 422.9 | QC1 |
| 336 | 1.89 | 380.0 | QC1 |
| 337 | 1.55 | 366.1 | QC1 |
| 338 | 1.66 | 380.1 | QC1 |
| 339 | 1.41 | 396.1 | QC1 |
| 340 | 1.44 | 410.1 | QC1 |
| 341 | 1.67 | 352.2 | QC1 |
| 342 | 1.78 | 366.1 | QC1 |
| 343 | 1.51 | 382.2 | QC1 |
| 344 | 1.54 | 395.9 | QC1 |
| 345 | 1.83 | 379.1 | QC1 |
| 346 | 1.93 | 393.0 | QC1 |
| 347 | 1.58 | 395.0 | QC1 |
| 348 | 1.61 | 409.1 | QC1 |
| 349 | 1.65 | 380.1 | QC1 |
| 350 | 1.79 | 468.1 | QC1 |
| 351 | 1.73 | 365.1 | QC1 |
| 352 | 1.46 | 426.1 | QC1 |
| 353 | 1.76 | 394.1 | QC1 |
| 354 | 1.66 | 392.1 | QC1 |
| 355 | 1.77 | 406.1 | QC1 |
| 356 | 1.58 | 424.1 | QC1 |
| 357 | 1.61 | 438.1 | QC1 |
| 358 | 1.56 | 500.1 | QC1 |
| 359 | 1.76 | 416.0 | QC1 |
| 360 | 1.86 | 430.0 | QC1 |
| 361 | 1.96 | 444.1 | QC1 |
| 362 | 1.61 | 446.0 | QC1 |
| 363 | 1.64 | 460.1 | QC1 |
| 364 | 1.69 | 393.1 | QC1 |
| 365 | 1.48 | 423.0 | QC1 |
| 366 | 1.79 | 407.1 | QC1 |
| 367 | 1.47 | 422.0 | QC1 |
| 368 | 1.27 | 392.1 | QC1 |
| 369 | 1.30 | 405.8 | QC1 |
| 370 | 1.77 | 404.0 | QC1 |
| 371 | 1.87 | 418.1 | QC1 |
| 372 | 1.96 | 432.1 | QC1 |
| 373 | 1.63 | 434.1 | QC1 |
| 374 | 1.43 | 411.0 | QC1 |
| 375 | 1.46 | 425.0 | QC1 |
| 376 | 1.48 | 422.1 | QC1 |
| 377 | 1.57 | 486.1 | QC1 |
| 378 | 1.53 | 408.1 | QC1 |
| 379 | 1.64 | 422.1 | QC1 |
| 380 | 1.31 | 424.1 | QC1 |
| 381 | 1.34 | 438.1 | QC1 |
| 382 | 1.66 | 448.1 | QC1 |
| 383 | 1.43 | 420.1 | QC1 |
| 384 | 1.43 | 390.1 | QC1 |
| 385 | 1.39 | 388.1 | QC1 |
| 386 | 1.34 | 406.1 | QC1 |
| 387 | 1.64 | 377.1 | QC1 |
| 388 | 1.68 | 379.1 | QC1 |
| 389 | 1.58 | 395.0 | QC1 |
| 390 | 1.60 | 410.1 | QC1 |
| 391 | 1.64 | 412.0 | QC1 |
| 392 | 1.63 | 351.1 | QC1 |
| 393 | 1.84 | 379.1 | QC1 |
| 394 | 1.48 | 381.1 | QC1 |
| 395 | 1.52 | 395.1 | QC1 |
| 396 | 1.69 | 398.1 | QC1 |
| 397 | 1.80 | 412.1 | QC1 |
| 398 | 1.48 | 428.1 | QC1 |
| 399 | 1.59 | 444.1 | QC1 |
| 400 | 1.55 | 442.1 | QC1 |
| 401 | 1.46 | 413.1 | QC1 |
| 402 | 1.49 | 427.1 | QC1 |
| 403 | 1.63 | 430.1 | QC1 |
| 404 | 1.73 | 444.1 | QC1 |
| 405 | 1.45 | 460.1 | QC1 |
| 406 | 1.59 | 390.2 | QC1 |
| 407 | 1.38 | 362.1 | QC1 |
| 408 | 1.49 | 376.1 | QC1 |
| 409 | 1.52 | 412.0 | QC1 |
| 410 | 1.31 | 428.1 | QC1 |
| 411 | 1.34 | 442.0 | QC1 |
| 412 | 1.70 | 460.0 | QC1 |
| 413 | 1.66 | 458.0 | QC1 |
| 414 | 1.61 | 476.0 | QC1 |
| 415 | 1.48 | 426.1 | QC1 |
| 416 | 1.48 | 483.1 | QC1 |
| 417 | 2.08 | 456.1 | QC2 |
| 418 | 1.91 | 472.1 | QC2 |
| 419 | 1.59 | 361.1 | QC1 |
| 420 | 1.64 | 363.2 | QC1 |
| 421 | 1.59 | 335.1 | QC1 |
| 422 | 1.69 | 349.1 | QC1 |
| 423 | 1.80 | 363.1 | QC1 |
| 424 | 1.47 | 379.1 | QC1 |
| 425 | 1.56 | 456.1 | QC1 |
| 426 | 1.44 | 472.1 | QC1 |
| 427 | 1.56 | 381.1 | QC1 |
| 428 | 1.59 | 383.1 | QC1 |
| 429 | 1.67 | 400.0 | QC1 |
| 430 | 1.66 | 395.1 | QC1 |
| 431 | 1.69 | 396.9 | QC1 |
| 432 | 1.76 | 413.9 | QC1 |
| 433 | 1.58 | 394.1 | QC1 |
| 434 | 1.68 | 408.1 | QC1 |
| 435 | 1.43 | 465.1 | QC1 |
| 436 | 1.45 | 424.0 | QC1 |
| 437 | 1.48 | 438.1 | QC1 |
| 438 | 1.51 | 438.1 | QC1 |
| 439 | 1.52 | 378.1 | QC1 |
| 440 | 1.63 | 392.2 | QC1 |
| 441 | 1.74 | 406.1 | QC1 |
| 442 | 1.39 | 408.1 | QC1 |
| 443 | 1.42 | 422.1 | QC1 |
| 444 | 1.52 | 394.2 | QC1 |
| 445 | 1.62 | 408.1 | QC1 |
| 446 | 1.40 | 424.1 | QC1 |
| 447 | 1.72 | 422.1 | QC1 |
| 448 | 1.67 | 431.8 | QC1 |
| 449 | 1.76 | 446.0 | QC1 |
| 450 | 1.86 | 460.1 | QC1 |
| 451 | 1.53 | 462.0 | QC1 |
| 452 | 1.56 | 476.0 | QC1 |
| 453 | 1.59 | 476.0 | QC1 |
| 454 | 1.59 | 476.0 | QC1 |
| 455 | 1.47 | 492.0 | QC1 |
| 456 | 1.47 | 491.9 | QC1 |
| 457 | 1.60 | 475.9 | QC1 |
| 458 | 1.51 | 503.1 | QC1 |
| 459 | 1.62 | 422.1 | QC1 |
| 460 | 1.68 | 440.1 | QC1 |
| 461 | 1.64 | 438.1 | QC1 |
| 462 | 1.59 | 456.0 | QC1 |
| 463 | 1.65 | 412.1 | QC1 |
| 464 | 1.74 | 426.1 | QC1 |
| 465 | 1.57 | 422.1 | QC1 |
| 466 | 1.53 | 420.1 | QC1 |
| 467 | 1.53 | 404.1 | QC1 |
| 468 | 1.57 | 406.1 | QC1 |

TABLE 9-continued

| Ex. | tR (min) | m/z | Method |
|---|---|---|---|
| 469 | 2.14 | 396.1 | QC2 |
| 470 | 2.31 | 410.2 | QC2 |
| 471 | 2.48 | 424.2 | QC2 |
| 472 | 2.03 | 440.1 | QC2 |
| 473 | 1.98 | 426.2 | QC2 |
| 474 | 2.49 | 440.3 | QC2 |
| 475 | 2.11 | 456.2 | QC2 |
| 476 | 2.31 | 442.2 | QC2 |
| 477 | 2.23 | 440.2 | QC2 |
| 478 | 2.16 | 458.2 | QC2 |
| 479 | 1.94 | 415.2 | QC2 |
| 480 | 2.01 | 417.2 | QC2 |
| 481 | 2.21 | 414.0 | QC2 |
| 482 | 2.38 | 428.2 | QC2 |
| 483 | 2.53 | 442.2 | QC2 |
| 484 | 2.04 | 444.1 | QC2 |
| 485 | 2.09 | 458.1 | QC2 |
| 486 | 2.13 | 409.2 | QC2 |
| 487 | 2.06 | 407.2 | QC2 |
| 488 | 1.93 | 389.2 | QC2 |
| 489 | 2.08 | 403.1 | QC2 |
| 490 | 2.23 | 417.2 | QC2 |
| 491 | 1.78 | 419.2 | QC2 |
| 492 | 1.83 | 433.2 | QC2 |
| 493 | 2.14 | 389.3 | QC2 |
| 494 | 2.08 | 387.3 | QC2 |
| 495 | 2.01 | 405.3 | QC2 |
| 496 | 2.16 | 423.2 | QC2 |
| 497 | 2.21 | 409.2 | QC2 |
| 498 | 2.08 | 409.2 | QC2 |
| 499 | 1.93 | 426.2 | QC2 |
| 500 | 2.04 | 361.2 | QC2 |
| 501 | 2.19 | 375.2 | QC2 |
| 502 | 2.14 | 422.2 | QC2 |
| 503 | 2.23 | 424.2 | QC2 |
| 504 | 1.54 | 465.1 | QC1 |
| 505 | 1.60 | 479.1 | QC1 |
| 506 | 1.58 | 477.1 | QC1 |
| 507 | 1.67 | 481.1 | QC1 |
| 508 | 1.69 | 513.1 | QC1 |
| 509 | 1.50 | 495.1 | QC1 |
| 510 | 1.54 | 465.0 | QC1 |
| 511 | 1.60 | 479.1 | QC1 |
| 512 | 1.63 | 491.1 | QC1 |
| 513 | 1.74 | 519.2 | QC1 |
| 514 | 1.52 | 480.1 | QC1 |
| 515 | 1.50 | 471.0 | QC1 |
| 516 | 1.48 | 423.2 | QC1 |
| 517 | 1.54 | 436.1 | QC1 |
| 518 | 1.51 | 450.1 | QC1 |
| 519 | 1.42 | 432.1 | QC1 |
| 520 | 1.51 | 485.0 | QC1 |
| 521 | 1.60 | 475.1 | QC1 |
| 522 | 1.93 | 438.2 | QC2 |
| 523 | 1.66 | 514.0 | QC1 |
| 524 | 1.52 | 514.0 | QC1 |
| 525 | 1.53 | 514.0 | QC1 |
| 526 | 1.63 | 535.0 | QC1 |
| 527 | 1.49 | 469.9 | QC1 |
| 528 | 1.51 | 438.0 | QC1 |
| 529 | 1.46 | 456.0 | QC1 |
| 530 | 1.75 | 400.0 | QC1 |
| 531 | 1.70 | 398.0 | QC1 |
| 532 | 1.64 | 416.0 | QC1 |
| 533 | 1.51 | 412.0 | QC1 |
| 534 | 1.60 | 426.0 | QC1 |
| 535 | 1.69 | 440.0 | QC1 |
| 536 | 1.38 | 483.0 | QC1 |
| 537 | 1.39 | 442.0 | QC1 |
| 538 | 1.42 | 456.0 | QC1 |
| 539 | 1.58 | 394.0 | QC1 |
| 540 | 1.68 | 408.0 | QC1 |
| 541 | 1.79 | 422.0 | QC1 |
| 542 | 1.49 | 451.0 | QC1 |
| 543 | 1.46 | 435.9 | QC1 |
| 544 | 1.40 | 452.9 | QC1 |
| 545 | 1.58 | 487.0 | QC1 |
| 546 | 1.44 | 454.0 | QC1 |
| 547 | 1.50 | 467.0 | QC1 |
| 548 | 1.44 | 447.0 | QC1 |
| 549 | 1.38 | 437.0 | QC1 |
| 550 | 1.58 | 420.0 | QC1 |
| 551 | 1.62 | 422.0 | QC1 |
| 552 | 1.71 | 372.0 | QC1 |
| 553 | 1.81 | 386.0 | QC1 |
| 554 | 1.52 | 443.0 | QC1 |
| 555 | 1.92 | 400.0 | QC1 |
| 556 | 1.55 | 402.0 | QC1 |
| 557 | 1.58 | 416.0 | QC1 |
| 558 | 1.81 | 434.1 | QC1 |
| 559 | 1.76 | 432.1 | QC1 |
| 560 | 1.71 | 450.1 | QC1 |
| 561 | 1.77 | 406.1 | QC1 |
| 562 | 1.86 | 420.1 | QC1 |
| 563 | 1.59 | 477.1 | QC1 |
| 564 | 1.96 | 434.1 | QC1 |
| 565 | 1.62 | 436.1 | QC1 |
| 566 | 1.65 | 450.1 | QC1 |
| 567 | 1.78 | 380.2 | QC1 |
| 568 | 1.73 | 378.2 | QC1 |
| 569 | 1.66 | 396.2 | QC1 |
| 570 | 1.55 | 440.0 | QC1 |
| 571 | 1.73 | 352.0 | QC1 |
| 572 | 1.84 | 366.1 | QC1 |
| 573 | 1.52 | 423.0 | QC1 |
| 574 | 1.96 | 380.1 | QC1 |
| 575 | 1.56 | 382.0 | QC1 |
| 576 | 1.59 | 396.0 | QC1 |
| 577 | 1.59 | 380.1 | QC1 |
| 578 | 1.54 | 378.0 | QC1 |
| 579 | 1.48 | 396.0 | QC1 |
| 580 | 1.53 | 352.0 | QC1 |
| 581 | 1.64 | 366.1 | QC1 |
| 582 | 1.38 | 423.0 | QC1 |
| 583 | 1.75 | 380.1 | QC1 |
| 584 | 1.40 | 382.0 | QC1 |
| 585 | 1.43 | 396.0 | QC1 |
| 586 | 1.47 | 413.2 | QC1 |
| 587 | 1.56 | 427.2 | QC1 |
| 588 | 1.66 | 441.2 | QC1 |
| 589 | 1.36 | 443.2 | QC1 |
| 590 | 1.38 | 457.2 | QC1 |
| 591 | 1.52 | 404.3 | QC1 |
| 592 | 1.48 | 402.3 | QC1 |
| 593 | 1.47 | 376.3 | QC1 |
| 594 | 1.57 | 390.3 | QC1 |
| 595 | 1.34 | 447.3 | QC1 |
| 596 | 1.67 | 404.4 | QC1 |
| 597 | 1.36 | 406.3 | QC1 |
| 598 | 1.38 | 420.3 | QC1 |
| 599 | 1.84 | 418.2 | QC2 |
| 600 | 1.51 | 420.2 | QC1 |
| 601 | 1.51 | 420.2 | QC1 |
| 602 | 1.53 | 420.2 | QC1 |
| 603 | 1.39 | 436.2 | QC1 |
| 604 | 1.39 | 436.2 | QC1 |
| 605 | 1.59 | 415.2 | QC1 |
| 606 | 1.70 | 403.3 | QC1 |
| 607 | 1.65 | 401.2 | QC1 |
| 608 | 1.60 | 419.3 | QC1 |
| 609 | 1.65 | 375.2 | QC1 |
| 610 | 1.75 | 389.3 | QC1 |
| 611 | 1.49 | 446.2 | QC1 |
| 612 | 1.84 | 403.2 | QC1 |
| 613 | 1.51 | 405.2 | QC1 |
| 614 | 1.54 | 419.2 | QC1 |
| 615 | 1.62 | 447.1 | QC1 |
| 616 | 1.67 | 438.2 | QC1 |
| 617 | 1.48 | 403.3 | QC1 |
| 618 | 1.48 | 403.3 | QC1 |
| 619 | 1.55 | 417.4 | QC1 |
| 620 | 1.52 | 417.4 | QC1 |
| 621 | 1.51 | 405.3 | QC1 |
| 622 | 1.64 | 431.4 | QC1 |
| 623 | 1.55 | 417.3 | QC1 |
| 624 | 1.56 | 417.4 | QC1 |

TABLE 9-continued

| Ex. | tR (min) | m/z | Method |
|---|---|---|---|
| 625 | 1.56 | 417.4 | QC1 |
| 626 | 1.55 | 417.4 | QC1 |
| 627 | 1.52 | 417.4 | QC1 |
| 628 | 1.51 | 405.3 | QC1 |
| 629 | 1.64 | 431.1 | QC1 |
| 630 | 1.56 | 417.1 | QC1 |
| 631 | 1.50 | 403.1 | QC1 |
| 632 | 1.47 | 403.1 | QC1 |
| 633 | 1.46 | 389.1 | QC1 |
| 634 | 1.58 | 417.1 | QC1 |
| 635 | 1.50 | 403.1 | QC1 |
| 636 | 1.53 | 417.1 | QC1 |
| 637 | 1.50 | 417.1 | QC1 |
| 638 | 1.49 | 403.1 | QC1 |
| 639 | 1.61 | 431.1 | QC1 |
| 640 | 1.53 | 417.2 | QC1 |
| 641 | 2.03 | 359.2 | QC2 |
| 642 | 1.56 | 345.2 | QC1 |
| 643 | 1.66 | 359.2 | QC1 |
| 644 | 1.40 | 416.3 | QC1 |
| 645 | 1.42 | 375.3 | QC1 |
| 646 | 1.45 | 389.3 | QC1 |
| 647 | 1.48 | 389.3 | QC1 |
| 648 | 1.48 | 389.3 | QC1 |
| 649 | 1.76 | 373.3 | QC1 |

| Ex | 1H-NMR data | Salt |
|---|---|---|
| | Table 10-1 | |
| 1 | (300 MHz, CDCl$_3$) δ 8.83 (1H, s), 8.39 (1H, br), 8.03 (1H, d, J = 2.2 Hz), 7.85 (1H, br), 7.45 (1H, s), 7.30 (1H, d, J = 6.6 Hz), 5.48 (2H, s), 4.75 (2H, q, J = 8.6 Hz), 2.65 (1H, septet, 6.6 Hz), 2.19 (3H, s), 1.30 (6H, d, J = 6.6 Hz) | free |
| 2 | (300 MHz, DMSO-d$_6$) δ 9.68 (1H, s), 9.00 (1H, s), 8.16 (1H, s), 7.86 (1H, d, J = 5.9 Hz), 7.69 (1H, s), 7.29 (1H, d, J = 5.9 Hz), 6.14 (1H, s), 5.66 (2H, s), 4.99 (2H, q, J = 8.8 Hz), 2.15 (3H, s), 1.43 (6H, s). | free |
| 69 | (300 MHz, CDCl$_3$) δ 8.84 (1H, s), 8.25 (1H, dd, J = 5.8 and 2.2 Hz), 8.06 (2H, s), 7.68 (1H, d, J = 5.8 Hz), 7.45 (1H, s), 5.55 (2H, s), 4.81-4.71 (2H, m), 3.58-3.48 (2H, m), 2.20 (3H, s), 1.33-1.27 (3H, m) | free |
| 141 | (300 MHz, DMSO-d$_6$) δ 9.17 (1H, s), 8.76 (1H, t, J = 5.9 Hz), 8.25 (1H, d, J = 5.9 Hz), 8.19 (1H, s), 7.76-7.73 (2H, m), 5.73 (2H, s), 4.99 (2H, q, J = 8.8 Hz), 4.83 (1H, t, J = 5.1 Hz), 3.60-3.52 (2H, m), 3.45-3.38 (2H, m), 2.15 (3H, s) | free |
| 149 | (300 MHz, CDCl$_3$) δ 8.79 (1H, s), 8.45 (1H,br), 8.24 (1H, d, J = 6.6 Hz), 8.06 (1H, d, J = 2.2 Hz), 7.69 (1H, d, J = 6.6 Hz), 7.41 (1H, s), 5.54 (2H, s), 4.56 (2H, t, J = 6.2 Hz), 3.90-3.84 (2H, m), 3.70-3.64 (2H, m), 2.75 (1H, t, J = 5.1 Hz), 2.69-2.54 (2H, m), 2.15 (3H, s) | free |
| 158 | (300 MHz, CDCl$_3$) δ 10.03 (1H, br s), 8.87 (1H, s), 7.90-7.82 (1H, m), 7.29-7.24 (2H, m), 5.79 (2H, s), 4.93 (2H, q, J = 8.1 Hz), 2.22 (3H, s), 1.81-1.70 (1H, m), 1.18-1.11 (2H, m), 0.97-0.90 (2H, m) | free |
| 166 | (300 MHz, CDCl$_3$) δ 8.80 (1H, s), 8.47-8.41 (1H, m), 8.23 (1H, d, J = 5.9 Hz), 8.06 (1H, d, J = 1.5 Hz), 7.68 (1H, d, J = 5.9 Hz), 7.46 (1H, s), 5.55 (2H, s), 4.76 (2H, q, J = 8.8 Hz), 4.12-4.04 (1H, m), 3.68-3.60 (1H, m), 3.45-3.35 (1H, m), 2.91 (1H, d, J = 4.4 Hz), 2.20 (3H, s), 1.28 (3H, d, J = 5.9 Hz) | free |
| 172 | (300 MHz, CDCl$_3$) δ 8.95 (1H, s), 8.23 (1H, d, J = 6.6 Hz), 8.12 (1H, s), 8.07 (1H, br), 7.68 (1H, d, J = 6.6 Hz), 7.08 (1H, s), 5.69 (2H, s), 4.43 (2H, q, J = 8.0 Hz), 3.54 (2H, quintet, J = 6.6 Hz), 2.23 (3H, s), 1.30 (3H, t, J = 7.3 Hz) | free |
| 174 | (300 MHz, CDCl$_3$) δ 8.93 (1H, s), 8.45 (1H, br), 8.24 (1H, d, J = 6.6 Hz), 8.12 (1H, s), 7.70 (1H, d, J = 6.6 Hz), 7.09 (1H, s), 4.43 (2H, q, J = 8.0 Hz), 3.92-3.84 (2H, m), 3.72-3.65 (2H, m), 2.77 (1H, t, J = 5.1 Hz), 2.24 (3H, s) | free |
| 179 | (270 MHz, DMSO-d$_6$) δ 9.17 (1H, s), 8.90 (1H, t, J = 5.3 Hz), 8.25-8.20 (2H, m), 7.75-7.73 (2H, m), 5.73 (2H, s), 5.00 (2H, q, J = 9.2 Hz), 4.55 (1H, t, J = 5.3 Hz), 3.52-3.34 (4H, m), 2.15 (3H, s), 1.71 (2H, quintet, J = 6.6 Hz) | free |
| 183 | (300 MHz, CDCl$_3$) δ 8.80 (1H, s), 8.40 (1H, br), 8.27 (1H, d, J = 5.8 Hz), 8.07 (1H, s), 7.70 (1H, d, J = 5.8 Hz), 7.47 (1H, s), 6.20 (1H, br), 5.57 (2H, s), 4.76 (2H, q, J = 8.8 Hz), 3.68-3.61 (2H, m), 3.55-3.49 (2H, m), 2.20 (3H, s), 1.99 (3H, s) | free |
| 199 | (300 MHz, CDCl$_3$) δ 8.80 (1H, s), 8.47 (1H, br), 8.25 (1H, d, J = 6.6 Hz), 8.07 (1H, d, J = 2.2 Hz), 7.71 (1H, d, J = 6.6 Hz), 7.46 (1H, d, J = 2.2 Hz), 5.56 (2H, s), 4.76 (2H, q, J = 8.8 Hz), 3.96-3.86 (1H, m), 3.75-3.58 (4H, m), 3.09-3.01 (2H, m), 2.21 (3H, s) | free |
| | Table 10-2 | |
| 220 | (300 MHz, CDCl$_3$) δ 8.76 (1H, s), 8.52-8.40 (1H, m), 8.24 (1H, d, J = 6.2 Hz), 7.70 (1H, d, J = 6.2 Hz), 7.27-7.15 (2H, m), 6.78 (1H, d, J = 8.1 Hz), 6.10 (1H, tt, J = 55.0, 4.0 Hz), 5.55 (2H, s), 4.18 (2H, td, J = 13.0, 4.0 Hz), 3.91-3.80 (2H, m), 3.72-3.61 (2H, m), 2.22 (3H, s) (a signal due to OH is not observed) | free |
| 222 | (300 MHz, CDCl$_3$) δ 8.81 (1H, s), 8.48-8.42 (1H, m), 8.25 (1H, d, J = 5.9 Hz), 8.07 (1H, d, J = 2.2 Hz), 7.69 (1H, d, J = 5.9 Hz), 7.45 (1H, s), 5.99 (1H, tt, J = 52.8 and 4.4 Hz), 5.56 (2H, s), 4.74 (2H, t, J = 12.5 Hz), 3.91-3.85 (2H, m), 3.70-3.64 (2H, m), 2.74 (1H, t, J = 5.9 Hz), 2.18 (3H, s) | free |
| 223 | (300 MHz, CDCl$_3$) δ 8.83 (1H, s), 8.36-8.28 (1H, m), 8.25 (1H, d, J = 5.9 Hz), 8.07 (1H, s), 7.70 (1H, d, J = 5.9 Hz), 7.46 (1H, s), 5.98 (1H, tt, J = 53.6 and 4.4 Hz), 5.56 (2H, s), 4.74 (2H, t, J = 12.5 Hz), 3.70-63 (4H, m), 3.30 (1H, br s), 2.19 (3H, s), 1.87-1.79 (2H, m) | free |
| 288 | (300 MHz, DMSO-d$_6$) δ 9.67 (1H, s), 8.98 (1H, s), 8.13 (1H, s), 7.85 (1H, d, J = 5.9 Hz), 7.63 (1H, s), 7.28 (1H, d, J = 5.9 Hz), 6.14 (1H, s), 5.63 (2H, s), 4.54 (2H, t, J = 13.2 Hz), 2.12 (3H, s), 1.71 (3H, t, J = 19.1 Hz), 1.41 (6H, s) | free |

| Ex | 1H-NMR data | Salt |
|---|---|---|
| 301 | (300 MHz, CDCl$_3$) δ 8.79 (1H, s), 8.45 (1H, br s), 8.24 (1H, d, J = 6.6 Hz), 8.07 (1H, s), 7.69 (1H, d, J = 6.6 Hz), 7.43 (1H, s), 5.55 (2H, s), 4.50 (2H, t, J = 11.7 Hz), 3.90-3.85 (2H, m), 3.70-3.64 (2H, m), 2.83 (1H, t, J = 5.5 Hz), 2.19 (3H, s), 1.74 (3H, t, J = 19.1 Hz) | free |
| 343 | (300 MHz, CDCl$_3$) δ 8.75 (1H, s), 8.51-8.39 (1H, m), 8.23-8.19 (1H, m), 8.05 (1H, d, J = 2.2 Hz), 7.67 (1H, d, J = 6.6 Hz), 7.38 (1H, s), 5.22 (2H, s), 4.16-4.14 (2H, m), 3.89-3.85 (2H, m), 3.69-3.63 (2H, m), 3.02 (1H, br s), 2.17 (3H, s), 1.35-1.21 (1H, m), 0.61-0.56 (2H, m), 0.37-0.32 (2H, m) | free |
| 462 | (300 MHz, DMSO-d$_6$) δ 9.67 (1H, s), 9.00 (1H, s), 8.15 (1H, s), 7.85 (1H, d, J = 5.9 Hz), 7.66 (1H, s), 7.28 (1H, d, J = 5.9 Hz), 6.66 (1H, tt, J = 52.1, 5.1 Hz), 6.14 (1H, s), 5.64 (2H, s), 4.83 (2H, t, J = 13.9 Hz), 2.13 (3H, s), 1.41 (6H, s) | free |
| 518 | (300 MHz, DMSO-d$_6$) δ 9.07 (1H, s), 8.93 (1H, t, J = 5.9 Hz), 8.24 (1H, d, J = 5.9 Hz), 8.02-7.94 (1H, m), 7.73 (1H, d, J = 5.9 Hz), 7.28 (2H, s), 7.03 (1H, d, J = 8.8 Hz), 5.65 (2H, s), 4.73 (2H, q, J = 8.1 Hz), 3.41-3.19 (4H, m), 2.13 (3H, s), 1.78 (3H, s) | free |

Pharmacological Assays

In vitro human voltage gated sodium channels activity

The inhibitory activities of compounds against voltage gated sodium channels are determined by methodology well known in the art.

The ability of the pyrazolopyridine derivatives of the formula (I) to inhibit the Na$_{v1.3}$, Na$_{v1.7}$ and Na$_{v1.5}$ channels is measured by Fluorescence Resonance Energy Transfer (FRET) assay and electrophysiology assay described below.

FRET Assay

This screen is used to determine the effects of compounds on human Na$_{v1.3}$, human Na$_{v1.7}$, and human Na$_{v1.5}$ channels, utilising electrical field stimulation (EFS) system in 96-well plate format on FDSS (Hamamatsu Photonics) platform. The change of membrane potential is monitored with FRET dye pair, oxonol (DiSBAC2(3)) and coumarin (CC2-DMPE).

Cell Maintenance:

Each HEK293 cells expressing human Na$_{v1.3}$ channels and HEK293 cells expressing human Na$_{v1.5}$ channels are grown in T225 flasks, in a 5% CO$_2$ humidified incubator to about 80% confluence. Media composition consists of Dulbecco's Modified Eagle Medium (high glucose), 10% FCS, 100 units/mL penicillin, 100 microgram/mL streptomycin and 500 microgram/mL Geneticine.

CHO cells expressing human Na$_{v1.7}$ channels are grown in T225 flasks, in a 5% CO$_2$ humidified incubator to about 80% confluence. Media composition consists of HAM/F12 with Glutamax I, 10% FCS, 100 units/mL penicillin and 100 microgram/mL hygromycin.

Protocol:

Seed each cell lines (1×10$^5$ cell/swell) into poly-D-lysine coated 96-well plates prior to experimentation.

Incubate at 37° C. in 5% CO$_2$ for 24 hours.

Wash each well with assay buffer (140 mM NaCl, 4.5 mM KCl, 10 mM D-Glucose, 2 mM CaCl$_2$, 1 mM MgCl$_2$, 10 mM HEPES, pH 7.4 adjusted with NaOH) twice.

Add 1st loading solution containing 10 microM CC2-DMPE and 0.06% Pluronic F-127 in assay buffer.

Incubate the plate at room temperature in dark for 1 hour.

Remove 1st loading solution and added 2nd loading solution containing 15 microM DiSBAC2(3), 0.555 mM VABSC-1 and 0.004% Pluronic F-127 in assay buffer.

Place the plate under the dark at room temperature for 25 minutes.

Add compound solutions into the assay plate.

Set the assay plate in FDSS and placed an EFS device on the plate.

Measure EFS-induced fluorescent response by FDSS.

The data are analyzed and reported as normalized ratios of intensities measured at 440 nm. The process of calculating these ratios is performed as follows:

$FIR$ = Fluorescence Integration Ratio = the integral of [Math. 1]

the ratio normalized by baseline (before $EFS$)

% inhibition=

$$\left\{1 - \frac{(FIR \text{ of each well} - \text{median } FIR \text{ in } 100\% \text{ Inh.})}{\left(\begin{array}{c}\text{median } FIR \text{ in } 0\% \text{ Inh.} - \\ \text{median } FIR \text{ in } 100\% \text{ Inh.}\end{array}\right)}\right\} \times 100$$

This analysis is performed using a computerized specific program designed for FDSS generated data. Fluorescence ratio values are plotted using XLfit to determine an IC$_{50}$ value for each compound.

All tested compounds show less than about 3 microM of IC$_{50}$ against Na$_{v1.3}$ and/or Na$_{v1.7}$ in the above assays. Preferable compounds show less than about 1 microM of IC$_{50}$ against Na$_{v1.7}$ and/or Na$_{v1.3}$ in the above assays.

Compounds with IC$_{50}$ against Na$_{v1.7}$<1 microM and/or Na$_{v1.3}$<1 microM are: Examples 1, 2, 3, 4, 6, 7, 9, 10, 11, 14, 15, 16, 18, 19, 20, 21, 22, 25, 27, 32, 33, 34, 38, 41, 42, 43, 44, 45, 46, 47, 51, 52, 61, 65, 69, 71, 75, 80, 82, 85, 88, 89, 92, 93, 96, 98, 103, 104, 106, 107, 108, 109, 112, 113, 119, 120, 125, 126, 128, 129, 134, 139, 141, 145, 147, 148, 149, 151, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 187, 190, 191, 194, 195, 196, 197, 199, 201, 202, 203, 204, 207, 209, 212, 214, 215, 216, 217, 218, 219, 220, 221, 222, 223, 224, 227, 228, 229, 230, 231, 232, 238, 239, 240, 241, 242, 245, 246, 247, 248, 251, 252, 254, 255, 256, 257, 258, 259, 260, 261, 262, 264, 265, 267, 268, 269, 270, 271, 272, 273, 274, 275, 276, 277, 278, 280, 281, 282, 283, 284, 285, 286, 287, 288, 289, 290, 292, 293, 294, 295, 296, 297, 298, 299, 300, 301, 302, 304, 306, 307, 308, 309, 310, 311, 312, 313, 314, 315, 316, 317, 320, 321, 322, 326, 327, 328, 329, 330, 331, 332, 333, 335, 336, 337, 338, 341, 342, 343, 344, 345, 347, 348, 349, 350, 351, 352, 355, 356, 357, 358, 359, 360, 362, 363, 364, 367, 369, 370, 371, 372, 373, 374, 375, 376, 377, 378, 380, 382, 383, 384, 385, 386, 387, 391, 392, 394, 395, 399, 400, 401, 402, 403, 406, 407, 408, 409, 412, 413, 414, 415, 416, 417, 418, 420, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 489, 492, 493, 494, 495, 496, 497, 500, 501, 502, 503, 504, 506, 507, 508, 512, 513, 515, 516, 517, 518, 519, 521, 522, 523, 524, 525, 527, 528, 529, 530, 531, 532, 533, 534, 535, 537, 538, 540, 545, 548, 549, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 596, 597, 598, 599, 600, 602, 603, 605, 606, 607, 608, 609, 610, 611, 612, 613, 614, 616, 617, 618, 619, 620, 622, 624, 625, 626, 627, 629, 631, 632, 633, 634, 636, 637, 639, 640, 641, 642, 643, 645, 646, and 649. Regarding all tested compounds, the ratio of activities against $Na_{v1.5}$ vs. $Na_{v1.3}$ or $Na_{v1.7}$ is more than three times. For example, the activities of Example 2 against $Na_{v1.5}$ and $Na_{v1.7}$ are more than 30 microM and 0.38 microM, respectively.

Electrophysiology Assay for Nays

Whole cell patch clamp recording is used to assess the efficacy or selectivity of Na channel blocker on human $Na_{v1.3}$ (hSCN3A) expressing HEK293 cells or human $Na_{v1.7}$ (hSCN9A) expressing CHO cells. Human $Na_{v1.3}$ expressing HEK293 cells are grown in growth media which contain: DMEM, 10% heat-inactivated FBS (Hyclone Laboratories Inc), 100 microgram/mL penicillin/100U/mL streptomycin, 150 microgram/mL Zeocin, and 3 microgram/mL Geneticin. Human $Na_{v1.7}$ expressing CHO cells are grown in growth media which contain: HAMF-12, 9% heat-inactivated FBS (Hyclone Laboratories Inc), and 100 microgram/mL penicillin/100 U/mL streptomycin, and 100 microgram/mL hygromycin.

Na channel expressing cells are dissociated by 0.05% Trypsine-EDTA, and then seeded on cover glass for 24-48 hr.

Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier (Axon Instruments or HEKA electronik). The extracellular recording solution consists of (mM): 140 NaCl, 5 KCl, 2 $CaCl_2$, 1 $MgCl_2$, 10 HEPES, and 10 Glucose, pH 7.4 adjusted with NaOH. The internal solution consists of (mM): 120 CsF, 15 NaCl, 10 EGTA, and 10 HEPES, pH 7.2 adjusted with CsOH; Upon insertion of the pipette tip into the bath, the pipette resistance is noted (acceptable range is between 1-3 megaohm). The junction potential between the pipette and bath solutions is zeroed on the amplifier. After establishing the whole-cell configuration, approximately 10 minutes are allowed for the pipette solution to equilibrate within the cell before beginning recording. Currents are lowpass filtered between 2-5 kHz and digitally sampled at 10 kHz.

The normalized steady-state inactivation curve is constructed using 2 sec (for vehicle) or 60 sec (for drugs) conditioning pulse to different potentials followed immediately by the test pulse to −10 mV. Peak currents are plotted as fraction of the maximum current at the conditioning potentials ranging from −120 mV to −40 mV for $Na_{v1.3}$ and from −130 mV to −60 mV for $Na_{v1.7}$. V1/2 or k values are estimated from Boltzmann fits. The affinity of drugs to resting state of Na channels ($K_{resting}$ or $K_r$) is assessed by 30 msec test pulse from a negative holding potential of −120 or −130 mV, where virtually all channels are in the resting state. $K_r$ value is calculated by a conventional 1:1 binding model:

$$K_{resting}(K_r) = \{[\text{drug}]I_{max},\text{drug}/(I_{max},\text{control} - I_{max},\text{drug})\} \qquad [\text{Math.2}]$$

where $K_{resting}(=K_r)$ is a dissociation constant for the resting state and [drug] is compound concentration. $I_{max}$,control and $I_{max}$,drug are peak currents in the absence and presence of compound, respectively.

The affinity of drug to inactivated state of Na channels ($K_{inact}$ or $K_i$) is estimated from the shift of the availability curve by compound. Interaction of the compound with the channel on inactivated state is evaluated by the following equation:

$$K_{inact}(K_i) = \{[\text{drug}]/((1+[\text{drug}]/Kr)*\exp(-\Delta V/k)-1)\} \qquad [\text{Math.3}]$$

where $K_{inact}(=K_i)$ is a dissociation constant for the inactivated state. $\Delta V$ is the compound-induced voltage shift of half maximal voltage of Boltzmann curve and k is the slop factor on presense of compound.

All tested compounds of the invention show potent activities in this model. For example, the activities (Ki) of example 2 against $Nav_{1.3}$ and $Nav_{1.7}$ are 0.57 microM and 0.34 microM, respectively.

In Vivo Assay

Chronic Constriction Injury (CCI)-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. CCI-induced static allodynia is assessed by von Frey hair (VFH) test. Surgery is performed according to the method of Bennett G J and Xie Y K (Pain 1988, 33: 87-107). The animals are anesthetized with intraperitoneal injection of pentobarbital sodium. The left common sciatic nerve is exposed at the level of the middle of the thigh, freed of adhering tissue, and four ligatures are loosely tided around it by using 4-0 silk thread. The incision is sutured, and the rats are allowed to recover in their cages with soft bedding. Sham operation is performed in the same manner except of sciatic nerve ligation. The animals are individually placed in a Plexiglas test chamber on an elevated grid to acclimate before the day of testing. On postoperative day (POD) 14-28, evaluation is performed using a series of calibrated VFH (Semmes-Winstein monofilaments) with 0.4, 0.6, 1, 2, 4, 6, 8 and 15 g force. VFH starting with the 2 g force is applied in an ascending or descending fashion according to a modified Dixon up-down method described by Chaplan SR et al. (J Neurosci Methods 1994, 53: 55-63). Each VFH is presented to the plantar surface of the operated hind paw with steady upward pressure until bent for approximately 6 seconds. In the absence of a paw withdrawal, a stronger stimulus is presented. In the event of a paw withdrawal, the next weaker stimulus is chosen. After the initial change from positive to negative or vice versa 4 more stimulations are applied. The 6-score pattern of positive and negative responses is converted into a 50% paw withdrawal threshold (PWT) using the following formula:

$$50\% \text{ PWT}(g) = (10^{[Xf+\kappa\delta]})/10{,}000 \qquad [\text{Math.4}]$$

where Xf is the value (in log units) of the final VFH used, κ is the tabular value for the pattern of positive/negative responses and δ is the mean difference between stimuli in log units (here, 0.224).

In the cases where continuous positive or negative responses are observed all the way out to the end of the stimulus spectrum, values of 0.25 and 15 g are assigned, respectively. The animals showing static allodynia (<4 g of 50% PWT) by CCI surgery are selected for evaluation and randomized to be nearly equal mean 50% PWT across all groups. The compounds of the invention or their vehicles are administered systemically. The rats are habituated to the chamber for at least 20 minutes before the measurement. The 50% PWT is measured at the appropriated time after compound administration. Statistical analysis is performed by unpaired t-test or one-way analysis of variance (ANOVA) with Dunnett's post-hoc test compared to the vehicle group.

All tested compounds of the invention show potent activities in this model.

Complete Freund's Adjuvant (CFA)-Induced Thermal Hyperalgesia in Rats

Male Sprague-Dawley rats at 6 weeks old are purchased from Charles River Japan Inc., and housed in groups of two per cage under a 12-h light/dark cycle (lights on at 07:00) with access to food and water ad libitum. CFA-induced thermal hyperalgesia is assessed using the plantar test apparatus (Ugo Basile) as described by Hargreaves K et al. (Pain 1988, 32: 77-88). The animals are placed in an apparatus consisting of individual testing box on an elevated glass table and allowed to acclimate for at least 10 minutes. Following the habituation, a mobile radiant heat source is located under the table and heat stimulation is applied to the plantar surface of the right hind paw. The latency to remove its hind paw is defined as paw withdrawal latency (PWL) in sec. The cut-off point is set at 30 seconds to prevent tissue damage. CFA is prepared at a concentration of 2-3 mg/mL of *Mycobacterium tuberculosis* H37 RA in liquid paraffin. After disinfections with 70% ethanol, the rats are injected intraplantarly with 100 microL of CFA (200-300 microgram) into the right hind paw. Two days after CFA injection, PWL is measured in the same manner as mentioned above. The animals showing decrease of the PWL (hyperalgesia) by CFA injection are selected for evaluation and randomized to be nearly equal mean PWL across all groups. The compounds of the invention or their vehicles are administered systemically. The rats are habituated to the apparatus for at least 10 minutes before each measurement. The PWL is measured at the appropriated time after compound administration. Statistical analysis is performed by unpaired t-test or ANOVA with Dunnett's post-hoc test compared to the vehicle group.

All tested compounds of the invention show potent activities in this model.

CFA-Induced Weight Bearing Deficit in Rats

Male Sprague-Dawley rats at 7 weeks old are purchased from Charles River Japan Inc., and housed in groups of two per cage under a 12-h light/dark cycle (lights on at 07:00) with access to food and water ad libitum. CFA-induced weight bearing (WB) deficit is assessed using Incapacitance tester (Linton Instrumentation). The animals are habituated to a plastic case that comes with Incapacitance tester before the day of CFA injection. On the day of CFA injection, the weight distribution of each hind paw is measured 3 times per rat using the tester, and the difference of weight distribution, weight on the right (injected) paw minus weight on left (non-injected) paw, is defined as WB deficit value in g. The duration of the each measurement is adjusted to 3 seconds. CFA is prepared at a concentration of 2-3 mg/mL of *Mycobacterium* tuberculosis H37 RA in liquid paraffin. After disinfections with 70% ethanol, the rats are injected intraplantarly with 100 microL of CFA (200-300 microgram) into the right hind paw. Two days after CFA injection, the weight distribution of each hind paw is measured and the WB deficit value is calculated in the same manner as mentioned above. The animals showing decrease of the WB deficit (>30%) by CFA injection are selected for evaluation and randomized to be nearly equal across all groups. The compounds of the invention or their vehicles are administered systemically. The weight distribution of each hind paw is measured at the appropriated time after compound administration, and the WB deficit value is calculated as previously explained. Statistical analysis is performed by unpaired t-test or ANOVA with Dunnett's post-hoc test compared to the vehicle group.

All tested compounds of the invention show potent activities in this model.

Paw Incision-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. Paw incision-induced static allodynia is assessed by VFH test. Surgery is performed according to the procedure described by Brennan et al. (Pain 1996, 64: 493-501). The animals are initially anesthetized with 3-4% isoflurane/$O_2$ mixture in an anesthetic chamber and maintained with 2-3% delivered through a nose cone. The plantar surface of the right hind paw is sterilized with 7.5% povidone-iodine solution. A 1-cm longitudinal incision is made with a number 11 blade, through skin and fascia of the plantar aspect of the paw, starting 0.5 cm from the proximal edge of the heel and extending toward the toes. The plantaris muscle is elevated using forceps and retracted. The muscle origin and insertion remain intact. After hemostasis with gentle pressure, the skin is apposed with 2 sutures of 5-0 nylon. The wound site is covered with Terramycin ointment, and the rats are allowed to recover in their cages with soft bedding. The animals are individually placed in a Plexiglas test chamber on an elevated grid to acclimate for 1 hour before the day of surgery. On POD1, evaluation is performed using a series of calibrated VFH (0.008, 0.02, 0.04, 0.07, 0.16, 0.4, 0.6, 1, 1.4, 2, 4, 6, 8, 10, 15 and 26 g). Starting with the 0.16 g force in an ascending or descending fashion, each VFH is presented to the proximal end of the wound near the lateral heel with steady upward pressure until bent for approximately 6 seconds. In the absence of a paw withdrawal (negative response), a stronger stimulus is presented. In the event of a paw withdrawal (positive response), the next weaker stimulus is chosen. The lowest amount of force required to elicit two positive responses is defined as PWT in g. In the cases where continuous positive or negative responses are observed all the way out to the end of the stimulus spectrum, values of 0.008 and 26 g are assigned, respectively. The animals showing <1.4 g of PWT by incisional surgery are selected for evaluation and randomized to be nearly equal median PWT across all groups. The compounds of the invention or their vehicles are administered systemically. The rats are habituated to the chamber for at least 20 minutes before the measurement. The PWT is measured at the appropriated time after compound administration. Statistical analysis is performed by Mann-Whitney U-test or Kruskcal-Wallis with Dunn's post-hoc test compared to the vehicle group.

All tested compounds of the invention show potent activities in this model.

Paclitaxel-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. Paclitaxel-induced static allodynia is assessed by VFH test. Treatment of paclitaxel is performed according to the method of Polomano R C et al. (Pain 2001, 94: 293-304). Paclitaxel (2 mg) is injected intraperitoneally on four alternate days (Days 1, 3, 5 and 7) in a volume of 1 mL/kg. Cumulative dose is 8 mg/kg. In sham group, the vehicle (a mixture of 16.7% Cremophor EL and 16.7% ethanol in saline) is treated as the same schedule. The animals are individually placed in a Plexiglas test chamber on an elevated grid to acclimate before the day of testing. On Days 15-29, evaluation is performed using a series of calibrated VFH with 0.4, 0.6, 1, 2, 4, 6, 8 and 15 g force. VFH starting with the 2 g force is applied in an ascending or descending fashion according to a modified Dixon up-down method described by Chaplan S R et al. (J Neurosci Methods 1994, 53: 55-63). Each VFH is presented to the plantar surface of the operated hind paw with steady upward pressure until bent for approximately 6 seconds. In the absence of a paw withdrawal, a stronger stimulus is presented. In the event of a paw withdrawal, the next weaker stimulus is chosen. After the initial change from positive to negative or vice versa 4 more stimulations are applied. The 6-score pattern of positive and negative responses is converted into a 50% PWT using the following formula:

$$50\% \ PWT(g) = (10^{[Xf+\kappa\delta]})/10{,}000 \qquad [\text{Math.5}]$$

where Xf is the value (in log units) of the final VFH used, κ is the tabular value for the pattern of positive/negative responses and δ is the mean difference between stimuli in log units (here, 0.224).

In the cases where continuous positive or negative responses are observed all the way out to the end of the stimulus spectrum, values of 0.25 and 15 g are assigned, respectively. The animals showing static allodynia (<4 g of 50% PWT) by paclitaxel treatment are selected for evaluation and randomized to be nearly equal mean 50% PWT across all groups. The compounds of the invention or their vehicles are administered systemically. The rats are habituated to the chamber for at least 20 minutes before the measurement. The 50% PWT is measured at the appropriated time after compound administration. Statistical analysis is performed by unpaired t-test or ANOVA with Dunnett's post-hoc test compared to the vehicle group.

All tested compounds of the invention show potent activities in this model.

Formalin-Induced Nociceptive Behaviors in Rats

Male Sprague-Dawley rats at 6 weeks old are purchased from Charles River Japan Inc., and housed in groups of two per cage under a 12-h light/dark cycle (lights on at 07:00) with access to food and water ad libitum. Formalin test is performed during the light cycle. The animals are acclimated to the testing chamber for at least 30 minutes prior to formalin injection. A mirror is placed behind and/or under the chamber to aid observation. The 50 microL of 5% formalin solution is injected subcutaneously into the plantar surface of the right hind paw. Immediately after the injection, the rats are individually placed in the chamber, and the pain-related behaviors are recorded. After the testing, the time spent licking and/or biting of the injected paw are counted in 5-minutes bins for 45 minutes following the formalin treatment. The sum of time spent licking/biting in seconds from time 0 to 5 minutes is considered as the early phase, whereas the late phase is taken as the sum of time spent licking/biting typically from 15 to 45 minutes. The compounds of the invention or their vehicles are administered systemically at the appropriated time point before the formalin injection. Statistical analysis is performed by unpaired t-test or ANOVA with Dunnett's post-hoc test compared to the vehicle group.

All tested compounds of the invention show potent activities in this model.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centri-fuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM $MgCl_2$ (pH 7.4 at 4° C.), homogenized, ali-quoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher $IC_{50}$ values in human dofetilide binding than $IC_{50}$ values in $Na_{v1.3}$ or $Na_{v1.7}$ FRET Assay. The high $IC_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM $MgCl_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at -10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations: Half-life=ln 2/k The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam(ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM MgCl$_2$ and probes as substrate for 5 min. Reaction is started by adding a 20 microL of 10 mM NADPH (20 microL of NADPH generating system, which consist of 10 mM NADP$^+$, 50 mM DL-lsocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment. HTD96a(registeredtrademark), regenerated cellulose membranes (molecular weight cut-off 12,000-14,000, 22 mm×120 mm) are soaked for over night in distilled water, then for 15 minutes in 30% ethanol, and finally for 20 minutes in dialysis buffer (Dulbecco's phosphate buffered saline, pH7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing internal standard compounds for analysis. The concentration of the compound is determined with LC/MS/MS analysis.

The fraction of the compound unbound is calculated by the following equation (A) or (B):

$$fu = 1 - \{([plasma]_{eq} - [buffer]_{eq})/([plasma]_{eq})\} \quad (A)$$

wherein [plasma]$_{eq}$ and [buffer]$_{eq}$ are the concentrations of the compound in plasma and buffer, respectively.

[Math. 6]

$$fu(\%) = \frac{Cb/Cis, b \times 4}{Cp/Cis, p \times 4/3} \times 100 \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The pyrazolopyridine derivatives of the present invention are useful in the treatment of a wide range of disorders, particularly pain, such as acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back pain, orofacial pain and chemo-induced pain.

The invention claimed is:
1. A compound of the following formula (I):

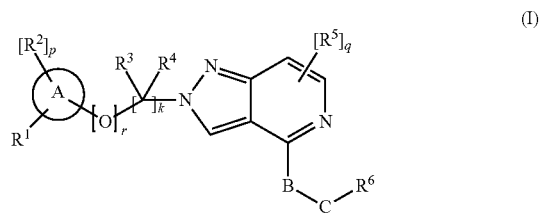

wherein:
A is a 5 to 6-membered aromatic ring which may contain 0 to 3 heteroatoms independently selected from the group consisting of O, N and S, or a 9 to 10-membered bicyclic aromatic ring which may contain 0 to 2 heteroatoms independently selected from the group consisting of O, N and S;

—B—C— is —NH—(C=O)— or —(C=O)—NH—;

R$^1$ is independently selected from the group consisting of:
(1) hydrogen, (2) —O$_n$—C$_{1-6}$ alkyl where the alkyl is unsubstituted or substituted with one or more substituents independently selected from R$^{11}$, (3) —O$_n$—C$_{3-7}$ cycloalkyl where the cycloalkyl is unsubstituted or substituted with one or more substituents independently selected from R$^{11}$, (4) —O-$_n$-phenyl, —O-$_n$-pyridyl or —O-$_a$-pyrazolyl, wherein the phenyl, the pyridyl or the pyrazolyl is unsubstittned or substituted with one or more substituents independently selected from R$^{11}$, and (5) —NH—C$_{1-6}$ alkyl, where the alkyl is unsubstituted or substituted with one or more substituents independently selected from R$^{11}$;

wherein n is independently 0 or 1, when n is 0, a chemical bond is present in the place of —O$_n$—;

R$^2$ is independently selected from the group consisting of:
(1) hydrogen, (2) halogen, (3) hydroxyl, (4) —O$_n$—C$_{1-6}$ alkyl, where the alkyl is unsubstituted or substituted with one or more substituents independently selected from R⁷, (5) —Oₙ—C₃₋₆ cycloalkyl, where the cycloalkyl is unsubstituted or substituted with one or more substituents independently selected from R⁷, and (6) —Oₙ-phenyl, where the phenyl is unsubstituted or substituted with ore or more substituents independently selected from R⁷;

wherein n is independently 0 or 1, when n is 0, a chemical bond is present in the place of —Oₙ—;

p is 1, 2, 3, or 4; when p is two or more than two, R² may be same or different;

R³ and R⁴ are independently hydrogen or C₁₋₆ alkyl;

R⁵ is independently selected from die group consisting of:
(1) hydrogen, (2) halogen, and (3) —Oₙ—C₁₋₆ alkyl, where the alkyl is unsubstituted or substituted with one or more substituents independently selected from R⁷;

wherein n is independently 0 or 1, when n is 0, a chemical bond is present in the place of —Oₙ—;

R⁵ may be anywhere on the pyrazolopyridine ring;

q is 1, 2 or 3; when q is two or more than two, R⁵ may be the same or different;

R⁶ is independently hydrogen, C₁₋₆ alkyl, C₁₋₆ alkoxy, C₃₋₇ cycloalkyl, —NR⁸R⁹, heterocyclyl, aryl, aryl-C₁₋₆ alkyl, or heterocyclyl-C₁₋₆ alkyl, wherein the C₁₋₆ alkyl, the C₁₋₆ alkoxy, the C₃₋₇ cycloalkyl, the heterocyclyl, the aryl, the aryl-C₁₋₆ alkyl, or the heterocyclyl-C₁₋₆ alkyl, is unsubstituted or substituted with one or more substituents independently selected from the group consisting of halogen, hydroxyl, C₁₋₆ alkyl, —O—C₁₋₆ alkyl, —C₃₋₇ cycloalkyl, hydroxyl-C₁₋₆ alkoxy, —CN, —NR⁸R⁹, —(C=O)—R⁸, —(C=O)—NR⁸R⁹, —NR⁸—(C=O)—R⁹, —NR⁸—(C=O)—OR⁹, —NR⁸—S(O)₂—R⁹, and —S(O)₂—R⁸;

R⁷ is selected from the group consisting of:
(1) hydrogen, (2) halogen, (3) hydroxyl, and (8) —(C=O)ₘ—Oₗ-phenyl wherein the phenyl is unsubstituted or substituted with one or more substituents independently selected from R¹¹;

wherein l is 0 or 1 and m is 0 or 1; when l is 0 or m is 0, a chemical bond is present in the place of —Oₗ— or —(C=O)ₘ—, and when l is 0 and m is 0, a chemical bond is present in the place of —(C=O)ₘ—Oₗ—;

R⁸ and R⁹ are independently hydrogen, C₁₋₆ alkyl, C₃₋₇ cycloalkyl, or aryl, wherein the C₁₋₆ alkyl, the C₃₋₇ cycloalkyl, or the aryl is unsubstituted or substituted with one or more substituents independently selected from the group consisting of halogen and hydroxyl; or R⁸ forms a 4 to 7 membered ring with R⁹ which may contain a nitrogen atom, an oxygen atom, a sulfur atom or a double bond, wherein the 4 to 7 membered ring is optionally substituted with 1 to 6 substituents independently selected from the group consisting of:(1) hydrogen, (2) hydroxyl, and (3) halogen;

R¹¹ is independently selected from the group consisting of:
(1) hydrogen, (2) hydroxyl, (3) halogen, (4) C₁₋₆ alkyl, wherein the alkyl is unsubstituted or substituted with one or more halogens, (5) C₃₋₆ cycloalkyl, and (6) —O—C₁₋₆ alkyl, where the alkyl is unsubstituted or substituted with one or more, halogens;

k is 1 or 2; and r is 0 or 1, when r is 0, a chemical bond is present in the place of —[O]ᵣ—;

wherein, in the R⁶, R⁸ and R⁹, the aryl is independently a 5 to 6-membered aromatic ring which may contain 0 to 3 heteroatoms independently selected from the group consisting of O, N and S; and wherein the heterocyclyl is a saturated 4 to 10-membered ring which may contain 1 to 2 heteroatoms independently selected from the group consisting of O, N and S;

or a pharmaceutically acceptable salt thereof.

2. The compound described in claim 1 wherein
k is 1;
r is 0;
or a pharmaceutically acceptable salt thereof.

3. A compound of the following formula (II)

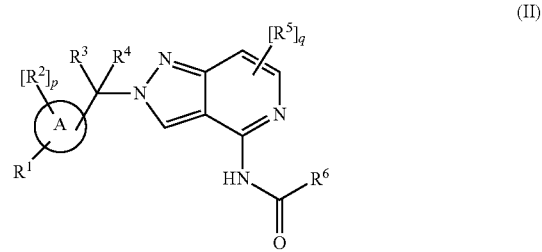

(II)

wherein:

A is a 5 to 6-membered aromatic ring which may contain 0 to 3 heteroatoms independently selected from the group consisting of O, N and S, or a 9 to 10-membered bicyclic aromatic ring which may contain 0 to 2 heteroatoms independently selected from the group consisting of O, N and S;

R¹ is independently selected from the group consisting of:
(1) hydrogen (2) —Oₙ—C₁₋₆ alkyl where the alkyl is unsubstituted or substituted with one or more substituents independently selected from R¹¹, (3) —Oₙ—C₃₋₇ cycloalkyl where the cycloalkyl is unsubstituted or substituted with one or more substituents independently selected from R¹¹, (4) —O-ₙ-phenyl, —O-ₙ-pyridyl or —O-ₙ-pyrazolyl, wherein the phenyl, the pyridyl or the pyrazolyl is unsubstituted or substituted with one or more substituents independently selected from R¹¹;

wherein n is independently 0 or 1, when n is 0, a chemical bond is present in the place of —Oₙ—;

R² is independently selected from the group consisting of:
(1) hydrogen, (2) halogen, (3) hydroxyl, (4) —Oₙ—C₁₋₆ alkyl, where the alkyl is unsubstituted or substituted with one or more substituents independently selected from R⁷, (5 ) —Oₙ—C₃₋₆ cycloalkyl, where the cycloalkyl is unsubstituted or substituted with one or more substituents independently selected from R⁷, and (6) —Oₙ-phenyl, where the phenyl is unsubstituted or substituted with one or more substituents independently selected from R⁷;

wherein n is independently 0 or 1, when n is 0, a chemical bond is present in the place of —Oₙ—;

p is 1, 2, 3, or 4; when p is two or more than two, R² may be the same or different;

R³ and R⁴ are independently hydrogen or C₁₋₆ alkyl;

R⁵ is independently selected from the group consisting of:
(1) hydrogen, (2) halogen, and (3) —Oₙ—C₁₋₆ alkyl, where the alkyl is unsubstituted or substituted with one or more substituents independently selected from R⁷;

wherein n is independently 0 or 1, when n is 0, a chemical bond is present in the place of —Oₙ—;

R⁵ may be anywhere on the pyrazolopyridine ring;

q is 1, 2 or 3; when q is two or more than two, R⁵ may be the same or different;

R⁶ is independently hydrogen, $C_{1-6}$ alkyl, $C_{1-6}$ alkoxy, $C_{3-7}$ cycloalkyl, 13 NR⁸R⁹, heterocyclyl, aryl, aryl-$C_{1-6}$ alkyl, or heterocyclyl-$C_{1-6}$ alkyl, wherein the $C_{1-6}$ alkyl, the $C_{1-6}$ alkoxy, the $C_{3-7}$ cycloalkyl, the heterocyclyl, the aryl, the aryl-$C_{1-6}$ alkyl, or the heterocyclyl-$C_{1-6}$ alkyl, is unsubstituted or substituted with one or more substituents independently selected from the group consisting of halogen, hydroxyl, $C_{1-6}$ alkyl, —O—$C_{1-6}$ alkyl, —$C_{3-7}$ cycloalkyl, —CN, —(C=O)—R⁸, —(C=O)—NR⁸R⁹, —NR⁸—(C=O)—R⁹, and —S(O)₂—R⁸;

R⁷ is selected from theroup consisting of:
(1) hydrogen, (2) halogen, (3) hydroxyl, and (8) —(C=O)$_m$—O$_l$-phenyl wherein the phenyl is unsubstituted or substituted with one or more substituents independently selected from R¹¹;
wherein l is 0 or 1 and m is 0 or 1; when l is 0 or m is 0, a chemical bond is present in the place of —O$_l$— or —(C=O)$_m$— and when l is 0 and m is 0, a chemical bond is present in the place of —(C=O)$_m$—O$_l$;

R⁸ and R⁹ are independently hydrogen, $C_{1-6}$ alkyl, Chd 3-7 cycloalkyl, or aryl, wherein the $C_{1-6}$ alkyl, the $C_{3-7}$ cycloalkyl, or the aryl is unsubstituted or substituted with one or more substituents independently selected from the group consisting of halogen and hydroxyl; or R⁸ forms a 4 to 7 membered ring with R⁹ which may contain a nitrogen atom, an oxygen atom, a sulfur atom or a double bond, wherein the 4 to 7 membered ring is optionally substituted with 1 to 6 substituents independently selected from the group consisting of: (1) hydrogen, (2) hydroxyl, and (3) halogen;

R¹¹ is independently selected from the group consisting of:
(1) hydrogen, (2) hydroxyl, (3) halogen, (4) —$C_{1-6}$, alkyl, where the alkyl is unsubstituted or substituted with one or more halogens (5) cycloalkyl, (6) —O—$C_{1-6}$ alkyl, where the alkyl is unsubstituted or substituted with one or more halogens;

wherein, in the R⁶, R⁸ and R⁹, the aryl is independently a 5 to 6-membered aromatic ring which may contain 0 to 3 heteroatoms independently selected from the group consisting of O, N and S; and
wherein the heterocyclyl is a saturated 4 to 10-membered ring which may contain 1 to 2 heteroatoms independently selected from the group consisting of O, N and S;
or a pharmaceutically acceptable salt thereof.

4. The compound according to claim 3, wherein:
R² is independently selected from the group consisting of:
(1) hydrogen, (2) halogen, (3) methyl, and (4) methoxy;
p is 1;
R³ is hydrogen;
R⁴ is hydrogen or methyl; and
R⁶ is selected from the group consisting of methyl, ethyl, isopropyl, cyclopropyl, heterocyclyl, aryl, and aryl-$C_{1-6}$ alkyl, wherein the methyl, the ethyl, the isopropyl, the cyclopropyl, the heterocyclyl, the aryl, or the aryl-$C_{1-6}$ alkyl is unsubstituted or substituted with one or more substituents independently selected from the group consisting of halogen, hydroxyl, $C_{1-6}$ alkyl, —O—$C_{1-6}$ alkyl, and —CN;
wherein the aryl is independently selected from the group consisting of pyridyl, oxazolyl, isoxazolyl and thiazolyl; and wherein the heterocyclyl is selected from the group consisting of piperidinyl, pyrrolidinyl, tetrahydrofuranyl and tetrahydropyranyl;
or a pharmaceutically acceptable salt thereof.

5. A compound of the following formula (III)

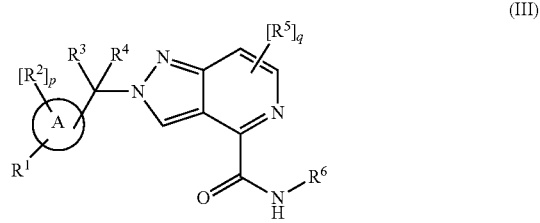

(III)

wherein:
A is a 5 to 6-membered aromatic ring which may contain 0 to 3 heteroatoms independently selected from the group consisting of O, N and S, or a 9 to 10-membered bicyclic aromatic ring which may contain 0 to 2 heteroatoms independently selected from the group consisting of O, N and S;
R¹ is independently selected from the group consisting of:
(1) hydrogen, (2) —O$_n$—$C_{1-6}$ alkyl where the alkyl is unsubstituted or substituted with one or more substituents independently selected from R¹¹, (3) —O$_n$—$C_{3-7}$ cycloalkyl where the cycloalkyl is unsubstituted or substituted with one or more substituents independently selected from R¹¹, (4) —O-$_n$-phenyl, —O-$_n$-pyridyl or —O-$_n$-pyrazolyl, wherein the phenyl, the pyridyl or the pyrazolyl is unsubstituted or substituted with one or more substituents independently selected from R¹¹, and (5) —NH—$C_{1-6}$ alkyl, where the alkyl is unsubstituted or substituted with one or more substituents independently selected from R¹¹;
wherein n is independently 0 or 1, when n is 0, a chemical bond is present in the place of —O$_n$—;
R² is independently selected from the group consisting of:
(1) hydrogen, (2) halogen, (3) hydroxyl, (4) —O$_n$—$C_{1-6}$ alkyl, where the alkyl is unsubstituted or substituted with one or more substituents independently selected from R⁷, (5) —O$_n$—$C_{3-6}$ cycloalkyl, where the cycloalkyl is unsubstituted or substituted with one or more substituents independently selected from R⁷, and (6) —O$_n$-phenyl, where the phenyl is unsubstituted or substituted with one or more substituents independently selected from R⁷;
wherein n is independently 0 or 1, when n is 0, a chemical bond is present in the place of —O$_n$—;
p is 1, 2, 3, or 4; when p is two or more than two, R² may be the same or different;
R³ and R⁴ are independently hydrogen or $C_{1-6}$ alkyl;
R⁵ is independently selected from the group consisting of:
(1) hydrogen, (2) halogen, and (3) —O$_n$—$C_{1-6}$ alkyl, where the alkyl is unsubstituted or substituted with one or more substituents independently selected from R⁷;
wherein n is independently 0 or 1, when n is 0, a chemical bond is present in the place of —O$_n$—;
R⁵ may be anywhere on the pyrazolopyridine ring;
q is 1, 2 or 3; when q is two or more than two, R⁵ may be the same or different;
R⁶ is independently hydrogen, $C_{1-6}$ alkyl, $C_{3-7}$ cycloalkyl, heterocyclyl, aryl, aryl-$C_{1-6}$ alkyl, or heterocyclyl-$C_{1-6}$ alkyl, wherein the $C_{1-6}$ alkyl, the $C_{3-7}$ cycloalkyl, the heterocyclyl, the aryl, the aryl-$C_{1-6}$ alkyl, or the heterocyclyl-$C_{1-6}$ alkyl, is unsubstituted or substituted with one or more substituents independently selected from the group consisting of halogen, hydroxyl, $C_{1-6}$ alkyl, —O—$C_{1-6}$ alkyl, —$C_{3-7}$ cycloalkyl, —O—$C_{3-7}$ cycloalkyl, hydroxyl-$C_{1-6}$ alkoxy, —CN, —$NR^8R^9$, —(C=O)—$R^8$, —(C=O)—$NR^8R^9$, —$NR^8$—(C=O)—$R^9$, —$NR^8$—(C=O)—$OR^9$, —$NR^8$—$S(O)_2$—$R^9$; and —$S(O)_2$—$R^8$;

$R^7$ is selected from the group consisting of:
(1) hydrogen, (2) halogen, (3) hydroxyl, and (8) —(C=O)$_m$—$O_l$-phenyl where the phenyl is unsubstituted or substituted with one or more substituents independently selected from $R^{11}$;
wherein l is 0 or 1 and m is 0 or 1; when l is 0 or m is 0, a chemical bond is present in the place of —$O_l$— or —(C=O)$_m$—, and when l is 0 and m is 0, a chemical bond is present in the place of —(C=O)$_m$—$O_l$—;
$R^8$ and $R^9$ are independently hydrogen, $C_{1-6}$ alkyl, $C_{3-7}$ cycloalkyl, or aryl, wherein the $C_{1-6}$ alkyl, the $C_{3-7}$ cycloalkyl, or the aryl is unsubstituted or substituted with one or more substituents independently selected from the group consisting of halogen and hydroxyl; or $R^8$ forms a 4 to 7 membered ring with $R^9$ which may contain a nitrogen atom, an oxygen atom, a sulfur atom or a double bond, wherein the 4 to 7 membered ring is optionally substituted with 1 to 6 substituents independently selected from the group consisting of:
(1) hydrogen, (2) hydroxyl, and (3) halogen;
$R^{11}$ is independently selected from the group consisting of:
(1) hydrogen, (2) hydroxyl, (3) halogen, (4) —$C_{1-6}$ alkyl, where the alkyl is unsubstituted or substituted with one or more halogens, (5) —$C_{3-6}$ cycloalkyl, and (6) —O—$C_{1-6}$ alkyl, where the alkyl is unsubstituted or substituted with one or more, halogens;
wherein, in the $R^6$, $R^8$ and $R^9$, the aryl is independently a 5 to 6-membered aromatic ring which may contain 0 to 3 heteroatoms independently selected from the group consisting of O, N and S; and
wherein the heterocyclyl is a saturated 4 to 10-membered ring which may contain 1 to 2 heteroatoms selected from the group consisting of O, N and S;
or a pharmaceutically acceptable salt thereof.

6. The compound described in claim 5 wherein:
$R^2$ is independently selected from the group consisting of:
(1) hydrogen, (2) halogen, (3) methyl, and (4) methoxy;
p is 1;
$R^3$ is hydrogen;
$R^4$ is hydrogen or methyl;
$R^6$ is selected from the group consisting of methyl, ethyl, isopropyl, propyl, and butyl wherein the methyl, the ethyl, the isopropyl, the propyl, or the butyl is unsubstituted or substituted with one or more substituents independently selected from the group consisting of hydroxyl, $C_{1-6}$ alkyl, $C_{3-7}$ cycloalkyl, —O—$C_{1-6}$ alkyl, —CN, and —$NR^8$—(C=O)—$R^9$ in which each of $R^8$ and $R^9$ is as defined in claim 5;
or a pharmaceutically acceptable salt thereof.

7. A compound which is selected from the group consisting of:
N-(2-((5-methyl-6-(2,2,2-trifluoroethoxy)pyridin-3-yl)methyl)-2H-pyrazolo[4,3-c]pyridin-4-yl)isobutyramide;
2-hydroxy-2-methyl-N-(2-((5-methyl-6-(2,2,2-trifluoroethoxy)pyridin-3-yl)methyl)-2H-pyrazolo[4,3-c]pyridin-4-yl)propanamide;
N-(2-((5-methyl-6-(2,2,2-trifluoroethoxy)pyridin-3-yl)methyl)-2H-pyrazolo[4,3-c]pyridin-4-yl)acetamide;
N-(2-((6-(2,2-difluoroethoxy)-5-methylpyridin-3-yl)methyl)-2H-pyrazolo[4,3-c]pyridin-4-yl)isobutyramide;
N-(2-((6-(2,2-difluoroethoxy)-5-methylpyridin-3-yl)methyl)-2H-pyrazolo[4,3-c]pyridin-4-yl)acetamide;
N-(2-((6-(2,2-difluoroethoxy)-5-methylpyridin-3-yl)methyl)-2H-pyrazolo[4,3-c]pyridin-4-yl)propionamide;
N-(2-((6-(2,2-difluoroethoxy)-5-methylpyridin-3-yl)methyl)-2H-pyrazolo[4,3-c]pyridin-4-yl)cyclopropanecarboxamide;
N-(2-((6-(2,2-difluoroethoxy)-5-methylpyridin-3-yl)methyl)-2H-pyrazolo[4,3-c]pyridin-4-yl)-2-hydroxy-2-methylpropanamide;
N-(2-(1-(5-methyl-6-(2,2,2-trifluoroethoxy)pyridin-3-yl)ethyl)-2H-pyrazolo[4,3-c]pyridin-4-yl)acetamide;
N-(2-(1-(5-methyl-6-(2,2,2-trifluoroethoxy)pyridin-3-yl)ethyl)-2H-pyrazolo[4,3-c]pyridin-4-yl)propionamide;
N-(2-(1-(5-methyl-6-(2,2,2-trifluoroethoxy)pyridin-3-yl)ethyl)-2H-pyrazolo[4,3-c]pyridin-4-yl)isobutyramide;
N-(2-(1-(5-methyl-6-(2,2,2-trifluoroethoxy)pyridin-3-yl)ethyl)-2H-pyrazolo[4,3-c]pyridin-4-yl)tetrahydro-2H-pyran-4-carboxamide;
N-(2-((6-(2,2,2-trifluoroethoxy)pyridin-3-yl)methyl)-2H-pyrazolo[4,3-c]pyridin-4-yl)cyclopropanecarboxamide;
N-(2-((6-(2,2,2-trifluoroethoxy)pyridin-3-yl)methyl)-2H-pyrazolo[4,3-c]pyridin-4-yl)isobutyramide;
N-(2-((5-chloro-6-(2,2,2-trifluoroethoxy)pyridin-3-yl)methyl)-2H-pyrazolo[4,3-c]pyridin-4-yl)isobutyramide;
N-(2-((5-chloro-6-(2,2,2-trifluoroethoxy)pyridin-3-yl)methyl)-2H-pyrazolo[4,3-c]pyridin-4-yl)propionamide;
N-(2-((5-chloro-6-(2,2,2-trifluoroethoxy)pyridin-3-yl)methyl)-2H-pyrazolo[4,3-c]pyridin-4-yl)tetrahydro-2H-pyran-4-carboxamide;
N-(2-((5-chloro-6-(2,2-difluoroethoxy)pyridin-3-yl)methyl)-2H-pyrazolo[4,3-c]pyridin-4-yl)acetamide;
N-(2-((5-chloro-6-(2,2-difluoroethoxy)pyridin-3-yl)methyl)-2H-pyrazolo[4,3-c]pyridin-4-yl)propionamide;
N-(2-((5-chloro-6-(2,2-difluoroethoxy)pyridin-3-yl)methyl)-2H-pyrazolo[4,3-c]pyridin-4-yl)isobutyramide;
N-(2-((5-chloro-6-(2,2,2-trifluoroethoxy)pyridin-3-yl)methyl)-2H-pyrazolo[4,3-c]pyridin-4-yl)acetamide;
N-(2-((5-methyl-6-(2,2,2-trifluoroethoxy)pyridin-3-yl)methyl)-2H-pyrazolo[4,3-c]pyridin-4-yl)tetrahydro-2H-pyran-4-carboxamide;
N-(2-((5-methyl-6-(2,2,2-trifluoroethoxy)pyridin-3-yl)methyl)-2H-pyrazolo[4,3-c]pyridin-4-yl)oxazole-5-carboxamide;
1,1-dimethyl-3-(2-((5-methyl-6-(2,2,2-trifluoroethoxy)pyridin-3-yl)methyl)-2H-pyrazolo[4,3-c]pyridin-4-yl)urea;
2-((5-methyl-6-(2,2,2-trifluoroethoxy)pyridin-3-yl)methyl)-2H-pyrazolo[4,3-c]pyridin-4-amine;
ethyl (2-((5-methyl-6-(2,2,2-trifluoroethoxy)pyridin-3-yl)methyl)-2H-pyrazolo[4,3-c]pyridin-4-yl)carbamate;
N-(2-((6-(2,2-trifluoroethoxy)pyridin-3-yl)methyl)-2H-pyrazolo[4,3-c]pyridin-4-yl)acetamide;
N-(2-((6-(2,2,2-trifluoroethoxy)pyridin-3-yl)methyl)-2H-pyrazolo[4,3-c]pyridin-4-yl)propionamide;

2-((5-methyl-6-(2,2,2-trifluoroethoxy)pyridin-3-yl)
methyl)-2H-pyrazolo[4,3-c]pyridine-4-carboxamide;
N-methyl-2-((5-methyl-6-(2,2,2-trifluoroethoxy)pyridin-
3-yl)methyl)-2H-pyrazolo[4,3-c]pyridine-4-carboxam-
ide;
N-isopropyl-2-((5-methyl-6-(2,2,2-trifluoroethoxy)pyri-
din-3-yl)methyl)-2H-pyrazolo[4,3-c]pyridine-4-car-
boxamide;
N-(2-((5-methyl-6-(2,2,2-trifluoroethoxy)pyridin-3-yl)
methyl)-2H-pyrazolo[4,3-c]pyridin-4-yl)cyclopropan-
ecarboxamide;
N-(2-((6-(2,2-difluoroethoxy)-5-fluoropyridin-3-yl)
methyl)-2H-pyrazolo[4,3-c]pyridin-4-yl)cyclopropan-
ecarboxamide;
N-(2-((6-(2,2-difluoroethoxy)-5-fluoropyridin-3-yl)
methyl)-2H-pyrazolo[4,3-c]pyridin-4-yl)isobutyr-
amide;
N-(2-((6-(2,2,2-trifluoroethoxy)pyridazin-3-yl)methyl)-
2H-pyrazolo[4,3-c]pyridin-4-yl)isobutyramide;
N-(2-((6-(2,2,2-trifluoroethoxy)pyridazin-3-yl)methyl)-
2H-pyrazolo[4,3-c]pyridin-4-yl)cyclopropanecarbox-
amide;
N-(2-((5-(2,2,2-trifluoroethoxy)pyridin-2-yl)methyl)-2H-
pyrazolo[4,3-c]pyridin-4-yl)isobutyramide;
N-(2-((5-(2,2,2-trifluoroethoxy)pyridin-2-yl)methyl)-2H-
pyrazolo[4,3-c]pyridin-4-yl)cyclopropanecarboxam-
ide;
N-(2-((6-(3,3,3-trifluoropropoxy)pyridin-3-yl)methyl)-
2H-pyrazolo[4,3-c]pyridin-4-yl)isobutyramide;
N-(2-((6-(3,3,3-trifluoropropoxy)pyridin-3-yl)methyl)-
2H-pyrazolo[4,3-c]pyridin-4-yl)cyclopropanecarbox-
amide;
N-(2-(1-(5-methyl-6-(2,2,2-trifluoroethoxy)pyridin-3-yl)
ethyl)-2H-pyrazolo[4,3-c]pyridin-4-yl)cyclopropan-
ecarboxamide;
N-(2-((5-fluoro-6-(2,2,2-trifluoroethoxy)pyridin-3-yl)
methyl)-2H-pyrazolo[4,3-c]pyridin-4-yl)propiona-
mide;
N-(2-((5-fluoro-6-(2,2,2-trifluoroethoxy)pyridin-3-yl)
methyl)-2H-pyrazolo[4,3-c]pyridin-4-yl)cyclopropan-
ecarboxamide;
N-(2-((5-fluoro-6-(2,2,2-trifluoroethoxy)pyridin-3-yl)
methyl)-2H-pyrazolo[4,3-c]pyridin-4-yl)isobutyr-
amide;
N-(2-((5-methyl-6-(2,2,2-trifluoroethoxy)pyridin-3-yl)
methyl)-2H-pyrazolo[4,3-c]pyridin-4-yl)pivalamide;
N-(2-((5-methyl-6-(2,2,2-trifluoroethoxy)pyridin-3-yl)
methyl)-2H-pyrazolo[4,3-c]pyridin-4-yl)nicotinamide;
N-(2-((6-(2,2,3,3-tetrafluoropropoxy)pyridin-3-yl)
methyl)-2H-pyrazolo[4,3-c]pyridin-4-yl)cyclopropan-
ecarboxamide;
N-(2-((6-(2,2-difluoroethoxy)-5-methylpyridin-3-yl)
methyl)-2H-pyrazolo[4,3-c]pyridin-4-yl)tetrahydro-
2H-pyran-4-carboxamide;
3-(2-((6-(2,2-difluoroethoxy)-5-methylpyridin-3-yl)
methyl)-2H-pyrazolo[4,3-c]pyridin-4-yl)-1,1-dimethy-
lurea;
N-(2-((6-(2,2-difluoroethoxy)-5-methylpyridin-3-yl)
methyl)-2H-pyrazolo[4,3-c]pyridin-4-yl)pivalamide;
N-(2-(4-(2,2,2-trifluoroethoxy)benzyl)-2H-pyrazolo[4,3-
c]pyridin-4-yl)isobutyramide;
N-(2-(4-(2,2,2-trifluoroethoxy)benzyl)-2H-pyrazolo[4,3-
c]pyridin-4-yl)cyclopropanecarboxamide;
N-(2-((6-(2,2,3,3,3-pentafluoropropoxy)pyridin-3-yl)
methyl)-2H-pyrazolo[4,3-c]pyridin-4-yl)isobutyr-
amide;
N-(2-((6-(2,2,3,3,3-pentafluoropropoxy)pyridin-3-yl)
methyl)-2H-pyrazolo[4,3-c]pyridin-4-yl)cyclopropan-
ecarboxamide;
N-(2-(4-(trifluoromethoxy)benzyl)-2H-pyrazolo[4,3-c]
pyridin-4-yl)isobutyramide;
2-(1-(5-methyl-6-(2,2,2-trifluoroethoxy)pyridin-3-yl)
ethyl)-2H-pyrazolo[4,3-c]pyridine-4-carboxamide;
N-ethyl-2-((5-methyl-6-(2,2,2-trifluoroethoxy)pyridin-3-
yl)methyl)-2H-pyrazolo[4,3-c]pyridine-4-carboxam-
ide;
(S)-2-((5-methyl-6-(2,2,2-trifluoroethoxy)pyridin-3-yl)
methyl)-N-(tetrahydrofuran-3-yl)-2H-pyrazolo[4,3-c]
pyridine-4-carboxamide;
N-cyclopropyl-2-((5-methyl-6-(2,2,2-trifluoroethoxy)
pyridin-3-yl)methyl)-2H-pyrazolo[4,3-c]pyridine-4-
carboxamide;
N-cyclobutyl-2-((5-methyl-6-(2,2,2-trifluoroethoxy)pyri-
din-3-yl)methyl)-2H-pyrazolo[4,3-c]pyridine-4-car-
boxamide;
N-(cyclopropylmethyl)-2-((5-methyl-6-(2,2,2-trifluo-
roethoxy)pyridin-3-yl)methyl)-2H-pyrazolo[4,3-c]
pyridine-4-carboxamide;
2-((5-methyl-6-(2,2,2-trifluoroethoxy)pyridin-3-yl)
methyl)-N-((tetrahydro-2H-pyran-4-yl)methyl)-2H-
pyrazolo[4,3-c]pyridine-4-carboxamide;
N-(2-methoxyethyl)-2-((5-methyl-6-(2,2,2-trifluoroeth-
oxy)pyridin-3-yl)methyl)-2H-pyrazolo[4,3-c]pyridine-
4-carboxamide;
(R)-N-(1-hydroxypropan-2-yl)-2-((5-methyl-6-(2,2,2-tri-
fluoroethoxy)pyridin-3-yl)methyl)-2H-pyrazolo[4,3-c]
pyridine-4-carboxamide;
N-(3-methyl-2-((5-methyl-6-(2,2,2-trifluoroethoxy)pyri-
din-3-yl)methyl)-2H-pyrazolo[4,3-c]pyridin-4-yl)pro-
pionamide;
N-(3-methyl-2-((5-methyl-6-(2,2,2-trifluoroethoxy)pyri-
din-3-yl)methyl)-2H-pyrazolo[4,3-c]pyridin-4-yl)cy-
clopropanecarboxamide;
N-(2-((6-(2,2,3,3-tetrafluoropropoxy)pyridin-3-yl)
methyl)-2H-pyrazolo[4,3-c]pyridin-4-yl)isobutyr-
amide;
N-(2-(1-(6-(2,2-difluoroethoxy)-5-methylpyridin-3-yl)
ethyl)-2H-pyrazolo[4,3-c]pyridin-4-yl)cyclopropan-
ecarboxamide;
N-(2-(2-(6-(2,2,2-trifluoroethoxy)pyridin-3-yl)ethyl)-2H-
pyrazolo[4,3-c]pyridin-4-yl)cyclopropanecarboxam-
ide;
N-(2-((6-(4-fluorophenoxy)-5-methylpyridin-3-yl)
methyl)-2H-pyrazolo[4,3-c]pyridin-4-yl)isobutyr-
amide;
N-(2-((6-(4-fluorophenoxy)-5-methylpyridin-3-yl)
methyl)-2H-pyrazolo[4,3-c]pyridin-4-yl)cyclopropan-
ecarboxamide;
(S)-N-(2-((5-methyl-6-(2,2,2-trifluoroethoxy)pyridin-3-
yl)methyl)-2H-pyrazolo[4,3-c]pyridin-4-yl)tetrahydro-
furan-2-carboxamide;
(S)-N-(2-((6-(2,2-difluoroethoxy)-5-methylpyridin-3-yl)
methyl)-2H-pyrazolo[4,3-c]pyridin-4-yl)tetrahydro-
furan-2-carboxamide;
N-(2-((6-(2,2-difluoroethoxy)-5-methylpyridin-3-yl)
methyl)-2H-pyrazolo[4,3-c]pyridin-4-yl)nicotinamide;
(R)-2-hydroxy-N-(2-((5-methyl-6-(2,2,2-trifluoroethoxy)
pyridin-3-yl)methyl)-2H-pyrazolo[4,3-c]pyridin-4-yl)
propanamide;
(S)-2-hydroxy-N-(2-((5-methyl-6-(2,2,2-trifluoroethoxy)
pyridin-3-yl)methyl)-2H-pyrazolo[4,3-c]pyridin-4-yl)
propanamide;

N-(2-((5-methyl-6-(2,2,2-trifluoroethoxy)pyridin-3-yl)methyl)-2H-pyrazolo[4,3-c]pyridin-4-yl)pyrrolidine-1-carboxamide;
1-acetyl-N-(2-((5-methyl-6-(2,2,2-trifluoroethoxy)pyridin-3-yl)methyl)-2H-pyrazolo[4,3-c]pyridin-4-yl)piperidine-4-carboxamide;
N-isopropyl-2-(1-(5-methyl-6-(2,2,2-trifluoroethoxy)pyridin-3-yl)ethyl)-2H-pyrazolo[4,3-c]pyridine-4-carboxamide;
2-((5-methyl-6-(2,2,2-trifluoroethoxy)pyridin-3-yl)methyl)-N-propyl-2H-pyrazolo[4,3-c]pyridine-4-carboxamide;
N-isobutyl-2-((5-methyl-6-(2,2,2-trifluoroethoxy)pyridin-3-yl)methyl)-2H-pyrazolo[4,3-c]pyridine-4-carboxamide;
N-(2-ethoxyethyl)-2-((5-methyl-6-(2,2,2-trifluoroethoxy)pyridin-3-yl)methyl)-2H-pyrazolo[4,3-c]pyridine-4-carboxamide;
N-(cyanomethyl)-2-((5-methyl-6-(2,2,2-trifluoroethoxy)pyridin-3-yl)methyl)-2H-pyrazolo[4,3-c]pyridine-4-carboxamide;
(S)-2-((5-methyl-6-(2,2,2-trifluoroethoxy)pyridin-3-yl)methyl)-N-((tetrahydrofuran-2-yl)methyl)-2H-pyrazolo[4,3-c]pyridine-4-carboxamide;
N-(2-(dimethylamino)ethyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(pyridin-3-ylmethyl)-2H-pyrazolo[4,3-c]pyridine-4-carboxamide;
N-((5-methyl-1,2,4-oxadiazol-3-yl)methyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(pyridin-3-yl)-2H-pyrazolo[4,3-c]pyridine-4-carboxamide;
(R)-N-(2-((5-methyl-6-(2,2,2-trifluoroethoxy)pyridin-3-yl)methyl)-2H-pyrazolo[4,3-c]pyridin-4-yl)tetrahydrofuran-2-carboxamide;
(R)-N-(2-((6-(2,2-difluoroethoxy)-5-methylpyridin-3-yl)methyl)-2H-pyrazolo[4,3-c]pyridin-4-yl)tetrahydrofuran-2-carboxamide;
N-(3-methoxypropyl)-2-((5-methyl-6-(2,2,2-trifluoroethoxy)pyridin-3-yl)methyl)-2H-pyrazolo[4,3-c]pyridine-4-carboxamide;
N-((1-hydroxycyclohexyl)methyl)-2-((5-methyl-6-(2,2,2-trifluoroethoxy)pyridin-3-yl)methyl)-2H-pyrazolo[4,3-c]pyridine-4-carboxamide;
N-(6-methyl-2-((5-methyl-6-(2,2,2-trifluoroethoxy)pyridin-3-yl)methyl)-2H-pyrazolo[4,3-c]pyridin-4-yl)propionamide;
N-(6-methyl-2-((5-methyl-6-(2,2,2-trifluoroethoxy)pyridin-3-yl)methyl)-2H-pyrazolo[4,3-c]pyridin-4-yl)cyclopropanecarboxamide;
N-(6-methyl-2-((5-methyl-6-(2,2,2-trifluoroethoxy)pyridin-3-yl)methyl)-2H-pyrazolo[4,3-c]pyridin-4-yl)isobutyramide;
2-hydroxy-2-methyl-N-(6-methyl-2-((5-methyl-6-(2,2,2-trifluoroethoxy)pyridin-3-yl)methyl)-2H-pyrazolo[4,3-c]pyridin-4-yl)propanamide;
N-(7-methyl-2-((5-methyl-6-(2,2,2-trifluoroethoxy)pyridin-3-yl)methyl)-2H-pyrazolo[4,3-c]pyridin-4-yl)propionamide;
N-(7-methyl-2-((5-methyl-6-(2,2,2-trifluoroethoxy)pyridin-3-yl)methyl)-2H-pyrazolo[4,3-c]pyridin-4-yl)isobutyramide;
2-((6-(2,2-difluoroethoxy)-5-methylpyridin-3-yl)methyl)-N-ethyl-2H-pyrazolo[4,3-c]pyridine-4-carboxamide;
2-((6-(2,2-difluoroethoxy)-5-methylpyridin-3-yl)methyl)-N-methyl-2H-pyrazolo[4,3-c]pyridine-4-carboxamide;
1-isobutyryl-N-(2-((5-methyl-6-(2,2,2-trifluoroethoxy)pyridin-3-yl)methyl)-2H-pyrazolo[4,3-c]pyridin-4-yl)piperidine-4-carboxamide;
N-(2-((5-methyl-6-(2,2,2-trifluoroethoxy)pyridin-3-yl)methyl)-2H-pyrazolo[4,3-c]pyridin-4-yl)-1-(methylsulfonyl)piperidine-4-carboxamide;
(S)-1-acetyl-N-(2-((5-methyl-6-(2,2,2-trifluoroethoxy)pyridin-3-yl)methyl)-2H-pyrazolo[4,3-c]pyridin-4-yl)pyrrolidine-2-carboxamide;
(R)-1-acetyl-N-(2-((5-methyl-6-(2,2,2-trifluoroethoxy)pyridin-3-yl)methyl)-2H-pyrazolo[4,3-c]pyridin-4-yl)pyrrolidine-2-carboxamide;
N-methyl-N-(2-((2-((5-methyl-6-(2,2,2-trifluoroethoxy)pyridin-3-yl)methyl)-2H-pyrazolo[4,3-c]pyridin-4-yl)amino)-2-oxoethyl)acetamide;
(S)-2-methoxy-N-(2-((5-methyl-6-(2,2,2-trifluoroethoxy)pyridin-3-yl)methyl)-2H-pyrazolo[4,3-c]pyridin-4-yl)propanamide;
(S)-N-(2-((6-(2,2-difluoroethoxy)-5-methylpyridin-3-yl)methyl)-2H-pyrazolo[4,3-c]pyridin-4-yl)-2-methoxypropanamide;
(R)-N-(2-((6-(2,2-difluoroethoxy)-5-methylpyridin-3-yl)methyl)-2H-pyrazolo[4,3-c]pyridin-4-yl)-2-hydroxypropanamide;
(S)-N-(2-((6-(2,2-difluoroethoxy)-5-methylpyridin-3-yl)methyl)-2H-pyrazolo[4,3-c]pyridin-4-yl)-2-hydroxypropanamide;
2-((6-(2,2-difluoroethoxy)-5-methylpyridin-3-yl)methyl)-N-isopropyl-2H-pyrazolo[4,3-c]pyridine-4-carboxamide;
N-cyclopropyl-2-((6-(2,2-difluoroethoxy)-5-methylpyridin-3-yl)methyl)-2H-pyrazolo[4,3-c]pyridine-4-carboxamide;
N-(cyclopropylmethyl)-2-((6-(2,2-difluoroethoxy)-5-methylpyridin-3-yl)methyl)-2H-pyrazolo[4,3-c]pyridine-4-carboxamide;
2-((6-(2,2-difluoroethoxy)-5-methylpyridin-3-yl)methyl)-N-(2-(dimethylamino)ethyl)-2H-pyrazolo[4,3-c]pyridine-4-carboxamide;
2-((5-methyl-6-(2,2,2-trifluoroethoxy)pyridin-3-yl)methyl)-N-(2-morpholinoethyl)-2H-pyrazolo[4,3-c]pyridine-4-carboxamide;
N-(2-((5-methyl-6-(2,2,2-trifluoroethoxy)pyridin-3-yl)methyl)-2H-pyrazolo[4,3-c]pyridin-4-yl)-2-(pyridin-2-yl)acetamide;
N-(2-((5-methyl-6-(2,2,2-trifluoroethoxy)pyridin-3-yl)methyl)-2H-pyrazolo[4,3-c]pyridin-4-yl)-2-(pyridin-3-yl)acetamide;
N-isopropyl-2-((6-(2,2,2-trifluoroethoxy)pyridin-3-yl)methyl)-2H-pyrazolo[4,3-c]pyridine-4-carboxamide;
N-ethyl-2-((6-(2,2,2-trifluoroethoxy)pyridin-3-yl)methyl)-2H-pyrazolo[4,3-c]pyridine-4-carboxamide;
N-cyclopropyl-2-((6-(2,2,2-trifluoroethoxy)pyridin-3-yl)methyl)-2H-pyrazolo[4,3-c]pyridine-4-carboxamide;
N-(cyclopropylmethyl)-2-((6-(2,2,2-trifluoroethoxy)pyridin-3-yl)methyl)-2H-pyrazolo[4,3-c]pyridine-4-carboxamide;
N-(2-((5-methyl-6-(2,2,2-trifluoroethoxy)pyridin-3-yl)methyl)-2H-pyrazolo[4,3-c]pyridin-4-yl)-2-(pyridin-4-yl)acetamide;

N-(cyanomethyl)-2-((6-(2,2-difluoroethoxy)-5-methyl-pyridin-3-yl)methyl)-2H-pyrazolo[4,3-c]pyridine-4-carboxamide;

2-((6-(2,2-difluoroethoxy)-5-methylpyridin-3-yl)methyl)-N-propyl-2H-pyrazolo[4,3-c]pyridine-4-carboxamide;

N-(2-cyanopropan-2-yl)-2-((5-methyl-6-(2,2,2-trifluoroethoxy)pyridin-3-yl)methyl)-2H-pyrazolo[4,3-c]pyridine-4-carboxamide;

N-(2-hydroxy-2-methylpropyl)-2-((5-methyl-6-(2,2,2-trifluoroethoxy)pyridin-3-yl)methyl)-2H-pyrazolo[4,3-c]pyridine-4-carboxamide;

N-(3-(dimethylamino)propyl)-2-((5-methyl-6-(2,2,2-trifluoroethoxy)pyridin-3-yl)methyl)-2H-pyrazolo[4,3-c]pyridine-4-carboxamide;

N-(2-aminoethyl)-2-((5-methyl-6-(2,2,2-trifluoroethoxy)pyridin-3-yl)methyl)-2H-pyrazolo[4,3-c]pyridine-4-carboxamide;

N-(2-hydroxyethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-(oxetan-3-yl)-2H-pyrazolo[4,3-c]pyridine-4-carboxamide;

N-methyl-2-((4-methyl-6-(2,2,2-trifluoroethoxy)pyridin-3-yl)methyl)-2H-pyrazolo[4,3-c]pyridine-4-carboxamide;

N-ethyl-2-((4-methyl-6-(2,2,2-trifluoroethoxy)pyridin-3-yl)methyl)-2H-pyrazolo[4,3-c]pyridine-4-carboxamide;

N-(2-((6-(2,2-difluoroethoxy)-5-methylpyridin-3-yl)methyl)-2H-pyrazolo[4,3-c]pyridin-4-yl)-2-(pyridin-4-yl)acetamide;

2-(pyridin-4-yl)-N-(2-((6-(2,2,2-trifluoroethoxy)pyridin-3-yl)methyl)-2H-pyrazolo[4,3-c]pyridin-4-yl)acetamide;

N-(2-((6-(2,2-difluoroethoxy)-5-methylpyridin-3-yl)methyl)-2H-pyrazolo[4,3-c]pyridin-4-yl)-2-(pyridin-3-yl)acetamide;

2-((6-(2,2-difluoroethoxy)-5-methylpyridin-3-yl)methyl)-N-(2-hydroxyethyl)-2H-pyrazolo[4,3-c]pyridine-4-carboxamide;

N-(2-hydroxyethyl)-2-((5-methyl-6-(3,3,3-trifluoropropoxy)pyridin-3-yl)methyl)-2H-pyrazolo[4,3-c]pyridine-4-carboxamide;

N-(2-hydroxyethyl)-2-((4-methyl-6-(2,2,2-trifluoroethoxy)pyridin-3-yl)methyl)-2H-pyrazolo[4,3-c]pyridine-4-carboxamide;

N-(2-((5-methyl-6-(3,3,3-trifluoropropoxy)pyridin-3-yl)methyl)-2H-pyrazolo[4,3-c]pyridin-4-yl)isobutyramide;

N-(2-((5-methyl-6-(3,3,3-trifluoropropoxy)pyridin-3-yl)methyl)-2H-pyrazolo[4,3-c]pyridin-4-yl)cyclopropanecarboxamide;

2-hydroxy-2-methyl-N-(2-((5-methyl-6-(3,3,3-trifluoropropoxy)pyridin-3-yl)methyl)-2H-pyrazolo[4,3-c]pyridin-4-yl)propanamide;

N-methyl-2-((5-methyl-6-(3,3,3-trifluoropropoxy)pyridin-3-yl)methyl)-2H-pyrazolo[4,3-c]pyridine-4-carboxamide;

N-ethyl-2-((5-methyl-6-(3,3,3-trifluoropropoxy)pyridin-3-yl)methyl)-2H-pyrazolo[4,3-c]pyridine-4-carboxamide;

N-isopropyl-2-((5-methyl-6-(3,3,3-trifluoropropoxy)pyridin-3-yl)methyl)-2H-pyrazolo[4,3-c]pyridine-4-carboxamide;

N-(2-((5-methyl-6-(2,2,2-trifluoroethoxy)pyridazin-3-yl)methyl)-2H-pyrazolo[4,3-c]pyridin-4-yl)isobutyramide;

N-(2-((5-methyl-6-(2,2,2-trifluoroethoxy)pyridazin-3-yl)methyl)-2H-pyrazolo[4,3-c]pyridin-4-yl)cyclopropanecarboxamide;

N-methyl-2-((5-methyl-6-(2,2,2-trifluoroethoxy)pyridazin-3-yl)methyl)-2H-pyrazolo[4,3-c]pyridine-4-carboxamide;

N-ethyl-2-((5-methyl-6-(2,2,2-trifluoroethoxy)pyridazin-3-yl)methyl)-2H-pyrazolo[4,3-c]pyridine-4-carboxamide;

N-(2-((5-methyl-6-(2,2,2-trifluoroethoxy)pyridin-3-yl)methyl)-2H-pyrazolo[4,3-c]pyridin-4-yl)-2-(2-methylthiazol-4-yl)acetamide;

N-(2-((5-methyl-6-(3,3,3-trifluoropropoxy)pyridin-3-yl)methyl)-2H-pyrazolo[4,3-c]pyridin-4-yl)-2-(pyridin-3-yl)acetamide;

N-(2-((5-methyl-6-(3,3,3-trifluoropropoxy)pyridin-3-yl)methyl)-2H-pyrazolo[4,3-c]pyridin-4-yl)-2-(pyridin-4-yl)acetamide;

2-(3,5-dimethylisoxazol-4-yl)-N-(2-((5-methyl-6-(2,2,2-trifluoroethoxy)pyridin-3-yl)methyl)-2H-pyrazolo[4,3-c]pyridin-4-yl)acetamide;

N-isopropyl-2-((5-methyl-6-(2,2,2-trifluoroethoxy)pyridazin-3-yl)methyl)-2H-pyrazolo[4,3-c]pyridine-4-carboxamide;

(R)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;

N-(2-((4-methyl-5-(2,2,2-trifluoroethoxy)pyridin-2-yl)methyl)-2H-pyrazolo[4,3-c]pyridin-4-yl)cyclopropanecarboxamide;

2-hydroxy-2-methyl-N-(2-((4-methyl-5-(2,2,2-trifluoroethoxy)pyridin-2-yl)methyl)-2H-pyrazolo[4,3-c]pyridin-4-yl)propanamide;

N-methyl-2-((4-methyl-5-(2,2,2-trifluoroethoxy)pyridin-2-yl)methyl)-2H-pyrazolo[4,3-c]pyridine-4-carboxamide;

N-ethyl-2-((4-methyl-5-(2,2,2-trifluoroethoxy)pyridin-2-yl)methyl)-2H-pyrazolo[4,3-c]pyridine-4-carboxamide;

N-isopropyl-2-((4-methyl-5-(2,2,2-trifluoroethoxy)pyridin-2-yl)methyl)-2H-pyrazolo[4,3-c]pyridine-4-carboxamide;

N-(2-hydroxyethyl)-2-((4-methyl-5-(2,2,2-trifluoroethoxy)pyridin-2-yl)methyl)-2H-pyrazolo[4,3-c]pyridine-4-carboxamide;

(S)-N-(1-hydroxypropan-2-yl)-2-((5-methyl-6-(2,2,2-trifluoroethoxy)pyridin-3-yl)methyl)-2H-pyrazolo[4,3-c]pyridine-4-carboxamide;

N-(2-amino-2-oxoethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-(2-(methylsulfonamido)ethyl)-2H-pyrazolo[4,3-c]pyridine-4-carboxamide;

N-(2-hydroxyethyl)-2-((5-methyl-6-(2,2,2-trifluoroethoxy)pyridazin-3-yl)methyl)-2H-pyrazolo[4,3-c]pyridine-4-carboxamide;

N-(3-hydroxypropyl)-2-((5-methyl-6-(2,2,2-trifluoroethoxy)pyridin-3-yl)methyl)-2H-pyrazolo[4,3-c]pyridine-4-carboxamide;
2-((6-(2,2-difluoroethoxy)-5-methylpyridin-3-yl)methyl)-N-(3-hydroxypropyl)-2H-pyrazolo[4,3-c]pyridine-4-carboxamide;
N-(2-cyanoethyl)-2-((5-methyl-6-(2,2,2-trifluoroethoxy)pyridin-3-yl)methyl)-2H-pyrazolo[4,3-c]pyridine-4-carboxamide;
N-(2-cyanoethyl)-2-((6-(2,2-difluoroethoxy)-5-methylpyridin-3-yl)methyl)-2H-pyrazolo[4,3-c]pyridine-4-carboxamide;
N-(2-acetamidoethyl)-2-((5-methyl-6-(2,2,2-trifluoroethoxy)pyridin-3-yl)methyl)-2H-pyrazolo[4,3-c]pyridine-4-carboxamide;
N-(2-((5-methoxy-6-(2,2,2-trifluoroethoxy)pyridin-3-yl)methyl)-2H-pyrazolo[4,3-c]pyridin-4-yl)isobutyramide;
N-(2-((5-methoxy-6-(2,2,2-trifluoroethoxy)pyridin-3-yl)methyl)-2H-pyrazolo[4,3-c]pyridin-4-yl)cyclopropanecarboxamide;
2-((5-methoxy-6-(2,2,2-trifluoroethoxy)pyridin-3-yl)methyl)-N-methyl-2H-pyrazolo[4,3-c]pyridine-4-carboxamide;
N-ethyl-2-((5-methoxy-6-(2,2,2-trifluoroethoxy)pyridin-3-yl)methyl)-2H-pyrazolo[4,3-c]pyridine-4-carboxamide;
N-isopropyl-2-((5-methoxy-6-(2,2,2-trifluoroethoxy)pyridin-3-yl)methyl)-2H-pyrazolo[4,3-c]pyridine-4-carboxamide;
N-(2-hydroxyethyl)-2-((5-methoxy-6-(2,2,2-trifluoroethoxy)pyridin-3-yl)methyl)-2H-pyrazolo[4,3-c]pyridine-4-carboxamide;
N-(2-(2-hydroxyethoxy)ethyl)-2-((5-methyl-6-(2,2,2-trifluoroethoxy)pyridin-3-yl)methyl)-2H-pyrazolo[4,3-c]pyridine-4-carboxamide;
N-(2-((4-methyl-5-(2,2,2-trifluoroethoxy)pyridin-2-yl)methyl)-2H-pyrazolo[4,3-c]pyridin-4-yl)isobutyramide;
N-ethyl-2-((5-fluoro-6-(2,2,2-trifluoroethoxy)pyridin-3-yl)methyl)-2H-pyrazolo[4,3-c]pyridine-4-carboxamide;
2-((5-fluoro-6-(2,2,2-trifluoroethoxy)pyridin-3-yl)methyl)-N-isopropyl-2H-pyrazolo[4,3-c]pyridine-4-carboxamide;
2-((5-chloro-6-(2,2,2-trifluoroethoxy)pyridin-3-yl)methyl)-N-(2-hydroxyethyl)-2H-pyrazolo[4,3-c]pyridine-4-carboxamide;
2-((5-chloro-6-(2,2-difluoroethoxy)pyridin-3-yl)methyl)-N-methyl-2H-pyrazolo[4,3-c]pyridine-4-carboxamide;
2-((5-chloro-6-(2,2-difluoroethoxy)pyridin-3-yl)methyl)-N-ethyl-2H-pyrazolo[4,3-c]pyridine-4-carboxamide;
2-((5-chloro-6-(2,2-difluoroethoxy)pyridin-3-yl)methyl)-N-(2-hydroxyethyl)-2H-pyrazolo[4,3-c]pyridine-4-carboxamide;
2-((5-chloro-6-(2,2-difluoroethoxy)pyridin-3-yl)methyl)-N-isopropyl-2H-pyrazolo[4,3-c]pyridine-4-carboxamide;
(R)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;
N-(2-hydroxyethyl)-2-(4-(2,2,2-trifluoroethoxy)benzyl)-2H-pyrazolo[4,3-c]pyridine-4-carboxamide;
2-((6-(4-fluorophenoxy)-5-methylpyridin-3-yl)methyl)-N-(2-hydroxyethyl)-2H-pyrazolo[4,3-c]pyridine-4-carboxamide;
N-(2-hydroxyethyl)-2-((6-(2,2,3,3,3-pentafluoropropoxy)pyridin-3-yl)methyl)-2H-pyrazolo[4,3-c]pyridine-4-carboxamide;
N-methyl-2-((6-(3,3,3-trifluoropropoxy)pyridin-3-yl)methyl)-2H-pyrazolo[4,3-c]pyridine-4-carboxamide;
N-ethyl-2-((6-(3,3,3-trifluoropropoxy)pyridin-3-yl)methyl)-2H-pyrazolo[4,3-c]pyridine-4-carboxamide;
N-isopropyl-2-((6-(3,3,3-trifluoropropoxy)pyridin-3-yl)methyl)-2H-pyrazolo[4,3-c]pyridine-4-carboxamide;
N-(2-hydroxyethyl)-2-((6-(3,3,3-trifluoropropoxy)pyridin-3-yl)methyl)-2H-pyrazolo[4,3-c]pyridine-4-carboxamide;
(S)-N-(1-amino-1-oxopropan-2-yl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(2-(methylamino)-2-oxoethyl)-2H-pyrazolo[4,3-c]pyridine-4-carboxamide;
N-(3-amino-3-oxopropyl)-2-((5-methyl-6-(2,2,2-trifluoroethoxy)pyridin-3-yl)methyl)-2H-pyrazolo[4,3-c]pyridine-4-carboxamide;
N-(3-hydroxy-2,2-dimethylpropyl)-2-((5-methyl-6-(2,2,2-trifluoroethoxy)pyridin-3-yl)methyl)-2H-pyrazolo[4,3-c]pyridine-4-carboxamide;
N-(2-hydroxyethyl)-2-((6-(2,2,2-trifluoroethoxy)pyridin-3-yl)methyl)-2H-pyrazolo[4,3-c]pyridine-4-carboxamide;
N-(4-hydroxybutyl)-2-((5-methyl-6-(2,2,2-trifluoroethoxy)pyridin-3-yl)methyl)-2H-pyrazolo[4,3-c]pyridine-4-carboxamide;
N-(3-hydroxypropyl)-2-((6-(2,2,2-trifluoroethoxy)pyridin-3-yl)methyl)-2H-pyrazolo[4,3-c]pyridine-4-carboxamide;
N-(2-hydroxyethyl)-2-(3-methyl-4-(2,2,2-trifluoroethoxy)benzyl)-2H-pyrazolo[4,3-c]pyridine-4-carboxamide;
N-ethyl-2-((6-(2,2,3,3-tetrafluoropropoxy)pyridin-3-yl)methyl)-2H-pyrazolo[4,3-c]pyridine-4-carboxamide;
N-(2-hydroxyethyl)-2-((6-(2,2,3,3-tetrafluoropropoxy)pyridin-3-yl)methyl)-2H-pyrazolo[4,3-c]pyridine-4-carboxamide;
N-(3-acetamidopropyl)-2-((5-methyl-6-(2,2,2-trifluoroethoxy)pyridin-3-yl)methyl)-2H-pyrazolo[4,3-c]pyridine-4-carboxamide;
2-((5-methyl-6-(2,2,2-trifluoroethoxy)pyridin-3-yl)methyl)-N-(3-(methylsulfonamido)propyl)-2H-pyrazolo[4,3-c]pyridine-4-carboxamide;
N-isopropyl-2-((6-(2,2,3,3-tetrafluoropropoxy)pyridin-3-yl)methyl)-2H-pyrazolo[4,3-c]pyridine-4-carboxamide;
2-(4-(2,2-difluoroethoxy)-3-methylbenzyl)-N-(2-hydroxyethyl)-2H-pyrazolo[4,3-c]pyridine-4-carboxamide;
2-(4-(2,2-difluoroethoxy)-3-methylbenzyl)-N-(3-hydroxypropyl)-2H-pyrazolo[4,3-c]pyridine-4-carboxamide;
N-(2-hydroxyethyl)-2-((5-methyl-6-(2,2,3,3-tetrafluoropropoxy)pyridin-3-yl)methyl)-2H-pyrazolo[4,3-c]pyridine-4-carboxamide;
N-(3-hydroxypropyl)-2-((5-methyl-6-(2,2,3,3-tetrafluoropropoxy)pyridin-3-yl)methyl)-2H-pyrazolo[4,3-c]pyridine-4-carboxamide;
2-((5-chloro-6-(2,2,2-trifluoroethoxy)pyridin-3-yl)methyl)-N-(3-hydroxypropyl)-2H-pyrazolo[4,3-c]pyridine-4-carboxamide;

2-((5-chloro-6-(2,2-difluoroethoxy)pyridin-3-yl)methyl)-N-(3-hydroxypropyl)-2H-pyrazolo[4,3-c]pyridine-4-carboxamide;

N-(3-hydroxypropyl)-2-(4-(2,2,2-trifluoroethoxy)benzyl)-2H-pyrazolo[4,3-c]pyridine-4-carboxamide;

N-(2-((2-methyl-6-(2,2,2-trifluoroethoxy)pyridin-4-yl)methyl)-2H-pyrazolo[4,3-c]pyridin-4-yl)isobutyramide;

N-(2-((2-methyl-6-(2,2,2-trifluoroethoxy)pyridin-4-yl)methyl)-2H-pyrazolo[4,3-c]pyridin-4-yl)cyclopropanecarboxamide;

N-(3-hydroxypropyl)-2-(3-methyl-4-(2,2,2-trifluoroethoxy)benzyl)-2H-pyrazolo[4,3-c]pyridine-4-carboxamide;

N-(3-hydroxypropyl)-2-((5-methyl-6-(3,3,3-trifluoropropoxy)pyridin-3-yl)methyl)-2H-pyrazolo[4,3-c]pyridine-4-carboxamide;

N-(3-hydroxypropyl)-2-((5-methyl-6-(2,2,2-trifluoroethoxy)pyridazin-3-yl)methyl)-2H-pyrazolo[4,3-c]pyridine-4-carboxamide;

N-(3-hydroxypropyl)-2-((4-methyl-5-(2,2,2-trifluoroethoxy)pyridin-2-yl)methyl)-2H-pyrazolo[4,3-c]pyridine-4-carboxamide;

N-(3-hydroxypropyl)-2-((5-methoxy-6-(2,2,2-trifluoroethoxy)pyridin-3-yl)methyl)-2H-pyrazolo[4,3-c]pyridine-4-carboxamide;

2-((5-fluoro-6-(2,2,2-trifluoroethoxy)pyridin-3-yl)methyl)-N-(3-hydroxypropyl)-2H-pyrazolo[4,3-c]pyridine-4-carboxamide;

2-((6-(4-fluorophenoxy)-5-methylpyridin-3-yl)methyl)-N-(3-hydroxypropyl)-2H-pyrazolo[4,3-c]pyridine-4-carboxamide;

N-(3-hydroxypropyl)-2-((6-(2,2,3,3,3-pentafluoropropoxy)pyridin-3-yl)methyl)-2H-pyrazolo[4,3-c]pyridine-4-carboxamide;

N-(3-hydroxypropyl)-2-((6-(3,3,3-trifluoropropoxy)pyridin-3-yl)methyl)-2H-pyrazolo[4,3-c]pyridine-4-carboxamide;

N-methyl-2-((2-methyl-6-(2,2,2-trifluoroethoxy)pyridin-4-yl)methyl)-2H-pyrazolo[4,3-c]pyridine-4-carboxamide;

N-ethyl-2-((2-methyl-6-(2,2,2-trifluoroethoxy)pyridin-4-yl)methyl)-2H-pyrazolo[4,3-c]pyridine-4-carboxamide;

N-isopropyl-2-((2-methyl-6-(2,2,2-trifluoroethoxy)pyridin-4-yl)methyl)-2H-pyrazolo[4,3-c]pyridine-4-carboxamide;

N-(2-hydroxyethyl)-2-((2-methyl-6-(2,2,2-trifluoroethoxy)pyridin-4-yl)methyl)-2H-pyrazolo[4,3-c]pyridine-4-carboxamide;

N-(3-hydroxypropyl)-2-((2-methyl-6-(2,2,2-trifluoroethoxy)pyridin-4-yl)methyl)-2H-pyrazolo[4,3-c]pyridine-4-carboxamide;

N-(2-((6-methyl-5-(2,2,2-trifluoroethoxy)pyridin-2-yl)methyl)-2H-pyrazolo[4,3-c]pyridin-4-yl)isobutyramide;

N-(2-((6-methyl-5-(2,2,2-trifluoroethoxy)pyridin-2-yl)methyl)-2H-pyrazolo[4,3-c]pyridin-4-yl)cyclopropanecarboxamide;

(S)-N-(2-hydroxypropyl)-2-((5-methyl-6-(3,3,3-trifluoropropoxy)pyridin-3-yl)methyl)-2H-pyrazolo[4,3-c]pyridine-4-carboxamide;

(R)-N-(2-hydroxypropyl)-2-((5-methyl-6-(3,3,3-trifluoropropoxy)pyridin-3-yl)methyl)-2H-pyrazolo[4,3-c]pyridine-4-carboxamide;

(S)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;

(R)-N-(2,3-dihydroxypropyl)-2-((5-methyl-6-(3,3,3-trifluoropropoxy)pyridin-3-yl)methyl)-2H-pyrazolo[4,3-c]pyridine-4-carboxamide;

(S)-N-(2,3-dihydroxypropyl)-2-((4-methyl-5-(2,2,2-trifluoroethoxy)pyridin-2-yl)methyl)-2H-pyrazolo[4,3-c]pyridine-4-carboxamide;

N-isopropyl-2-((1-(5-(trifluoromethyl)pyridin-2-yl)-1H-pyrazol-3-yl)methyl)-2H-pyrazolo[4,3-c]pyridine-4-carboxamide;

N-(2-hydroxyethyl)-2-((1-(5-(trifluoromethyl)pyridin-2-yl)-1H-pyrazol-3-yl)methyl)-2H-pyrazolo[4,3-c]pyridine-4-carboxamide;

N-(3-hydroxypropyl)-2-((1-(5-(trifluoromethyl)pyridin-2-yl)-1H-pyrazol-3-yl)methyl)-2H-pyrazolo[4,3-c]pyridine-4-carboxamide;

N-methyl-2-((1-(5-(trifluoromethyl)pyridin-2-yl)-1H-pyrazol-3-yl)methyl)-2H-pyrazolo[4,3-c]pyridine-4-carboxamide;

N-ethyl-2-((1-(5-(trifluoromethyl)pyridin-2-yl)-1H-pyrazol-3-yl)methyl)-2H-pyrazolo[4,3-c]pyridine-4-carboxamide;

(S)-N-(2-hydroxypropyl)-2-((4-methyl-5-(2,2,2-trifluoroethoxy)pyridin-2-yl)methyl)-2H-pyrazolo[4,3-c]pyridine-4-carboxamide;

(R)-N-(2-hydroxypropyl)-2-((4-methyl-5-(2,2,2-trifluoroethoxy)pyridin-2-yl)methyl)-2H-pyrazolo[4,3-c]pyridine-4-carboxamide;

(S)-N-(1-hydroxypropan-2-yl)-2-((5-methyl-6-(3,3,3-trifluoropropoxy)pyridin-3-yl)methyl)-2H-pyrazolo[4,3-c]pyridine-4-carboxamide;

(S)-N-(1-hydroxypropan-2-yl)-2-((4-methyl-5-(2,2,2-trifluoroethoxy)pyridin-2-yl)methyl)-2H-pyrazolo[4,3-c]pyridine-4-carboxamide;

N-(2-cyanoethyl)-2-((4-methyl-5-(2,2,2-trifluoroethoxy)pyridin-2-yl)methyl)-2H-pyrazolo[4,3-c]pyridine-4-carboxamide;

N-(2-cyanoethyl)-2-((5-methyl-6-(3,3,3-trifluoropropoxy)pyridin-3-yl)methyl)-2H-pyrazolo[4,3-c]pyridine-4-carboxamide;

N-(2-acetamidoethyl)-2-((5-methyl-6-(3,3,3-trifluoropropoxy)pyridin-3-yl)methyl)-2H-pyrazolo[4,3-c]pyridine-4-carboxamide;

N-(2-amino-2-oxoethyl)-2-((5-methyl-6-(3,3,3-trifluoropropoxy)pyridin-3-yl)methyl)-2H-pyrazolo[4,3-c]pyridine-4-carboxamide;

N-(2-methoxyethyl)-2-((5-methyl-6-(3,3,3-trifluoropropoxy)pyridin-3-yl)methyl)-2H-pyrazolo[4,3-c]pyridine-4-carboxamide;

N-(2-((5-methyl-6-(2-(2,2,2-trifluoroethoxy)ethoxy)pyridin-3-yl)methyl)-2H-pyrazolo[4,3-c]pyridin-4-yl)isobutyramide;

N-(2-((5-methyl-6-(2-(2,2,2-trifluoroethoxy)ethoxy)pyridin-3-yl)methyl)-2H-pyrazolo[4,3-c]pyridin-4-yl)cyclopropanecarboxamide;

2-hydroxy-2-methyl-N-(2-((5-methyl-6-(2-(2,2,2-trifluoroethoxy)ethoxy)pyridin-3-yl)methyl)-2H-pyrazolo[4,3-c]pyridin-4-yl)propanamide;

N-(2-((2-methoxy-6-(2,2,2-trifluoroethoxy)pyridin-3-yl)methyl)-2H-pyrazolo[4,3-c]pyridin-4-yl)isobutyramide;

N-(2-((2-methoxy-6-(2,2,2-trifluoroethoxy)pyridin-3-yl)methyl)-2H-pyrazolo[4,3-c]pyridin-4-yl)cyclopropanecarboxamide;

N-(2-hydroxyethyl)-2-((5-methyl-6-(2-(2,2,2-trifluoroethoxy)ethoxy)pyridin-3-yl)methyl)-2H-pyrazolo[4,3-c]pyridine-4-carboxamide;

N-(3-hydroxypropyl)-2-((5-methyl-6-(2-(2,2,2-trifluoroethoxy)ethoxy)pyridin-3-yl)methyl)-2H-pyrazolo[4,3-c]pyridine-4-carboxamide;

N-methyl-2-((5-methyl-6-(2-(2,2,2-trifluoroethoxy)ethoxy)pyridin-3-yl)methyl)-2H-pyrazolo[4,3-c]pyridine-4-carboxamide;

N-ethyl-2-((5-methyl-6-(2-(2,2,2-trifluoroethoxy)ethoxy)pyridin-3-yl)methyl)-2H-pyrazolo[4,3-c]pyridine-4-carboxamide;

N-(2-hydroxyethyl)-2-((2-methoxy-6-(2,2,2-trifluoroethoxy)pyridin-3-yl)methyl)-2H-pyrazolo[4,3-c]pyridine-4-carboxamide;

N-(3-hydroxypropyl)-2-((2-methoxy-6-(2,2,2-trifluoroethoxy)pyridin-3-yl)methyl)-2H-pyrazolo[4,3-c]pyridine-4-carboxamide;

2-((2-methoxy-6-(2,2,2-trifluoroethoxy)pyridin-3-yl)methyl)-N-methyl-2H-pyrazolo[4,3-c]pyridine-4-carboxamide;

N-ethyl-2-((2-methoxy-6-(2,2,2-trifluoroethoxy)pyridin-3-yl)methyl)-2H-pyrazolo[4,3-c]pyridine-4-carboxamide;

N-isopropyl-2-((5-methyl-6-(2-(2,2,2-trifluoroethoxy)ethoxy)pyridin-3-yl)methyl)-2H-pyrazolo[4,3-c]pyridine-4-carboxamide;

N-isopropyl-2-((2-methoxy-6-(2,2,2-trifluoroethoxy)pyridin-3-yl)methyl)-2H-pyrazolo[4,3-c]pyridine-4-carboxamide;

N-methyl-2-(2-(4-(trifluoromethyl)phenoxy)ethyl)-2H-pyrazolo[4,3-c]pyridine-4-carboxamide;

N-ethyl-2-(2-(4-(trifluoromethyl)phenoxy)ethyl)-2H-pyrazolo[4,3-c]pyridine-4-carboxamide;

N-isopropyl-2-(2-(4-(trifluoromethyl)phenoxy)ethyl)-2H-pyrazolo[4,3-c]pyridine-4-carboxamide;

N-(2-hydroxyethyl)-2-(2-(4-(trifluoromethyl)phenoxy)ethyl)-2H-pyrazolo[4,3-c]pyridine-4-carboxamide;

N-(3-hydroxypropyl)-2-(2-(4-(trifluoromethyl)phenoxy)ethyl)-2H-pyrazolo[4,3-c]pyridine-4-carboxamide;

N-(2-((6-methyl-5-(2,2,2-trifluoroethoxy)pyrazin-2-yl)methyl)-2H-pyrazolo[4,3-c]pyridin-4-yl)isobutyramide;

N-(2-((6-methyl-5-(2,2,2-trifluoroethoxy)pyrazin-2-yl)methyl)-2H-pyrazolo[4,3-c]pyridin-4-yl)cyclopropanecarboxamide;

N-(2-((6-(2,2-difluoropropoxy)-5-methylpyridin-3-yl)methyl)-2H-pyrazolo[4,3-c]pyridin-4-yl)isobutyramide;

N-(2-((6-(2,2-difluoropropoxy)-5-methylpyridin-3-yl)methyl)-2H-pyrazolo[4,3-c]pyridin-4-yl)cyclopropanecarboxamide;

N-(2-((6-(2,2-difluoropropoxy)-5-methylpyridin-3-yl)methyl)-2H-pyrazolo[4,3-c]pyridin-4-yl)-2-hydroxy-2-methylpropanamide;

2-(2-((3-chloro-5-(trifluoromethyl)pyridin-2-yl)oxy)ethyl)-N-methyl-2H-pyrazolo[4,3-c]pyridine-4-carboxamide;

2-(2-((3-chloro-5-(trifluoromethyl)pyridin-2-yl)oxy)ethyl)-N-ethyl-2H-pyrazolo[4,3-c]pyridine-4-carboxamide;

2-(2-((3-chloro-5-(trifluoromethyl)pyridin-2-yl)oxy)ethyl)-N-isopropyl-2H-pyrazolo[4,3-c]pyridine-4-carboxamide;

2-(2-((3-chloro-5-(trifluoromethyl)pyridin-2-yl)oxy)ethyl)-N-(2-hydroxyethyl)-2H-pyrazolo[4,3-c]pyridine-4-carboxamide;

2-(2-((3-chloro-5-(trifluoromethyl)pyridin-2-yl)oxy)ethyl)-N-(3-hydroxypropyl)-2H-pyrazolo[4,3-c]pyridine-4-carboxamide;

2-((5-cyclopropyl-6-(2,2,2-trifluoroethoxy)pyridin-3-yl)methyl)-N-methyl-2H-pyrazolo[4,3-c]pyridine-4-carboxamide;

2-((5-cyclopropyl-6-(2,2,2-trifluoroethoxy)pyridin-3-yl)methyl)-N-ethyl-2H-pyrazolo[4,3-c]pyridine-4-carboxamide;

2-((5-cyclopropyl-6-(2,2,2-trifluoroethoxy)pyridin-3-yl)methyl)-N-isopropyl-2H-pyrazolo[4,3-c]pyridine-4-carboxamide;

2-((5-cyclopropyl-6-(2,2,2-trifluoroethoxy)pyridin-3-yl)methyl)-N-(2-hydroxyethyl)-2H-pyrazolo[4,3-c]pyridine-4-carboxamide;

2-((5-cyclopropyl-6-(2,2,2-trifluoro ethoxy)pyridin-3-yl)methyl)-N-(3-hydroxypropyl)-2H-pyrazolo[4,3-c]pyridine-4-carboxamide;

2-((6-(2,2-difluoropropoxy)-5-methylpyridin-3-yl)methyl)-N-methyl-2H-pyrazolo[4,3-c]pyridine-4-carboxamide;

2-((6-(2,2-difluoropropoxy)-5-methylpyridin-3-yl)methyl)-N-ethyl-2H-pyrazolo[4,3-c]pyridine-4-carboxamide;

2-((6-(2,2-difluoropropoxy)-5-methylpyridin-3-yl)methyl)-N-(2-hydroxyethyl)-2H-pyrazolo[4,3-c]pyridine-4-carboxamide;

2-((6-(2,2-difluoropropoxy)-5-methylpyridin-3-yl)methyl)-N-(3-hydroxypropyl)-2H-pyrazolo[4,3-c]pyridine-4-carboxamide;

N-methyl-2-((6-methyl-5-(2,2,2-trifluoroethoxy)pyrazin-2-yl)methyl)-2H-pyrazolo[4,3-c]pyridine-4-carboxamide;

N-ethyl-2-((6-methyl-5-(2,2,2-trifluoroethoxy)pyrazin-2-yl)methyl)-2H-pyrazolo[4,3-c]pyridine-4-carboxamide;

N-(3-hydroxypropyl)-2-((6-methyl-5-(2,2,2-trifluoroethoxy)pyrazin-2-yl)methyl)-2H-pyrazolo[4,3-c]pyridine-4-carboxamide;

2-((6-(2,2-difluoropropoxy)-5-methylpyridin-3-yl)methyl)-N-isopropyl-2H-pyrazolo[4,3-c]pyridine-4-carboxamide;

N-isopropyl-2-((6-methyl-5-(2,2,2-trifluoroethoxy)pyrazin-2-yl)methyl)-2H-pyrazolo[4,3-c]pyridine-4-carboxamide;

2-((6-(4-chloro-1H-pyrazol-1-yl)-5-methylpyridin-3-yl)methyl)-N-methyl-2H-pyrazolo[4,3-c]pyridine-4-carboxamide;

2-((6-(4-chloro-1H-pyrazol-1-yl)-5-methylpyridin-3-yl)methyl)-N-ethyl-2H-pyrazolo[4,3-c]pyridine-4-carboxamide;

N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide;

N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide;

N-methyl-2-(1-(5-methyl-6-(2,2,2-trifluoroethoxy)pyridin-3-yl)ethyl)-2H-pyrazolo[4,3-c]pyridine-4-carboxamide;

N-ethyl-2-(1-(5-methyl-6-(2,2,2-trifluoroethoxy)pyridin-3-yl)ethyl)-2H-pyrazolo[4,3-c]pyridine-4-carboxamide;

N-methyl-2-((5-methyl-2-phenyl-2H-1,2,3-triazol-4-yl)methyl)-2H-pyrazolo[4,3-c]pyridine-4-carboxamide;

N-(2-methoxyethyl)-2-((4-methyl-5-(2,2,2-trifluoroethoxy)pyridin-2-yl)methyl)-2H-pyrazolo[4,3-c]pyridine-4-carboxamide;
2-((6-(4-chloro-1H-pyrazol-1-yl)-5-methylpyridin-3-yl)methyl)-N-isopropyl-2H-pyrazolo[4,3-c]pyridine-4-carboxamide;
2-((6-(4-chloro-1H-pyrazol-1-yl)-5-methylpyridin-3-yl)methyl)-N-(2-hydroxyethyl)-2H-pyrazolo[4,3-c]pyridine-4-carboxamide;
2-hydroxy-2-methyl-N-(2-(1-(5-methyl-6-(2,2,2-trifluoroethoxy)pyridin-3-yl)ethyl)-2H-pyrazolo[4,3-c]pyridin-4-yl)propanamide;
N-(2-((5-methyl-2-phenyl-2H-1,2,3-triazol-4-yl)methyl)-2H-pyrazolo[4,3-c]pyridin-4-yl)cyclopropanecarboxamide;
N-(2-((6-(2,2,2-trifluoroethoxy)pyridin-2-yl)methyl)-2H-pyrazolo[4,3-c]pyridin-4-yl)isobutyramide;
N-(2-((6-(2,2,2-trifluoroethoxy)pyridin-2-yl)methyl)-2H-pyrazolo[4,3-c]pyridin-4-yl)cyclopropanecarboxamide;
N-(2-((6-(cyclopropylmethoxy)-5-methylpyridin-3-yl)methyl)-2H-pyrazolo[4,3-c]pyridin-4-yl)isobutyramide;
N-(2-((6-(cyclopropylmethoxy)-5-methylpyridin-3-yl)methyl)-2H-pyrazolo[4,3-c]pyridin-4-yl)cyclopropanecarboxamide;
N-(2-((6-(cyclopropylmethoxy)-5-methylpyridin-3-yl)methyl)-2H-pyrazolo[4,3-c]pyridin-4-yl)-2-hydroxy-2-methylpropanamide;
N,6-dimethyl-2-((5-methyl-6-(2,2,2-trifluoroethoxy)pyridin-3-yl)methyl)-2H-pyrazolo[4,3-c]pyridine-4-carboxamide;
N-ethyl-6-methyl-2-((5-methyl-6-(2,2,2-trifluoroethoxy)pyridin-3-yl)methyl)-2H-pyrazolo[4,3-c]pyridine-4-carboxamide;
N-ethyl-2-((5-methyl-6-((2,2,2-trifluoroethyl)amino)pyridin-3-yl)methyl)-2H-pyrazolo[4,3-c]pyridine-4-carboxamide;
N-isopropyl-2-((5-methyl-6-((2,2,2-trifluoroethyl)amino)pyridin-3-yl)methyl)-2H-pyrazolo[4,3-c]pyridine-4-carboxamide;
N-(2-hydroxyethyl)-2-((5-methyl-6-((2,2,2-trifluoroethyl)amino)pyridin-3-yl)methyl)-2H-pyrazolo[4,3-c]pyridine-4-carboxamide;
N-(3-hydroxypropyl)-2-((5-methyl-6-((2,2,2-trifluoroethyl)amino)pyridin-3-yl)methyl)-2H-pyrazolo[4,3-c]pyridine-4-carboxamide;
2-((6-(cyclopropylmethoxy)-5-methylpyridin-3-yl)methyl)-N-isopropyl-2H-pyrazolo[4,3-c]pyridine-4-carboxamide;
N-methyl-2-((6-(2,2,2-trifluoroethoxy)pyridin-2-yl)methyl)-2H-pyrazolo[4,3-c]pyridine-4-carboxamide;
N-ethyl-2-((6-(2,2,2-trifluoroethoxy)pyridin-2-yl)methyl)-2H-pyrazolo[4,3-c]pyridine-4-carboxamide;
N-(2-hydroxyethyl)-2-((6-(2,2,2-trifluoroethoxy)pyridin-2-yl)methyl)-2H-pyrazolo[4,3-c]pyridine-4-carboxamide;
N-(3-hydroxypropyl)-2-((6-(2,2,2-trifluoroethoxy)pyridin-2-yl)methyl)-2H-pyrazolo[4,3-c]pyridine-4-carboxamide;
2-((6-(cyclopropylmethoxy)-5-methylpyridin-3-yl)methyl)-N-methyl-2H-pyrazolo[4,3-c]pyridine-4-carboxamide;
2-((6-(cyclopropylmethoxy)-5-methylpyridin-3-yl)methyl)-N-ethyl-2H-pyrazolo[4,3-c]pyridine-4-carboxamide;
2-((6-(cyclopropylmethoxy)-5-methylpyridin-3-yl)methyl)-N-(2-hydroxyethyl)-2H-pyrazolo[4,3-c]pyridine-4-carboxamide;
2-((6-(cyclopropylmethoxy)-5-methylpyridin-3-yl)methyl)-N-(3-hydroxypropyl)-2H-pyrazolo[4,3-c]pyridine-4-carboxamide;
N-ethyl-2-(3-methyl-4-(trifluoromethoxy)benzyl)-2H-pyrazolo[4,3-c]pyridine-4-carboxamide;
N-isopropyl-2-(3-methyl-4-(trifluoromethoxy)benzyl)-2H-pyrazolo[4,3-c]pyridine-4-carboxamide;
N-(2-hydroxyethyl)-2-(3-methyl-4-(trifluoromethoxy)benzyl)-2H-pyrazolo[4,3-c]pyridine-4-carboxamide;
N-(3-hydroxypropyl)-2-(3-methyl-4-(trifluoromethoxy)benzyl)-2H-pyrazolo[4,3-c]pyridine-4-carboxamide;
N-ethyl-2-((2-(2,2,2-trifluoroethoxy)pyridin-4-yl)methyl)-2H-pyrazolo[4,3-c]pyridine-4-carboxamide;
N-(2-((5-phenyl-6-(2,2,2-trifluoroethoxy)pyridin-3-yl)methyl)-2H-pyrazolo[4,3-c]pyridin-4-yl)cyclopropanecarboxamide;
N-methyl-2-(3-methyl-4-(trifluoromethoxy)benzyl)-2H-pyrazolo[4,3-c]pyridine-4-carboxamide;
2-((6-(4-chloro-1H-pyrazol-1-yl)-5-methylpyridin-3-yl)methyl)-N-(3-hydroxypropyl)-2H-pyrazolo[4,3-c]pyridine-4-carboxamide;
N-isopropyl-2-((2-(2,2,2-trifluoroethoxy)pyridin-4-yl)methyl)-2H-pyrazolo[4,3-c]pyridine-4-carboxamide;
2-((6-(4-fluorophenoxy)-5-methylpyridin-3-yl)methyl)-N-methyl-2H-pyrazolo[4,3-c]pyridine-4-carboxamide;
N-ethyl-2-((6-(4-fluorophenoxy)-5-methylpyridin-3-yl)methyl)-2H-pyrazolo[4,3-c]pyridine-4-carboxamide;
N-(2-hydroxyethyl)-6-methyl-2-((5-methyl-6-(2,2,2-trifluoroethoxy)pyridin-3-yl)methyl)-2H-pyrazolo[4,3-c]pyridine-4-carboxamide;
N-(3-hydroxypropyl)-6-methyl-2-((5-methyl-6-(2,2,2-trifluoroethoxy)pyridin-3-yl)methyl)-2H-pyrazolo[4,3-c]pyridine-4-carboxamide;
2-((5-methyl-6-(3,3,3-trifluoropropoxy)pyridin-3-yl)methyl)-N-(3-(methylsulfonyl)propyl)-2H-pyrazolo[4,3-c]pyridine-4-carboxamide;
N-methyl-2-((1-(2,2,2-trifluoroethoxy)isoquinolin-4-yl)methyl)-2H-pyrazolo[4,3-c]pyridine-4-carboxamide;
N-ethyl-2-((1-(2,2,2-trifluoroethoxy)isoquinolin-4-yl)methyl)-2H-pyrazolo[4,3-c]pyridine-4-carboxamide;
N-isopropyl-2-((1-(2,2,2-trifluoroethoxy)isoquinolin-4-yl)methyl)-2H-pyrazolo[4,3-c]pyridine-4-carboxamide;
N-(2-hydroxyethyl)-2-((1-(2,2,2-trifluoroethoxy)isoquinolin-4-yl)methyl)-2H-pyrazolo[4,3-c]pyridine-4-carboxamide;
N-(3-hydroxypropyl)-2-((1-(2,2,2-trifluoroethoxy)isoquinolin-4-yl)methyl)-2H-pyrazolo[4,3-c]pyridine-4-carboxamide;
N-ethyl-2-(4-((2,2,2-trifluoroethoxy)methyl)benzyl)-2H-pyrazolo[4,3-c]pyridine-4-carboxamide;
N-isopropyl-2-(4-((2,2,2-trifluoroethoxy)methyl)benzyl)-2H-pyrazolo[4,3-c]pyridine-4-carboxamide;
2-((5-(2,2-difluoroethoxy)-4-methylpyridin-2-yl)methyl)-N-(2-hydroxyethyl)-2H-pyrazolo[4,3-c]pyridine-4-carboxamide;
2-((5-(2,2-difluoroethoxy)-4-methylpyridin-2-yl)methyl)-N-(3-hydroxypropyl)-2H-pyrazolo[4,3-c]pyridine-4-carboxamide;
N-methyl-2-((1-methyl-5-(trifluoromethoxy)-1H-indol-2-yl)methyl)-2H-pyrazolo[4,3-c]pyridine-4-carboxamide;

N-ethyl-2-((1-methyl-5-(trifluoromethoxy)-1H-indol-2-yl)methyl)-2H-pyrazolo[4,3-c]pyridine-4-carboxamide;

N-isopropyl-2-((1-methyl-5-(trifluoromethoxy)-1H-indol-2-yl)methyl)-2H-pyrazolo[4,3-c]pyridine-4-carboxamide;

N-(2-hydroxyethyl)-2-((1-methyl-5-(trifluoromethoxy)-1H-indol-2-yl)methyl)-2H-pyrazolo[4,3-c]pyridine-4-carboxamide;

2-(3-chloro-4-(2,2-difluoroethoxy)benzyl)-N-(2-hydroxyethyl)-2H-pyrazolo[4,3-c]pyridine-4-carboxamide;

2-(3-chloro-4-(2,2-difluoroethoxy)benzyl)-N-(3-hydroxypropyl)-2H-pyrazolo[4,3-c]pyridine-4-carboxamide;

N-(2-((5-methyl-6-((2,2,2-trifluoroethoxy)methyl)pyridin-3-yl)methyl)-2H-pyrazolo[4,3-c]pyridin-4-yl)isobutyramide;

2-((5-methyl-6-(2,2,2-trifluoroethoxy)pyridin-3-yl)methyl)-N-(3-(methylsulfonyl)propyl)-2H-pyrazolo[4,3-c]pyridine-4-carboxamide;

N-ethyl-2-((5-methyl-6-((2,2,2-trifluoroethoxy)methyl)pyridin-3-yl)methyl)-2H-pyrazolo[4,3-c]pyridine-4-carboxamide;

N-isopropyl-2-((5-methyl-6-((2,2,2-trifluoroethoxy)methyl)pyridin-3-yl)methyl)-2H-pyrazolo[4,3-c]pyridine-4-carboxamide;

N-(2-hydroxyethyl)-2-((5-methyl-6-((2,2,2-trifluoroethoxy)methyl)pyridin-3-yl)methyl)-2H-pyrazolo[4,3-c]pyridine-4-carboxamide;

N-(3-hydroxypropyl)-2-((5-methyl-6-((2,2,2-trifluoroethoxy)methyl)pyridin-3-yl)methyl)-2H-pyrazolo[4,3-c]pyridine-4-carboxamide;

N-(3-hydroxypropyl)-2-((1-methyl-5-(trifluoromethoxy)-1H-indol-2-yl)methyl)-2H-pyrazolo[4,3-c]pyridine-4-carboxamide;

N-(2-((5-methyl-6-((2,2,2-trifluoroethoxy)methyl)pyridin-3-yl)methyl)-2H-pyrazolo[4,3-c]pyridin-4-yl)cyclopropanecarboxamide;

N-(2-((5-(2,2-difluoroethoxy)-4-methylpyridin-2-yl)methyl)-2H-pyrazolo[4,3-c]pyridin-4-yl)isobutyramide;

N-(2-((5-(2,2-difluoroethoxy)-4-methylpyridin-2-yl)methyl)-2H-pyrazolo[4,3-c]pyridin-4-yl)cyclopropanecarboxamide;

N-(2-((5-(2,2-difluoroethoxy)-4-methylpyridin-2-yl)methyl)-2H-pyrazolo[4,3-c]pyridin-4-yl)-2-hydroxy-2-methylpropanamide;

N-(2-(3-(trifluoromethoxy)benzyl)-2H-pyrazolo[4,3-c]pyridin-4-yl)cyclopropanecarboxamide;

N-(2-(3-(trifluoromethoxy)benzyl)-2H-pyrazolo[4,3-c]pyridin-4-yl)isobutyramide;

2-hydroxy-2-methyl-N-(2-(3-(trifluoromethoxy)benzyl)-2H-pyrazolo[4,3-c]pyridin-4-yl)propanamide;

N-(2-(2-((3-fluoro-5-(trifluoromethyl)pyridin-2-yl)oxy)ethyl)-2H-pyrazolo[4,3-c]pyridin-4-yl)cyclopropanecarboxamide;

N-(2-(2-((3-fluoro-5-(trifluoromethyl)pyridin-2-yl)oxy)ethyl)-2H-pyrazolo[4,3-c]pyridin-4-yl)isobutyramide;

N-methyl-2-(3-(trifluoromethoxy)benzyl)-2H-pyrazolo[4,3-c]pyridine-4-carboxamide;

N-isopropyl-2-(3-(trifluoromethoxy)benzyl)-2H-pyrazolo[4,3-c]pyridine-4-carboxamide;

N-(2-hydroxyethyl)-2-(3-(trifluoromethoxy)benzyl)-2H-pyrazolo[4,3-c]pyridine-4-carboxamide;

N-(3-hydroxypropyl)-2-(3-(trifluoromethoxy)benzyl)-2H-pyrazolo[4,3-c]pyridine-4-carboxamide;

N-ethyl-2-(2-((3-fluoro-5-(trifluoromethyl)pyridin-2-yl)oxy)ethyl)-2H-pyrazolo[4,3-c]pyridine-4-carboxamide;

2-(2-((3-fluoro-5-(trifluoromethyl)pyridin-2-yl)oxy)ethyl)-N-isopropyl-2H-pyrazolo[4,3-c]pyridine-4-carboxamide;

2-(2-((3-fluoro-5-(trifluoromethyl)pyridin-2-yl)oxy)ethyl)-N-(3-hydroxypropyl)-2H-pyrazolo[4,3-c]pyridine-4-carboxamide;

N-(2-((5-(2,2,3,3,3-pentafluoropropoxy)pyridin-2-yl)methyl)-2H-pyrazolo[4,3-c]pyridin-4-yl)isobutyramide;

N-(2-((5-(2,2,3,3,3-pentafluoropropoxy)pyridin-2-yl)methyl)-2H-pyrazolo[4,3-c]pyridin-4-yl)cyclopropanecarboxamide;

N-(2-hydroxyethyl)-2-(4-(1,1,2,2-tetrafluoroethoxy)benzyl)-2H-pyrazolo[4,3-c]pyridine-4-carboxamide;

N-(3-hydroxypropyl)-2-(4-(1,1,2,2-tetrafluoroethoxy)benzyl)-2H-pyrazolo[4,3-c]pyridine-4-carboxamide;

N-ethyl-2-((5-(2,2,3,3,3-pentafluoropropoxy)pyridin-2-yl)methyl)-2H-pyrazolo[4,3-c]pyridine-4-carboxamide;

N-isopropyl-2-((5-(2,2,3,3,3-pentafluoropropoxy)pyridin-2-yl)methyl)-2H-pyrazolo[4,3-c]pyridine-4-carboxamide;

N-(3-hydroxypropyl)-2-((5-(2,2,3,3,3-pentafluoropropoxy)pyridin-2-yl)methyl)-2H-pyrazolo[4,3-c]pyridine-4-carboxamide;

2-((5-(2,2-difluoroethoxy)-4-methylpyridin-2-yl)methyl)-N-isopropyl-2H-pyrazolo[4,3-c]pyridine-4-carboxamide;

2-((5-(2,2-difluoroethoxy)-4-methylpyridin-2-yl)methyl)-N-methyl-2H-pyrazolo[4,3-c]pyridine-4-carboxamide;

2-((5-(2,2-difluoroethoxy)-4-methylpyridin-2-yl)methyl)-N-ethyl-2H-pyrazolo[4,3-c]pyridine-4-carboxamide;

N-ethyl-2-((5-(2,2,3,3-tetrafluoropropoxy)pyridin-2-yl)methyl)-2H-pyrazolo[4,3-c]pyridine-4-carboxamide;

N-(2-hydroxyethyl)-2-((5-(2,2,3,3-tetrafluoropropoxy)pyridin-2-yl)methyl)-2H-pyrazolo[4,3-c]pyridine-4-carboxamide;

N-(3-hydroxypropyl)-2-((5-(2,2,3,3-tetrafluoropropoxy)pyridin-2-yl)methyl)-2H-pyrazolo[4,3-c]pyridine-4-carboxamide;

N-(2-((5-chloro-6-(2,2,3,3-tetrafluoropropoxy)pyridin-3-yl)methyl)-2H-pyrazolo[4,3-c]pyridin-4-yl)isobutyramide;

N-(2-((5-chloro-6-(2,2,3,3-tetrafluoropropoxy)pyridin-3-yl)methyl)-2H-pyrazolo[4,3-c]pyridin-4-yl)cyclopropanecarboxamide;

N-(2-((5-chloro-6-(2,2,3,3-tetrafluoropropoxy)pyridin-3-yl)methyl)-2H-pyrazolo[4,3-c]pyridin-4-yl)-2-hydroxy-2-methylpropanamide;

N-(2-((5-(2,2,3,3-tetrafluoropropoxy)pyridin-2-yl)methyl)-2H-pyrazolo[4,3-c]pyridin-4-yl)isobutyramide;

N-(2-acetamidoethyl)-2-((5-methyl-6-(2,2,3,3-tetrafluoropropoxy)pyridin-3-yl)methyl)-2H-pyrazolo[4,3-c]pyridine-4-carboxamide;

(S)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;

(S)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;

N-(2-(3-(trifluoromethyl)benzyl)-2H-pyrazolo[4,3-c]
  pyridin-4-yl)cyclopropanecarboxamide;
N-(2-(3-(trifluoromethyl)benzyl)-2H-pyrazolo[4,3-c]
  pyridin-4-yl)isobutyramide;
N-methyl-2-(3-(trifluoromethyl)benzyl)-2H-pyrazolo[4,
  3-c]pyridine-4-carboxamide;
N-ethyl-2-(3-(trifluoromethyl)benzyl)-2H-pyrazolo[4,3-
  c]pyridine-4-carboxamide;
N-isopropyl-2-(3-(trifluoromethyl)benzyl)-2H-pyrazolo
  [4,3-c]pyridine-4-carboxamide;
N-(3-hydroxypropyl)-2-(3-(trifluoromethyl)benzyl)-2H-
  pyrazolo[4,3-c]pyridine-4-carboxamide;
(R)-N-(2-hydroxypropyl)-2-((5-methyl-6-(2,2,3,3-tetra-
  fluoropropoxy)pyridin-3-yl)methyl)-2H-pyrazolo[4,3-
  c]pyridine-4-carboxamide;
(R)-N-(2,3-dihydroxypropyl)-2-((5-methyl-6-(2,2,3,3-
  tetrafluoropropoxy)pyridin-3-yl)methyl)-2H-pyrazolo
  [4,3-c]pyridine-4-carboxamide;
2-(3-chloro-4-(2,2-difluoroethoxy)benzyl)-N-methyl-2H-
  pyrazolo[4,3-c]pyridine-4-carboxamide;
N-methyl-2-(4-(1,1,2,2-tetrafluoroethoxy)benzyl)-2H-
  pyrazolo[4,3-c]pyridine-4-carboxamide;
2-((5-chloro-6-(2,2,2-trifluoroethoxy)pyridin-3-yl)
  methyl)-N-methyl-2H-pyrazolo[4,3-c]pyridine-4-car-
  boxamide;
2-(3-chloro-4-(2,2-difluoroethoxy)benzyl)-N-ethyl-2H-
  pyrazolo[4,3-c]pyridine-4-carboxamide;
N-ethyl-2-(4-(1,1,2,2-tetrafluoroethoxy)benzyl)-2H-
  pyrazolo[4,3-c]pyridine-4-carboxamide;
2-((5-chloro-6-(2,2,2-trifluoroethoxy)pyridin-3-yl)
  methyl)-N-ethyl-2H-pyrazolo[4,3-c]pyridine-4-car-
  boxamide;
N-(2-acetamidoethyl)-2-(1-(4-methyl-5-(2,2,2-trifluo-
  roethoxy)pyridin-2-yl)ethyl)-2H-pyrazolo[4,3-c]pyri-
  dine-4-carboxamide;
N-(2-hydroxyethyl)-2-(1-(4-methyl-5-(2,2,2-trifluoroeth-
  oxy)pyridin-2-yl)ethyl)-2H-pyrazolo[4,3-c]pyridine-4-
  carboxamide;
N-(3-hydroxypropyl)-2-(1-(4-methyl-5-(2,2,2-trifluo-
  roethoxy)pyridin-2-yl)ethyl)-2H-pyrazolo[4,3-c]pyri-
  dine-4-carboxamide;
N-((S)-2-hydroxypropyl)-2-(1-(4-methyl-5-(2,2,2-trifluo-
  roethoxy)pyridin-2-yl)ethyl)-2H-pyrazolo[4,3-c]pyri-
  dine-4-carboxamide;
N-methyl-2-((5-methyl-6-(3,3,3-trifluoropropyl)pyridin-
  3-yl)methyl)-2H-pyrazolo[4,3-c]pyridine-4-carboxam-
  ide;
N-ethyl-2-((5-methyl-6-(3,3,3-trifluoropropyl)pyridin-3-
  yl)methyl)-2H-pyrazolo[4,3-c]pyridine-4-carboxam-
  ide;
N-isopropyl-2-((5-methyl-6-(3,3,3-trifluoropropyl)pyri-
  din-3-yl)methyl)-2H-pyrazolo[4,3-c]pyridine-4-car-
  boxamide;
N-(2-hydroxyethyl)-2-((5-methyl-6-(3,3,3-trifluoropro-
  pyl)pyridin-3-yl)methyl)-2H-pyrazolo[4,3-c]pyridine-
  4-carboxamide;
N-(3-hydroxypropyl)-2-((5-methyl-6-(3,3,3-trifluoropro-
  pyl)pyridin-3-yl)methyl)-2H-pyrazolo[4,3-c]pyridine-
  4-carboxamide;
N-methyl-2-((4-methyl-5-(3,3,3-trifluoropropoxy)pyri-
  din-2-yl)methyl)-2H-pyrazolo[4,3-c]pyridine-4-car-
  boxamide;
N-ethyl-2-((4-methyl-5-(3,3,3-trifluoropropoxy)pyridin-
  2-yl)methyl)-2H-pyrazolo[4,3-c]pyridine-4-carboxam-
  ide;
N-(2-hydroxyethyl)-2-((4-methyl-5-(3,3,3-trifluoro-
  propoxy)pyridin-2-yl)methyl)-2H-pyrazolo[4,3-c]pyri-
  dine-4-carboxamide;
N-isopropyl-2-((4-methyl-5-(3,3,3-trifluoropropoxy)
  pyridin-2-yl)methyl)-2H-pyrazolo[4,3-c]pyridine-4-
  carboxamide;
2-((5-chloro-6-(2,2,3,3-tetrafluoropropoxy)pyridin-3-yl)
  methyl)-N-methyl-2H-pyrazolo[4,3-c]pyridine-4-car-
  boxamide;
2-((5-chloro-6-(2,2,3,3-tetrafluoropropoxy)pyridin-3-yl)
  methyl)-N-ethyl-2H-pyrazolo[4,3-c]pyridine-4-car-
  boxamide;
2-((5-chloro-6-(2,2,3,3-tetrafluoropropoxy)pyridin-3-yl)
  methyl)-N-isopropyl-2H-pyrazolo[4,3-c]pyridine-4-
  carboxamide;
2-((5-chloro-6-(2,2,3,3-tetrafluoropropoxy)pyridin-3-yl)
  methyl)-N-(2-hydroxyethyl)-2H-pyrazolo[4,3-c]pyri-
  dine-4-carboxamide;
2-((5-chloro-6-(2,2,3,3-tetrafluoropropoxy)pyridin-3-yl)
  methyl)-N-(3-hydroxypropyl)-2H-pyrazolo[4,3-c]pyri-
  dine-4-carboxamide;
(S)-2-((5-chloro-6-(2,2,3,3-tetrafluoropropoxy)pyridin-3-
  yl)methyl)-N-(2-hydroxypropyl)-2H-pyrazolo[4,3-c]
  pyridine-4-carboxamide;
(R)-2-((5-chloro-6-(2,2,3,3-tetrafluoropropoxy)pyridin-
  3-yl)methyl)-N-(2-hydroxypropyl)-2H-pyrazolo[4,3-c]
  pyridine-4-carboxamide;
(S)-2-((5-chloro-6-(2,2,3,3-tetrafluoropropoxy)pyridin-3-
  yl)methyl)-N-(2,3-dihydroxypropyl)-2H-pyrazolo[4,3-
  c]pyridine-4-carboxamide;
(R)-2-((5-chloro-6-(2,2,3,3-tetrafluoropropoxy)pyridin-
  3-yl)methyl)-N-(2,3-dihydroxypropyl)-2H-pyrazolo[4,
  3-c]pyridine-4-carboxamide;
(S)-2-((5-chloro-6-(2,2,3,3-tetrafluoropropoxy)pyridin-3-
  yl)methyl)-N-(1-hydroxypropan-2-yl)-2H-pyrazolo[4,
  3-c]pyridine-4-carboxamide;
N-(2-acetamidoethyl)-2-((5-chloro-6-(2,2,3,3-tetrafluo-
  ropropoxy)pyridin-3-yl)methyl)-2H-pyrazolo[4,3-c]
  pyridine-4-carboxamide;
N-(2-((5-methyl-6-(2,2,3,3-tetrafluoropropoxy)pyridin-
  3-yl)methyl)-2H-pyrazolo[4,3-c]pyridin-4-yl)isobutyr-
  amide;
N-(2-((5-methyl-6-(2,2,3,3-tetrafluoropropoxy)pyridin-
  3-yl)methyl)-2H-pyrazolo[4,3-c]pyridin-4-yl)cyclo-
  propanecarboxamide;
2-hydroxy-2-methyl-N-(2-((5-methyl-6-(2,2,3,3-tetra-
  fluoropropoxy)pyridin-3-yl)methyl)-2H-pyrazolo[4,3-
  c]pyridin-4-yl)propanamide;
N-methyl-2-((5-methyl-6-(2,2,3,3-tetrafluoropropoxy)
  pyridin-3-yl)methyl)-2H-pyrazolo[4,3-c]pyridine-4-
  carboxamide;
N-ethyl-2-((5-methyl-6-(2,2,3,3-tetrafluoropropoxy)pyri-
  din-3-yl)methyl)-2H-pyrazolo[4,3-c]pyridine-4-car-
  boxamide;
N-(2-((4-methyl-5-(3,3,3-trifluoropropoxy)pyridin-2-yl)
  methyl)-2H-pyrazolo[4,3-c]pyridin-4-yl)isobutyr-
  amide;
N-(2-((4-methyl-5-(3,3,3-trifluoropropoxy)pyridin-2-yl)
  methyl)-2H-pyrazolo[4,3-c]pyridin-4-yl)cyclopropan-
  ecarboxamide;
N-(2-((5-methyl-6-(3,3,3-trifluoropropyl)pyridin-3-yl)
  methyl)-2H-pyrazolo[4,3-c]pyridin-4-yl)cyclopropan-
  ecarboxamide;
N-(2-((5-methyl-6-(3,3,3-trifluoropropyl)pyridin-3-yl)
  methyl)-2H-pyrazolo[4,3-c]pyridin-4-yl)isobutyr-
  amide;

2-((5-chloro-6-(2,2-difluoropropoxy)pyridin-3-yl)methyl)-N-methyl-2H-pyrazolo[4,3-c]pyridine-4-carboxamide;

2-((5-chloro-6-(2,2-difluoropropoxy)pyridin-3-yl)methyl)-N-ethyl-2H-pyrazolo[4,3-c]pyridine-4-carboxamide;

2-((5-chloro-6-(2,2-difluoropropoxy)pyridin-3-yl)methyl)-N-isopropyl-2H-pyrazolo[4,3-c]pyridine-4-carboxamide;

2-((5-chloro-6-(2,2-difluoropropoxy)pyridin-3-yl)methyl)-N-(3-hydroxypropyl)-2H-pyrazolo[4,3-c]pyridine-4-carboxamide;

2-((5-chloro-6-(2,2-difluoropropoxy)pyridin-3-yl)methyl)-N-(2-hydroxyethyl)-2H-pyrazolo[4,3-c]pyridine-4-carboxamide;

N-isopropyl-2-((5-methyl-6-(2,2,3,3-tetrafluoropropoxy)pyridin-3-yl)methyl)-2H-pyrazolo[4,3-c]pyridine-4-carboxamide;

(S)-N-(1-hydroxypropan-2-yl)-2-((5-methyl-6-(2,2,3,3-tetrafluoropropoxy)pyridin-3-yl)methyl)-2H-pyrazolo[4,3-c]pyridine-4-carboxamide;

N-(2-((5-chloro-6-(3,3,3-trifluoropropoxy)pyridin-3-yl)methyl)-2H-pyrazolo[4,3-c]pyridin-4-yl)isobutyramide;

N-(2-((5-chloro-6-(3,3,3-trifluoropropoxy)pyridin-3-yl)methyl)-2H-pyrazolo[4,3-c]pyridin-4-yl)cyclopropanecarboxamide;

N-(2-((5-chloro-6-(3,3,3-trifluoropropoxy)pyridin-3-yl)methyl)-2H-pyrazolo[4,3-c]pyridin-4-yl)-2-hydroxy-2-methylpropanamide;

N-(2-((1-methyl-5-(trifluoromethyl)-1H-benzo[d]imidazol-2-yl)methyl)-2H-pyrazolo[4,3-c]pyridin-4-yl)cyclopropanecarboxamide;

N-(2-((1-methyl-5-(trifluoromethyl)-1H-benzo[d]imidazol-2-yl)methyl)-2H-pyrazolo[4,3-c]pyridin-4-yl)isobutyramide;

2-((5-chloro-6-(3,3,3-trifluoropropoxy)pyridin-3-yl)methyl)-N-methyl-2H-pyrazolo[4,3-c]pyridine-4-carboxamide;

2-((5-chloro-6-(3,3,3-trifluoropropoxy)pyridin-3-yl)methyl)-N-ethyl-2H-pyrazolo[4,3-c]pyridine-4-carboxamide;

2-((5-chloro-6-(3,3,3-trifluoropropoxy)pyridin-3-yl)methyl)-N-isopropyl-2H-pyrazolo[4,3-c]pyridine-4-carboxamide;

2-((5-chloro-6-(3,3,3-trifluoropropoxy)pyridin-3-yl)methyl)-N-(2-hydroxyethyl)-2H-pyrazolo[4,3-c]pyridine-4-carboxamide;

2-((5-chloro-6-(3,3,3-trifluoropropoxy)pyridin-3-yl)methyl)-N-(3-hydroxypropyl)-2H-pyrazolo[4,3-c]pyridine-4-carboxamide;

N-(2-(3-chloro-4-(2,2-difluoroethoxy)benzyl)-2H-pyrazolo[4,3-c]pyridin-4-yl)isobutyramide;

N-(2-(3-chloro-4-(2,2-difluoroethoxy)benzyl)-2H-pyrazolo[4,3-c]pyridin-4-yl)cyclopropanecarboxamide;

N-methyl-2-((1-methyl-5-(trifluoromethyl)-1H-benzo[d]imidazol-2-yl)methyl)-2H-pyrazolo[4,3-c]pyridine-4-carboxamide;

N-ethyl-2-((1-methyl-5-(trifluoromethyl)-1H-benzo[d]imidazol-2-yl)methyl)-2H-pyrazolo[4,3-c]pyridine-4-carboxamide;

N-isopropyl-2-((1-methyl-5-(trifluoromethyl)-1H-benzo[d]imidazol-2-yl)methyl)-2H-pyrazolo[4,3-c]pyridine-4-carboxamide;

N-(2-hydroxyethyl)-2-((1-methyl-5-(trifluoromethyl)-1H-benzo[d]imidazol-2-yl)methyl)-2H-pyrazolo[4,3-c]pyridine-4-carboxamide;

N-(3-hydroxypropyl)-2-((1-methyl-5-(trifluoromethyl)-1H-benzo[d]imidazol-2-yl)methyl)-2H-pyrazolo[4,3-c]pyridine-4-carboxamide;

N-(2-(4-(2,2-difluoroethoxy)-3-methylbenzyl)-2H-pyrazolo[4,3-c]pyridin-4-yl)isobutyramide;

N-(2-(4-(2,2-difluoroethoxy)-3-methylbenzyl)-2H-pyrazolo[4,3-c]pyridin-4-yl)cyclopropanecarboxamide;

N-(2-(4-(2,2-difluoroethoxy)-3-methylbenzyl)-2H-pyrazolo[4,3-c]pyridin-4-yl)-2-hydroxy-2-methylpropanamide;

2-hydroxy-2-methyl-N-(2-(3-methyl-4-(2,2,2-trifluoroethoxy)benzyl)-2H-pyrazolo[4,3-c]pyridin-4-yl)propanamide;

2-hydroxy-2-methyl-N-(2-(3-methyl-4-(trifluoromethoxy)benzyl)-2H-pyrazolo[4,3-c]pyridin-4-yl)propanamide;

2-hydroxy-2-methyl-N-(2-(2-(4-(trifluoromethyl)phenoxy)ethyl)-2H-pyrazolo[4,3-c]pyridin-4-yl)propanamide;

N-(2-((6-(4-chloro-1H-pyrazol-1-yl)-5-methylpyridin-3-yl)methyl)-2H-pyrazolo[4,3-c]pyridin-4-yl)-2-hydroxy-2-methylpropanamide;

2-(4-(2,2-difluoroethoxy)-3-methylbenzyl)-N-methyl-2H-pyrazolo[4,3-c]pyridine-4-carboxamide;

2-(4-(2,2-difluoroethoxy)-3-methylbenzyl)-N-ethyl-2H-pyrazolo[4,3-c]pyridine-4-carboxamide;

N-(2-((5-chloro-6-(2,2-difluoropropoxy)pyridin-3-yl)methyl)-2H-pyrazolo[4,3-c]pyridin-4-yl)cyclopropanecarboxamide;

N-(2-((5-chloro-6-(2,2-difluoropropoxy)pyridin-3-yl)methyl)-2H-pyrazolo[4,3-c]pyridin-4-yl)isobutyramide;

2-((5-methyl-6-(2,2,2-trifluoroethoxy)pyridin-3-yl)methyl)-N-(2-propionamidoethyl)-2H-pyrazolo[4,3-c]pyridine-4-carboxamide;

N-(2-isobutyramidoethyl)-2-((5-methyl-6-(2,2,2-trifluoroethoxy)pyridin-3-yl)methyl)-2H-pyrazolo[4,3-c]pyridine-4-carboxamide;

N-(2-(cyclopropanecarboxamido)ethyl)-2-((5-methyl-6-(2,2,2-trifluoroethoxy)pyridin-3-yl)methyl)-2H-pyrazolo[4,3-c]pyridine-4-carboxamide;

ethyl (2-(2-((5-methyl-6-(2,2,2-trifluoroethoxy)pyridin-3-yl)methyl)-2H-pyrazolo[4,3-c]pyridine-4-carboxamido)ethyl)carbamate;

N-(2-benzamidoethyl)-2-((5-methyl-6-(2,2,2-trifluoroethoxy)pyridin-3-yl)methyl)-2H-pyrazolo[4,3-c]pyridine-4-carboxamide;

N-(2-(2-hydroxy-2-methylpropanamido)ethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-(2-(N-methylacetamido)ethyl)-2H-pyrazolo[4,3-c]pyridine-4-carboxamide;

N-(2-butyramidoethyl)-2-((5-methyl-6-(2,2,2-trifluoroethoxy)pyridin-3-yl)methyl)-2H-pyrazolo[4,3-c]pyridine-4-carboxamide;

N-(2-(cyclobutanecarboxamido)ethyl)-2-((5-methyl-6-(2,2,2-trifluoroethoxy)pyridin-3-yl)methyl)-2H-pyrazolo[4,3-c]pyridine-4-carboxamide;

N-(2-(cyclohexanecarboxamido)ethyl)-2-((5-methyl-6-(2,2,2-trifluoroethoxy)pyridin-3-yl)methyl)-2H-pyrazolo[4,3-c]pyridine-4-carboxamide;

N-(2-(3-ethylureido)ethyl)-2-((5-methyl-6-(2,2,2-trifluoroethoxy)pyridin-3-yl)methyl)-2H-pyrazolo[4,3-c]pyridine-4-carboxamide;

N-(2-acetamidoethyl)-2-((5-chloro-6-(2,2,2-trifluoroethoxy)pyridin-3-yl)methyl)-2H-pyrazolo[4,3-c]pyridine-4-carboxamide;
N-(2-acetamidoethyl)-2-((6-(cyclopropylmethoxy)-5-methylpyridin-3-yl)methyl)-2H-pyrazolo[4,3-c]pyridine-4-carboxamide;
N-(2-acetamidoethyl)-2-(3-methyl-4-(trifluoromethoxy)benzyl)-2H-pyrazolo[4,3-c]pyridine-4-carboxamide;
N-(2-acetamidoethyl)-2-(3-methyl-4-(2,2,2-trifluoroethoxy)benzyl)-2H-pyrazolo[4,3-c]pyridine-4-carboxamide;
N-(2-acetamidoethyl)-2-(4-(2,2-difluoroethoxy)-3-methylbenzyl)-2H-pyrazolo[4,3-c]pyridine-4-carboxamide;
N-(2-acetamidoethyl)-2-((5-chloro-6-(3,3,3-trifluoropropoxy)pyridin-3-yl)methyl)-2H-pyrazolo[4,3-c]pyridine-4-carboxamide;
N-(2-acetamidoethyl)-2-((1-methyl-5-(trifluoromethoxy)-1H-indol-2-yl)methyl)-2H-pyrazolo[4,3-c]pyridine-4-carboxamide;
2-hydroxy-2-methyl-N-(2-((4-methyl-5-(3,3,3-trifluoropropoxy)pyridin-2-yl)methyl)-2H-pyrazolo[4,3-c]pyridin-4-yl)propanamide;
2-((5-methyl-6-(2,2,2-trifluoroethoxy)pyridin-3-yl)methyl)-N-(2-(picolinamido)ethyl)-2H-pyrazolo[4,3-c]pyridine-4-carboxamide;
2-((5-methyl-6-(2,2,2-trifluoroethoxy)pyridin-3-yl)methyl)-N-(2-(nicotinamido)ethyl)-2H-pyrazolo[4,3-c]pyridine-4-carboxamide;
N-(2-(isonicotinamido)ethyl)-2-((5-methyl-6-(2,2,2-trifluoroethoxy)pyridin-3-yl)methyl)-2H-pyrazolo[4,3-c]pyridine-4-carboxamide;
N-(2-(1-hydroxycyclohexanecarboxamido)ethyl)-2-((5-methyl-6-(2,2,2-trifluoroethoxy)pyridin-3-yl)methyl)-2H-pyrazolo[4,3-c]pyridine-4-carboxamide;
N-(2-acetamidoethyl)-2-(3-chloro-4-(2,2,2-trifluoroethoxy)benzyl)-2H-pyrazolo[4,3-c]pyridine-4-carboxamide;
N-(2-((4-methyl-5-(2,2,3,3-tetrafluoropropoxy)pyridin-2-yl)methyl)-2H-pyrazolo[4,3-c]pyridin-4-yl)cyclopropanecarboxamide;
2-hydroxy-2-methyl-N-(2-((4-methyl-5-(2,2,3,3-tetrafluoropropoxy)pyridin-2-yl)methyl)-2H-pyrazolo[4,3-c]pyridin-4-yl)propanamide;
N-(2-((5-chloro-6-(cyclopropylmethoxy)pyridin-3-yl)methyl)-2H-pyrazolo[4,3-c]pyridin-4-yl)isobutyramide;
N-(2-((5-chloro-6-(cyclopropylmethoxy)pyridin-3-yl)methyl)-2H-pyrazolo[4,3-c]pyridin-4-yl)cyclopropanecarboxamide;
N-(2-((5-chloro-6-(cyclopropylmethoxy)pyridin-3-yl)methyl)-2H-pyrazolo[4,3-c]pyridin-4-yl)-2-hydroxy-2-methylpropanamide;
N-methyl-2-((4-methyl-5-(2,2,3,3-tetrafluoropropoxy)pyridin-2-yl)methyl)-2H-pyrazolo[4,3-c]pyridine-4-carboxamide;
N-ethyl-2-((4-methyl-5-(2,2,3,3-tetrafluoropropoxy)pyridin-2-yl)methyl)-2H-pyrazolo[4,3-c]pyridine-4-carboxamide;
N-isopropyl-2-((4-methyl-5-(2,2,3,3-tetrafluoropropoxy)pyridin-2-yl)methyl)-2H-pyrazolo[4,3-c]pyridine-4-carboxamide;
N-(2-acetamidoethyl)-2-((4-methyl-5-(2,2,3,3-tetrafluoropropoxy)pyridin-2-yl)methyl)-2H-pyrazolo[4,3-c]pyridine-4-carboxamide;
N-(2-hydroxyethyl)-2-((4-methyl-5-(2,2,3,3-tetrafluoropropoxy)pyridin-2-yl)methyl)-2H-pyrazolo[4,3-c]pyridine-4-carboxamide;
N-(3-hydroxypropyl)-2-((4-methyl-5-(2,2,3,3-tetrafluoropropoxy)pyridin-2-yl)methyl)-2H-pyrazolo[4,3-c]pyridine-4-carboxamide;
N-methyl-2-(1-(4-methyl-5-(2,2,2-trifluoroethoxy)pyridin-2-yl)ethyl)-2H-pyrazolo[4,3-c]pyridine-4-carboxamide;
N-ethyl-2-(1-(4-methyl-5-(2,2,2-trifluoroethoxy)pyridin-2-yl)ethyl)-2H-pyrazolo[4,3-c]pyridine-4-carboxamide;
N-isopropyl-2-(1-(4-methyl-5-(2,2,2-trifluoroethoxy)pyridin-2-yl)ethyl)-2H-pyrazolo[4,3-c]pyridine-4-carboxamide;
N-(2-acetamidoethyl)-2-((2-methyl-6-(2,2,2-trifluoroethoxy)pyridin-4-yl)methyl)-2H-pyrazolo[4,3-c]pyridine-4-carboxamide;
N-(2-acetamidoethyl)-2-(2-(4-(trifluoromethyl)phenoxy)ethyl)-2H-pyrazolo[4,3-c]pyridine-4-carboxamide;
N-(2-acetamidoethyl)-2-((6-(4-chloro-1H-pyrazol-1-yl)-5-methylpyridin-3-yl)methyl)-2H-pyrazolo[4,3-c]pyridine-4-carboxamide;
N-(2-acetamidoethyl)-2-((1-(2,2,2-trifluoroethoxy)isoquinolin-4-yl)methyl)-2H-pyrazolo[4,3-c]pyridine-4-carboxamide;
N-(2-acetamidoethyl)-2-(4-(1,1,2,2-tetrafluoroethoxy)benzyl)-2H-pyrazolo[4,3-c]pyridine-4-carboxamide;
N-(2-acetamidoethyl)-2-((2-methoxy-6-(2,2,2-trifluoroethoxy)pyridin-3-yl)methyl)-2H-pyrazolo[4,3-c]pyridine-4-carboxamide;
N-(2-acetamidoethyl)-2-((6-(2,2-difluoropropoxy)-5-methylpyridin-3-yl)methyl)-2H-pyrazolo[4,3-c]pyridine-4-carboxamide;
N-(2-acetamidoethyl)-2-((6-(2,2,2-trifluoroethoxy)pyridin-2-yl)methyl)-2H-pyrazolo[4,3-c]pyridine-4-carboxamide;
N-(2-(1-(4-methyl-5-(2,2,2-trifluoroethoxy)pyridin-2-yl)ethyl)-2H-pyrazolo[4,3-c]pyridin-4-yl)cyclopropanecarboxamide;
N-(2-(1-(4-methyl-5-(2,2,2-trifluoroethoxy)pyridin-2-yl)ethyl)-2H-pyrazolo[4,3-c]pyridin-4-yl)isobutyramide;
2-((5-chloro-6-(cyclopropylmethoxy)pyridin-3-yl)methyl)-N-methyl-2H-pyrazolo[4,3-c]pyridine-4-carboxamide;
2-((5-chloro-6-(cyclopropylmethoxy)pyridin-3-yl)methyl)-N-ethyl-2H-pyrazolo[4,3-c]pyridine-4-carboxamide;
N-(2-acetamidoethyl)-2-((5-chloro-6-(cyclopropylmethoxy)pyridin-3-yl)methyl)-2H-pyrazolo[4,3-c]pyridine-4-carboxamide;
2-((5-chloro-6-(cyclopropylmethoxy)pyridin-3-yl)methyl)-N-isopropyl-2H-pyrazolo[4,3-c]pyridine-4-carboxamide;
2-((5-chloro-6-(cyclopropylmethoxy)pyridin-3-yl)methyl)-N-(2-hydroxyethyl)-2H-pyrazolo[4,3-c]pyridine-4-carboxamide;
2-((5-chloro-6-(cyclopropylmethoxy)pyridin-3-yl)methyl)-N-(3-hydroxypropyl)-2H-pyrazolo[4,3-c]pyridine-4-carboxamide;
N-(2-((6-((4-fluorobenzyl)oxy)-5-methylpyridin-3-yl)methyl)-2H-pyrazolo[4,3-c]pyridin-4-yl)isobutyramide;
N-(2-((6-((4-fluorobenzyl)oxy)-5-methylpyridin-3-yl)methyl)-2H-pyrazolo[4,3-c]pyridin-4-yl)cyclopropanecarboxamide;
N-(2-((6-((4-fluorobenzyl)oxy)-5-methylpyridin-3-yl)methyl)-2H-pyrazolo[4,3-c]pyridin-4-yl)-2-hydroxy-2-methylpropanamide;

2-((6-((4-fluorobenzyl)oxy)-5-methylpyridin-3-yl)methyl)-N-methyl-2H-pyrazolo[4,3-c]pyridine-4-carboxamide;
N-ethyl-2-((6-((4-fluorobenzyl)oxy)-5-methylpyridin-3-yl)methyl)-2H-pyrazolo[4,3-c]pyridine-4-carboxamide;
N-(2-acetamidoethyl)-2-((6-((4-fluorobenzyl)oxy)-5-methylpyridin-3-yl)methyl)-2H-pyrazolo[4,3-c]pyridine-4-carboxamide;
2-((6-((4-fluorobenzyl)oxy)-5-methylpyridin-3-yl)methyl)-N-isopropyl-2H-pyrazolo[4,3-c]pyridine-4-carboxamide;
2-((6-((4-fluorobenzyl)oxy)-5-methylpyridin-3-yl)methyl)-N-(2-hydroxyethyl)-2H-pyrazolo[4,3-c]pyridine-4-carboxamide;
2-((6-((4-fluorobenzyl)oxy)-5-methylpyridin-3-yl)methyl)-N-(3-hydroxypropyl)-2H-pyrazolo[4,3-c]pyridine-4-carboxamide;
N-(2-((6-cyclobutoxy-5-methylpyridin-3-yl)methyl)-2H-pyrazolo[4,3-c]pyridin-4-yl)isobutyramide;
N-(2-((6-cyclobutoxy-5-methylpyridin-3-yl)methyl)-2H-pyrazolo[4,3-c]pyridin-4-yl)cyclopropanecarboxamide;
N-(2-((6-cyclobutoxy-5-methylpyridin-3-yl)methyl)-2H-pyrazolo[4,3-c]pyridin-4-yl)-2-hydroxy-2-methylpropanamide;
N-(2-((4-methyl-5-(2,2,3,3-tetrafluoropropoxy)pyridin-2-yl)methyl)-2H-pyrazolo[4,3-c]pyridin-4-yl)isobutyramide;
2-((6-cyclobutoxy-5-methylpyridin-3-yl)methyl)-N-methyl-2H-pyrazolo[4,3-c]pyridine-4-carboxamide;
2-((6-cyclobutoxy-5-methylpyridin-3-yl)methyl)-N-ethyl-2H-pyrazolo[4,3-c]pyridine-4-carboxamide;
N-(2-acetamidoethyl)-2-((6-cyclobutoxy-5-methylpyridin-3-yl)methyl)-2H-pyrazolo[4,3-c]pyridine-4-carboxamide;
2-((6-cyclobutoxy-5-methylpyridin-3-yl)methyl)-N-isopropyl-2H-pyrazolo[4,3-c]pyridine-4-carboxamide;
2-((6-cyclobutoxy-5-methylpyridin-3-yl)methyl)-N-(2-hydroxyethyl)-2H-pyrazolo[4,3-c]pyridine-4-carboxamide;
2-((6-cyclobutoxy-5-methylpyridin-3-yl)methyl)-N-(3-hydroxypropyl)-2H-pyrazolo[4,3-c]pyridine-4-carboxamide;
N-(2-((5-(cyclopropylmethoxy)-4-methylpyridin-2-yl)methyl)-2H-pyrazolo[4,3-c]pyridin-4-yl)isobutyramide;
N-(2-((5-(cyclopropylmethoxy)-4-methylpyridin-2-yl)methyl)-2H-pyrazolo[4,3-c]pyridin-4-yl)cyclopropanecarboxamide;
N-(2-((5-(cyclopropylmethoxy)-4-methylpyridin-2-yl)methyl)-2H-pyrazolo[4,3-c]pyridin-4-yl)-2-hydroxy-2-methylpropanamide;
2-((5-(cyclopropylmethoxy)-4-methylpyridin-2-yl)methyl)-N-methyl-2H-pyrazolo[4,3-c]pyridine-4-carboxamide;
2-((5-(cyclopropylmethoxy)-4-methylpyridin-2-yl)methyl)-N-ethyl-2H-pyrazolo[4,3-c]pyridine-4-carboxamide;
N-(2-acetamidoethyl)-2-((5-(cyclopropylmethoxy)-4-methylpyridin-2-yl)methyl)-2H-pyrazolo[4,3-c]pyridine-4-carboxamide;
2-((5-(cyclopropylmethoxy)-4-methylpyridin-2-yl)methyl)-N-isopropyl-2H-pyrazolo[4,3-c]pyridine-4-carboxamide;
2-((5-(cyclopropylmethoxy)-4-methylpyridin-2-yl)methyl)-N-(2-hydroxyethyl)-2H-pyrazolo[4,3-c]pyridine-4-carboxamide;
2-((5-(cyclopropylmethoxy)-4-methylpyridin-2-yl)methyl)-N-(3-hydroxypropyl)-2H-pyrazolo[4,3-c]pyridine-4-carboxamide;
N-methyl-2-((5-methyl-6-(2,2,3,3-tetrafluoropropoxy)pyridazin-3-yl)methyl)-2H-pyrazolo[4,3-c]pyridine-4-carboxamide;
N-ethyl-2-((5-methyl-6-(2,2,3,3-tetrafluoropropoxy)pyridazin-3-yl)methyl)-2H-pyrazolo[4,3-c]pyridine-4-carboxamide;
N-isopropyl-2-((5-methyl-6-(2,2,3,3-tetrafluoropropoxy)pyridazin-3-yl)methyl)-2H-pyrazolo[4,3-c]pyridine-4-carboxamide;
N-(2-hydroxyethyl)-2-((5-methyl-6-(2,2,3,3-tetrafluoropropoxy)pyridazin-3-yl)methyl)-2H-pyrazolo[4,3-c]pyridine-4-carboxamide;
N-(3-hydroxypropyl)-2-((5-methyl-6-(2,2,3,3-tetrafluoropropoxy)pyridazin-3-yl)methyl)-2H-pyrazolo[4,3-c]pyridine-4-carboxamide;
N-(2-((5-(2,2-difluoropropoxy)-4-methylpyridin-2-yl)methyl)-2H-pyrazolo[4,3-c]pyridin-4-yl)isobutyramide;
N-(2-((5-(2,2-difluoropropoxy)-4-methylpyridin-2-yl)methyl)-2H-pyrazolo[4,3-c]pyridin-4-yl)cyclopropanecarboxamide;
2-(5-(2,2-difluoropropoxy)-4-methylpyridin-2-yl)methyl)-N-methyl-2H-pyrazolo[4,3-c]pyridine-4-carboxamide;
2-(5-(2,2-difluoropropoxy)-4-methylpyridin-2-yl)methyl)-N-ethyl-2H-pyrazolo[4,3-c]pyridine-4-carboxamide;
N-(2-acetamidoethyl)-2-((5-(2,2-difluoropropoxy)-4-methylpyridin-2-yl)methyl)-2H-pyrazolo[4,3-c]pyridine-4-carboxamide;
2-((5-(2,2-difluoropropoxy)-4-methylpyridin-2-yl)methyl)-N-isopropyl-2H-pyrazolo[4,3-c]pyridine-4-carboxamide;
2-((5-(2,2-difluoropropoxy)-4-methylpyridin-2-yl)methyl)-N-(2-hydroxyethyl)-2H-pyrazolo[4,3-c]pyridine-4-carboxamide;
2-((5-(2,2-difluoropropoxy)-4-methylpyridin-2-yl)methyl)-N-(3-hydroxypropyl)-2H-pyrazolo[4,3-c]pyridine-4-carboxamide;
N-(2-((5-(2,2-difluoropropoxy)-4-methylpyridin-2-yl)methyl)-2H-pyrazolo[4,3-c]pyridin-4-yl)-2-hydroxy-2-methylpropanamide;
(R)-2-((6-(2,2-difluoropropoxy)-5-methylpyridin-3-yl)methyl)-N-(2-hydroxypropyl)-2H-pyrazolo[4,3-c]pyridine-4-carboxamide;
(S)-2-((6-(2,2-difluoropropoxy)-5-methylpyridin-3-yl)methyl)-N-(2-hydroxypropyl)-2H-pyrazolo[4,3-c]pyridine-4-carboxamide;
(S)-2-((6-(2,2-difluoropropoxy)-5-methylpyridin-3-yl)methyl)-N-(1-hydroxypropan-2-yl)-2H-pyrazolo[4,3-c]pyridine-4-carboxamide;
(S)-2-((6-(2,2-difluoropropoxy)-5-methylpyridin-3-yl)methyl)-N-(2,3-dihydroxypropyl)-2H-pyrazolo[4,3-c]pyridine-4-carboxamide;
(R)-2-((6-(2,2-difluoropropoxy)-5-methylpyridin-3-yl)methyl)-N-(2,3-dihydroxypropyl)-2H-pyrazolo[4,3-c]pyridine-4-carboxamide;
N-(2-cyanoethyl)-2-((6-(2,2-difluoropropoxy)-5-methylpyridin-3-yl)methyl)-2H-pyrazolo[4,3-c]pyridine-4-carboxamide;

N-(2-(4-(2,2-difluoropropoxy)-3-methylbenzyl)-2H-pyrazolo[4,3-c]pyridin-4-yl)isobutyramide;
N-(2-(4-(2,2-difluoropropoxy)-3-methylbenzyl)-2H-pyrazolo[4,3-c]pyridin-4-yl)cyclopropanecarboxamide;
N-(2-(4-(2,2-difluoropropoxy)-3-methylbenzyl)-2H-pyrazolo[4,3-c]pyridin-4-yl)-2-hydroxy-2-methylpropanamide;
2-(4-(2,2-difluoropropoxy)-3-methylbenzyl)-N-methyl-2H-pyrazolo[4,3-c]pyridine-4-carboxamide;
2-(4-(2,2-difluoropropoxy)-3-methylbenzyl)-N-ethyl-2H-pyrazolo[4,3-c]pyridine-4-carboxamide;
N-(2-acetamidoethyl)-2-(4-(2,2-difluoropropoxy)-3-methylbenzyl)-2H-pyrazolo[4,3-c]pyridine-4-carboxamide;
2-(4-(2,2-difluoropropoxy)-3-methylbenzyl)-N-isopropyl-2H-pyrazolo[4,3-c]pyridine-4-carboxamide;
2-(4-(2,2-difluoropropoxy)-3-methylbenzyl)-N-(2-hydroxyethyl)-2H-pyrazolo[4,3-c]pyridine-4-carboxamide;
2-(4-(2,2-difluoropropoxy)-3-methylbenzyl)-N-(3-hydroxypropyl)-2H-pyrazolo[4,3-c]pyridine-4-carboxamide;
N-(2-(1-(5-methyl-6-(2,2,2-trifluoroethoxy)pyridin-3-yl)ethyl)-2H-pyrazolo[4,3-c]pyridin-4-yl)oxazole-5-carboxamide;
(S)-2-(4-(2,2-difluoroethoxy)-3-methylbenzyl)-N-(2-hydroxypropyl)-2H-pyrazolo[4,3-c]pyridine-4-carboxamide;
(R)-2-(4-(2,2-difluoroethoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((R)-2-hydroxypropyl)-2H-pyrazolo[4,3-c]pyridine-4-carboxamide;
(R)-2-(4-(2,2-difluoroethoxy)-3,5-dimethylbenzyl)-N-(2-hydroxypropyl)-2H-pyrazolo[4,3-c]pyridine-4-carboxamide;
(R)-2-(3-(2,2-difluoroethoxy)-4-methylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((R)-2-hydroxypropyl)-2H-pyrazolo[4,3-c]pyridine-4-carboxamide;
(S)-2-(4-(2,2-difluoropropoxy)-3-methylbenzyl)-N-(2-hydroxypropyl)-2H-pyrazolo[4,3-c]pyridine-4-carboxamide;
(R)-2-(4-(2,2-difluoropropoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((S)-2-hydroxypropyl)-2H-pyrazolo[4,3-c]pyridine-4-carboxamide;
(S)-2-(4-(2,2-difluoroethoxy)-3,5-dimethylbenzyl)-N-(2-hydroxypropyl)-2H-pyrazolo[4,3-c]pyridine-4-carboxamide;
(S)-2-(3-(2,2-difluoroethoxy)-4-methylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((S)-2-hydroxypropyl)-2H-pyrazolo[4,3-c]pyridine-4-carboxamide;
2-(1-(4-(2,2-difluoroethoxy)-3-methylphenyl)ethyl)-N-((S)-2-hydroxypropyl)-2H-pyrazolo[4,3-c]pyridine-4-carboxamide;
2-(4-(2,2-difluoroethoxy)-3,5-dimethylbenzyl)-N-(2-hydroxyethyl)-2H-pyrazolo[4,3-c]pyridine-4-carboxamide;
2-(3-(2,2-difluoroethoxy)-4-methylbenzyl)-N-(2-hydroxyethyl)-2H-pyrazolo[4,3-c]pyridine-4-carboxamide;
2-(1-(4-(2,2-difluoroethoxy)-3-methylphenyl)ethyl)-N-(2-hydroxyethyl)-2H-pyrazolo[4,3-c]pyridine-4-carboxamide;
2-(1-(4-(2,2-difluoroethoxy)-3-methylphenyl)ethyl)-N-(3-hydroxypropyl)-2H-pyrazolo[4,3-c]pyridine-4-carboxamide;
2-(4-(2,2-difluoroethoxy)-3,5-dimethylbenzyl)-N-(3-hydroxypropyl)-2H-pyrazolo[4,3-c]pyridine-4-carboxamide;
2-(3-(2,2-difluoroethoxy)-4-methylbenzyl)-N-(3-hydroxypropyl)-2H-pyrazolo[4,3-c]pyridine-4-carboxamide;
2-(1-(4-(2,2-difluoropropoxy)-3-methylphenyl)ethyl)-N-(3-hydroxypropyl)-2H-pyrazolo[4,3-c]pyridine-4-carboxamide;
2-(4-(2,2-difluoropropoxy)-3-methylbenzyl)-2H-pyrazolo[4,3-c]pyridine-4-carboxamide;
2-(4-(difluoromethoxy)-3-methylbenzyl)-N-methyl-2H-pyrazolo[4,3-c]pyridine-4-carboxamide;
2-(4-(difluoromethoxy)-3-methylbenzyl)-N-ethyl-2H-pyrazolo[4,3-c]pyridine-4-carboxamide;
N-(2-acetamidoethyl)-2-(4-(difluoromethoxy)-3-methylbenzyl)-2H-pyrazolo[4,3-c]pyridine-4-carboxamide;
2-(4-(difluoromethoxy)-3-methylbenzyl)-N-(2-hydroxyethyl)-2H-pyrazolo[4,3-c]pyridine-4-carboxamide;
2-(4-(difluoromethoxy)-3-methylbenzyl)-N-(3-hydroxypropyl)-2H-pyrazolo[4,3-c]pyridine-4-carboxamide;
(R)-2-(4-(difluoromethoxy)-3-methylbenzyl)-N-(2-hydroxypropyl)-2H-pyrazolo[4,3-c]pyridine-4-carboxamide;
(S)-2-(4-(difluoromethoxy)-3-methylbenzyl)-N-(2-hydroxypropyl)-2H-pyrazolo[4,3-c]pyridine-4-carboxamide; and
2-(4-(difluoromethoxy)-3-methylbenzyl)-N-isopropyl-2H-pyrazolo[4,3-c]pyridine-4-carboxamide;
or a pharmaceutically acceptable salt thereof.

8. The compound as claimed in claim 7, which is selected from the group consisting of:
N-(2-((5-methyl-6-(2,2,2-trifluoroethoxy)pyridin-3-yl)methyl)-2H-pyrazolo[4,3-c]pyridin-4-yl)isobutyramide;
2-hydroxy-2-methyl-N-(2-((5-methyl-6-(2,2,2-trifluoroethoxy)pyridin-3-yl)methyl)-2H-pyrazolo[4,3-c]pyridin-4-yl)propanamide;
N-(2-((6-(2,2-difluoroethoxy)-5-methylpyridin-3-yl)methyl)-2H-pyrazolo[4,3-c]pyridin-4-yl)isobutyramide;
N-(2-((6-(2,2,2-trifluoroethoxy)pyridin-3-yl)methyl)-2H-pyrazolo[4,3-c]pyridin-4-yl)isobutyramide;
N-(2-((5-chloro-6-(2,2,2-trifluoroethoxy)pyridin-3-yl)methyl)-2H-pyrazolo[4,3-c]pyridin-4-yl)acetamide;
N-methyl-2-((5-methyl-6-(2,2,2-trifluoroethoxy)pyridin-3-yl)methyl)-2H-pyrazolo[4,3-c]pyridine-4-carboxamide;
N-isopropyl-2-((5-methyl-6-(2,2,2-trifluoroethoxy)pyridin-3-yl)methyl)-2H-pyrazolo[4,3-c]pyridine-4-carboxamide;
N-(2-(1-(5-methyl-6-(2,2,2-trifluoroethoxy)pyridin-3-yl)ethyl)-2H-pyrazolo[4,3-c]pyridin-4-yl)isobutyramide;
N-(2-(1-(5-methyl-6-(2,2,2-trifluoroethoxy)pyridin-3-yl)ethyl)-2H-pyrazolo[4,3-c]pyridin-4-yl)acetamide;

N-(2-(1-(5-methyl-6-(2,2,2-trifluoroethoxy)pyridin-3-yl)ethyl)-2H-pyrazolo[4,3-c]pyridin-4-yl)tetrahydro-2H-pyran-4-carboxamide;

N-(2-((6-(2,2-difluoroethoxy)-5-methylpyridin-3-yl)methyl)-2H-pyrazolo[4,3-c]pyridin-4-yl)pivalamide;

N-ethyl-2-((5-methyl-6-(2,2,2-trifluoroethoxy)pyridin-3-yl)methyl)-2H-pyrazolo[4,3-c]pyridine-4-carboxamide;

N-(2-methoxyethyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)methyl)-N-propyl-2H-pyrazolo[4,3-c]pyridine-4-carboxamide;

N-(2-(dimethylamino)ethyl)-2-((5-methyl-6-(2,2,2-trifluoroethoxy)pyridin-3-yl)methyl)-2H-pyrazolo[4,3-c]pyridine-4-carboxamide;

2-hydroxy-2-methyl-N-(6-methyl-2-((5-methyl-6-(2,2,2-trifluoroethoxy)pyridin-3-yl)methyl)-2H-pyrazolo[4,3-c]pyridin-4-yl)propanamide;

2-((6-(2,2-difluoroethoxy)-5-methylpyridin-3-yl)methyl)-N-ethyl-2H-pyrazolo[4,3-c]pyridine-4-carboxamide;

N-(2-hydroxyethyl)-2-((5-methyl-6-(2,2,2-trifluoroethoxy)pyridin-3-yl)methyl)-2H-pyrazolo[4,3-c]pyridine-4-carboxamide;

2-((6-(2,2-difluoroethoxy)-5-methylpyridin-3-yl)methyl)-N-(2-hydroxyethyl)-2H-pyrazolo[4,3-c]pyridine-4-carboxamide;

N-(2-hydroxyethyl)-2-((5-methyl-6-(3,3,3-trifluoropropoxy)pyridin-3-yl)methyl)-2H-pyrazolo[4,3-c]pyridine-4-carboxamide;

N-(2-((5-methyl-6-(3,3,3-trifluoropropoxy)pyridin-3-yl)methyl)-2H-pyrazolo[4,3-c]pyridin-4-yl)isobutyramide;

2-hydroxy-2-methyl-N-(2-((5-methyl-6-(3,3,3-trifluoropropoxy)pyridin-3-yl)methyl)-2H-pyrazolo[4,3-c]pyridin-4-yl)propanamide;

N-isopropyl-2-((5-methyl-6-(3,3,3-trifluoropropoxy)pyridin-3-yl)methyl)-2H-pyrazolo[4,3-c]pyridine-4-carboxamide;

N-(2-((5-methyl-6-(2,2,2-trifluoroethoxy)pyridazin-3-yl)methyl)-2H-pyrazolo[4,3-c]pyridin-4-yl)isobutyramide;

N-(2-((5-methyl-6-(2,2,2-trifluoroethoxy)pyridazin-3-yl)methyl)-2H-pyrazolo[4,3-c]pyridin-4-yl)cyclopropanecarboxamide;

N-methyl-2-((5-methyl-6-(2,2,2-trifluoroethoxy)pyridazin-3-yl)methyl)-2H-pyrazolo[4,3-c]pyridine-4-carboxamide;

N-ethyl-2-((5-methyl-6-(2,2,2-trifluoroethoxy)pyridazin-3-yl)methyl)-2H-pyrazolo[4,3-c]pyridine-4-carboxamide;

(R)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2-hydroxypropyl)-2-((5-methyl-6-(2,2,2-trifluoroethoxy)pyridin-3-yl)methyl)-2H-pyrazolo[4,3-c]pyridine-4-carboxamide;

(S)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;

N-(2-((4-methyl-5-(2,2,2-trifluoroethoxy)pyridin-2-yl)methyl)-2H-pyrazolo[4,3-c]pyridin-4-yl)cyclopropanecarboxamide;

N-methyl-2-((4-methyl-5-(2,2,2-trifluoroethoxy)pyridin-2-yl)methyl)-2H-pyrazolo[4,3-c]pyridine-4-carboxamide;

N-ethyl-2-((4-methyl-5-(2,2,2-trifluoroethoxy)pyridin-2-yl)methyl)-2H-pyrazolo[4,3-c]pyridine-4-carboxamide;

N-isopropyl-2-((4-methyl-5-(2,2,2-trifluoroethoxy)pyridin-2-yl)methyl)-2H-pyrazolo[4,3-c]pyridine-4-carboxamide;

N-(2-hydroxyethyl)-2-((4-methyl-5-(2,2,2-trifluoroethoxy)pyridin-2-yl)methyl)-2H-pyrazolo[4,3-c]pyridine-4-carboxamide;

N-(2-hydroxyethyl)-2-((5-methyl-6-(2,2,2-trifluoroethoxy)pyridazin-3-yl)methyl)-2H-pyrazolo[4,3-c]pyridine-4-carboxamide;

N-(3-hydroxypropyl)-2-((5-methyl-6-(2,2,2-trifluoroethoxy)pyridin-3-yl)methyl)-2H-pyrazolo[4,3-c]pyridine-4-carboxamide;

2-((6-(2,2-difluoroethoxy)-5-methylpyridin-3-yl)methyl)-N-(3-hydroxypropyl)-2H-pyrazolo[4,3-c]pyridine-4-carboxamide;

N-(2-cyanoethyl)-2-((5-methyl-6-(2,2,2-trifluoroethoxy)pyridin-3-yl)methyl)-2H-pyrazolo[4,3-c]pyridine-4-carboxamide;

N-(2-cyanoethyl)-2-((6-(2,2-difluoroethoxy)-5-methylpyridin-3-yl)methyl)-2H-pyrazolo[4,3-c]pyridine-4-carboxamide;

N-(2-acetamidoethyl)-2-((5-methyl-6-(2,2,2-trifluoroethoxy)pyridin-3-yl)methyl)-2H-pyrazolo[4,3-c]pyridine-4-carboxamide;

N-(2-((5-methoxy-6-(2,2,2-trifluoroethoxy)pyridin-3-yl)methyl)-2H-pyrazolo[4,3-c]pyridin-4-yl)isobutyramide;

N-ethyl-2-((5-methoxy-6-(2,2,2-trifluoroethoxy)pyridin-3-yl)methyl)-2H-pyrazolo[4,3-c]pyridine-4-carboxamide;

N-(2-(2-hydroxyethoxy)ethyl)-2-((5-methyl-6-(2,2,2-trifluoroethoxy)pyridin-3-yl)methyl)-2H-pyrazolo[4,3-c]pyridine-4-carboxamide;

N-(2-((4-methyl-5-(2,2,2-trifluoroethoxy)pyridin-2-yl)methyl)-2H-pyrazolo[4,3-c]pyridin-4-yl)isobutyramide;

2-((5-chloro-6-(2,2,2-trifluoroethoxy)pyridin-3-yl)methyl)-N-(2-hydroxyethyl)-2H-pyrazolo[4,3-c]pyridine-4-carboxamide;

2-((5-chloro-6-(2,2-difluoroethoxy)pyridin-3-yl)methyl)-N-ethyl-2H-pyrazolo[4,3-c]pyridine-4-carboxamide;

2-((5-chloro-6-(2,2-difluoroethoxy)pyridin-3-yl)methyl)-N-(2-hydroxyethyl)-2H-pyrazolo[4,3-c]pyridine-4-carboxamide;

(R)-N-(2,3-dihydroxypropyl)-2-((5-methyl-6-(2,2,2-trifluoroethoxy)pyridin-3-yl)methyl)-2H-pyrazolo[4,3-c]pyridine-4-carboxamide;

N-(2-hydroxyethyl)-2-((6-(2,2,3,3,3-pentafluoropropoxy)pyridin-3-yl)methyl)-2H-pyrazolo[4,3-c]pyridine-4-carboxamide;

N-(4-hydroxybutyl)-2-((5-methyl-6-(2,2,2-trifluoroethoxy)pyridin-3-yl)methyl)-2H-pyrazolo[4,3-c]pyridine-4-carboxamide;

N-(2-hydroxyethyl)-2-(3-methyl-4-(2,2,2-trifluoroethoxy)benzyl)-2H-pyrazolo[4,3-c]pyridine-4-carboxamide;

N-(3-acetamidopropyl)-2-((5-methyl-6-(2,2,2-trifluoroethoxy)pyridin-3-yl)methyl)-2H-pyrazolo[4,3-c]pyridine-4-carboxamide;

2-((5-methyl-6-(2,2,2-trifluoroethoxy)pyridin-3-yl)
methyl)-N-(3-(methylsulfonamido)propyl)-2H-pyra-
zolo[4,3-c]pyridine-4-carboxamide;

2-(4-(2,2-difluoroethoxy)-3-methylbenzyl)-N-(2-hy-
droxyethyl)-2H-pyrazolo[4,3-c]pyridine-4-carboxam-
ide;

2-(4-(2,2-difluoroethoxy)-3-methylbenzyl)-N-(3-hy-
droxypropyl)-2H-pyrazolo[4,3-c]pyridine-4-carbox-
amide;

N-(2-hydroxyethyl)-2-((5-methyl-6-(2,2,3,3-tetrafluoro-
propoxy)pyridin-3-yl)methyl)-2H-pyrazolo[4,3-c]pyri-
dine-4-carboxamide;

N-(3-hydroxypropyl)-2-((5-methyl-6-(2,2,3,3-tetrafluo-
ropropoxy)pyridin-3-yl)methyl)-2H-pyrazolo[4,3-c]
pyridine-4-carboxamide;

2-((5-chloro-6-(2,2,2-trifluoroethoxy)pyridin-3-yl)
methyl)-N-(3-hydroxypropyl)-2H-pyrazolo[4,3-c]pyri-
dine-4-carboxamide;

N-(2-((2-methyl-6-(2,2,2-trifluoroethoxy)pyridin-4-yl)
methyl)-2H-pyrazolo[4,3-c]pyridin-4-yl)isobutyr-
amide;

N-(3-hydroxypropyl)-2-(3-methyl-4-(2,2,2-trifluoroeth-
oxy)benzyl)-2H-pyrazolo[4,3-c]pyridine-4-carboxam-
ide;

N-(3-hydroxypropyl)-2-((5-methyl-6-(3,3,3-trifluoro-
propoxy)pyridin-3-yl)methyl)-2H-pyrazolo[4,3-c]pyri-
dine-4-carboxamide;

N-(3-hydroxypropyl)-2-((4-methyl-5-(2,2,2-trifluoroeth-
oxy)pyridin-2-yl)methyl)-2H-pyrazolo[4,3-c]pyridine-
4-carboxamide;

N-methyl-2-((2-methyl-6-(2,2,2-trifluoroethoxy)pyridin-
4-yl)methyl)-2H-pyrazolo[4,3-c]pyridine-4-carboxam-
ide;

N-ethyl-2-((2-methyl-6-(2,2,2-trifluoroethoxy)pyridin-4-
yl)methyl)-2H-pyrazolo[4,3-c]pyridine-4-carboxam-
ide;

N-isopropyl-2-((2-methyl-6-(2,2,2-trifluoroethoxy)pyri-
din-4-yl)methyl)-2H-pyrazolo[4,3-c]pyridine-4-car-
boxamide;

N-(2-hydroxyethyl)-2-((2-methyl-6-(2,2,2-trifluoroeth-
oxy)pyridin-4-yl)methyl)-2H-pyrazolo[4,3-c]pyridine-
4-carboxamide;

N-(3-hydroxypropyl)-2-((2-methyl-6-(2,2,2-trifluoroeth-
oxy)pyridin-4-yl)methyl)-2H-pyrazolo[4,3-c]pyridine-
4-carboxamide;

(S)-N-(2-hydroxypropyl)-2-((5-methyl-6-(3,3,3-trifluoro-
propoxy)pyridin-3-yl)methyl)-2H-pyrazolo[4,3-c]pyri-
dine-4-carboxamide;

(R)-N-(2-hydroxypropyl)-2-((5-methyl-6-(3,3,3-trifluo-
ropropoxy)pyridin-3-yl)methyl)-2H-pyrazolo[4,3-c]
pyridine-4-carboxamide;

(S)-N-(2,3-dihydroxypropyl)-2-((5-methyl-6-(3,3,3-trif-
luoropropoxy)pyridin-3-yl)methyl)-2H-pyrazolo[4,3-
c]pyridine-4-carboxamide;

(R)-N-(2,3-dihydroxypropyl)-2-((5-methyl-6-(3,3,3-trif-
luoropropoxy)pyridin-3-yl)methyl)-2H-pyrazolo[4,3-
c]pyridine-4-carboxamide;

N-(3-hydroxypropyl)-2-((1-(5-(trifluoromethyl)pyridin-
2-yl)-1H-pyrazol-3-yl)methyl)-2H-pyrazolo[4,3-c]
pyridine-4-carboxamide;

N-ethyl-2-((1-(5-(trifluoromethyl)pyridin-2-yl)-1H-pyra-
zol-3-yl)methyl)-2H-pyrazolo[4,3-c]pyridine-4-car-
boxamide;

(S)-N-(2-hydroxypropyl)-2-((4-methyl-5-(2,2,2-trifluo-
roethoxy)pyridin-2-yl)methyl)-2H-pyrazolo[4,3-c]
pyridine-4-carboxamide;

(S)-N-(1-hydroxypropan-2-yl)-2-((5-methyl-6-(3,3,3-trif-
luoropropoxy)pyridin-3-yl)methyl)-2H-pyrazolo[4,3-
c]pyridine-4-carboxamide;

N-(2-cyanoethyl)-2-((4-methyl-5-(2,2,2-trifluoroethoxy)
pyridin-2-yl)methyl)-2H-pyrazolo[4,3-c]pyridine-4-
carboxamide;

N-(2-cyanoethyl)-2-((5-methyl-6-(3,3,3-trifluoro-
propoxy)pyridin-3-yl)methyl)-2H-pyrazolo[4,3-c]pyri-
dine-4-carboxamide;

N-(2-acetamidoethyl)-2-((5-methyl-6-(3,3,3-trifluoro-
propoxy)pyridin-3-yl)methyl)-2H-pyrazolo[4,3-c]pyri-
dine-4-carboxamide;

N-(2-hydroxyethyl)-2-((5-methyl-6-(2-(2,2,2-trifluo-
roethoxy)ethoxy)pyridin-3-yl)methyl)-2H-pyrazolo[4,
3-c]pyridine-4-carboxamide;

N-(2-hydroxyethyl)-2-((2-methoxy-6-(2,2,2-trifluoroeth-
oxy)pyridin-3-yl)methyl)-2H-pyrazolo[4,3-c]pyridine-
4-carboxamide;

N-(3-hydroxypropyl)-2-((2-methoxy-6-(2,2,2-trifluo-
roethoxy)pyridin-3-yl)methyl)-2H-pyrazolo[4,3-c]
pyridine-4-carboxamide;

2-((2-methoxy-6-(2,2,2-trifluoroethoxy)pyridin-3-yl)
methyl)-N-methyl-2H-pyrazolo[4,3-c]pyridine-4-car-
boxamide;

N-ethyl-2-((2-methoxy-6-(2,2,2-trifluoroethoxy)pyridin-
3-yl)methyl)-2H-pyrazolo[4,3-c]pyridine-4-carboxam-
ide;

N-isopropyl-2-(2-(4-(trifluoromethyl)phenoxy)ethyl)-
2H-pyrazolo[4,3-c]pyridine-4-carboxamide;

N-(3-hydroxypropyl)-2-(2-(4-(trifluoromethyl)phenoxy)
ethyl)-2H-pyrazolo[4,3-c]pyridine-4-carboxamide;

N-(2-((6-methyl-5-(2,2,2-trifluoroethoxy)pyrazin-2-yl)
methyl)-2H-pyrazolo[4,3-c]pyridin-4-yl)isobutyr-
amide;

N-(2-((6-(2,2-difluoropropoxy)-5-methylpyridin-3-yl)
methyl)-2H-pyrazolo[4,3-c]pyridin-4-yl)-2-hydroxy-
2-methylpropanamide;

2-(2-((3-chloro-5-(trifluoromethyl)pyridin-2-yl)oxy)
ethyl)-N-(2-hydroxyethyl)-2H-pyrazolo[4,3-c]pyri-
dine-4-carboxamide;

2-((5-cyclopropyl-6-(2,2,2-trifluoroethoxy)pyridin-3-yl)
methyl)-N-ethyl-2H-pyrazolo[4,3-c]pyridine-4-car-
boxamide;

2-((5-cyclopropyl-6-(2,2,2-trifluoroethoxy)pyridin-3-yl)
methyl)-N-isopropyl-2H-pyrazolo[4,3-c]pyridine-4-
carboxamide;

2-((5-cyclopropyl-6-(2,2,2-trifluoroethoxy)pyridin-3-yl)
methyl)-N-(2-hydroxyethyl)-2H-pyrazolo[4,3-c]pyri-
dine-4-carboxamide;

2-((6-(2,2-difluoropropoxy)-5-methylpyridin-3-yl)
methyl)-N-methyl-2H-pyrazolo[4,3-c]pyridine-4-car-
boxamide;

2-((6-(2,2-difluoropropoxy)-5-methylpyridin-3-yl)
methyl)-N-ethyl-2H-pyrazolo[4,3-c]pyridine-4-car-
boxamide;

2-((6-(2,2-difluoropropoxy)-5-methylpyridin-3-yl)
methyl)-N-(2-hydroxyethyl)-2H-pyrazolo[4,3-c]pyri-
dine-4-carboxamide;

2-((6-(2,2-difluoropropoxy)-5-methylpyridin-3-yl)
methyl)-N-(3-hydroxypropyl)-2H-pyrazolo[4,3-c]pyri-
dine-4-carboxamide;

N-ethyl-2-((6-methyl-5-(2,2,2-trifluoroethoxy)pyrazin-2-
yl)methyl)-2H-pyrazolo[4,3-c]pyridine-4-carboxam-
ide;

2-((6-(2,2-difluoropropoxy)-5-methylpyridin-3-yl)
methyl)-N-isopropyl-2H-pyrazolo[4,3-c]pyridine-4-
carboxamide;

N-isopropyl-2-((6-methyl-5-(2,2,2-trifluoroethoxy)pyrazin-2-yl)methyl)-2H-pyrazolo[4,3-c]pyridine-4-carboxamide;
2-((6-(4-chloro-1H-pyrazol-1-yl)-5-methylpyridin-3-yl)methyl)-N-methyl-2H-pyrazolo[4,3-c]pyridine-4-carboxamide;
2-((6-(4-chloro-1H-pyrazol-1-yl)-5-methylpyridin-3-yl)methyl)-N-ethyl-2H-pyrazolo[4,3-c]pyridine-4-carboxamide;
N-(2-hydroxyethyl)-2-(1-(5-methyl-6-(2,2,2-trifluoroethoxy)pyridin-3-yl)ethyl)-2H-pyrazolo[4,3-c]pyridine-4-carboxamide;
N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide;
N-methyl-2-(1-(5-methyl-6-(2,2,2-trifluoroethoxy)pyridin-3-yl)ethyl)-2H-pyrazolo[4,3-c]pyridine-4-carboxamide;
N-ethyl-2-(1-(5-methyl-6-(2,2,2-trifluoroethoxy)pyridin-3-yl)ethyl)-2H-pyrazolo[4,3-c]pyridine-4-carboxamide;
2-((6-(4-chloro-1H-pyrazol-1-yl)-5-methylpyridin-3-yl)methyl)-N-isopropyl-2H-pyrazolo[4,3-c]pyridine-4-carboxamide;
2-((6-(4-chloro-1H-pyrazol-1-yl)-5-methylpyridin-3-yl)methyl)-N-(2-hydroxyethyl)-2H-pyrazolo[4,3-c]pyridine-4-carboxamide;
N-(2-((6-(cyclopropylmethoxy)-5-methylpyridin-3-yl)methyl)-2H-pyrazolo[4,3-c]pyridin-4-yl)-2-hydroxy-2-methylpropanamide;
N,6-dimethyl-2-((5-methyl-6-(2,2,2-trifluoroethoxy)pyridin-3-yl)methyl)-2H-pyrazolo[4,3-c]pyridine-4-carboxamide;
N-ethyl-6-methyl-2-((5-methyl-6-(2,2,2-trifluoroethoxy)pyridin-3-yl)methyl)-2H-pyrazolo[4,3-c]pyridine-4-carboxamide;
N-ethyl-2-((5-methyl-6-((2,2,2-trifluoroethyl)amino)pyridin-3-yl)methyl)-2H-pyrazolo[4,3-c]pyridine-4-carboxamide;
N-(3-hydroxypropyl)-2-((5-methyl-6-((2,2,2-trifluoroethyl)amino)pyridin-3-yl)methyl)-2H-pyrazolo[4,3-c]pyridine-4-carboxamide;
2-((6-(cyclopropylmethoxy)-5-methylpyridin-3-yl)methyl)-N-isopropyl-2H-pyrazolo[4,3-c]pyridine-4-carboxamide;
2-((6-(cyclopropylmethoxy)-5-methylpyridin-3-yl)methyl)-N-methyl-2H-pyrazolo[4,3-c]pyridine-4-carboxamide;
2-((6-(cyclopropylmethoxy)-5-methylpyridin-3-yl)methyl)-N-ethyl-2H-pyrazolo[4,3-c]pyridine-4-carboxamide;
2-((6-(cyclopropylmethoxy)-5-methylpyridin-3-yl)methyl)-N-(2-hydroxyethyl)-2H-pyrazolo[4,3-c]pyridine-4-carboxamide;
2-((6-(cyclopropylmethoxy)-5-methylpyridin-3-yl)methyl)-N-(3-hydroxypropyl)-2H-pyrazolo[4,3-c]pyridine-4-carboxamide;
N-(2-hydroxyethyl)-2-(3-methyl-4-(trifluoromethoxy)benzyl)-2H-pyrazolo[4,3-c]pyridine-4-carboxamide;
N-(3-hydroxypropyl)-2-(3-methyl-4-(trifluoromethoxy)benzyl)-2H-pyrazolo[4,3-c]pyridine-4-carboxamide;
2-((6-(4-chloro-1H-pyrazol-1-yl)-5-methylpyridin-3-yl)methyl)-N-(3-hydroxypropyl)-2H-pyrazolo[4,3-c]pyridine-4-carboxamide;
N-ethyl-2-((6-(4-fluorophenoxy)-5-methylpyridin-3-yl)methyl)-2H-pyrazolo[4,3-c]pyridine-4-carboxamide;
N-(2-hydroxyethyl)-6-methyl-2-((5-methyl-6-(2,2,2-trifluoroethoxy)pyridin-3-yl)methyl)-2H-pyrazolo[4,3-c]pyridine-4-carboxamide;
N-(3-hydroxypropyl)-6-methyl-2-((5-methyl-6-(2,2,2-trifluoroethoxy)pyridin-3-yl)methyl)-2H-pyrazolo[4,3-c]pyridine-4-carboxamide;
2-((5-methyl-6-(3,3,3-trifluoropropoxy)pyridin-3-yl)methyl)-N-(3-(methylsulfonyl)propyl)-2H-pyrazolo[4,3-c]pyridine-4-carboxamide;
N-methyl-2-((1-(2,2,2-trifluoroethoxy)isoquinolin-4-yl)methyl)-2H-pyrazolo[4,3-c]pyridine-4-carboxamide;
N-ethyl-2-((1-(2,2,2-trifluoroethoxy)isoquinolin-4-yl)methyl)-2H-pyrazolo[4,3-c]pyridine-4-carboxamide;
N-(2-hydroxyethyl)-2-((1-(2,2,2-trifluoroethoxy)isoquinolin-4-yl)methyl)-2H-pyrazolo[4,3-c]pyridine-4-carboxamide;
N-(3-hydroxypropyl)-2-(1-(2,2,2-trifluoroethoxy)isoquinolin-4-yl)methyl)-2H-pyrazolo[4,3-c]pyridine-4-carboxamide;
2-(3-chloro-4-(2,2-difluoroethoxy)benzyl)-N-(3-hydroxypropyl)-2H-pyrazolo[4,3-c]pyridine-4-carboxamide;
N-(2-((5-methyl-6-((2,2,2-trifluoroethoxy)methyl)pyridin-3-yl)methyl)-2H-pyrazolo[4,3-c]pyridin-4-yl)isobutyramide;
2-((5-methyl-6-(2,2,2-trifluoroethoxy)pyridin-3-yl)methyl)-N-(3-(methylsulfonyl)propyl)-2H-pyrazolo[4,3-c]pyridine-4-carboxamide;
N-(3-hydroxypropyl)-2-((1-methyl-5-(trifluoromethoxy)-1H-indol-2-yl)methyl)-2H-pyrazolo[4,3-c]pyridine-4-carboxamide;
N-(2-((5-(2,2-difluoroethoxy)-4-methylpyridin-2-yl)methyl)-2H-pyrazolo[4,3-c]pyridin-4-yl)isobutyramide;
N-(2-((5-(2,2-difluoroethoxy)-4-methylpyridin-2-yl)methyl)-2H-pyrazolo[4,3-c]pyridin-4-yl)cyclopropanecarboxamide;
N-(2-hydroxyethyl)-2-(3-(trifluoromethoxy)benzyl)-2H-pyrazolo[4,3-c]pyridine-4-carboxamide;
N-(2-((5-(2,2,3,3,3-pentafluoropropoxy)pyridin-2-yl)methyl)-2H-pyrazolo[4,3-c]pyridin-4-yl)isobutyramide;
N-ethyl-2-((5-(2,2,3,3,3-pentafluoropropoxy)pyridin-2-yl)methyl)-2H-pyrazolo[4,3-c]pyridine-4-carboxamide;
2-((5-(2,2-difluoroethoxy)-4-methylpyridin-2-yl)methyl)-N-isopropyl-2H-pyrazolo[4,3-c]pyridine-4-carboxamide;
2-((5-(2,2-difluoroethoxy)-4-methylpyridin-2-yl)methyl)-N-methyl-2H-pyrazolo[4,3-c]pyridine-4-carboxamide;
2-((5-(2,2-difluoroethoxy)-4-methylpyridin-2-yl)methyl)-N-ethyl-2H-pyrazolo[4,3-c]pyridine-4-carboxamide;
N-ethyl-2-((5-(2,2,3,3-tetrafluoropropoxy)pyridin-2-yl)methyl)-2H-pyrazolo[4,3-c]pyridine-4-carboxamide;
N-(2-((5-chloro-6-(2,2,3,3-tetrafluoropropoxy)pyridin-3-yl)methyl)-2H-pyrazolo[4,3-c]pyridin-4-yl)-2-hydroxy-2-methylpropanamide;
N-(2-((5-(2,2,3,3-tetrafluoropropoxy)pyridin-2-yl)methyl)-2H-pyrazolo[4,3-c]pyridin-4-yl)isobutyramide;
N-(2-acetamidoethyl)-2-((5-methyl-6-(2,2,3,3-tetrafluoropropoxy)pyridin-3-yl)methyl)-2H-pyrazolo[4,3-c]pyridine-4-carboxamide;

(S)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;
(S)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;
N-(3-hydroxypropyl)-2-(3-(trifluoromethyl)benzyl)-2H-pyrazolo[4,3-c]pyridine-4-carboxamide;
(R)-N-(2-hydroxypropyl)-2-((5-methyl-6-(2,2,3,3-tetrafluoropropoxy)pyridin-3-yl)methyl)-2H-pyrazolo[4,3-c]pyridine-4-carboxamide;
(R)-N-(2,3-dihydroxypropyl)-2-((5-methyl-6-(2,2,3,3-tetrafluoropropoxy)pyridin-3-yl)methyl)-2H-pyrazolo[4,3-c]pyridine-4-carboxamide;
2-(3-chloro-4-(2,2-difluoroethoxy)benzyl)-N-methyl-2H-pyrazolo[4,3-c]pyridine-4-carboxamide;
2-((5-chloro-6-(2,2,2-trifluoroethoxy)pyridin-3-yl)methyl)-N-methyl-2H-pyrazolo[4,3-c]pyridine-4-carboxamide;
2-(3-chloro-4-(2,2-difluoroethoxy)benzyl)-N-ethyl-2H-pyrazolo[4,3-c]pyridine-4-carboxamide;
N-ethyl-2-(4-(1,1,2,2-tetrafluoroethoxy)benzyl)-2H-pyrazolo[4,3-c]pyridine-4-carboxamide;
2-((5-chloro-6-(2,2,2-trifluoroethoxy)pyridin-3-yl)methyl)-N-ethyl-2H-pyrazolo[4,3-c]pyridine-4-carboxamide;
N-methyl-2-(1-(4-methyl-5-(2,2,2-trifluoroethoxy)pyridin-2-yl)ethyl)-2H-pyrazolo[4,3-c]pyridine-4-carboxamide;
N-ethyl-2-(1-(4-methyl-5-(2,2,2-trifluoroethoxy)pyridin-2-yl)ethyl)-2H-pyrazolo[4,3-c]pyridine-4-carboxamide;
N-(2-acetamidoethyl)-2-(1-(4-methyl-5-(2,2,2-trifluoroethoxy)pyridin-2-yl)ethyl)-2H-pyrazolo[4,3-c]pyridine-4-carboxamide;
N-(2-hydroxyethyl)-2-(1-(4-methyl-5-(2,2,2-trifluoroethoxy)pyridin-2-yl)ethyl)-2H-pyrazolo[4,3-c]pyridine-4-carboxamide;
N-(3-hydroxypropyl)-2-(1-(4-methyl-5-(2,2,2-trifluoroethoxy)pyridin-2-yl)ethyl)-2H-pyrazolo[4,3-c]pyridine-4-carboxamide;
N-((S)-2-hydroxypropyl)-2-(1-(4-methyl-5-(2,2,2-trifluoroethoxy)pyridin-2-yl)ethyl)-2H-pyrazolo[4,3-c]pyridine-4-carboxamide;
N-methyl-2-((5-methyl-6-(3,3,3-trifluoropropyl)pyridin-3-yl)methyl)-2H-pyrazolo[4,3-c]pyridine-4-carboxamide;
N-ethyl-2-((5-methyl-6-(3,3,3-trifluoropropyl)pyridin-3-yl)methyl)-2H-pyrazolo[4,3-c]pyridine-4-carboxamide;
N-isopropyl-2-((5-methyl-6-(3,3,3-trifluoropropyl)pyridin-3-yl)methyl)-2H-pyrazolo[4,3-c]pyridine-4-carboxamide;
N-(2-hydroxyethyl)-2-((5-methyl-6-(3,3,3-trifluoropropyl)pyridin-3-yl)methyl)-2H-pyrazolo[4,3-c]pyridine-4-carboxamide;
N-(3-hydroxypropyl)-2-((5-methyl-6-(3,3,3-trifluoropropyl)pyridin-3-yl)methyl)-2H-pyrazolo[4,3-c]pyridine-4-carboxamide;
N-methyl-2-((4-methyl-5-(3,3,3-trifluoropropoxy)pyridin-2-yl)methyl)-2H-pyrazolo[4,3-c]pyridine-4-carboxamide;
N-ethyl-2-((4-methyl-5-(3,3,3-trifluoropropoxy)pyridin-2-yl)methyl)-2H-pyrazolo[4,3-c]pyridine-4-carboxamide;
N-(2-hydroxyethyl)-2-((4-methyl-5-(3,3,3-trifluoropropoxy)pyridin-2-yl)methyl)-2H-pyrazolo[4,3-c]pyridine-4-carboxamide;
N-isopropyl-2-((4-methyl-5-(3,3,3-trifluoropropoxy)pyridin-2-yl)methyl)-2H-pyrazolo[4,3-c]pyridine-4-carboxamide;
2-((5-chloro-6-(2,2,3,3-tetrafluoropropoxy)pyridin-3-yl)methyl)-N-methyl-2H-pyrazolo[4,3-c]pyridine-4-carboxamide;
2-((5-chloro-6-(2,2,3,3-tetrafluoropropoxy)pyridin-3-yl)methyl)-N-ethyl-2H-pyrazolo[4,3-c]pyridine-4-carboxamide;
2-((5-chloro-6-(2,2,3,3-tetrafluoropropoxy)pyridin-3-yl)methyl)-N-isopropyl-2H-pyrazolo[4,3-c]pyridine-4-carboxamide;
2-((5-chloro-6-(2,2,3,3-tetrafluoropropoxy)pyridin-3-yl)methyl)-N-(2-hydroxyethyl)-2H-pyrazolo[4,3-c]pyridine-4-carboxamide;
2-((5-chloro-6-(2,2,3,3-tetrafluoropropoxy)pyridin-3-yl)methyl)-N-(3-hydroxypropyl)-2H-pyrazolo[4,3-c]pyridine-4-carboxamide;
(S)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;
(R)-2-((5-chloro-6-(2,2,3,3-tetrafluoropropoxy)pyridin-3-yl)methyl)-N-(2-hydroxypropyl)-2H-pyrazolo[4,3-c]pyridine-4-carboxamide;
(S)-2-((5-chloro-6-(2,2,3,3-tetrafluoropropoxy)pyridin-3-yl)methyl)-N-(1-hydroxypropan-2-yl)-2H-pyrazolo[4,3-c]pyridine-4-carboxamide;
N-(2-acetamidoethyl)-2-((5-chloro-6-(2,2,3,3-tetrafluoropropoxy)pyridin-3-yl)methyl)-2H-pyrazolo[4,3-c]pyridine-4-carboxamide;
N-(2-(1-(4-methyl-5-(2,2,2-trifluoroethoxy)pyridin-2-yl)ethyl)-2H-pyrazolo[4,3-c]pyridin-4-yl)isobutyramide;
2-hydroxy-2-methyl-N-(2-((5-methyl-6-(2,2,3,3-tetrafluoropropoxy)pyridin-3-yl)methyl)-2H-pyrazolo[4,3-c]pyridin-4-yl)propanamide;
N-methyl-2-((5-methyl-6-(2,2,3,3-tetrafluoropropoxy)pyridin-3-yl)methyl)-2H-pyrazolo[4,3-c]pyridine-4-carboxamide;
N-ethyl-2-((5-methyl-6-(2,2,3,3-tetrafluoropropoxy)pyridin-3-yl)methyl)-2H-pyrazolo[4,3-c]pyridine-4-carboxamide;
N-(2-((4-methyl-5-(3,3,3-trifluoropropoxy)pyridin-2-yl)methyl)-2H-pyrazolo[4,3-c]pyridin-4-yl)cyclopropanecarboxamide;
N-(2-((5-methyl-6-(3,3,3-trifluoropropyl)pyridin-3-yl)methyl)-2H-pyrazolo[4,3-c]pyridin-4-yl)cyclopropanecarboxamide;
2-((5-chloro-6-(2,2-difluoropropoxy)pyridin-3-yl)methyl)-N-methyl-2H-pyrazolo[4,3-c]pyridine-4-carboxamide;
2-((5-chloro-6-(2,2-difluoropropoxy)pyridin-3-yl)methyl)-N-ethyl-2H-pyrazolo[4,3-c]pyridine-4-carboxamide;
2-((5-chloro-6-(2,2-difluoropropoxy)pyridin-3-yl)methyl)-N-(3-hydroxypropyl)-2H-pyrazolo[4,3-c]pyridine-4-carboxamide;
2-((5-chloro-6-(2,2-difluoropropoxy)pyridin-3-yl)methyl)-N-(2-hydroxyethyl)-2H-pyrazolo[4,3-c]pyridine-4-carboxamide;
N-isopropyl-2-((5-methyl-6-(2,2,3,3-tetrafluoropropoxy)pyridin-3-yl)methyl)-2H-pyrazolo[4,3-c]pyridine-4-carboxamide;

(S)-N-(1-hydroxypropan-2-yl)-2-((5-methyl-6-(2,2,3,3-tetrafluoropropoxy)pyridin-3-yl)methyl)-2H-pyrazolo[4,3-c]pyridine-4-carboxamide;

2-((5-chloro-6-(3,3,3-trifluoropropoxy)pyridin-3-yl)methyl)-N-methyl-2H-pyrazolo[4,3-c]pyridine-4-carboxamide;

2-((5-chloro-6-(3,3,3-trifluoropropoxy)pyridin-3-yl)methyl)-N-ethyl-2H-pyrazolo[4,3-c]pyridine-4-carboxamide;

2-((5-chloro-6-(3,3,3-trifluoropropoxy)pyridin-3-yl)methyl)-N-isopropyl-2H-pyrazolo[4,3-c]pyridine-4-carboxamide;

2-((5-chloro-6-(3,3,3-trifluoropropoxy)pyridin-3-yl)methyl)-N-(2-hydroxyethyl)-2H-pyrazolo[4,3-c]pyridine-4-carboxamide;

2-((5-chloro-6-(3,3,3-trifluoropropoxy)pyridin-3-yl)methyl)-N-(3-hydroxypropyl)-2H-pyrazolo[4,3-c]pyridine-4-carboxamide;

N-ethyl-2-((1-methyl-5-(trifluoromethyl)-1H-benzo[d]imidazol-2-yl)methyl)-2H-pyrazolo[4,3-c]pyridine-4-carboxamide;

N-(3-hydroxypropyl)-2-((1-methyl-5-(trifluoromethyl)-1H-benzo[d]imidazol-2-yl)methyl)-2H-pyrazolo[4,3-c]pyridine-4-carboxamide;

2-hydroxy-2-methyl-N-(2-(3-methyl-4-(2,2,2-trifluoroethoxy)benzyl)-2H-pyrazolo[4,3-c]pyridin-4-yl)propanamide;

2-hydroxy-2-methyl-N-(2-(3-methyl-4-(trifluoromethoxy)benzyl)-2H-pyrazolo[4,3-c]pyridin-4-yl)propanamide;

2-(4-(2,2-difluoroethoxy)-3-methylbenzyl)-N-methyl-2H-pyrazolo[4,3-c]pyridine-4-carboxamide;

2-(4-(2,2-difluoroethoxy)-3-methylbenzyl)-N-ethyl-2H-pyrazolo[4,3-c]pyridine-4-carboxamide;

N-(2-acetamidoethyl)-2-((6-(cyclopropylmethoxy)-5-methylpyridin-3-yl)methyl)-2H-pyrazolo[4,3-c]pyridine-4-carboxamide;

N-(2-acetamidoethyl)-2-(3-methyl-4-(2,2,2-trifluoroethoxy)benzyl)-2H-pyrazolo[4,3-c]pyridine-4-carboxamide;

N-(2-acetamidoethyl)-2-(4-(2,2-difluoroethoxy)-3-methylbenzyl)-2H-pyrazolo[4,3-c]pyridine-4-carboxamide;

2-hydroxy-2-methyl-N-(2-((4-methyl-5-(3,3,3-trifluoropropoxy)pyridin-2-yl)methyl)-2H-pyrazolo[4,3-c]pyridin-4-yl)propanamide;

N-(2-acetamidoethyl)-2-((6-(2,2-difluoropropoxy)-5-methylpyridin-3-yl)methyl)-2H-pyrazolo[4,3-c]pyridine-4-carboxamide;

2-((5-chloro-6-(cyclopropylmethoxy)pyridin-3-yl)methyl)-N-methyl-2H-pyrazolo[4,3-c]pyridine-4-carboxamide;

2-((5-chloro-6-(cyclopropylmethoxy)pyridin-3-yl)methyl)-N-ethyl-2H-pyrazolo[4,3-c]pyridine-4-carboxamide;

2-((5-chloro-6-(cyclopropylmethoxy)pyridin-3-yl)methyl)-N-isopropyl-2H-pyrazolo[4,3-c]pyridine-4-carboxamide;

2-((5-chloro-6-(cyclopropylmethoxy)pyridin-3-yl)methyl)-N-(2-hydroxyethyl)-2H-pyrazolo[4,3-c]pyridine-4-carboxamide;

2-((5-chloro-6-(cyclopropylmethoxy)pyridin-3-yl)methyl)-N-(3-hydroxypropyl)-2H-pyrazolo[4,3-c]pyridine-4-carboxamide;

2-((6-((4-fluorobenzyl)oxy)-5-methylpyridin-3-yl)methyl)-N-(2-hydroxyethyl)-2H-pyrazolo[4,3-c]pyridine-4-carboxamide;

N-(2-((6-cyclobutoxy-5-methylpyridin-3-yl)methyl)-2H-pyrazolo[4,3-c]pyridin-4-yl)-2-hydroxy-2-methylpropanamide;

2-((6-cyclobutoxy-5-methylpyridin-3-yl)methyl)-N-ethyl-2H-pyrazolo[4,3-c]pyridine-4-carboxamide;

N-(2-acetamidoethyl)-2-((6-cyclobutoxy-5-methylpyridin-3-yl)methyl)-2H-pyrazolo[4,3-c]pyridine-4-carboxamide;

2-((6-cyclobutoxy-5-methylpyridin-3-yl)methyl)-N-isopropyl-2H-pyrazolo[4,3-c]pyridine-4-carboxamide;

2-((6-cyclobutoxy-5-methylpyridin-3-yl)methyl)-N-(2-hydroxyethyl)-2H-pyrazolo[4,3-c]pyridine-4-carboxamide;

2-((6-cyclobutoxy-5-methylpyridin-3-yl)methyl)-N-(3-hydroxypropyl)-2H-pyrazolo[4,3-c]pyridine-4-carboxamide;

N-(2-((5-(cyclopropylmethoxy)-4-methylpyridin-2-yl)methyl)-2H-pyrazolo[4,3-c]pyridin-4-yl)-2-hydroxy-2-methylpropanamide;

2-((5-(cyclopropylmethoxy)-4-methylpyridin-2-yl)methyl)-N-ethyl-2H-pyrazolo[4,3-c]pyridine-4-carboxamide;

2-((5-(cyclopropylmethoxy)-4-methylpyridin-2-yl)methyl)-N-isopropyl-2H-pyrazolo[4,3-c]pyridine-4-carboxamide;

2-((5-(cyclopropylmethoxy)-4-methylpyridin-2-yl)methyl)-N-(2-hydroxyethyl)-2H-pyrazolo[4,3-c]pyridine-4-carboxamide;

2-((5-(cyclopropylmethoxy)-4-methylpyridin-2-yl)methyl)-N-(3-hydroxypropyl)-2H-pyrazolo[4,3-c]pyridine-4-carboxamide;

N-methyl-2-((5-methyl-6-(2,2,3,3-tetrafluoropropoxy)pyridazin-3-yl)methyl)-2H-pyrazolo[4,3-c]pyridine-4-carboxamide;

N-ethyl-2-((5-methyl-6-(2,2,3,3-tetrafluoropropoxy)pyridazin-3-yl)methyl)-2H-pyrazolo[4,3-c]pyridine-4-carboxamide;

N-(3-hydroxypropyl)-2-((5-methyl-6-(2,2,3,3-tetrafluoropropoxy)pyridazin-3-yl)methyl)-2H-pyrazolo[4,3-c]pyridine-4-carboxamide;

N-(2-((5-(2,2-difluoropropoxy)-4-methylpyridin-2-yl)methyl)-2H-pyrazolo[4,3-c]pyridin-4-yl)isobutyramide;

2-((5-(2,2-difluoropropoxy)-4-methylpyridin-2-yl)methyl)-N-methyl-2H-pyrazolo[4,3-c]pyridine-4-carboxamide;

2-((5-(2,2-difluoropropoxy)-4-methylpyridin-2-yl)methyl)-N-ethyl-2H-pyrazolo[4,3-c]pyridine-4-carboxamide;

2-((5-(2,2-difluoropropoxy)-4-methylpyridin-2-yl)methyl)-N-isopropyl-2H-pyrazolo[4,3-c]pyridine-4-carboxamide;

2-((5-(2,2-difluoropropoxy)-4-methylpyridin-2-yl)methyl)-N-(2-hydroxyethyl)-2H-pyrazolo[4,3-c]pyridine-4-carboxamide;

2-((5-(2,2-difluoropropoxy)-4-methylpyridin-2-yl)methyl)-N-(3-hydroxypropyl)-2H-pyrazolo[4,3-c]pyridine-4-carboxamide;

N-(2-cyanoethyl)-2-((6-(2,2-difluoropropoxy)-5-methylpyridin-3-yl)methyl)-2H-pyrazolo[4,3-c]pyridine-4-carboxamide;

2-(4-(2,2-difluoropropoxy)-3-methylbenzyl)-N-methyl-2H-pyrazolo[4,3-c]pyridine-4-carboxamide;

2-(4-(2,2-difluoropropoxy)-3-methylbenzyl)-N-ethyl-2H-pyrazolo[4,3-c]pyridine-4-carboxamide;

2-(4-(2,2-difluoropropoxy)-3-methylbenzyl)-N-isopropyl-2H-pyrazolo[4,3-c]pyridine-4-carboxamide;

2-(4-(2,2-difluoropropoxy)-3-methylbenzyl)-N-(2-hydroxyethyl)-2H-pyrazolo[4,3-c]pyridine-4-carboxamide;
2-(4-(2,2-difluoropropoxy)-3-methylbenzyl)-N-(3-hydroxypropyl)-2H-pyrazolo[4,3-c]pyridine-4-carboxamide;
(R)-2-(4-(2,2-difluoroethoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((R)-2-hydroxypropyl)-2H-pyrazolo[4,3-c]pyridine-4-carboxamide;
(R)-2-(4-(2,2-difluoroethoxy)-3,5-dimethylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((R)-2-hydroxypropyl)-2H-pyrazolo[4,3-c]pyridine-4-carboxamide;
(S)-2-(4-(2,2-difluoropropoxy)-3-methylbenzyl)-N-(2-hydroxypropyl)-2H-pyrazolo[4,3-c]pyridine-4-carboxamide;
(R)-2-(4-(2,2-difluoropropoxy)-3-methylbenzyl)-N-(2-hydroxypropyl)-2H-pyrazolo[4,3-c]pyridine-4-carboxamide;
2-(1-(4-(2,2-difluoroethoxy)-3-methylphenyl)ethyl)-N-((S)-2-hydroxypropyl)-2H-pyrazolo[4,3-c]pyridine-4-carboxamide;
(S)-2-(4-(2,2-difluoroethoxy)-3,5-dimethylbenzyl)-N-(2-hydroxypropyl)-2H-pyrazolo[4,3-c]pyridine-4-carboxamide;
2-(1-(4-(2,2-difluoropropoxy)-3-methylphenyl)ethyl)-N-((S)-2-hydroxypropyl)-2H-pyrazolo[4,3-c]pyridine-4-carboxamide;
2-(1-(4-(2,2-difluoroethoxy)-3-methylphenyl)ethyl)-N-2-hydroxyethoxy)-2H-pyrazolo[4,3-c]pyridine-4-carboxamide;
2-(4-(2,2-difluoroethoxy)-3,5-dimethylbenzyl)-N-(2-hydroxyethyl)-2H-pyrazolo[4,3-c]pyridine-4-carboxamide;
2-(1-(4-(2,2-difluoropropoxy)-3-methylphenyl)ethyl)-N-(2-hydroxyethyl)-2H-pyrazolo[4,3-c]pyridine-4-carboxamide;
2-(1-(4-(2,2-difluoroethoxy)-3-methylphenyl)ethyl)-N-(3-hydroxypropyl)-2H-pyrazolo[4,3-c]pyridine-4-carboxamide;
2-(4-(2,2-difluoroethoxy)-3,5-dimethylbenzyl)-N-(3-hydroxypropyl)-2H-pyrazolo[4,3-c]pyridine-4-carboxamide;
2-(1-(4-(2,2-difluoropropoxy)-3-methylphenyl)ethyl)-N-(3-hydroxypropyl)-2H-pyrazolo[4,3-c]pyridine-4-carboxamide;
2-(4-(2,2-difluoropropoxy)-3-methylbenzyl)-2H-pyrazolo[4,3-c]pyridine-4-carboxamide;
2-(4-(difluoromethoxy)-3-methylbenzyl)-N-(3-hydroxypropyl)-2H-pyrazolo[4,3-c]pyridine-4-carboxamide; and
2-(4-(difluoromethoxy)-3-methylbenzyl)-N-isopropyl-2H-pyrazolo[4,3-c]pyridine-4-carboxamide;
or a pharmaceutically acceptable salt thereof.

9. A pharmaceutical composition comprising the compound or the pharmaceutically acceptable salt thereof, according to claim 1, and a pharmaceutically acceptable carrier.

10. The pharmaceutical composition according to claim 9, further comprising another pharmacologically active agent.

11. A method for the treatment of a condition or disorder in which a TTX-S channel blocker is involved, in an animal or a human, which comprises administering to the animal or human in need of such treatment a therapeutically effective amount of the compound or the pharmaceutically acceptable salt thereof according to claim 1, wherein the condition or disorder is selected from the group consisting of: acute pain, chronic pain, neuropathic pain, inflammatory pain, visceral pain, nociceptive pain, multiple sclerosis, irritable bowel syndrome, osteoarthritis, rheumatoid arthritis, a functional bowel disorder, an inflammatory bowel disease, pain associated with dysmenorrhea, pelvic pain, cystitis, pancreatitis, migraine, a cluster and tension headache, diabetic neuropathy, peripheral neuropathic pain, sciatica, fibromyalgia, Crohn's disease, epilepsy or an epileptic condition, bipolar depression, tachyarrhythmias, mood disorder, bipolar disorder, myotonia, arrhythmia, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder, causalgia, chemo-induced pain, anxiety, and depression; and combination thereof.

12. A process for preparing a pharmaceutical composition comprising mixing the compound or the pharmaceutically acceptable salt thereof according to claim 1, and a pharmaceutically acceptable carrier or excipient.

13. The method according to claim 11, wherein the condition or disorder is anxiety or depression.

14. The compound according to claim 1,
wherein A is selected from the group consisting of pyridyl, pyridazinyl, phenyl, pyrazolyl, pyrazinyl, triazolyl, isoquinolyl, indolyl, and benzoimidazolyl;
or a pharmaceutically acceptable salt thereof.

15. A single enantiomer of a compound selected from the group consisting of:
(1) N-(2-(1-(5-methyl-6-(2,2,2-trifluoroethoxy)pyridin-3-yl)ethyl)-2H-pyrazolo[4,3-c]pyridin-4-yl)isobutyramide;
(2) N-(2-(1-(5-methyl-6-(2,2,2-trifluoroethoxy)pyridin-3-yl)ethyl)-2H-pyrazolo[4,3-c]pyridin-4-yl)acetamide;
(3) N-(2-(1-(5-methyl-6-(2,2,2-trifluoroethoxy)pyridin-3-yl)ethyl)-2-pyrazolo[4,3-c]pyridin-4-yl)propionamide;
(4) N-(2-(1-(5-methyl-6-(2,2,2-trifluoroethoxy)pyridin-3-yl)ethyl)-2H-pyrazolo[4,3-c]pyridin-4-yl)tetrahydro-2H-pyran-4-carboxamide;
(5) N-(2-hydroxyethy)-2H-(5-methyl-6-(2,2,2-trifluoroethoxy)pyridin-3-yl)ethyl)-2H-pyrazolo[4,3-c]pyridine-4-carboxamide;
(6) N-(3-hydroxypropyl)-2-(1-(5-methyl-6-(2,2,2-trifluoroethoxy)pyridin-3-yl)ethyl)-2H-pyrazolo[4,3-c]pyridine-4-carboxamide;
(7) N-methyl-2-(1-(5-methyl-6-(2,2,2-trifluoroethoxy)pyridin-3-yl)ethyl)-2H-pyrazolo[4,3-c]pyridine-4-carboxmide;
(8) N-ethyl-2-(1-(5-methyl-6-(2,2,2-trifluoroethoxy)pyridin-3-yl)ethyl)-2H-pyrazolo[4,3-c]pyridine-4-carboxamide;
(9) N-methyl-2-(1-(4-methyl-5-(2,2,2-trifluoroethoxy)pyridin-2-yl)ethyl)-2H-pyrazolo[4,3-c]pyridine-4-carboxamide;
(10) N-ethyl-2-(1-(4-methyl-5-(2,2,2trifluoroethoxy)pyridin-2-yl)ethyl)-2H-pyrazolo[4,3-c]pyridine-4-carboxamide;
(11) N-(2-(1-(4-methyl-5-(2,2,2trifluoroethoxy)pyridin-2-yl)ethyl)-2H-pyrazolo[4,3-c]pyridin-4-yl)isobutyramide;

(12) 2-hydroxy-2-methyl-N-(2-(1-(5-methyl-6-(2,2,2-trifluoroethoxy)pyridin-2-yl)ethyl)-2H-pyrazolo[4,3-c]pyridin-4-yl)-yl)propanamide;
(13) 2-(1-(4-(2,2-difluoroethoxy)-3-methylphenyl)ethyl)-N-((R)-2-hydroxypropyl)-2H-pyrazolo[4,3-c]pyridine-4-carboxamide;
(14) 2-(1-(4-(2,2-difluoroethoxy)-3-methylphenyl)ethyl)-N-((S)-2-hydroxypropyl)-2H-pyrazolo[4,3-c]pyridine-4-carboxamide;
(15) 2-(1-(4-(2,2-difluoroethoxy)-3-methylphenyl)ethyl)-N-(2-hydroxyethyl)-2H-pyrazolo[4,3-c]pyridine-4-carboxamide;
(16) 2-(1-(4-(2,2-difluoroethoxy)-3-methylphenyl)ethyl)-N-hydroxypropyl)-2H-parazolo[4,3-c]pyridine-4-carboxamide;
(17) 2-(1-(5-methyl-6-(2,2,2- trifluoroethoxy)pyridin-3-yl)ethyl)-2H-pyrazolo[4,3-c]pyridin-4-carboxamide;
(18) N-(2-(1-(6-(2,2-difluoroethoxy)-5-methylpyridin-3-yl)ethyl)-2H-parazolo[4,3-c]pyridine-4-yl)cyclopropanecarboxamide;
(19) N-isopropyl-2-(1-(5-methyl-5-(2,2,2-trifluoroethoxy)pyridin-3-yl)ethyl)-2H-pyrazolo[4,3-c]pyridine-4-carboxamide;
(20) N-(2-acetamidoethyl)-2-(1-(4-methyl-5-(2,2,2-trifluoroethoxy)pyridin-3-yl)ethyl)-2H-pyrazolo[4,3-c]pyridine-4-carboxamide;
(21) N-(2-hydroxyethyl)-2-(1-(4-methyl-5-(2,2,2-trifluoroethoxy)pyridin-3-yl)ethyl)-2H-pyrazolo[4,3-c]pyridine-4-carboxamide;
(22) N-(3-hydroxypropyl)-2-(1-(4-methyl-5-(2,2,2-trifluoroethoxy)pyridin-2-yl)ethyl)-2H-pyrazolo[4,3-c]pyridine-4-carboxamide;
(23) N-((S)-2-hydroxypropyl)-2-(1-(4-methyl-5-(2,2,2-trifluoroethoxy)pyridin-2-yl)ethyl)-2H-pyrazolo[4,3-c]pyridine-4-carboxamide;
(24) N-isopropyl-2-(1-(4-methyl-5-(2,2,2-trifluoroethoxy)pyridin-2-yl)ethyl)-2H-pyrazolo[4,3-c]pyridine-4-carboxamide;
(25) N-(2-(1-(4-methyl-5-(2,2,2-trifluoroethoxy)pyridin-2-yl)ethyl)-2H-pyrazolo[4,3-c]pyridine-4-yl)cyclopropanecarboxamide;
(26) N-(2-(1-(5-methyl-6-(2,2,2-trifluoroethoxy)pyridin-2-yl)ethyl)-2H-pyrazolo[4,3-c]pyridine-4-yl)oxazole-5-carboxamide;
(27) 2-(1-(4-(2,2-difluoropropoxy)-3-methylphenyl)ethyl)-N-((R)-2-hydroxypropyl)-2H-pyrazolo[4,3-c]pyridine-4-carboxamide;
(28) 2-(1-(4-(2,2-difluoropropoxy)-3-methylphenyl)ethyl-N-((S)-2-hydroxypropyl)-2H-pyrazolo[4,3-c]pyridine-4-carboxamide;
(29) 2-(1-(4-(2,2-difluoropropoxy)-3-methylphenyl)ethyl)-N-(2-hydroxyethyl)-2H-pyrazolo[4,3-c]pyridine-4-carboxamide;
(30) 2-(1-(4-(2,2-difluoropropoxy)-3-methylphenyl)ethyl)-N-(2-hydroxyethyl)-2H-pyrazolo[4,3-c]pyridine-4-carboxamide; and
(34) N-(2-(1-(5-methyl-6-(2,2,2-trifluoroethoxy)pyridine-3-yl)ethyl)-2H-pyrazolo[4,3-c]pyridin-4-yl)cycopropanecarboxamide;

or a pharmaceutically acceptable salt thereof.

* * * * *

UNITED STATES PATENT AND TRADEMARK OFFICE
CERTIFICATE OF CORRECTION

PATENT NO. : 9,944,634 B2
APPLICATION NO. : 14/434203
DATED : April 17, 2018
INVENTOR(S) : Kiyoshi Kawamura et al.

Page 1 of 1

It is certified that error appears in the above-identified patent and that said Letters Patent is hereby corrected as shown below:

In the Claims

In Column 644, Line 56 (Claim 1), "pyridyl or -O-$_a$-pyrazolyl, wherein the phenyl, the" should read --pyridyl or -O-$_n$-pyrazolyl, wherein the phenyl, the--.

In Column 645, Line 13 (Claim 1), "$R^5$ is independently selected from die group consisting of:" should read --$R^5$ is independently selected from the group consisting of:--.

In Column 645, Line 30 (Claim 1), "-O-$C_{1-6}$ alkyl, -$C_{3-7}$ cycloalkyl, hydroxyl-$C_{1-6}$" should read -- -O-$C_{1-6}$ alkyl, -$C_{3-7}$ cycloalkyl, -O-$C_{3-7}$ cycloalkyl, hydroxyl-$C_{1-6}$--.

In Column 645, Line 60 (Claim 1), "substituted with one or more, halogens;" should read --substituted with one or more halogens;--.

In Column 647, Line 2 (Claim 3), "$C_{3-7}$ cycloalkyl, 13 $NR^8R^9$, heterocyclyl, aryl, aryl-$C_{1-6}$" should read --$C_{3-7}$ cycloalkyl, -$NR^8R^9$, heterocyclyl, aryl, aryl-$C_{1-6}$--.

In Column 647, Lines 22-23 (Claim 3), "$R^8$ and $R^9$ are independently hydrogen, $C_{1-6}$ alkyl, Chd 3-7 cycloalkyl, or aryl, wherein the $C_{1-6}$ alkyl, the $C_{3-7}$" should read --$R^8$ and $R^9$ are independently hydrogen, $C_{1-6}$ alkyl, $C_{3-7}$ cycloalkyl, or aryl, wherein the $C_{1-6}$ alkyl, the $C_{3-7}$--.

In Column 647, Line 38 (Claim 3), "or more halogens (5) cycloalkyl, (6) -O-$C_{1-6}$ alkyl," should read --or more halogens, (5) -$C_{3-6}$ cycloalkyl, (6) -O-$C_{1-6}$ alkyl,--.

Signed and Sealed this
Third Day of July, 2018

Andrei Iancu
*Director of the United States Patent and Trademark Office*